(12) United States Patent
Sherman et al.

(10) Patent No.: US 6,495,348 B1
(45) Date of Patent: Dec. 17, 2002

(54) MITOMYCIN BIOSYNTHETIC GENE CLUSTER

(75) Inventors: David H. Sherman, St. Louis Park, MN (US); Yingqing Mao, St. Paul, MN (US); Mustafa Varoglu, St. Paul, MN (US); Min He, St. Paul, MN (US); Paul Sheldon, Fitchburg, WI (US)

(73) Assignee: Regents of the University of Minnesota, Minneapolis, MN (US)

(*) Notice: Subject to any disclaimer, the term of this patent is extended or adjusted under 35 U.S.C. 154(b) by 0 days.

(21) Appl. No.: 09/266,965

(22) Filed: Mar. 12, 1999

Related U.S. Application Data

(63) Continuation-in-part of application No. 08/624,447, filed as application No. PCT/US94/11279 on Oct. 6, 1994, which is a continuation-in-part of application No. 08/133,963, filed on Oct. 7, 1993, now abandoned.

(51) Int. Cl.⁷ .................................................. C12P 19/62
(52) U.S. Cl. ........................ 435/76; 435/183; 435/320.1; 435/252.3; 435/252.35; 536/23.1; 536/23.2
(58) Field of Search .............................. 536/23.1, 23.2; 435/252.35, 76, 320.1, 252.3, 183

(56) References Cited

U.S. PATENT DOCUMENTS

| | | | |
|---|---|---|---|
| 3,214,440 A | 10/1965 | Cosulich et al. | |
| 3,219,530 A | 11/1965 | Bohonos et al. | |

(List continued on next page.)

FOREIGN PATENT DOCUMENTS

| | | | | |
|---|---|---|---|---|
| EP | 0238323 | 9/1987 | ........... | C12N/15/00 |
| EP | 0361905 | 4/1990 | ........... | C12N/15/52 |
| EP | 0 468 217 | 1/1992 | ........... | C12N/15/76 |
| EP | 0468220 | 1/1992 | ........... | C12N/15/52 |
| EP | 0 791 655 | 8/1997 | ........... | C12N/15/52 |
| EP | 0 791 656 | 8/1997 | ........... | C12N/15/52 |
| FR | 2696189 | 4/1994 | ........... | C12N/15/31 |
| JP | 61205484 | 9/1986 | ........... | C12N/15/00 |
| JP | 63313589 | 12/1988 | ........... | C12N/1/20 |
| JP | 6261765 | 9/1994 | ........... | C12N/15/54 |
| JP | 9268190 | 10/1997 | ........ | C07D/487/14 |
| JP | 10094395 | 4/1998 | ........... | C12N/15/09 |
| TW | 202481 | 3/1993 | ........... | C12N/15/10 |
| WO | 92/20698 | 11/1992 | ........... | C07H/21/04 |
| WO | 93/13663 | 7/1993 | ........... | A01N/43/22 |
| WO | 95/09926 | 4/1995 | ............ | C12Q/1/18 |
| WO | 96/01901 | 1/1996 | ........... | C12N/15/52 |
| WO | 96/10084 | 4/1996 | ........... | C12N/15/52 |
| WO | 97/02358 | 1/1997 | ........... | C12P/19/62 |
| WO | 97/04077 | 2/1997 | ............ | C12N/9/00 |
| WO | 97/08323 | 3/1997 | ........... | C12N/15/52 |
| WO | 97/23630 | 7/1997 | ........... | C12N/15/54 |
| WO | 97/36904 | 10/1997 | ........ | C07D/487/04 |
| WO | 97/39135 | 10/1997 | ........... | C12N/15/87 |
| WO | 98/00121 | 1/1998 | ........... | A61K/31/12 |
| WO | 98/00557 | 1/1998 | ........... | C12N/15/82 |
| WO | 98/01546 | 1/1998 | ........... | C12N/15/00 |
| WO | 98/01571 | 1/1998 | ........... | C12N/15/62 |

(List continued on next page.)

OTHER PUBLICATIONS

Adler, T., "Plants: The New Plastics Makers", *Science News of the Week*, 146(26–27), 420 (1994).

(List continued on next page.)

*Primary Examiner*—Ponnathapu Achutamurthy
*Assistant Examiner*—Kathleen Kerr
(74) *Attorney, Agent, or Firm*—Schwegman, Lundberg, Woessner & Kluth, P.A.

(57) ABSTRACT

The invention provides a biosynthetic gene cluster for mitomycin, for example, a mitomycin biosynthetic cluster from organisms such as Streptomyces, for instance, *S. lavendulae*, as well as methods of using gene(s) within the cluster to alter antibiotic biosynthesis and to prepare a polyketide synthase.

25 Claims, 78 Drawing Sheets

U.S. PATENT DOCUMENTS

| | | | |
|---|---|---|---|
| 3,272,696 A | 9/1966 | O'Connell et al. | |
| 3,306,821 A | 2/1967 | Scroeder | |
| 3,332,944 A | 7/1967 | Cosulich et al. | |
| 4,395,558 A | 7/1983 | Kasai et al. | 548/422 |
| 4,885,251 A | 12/1989 | Inoglia et al. | 435/183 |
| 4,892,819 A | 1/1990 | Carr et al. | 435/69.1 |
| 4,935,340 A | 6/1990 | Baltz et al. | 435/6 |
| 4,975,278 A | 12/1990 | Senter et al. | 424/94.3 |
| 5,023,253 A | 6/1991 | William et al. | 514/228.2 |
| 5,032,512 A | 7/1991 | Witholt et al. | 435/123 |
| 5,108,918 A | 4/1992 | Groenen et al. | 435/172.3 |
| 5,140,013 A | 8/1992 | Gaudreault et al. | 514/21 |
| 5,229,279 A | 7/1993 | Peoples et al. | 435/135 |
| 5,245,023 A | 9/1993 | Peoples et al. | 536/23.2 |
| 5,250,430 A | 10/1993 | Peoples et al. | 435/232 |
| 5,252,673 A | 10/1993 | Hirano et al. | 525/183 |
| 5,256,685 A | 10/1993 | Arai et al. | 514/410 |
| 5,334,611 A | 8/1994 | Arai et al. | 514/410 |
| 5,352,798 A | 10/1994 | Benigni et al. | 548/422 |
| 5,374,739 A | 12/1994 | Kaneko et al. | 548/422 |
| 5,462,862 A | 10/1995 | Groenen et al. | 435/69.1 |
| 5,514,544 A | 5/1996 | Rao et al. | 435/6 |
| 5,545,553 A | 8/1996 | Gotschlich | 435/252.33 |
| 5,554,638 A | 9/1996 | Dewhirst et al. | 514/398 |
| 5,589,385 A | 12/1996 | Ryan et al. | 435/258.35 |
| 5,629,427 A | 5/1997 | Peterson | 546/276.7 |
| 5,665,564 A | 9/1997 | Caruso et al. | 435/69.1 |
| 5,672,497 A | 9/1997 | Cox et al. | 435/320.1 |
| 5,716,849 A | 2/1998 | Ligon et al. | 435/419 |
| 5,744,350 A | 4/1998 | Vinci et al. | 435/254.11 |
| 5,744,460 A | 4/1998 | Muller et al. | 514/44 |
| 5,747,469 A | 5/1998 | Roth et al. | 514/44 |
| 5,763,239 A | 6/1998 | Short et al. | 435/172.1 |
| 5,788,958 A | 8/1998 | Dewhirst et al. | 424/78.38 |
| 5,824,513 A | 10/1998 | Katz et al. | 435/76 |
| 5,830,750 A * | 11/1998 | Khosla et al. | 435/252.35 |
| 5,866,410 A | 2/1999 | Ryan et al. | 435/320.1 |
| 5,962,290 A | 10/1999 | Khosla et al. | 435/183 |
| 6,022,731 A | 2/2000 | Khosla et al. | 435/252.35 |
| 6,033,883 A | 3/2000 | Barr et al. | 435/148 |
| 6,077,696 A | 6/2000 | Khosla et al. | 435/135 |
| 6,090,601 A | 7/2000 | Gustafsson et al. | 435/183 |
| 6,117,659 A | 9/2000 | Ashley et al. | 435/155 |
| 6,210,935 B1 | 4/2001 | Schupp et al. | |

FOREIGN PATENT DOCUMENTS

| | | | |
|---|---|---|---|
| WO | 98/04713 | 2/1998 | C12N/15/52 |
| WO | 98/07868 | 2/1998 | C12N/15/52 |
| WO | 98/09978 | 3/1998 | C07H/17/08 |
| WO | 98/11230 | 3/1998 | C12N/15/52 |
| WO | 98/27203 | 6/1998 | C12N/15/00 |
| WO | 98/36078 | 8/1998 | C12N/15/52 |
| WO | 98/49315 | 11/1998 | C12N/15/52 |
| WO | 98/53097 | 11/1998 | C12Q/1/68 |
| WO | 98/54308 | 12/1998 | C12N/15/52 |
| WO | 99/03986 | 1/1999 | C12N/15/00 |

OTHER PUBLICATIONS

Andersen, J.F., et al., "Characterization of *Saccharopolyspora erythraea* Cytochrome P–450 Genes and Enzymes, Including 6–Deoxyerythronolide B Hydroxylase", *Journal of Bacteriology*, 174, 725–735 (1992).

Anderson, A.J., et al., "Occurrence, Metabolism, Metabolic Role, and Industrial Uses of Bacterial Polyhydroxyalkanoates", *Microbiological Review*, 54(4), 450–472 (1990).

August, et al., "Cloning and Expression of the *Streptomyces lavendulae* Mitomycin C Resistance Genes in *Streptomyces lividans*", *92nd General Meeting of the American Society for Microbiology*, New Orleans, Louisiana, Abstract No. B19, 16 (1992).

August, P.R., et al., "Cloning and Analysis of a Locus (mcr) Involved in Mitomycin C Resistance in *Streptomyces lavendulae*", *Journal of Bacteriology*, 176(14), 4448–4454 (1994).

August, R.P., et al., "Cloning and Expression of *Streptomyces lavendulae* Mitomycin C Resistance Gene in *Streptomyces lividans* 1326", *92nd General Meeting of the American Society for Microbiology*, New Orleans, Louisiana, Abstract No. O–12, 31 (1992).

August, P.R., et al., "Inducible Synthesis of the Mitomycin C Resistance Gene Product (MCRA) from *Streptomyces lavendulae*", *Gene*, 175, 261–267 (1996).

Beijnen, et al., "Mitomycin Antitumor Agents: A Review of Their Physico–Chemical and Analytical Properties and Stability", *Journal of Pharmaceutical & Biomedical Analysis*, 4, 275–295 (1986).

Bevitt, D.J., et al., "6–Deoxyerythronolide–B synthase 2 from *Saccharopolyspora erythraea*; cloning of the structural gene, sequence analysis and inferred domain structure of the multifunctional enzyme", *European Journal of Biochemistry*, 204, 39–49 (1992).

Brandl, H., et al., "Plastics from Bacteria and for Bacteria: Poly(β–hydroxy–alkanoates) as Natural, Biocompatible, and Biodegradable Polyesters", *Advances in Biochemical Engineering Biotechnology*, 41, 77–93 (1990).

Brandsch, R., et al., "6–Hydroxy–D–nicotine oxidase of *Arthrobacter oxidans*: Gene structure of the flavoenzyme and its relationship to 6–hydroxy–L–nicotine oxidase", *Eur. J. Biochem.*, 167, 315–320 (1987).

Byrom, D., "Polymer synthesis by micro–organisms: technology and economics", *Tibtech*, 5, 246–250 (1987).

Cera, C., et al., "Modulation of Mitomycin Cross–Linking by DNA Bending in the *Escherichia coli* CAP Protein–DNA Complex", *Biochemistry*, 28, 3908–3911 (1989).

Claridge, C.A., et al., "New Mitomycin Analogs Produced by Directed Biosynthesis", *The Journal of Antibiotics*, 39, 437–446 (1986).

Cortes, J., et al., "Repositioning of a Domain in a Modular Polyketide Synthase to Promote Specific Chain Cleavage", *Science*, 268, 1487–1489 (1995).

Davies, J., et al., "A New Look at Antibiotic Resistance", *FEMS Microbiology Reviews*, 39, 363–371 (1986).

Donadio, S., et al., "An erythromycin analog produced by reprogramming of polyketide synthesis", *Proceedings of the National Academy of Sciences*, 90, 7119–7123 (1993).

Donadio, S., et al., "Modular Organization of Genes Required for Complex Polyketide Biosynthesis", *Science*, 252, 675–679 (1991).

Donadio, S., et al., "Organization of the enzymatic domains in the multifunctional polyketide synthase involved in erythromycin formation in *Saccharopolyspora erythraea*", *Gene*, 111(1), 51–60 (1992).

Fernandez–Moreno, M.A., et al., "Streptothricin Biosyntheses Is Catalyzed by Enzymes Related to Nonribosomal Peptide Bond Formation", *Journal of Bacteriology*, 179(22), 6929–6936 (1997).

Gaisser, S., et al., "Analysis of Seven Genes from the eryAI–eryK Region of the Erythromycin Biosynthetic Gene Cluster in *Saccharopolyspora erythraea*", *Mol. Gen. Genet.*, 256, 239–251 (1997).

Han, L., et al., "Cloning and Characterization of Polyketide Synthase Genes for Jadomycin B Biosynthesis in *Streptomyces venezuelae* ISP5230", *Microbiology*, 140, 3379–3389 (1994).

Herr, R.R., et al., "Porfiromycin, a New Antibiotic II. Isolation and Characterization", *Antimicrobial Agents Annual*, Plenum Press, NY, 23–26 (1990).

Hoey, B.M., et al., "Reductive Activation of Mitomycin C", *Biochemistry*, 27, 2608–2614 (1988).

Hopwood, et al., "Genetic Manipulation of Streptomyces: A Laboratory Manual", 77–78; 292–293; 214–224 (1985).

Hopwood, D.A., et al., "Molecular Genetics of Polyketides and its Comparison to Fatty Acid Biosynthesis", *Annu. Rev. Genet.*, 24, 37–66 (1990).

Iyer, V.N., et al., "Mitomycins and Porfiromycin: Chemical Mechanism of Activation and Cross–linking of DNA", *Science*, 145, 55–58 (1964).

Jacobsen, J.R., et al., "Precursor–Directed Biosynthesis of Erythromycin Analogs by an Engineered Polyketide Synthase", *Science*, 277, 367–369 (1997).

Kao, C.M., et al., "Engineered Biosynthesis of a Complete Macrolactone in a Heterologous Host", *Science*, 265, 509–512 (1994).

Kao, C.M., et al., "Manipulation of Macrolide Ring Size by Directed Mutagenesis of a Modular Polyketide Synthase", *J. Am. Chem. Soc.*, 117, 9105–9106 (1995).

Kasai, M., et al., "Studies on the Chemistry of Mitomycins", *Synlett*, 10, 778–790 (1992).

Katz, L., "Manipulation of Modular Polyketide Synthases", *Chem. Rev.*, 97, 2557–2575 (1997).

Kealey, J.T., et al., "Production of a Polyketide Natural Product in Nonpolyketide–Producing Prokaryotic and Eurkaryotic Hosts", *Proc. Natl. Acad. Sci. USA*, 95, 505–509 (1998).

Khosla, C., "Harnessing the Biosynthetic Potential of Modular Polyketide Synthases", *Chem. Rev.*, 97, 2577–2590 (1997).

Kiyoto, S., et al., "A New Antitumor Antibiotic, FR–900482 II. Production, Isolation, Characterization and Biological Activity", *The Journal of Antibiotics*, 40, 594–599 (1987).

Kumar, S., et al., "Orientation Isomers of the Mitomycin C Interstrand Cross–Link in Non–Self–Complementary DNA. Differential Effect of the Two Isomers on Restriction Endonuclease Cleavage at the Nearby Site", *Biochemistry*, 32, 1364–1372 (1993).

Liu, L., et al., "Biosynthesis of 2–Nor–6–deoxyerythronolide B by Rationally Designed Domain Substitution", *J. Am. Chem. Soc.*, 119, 10553–10554 (1997).

Marahiel, M.A., et al., "Modular Peptide Synthetases Involved in Nonribosomal Peptide Synthesis", *Chemical Reviews*, 97, 2651–2673 (1997).

Masuda, K., et al., "Interstrand DNA–DNA and DNA–Protein Cross–Links by a New Antitumor Antibiotic, FK973, in L1210 Cells", *Cancer Research*, 48, 5172–5177 (1988).

McDaniel, R., et al., "Engineered Intermodular and Intramodular Polyketide Synthase Fusions", *Chemistry and Biology*, 4, 667–674 (1997).

McDaniel, R., et al., "Rational Design of Aromatic Polyketide Natural Products by Recombinant Assembly of Enzymatic Subunits", *Nature*, 375, 549–554 (1995).

Mohler, H., et al., "Covalently Bound Flavin on D–6–Hydroxynicotine Oxidase from Arthrobacter oxidans", *Eur. J. Biochem.*, 29, 152–155 (1972).

Moscow, J.A., et al., "Chapter 9: Multidrug Resistance." *In: Cancer Chemotherapy and Biological Response Modifiers Annual 11*, Elsevier Science Publishers B.V., Editors: Pinedo, H.M. et al., 97–114 (1990).

Nicolaou, K.C., et al., "Chemistry and Biology of the Enediyne Anticancer Antibiotics", *Angewandte Chemie*, 30, 1387–1416 (1991).

Pan, S., et al., "The role of NAD(P)H:Quinone Oxidoreductase in Mitomycin C– and Porfiromycin–Resistant HCT 116 Human Colon–Cancer Cells", *Cancer Chemother. Pharmacol.*, 31, 23–31 (1992).

Peoples, O.P., et al., "Poly–β–hydroxybutyrate Biosynthesis in *Alcaligenes eutrophus* H16 characterization of the genes encoding β–Ketothiolase and acetoacetyl–CoA", *The Journal of Biological Chemistry*, 264(26), 15293–15297 (1989).

Poirier, Y., et al., "Polyhydroxybutyrate, a Bioderadable Thermoplastic, Produced in Transgenic Plants", *Science*, 256, 520–523 (1992).

Poirier, Y., et al., "Production of Polyhydroxyalkanoates, a Family of Biodegradable Plastics and Elastomers, in Bacteria Plants", *Bio/Technology*, 13, 142–150 (1995).

Schwartz, H.S., et al., "Mitomycin C: Chemical and Biological Studies on Alkylation", *Science*, 142, 1181–1183 (1963).

Service, R.F., "Hijacking a Cell's Chemical Paths to Make New Antibiotics", *Science*, 277, 319 (1997).

Sheldon, P.C., "Analysis of Antibiotic Resistance and Biosynthetic Gene Function and Regulation in the Mitomycin C Producing Organism, *Streptomyces lavendulae*", Ph.D. Thesis, University of Minnesota, Abstract only, (1997).

Sheldon, P.J., et al., "Characterization of a Mitomycin–Binding Drug Resistance Mechanism from the Producing Organism, *Streptomyces lavendulae*", *Journal of Bacteriology*, 179(5), 1796–1804 (1997).

Stassi, D., et al., "Identification fo a *Saccharopolyspora erythraea* Gene Required for the Final Hydroxylation Step in Erythromycin Biosynthesis", *Journal of Bacteriology*, 175, 182–189 (1993).

Staunton, J., et al., "Biosynthesis of Erythromycin and Rapamycin", *Chem. Rev.*, 97, 2611–2629 (1997).

Teng, S.P., et al., "DNA Sequence Specificity of Mitomycin Cross–Linking", *Biochemistry*, 28, 3901–3907 (1989).

Tomasz, M., et al., "Isolation and Structures of a Covalent Cross–Link Adduct Between Mitomycin C and DNA", *Science*, 235, 1204–1208 (1987).

Tsoi, C.J., et al., "Combinatorial Biosynthesis of 'Unnatural' Natural Products: The Polyketide Example", *Chemistry and Biology*, 2, 355–362 (1995).

Uchida, I., et al., "Structure of FR 900482, a Novel Antitumor Antibiotic from a Streptomyces", *J. Am. Chem. Soc.*, 109, 4108–4109 (1987).

Verdine, G.L., et al., "The Combinatorial Chemistry of Nature", *Nature*, 384, 11–13 (1996).

Witt, D., et al., "Unification of the Genera Streptoverticillum and Streptomyces, and Amendation of Streptomyces Waksman and Henrici 1943, 339", *System. Appl. Microbiol.*, 13, 361–371 (1990).

Woo, J., et al., "DNA Interstrand Cross–Linking by Reductively Activated FR900482 and FR66979", *J. Am. Chem. Soc.*, 115, 1199–1200 (1993).

Yang, K., et al., "Accumulation of the angucycline antibiotic rabelomycin after disruption of an oxygenase gene in the jadomycin B biosynthetic gene cluster of *Stretomyces venezuelae*", *Microbiology*, 142(1), 123–132 (1996).

August, P., et al., "Biosynthesis of the ansamycin antibiotic rifamycin: deductions from the molecular analysis of the rif biosynthetic gene cluster of *Amycolatopsis mediterranei* S699", *Chemistry & Biology*, 5, 69–79 (Feb. 1998).

August, P., et al., "Cloning and Analysis of a Locus (mcr) Involved in Mitomycin C Resistance in *Streptomyces lavendulae*", *Journal of Bacteriology*, 176, 4448–4454 (Jul. 1994).

Becker, A.M., et al., "3–Amino–5–Hydroxybenzoic Acid in Antibiotic Biosynthesis VI. Directed Biosynthesis Studies with Ansamycin Antibiotics", *The Journal of Antibiotics*, XXXVI No. 10, 1323–1328 (Oct. 1983).

Fu, H., et al., "Antibiotic activity of polyketide products derived from combinatorial biosynthesis: Implications for directed evolution", *Molecular Diversity*, 1, 121–124, (1995).

Gaisser, S., et al., "Cloning of an Avilamycin Biosynthetic Gene Cluster from *Streptomyces viridochromogenes* Tu57", *Journal of Bacteriology*, 179, 6271–6278 (Oct. 1997).

Gaisser, S., et al., "Analysis of eryBI, eryBIII and EryBVII from the erythromycin biosynthetic gene cluster in *Saccharopolyspora erthraea*", *Molecular & General Genetics*, 258, 78–88, (1998).

Hopwood, D.A., "Antibiotics: opportunities for genetic manipulation", *Philosophical Transactions of the Royal Society of London*, 324, 549–562, (1989).

Lomovskaya, N., et al., "Gene disruption and replacement in the rapamycin–producing *Streptomyces hygroscopicus* strain ATCC 29253", *Microbiology*, 143, 875–883, (1997).

Quiros, L.M., et al., "Two glycosyltransferases and a glycosidase are involved in oleandomycin modification during its biosynthesis by *Streptomyces antibioticus*", *Molecular Microbiology*, 28, 1177–1185, (1998).

Sheldon, P.J., et at., "Characterization of a Mitomycin–Binding Drug Resistance Mechanism from the Producing Organism, *Streptomyces lavendulae*", *Journal of Baceriology*, 179, 1796–1804, (Mar. 1997).

Bierman, M., et al., "Plasmid cloning vectors for the conjugal transfer of DNA from *Escherichia coli* to Streptomyces spp.", *Gene*, 116 (1), pp. 43–49, (Jul. 1, 1992).

Kim, C., et al., "3–Amino–5–hydroxybenzoic acid synthase, the terminal enzyme in the formation of the precursor of $mC_7N$ units in rifamycin and related antibiotics", *Journal of Biological Chemistry*, 273 (11), pp. 6030–6040, (Mar. 13, 1998).

Mao, Y., et al., "Molecular characterization and analysis of the biosynthetic gene cluster for the antitumor antibiotic mitromycin C from *Streptomyces lavendulae* NRRL 2564", *Chemistry & Biology*, 6 (4), pp. 251–263, (Mar. 23, 1999).

Ruan, X., et al., "A second type–I PKS gene cluster isolated from *Streptomyces hygroscopicus* ATCC 29253, a rapamycin–producing strain", *Gene*, 203, pp. 1–9, (1997).

Xue, Y., et al., "A gene cluster for macrolide antibiotic biosynthesis in *Streptomyces venezuelae*: architecture of metabolic diversity", *Proceedings of the National Academy of Sciences*, 95 (21), pp. 12111–12116, (Oct. 1998).

Chen, C.W., et al., "Cloning and Expression of a DNA Sequence Conferring Cephamycin C Production", *Bio/Technology*, 6, 1222, (1988).

Gould, S.J., et al., "Cloning and Heterologous Expression of Genes fromthe Kinamycin Biosynthetic Pathway of *Streptomyces murayamaensis*", *J. Antibiot.*, 51, 50–57.

August, P.R., et al., "Cloning and expression of the *Streptomyces lavendulae* mitomycin C resistance genes in *Streptomyces lividans*", Fifth ASM Conference on Genetics and Molecular Biology of Industrial Microorganisms, Bloomington, Indiana, Absract B19, p. 16, (1992).

August, R.P., et al., "Cloning, expression and nucleotide sequence of the *Streptomyces lavendulae* mitomycin C resistance genes in *Streptomyces lividans*", Draft of Abstract for Submission to Combined Canadian Society for Microbiology and Society for Industrial Microorganisms Meeting, (Aug., 1993).

August, R.P., et al., "Molecular genetics and biochemistry of mitomycin C resistance", $205^{th}$ ACS National Meeting, Denver, Colorado, Abstract 14, (1993).

\* cited by examiner

METHYTRANSFERASE ALIGNMENT

```
TcmN    324  G M E R F S R I A D L G G G D G W F L A Q I L R R H P H A T
ORF14    56  P L R A G D R L L D I G C G N G - E P A I R M A T A N D V M
MmcR    181  D F S G A A T A V D I G G G R G S L M A A V L D A F P G L R
MitM     68  R I G A G S R V L D L G C G V G - T P G V R I A R L S G A H
MitN     60  R L A P G E R V L D V G S G N G - K A T L R I A A R H G V R
EryG     78  G I S E G D E V L D V G F G L G A Q D F F W L E T R K P A R
DmpM    201  D F S S Y G T V V D I G G A D G S L L A A V L S A H P G V E

Consen        . .   G   R . L D . G   G   G         A     . . . .   G . .
                        ─────────────────────────
                             motif I TcmN    354  G L L M D L - P R V A A S A G P V L E E A K V A D R V T V L
ORF14    85  V T G I S I S E K Q V E R A N D R A Y K A D V D D R V V F E
MmcR    211  G T L L E R - P P V A E E A R E L L T G R G L A D R C E I L
MitM     97  V T G I S V S H E Q V R A N A L A E A G L A D R A R F Q
MitN     89  A T G V S I N P Y Q V G L S R Q L A E K G - D E A T E F R
EryG    108  I V G V D L T P S H V R I A S E R A E R E N V Q D R L Q F K
DmpM    231  G V V F D S - P E G A R D A A A T L D A A G V G E R G R V E Consen         T G . . .   P   . V       A       . A E   A G V   D R       F TcmN    383  P G D F F T D P V P T G - Y D - A Y L F K G V L H N W S D E
ORF14   115  Y A D A M E L P Y P D A S F D V V W A L E S L H H M P D R -
MmcR    240  P G D F F E T - I P D G - A D - V Y L I K H V L H D W D D D
MitM    127  R A D A M D L P F E D E S F D A V I A L E S I I H M P D R -
MitN    118  I G D M L A L P F P D G S F D A C Y A I E S I C H A L E R -
EryG    138  E G S A T D L P F G A E T F D R V T S L E S A L H Y E P R -
DmpM    260  T G D F F T R - V P G G - G D - L Y V L K S I L H D W S D A Consen        G D       . L P . P D G . F D   V Y . L E S . L H       . R
                                              ─────────────────
                                                  motif II TcmN    411  R A V T V L R R V R E A I G D D D A R L I F D Q V M A P E
ORF14   144  - - W H V I R Q A A R V L R P G - G R L A L G D F L L V P S
MmcR    267  D V V R I L R R I A T A M K P D - S R L L V I D N L I D E R
MitM    156  - - A Q V L A Q V G R V L R P G - G R L V L T D F F E R A P
MitN    147  - - A D V F T E I A R V L R P G - G R V T V T D F V L R R P
EryG    167  - - T D F F K G A F E V L K P G - G V L A I G D I I P L D L
DmpM    287  R S A D I L R T V R A A M P A H - A R L L V E V L L P D T Consen        . V . R . .         V L . P G   G R L . . .   D       . . .
                                  ─────────────────
                                      motif III
```

FIG. 3

Dendrogram of MitM, MitN and MmcR with other methyltransferases

| GENE | AMINO ACIDS | ACCESSION NUMBERS OF HOMOLOGOUS PROTEINS | TYPICAL HOMOLOGY (% IDENTITY, % SIMILARITY) | PROPOSED FUNCTION |
|---|---|---|---|---|
| orf6 | 414 | 1020391, 3114701 | (54%, 74%) | DEHYDROGENASE |
| orf5 | 176 | 2496757, 2104395 | (38%, 57%) | LINA HOMOLOGUE |
| orf4 | 407 | 99020, 117302 | (47%, 66%) | CYTOCHROME P450 HYDROXYLASE |
| orf3 | 410 | 561882, 987105 | (51%, 63%) | CYTOCHROME P450 HYDROXYLASE |
| orf2 | 368 | 1552858, 1502425 | (38%, 54%) | ESTERASE |
| orf1 | 285 | 118783, 1168271 | (39%, 45%) | TRANSCRIPTIONAL ACTIVATOR |
| mitT | 270 | 2792323, 2492956 | (56%, 67%) | AMINOQUINATE DEHYDROGENASE (RIFI HOMOLOGUE) |
| mitS | 315 | 2792326, 729585 | (53%, 63%) | KINASE (RIFN HOMOLOGUE) |
| mitR | 514 | 1170892, 3282517 | (26%, 33%) | MCRA HOMOLOGUE |
| mitQ | 164 | 152404, 2982999 | (43%, 50%) | PUTATIVE REGULATOR |
| mitP | 343 | 3056886, 2792321 | (70%, 77%) | AMINODHQ SYNTHASE (RIFG HOMOLOGUE) |
| mitO | 163 | 2791588 | (32%, 48%) | UNKNOWN |
| mitN | 275 | 2792343, 2246452 | (32%, 48%) | METHYLTRANSFERASE |
| mitM | 283 | 2792343, 1001725 | (40%, 49%) | METHYLTRANSFERASE |
| mitL | 520 | 1502425, 1552858 | (28%, 42%) | ESTERASE |
| mitK | 346 | 2826429, 2129143 | (36%, 51%) | F420 DEPENDENT $H_4MPT$ REDUCTASE |

FIG. 5A

| GENE | AMINO ACIDS | ACCESSION NUMBERS OF HOMOLOGOUS PROTEINS | TYPICAL HOMOLOGY (% IDENTITY, % SIMILARITY) | PROPOSED FUNCTION |
|---|---|---|---|---|
| mitJ | 235 | 2792325, 3056884 | (64%, 75%) | PHOSPHATASE (RIFM HOMOLOGUE) |
| mitI | 290 | - | - | UNKNOWN |
| mitH | 382 | 2129143, 2826429 | (40%, 49%) | F420 DEPENDENT H4MPT REDUCTASE |
| mitG | 404 | 3056883 | (46%, 61%) | OXIDOREDUCTASE (RIFL HOMOLOGUE) |
| mitF | 257 | 1841491, 2506147 | (39%, 51%) | REDUCTASE |
| mitE | 707 | 1040685, 665920 | (31%, 52%) | COA LIGASE |
| mitD | 383 | 2648528, 1806159 | (22%, 39%) | UNKNOWN |
| mitC | 260 | 2894171 | (54%, 62%) | UNKNOWN |
| mitB | 272 | 1314568, 1651894 | (36%, 43%) | GLYCOSYLTRANSFERASE |
| mitA | 388 | 2147019, 995684 | (67%, 76%) | AHBA SYNTHASE (RIFK HOMOLOGUE) |
| mmcA | 514 | - | - | UNKNOWN |
| mmcB | 93 | 2984024, 113194 | (29%, 61%) | ACYL CARRIER PROTEIN |
| mmcC | 470 | - | - | UNKNOWN |
| mmcD | 611 | 2622915, 3131076 | (34%, 53%) | METHYLTRANSFERASE |
| mmcE | 359 | 2622160, 2506843 | (36%, 56%) | H4MPT:COM METHYLTRANSFERASE |
| mmcF | 145 | 2792346, 1703004 | (74%, 81%) | AMINODHQ DEHYDRATASE (RIFJ HOMOLOGUE) |

FIG. 5B

| GENE | AMINO ACIDS | ACCESSION NUMBERS OF HOMOLOGOUS PROTEINS | TYPICAL HOMOLOGY (% IDENTITY, % SIMILARITY) | PROPOSED FUNCTION |
|---|---|---|---|---|
| mmcG | 177 | - | - | UNKNOWN |
| mmcH | 254 | 2105061, 2829569 | (36%, 50%) | UNKNOWN |
| mmcI | 264 | 1568583, 2649391 | (55%, 69%) | F420 DEPENDENT H4MPT REDUCTASE |
| mmcJ | 274 | 2829504, 2735505 | (36%, 47%) | F420 DEPENDENT H4MPT REDUCTASE |
| mmcK | 460 | 3218385 | (28%, 46%) | UNKNOWN |
| mmcL | 511 | 2829486, 2228233 | (43%, 61%) | ALDEHYDE DEHYDROGENASE |
| mmcM | 472 | 1170892, 3282517 | (54%, 69%) | McrA HOMOLOGUE |
| mmcN | 395 | 117302, 2147740 | (37%, 56%) | CYTOCHROME P450 HYDROXYLASE |
| mmcO | 474 | - | - | UNKNOWN |
| mrd | 130 | 1917021 | - | MITOMYCIN RESISTANCE DETERMINANT (MRD) |
| mmcP | 443 | - | - | UNKNOWN |
| mmcQ | 123 | 396392, 2851659 | (38%, 60%) | UNKNOWN |
| mmcR | 351 | 1169359, 730913 | (40%, 58%) | O-METHYLTRANSFERASE |
| mmcS | 546 | 2498662, 3328168 | (45%, 58%) | CARBAMOYL TRANSFERASE |
| mmcT | 568 | 730909, 769829 | (38%, 55%) | HYDROXYLASE |
| mmcU | 160 | 1652032, 2650349 | (52%, 69%) | SULFATE ADENYLATE TRANSFERASE UNIT 1 |

FIG. 5C

| GENE | AMINO ACIDS | ACCESSION NUMBERS OF HOMOLOGOUS PROTEINS | TYPICAL HOMOLOGY (% IDENTITY, % SIMILARITY) | PROPOSED FUNCTION |
|---|---|---|---|---|
| mmcV | 319 | 1706266, 882645 | (67%, 81%) | SULFATE ADENYLATE TRANSFERASE UNIT II |
| mct | 484 | 282580, 2995318 | (52%, 66%) | MITOMYCIN C TRANSLOCASE (MCT) |
| mmcW | 163 | 1172058, 127291 | (39%, 54%) | REPRESSOR |
| mmcX | 413 | - | - | UNKNOWN |
| mmcY | 271 | 2662299, 116329 | (75%, 85%) | CHITINASE |
| orf11 | 139 | 2879888 | (39%, 58%) | UNKNOWN |
| orf12 | 936 | 1061284, 1352001 | (42%, 57%) | ACID TREHALASE |

FIG. 5D

| Strains or Plasmids | Relevant Characteristics[a] |
|---|---|
| *E. coli* strains | |
| DH5α | F⁻ recA φ80 dlacZ ΔM15 |
| DH5αF' | F' φ80 dlacZ ΔM15 |
| S17-1 | Contains RP4 integrated into the chromosome; Str[R] |
| *A. mediterranei* | |
| ATCC 27643 | rifamycin producer |
| *S. lavendulae* | |
| NRRL 2564 | MC producer |
| MV100[b] | *mitA* insertional disruption mutant of NRRL 2564 |
| MV102[b] | *mitA* site directed mutant (K191A) of NRRL 2564 |
| MV103 | MV100 with plasmid pDHS2003 |
| MM101[b] | *mitB* insertional disruption mutant of NRRL 2564 |
| Plasmids | |
| pNJ1 | Th[R] Ap[R] bifunctional *E.coli* and *Streptomyces* shuttle vector |
| pUC119 | Ap[R] *lacZα* MCS, *E. coli* cloning vector |
| pKC1139 | Am[R] *lacZα* MCS oriT rep[ts] |
| pDHS3001 | pIJ702 with 4.1 kb *BclI* DNA insert, contains *mrd* locus |
| pKN108 | contains rifamycin AHBA synthase gene |
| pFD666 | Neo[R] bifunctional *E. coli* and *Streptomyces* shuttle cosmid |
| pDHS7529 | pNJ1 with 37 kb inserted fragment from *S. lavendulae*, contains *mrd* and *mitABC* locus |
| pDHS7601 | pUC119 with 3.8 kb *BamHI* subclone from pDHS7529, contains *mitABC* locus |
| pDHS5000 | pUC119 with 1.1 kb *SmaI-PstI* fragment of *tsr* gene from pNJ1, blunt-ended and subcloned in *SmaI* site |
| pDHS2001 | *mitA* disruption construct, 1.1 kb *SmaI-BamHI* (*tsr*) fragment from pDHS5000 was blunt-ended and inserted into the two *MscI* sites of pDHS7601 |
| pDHS2002 | *mitA* disruption vector, 4.9 kb *EcoRI-HindIII* insert from pDHS2001 was subcloned into pKC1139 |
| pDHS2015 | *mitA* site directed disruption vector with lysine191 replaced by alanine |
| PDHS2003 | pKC1139 with 3.8 kb *EcoRI-HindIII* insert from pDHS7601 |
| pDHS7701 | *mitB* disruption construct, 1.4 kb *neo* resistant fragment *ApaL1-HindIII* was blunt-ended and subcloned into the *BstBI* digested, blunt-ended pDHS7601 |
| pDHS7702 | *mitB* disruption vector, 5.2 kb *EcoRI-HindIII* insert from pDHS7701 subcloned into pKC1139 |

[a]Am[R], apramycin resistance; Ap[R], ampicillin resistance; Neo[R], neomycin resistance; rep[ts], temperature-sensitive replicon for *Streptomyces*; Str[R], streptomycin resistance; Th[R], thiostrepton resistance; *tsr*, thiostrepton resistance gene; [b]see Materials and Methods

FIG. 6

```
BamHI
▼
GGATCCGAGGGCCGGAGTGGGATTCGGCTCAATGAACCATGCACACAGCACATACCAGGACGGTGTCGCGCCCAC          75
CATACGCGACGCTTCCCGCTCCCTCCAGCCGTGCGGTTTGAGCCACTTCGACGCCGGATAACGTTGCCGACAGGC         150
CCGCCGAGCAGCCCCTGAACTGGATCAATTCCCTTGGGAATAAGGCAGTTTCACTGCTCAACCACCCTGCTGACG         225
AGAATCCACCGCCGACCGGCGGTCGGGGCAGACCTTCCCGGCAAGGGTGTTGACTCCGGCAACTGCCCTATGGAG         300
GCTCGTGTCTGGCATCCGATCCCGGCCTATGACCGGGGGCCGGATCACATGCCCGCTCCGGCCACCCCTCACACC         375
GCGGGCCGGATTTCCCGCCGCCCCCGAGGAACGGCGTTTCCCGTCGGGTCACGCACCACCCTTCCCGACGCGGGG         450
CGAACACAACGGAACCGGGCCGTGAAGCCACGGCCACCGAAGGCAAAGGCCTCGACACCCGCCCTCCCGCCGTAC         525 orf1 ▶
AGCGCCCCGAAGTCGACCGTGCCGCCGCACCCGCAGGACC GAAAGG CTGCTCAATGACACCTACGTCCGGTGATG         600
                                              M T P T S G D D
ACGTCCTGTCCTTTCCCTCATGGCCGCAACACGGCGCGGAGGAGCGCGCCGGACTCCTGCGGGCCCTGGACCAGA         675
 V L S F P S W P Q H G A E E R A G L L R A L D Q K
AGGGGTGGTGGCGCGACGCGGGGCAGGAGGTCGATCTCTTCGAGCGGGAGTTCGCCGACCACCACGGCGCCCCGC         750
 G W W R D A G Q E V D L F E R E F A D H H G A P H
ACGCGATCGCCACGACGAACGGCACCCACGCCCTGGAACTCGCCCTGGGGGTCATGGGGATCGGCCCCGGTGACG         825
 A I A T T N G T H A L E L A L G V M G I G P G D E
AGGTCATCGTCCCCGCGTTCACCTTCATCTCGTCGTCGCTGGCCGTGCAGCGCATGGGCGCGGTGCCGGTGCCGG         900
 V I V P A F T F I S S S L A V Q R M G A V P V P A
CGGACGTACGGCCCGACACCTACTGCCTCGATGCCGACGCGGCGGCGGCGCTGGTGACGCCACGCACCAAAGCGA         975
 D V R P D T Y C L D A D A A A A L V T P R T K A I
TCATGCCGGTCCACATGGCGGGCCAGTTCGCCGACATGGACGCCCTGGAGAAGCTCTCCGTCGCGACGGGCGTGC        1050
 M P V H M A G Q F A D M D A L E K L S V A T G V P
                                           SacI
                                            ▼
CGGTCCTCCAGGACGCCGCGCACGCCCACGGCGCGCAGTGGCAGGGCCGCCGGGTCGGGGAGCTCGGCTCGATCG        1125
 V L Q D A A H A H G A Q W Q G R R V G E L G S I A
CCGCCTTCAGCTTCCAGAACGGCAAGCTGATGACCGCCGGCGAGGGCGGCGCCCTGCTCCTGCCGGACGACGAGT        1200
 A F S F Q N G K L M T A G E G G A L L L P D D E S
CCTTCCACGAGGCGTTCCTCCAGCACTGCTGCGGCCGCCCGCCCGGGGACCGCGTCTACCGCCATCTGACGCAGG        1275
 F H E A F L Q H C C G R P P G D R V Y R H L T Q G
GCTCCAACTACCGCATGAACGAGTTCTCCGCGAGCGTCCTGCGTGCTCAACTGAAGCGCTTGAAGGATCAGTTGC        1350
 S N Y R M N E F S A S V L R A Q L K R L K D Q L R
GCATCAGGGAGGAGCGCTGGGCCCAGCTGCGTACGGCACTGGCCGCCATCGACGGCGTGGTGCCGCAGGGGCGCG        1425
 I R E E R W A Q L R T A L A A I D G V V P Q G R D
         MscI
          ▼
ACGAGCGCGGCGACCTCCACTCCCACTACATGGCCATGGTCCGGCTGCCCGGCATCTCGGCCCGGCGCCGCCTCG        1500
 E R G D L H S H Y M A M V R L P G I S A R R R L A
CGCTGGTGGACGCGCTGGTCGAGCGGGGAGTGCCCGCGTTCGTCGGCTTCCCGCCGGTCTACCGCACCGAGGGTT        1575
 L V D A L V E R G V P A F V G F P P V Y R T E G F
         MscI
          ▼
TCGCGCGCGGCCCGGCGCCGGCGGACGCCGAGGAGCTGGCCAAGAGCTGTCCCGTGGCGGAGGAGATCGGCAGCG        1650
 A R G P A P A D A E E L A K S C P V A E E I G S D
ACTGCCTCTGGCTGCACCATCGCGTCCTGCTCGCCGACGTGACCACGCTGGACCGGCTGGCGGAGGTCTTCTCCG        1725
 C L W L H H R V L L A D V T T L D R L A E V F S G
GCCTCGTCGGCGCGCTCTGACCCGATGCGGGCCCCCAACGGCACCACCGCCCCCCGGCTGAGCGTCGTCGTCCCC        1800
 L V G A L
                                        SphI
                                         ▼
AGCCGGGGGCCCGCGGCACGCCTGCGCGCGACCCTCGCATGCCTTGCCGGCCCCTCCCCG GGAACG CCGCCCTTC        1875
orf2 ▶
GAAGTGGTCGTCGTCGACGACAACGACGGGGGCGACGCCGGTGATCAACTGATCGCCGTGACAGGCGAGATGAGC        1950
     V V V V D D N D G G D A G D Q L I A V T G E M S
GGCCTTCTCCCGCTGCGCGTGGTGCGGGGACCGCTGCGGGGGCGGGCCGCCGCCCGGAACGCCGGGGCGGCCGCG        2025
 G L L P L R V V R G P L R G R A A A R N A G A A A
GCCCTCGCGCCCCGGCTGGTCTTCCTCGACGACGACGTCCTGGTGGGGCCCGGCTTCCTCGCCGCACACGCCGCG        2100
 A L A P R L V F L D D D V L V G P G F L A A H A A
```

FIG. 9A

```
GCCGCGGAACCGGACGCCTTCACCCACGGCCGGCTGCGCGAACTCCCCACCGCGGCGCGGTTCCTCGCCGCTGTC    2175
 A  A  E  P  D  A  F  T  H  G  R  L  R  E  L  P  T  A  A  R  F  L  A  A  V
GAGAAGGCCGCCCCGACCGAGGTCCGCCGCGCCCGCGCCGGACTCGAACCCGCTGCCCCGGCCGCCTCCGAGCGG    2250
 E  K  A  A  P  T  E  V  R  R  A  R  A  G  L  E  P  A  A  P  A  A  S  E  R
CGCCAACCGCACCGGCGGCTCGTCGCCAACGCCCTGGAGCGGGCCGTGGAGGCCATGGCCGGCGGCTCCCTGCCG    2325
 R  Q  P  H  R  R  L  V  A  N  A  L  E  R  A  V  E  A  M  A  G  G  S  L  P
GACGTCGCCCCCTGGCTCGGCTTCATCGGCGCGAACACCGCCCTCGACAAGGCCGCATGGGAGCATACCGGCGGA    2400
 D  V  A  P  W  L  G  F  I  G  A  N  T  A  L  D  K  A  A  W  E  H  T  G  G
TTCGACGAGGAGTTCGGGCTCACCTGGGGGTGCGAGGACCTGGAGTTCGGCTTCCGCCTGCACGCCGCCGGGCTG    2475
 F  D  E  E  F  G  L  T  W  G  C  E  D  L  E  F  G  F  R  L  H  A  A  G  L
                                ▼ApaLI
CGCAGGACCCTCGCCCCCGACGCCCTCGGTGTGCACCTCAGCCACGCCCGCCCCGGCCGCTGGGAGCAGCACCAC    2550
 R  R  T  L  A  P  D  A  L  G  V  H  L  S  H  A  R  P  G  R  W  E  Q  H  H
CGCAACCTCACGCACTTCTCCGCCGGCCACCCGCACCCGTCGGTACGCGCCTTGGAGGCCCTGCTCGGGCCCGAC    2625
 R  N  L  T  H  F  S  A  G  H  P  H  P  S  V  R  A  L  E  A  L  L  G  P  D
                                                                    orf3
GGCACGCCGGAGGCGTATGTGCGCGCCGTCCTGGCCGAAGAGGCCGCACCGGCAGGGACGCGGCGCGATGAGCG    2700
 G  T  P  E  A  Y  V  R  A  V  L  A  E  E  A  A  P  A R  D  A  A  R
                                                                   M  S  G
GCACACCGGCCACCGCGCCGTACGGTCCCGTGGTGCTCTCCCCGCACGCGGACGACGCCGTGTGGTCCCTGGGCG    2775
 T  P  A  T  A  P  Y  G  P  V  V  L  S  P  H  A  D  D  A  V  W  S  L  G  G
GGCGGCTGGCGCGCTGGGCCGCCGAGGGCCCGCGGCCGACCGTCGTCACGGTCTTCGCCGGGCCCGCGGCCGGGA    2850
 R  L  A  R  W  A  A  E  G  P  R  P  T  V  V  T  V  F  A  G  P  A  A  G  K
AGCCCGAGTCGTGGCGGAGCGCCGCCGATCCCGCGGTGCGCCGGGCCGAGGACCGGGCGGCATGTGCCGAACTGG    2925
 P  E  S  W  R  S  A  A  D  P  A  V  R  R  A  E  D  R  A  A  C  A  E  L  G
GCGTGCGCCACGTGCCGCTGGGCTTCACCGACGCGGCACTGCGTACGGCCTCGGGCGCCTATCTCTACGCTTCC    3000
 V  R  H  V  P  L  G  F  T  D  A  A  L  R  T  A  S  G  A  Y  L  Y  A  S  P
CGCGCCGGCTCTTCGGCCCCTGGCACCCGGCCGACCTCCCGCTGCTGGAGGAGGTGCGGGCGGCTCTGCTGCCGC    3075
 R  R  L  F  G  P  W  H  P  A  D  L  P  L  L  E  E  V  R  A  A  L  L  P  L
TGTGCGCGGGGGCGTCGAGCGTCCACGTTCCCCTGGCGGCGGGCCGGCACGTCGACCACCGCCTGGTCCGCGGCG    3150
 C  A  G  A  S  S  V  H  V  P  L  A  A  G  R  H  V  D  H  R  L  V  R  G  A
CGGTGGAGCCCCTGTCCCCCGCCCGTACCGTCTTCTACGAGGACTTCCCCTACCGGCTGCGCGAACGTGACCACA    3225
 V  E  P  L  S  P  A  R  T  V  F  Y  E  D  F  P  Y  R  L  R  E  R  D  H  T
CGAACCTGCGGCCGCGCACGGAACGGCTGCCGTCCGAGGCGGTGGACCGCTGGCTGACCGCCGCCGGTCACTACT    3300
 N  L  R  P  R  T  E  R  L  P  S  E  A  V  D  R  W  L  T  A  A  G  H  Y  S
CCAGCCAGGCGAGCGCCCACTTCGGCGGTGCGGCCGCCCTGCGCGAGGCCCTGTTCGCCCGCGCCCGCGCACACG    3375
 S  Q  A  S  A  H  F  G  G  A  A  L  R  E  A  L  F  A  R  A  R  A  H  G
GCGGGCCCGGCCGGCCCGGCCACGCCGACCGCCACTGGGTGCCCGTCGGCCAGGACGACCGGGGCGAGGCCCGGC    3450
 G  P  G  R  P  G  H  A  D  R  H  W  V  P  V  G  Q  D  D  R  G  E  A  R  P
CGGCACCCGTGGAAAGGGGGCCGTGACCCACGCCGTGCGCAGCCCCACCACGAGAGAGGCCACTCATGTCCCGTA    3525
 A  P  V  E  R  G  P
GCACCCACCCGCCGACAGCCACCCCCGACGCGGGCACCAGGCGACGCCTGCCGCTGATCGGCAACGACCTGGTCA    3600
TCAACGAGGACTCCTGCAACCTCAGCTGCACCTACTGCCTCACCGGACAGAGCAACCTCAAGGAGGGCCACTCCC    3675
TTCAACTGATCTTCGAGCCCCCGCGGCGCGACAGCTACGCCAAGGACAGCGGGCTGGGGCAGCGCATGGACAAGG    3750
 ▼BamHI
TCGCCGACCGGATCC                                                              3765
```

FIG. 9B

```
S.lave     MTPTS  OVL  SPPSWPQHGA  EERAGLLRAL  DQKGWM   AG  QEVDLFEREF    50
S.coli     M-SSGV LGS  APRVWPQYDD  AERTGLIRAL  EQGQWWRMGG  GEVERFEREF    49
A.pret     M-GSSPDAGI  DFPAWPQHDD  AERAALLRAL  DQGQWWRVGG  SEVDEFEREF    49
A.medi     M---NARKAP  EFPAWPQYDD  AERNGLVRAL  EQGQWWRMGG  DEVNSFEREF    47
Consensus  M-........  .FP.WPQ.DD  AER.GL.RAL  .QGQWWR.GG  .EV...FEREF   50

S.lave     ADHHGAPHAI  ATTNGTHALE  LALGVMGIGP  GDEVIVPAFT  FISSSLAVQR    100
S.coli     AEYHGGEHAL  AVTNGTHALE  LALEVMGVGP  GTEVIVPAFT  FISSSQAAQR    99
A.pret     AEYHGAGHAL  AVTNGTHALE  LALQVLDVGP  GTEVIVPAFT  FISSSQAVQR    99
A.medi     AAHHGAAHGL  AVTNGTHALE  LALQVMGVGP  GTEVIVPAFT  FISSSQAAQR    97
Consensus  A..HGA.HAL  AVTNGTHALE  LAL.VMGVGP  GTEVIVPAFT  FISSSQA.QR    100

S.lave     MGAVPVPADV  RPDTYCLDAD  AAAALVTPRT  KAIMPVHMAG  QFADMDALEK    150
S.coli     LGAVVVPVDV  DPETYCIDPA  EAAKAITPRT  RAIMPVHMAG  QLADMDALEK    149
A.pret     LGAVAVPVDV  DPDTYCLDVA  AAEDAVTSRT  SAIMPVHMAG  QFADMDRLDK    149
A.medi     LGAVTVPVDV  DAATYNLDPE  AVAAAVTPRT  KVIMPVHMAG  LMADMDALAK    147
Consensus  LGAV.VPVDV  DP.TYCLD..  AAA.AVTPRT  .AIMPVHMAG  Q.ADMDAL.K    150

S.lave     LSVATGVPVL  QDAAHAHGAQ  WQGRRVGELG  SIAAFSFQNG  KLMTAGEGGA    200
S.col      VAADSGVPLI  QDAAHAQGAT  WNGRRLGELG  SVAAFSFQNG  KLMTAGEGGA    199
A.pret     LSASTGVPVV  QDAAHAHGAH  WRGKRVGELG  SIATFSFQNG  KLMTAGEGGA    199
A.medi     ISADTGVPLL  QDAAHAHGAR  WQGKRVGELD  SIATFSFQNG  KLMTAGEGGA    197
Consensus  .SA.TGVP..  QDAAHAHGA.  W.G.RVGELG  SIA.FSFQNG  KLMTAGEGGA    200

S.lave     LLLPDDESFH  --EAFLQHCC  GRPPGDRVYR  HLTQGSNYRM  NEFSASVLRA    248
S.coli     VLFPTAE--M  AEHAFLRHSC  GRPRNDRGYF  HRTSGSNFRL  NEFSASVLRA    247
A.pret     VLFADQA--Q  WEKAFVLHSC  GRPKGDRGYF  HLTSGSNFRM  NEFSAAVLRA    247
A.medi     VVFPDGETEK  YETAFLRHSC  GRPRDDRRYF  HKIAGSNMRL  NEFSASVLRA    247
Consensus  VLFPD.E...  .E.AFL.HSC  GRP..DR.YF  H.T.GSN.R.  NEFSASVLRA    250

S.lave     QLKRLKDQLR  IREERWAQLR  TALAAIDGVV  PQGRDERGDL  HSHYMAMVRL    298
S.coli     QLARLDGQIR  TREERWPLLS  SLLAEIPGVV  PQRLDRRPDR  NPHYMAMFRV    297
A.pret     QLGRLDSQIA  TRQARWPVLS  ALLAGIDGVV  PQTVDPRSDR  NPSYMAMFRM    297
A.medi     QLARLDEQIA  VRDEPWTLLS  RLLGAIDGVV  PQGGDVRADR  NSHYMAMFRI    297
Consensus  QL.RLD.QI.  .R.ERW..LS  .LLA.IDGVV  PQ..D.R.DR  N.HYMAMFR.    300

S.lave     PGISARRRLA  LVDALVERGV  PAFVGFPPVY  RTEGF-ARGP  APADAEELAK    347
S.coli     PRITEERRAR  VVDTLVERGV  PAFVAFRSVY  RTDAFWEMGA  PDLSVDELA-    346
A.pret     PGVTEERRNA  VVDELVRRGI  PAFMAFRAVY  RTQAFWETGA  PDLTPEELAA    347
A.medi     PGLTEERRNA  LVDRLVEAGL  PAFAAFRAIY  RTDAFWELGA  PDESVDAIAR    347
Consensus  PG.TEERR.A  .VD.LVERG.  PAF.AFR.VY  RT.AFWE.GA  PD....ELA.    350

S.lave     SCPVAEEIGS  DCLWLHHRVL  LADVTTLDRL  AEVFSGLVGA  L             388
S.coli     RLPPLRGLTT  DCLWLHHRTL  LGTEEQMHEV  AAVIADVL-G  S             386
A.pret     RCPVSEEITR  DCVWLHHRVL  LGAEEQVRRL  AAVVADVVAG  A             388
A.medi     RCPNTDAISS  DCVWLHHRVL  LAGEPELHAT  AEIIADAVGR  A             388
Consensus  RCP....I..  DC.WLHHRVL  L..E......  A.V.AD.V..  .             391
```

FIG. 10

| Strain or plasmid | Relevant characteristic(s)[a] |
|---|---|
| Bacterial strains | |
| *S. lavendulae* | |
| NRRL 2564 | MC[+] Mc[r] |
| *mct* mutant | *mct* |
| | |
| *E. coli* | |
| S17-1 | RP4 derivative integrated on chromosome |
| DH5α | F[−] *recA* φ80 *dlacZ* ΔM15 |
| BL21(DE3) | F[−] *ompT hsdS gal dcm* (DE3) |
| PJS100 | BL21(DE3) containing pDHS7006 |
| PJS102 | BL21(DE3) containing pDHS7023 |
| PJS103 | BL21(DE3) containing pDHS7024 |
| | |
| Plasmids | |
| pUC119 | High copy *E. coli* vector; Ap[r] |
| pKC1139 | *Streptomyces-E. coli* conjugal transfer vector; Am[r] *oriT* |
| pET17b | Protein expression vector; Ap[r] |
| pDHS7006[b] | pT7SC (4) with 0.7-kb insert containing *mrd* |
| pDHS7023[c] | pET17b with 1.45-kb insert containing *mct* |
| pDHS7024[d] | pDHS7023 with 2.1-kb *Ssp*I fragment from pDHS7006 |
| pDHS7547 | pNJ1 with 25-kb *Sau*3A insert from *S. lavendulae* |
| pDHS7661 | pUC119 with 3.5-kb *Bam*HI subclone from pDHS7547 |
| pDHS7703 | pDHS7661 with *aph*II gene within the *mct* sequence |
| pDHS7704 | pKC1139 with 5.4-kb *Eco*RI-*Hin*dIII fragment from pDHS7703 |

[a] Mc[s], MC sensitive; Mc[r], MC resistant; MC[+], MC production.
[b] Confers resistance to 30 μg of MC per ml of medium in *E. coli*.
[c] Confers resistance to 2.5 μg of MC per ml of medium in *E. coli*.
[d] Confers resistance to 150 μg of MC per ml of medium in *E. coli*.

FIG. 14

```
  0 ATGGAGGACGGCAAGCGC   GGGTATTTCTAGCGCGGCGGGCCGGTGCGG   ACAAGCGGAGGACTAGTCCC    74
 75 TAAGTATGAAGTCCCCTACTCCGTTTGTCTGTTGAGGGCAGGGCGCCGTCTGAGGATGATGCAGTCCATGTCAC   149
                                          MCT → M  M  Q  S  M  S  Q
150 AGTTACTTTCCGGGAAGGACGGCGCCCAGGAGGCGCCAAGTCGCGGCGGGTCCACGTGGGTGGCCGTCCTCGCCG   224
     L  L  S  G  K  D  G  A  Q  E  A  P  S  R  G  G  S  T  W  V  A  V  L  A  A
225 CGTGGTGGGGCAGTTCGTGGTGGTCCTCGACGTGTCCGTCATCAATGTCGCGCTGCCGTCGATCCGTTCCGGCC   299
     C  V  G  Q  F  V  V  V  L  D  V  S  V  I  N  V  A  L  P  S  I  R  S  G  L
300 TCGACATCGGCGAGACGGGCCTGCAGTGGGTGGTCAACGCCTACGTCATCGCCTTCGCGGGCTTCCTGCTGCTG   374
     D  I  G  E  T  G  L  Q  W  V  V  N  A  Y  V  I  A  F  A  G  F  L  L  L  G
375 GCGGCCGGGCTCCGACCTCTTCGGCCGCAAGGCCGTGTTCGTCTTCGGCCTCGGGGTGTTCACCGCCGCGAGCC   449
     G  R  A  S  D  L  F  G  R  K  A  V  F  V  F  G  L  G  V  F  T  A  A  S  L
450 TGCTCGGCGGCCTCGCGCAGGCGCCGTGGATGCTCATCGTCGCCCGCGCCCTGCAAGGCATCGGGGCGGCCGTGC   524
     L  G  G  L  A  Q  A  P  W  M  L  I  V  A  R  A  L  Q  G  I  G  A  A  V  L
525 TCTCACCCGCCACCCTCGCGATCCTCACCACCACGTTCCCCGAGGGTCCGGCGCGCATCAAAGCCGTCGCGATCT   599
     S  P  A  T  L  A  I  L  T  T  T  F  P  E  G  P  A  R  I  K  A  V  A  I  W
600 GGACGGCGGTGGGCACGGGCGGCGGCGCGGGCGGGGCCTCATGGCGGCCTGCTCACCGACTACCTCTCGTGGC   674
     T  A  V  G  T  G  G  A  A  G  G  L  I  G  G  L  L  T  D  Y  L  S  W  R
675 GCTGGGTGTTGCTGATCAACGTGCCGCTGGGCCTTGTCGTGATCGTCGCGACGGTCGCCTGGCTGGCCGAGAGCC   749
     W  V  L  L  I  N  V  P  L  G  V  V  I  V  A  T  V  A  W  L  A  E  S  R
750 GCAGCGACCAGGCACACCGACGCCGGCTGGACCTCCCGGGAGCGGTGCTGGTGACCCTGGGCGTCGGCAGCCTGG   824
     S  D  Q  A  H  R  R  R  L  D  L  P  G  A  V  L  V  T  L  G  V  G  S  L  A
825 CCTACGGCATCTCGCAGAGCGAGGGCCACGGCTGGGGCTCGCGCGGACGCTCACCTTCCTGATCGTCGGTGTCG   899
     Y  G  I  S  Q  S  E  G  H  G  W  G  S  P  R  T  L  T  F  L  I  V  G  V  V
900 TGGCGCTCCTCGCCTTCGTCGCCGTGGAGCAGCGCAGCGCGAGCCGTTGATGCCGCTCGGTGTCTTCCGGGTGC   974
     A  L  L  A  F  V  A  V  E  Q  R  T  R  E  P  L  M  P  L  G  V  F  R  V  R
975 GCTCGGTGTCGGCGGCCAACGCCATCACCATCGTCAGTGGCATGGGCTTCTACGCGATGTGGTACTTCCTCTCGC   1049
     S  V  S  A  A  N  A  I  T  I  V  S  G  M  G  F  Y  A  M  W  Y  F  L  S  L
1050 TCTACATGCAGAACGTGCTGAAATACTCCGCCGTACAGACCGGCCTGGCCCTGCTTCCCCACACCGCCACCATCA   1124
     Y  M  Q  N  V  L  K  Y  S  A  V  Q  T  G  L  A  L  L  P  H  T  A  T  I  I
1125 TCCTCTCCGCGCAGTTCGCACCCCGCCTGATGCGGTGGATCAAGGGCGCACCCTCCTCGTGATCGCGGGACTGC   1199
     L  S  A  Q  F  A  P  R  L  M  R  W  I  K  G  R  T  L  L  V  I  A  G  L  L
1200 TGACCGCCGCGGGCTTCATCTGGCAGGGAACATGGACGCCGACGGCTCCTTCCTGGCGACCCTGCTGGCCCGG   1274
     T  A  A  G  F  I  W  Q  G  N  M  D  A  D  G  S  F  L  A  T  L  L  G  P  G
1275 GAATCGTCTTCTCCTTCGGCGCGGGCCTGATGATGACGCTCCTCGCGGTCTCGGCCACGACGGCGTGGAGCTCT   1349
     I  V  F  S  F  G  A  G  L  M  M  T  L  L  A  V  S  A  T  T  G  V  E  L  S
1350 CCGAATCGGGCCTGGTGGCCGGCCTCGCCAACACCTCGCGCACCATGGGCGGCGCGCTGGCCTGTCGGTCCTCG   1424
     E  S  G  L  V  A  G  L  A  N  T  S  R  T  M  G  G  A  L  G  L  S  V  L  A
1425 CGTCCGTCGCCGGCCGCCACGGCCGACGTGGGCCCGGCGCGGAGGGCTGGCCTCCGGCTACGGTCGGGCGT   1499
     S  V  A  A  R  R  T  A  D  V  G  P  G  A  E  G  L  A  S  G  Y  G  R  A  F
1500 TCGTCGTGTCCGGGGCCATCATCCTCGTGAGCATGCTGATGATCCCTTCCTGCCCAAGCCCCAGCCCCAGACCC   1574
     V  V  S  G  A  I  I  L  V  S  M  L  M  I  P  F  L  P  K  P  Q  P  Q  T  P
1575 CGGCGGAATGACCTGTGAGCACGGACATACGAGGAGGCTTGGTGGGCAGGACAGCCGGCCGCGGTGGCTCACCG   1649
     A  E  *
1650 ACGAGGAACAACGCGTGTGGCGCGGCTATCTGCGGGCACCAGGCTGGTGGAGGACCACCTGGACCGCGCCTCC   1724
1725 AGCGGGAAGCGGACATGCCCGCACCTCTATTACGGTCTTCTCGTCCAGCTCTCCGAGGCCCGGCGCCGGGGATCC   1799
```

FIG. 16

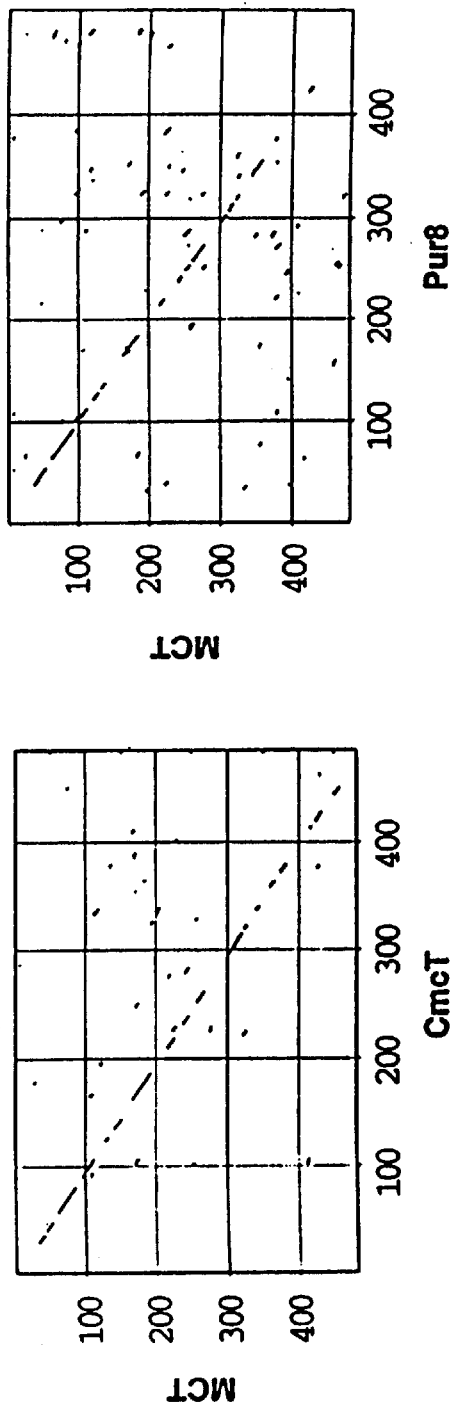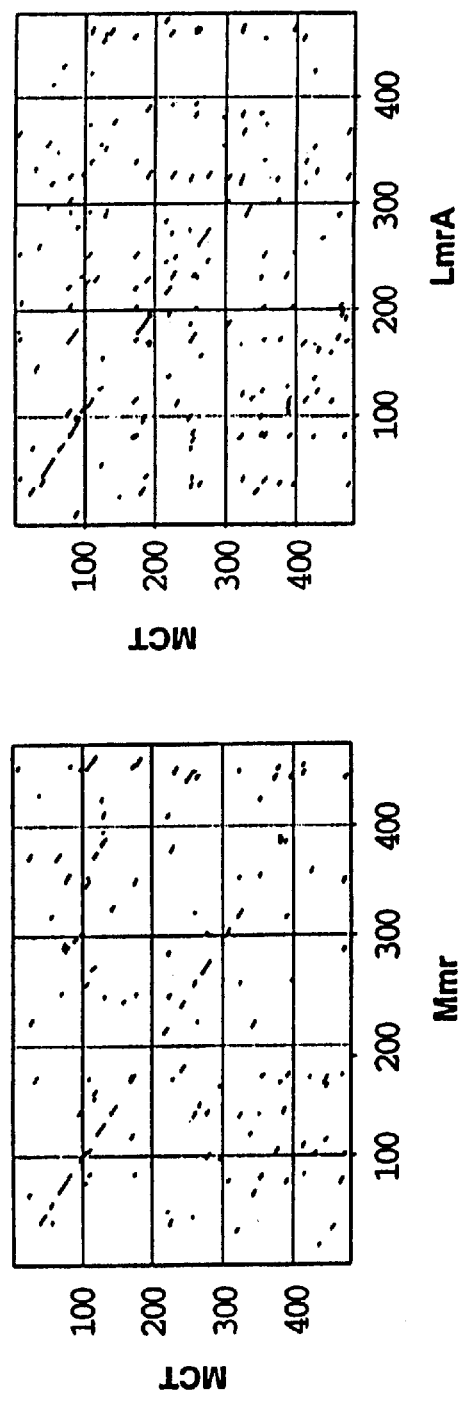
FIG. 17

MC-CLUSTER-TOTAL SEQUENCE

```
ggatcccgat cgtctcggac atgaccggcg accttctcgg cgcgcgggag gcccaggacc      60
ccgcctactg ggtgtcccac atccgccgcg cggtgcgctt ccacgaccag atccgccgtc     120
tgcagcgcta cggggccggg gccttcgtcg aggtcggccc ggacacggtg ctcagctcgg     180
ccggccaggc gtgcctgacg gaccaggcgg gcaggagcgc gcccgtcctg gtgtccctcg     240
cgcacgccga gcgcgcggag gtgcccgcgc tcctgaccgc tctggccacc ctgcacaccc     300
gtggcgtggc cgtggactgg cgggcgtggt tcggcgacgg gccgcgcgcg gccggcctgc     360
ccacatacgc gttccagaag cagcactact ggccgtcggg ccccaccggt tggcggtccg     420
ggcccgcccc cgtacccctg ccccaggccg gaacggagga cgccgaaagg cccggtcgcg     480
ccgcggagtg gcgggcgctg ccgcccggtg agcggtacga cgcgctgctg cggatggtgc     540
gcggcgaagc cgccgccgtg atggggcacg ccgggccgga ggcggtggag ccggagcgcg     600
gcttcctcga ccacggcttc gactcggtga tggccgtgaa gctgcgcgac cgtctcgtgg     660
ccgggacggg gcgggagctg ccgacgaccc tgctgttcga ccaccccacg cccgcggccg     720
tcgccgacta cctgctggcg ggacgggcg aggccgagac ggcgccgtcc gtgtccctgt     780
cggaccagct cgaccgcctg gaggccgacc tcgcgcggct gccggccgac gaccggcagc     840
gcgcccgcgt cgccgagcgg ctcaagggcc tgctcgcggt ccacgcgccg gaccggggcg     900
ccgggagcga ggacgcgccg gaccaggacg cgctggacac ggcgaccgac gacgagatgt     960
tcgagctgat cgagaaggaa ctccgccgtg gatgagacca acgagaccaa actccgcgag    1020
tacctgcggc tggtcacggc cgatctgcgg cgaacccgca ggcagttgga ggaggccgag    1080
gacgcggccc gcgagcccgt cgcgatcgtg ggcatggcgt gccgcttccc cggggacgtg    1140
gcatcgccgg acgacctgtg gcagctggtc gccgagggcc gggacgccgt caccgagttc    1200
cccgccgacc ggggctggga cgtcgacgcc gtctacacc ccgagccggg caccccgggc    1260
aggacgtacg cgcgccacgg cggcttcctc aaggacgccg ccggattcga cgccgccttc    1320
ttcggcatca cgccgcgcga ggcgctcgcc atggacccgc agcagcgcat gatcatggag    1380
gtctcctggg aggcgttcga gcaggcgggc ctcgacgcga ccaccctgcg gggcgaggac    1440
gtcggcgtct tcgtcggctc caacagcaac gactacctga tcaacgtgct cgacgcgcgg    1500
gacgtcgccg agggcttcat cgggaccggc aactccgcca gcatcctctc cggccgcgtc    1560
gcctacacct tcggcttcga gggcccggcc gtgtccgtcg acaccgcctg ctcctcctcg    1620
ctggtcgcgc tgcacctggc cgcgcagtcc ctgcggcagg gggagtgctc cctggcgctg    1680
gcgggcggcg cgacggtgat ggccacgccg accgccttca tcgagttcag ccgccagcgg    1740
ggcctggccc ccgacggccg ctgcaagtcc ttctcggcga ccgccgacgg caccacctgg    1800
tccgagggcg cggccgtgct gctgctggcc cggctctcgg acgcccgccg cctgggctac    1860
cccgtgcacg cggtcatccg gggcagcgcc gtcaaccagg acggcgcgag cgcgggcctg    1920
accgcgccca acggaccggc gcaacagcgg gtgatccggc aggcactggc caacgcacgg    1980
ctgacggccg acagcgtcga cgcggtcgag gcacacggca ccggcacccc gctgggcgac    2040
ccgatcgagg cccaggccct cctcgccacc tacgggcggg cccgcggcga gggcaggccg    2100
ctgtggctgg gctcgctgaa gtcgaacctg gccacaccc agtccgcggc cggcgcgggc    2160
ggcgtcatca agatggtgat ggccatgcgg cacgggacgc tgccccgcac gctgcacctc    2220
acggagccca ccccgcgcgt cgactggtcc gccggtgacg tacggctgct gaccgaggcc    2280
caggactggc cggacaccgg acagccgcgc cgtgcggccg tctcgtcctt cggcgtcagc    2340
ggcaccaacg cccatgtgat cctggagggc ccgcccgccg aggaggcacc ggacgcgccg    2400
ctgccggacg tctcctcgca gccgccgggc ccgctgccgt gggtcgtctc cggccgcagc    2460
gaggcggccg tccgagcgca ggccgacgc ctggcggccc acctgaccgc gcgcccgcac    2520
ctggcaccgg ccgacgtggc caccgcgctg gccaccacgc gggcggcctt cgaccaccgg    2580
gccgccgtcg tcggccggga ccgtgaggaa ctgctcgccg gcctcgcggc cctggccacc    2640
ggaacccgcg cgcccggcct ggtcaccggc cggaccccgc cgtccggccg caaggccgcc    2700
ttcctcttca ccggacaggg cagccagcag cccggcatgg gccgcgaact ggcggtcac    2760
agcaccgtgt tcgccgacgc cctggacgag gtctgcgccc agctcgaccg gcacctcgac    2820
cggccgctgc gcgaggtgct gttcgccgcg gacggcacgc ccgaggccgc cctgctcgac    2880
acgacggcct acacccagcc cgcgctgttc gccgtcgagg tcgcgctgct gcggctgctg    2940
gaggactggg gcttgcggcc cggcatggtc gcgggccact cggtcggcga actgaccgcc    3000
gcctacgccg ccggggtctg tcgctcgcc gacgcctgcg ccctggtcgc cgccgcggc    3060
cggctgaccc aggcactgcc gcgggcggc gccatggtcg ccgtgcaggc gaccgaggac    3120
gaggtgcgcg cccaactcgc cgacggccgc cccggcgtgg acatcgccgc cgtcaacgga    3180
ccggaagcgg tggtgctgtc cggcgacgag gccgccgtca ggacctggc gcgcgagtgg    3240
gccgcccgcg gccgggagac caggaggctg cgggtcagcc acgccttcca ctccgcccac    3300
ctggacgcca tgaccgaggc gttcgccgag gtcgcacgag gggtgcccta cagcgcgccg    3360
tccctcccgg tggtctccac gctcaccggg gccccgtca ccgacgagct ccgcaggccg    3420
gaacactggg tgcgcacgt ccgggagacg gtgcgcttcc acgacgcggt ccgcgccctg    3480
cgcgaccgcg gggccaccgc gttcctggag gtcgggcccg gcggcgtgct gacggccgcg    3540
gcacgccgat gcctgcccga cgccgccccc gagacgttcg tccccgtgct gcggcgccgc    3600
```

FIG. 21A

```
aggcccgaac ccgagtccgt gctgacggcc gtcgcgcagg cccacacgat cggcctctcg   3660
ccggcgtggg accgcctgct gcccaaggcc cggacgcgcg tggacctgcc cacgtacgcc   3720
ttccagcgcg gccactactg gctggcgggc atggccggag cgggcaccgc gcggccggtg   3780
cggccggaag tgcaggagcc caccgccccc tccggtacgc cgccgctgtc gcgacggctg   3840
gccgacgcgt cggaggagga gcgcggccac ctgctgctga cgctggtacg cgagcagtcg   3900
gccaccgtga tgggcggcgt cgaccccgcg caggtcgaac ccgaccgccc cttcctggag   3960
ctcggcttcg actccctgat gggcgtcgag ctgcgcaccg cgctcgccgc cgactgcgca   4020
ctgccccctgc cgcccggcct gatcttcgac caccccacgc ccgccgccct ggccgccttc   4080
ctcggcgagc agctcgcggc ggcggcctcc ggcaccccca cggcggcggc accctcgccg   4140
tactccctgg aggcgctgta ccgcaacgcc aacaccctcg accggcccga ggacgcgctc   4200
gccctcacca aggccgcctc ccggctgcgc ccggtcttcg ccagcgtggc cgaggcgggg   4260
caggacccgg tcacggtgga gctggcacag gccaccggcc ttccgggcct gatctgctgc   4320
ccggcacccg tgccgctgta cggggcacag cagtacagcc ggctcgcagc cgccttccgc   4380
ggcacgcgcg gagtctcggc cctgctcgcc cccggcttct ccccgggcga actgctgccc   4440
gccgacttcg aggtgatgca ggacttcctc gccgaggggg tccggcggca gaccgacggc   4500
gcgcccttcg tcctcctggg ccactcctcc ggggctggt  tcgcctacag cctggcggcc   4560
cacctggcgc gcaccgggcc gcgcccggag gccgtcgtgc tgctggacac ctatcagctg   4620
cacgcccggc cgctgcaccg catgcagcgc gaactcgccc agggcgtcct ggaccgcgag   4680
gaggacttcg gggcgatgac ggacgtacgg ctgagtgcca tgggcaaata cttcgacttc   4740
ttcaccgact gggtggccga ggacgccggt gtcccgacgc tgctgctgcg ggcctccgag   4800
cctctgggcg aggtcgtcga gggccaggag tggcgctcca cctggccgtt cgacagcacg   4860
gtcctcgaca cggaaggcga ccacttcgcc atggtcaacg accacgcgcc gcggacggcc   4920
caggccgtga acggctggct gtcgggcctc accggcggaa ggggctgagc gccggtggag   4980
acacgcaacg ccgaacggcc gtggatacgc agcttccacc ccgctcccca ggcccctgtg   5040
cggctgctgt gcctgccgca cgccggggggc tccgcgagcg cctacttcgc gctgtcgagg   5100
gaactggcgc cccgggtgga ggtgctcgcc gtgcagtacc ccgggcggca ggaccggcgc   5160
gacgagccgc tgctggactc gatcgaggcc ctgcgcgacg gggtcgccga ggccctgacg   5220
ccctggctgg accggccggt cgccctcttc ggccacagca tgggcgccgt ggtggcctac   5280
gagctggcgc ggctgctgtg ccaggacgcg ggcgtgccgc tcacccacct cttcgtctcc   5340
ggacgccggg gatccgaccg aagtctccgt ccttgccgcc gtgttccgga attcaccgtg   5400
acaccgccgc gcggctcttc ttccgaagtc ctccagatcc ggcacgagtt tgtatccgaa   5460
cgggggttctg cgtgcgaaat actctcttcg aattgggtga catacccccg atcggcaccg   5520
tacccgagca gatgtacgcc tcggtgatcc gacgggagcg ctacggacag ccccaccagg   5580
cgttccgcag cgaggtcgtg gacgtgccga aggtgggggcc cggtcaggcg ctggtcctcg   5640
tgatggccgc gggcatcaac tacaacaacg tctgggcctc cctggggcag ccggtcgacg   5700
tgatctccgc gcggcagaag cagggccaca gcgaggactt ccacatcggc gggtccgagg   5760
gctccggcgt ggtgtgggcg gtggggggagg gcgtcaccca ggtcgcggtg ggcgacgaag   5820
tgatcctctc cggctgccag tggacggaga cggccgccga catccggctc ggcgccgacc   5880
ccatgacctc cggctcgcag tcggtgtggg gatacgaggg caactacggc tccttcgccc   5940
agttcgccct cgtcgacgac tatcagtgcc accccaagcc gcccggcctg acctgggagg   6000
aagccgcctg cttcctgctc accggggcca ccgcctaccg ccagctgtgc ggctggcagc   6060
cgcacgacgt gcggccgggc gacccggtcc tcatctgggg cggggccggc gggctcggct   6120
ccatggccat ccagatcacc cgggcgcggg gcggcatccc cgtcgccgtg gtctccacg   6180
aggagcgggc ccgctactgc cgggagctcg gcgcccaggg caccatcaac cgcctggact   6240
tcgaccactg gggacggctg ccgacatcg gcgaccacga ggcgatgggc cgctggaccg   6300
agggtgtacg ggccttcggc cggcgcttct gggaggtgct gggcgagcgc aggtccccgc   6360
gcatcgtcct ggagcacagc ggccaggcca ccatccccac ctcgatgtac ctgtgcgaca   6420
acgcgggcat ggtcgtcatc tgcggcggca ccaccggcta caacgccgac atcgacctgc   6480
gcttcctgtg gatgcgtcag aagcgcttgc agggctcgca cttcgccaac ctgcggcagt   6540
gccgcgacgt catccacatg gtcgcgaacg gccagctcga cccgtgcctg tcgtggaccg   6600
gcggcttcga cgacatcggc aaggcacacc agctgatgca cgacaaccag cacccccagg   6660
gcaaccaggc cgtcctggtc aacgcgccgc ggaccggcct gaccaccttc gcctgaacca   6720
ccgccccggt gttccgacgt cttcccccca cacttaccga ccaaggagag atcaccatgg   6780
acaagctcga catcctctgg agcgagcgcg agatccgtgc cgtgctgcag cgctactgcc   6840
gcgggctcga ccgcctcgac gaggaactgg tcaagtccgc ctaccacgag gacgcgcacg   6900
acgaccgcgg cgtcatccgc ggcaacgcac acgacttcgt caagcagatc gtcccgctcc   6960
tgcgcgacgc ctacaccggc accctgcaca ccctgcacgg cagcacgatc gagatcgacg   7020
gggatgccgc gggcgtggag tcctactgca ccgcctacca ctaccgcgag agcgacggca   7080
tcaagcgggt ggagcagttc gccgggcgct acgtcgaccg cttcgagcgg cgcgacggcg   7140
tctggaagat cgcccgccgg ctcgtgctga acgacttcag cctcgcccag gaggtgccgc   7200
tcgaccccgc cgaggcccag gccggcttca accctccca ccgcgacctc accgacgcca   7260
gctaccaggt gctgccgctg cgcggcccgg acgcccccac cctctgagcc gtccggccgc   7320
```

FIG. 21B

```
cccaactcgc cccacctcac caggagtcac caccgtgtcc gacaccgagc agcacgcgcc   7380
cacgctgccg cggcagcgca cctgcccctt ctcgccgccg cccgagctcg aggagctgcg   7440
gcgcaccgat cccatcagca ggatgcggtt cgccgacgac tccccgggat ggctgctgac   7500
ccgccacgcc gacgtccgcg ccgcgctggc cgaccccggc gtcagctcgc accccggcaa   7560
ggcaccccag ccctggcgca acctcgcccc cgagatgcgc gccgagcact acctgccggg   7620
cttcctgatc ttcatggacc cgccggacca cacccgctac cgccgcctgc tcaccaagtg   7680
gttcaccatg cgggccatcc gcaagctcga acccaggatc gagcagatcg tcaccgagac   7740
cctcgacgcc atggaggccc agggcggcac cgtcgacctg gtgcagtcct tcgcgctgcc   7800
gatcccgctg ctggtcatct gcgagctgat gggcatccgc tacgaggagc gcgaggagtt   7860
catggacatg gtcctgcgac tccaggccct ggacgccacg cccgaggaac tcggggccct   7920
cggcgccagg atgaacgagt tcatgatgaa gctcgccgcc gccaagcgcg cgaaccccgg   7980
cgacgacctg ctcagccacc tcgcccacga ccccgacgcc gacccggcgc tcacggatct   8040
ggagatcgcc ggcatcggcg tgctgatgct catcgcgggg cacgagacct cggccaacat   8100
gctgggcgtc ggcacctaca ccctgctgga gaacgcgac cagtgggccc tgctccgtga   8160
cgacatcagc ctgatcgacc gggccgtcga ggagctgctg cgccaccaga ccatcgtcca   8220
gcagggcctg ccgcgcggcg tcacccggga catggagatc gccggacacc aggtgaagac   8280
cggggagtcc ctgctggcct cgctgcccgc cgccaaccgc gaccccgccg tcttccccga   8340
ccccgaccgc ctcgacatca cgcgcgagca aacccgcac ctcgccttcg gccacggcat   8400
ccacctctgc ctgggcatgg agctcgcccg gtggagatg cgccaggcgt ggcgcggcct   8460
cgtcacgcgc ttccccggcc tgcgcatggc cgccgcgccc gaggacatcc gctggcgcga   8520
cgaccagatc gtctacggcg tgtacaacct cccggtgacc tgggacgagg ccaagtgacc   8580
ggccccgagg ccgcggtgcg cgggtgcccc ttcggcgccg gcgaggcgcc cgcgtacccc   8640
ttccacgccc ccgaccggct ggagcccgac ccgtactggg agccgctgcg ccgcgagcgg   8700
ccgctgcaac gcgtcacgct gccgtacggc ggcgaggcgt ggctcgccac ccgctatcag   8760
gacgtgcgcg cggtcttcgc cgaccgcagg ttctcccggc agctcgccgt cgcgcccggc   8820
gctccgcgct tcctcccgca ccagccgccg ccggacgccg tcctgagcgt cgagggcccc   8880
gaccacgccg ggctgcgccg gctggtcggg aaggtcttca cgccgcgccg cgtggaggac   8940
atgcgtccgc tcatccagcg caccgccgac ggactcctcg acgcgatgga ggagatgggg   9000
ccgcccgcgg acctggtcga ggacttctcc ctgcccttcg ccgtgtccat gatctgcgag   9060
ctgctcggcg tgccgcccga ggaccgcaag cggttctgcg tctggtcgga cgcgctgctg   9120
acgaccaccg cgcacacccc cgcccaggtg cgcgactaca tgatgcagat gcacgactac   9180
ctcggcgggc tcgtcgcgca gcgccgggtg cggcccaccg cggacctgat cggctccctc   9240
gtgaccgcgc gcgacgagga ggacaagctc accgagggcg agctggtgcg gctggccgag   9300
gccatcctca tcgccggcta cgagacctcg gcgagccaga tccccaactt cctctacgtc   9360
ctcttccgcc acccgcagct gctggagcgg atcaggaacg accacgacct catccccgac   9420
gccgtcgagg aactgctgcg cttcgtgccc atcggcaccg tggacggctt tccccgtacg   9480
gccaccgagg acgtcgagct cggggagtc ctggtcaggg ccggggagac ggtcgtgccg   9540
tcgatgggcg ccgccaaccg cgaccccgag ctgttcacgg accccgacga gctggacctc   9600
gcgcggcggc cgaatccgca cctgggcttc ggcgcgggac cgcaccactg cctgggcgcc   9660
caactggccc gggtggagct ccagatcacg ctcacgacgc tgttccgcag ataccccgc   9720
ctgcggctgg ccgtgccgga ggagagcctc tcgtggaagg aggggctgat ggtccgcggc   9780
atgcacacca tgccggtcac ctggtgagga caccggcgtc ctcctgacct tcccggcgtt   9840
ctcacgccgt cccggcagcc ttccttccga cacgagcgca cagagggtga agcgaccgca   9900
atgagcacca tcgacgaatg gaacacagc acgaaggagg cgggcatgga ccccgcggcc   9960
ctcagacgcc tgaccgatgt ggtgcgggcg aggggcggc cggcgcagct gtgcgtcatg   10020
cggcggggca ccgtggtcct ggaccgctcg ttcggctgct cctccgactc cctcttcctc   10080
gtctacgcgg ccaccaagcc cgtcgccgc ctcgccgtgc acgcgctcgc cgagcggggc   10140
ctgatcgggc tggaccggcc ggtggccgaa tactggccgc agttcgccgg gcacggcaag   10200
ggtgacgtga ccgtccgtca tgtcctccag caccgggccg gggtgccggt cggccggggc   10260
atcgtgcgca cgatgcgcac cgccggcgac tgggagcgct ccgtgcgcga ccttgagcag   10320
tcccggccca agtggcccgg cggcgaggtc gccgcctacc acttcatgag tttcggattc   10380
attctcggcg aactggtgca gcgcgtcacc gggcggtcgt tccgagattt cgtgacttcc   10440
gagctcttcg ccccacttgg gctgaatgat ttgcacatgg gattgcccgg cagtgcctgg   10500
ccccggcatg tgcccgcgcg ggccgccac ccctccgaat ggcccaatca gtggatgagc   10560
aaccgccgcg gctaccgcca ggccgtcatt ccgtccgccg gtctttccgg aaccgccgca   10620
caaatggccc gctttacca gatgcttatg gagggcggct cgctcgacgg catccgcgtg   10680
ctgcggcccg aaactgtgga ggaagccaga aaaccgtcca atgacggcgg aatcgacgct   10740
tccctcaagc gtccggtccg ctggtcccac ggattcatgc tcggtggtcc gggcccggac   10800
ccgcgggggc tgtccaatgt gctgggccgc acgagcgacc cgagcgcctt cgggcacgcg   10860
ggcaccacgt ccagcgtcgt gtgggccgac cccacgcgcg agctggtcct cgcctacctc   10920
tccaacatcc agcccgagtt cggagcgggt atcgagcggc tccgcgaggt cagtgacctc   10980
gcgctcggtg cctgcgaggc aggctgaccc gagccgtgcc gccacggccc ggcgcccgcc   11040
```

FIG. 21C

```
cgatccgatc gggtccggtg ggggccggcc gggtccgggc ggggacgcac ttccccggc   11100
gtccccgccc gggccccggt gcgaaccggg cgcaaaggcg gccgatcgcc cggcgcggcc  11160
ggatgccccc gaacggtgtg aaacgttctt atcagcctct gaccagcacc gagtgatcta  11220
ctgcacagcc cgaggccgcg attccggcag tatcttgatc ttgacggggc accaatgcga  11280
gcgggctatt cgccgcggtt ttccctgacg tcggatgcag atgacaccgg aggagggcca  11340
gtgctgaatc tgcccaaagg aatggagcgc gcgcatccgc attctccgcc acaggtggga  11400
atactcggac ccttggaagt ccgctcggcc ggaggtgccg gaacgggagc cgcggtaagc  11460
ggtattcgcg tacgcacatt gcttgccgcg ttgactgccc gcctggggca ggcgatgtcg  11520
accgagcgca tcctcaaaga ggtctgggcc gacaacccgc ccgcgaccga tcgcaaggcg  11580
gtggccgtcg ccgtcctgcg gctgcggcgg gtcctcggcg acaacgaagg acggtggctg  11640
ctcacccgcc cctccggtta cgtcctggac atcccccgg  accacctcga cgccgtacgc  11700
gcggagaccc tggtgcggga aggccgggcc gccctggccg ccggcgaccc acgcgtcgcg  11760
gcccgccacc tcacgcgcgc cctcgaccag tggcggggcg agccctacgc ggacgccaac  11820
gccatctcga ccgtgtccca gcgcatcacg gagctggaga acctcaggtc cgaggccgtc  11880
caggcgcaca tcgacgccag gctcgaactg ggtcaccacc aggaactggt cggcgaactc  11940
cgctcgctga ccgccgcgaa ccccctgcac gagccgcact ggctgcagct gatgctcgcc  12000
ctctaccgct ccggcaagca ggccgaggct ctcgccgcct atatgcagct gcggcaggcg  12060
ctggccgaga acctgggcat cgaccccgggt cgtcagctcc aggaactgca cctgcggatc  12120
ctgcgcgccg acgcgggcct gctgacgggg tccgggccgg cggcaccggc cgagccactg  12180
ctcgtacggc agtcctgagg gctcacggcc acccgaagaa cgcgcggtag cacggaacct  12240
gctgctccag catatggatg ccgtggtgca cacggcgccc ggcggtggcg gccgcgctca  12300
gcagcgccgt ctcgtgcggc ttcatgacga cgtcgaccac cacggcatcc ggtcgcaccc  12360
tcgcggggtc gaagggcagc gggtcctcgg aacgcatgcc cagaggcgtc gcgttgacgg  12420
cgaaatcggc cgcctccaga tcgccgggcc ccagcgcccg gatcccgtcc ggccggcggg  12480
acccgagccg cagcagcagc gcgtcgagct gggcgcggtc ggtgtcgtgc acggacaccc  12540
gcgcggcgtc ggccatcagc agcgcgtgg cgatcgcgct gcccgcccct ccggcgccga   12600
ccagtgccac atgcctgtcg cgcaccgtgt gcccggccgc ctgaagaccc tggacgaacc  12660
cgagcccgtc gaagttctcg gcgtaccagc ggccgtcggg ttccgccgtc atcgcgttgg  12720
ccgtcccgat gagggcggcc gccggcccga gccgtccgc gagcccgcac agggccgcct   12780
tgtgcggcac ggtgaccagc agaccgtcca gattgccgat ccgcttgagc ccctcgacca  12840
cctcggcgag atcccgcgcc cggacgtgca ccggcaccac cacggcgtcc agaccgcttt  12900
cgctcagcag ggggttgagc agaccgggcg ccttgacctg gcgacggga  tcacccagca  12960
ccgcgtacag ccgcgtggcg cccgagacac cggccgccgg cccgaggaat tccatcagcc  13020
gatcctctct gtaccccga  cggatgttgc cctacggtgc tggagatgct ccacagcttt  13080
gccgtgaccg ccggtcggca aaccctgcg  tgcccctgac gcgccaggcc ctccaggtag  13140
ttgctcccgg cggatcccga cagctcccga ccggtcccga cggagggaag aagccatcag  13200
atacctggga atcgacgtcg gaggcacgaa ggtcgccctg cgggtgacgg gggacaccga  13260
cggtgcgggc ggcggcgacg tgacgttccg ctggcccgcc gccggcgacg tcaccgcgga  13320
tctggacctg ctcgccgcgc gggtccgcgg tcttctggga caccgcgagg acccctcgc   13380
cggggtcggc gtggccatgc ccgcgatctg cgacgcggcc gggacggtcc gcacgtggcc  13440
gggacggccg agctggcgg gcctgaacct gacgccgcc ttcgggcagt tgctgcccgg   13500
cacccccggtc gcctgcgccg acgacggtga cctggccgcg ctggcggagt cccgcgccgc  13560
cggctgccgg catctgctgt acgtggggt cggcacgggc atcggcggcg catcgtcca   13620
tgagggccgc gcctggccgg gccccggacg cggctcgtgc gaggtcggcc atgtcgtcgt  13680
cgaccgctcg gcccacgct gcgactgcgg gcgcgccggc tgcgtccagg cggtcgcgtc  13740
gggaccggcg accctccggc gggcgccga acggcggc cgggagaccg gcttcgacga   13800
actggcctcc ggggcgcgct tgcacgcccc gtgggcggaa gcggccgtcg acgagagcgc  13860
cgcggccctg gccaccgccg tgaccggcat ctgcgagctg gcccaccccg aactcgtcct  13920
cgtcggcggc gggttcgcgg cgggcgtgcc gggatacgtg gcctcggtcg cggcgcacgt  13980
cgagcggctg acccgcccgg gaacggatcc cgtgcgggtg cgccggcgg tgctcggcgg   14040
gcggtcctcc ctgcacggcg cactgctgct cgcgcgggag cacacgggc ggggaaaccg   14100
gccgccggag agtgaccgtg tttcttccga tgtttcttcc gatgtttctt tcggggagt   14160
gacagacagg gccgttggcc ggtccgactg agcacaatca caggtgattt cgcccaggtt  14220
caccacgcct cgtgtgctcg gggtcggcag aaggagtcag agtcatgctc gacaggcgga  14280
gcgtcattcg cgtcggcgcc ggggtggcgg cggccgccgc cgtggccggt acggccgcca  14340
ccggtgcggc ggccgtgggg ctgccgggtg tacgggacg cgcggcgtcg cgcggggtcg   14400
actgggcctc cttacgccgt catctgtcgg gcgagctcgt cctgccggcg gacaccggat  14460
acgagcgggc caggaagctc tacagcggcc agttcgacgg catccgcccg caggccgtcg  14520
cctactgccg gaccgaggag gacgtgcgga cgaccctcgc gttcgcccag gaccacgcgc  14580
tgcccctcac cccgcgcagt ggcgggcaca gcttcggcgg ctactccacg accgacggaa  14640
tcgtcctgga cgtctccggc ttccacgcgg tgagcctcac ccggaacacc gtcgtcatgg  14700
gcgcgggcac ccagcaggtg gacgccctca ccgccctgtc gccgcgcggt gtcgccgtgg  14760
```

FIG. 21D

```
cgagcggcaa ctgcgcgggc gtctgtcccg gcggcttcgt ccagggcggc ggactgggct    14820
ggcagagccg caagttcggc atggcgtgcg accggctcgt ctccgcccgg gtcgtgctcg    14880
ccgacggccg cgccgtgacc gcctccgcca ccgaacaccc cgaccttttc tgggcgatgc    14940
gcggcggagg cggcggcaac ttcggcgtcg tcaccggctt cgagctgcgc cccaccgacg    15000
tccccctccgt cgtcagctac aacctcacct ggccgtggga gtcggcgcgg cgcgtcatcg    15060
aggcgtggca gcactggatc atcgacggcc cccgcgacct cggtgccgcc atggccgtgc    15120
agtggcccga cgccgggacc ggcacgccgg tcgtggtcgt caccggcgcc tggctgggcg    15180
cggccgacgc gctcaccccc gtgctggact ccctggtggc ctccgtgggc agcgcgcccg    15240
ccacccgctc ggccaaggcg ctctcccagc acgacgcgat gatggcgcag tacggctgcg    15300
ccgacctcac gcccgagcag tgccacacgg tcggctactc gcccgaggcc gcgctgcccc    15360
ggcagaactt ctccatggac cgcaaccggc tcttctcccg ggccatcggg caaggaggcg    15420
tcgagcggat cctggaggcg ttcgccgccg accgcgcgc cggacagttc cgcttcctga    15480
gcttcttcgc cctcggcggc gccgccaacc gcccgaccg caccaccacc gcctacgttc    15540
accgcgacac cgagttctac ctcggtttct cgatcgggct gaacgacccg gagtacacgg    15600
cggaggacga gaggctcggc cgcgcctggg ccgcgcgagg actgcgcacg ctcgatcccc    15660
actccaacgg cgagagctac cagaacttca tcgacccgga gctcgacgac tggaagtcgg    15720
cctactacgc cgagaactac gtgcgcctgg ccgccgtcaa ggcggcctac gacccgcacc    15780
ggctcttctc cttcgcgcag gccgtctgac tctcccgaa agaccccctgc cggcctgctc    15840
ccctccgcgg ctcctgtggg cactggtgcg cccgcgcact tctgtgtgat tgagtgaagt    15900
ccgggcgtgc agagctcagt tgccgtggag ggggcgccag ttgcgagcat cagcggtgga    15960
gagggtggag ctgatccgct ggccggtgga gtccgagcgg cgggagcgct gccgcgaccg    16020
gggcgtcatg cggatcctgg tgctggaggc ggggggccgag gcacccttgt gcgtggaccc    16080
caaggaggac tgggtccgcg ctcccggcag caccgacgac ctgcggcgcc gcgtcgaggc    16140
cctgcgcctt cggggagccg ccgccgagtc ccggcccgag gtcgacccga acggagtgct    16200
gcgtttccgg tggcgctccg ccctgctctc gcccaccgag gcccggctcg tcgcccggct    16260
cgccgagtcc tatgccgagg tcgtcgcccg cgacgacctg ctccgcccgc ccccgggccg    16320
taccgtgccg agccgtaacg cgctcgacct ccacatcatg cggatccgac ggcgcctcgc    16380
cgcgctgggc ctgagggtgc gcaccgtccg ggggcgtggc tacgtcctgg agagcgcgga    16440
aggagtctga ccgacgggcg tggccgcgca ccgcaccgac cgccccgacg agcgaggagc    16500
ccgaagtgca gcagcctcat cacagccgcg tcgacgtgga actgggcgag aggtcctacc    16560
ccgtccacgt cggaccgggg gtccgccacc tcctgcccgg catcgtcgcc tccctcggcg    16620
cgcaccgcgc cgccgtcgtg accgcacggc ccccgacct ggtgcccgat cccggcgtgc    16680
ccgcgctgat cgtgcgggca cgtgacgcg agcggcacaa gacgctcgcc accgtcgagg    16740
acctgtgccg caagttcacc accttcggca tcacgcgcca cgacgtcgtc gtctcctgcg    16800
gaggaggctc gacgaccgac accgtcggcc tggcggcggc gctgcaccac cgtggggtgc    16860
cggtggtgca cctgccgacc accctcctgg cccaggtgga cgcgagcgtc ggcggcaaga    16920
cggcggtcaa cctgcccgag ggcaagaacc tcgtcggcgc ctactggcag cccaaggccg    16980
tgctgtgcga caccacgtat ctccagacgc tgcccgccga ggagtgggtc aacggctacg    17040
gcgagatagc gcgctgccac ttcatcggtg ccggcgacct ccgcggccgg gccgtccacg    17100
accaggtcac cgcgagcctg cggctgaagg cgtccgtcgt cgcggccgac gagcgggaca    17160
ccggcctgcg gcacatcctc aactacgacg atacgctggg ccacgcactg gagaccgcca    17220
ccggcttcgg gctgcggcac ggactcggcg tggcgatcgg gacggtcttc gcgggccggc    17280
tcgcggaggc gctgggccgc atcggcgccg accgcgcgcg ggagcacacc gaggtcgtcc    17340
gccactacgg acttcccgac agcctccgg gaaacaccga catcaccgag ctcgtcgcgc    17400
tgatgaggca cgacaagaag gccacgtcgg gactgacctt cgtgctcgac gggccttccg    17460
gcgtggagct ggtgtccggg atcccggagg acgtcgtcct gcgtacgctc gcggcgatgc    17520
cgcgaggaac ggcctgaccg agtgttccgt cttccgaggg gaagtgaccg tttcgtgtcg    17580
gcagagctgt cagaaccgct gaagaaggcc ctggactccc tggtgttcgg cgtcgtggcg    17640
acgaccgacc ccgacggccg cccgcaccag tcggtggtgt gggtccggcg cgagggctcc    17700
gacgtgctgt tctcgatcac gcgcggcagc cgcaaggaga ggaacatcct gcgcgacccg    17760
cgtgtgagcg tgctgatcag cccggcggac tcgccgtaca cctacgccgc gatccggggc    17820
accgcgcact tcgaggacgt gccggacccg ggcgcgtacc tcgacacgtt ctccataaag    17880
taccacggcg tgccctaccg ggagtcgttc cccgagccgc cggaggtgag caccattctc    17940
gccgtccggc tcgttccgac gtcggtctac gagcagtggt gagggcgtag gcgtcccgaa    18000
gccccggcag cgtcccgaat gccgctgccg gggcttcccg tgggagccct acgccggttt    18060
ccgcgcggtg accaccgagt agccgacctc ctccaccgag cccatgcggt cgatgccgtc    18120
gaccatgcgg tggaacgcct cgtcgtccat gtgggagccg agctcgtcgc tggccgcacg    18180
catcttcgcc gccaccgcct cgtaggaggg ccgcaccctg tccccgatgt cgaggaactc    18240
caccacctcc agccccaccg accgcatgca gtcctcgtac gcctcgcggg tgaggacggg    18300
gccctgctgg aagttgtcgt tggcggtgtc gacgatcgtc ctggacgcgt cgctcagggg    18360
ccggcgcagc acgaagtccg tcaccgtcac ccggccgccc gggcgcagca cccgggcgat    18420
ctcggtgaag acgtcggccc gttccagggc gtggcagatg ctctcgatcg cgtaacaggc    18480
```

FIG. 21E

```
gtcgaacgag ccgtcgggaa aggggagcgc gagcatgtca ccgatgcgga actcggtcgc 18540
ctcgtcgccc tccttctcgg cgagctgccg cgacagaccc acctggtagg ggttgatgga 18600
gaccccggtg gcccgcaccc cgtgccgggc ggcgatgcgc aaggtggcct tgccgttgcc 18660
cgaccccacg tcgagcaccc gctccccggg ggcgaggcgc aggcgctccg agacgtagtc 18720
ggtcagccgg tcgcctgcct cttccaccgt cgtggggacg tcgggtcccg cccagtagcc 18780
accgtgcatg tagccgcctt ccgcgtgcac catcaagtcg gtgacgcggt tgtagagttc 18840
gaccatccgg tcggaggcgg acgcggtttc cgtcatgccg ctcactttcc cgggcgctgg 18900
gcgaccagca gcagatagcc gaactccttg acgccgacga ggtcgccggg gtcgaactgg 18960
ttcaccatct cctcgccgaa ctgcgtctcc agcctctgct tcgaggagtt gatgcgctcc 19020
gagagcagcc tgaaggtctt ctccagggtc tggtcgctga tgtcgaggaa ctcctccagc 19080
cacaggcccg ccccccgcag caggggaggg tacgcctcgg cgctgaccat ggtcatcatg 19140
aagtcgtgga ggtagcgctg gacggcggcc cgcccctcgg gggcgagggg ggcccgctcg 19200
aagaagtcgg tgagcaccag acggccccg ggccgcagca cccggcgac ctgggcgagc 19260
acctgggcgc ggtcgggcat gtggatgatc gattcgaggg cgatgcgagc gtcgaagctc 19320
tcgtcctcga aggggaggtc catcgcgtcg gcccgctgga agcgcgcccg gtcggcgagc 19380
ccggcctcct cggccagcgc gttggcccgg acgacctgct catggctcac cgagatgccc 19440
gtgacatgcg ctccgctgag ccgggcgatg cgtacgcccg gggtccccac gccgcagccg 19500
aggtccagga cgcgggagcc ggcgccgatg cgcagccgct cggccatcat gtcggtgagc 19560
cggtcggtgg cctcggccag cggcacctgg ctgtcggggg agtcccagta gccgaagtgc 19620
aggttctcgc cgagggaggc ggctcccagc gcggtgaacc ggtcgtagag cgcgcccact 19680
tcctcggagg cgggtgaggg catgggagt tcggacagct cggagtgcgg catggacgat 19740
ccctctcgtg aaaggtcggg ggtgggtcgg gcagtcggtg tcaggagaga cggaggtcct 19800
ggtagacggc gtcggcgagg cggacgatgc gctcgcggtg ccgttcgtgc tccaccttcc 19860
cgttgaggtg gagggcgacg acgagagcgg cgtccgggtc ggcgaagacc acggcggtcc 19920
acagcccgtc gtgcccgaag gaccgggggg aggcgtacga gccgaagctg gtgaaccgcg 19980
gatccagctg acggcattcg aggcggaacc ccatgcccca gtcggcgttg ccgtagcggt 20040
cctggaggcc ggtgcggtgc cgggccgtga gggcggcgac ggtgggcggc gccaggacgc 20100
gcccgccggg agcgtccccg ccgcgcagca gcatctcgaa gagcctgccc atgtcccgca 20160
gcgggccacg ggtgttgacc cccgggatgc agcgtgtggt ggccgcctcc gtcgaccacc 20220
agtgggtggg cagcgggccg ccctcggggt tgctcacatg gatcagcggc agctcgcccc 20280
cgagcgcggc gaactcctcg cgatccaggt ggacacgggt gccggacatg ccgcacggcc 20340
cgaggatctc ctcctggacg tacgcgcggt actccctgcc gtcgacgacc ggaaggatgc 20400
gcgccaggac gaaccaggcc caccactggc tgtagttgat gccgggcgtg ccccccggac 20460
gcggtgccac cggcacctcg aaggcacggc gcacgcgctc ctcgtccggg ccggccacga 20520
tgccgtgcag cgggtcgtcg ccggtgggca gcgggcccgt atgcgtcagc agttccatcg 20580
aggtgatgga ctccttgccc cggttgccga actccggcag atagtgcgcg acgggcagat 20640
acgggtcgta cgctcccgcc tcccacagcc ggcccagggc gaccgacagc agtggcttgg 20700
cgcagcagta ccacggggc agcgaccggt gggtcatcgc caccccgggg cgggccagcc 20760
ccaacccggc gtccgccaga gggactccgt cgcgggagac gtagatctgc gcccccgggg 20820
tcgaggtgcc gacctcgcgc tccagctccc gcatggtgcc gggaagcgcc gcacgggcgc 20880
gccggacggc ctcggccgcg tcctcggtgc cgggcggcgg ggccgcttcc cgcgccgtgg 20940
taccgggcgt gcccctgagc gcggccacat ggcccgaggc gtcccgctcc agtgcggcgt 21000
cgatgaagaa cagcaggctg aaattgccct cggcccgtac gtcgccccgc tcgaatacgc 21060
cggtccgatc ccgcgcgggg ccgagcagca gggcgggcc ggcctccagg ggaagccgga 21120
tccgcagtcc cggactctca ccggccgcgg ccgcgaggcc gagcccgccg gcgacgaggt 21180
ccacctggac gtcgacggcc gggggttcgc cgggcggtgg gtcggtgagc tccaggcgga 21240
gcgcgaccgt gccgcgttcg cccacgggcg ggcgttcgag cctcgcggcc ccggcgagcc 21300
aggccgtgga caggaacggc gcggtggaca gggtgttcag cacgggctca ctcctccgct 21360
tccttggcgg cccccggcgc cacctggggg acgacctcct ggaacagccg ctccaggctg 21420
gtggtggccg ggtagtcgcg gaaccacagc acgaactccg ccacgcccgc ggcgaccagg 21480
cgccgggcgc gctcggtgag ctgttccggc gtcccgtaca ggctgccgcc gccagcagg 21540
tcgggatggt ggctccagaa cagcacctcg tgcggggtgg agagccagcg gtcgcgttcc 21600
aggacggagt cgaagatccg gcactccgcg gcccaggcgt gccggacgcc gtccggatcg 21660
agcccgagct ccgtgcgacg gcggcggaac gcggtgacgg ccgcggcgac ctgagcgggc 21720
tcaccggtcc actggacatg agcgcactcc cgcacggtgg cgtcggcggg ccgcagcgcg 21780
ccgctcccgg cgtccccggc cggggtgcgc agcgcgaggg ggaggggctg ctgccgtggg 21840
gcgggcacgc agtgccgga agtgaggcgg atgtgttccc cggtgaaggt gacgggctgt 21900
ccgccccaca gcgcgcggga ggctcgacc gtctcgccga gagcccggtg gccggcggcc 21960
tcctcctcgt ccgcctccag gcccgtgggc acctcgcgcc ccgtcgagtg gtgctccggc 22020
aggtactcgc gggccgggaa gccgagggtg agccggccgt cgcagacgac gtccagggtc 22080
gcggcccgct tggcgatcag cgcggcgttg cggaacggcg gggccgagga gagcagtccc 22140
agatccagac cgggcaccgc gcccgcgagg gccgccagcg ccgtccagcc ctcccagacc 22200
```

FIG. 21F

```
ggctcgggct cgcgccgggg cagggtgtcg gtgcggtcca gcagccagag ggcgccacgg 22260
ccgtgccggt ggacggtgcg ggcggtctcc aggaggagcc gccagccctc gcggccgccc 22320
gtaccggcca gttcgaggtt ggtgccctgc ggggcgacga cgctccagcg cggggtcgcg 22380
ggcgtcatgc gtggccgccg ctgcggacca gcgcgagcag gctctgcggc ttgtccagca 22440
ggcgtcgggg ccgctcggcg cgcagttggc cggccgcgcc ctcgccccag gtcgcgccca 22500
cggtggcggt cccggcggcg cggccgctgc ggatgtcgat caccgcgtcg ccgaccatga 22560
ccgcgtcctc gggcgccgcg tccagccggc gcagtgcctc ccgcacgatg tcggggtgcg 22620
gcttgggcct cggcacctcg tcgctgccca ccacctcgtc cagcaggggc agcagcccga 22680
ccgcctccag cacggcgcgc gcccgggagc cggacttgcc ggtggcgatc gcggtgccga 22740
cgccgtccgc gcgcagctcc gccagcaact gcggcacgtc cgggtacacc tcgacgcggt 22800
ccatcagccg gtggctctcc cggacgaacg gttcctccat ctcgccgggc aggcccatca 22860
gccgcatgat gtccgggaag tagcggccct ggtgcgtgcg gtactcctcg aagggcggct 22920
cgcccggccc caccacttcg cggtaggcca cggcgaacgc ctcgcgcatc accgcgaaac 22980
tgtcgatgag gacgccgtcg aggtcgaaga ccacggtggt gaaccggcac gggagagcgg 23040
tggcgggcgc gtccgccgcg gcccgcgagg cgggcggggg gttcaggggc atggcaggag 23100
ctccgtgggt agggacgtcg gggcccagac cccggcgtgg ctgacgactt tcgtgaagcg 23160
gcccgcgagc cggtggtaga cggccccggg cgagctgtgc ggcgggtggg ccgccgcgtc 23220
cagcccgccc caggcggcca tggccctcag cagcagcgga tcggccggca cccagcggcc 23280
gcccaccagg aactcggccc agcagtgcgg tgtggagtac ggcttggcca ccagcagccc 23340
gaaggagaac cgcacgtcga gcccgcgccg ccggccctcc gccaccagcc aggccgcggc 23400
gccgccgcag tcggccatgt gcgtgctcca caggaacccc gggtcccagc ggatcgcttc 23460
gggcagcagg aagaagccga ccggctccag ggtgcgcagc aggtcgagga cggccggggg 23520
gaagtccggc cagtggccgc gcgaccgtgt gtacagccgc gccagcgtgg tctcccgcgg 23580
cgaagccgcc tccaccgggc ggcgggcgcc gggcagcagc actccgtagc ggcacgggcc 23640
cgcgtggccg ggcaccgggc aggacgccgt gacgtcgacg cgccagcgcg ggctctccgc 23700
ggccgaggcg gtccgcaggg aaccggccca cgagcggatg gcccggcgct gcaccgagga 23760
caggccaagg tgcagggccg cgttgcccag gtcgtagccg tcgaagaggc gtcccgcgcc 23820
gcttcccacg aagggcacgc ccgcctcgca cagcgcggac agcagctccg gtccgatccg 23880
gtgcagccgg cgcgcgctct gctcgtcgac ggtgaaacgg cggtgctcgt cgggcacgag 23940
cttcagacgc tccacgagcg cctggagctc ctgggtggag ggggccgggc cggcaggta 24000
gacgctgatc tcctcaatcc tttcgccggg gcgggcagcc ggtgcgggac ggccggggcg 24060
gccgccggtg gggtgccggg tcagtcgatg tagcccgagc cctggaggcg ggccgccacc 24120
tgctgctcgt cgctcgcggt gtacgccggc tcctgcgggc gcggcgcgta gggggagaag 24180
gcgcgcagtg ccggggccac ctcgtgcgcg aacagttcca tggactcgat gcggtgccgg 24240
tccgccagct cgccgaaggt gaactcgccc agcagcgtgt cgaaatggcc ctccagggac 24300
gcggccctga tccggtcggc cacggtcgcc ggcgagccga cgaagacgag gttgttctcc 24360
agcaggaagc gcaggtcgcc ggagcccgcc aggatgtccg tcgtgctgag cctgctgggt 24420
ggggcgtgct gatcgcggga acgggacacc gagccgtacc gcagcgtctt ggtgaacgtc 24480
tcggtgatgt gcgcggccgc ccgctcctcc gcctcggcgt ccgtccgggc cacgtggacc 24540
agcgtccagt agccgatgcg cgggtcgctc gcgtggccgt ggccgcgcca ccagtcgagg 24600
tagtgccggt agaccagcgc catggaggcg cgcggcacga tcatcgtgga actggtgtgg 24660
gcaccggcct cgctgagata gcgcaaggtg ttgcggttgg tggtgggcac ccacatcggc 24720
gggtgcgggc gctgcaccgg cgggaaggac agggcgatgt cgcgcagccg gtgcgcgggc 24780
ccgtcgaagt cgaaggcgcc ccgcgcggcg aacgcggcac gcagcagctc cagggcctcc 24840
cgggtcagga ggtgacggtt gtcgaaatcg gcgtcgaagg gcaggaaggg gtcacggctg 24900
acgcccgagg cgagcccac ctccagccgc ccgcccagga gctggtccag ggtcgcgacc 24960
tcctcgacca ggtgcagcgg gtggcgcagc ggcgccaccc accccatcgg gccgacccgg 25020
atgcgctcgg tgcgcaccgc ggcgccgtg cagaagaccg cgggcgaggg catccagctc 25080
tcgtgcggcg tgcagtggtg ctccaccgag aacgcgtagt cgaagccgag ccggtcggcg 25140
tcctcgacct cgccgccacag ctcttcgtag cgctcgcccg gcgtgatacc gggacgtccc 25200
cagacatggg agaaataagc gaatttcatt ggcttccccg ggtgggcagg acacgtggac 25260
aactggacgt gctgggcgcc gcgtcgctct gcggccggtg caggggcgag ggagggtcga 25320
cgccggcggc cgaatagatg tggtcgatgc aggaggccag gatggtcact tcggccatcg 25380
accctcgcc caggcccgac accgggccct gcccgtcggc cgagccgccg agcctgcggg 25440
cgagttcgtc cacctgccgc cggtactcca cgcccacggg ctcgtcgggc agcgcgacgg 25500
tctcctccac cccctggcgc aggaccacga ggctcgactt ctgtagccgg tggggctga 25560
agccgaaggt gccgcgcagc gtcgccaccc cctcggtgcc ctccacggtg atcgtggtga 25620
cgtccagcgc ctggtgggag gcccagcgtg tctccaggga gatgcccacg tcggtgtcgg 25680
tgacgaggaa gccgcgggcg tgtcctcca ccgtctcccc ggggcctggc cgcgccgtgc 25740
cggaggagcg ccggctccag tcggccgtgg cctcgccccg gctcatccag tccgcggaca 25800
tcgtgctcgc cgcccggacc acgcgcggcc acccagcag gtgcaggccc acgtccagca 25860
ggtgccagcc caggtcgagc agcgcgccgc ccccggcgag ccggcggtcg acgaaccacc 25920
```

FIG. 21G

```
cggtgcgctg cgggatgccg gtggcccgga tccagctcag cccgacactg cgcacggtgc 25980
ccagcgaggg cagcagctcc gccaggcggc agacatcggt gcggtgccgg gcggcgctcc 26040
aggcgtagag ggtgatgtcc ccgatgctgt cgccccgcgc ctggtggtcc agggcgagcg 26100
cctgggcctc gaagagcgtg cggcacaccg gcttctcgac gaacaccggc acgtcccgct 26160
ccaggagggc cttggccacg gggagatgga ggtggttggg cagggcgatg atggccgcgt 26220
ccacgcttct ggggcgagc tcttccggtc tgctcaggac gcgggtccgc gcgccctccg 26280
gcagggccga cctggccgcc acggggtcgt cgtccacgag gaagtcgacc cggaacgccg 26340
ggtgttccgc cagcagcggc agccacacct tgcgcgagac ccatcccgcg cccagcactg 26400
ccatccggag gggttcgcga gctgtcgtcg gcggtgtcac gacgggtgcc ttctccgtga 26460
aagtcatcag aagcgggcac caccgtcgac gacgagcgta ttgccgttga cgtacgaggc 26520
cgacggcgac agcaggaacg acaccgccgc cgcgacctcc tccggctcac cgagccgccc 26580
cgccccgatg aactgcagga ccagatcgcg ctcggcctcc gagaagtcca tcacctcggc 26640
gcggatcgcc ccgggcgcga cgacgttgac ggtgatgccg tgcttgccga cctcacccgc 26700
caccgacgcc gcccacggct ggagcgcccc cttggtggcg gcgtacgcgc tgtggccggg 26760
cagcccgctg gtcccggccc gggagccgaa gagcacgatc cgcccgtacc tggcgcgcat 26820
catcggcttc aggcacgcct tggcgagacc cacggaaccg gccaggttga cccgcagcag 26880
cttctccagg ctccgggcgt ccgtggccat cgcgagccgg cgcgtacgca agcccgcagc 26940
agccacacag ccgtccaccc gcccgaaccg ttcgacggcc gccgccacca gcgcgtcggc 27000
gccctcgggt tcgctcaggt ccgccgccac gggcacgagg gtgccgccct ggccctccac 27060
ctgctcccgc agcttgcgga tcgcctgctc gccgctgtgg tagccggcga cgacggtggc 27120
gccgagcgcg gcgagctcca gcgcgcacgc gccgcctatc tgcccggacg cgcccgagac 27180
cacgaccacg cggccgctct gtcccaggcg ctccgtgcc cggtcggtga cggtgctcat 27240
gaaccggcct ccttggcgat gatcagatga caggggacg cgtccagcgg cacgtgccgt 27300
gcgacctccg ccccctcttg cagcagcccg gcgatcagct cgccggtggc cggccacgcg 27360
gtcccgccgt gcgtgagcca gtccagagcc agttcgctcc ccggcccgga cgccggcagg 27420
aagacgtcgt cgaccagcag ccgcccgccc ggccgcaggg agccgagcag ggcaccgaga 27480
gcgctgcccg gcccccggcc gtgcaggcg ttggcgacca cgcagaagtc ggcgtagccg 27540
acgggcagtt ccgtccccac ggtcaccctg ccctcctcga ccgccgcggc gacggccgag 27600
gagagcggcc cgctcagccg gccgacggtg accagatggc cgctcgcccc ggggtccgag 27660
gcgagcaggc gttccagata gcggcccggg ccgcggtca cctccaccac ccgggctccc 27720
ggcccggggcc gcaggagccg caggccgagc gcggcccggg ccgtgcgcc ggggccgtcc 27780
atcgcgccct ggtacagggc gacgagcgga ccgaggctct cgggggggacg ctcctcgaag 27840
ggacgccgcg ccgtcccgct ccgggccacc gcgacgagct cctcgcgcgt gaccagccca 27900
cgggagaggt gctcctccag cgccacgaac gcggccagct ccccggcccg gacccggtcc 27960
ccgggctctt gcgccccggt ggtcagcacc cccagagcgg tggccgtgcg cagcagccac 28020
tccagggcat ccgcgtcgca cccagctcc ccggcgagga gagccgtgcc ggcaccctgg 28080
gcgagtgcct ccaggggcgcc caagtcgtgc agcgcgaaga gcacttcgga tgccttgtac 28140
gcccgggcgg cctccgccgc gctccgggtg aggcggtaga cggacgccgc ccgcaccttg 28200
cccgcggcgt tgaccggcag gctctcccgc aggacgaact cgtcgggcac cttgtgcggg 28260
gccagctccc ggcgggcgtg ctcgcgcagc gcctcggggg tgagccccgg ccccgccgcc 28320
gagacctccg cgacgatccc gtcctcgccc cggtgccgcc cgccgggc gcccacccgc 28380
acattcacca cgtccggatg accgcgcagc acctcctcga tctccagcgg ggagacccag 28440
cgccccgccc ggcggatcgc ccggtcctcg cgtcccagga tgcgcaggcc cccgggcacg 28500
gccacggcga gatcgcccat ggcgtacggc cggccgtcga cccgtacgct cagcagcccc 28560
ggggtgccgg cgggcggcac cacgccctcc gggccggtca gttcgcactc caccccccggc 28620
aggggagcac cggcgcacaa gggctccagc cccgccggtc cggcgagcac ggcgcccgtc 28680
tccgtggaac cgtagttgcg ggcgagaccg gtcccgaacg cctcggtgaa cgcgcggtcc 28740
agctgctcgt ccaccggcc cgcacccacc atggccagcc ggagaccggg agcggcgggc 28800
gcccgcccgg ccgctgctcc ccgcagccgc cgggtcgcca gcagccggc cacactgggc 28860
accagggcca ccacggtcgc accaccggac agctccgcgg cgatgcggcc gagggcggtc 28920
ggcggtacgg ggcgcagcgc ggcacccgtc agcagtccgc cgaacagcca gcccagcgcg 28980
tacgcgtggg acagcggcac cggcagcagc agggtgtcct ctcccgtcag cccgaccccg 29040
tcgcggtagc ggcggccctc cgcgagcagg ctctcctcgc tgcgggcgac gagcttgctc 29100
gcaccggtcg accccgaggt cgggagcagc acggcgggcg gggcgccgga gggttctccg 29160
ggcgagccgg tcaacgtcag gcggaggccg tcgccggtcc ggggacgac cagggacctg 29220
ccgcccccgg cagcccgcag cagccgcgcg gtctcggggc cggggtgtc gggttcgagc 29280
agcagggccc tggcgccgga tgccagcagg gagaggaagg cgacgaccca ccgcgggctg 29340
ttgggcgcgc gcagggccac cgcctcgccc tccaccgcct cggccttgag ctgtgccgcg 29400
gccgtacgca cctgctccag cagggagttc acatcggtcc cgggcagcgg tatccggccg 29460
gacggcagcc gttccaccgc gcccaggagg tgtccgcct cgtgaccggt cgcctgttca 29520
gtcatggccg ccctgaggt agtcggcctt cgcgtcgctg agcatctgcc ggatgcgggg 29580
cggggagtag gtgggagcgg cgcacagctc gtcgagggtg atctcgtcct cgaagtacat 29640
```

```
cg agagcgtg tcccagggcg tgaagcagcc gtggcacgcc ttgagccggg gcttggggc    29700
gagcagggca cggtagaggc cgctggtgcc caccgtgtcc agcatctcgc tccagtcgtc    29760
ctccagggcg ttgcccatgt cggagaacca gatgttgggg cagggcgtga cgacgccgtc    29820
gctgaagctg gagacgacca gccgcggcag atggcagcgg aaggtgcggc ggccctcgcg    29880
gtagaagctc gtcagccggt cgaagtaggg ccgcggcggg aggacccgcg cgaactcgtc    29940
gtagcggtcg acgagttcct ggatgtggcc gaactgcccg ggccgcacct tgaagtcctc    30000
cgagtccggg ccccgcaccg ggaagggaa gtagacggga ggccgggaga atcccgacag    30060
ccactcggcg aacgcgcaga cctccgtgac gctccggtcg ttgagcactg aatagatctc    30120
caccggcagc cccgagtcca ggatccgggc gatggcggcg acgaccttct cgtgcaggct    30180
cccggacggc acacgatggc tgttgccgtg gtggaggtgg ctgtcgaggg agacctggag    30240
cacgacgttg ccccacgagc ggaaccgctc caggtgctcc tcgcgcacca ggacaccgtt    30300
ggtctggatg accagcacgt cgtatttacg ggcctcctgc tccaggaagt ccatgatccc    30360
ccggaccagg aagatctcgc ctccggtcac cttgagcagc ggcaggccga agcggtcccg    30420
gatccggtcg gcgaccttgt ccatgcgctg ccccagcccg ctgtccttgg cgtagctgtc    30480
gcgccgcggg ggctcgaaga tcagttgaag ggagtggccc tccttgaggt tgctctgtcc    30540
ggtgaggcag taggtgcagc tgaggttgca ggagtcctcg ttgatgacca ggtcgttgcc    30600
gatcagcggc aggcgtcgcc tggtgcccgc gtcggggtg gctgtcggcg ggtgggtgct    30660
acgggacatg agtggcctct ctcgtggtgg ggctgcgcac ggcgtgggtc acggcccct    30720
ttccacgggt gccggccggg cctcgccccg gtcgtcctgg ccgacgggca cccagtggcg    30780
gtcggcgtgg ccgggccggc cgggcccgcc gtgtgcgcgg gcgcgggcga cagggcctc    30840
gcgcagggcg gccgcaccgc cgaagtgggc gctcgcctgg ctggagtagt gaccggcggc    30900
ggtcagccag cggtccaccg cctcggacgg cagccgttcc gtgcgcggcc gcaggttcgt    30960
gtggtcacgt tcgcgcagcc ggtaggggaa gtcctcgtag aagacggtac gggcggggga    31020
caggggctcc accgcgccgc ggaccaggcg gtggtcgacg tgccggcccg ccgccagggg    31080
aacgtggacg ctcgacgccc ccgcgcacag cggcagcaga gccgcccgca cctcctccag    31140
cagcgggagg tcggccgggt gccaggggcc gaagagccgg cgcggggaag cgtagagata    31200
ggcgcccgag gccgtacgca gtgccgcgtc ggtgaagccc agcggcacgt ggcgcacgcc    31260
cagttcggca catgccgccc ggtcctcgcc ccggcgcacc gcggatcgg cggcgctccg    31320
ccacgactcg ggcttcccgg ccgcgggccc ggcgaagacc gtgacgacgg tcggccgccg    31380
gccctcggcg gcccagcgcg ccagccgccc gcccagggac cacacggcgt cgtccgcgtg    31440
cggggagagc accacgggac cgtacggcgc ggtggccggt gtgccgctca tcgcgccgcg    31500
tcccgtgccg gtgcggcctc ttcggccagg acggcgcgca catacgcctc cggcgtgccg    31560
tcgggcccga gcagggcctc caaggcgcgt accgacgggt gcgggtggcc ggcggagaag    31620
tgcgtgaggt tgcggtggtg ctgctcccag cggccggggc gggcgtggct gaggtgcaca    31680
ccgagggcgt cggggcgag ggtcctgcgc agcccggcgg cgtgcaggcg aagccgaac     31740
tccaggtcct cgcaccccca ggtgagcccg aactcctcgt cgaatccgcc ggtatgctcc    31800
catgcggcct tgtcgagggc ggtgttcgcg ccgatgaagc cgagccaggg ggcgacgtcc    31860
ggcagggagc cgccggccat ggcctccacg cccgctcca gggcgttggc gacgagccgc    31920
cggtgcggtt ggcgccgctc ggaggcggcc ggggcagcgg gttcgagtcc ggcgcgggcg    31980
cggcggacct cggtcggggc ggccttctcg acagcggcga ggaaccgcgc cgcggtgggg    32040
agttcgcgca gccggccgtg ggtgaaggcg tccggttccg cggccgcggc gtgtgcggcg    32100
aggaagccgg gccccaccag gacgtcgtcg tcgaggaaga ccagccgggg cgcgagggcc    32160
gcggccgccc cggcgttccg ggcggcggcc cgccccgca gcggtccccg caccacgcgc    32220
agcgggagaa ggccgctcat ctcgcctgtc acggcgatca gttgatcacc ggcgtcgccc    32280
ccgtcgttgt cgtcgacgac gaccacttcg aaggcggcg ttcccggga gggccggca     32340
aggcatgcga gggtcgcgcg caggcgtgcc gcgggccccc ggctggggac gacgacgctc    32400
agccgggggg cggtggtgcc gttgggggcc cgcatcgggt cagagcgcgc cgacgaggcc    32460
ggagaagacc tccgccagcc ggtccagcgt ggtcacgtcg gcgagcagga cgcgatggtg    32520
cagccagagg cagtcgctgc cgatctcctc cgccacggga cagctcttgg ccagctcctc    32580
ggcgtccgcc ggcgccgggc cgcgcgcgaa accctcggtg cggtagaccg gcgggaagcc    32640
gacaacgcg ggcactcccc gctcgaccag cgcgtccacc agcgcgaggc ggcgccggc     32700
cgagatgccg ggcagccgga ccatggccat gtagtgggag tggaggtcgc cgcgctcgtc    32760
gcgcccctgc ggcaccacgc cgtcgatggc ggccagtgcc gtacgcagct gggcccagcg    32820
ctcctccctg atgcgcaact gatccttcaa gcgcttcagt tgagcacgca ggacgctcgc    32880
ggagaactcg ttcatgcggt agttggagcc ctgcgtcaga tggcggtaga cgcggtcccc    32940
gggcgggcgg ccgcagcagt gctggaggaa cgcctcgtgg aaggactcgt cgtccggcag    33000
gagcagggcg ccgccctcgc cggcggtcat cagcttgccg ttctggaagc tgaaggcggc    33060
gatcgagccg agctcccga cccggcggcc ctgccactgc gcgccgtggg cgtgcgcggc    33120
gtcctggagg accggcacgc ccgtcgcgac ggagagcttc tccagggcgt ccatgtcggc    33180
gaactggccc gccatgtgga ccggcatgat cgctttggtg cgtggcgtca ccagcgccgc    33240
cgccgcgtcg gcatcgaggc agtaggtgtc gggccgtacg tccgccggca ccggcaccgc    33300
gcccatgcgc tgcacggcca gcgacgacga gatgaaggtg aacgcgggga cgatgacctc    33360
```

FIG. 21I

```
gtcaccgggg ccgatcccca tgaccccag  ggcgagttcc agggcgtggg tgccgttcgt 33420
cgtggcgatc gcgtgcgggg cgccgtggtg gtcggcgaac tcccgctcga agagatcgac 33480
ctcctgcccc gcgtcgcgcc accacccctt ctggtccagg gcccgcagga gtccggcgcg 33540
ctcctccgcg ccgtgttgcg gccatgaggg aaaggacagg acgtcatcac cggacgtagg 33600
tgtcattgag cagcctttcg gtcctgcggg tgcggcggca cggtcgactt cggggcgctg 33660
tacggcggga gggcgggtgt cgaggccttt gccttcggtg gccgtggctt cacggcccgg 33720
ttccgttgtg ttcgccccgc gtcgggaagg gtggtgcgtg acccgacggg aaacgccgtt 33780
cctcggggc  ggcgggaaat ccggcccgcg gtgtgagggg tggccggagc gggcatgtga 33840
tccggccccc ggtcataggc cgggatcgga tgccagacac gagcctccat agggcagttg 33900
ccggagtcaa cacccttgcc gggaaggtct gccccgaccg ccggtcggcg gtggattctc 33960
gtcagcaggg tggttgagca gtgaaactgc cttattccca agggaattga tccagttcag 34020
gggctgctcg gcgggcctgt cggcaacgtt atccggcgtc gaagtggctc aaaccgcacg 34080
gctggaggga gcgggaagcg tcgcgtatgg tgggcgcgac accgtcctgg tatgtgctgt 34140
gtgcatggtt cattgagccg aatcccactc cggccctcgg atccgggcgc catacgatca 34200
ccgttgtccg gtctgtggac gcaccggtga ggggctgtta cagtcctcgg atcatcgatg 34260
agcggcggca gtttctgcct gcaatcgtga tgagttctca gagctggagg caatttcgtg 34320
ccaccctctc cccgcgccct cgtcatcgga atcgacgag  gcacattcga tacggtcgac 34380
ccgctgatcg agtgcggtct gctgccccat atggcgaagt tgctgcgcga gagcgccagt 34440
gccgccacgg actgcacctg gcccgcccac acggcgccgg ggtgagcac  gttcgtctcc 34500
gccagcgatc ccggcggtca cgggatctat cagttctacg acccaggga  cccggcctac 34560
ggggcccgcg tcacgcgctc cggcgacctg gccggtcct  gcgcctggga ctggctcgcc 34620
gcgcaggaat attcgctggg cctcatcaac atcccgatgt cgcacccgcc ggccgacctc 34680
cccggctatc aggtcacctg gccgctggag cggacactca agcactgccg cccggattcc 34740
ctgctgcgcg aactcgccgc ggccaaggcc catttccagt cggacctcgc gaccatgttc 34800
cggggcgaca tggcctatct ggaggaggcc gagcgcaatg tggcggcgcg gtccgctcc  34860
gtacggcatc tgatgagcac ccggcccacc gatgtcgtga tggtcgtgct caccgaggcc 34920
gaccgggtcg gccaccacta ctggcactac ggcgaccccg gtcacccggg ccaccggccc 34980
gccccggagg gcagcggctg ggacgtcgcc atgccccgga tctaccaggc catcgaccac 35040
gcggtgggcg agctcctgga gctcgtcgac gaggacacct ccgtcgtgct cgtctccgac 35100
cacggcctgg gcaccgggcg ccacggcctg tcggtgcaca ccctcctgga ggaggccggg 35160
ctgctggcca ccgcaccggg ggaggagccg caggacgcgg cggcgagctg gttcgcgggc 35220
aacggccggc acgtcgactt ccgccgcacc agcgtctaca tgcccgtccc cggcagctac 35280
ggcctcaaca tcaacgtacg cggacgccag cagcgcggca ccgtcgcacc ccgcgaccgc 35340
gaacgcgtca tggacgaggt cacgggcctg ctctccgggc tgaccggccc cgagggacag 35400
caggtcttcc gggccgtccg cccgcgcgaa gaggcgtacc cagggccgca caccggccgg 35460
gcacccgacc tcctcctcgt cccgcgggac gagaccgtcc tgcccgtccc cgacctcggc 35520
ggtgacgtgt ggcggccgag cgcgcagacc ggcctgcacc gctaccgcgg cctgtgggcg 35580
caccgctcgc ccgcgtccg  ccccggccgc ctgcccggca ccgtcgcgct caccgacacc 35640
ctgcccaccc tgctcaccga cctcggggcc gcatggccca gcgacatcca cggccgcccc 35700
gtgaccgccg tcctcgacga cggcgtacgc gtcccgccct ccgaccccg  ggtcgaggcc 35760
accggcaccc cggccaccac gatcccggcc gccgcttcgg ccgctgatgc cgccgaggac 35820
gcgtacacca gcgaccgctt gcgcgaaatg ggctacctgt aagcaccgcc gggccgtacc 35880
ggcgcttgtc cccaccggag tcccgccgct cgcggcggcg tggaggagag aggtatttct 35940
gccatggaga ccctgacgac cgacaagatc aaggaccggc tgcgcaaggt gctcgtcgat 36000
tccctcgaac tgtccccgga ccctcggcc  gtacccgacg agggactcgt ggagaagctg 36060
ggcctggact cgatcaacac catcgaattc ctcatctgga tcgagagcga attcggcata 36120
gagatcgccg acgaggacct gtcgatcaag ctcatcgaca gtctcgacct cctcgccggc 36180
tatgtgtccg agcgcgtgaa cggcgtcacc gcaccgccg  aatgacggcc gtgcgcgcgc 36240
tcgcctcgg  gcccactccc cgcagcggaa ggacgtgagc acgatggacc ggcacgccct 36300
ggtgatcggg ctcgacggca tgccgaggac cctgctgacc gcctggccg  gcgacgggac 36360
catgccgcac accgcggcgc tgctcgccga gggccactgc gcggaactgc tggcacccgt 36420
accggagatc agctccacct cctgggccac cttcctcacc ggcaccaacc cgggccggca 36480
cggcatctac ggcttcaccg acctcgcccc cggcgacggc taccgcatca ccttccccgg 36540
tgtgcggcag ctgcgcgaac ccccgctgtg ggaactcgcc gcccgcgccg gccgcaggac 36600
cgtgtgcctg aacgtccgg  gcacctaccc cgccccgcc  atcgacggcg tgctggtctc 36660
cggcttcgtc gcgcccgaac tggagcgcgc cgtcagcccg ccacggctgc tgccgctgct 36720
gcgcggcctc gactacgaac tcgacgtcga ggtcggcgac gtcgccgccg acccggccgc 36780
cttcctcggg cgggccgtcc gggccctgcg cgcccgcacc cgggcgatgg aacacctgct 36840
gcgccaggag acctgggacc tcgcggtcgc cgtgctcacc gagaccgacc gcgtccacca 36900
cttcctgtgg cgcgcggtcg ccgaccccgc cgaccccctc cacggggacg tcctcgcctt 36960
ctaccgcctc gtggacgact gcgtcgccac cctggtgagc accctcccac cgggcggcga 37020
actcttcctg atgagcgacc acggcttcgg acccgccgcc tgtcaggtct atctgaacgc 37080
```

```
gtggctcagg gagtccggct ggctggccgg gctcgacgtc tgtccggacc tcaccgcggt   37140
cgacgctcgc agcaccgcct tcgcgctcga ccccgcccgc atccacctca accgcaagag   37200
ccgcttcccc ggcggcggcc tgaccgacgc ggaggcggac gaggccgccc acgagatcgc   37260
gcgcgagctg tccgccctgc gctgcgacgg cacccgcctg ggccccgacg tcgacggacc   37320
cctgctcgtc cgcgacctct accgcgctca ggagatctac cacggcccgc tgttgggcaa   37380
cgccccgac ctggtggccg taccggcccc cggggtgcag ctgcgcggcg gctggggcgg    37440
cacgcacacc gtacgcaacg acatcctcac cggcacccac acccgcgacg acgcggtctt   37500
ctaccggcgc ggcgcgcccg cgccgcccc ggggcggac gacggccccc tcgacatgac     37560
ggacgtcgcc ccgaccgtcc tcgcctccct gggcatccac cccggcgggc tcgacggcgc   37620
ggccgtactc ggcaccacgg gacccgcgtc cggtcacggc cgcacggacc cccctctcga   37680
catcagggag ctctgatgaa gcacgacctc ggtctggcac catcggcacc caaaccggga   37740
acactcgacc tgagcctgga cccacgcatc acggaccccg cttccttccg ggtcagtttc   37800
ctgatcctcc tcgacggcga cctcgtgatg tccccgaac acctcggcgt cgcctacatg   37860
gccggtgtgc tgcgccatac gggcttcacc gcggagatcc gggaggtgga gcacggcgac   37920
gaccaggcgg ccgccaccgt cgaggcgctc aaggagtacc ggcccgacct cgtctgcttc   37980
accctgatga gcctgaacct gggcagctgt ctgaccctgt gccggatgct gcgggaggag   38040
ctgccgggga cgacgatcgc ctgcggcggc ccagccggga ccttcgcggg cctggacgtc   38100
ctgcggaaca accccctggac cgacgtcgtc gccgtggggg agggcgagcc caccatcctc   38160
gacctcgtcc aacggctcta cctcaaggag ccgttgtccg cctgcaaggg gatctgctac   38220
cgcgacgagg acggcacacc gcgccagaac cccgccgcc cctgatcca aacctggag     38280
gacctcccct tccccgcccg ggaccagctg cgccagcacg gcgacaagct ggagtacgtc   38340
cgggtcagca ccagccgggg ctgcgtcgcc aactgcgcct tctgctccgc cccgcacctg   38400
aagaaccgcg tccaggcggg caaggcgtgg cgcggccgcg ggccggaaca gatcgtggac   38460
gaggtcgccg agatcgtcga acgccaccag ttccggacct tcgacttcgt cgactccacc   38520
ttcgaggacc ccgacggcgg ccgggtcggc aagaaacggg tcgccgccat cgcgaacggc   38580
atcctggagc gcggcctcga catctactac aacgtctgca tgcgggccga gaactggcac   38640
gacacccccg aggaccacgc cctgctcgac ctgctggtcg cctcgggcct ggagaaggtc   38700
aacgtcggca tcgaggccgg caccgccgga gaactgctcc tctgggagaa gcgcgccacc   38760
gtcgaggaca acgtcaccat catcaggatg ctgcggaac acggcactcta tctcgccatg   38820
ggattcattc ccttccaccc ctacgcgacc ctggagacca tcgtcaccaa cgcggccttc   38880
ctgcgcgaca attccggcca caacctccgg cgcatgaccg aacgcctgga gatctacccc   38940
ggaacggcca tcgtcagccg catgcgggcc gacggactcc tcggcgagag ctatctcgaa   39000
gggctcgacc cctacggcta cgcattcaag gatccccgcg tcggacggct cgccaagcat   39060
ttcgcccagc tctacaacaa cgacgactac caccggcacg gcgtcatcac cgagcagtcc   39120
tccgtcttcg ccttcgagac ctacaacgtc gtactccaga ccttcatctc ccggctgcac   39180
cgccggttca ccaccctgcc ggggtggac gaggtgatgg aggcattcaa ggcccgggtg    39240
cacgagatcc gccaggagat gggccggcac aactacggct tcttcatgtc caatgtcgag   39300
gcggtcatga acgacaccct cgacccggag aagcagcgcc ggcaggtggt ggacgtcgag   39360
cacttcttcc gcgaccgcct cgatgtgttg cgcagcgagc aattgcgcgt cggcaaggcc   39420
ctcacccggc tcggcgcccg ggtgacggag gtcagctcga ccattcccaa ggagcgcccc   39480
ggcggactgc cgcgccagta cacgggagag ggcagcggtg ccacgtggtg agacgggaac   39540
cgccgcggcg cgggtggcgg tctgcacgct gagcagcagg gaactggtcg gcccgctggc   39600
ccggttgccc ggtgtggcgg ccgcgggcac gctgatgacc gccaacctgg gcatcgagca   39660
ggtgatcaag gccctgccgg gcgaccggac ggtccgcggc ctgctcgtgt gcggccgcga   39720
ctcaccccgc ttccgcgccg gccagagcct gatcgccctc ttccgccacg gcctgcgccc   39780
cgaggacggg cacatccggg gagccaccgg ctatctcccc gtcctgaggt cggtgacggc   39840
gcgggagacc gaggaggtac gcgcccgcgt cgagctggtg gacgcccgtg gcgagcgcga   39900
cgtcgagacg ctgcgcgccg aggtcgcggc actcctcgcc cgcgtacggc gcaccccggc   39960
cctccccctcc cgcgagcacg acggcggcca acccagcttc gtggagccgg acttcggacg   40020
gctgcatcct gtcggccgcc gccgctccct ggacgcgggc atcggcgggt tcgtgctcat   40080
cagcgtcgac cgtgagcacc ggcggatcct gctgcgccac tacacctccg atgtgcggcc   40140
ccggcacgag atgtggggca cccgcgggga ggcgatgctg ctcgggctgc tggaggcgg   40200
cgtcatcgag gacccccgccc acgccggata cctcggcgcc gaactggcca aggccgagac   40260
ggcgctgcgg ctcggcctgc actacgaaca ggacctgccc ctgcgcccgc cggcaggcc    40320
gcccggccct gtgcggcgcc ggaccgcgaa ggagcgaacg accatggcgc aagcacccgc   40380
gctggaggac ttcctgcgtc tcgtgacgag gacgctgggg gccgaggacg ccgtcctgga   40440
cctgcacacg ccgctcggcg agcaactggc ggtggactcc gcccggctca tcgaactcac   40500
cgtcgtcctg gaggaggagc tcggcgcgga cctccccgac gacgccgacc tgccagggc    40560
caccccgcg gaactccaca aagcactcgt gggctgagga ggagaccgac atgcgcagcg    40620
tgctgttgct caacggaccc aacctgggga cgctcggcaa gcggcaaccg gagatctacg   40680
gaaccgacac cctggccgag atcgaggccg ccgtggccga ggaggtggga gcgcgcggct   40740
gggaggtggt ctccgaacag cgcaacggcg aggggaact ggtcgatgtg ctccagcgcc    40800
```

FIG. 21K

```
a cgacgacgt ggtgggcgcc gtggtcaacc ccggcgccct gatgatcgcc ggctggtcac   40860
tgcgcgacgc gctcgccgac ttcgccccgc cctgggtgga ggtgcacctg agcaacgtgt   40920
ggggacgcga ggcattccgg cacacctccg tcacggcccc gctggcctcc ggcgtcgtga   40980
tggggatggg ggcgctgggc taccggctgg cagcgcgcgc cctcaccggg ctggtccccg   41040
aggactgacg gtgacccggc ccggcccgta cgcacctcca gatgggaccg gcccgcccgg   41100
cagggacgcc acctcggcgc ccggcccgta cgcacgctca ggcgggccac acccgcagct   41160
cctccttgat cacctgagcg ccggcctggt cgcacgcccc gggcagcggg caggccgccg   41220
ggaggatccg cacggtgaac ggcccctcgg tcaggccgcg ccaggcgggg accaccggcgc   41280
gaccgcggtc cacctccgcg gacaccaagg ccgtgaccgg acagggaaat tgaccggaga   41340
cctccccgcc caccccttcg ccgggcccgc ggctgccgag ccacagcagc acatgcaccg   41400
gcgggcgcgc ggcccgctcg gcggcccgca gcgccgcgcc cagcccggca ccggcacaga   41460
ccagcgccca cggcccgccg tccccggccg cctccgcgat cgcctcgacg ccgtgctcca   41520
ccaccagttc ggggggcgagc gcctgccgcc agccctccgc gtccggcccg tccgtcacgg   41580
cgaccagccg gaccaccggc accaccacgc ctccggcgtt cccctcagcc gtacgcgaca   41640
tccccagacc ctctcttccg taccgtccca cccgccctcg ctctcccgcc cggcgccgct   41700
acggcaggcc gtcggtcatc ccgagggaga agtagttctc gtaccccagc agccggcgca   41760
gttcgggcgt cgcgcgggtg gcgacgtcct cccgcagacc cgagaagaag ttctgctgct   41820
gccggacgta ccgcgcggcag tagtagttga ggatgccgtg ccgcggccgg tcggtggtgt   41880
tggcgcccgt ctggtgccac aggcgcccgt cgaagaccat cacgctcccg gccggcgcgc   41940
acacggcgac cgtctcggtg ttccccctcgc cccggtcgta gtccggctgc cggcccagca   42000
gatgggagcc gggcaccagg cgggtcgcgc cgttgcctc ggtgaagtcg tccagcatcc   42060
acatgctgtt ggcaccagc ggatacgggg gccacggcgg gcgggcgaag gtctggtccg   42120
cgtgcagatg catccgggaa ccgccggggc ccgcgatatt ggcgtgcgtg ctggagagca   42180
ggaagccgaa gcccaggatc tcctccatca ggagcatgac ggtgggatcc tgcacgttct   42240
gctcgaattc ctcgccctg ttcagcaggc tgaagacgcg ttggttgccg ccgtcgtaga   42300
gaaaggccga gccgttctca cgctcctgct cggcgaccto cagcagccgc cctctgagct   42360
tttcgaagac cgcggccggc aaggggcact cgatcaggca gtatccggct tcgaccagat   42420
cccgggaggc tttctcgacg tcattcgtca aagtcgcatc catatggcga ggctagcagc   42480
cgaaatctcg gccgcaccat agcgcgaaaa cgccggtcca tgatttttc acgtgcggga   42540
aggacggatt ttccatggca cactcaccgc ggcggccgga cggccccctc cgcatcgggg   42600
tctggctggc ccccagcac acctcggtgg ccgaactgcg cgccgcctgg cgcgcggccg   42660
actccctggg cgtggactcg ctgtggctgt ggaccactt cttcccgctc accggggacc   42720
ccgacggcag ccacttcgag gcctggaccc tgctggcggc catggccgcc gacacccgcg   42780
ccgcccgcct gggcaccctg gtgtccaact acgcctaccg caaccccgac ctcctggccg   42840
acatggcccg cacggtcgac cacatcggcg acggccgcct gatcctcggc atgggcgccg   42900
gctgggtcga acgcgacctg aaggagtacg gctaccccac gcccggcgcg ggggagcggg   42960
tggacgggct catcgaggcg gtggagcgcg tcgaccgcag actcggccgg ctgcgccccg   43020
ggccgctcgg cgacctcccc ctgctcatcg gcggggacgg gcagcggcgc ctgctgcgct   43080
tcgccgccga acgggccgcc atctggaaca ccatgccctg gcgcttcgcc gagggcaatc   43140
gcgtgctgga cgagtggtgc gcgcgggtcg gccgcgaccc ggcggagatc gagcgcagcg   43200
ccttcgtcac ccgcgaccag accgacgagg agctgcgctg cctggtggcg acgggcgtcc   43260
agcacctgat cttccaggtc gggcacccct tccgcttcga cggcgtggag cgggccctgc   43320
gcttcgcggg cggctggagc aaggggtaag gccagggccc ggacgcgccc cgcgtcgcca   43380
ctagagcaac gcgtccgcca gccggtccac ttgggacagc gccgccgccg tgggtggag   43440
gacgacctcg tccaccccgc cgtcggcgag cgccgagacc gccgcgcgga gctgccccgc   43500
ggtgcgcggg gtcttcgcca cgaactcctc cgcctcctcg cccagcaccg cgaagtagtc   43560
ccggacgaag gccgccgact cctgggccac gtcctcgccc agggtgtagc gcgccagcgc   43620
caccacatgc ggcgccccgg cgcgtcccgc ctcgctccag gcgcggcgca cccgttccgc   43680
gaccggcacg atccgctccg gctccaggcc gggcgccgtc cagccgtcgg cccagcgcgc   43740
cacgcggcgc acggccgccg cgctgacccc gccgacgagg accggcacac cggggccctc   43800
cgcgcccggc cgggcgcccc ggccgagcag ctccagctgc tcctcgaacg ccgcgccgcg   43860
gtcgtcgaag gcgcggccgg cggcctcgaa gtcgtcctcg cgcacgccgg gcccgacccc   43920
cagggtgaac cgcccgcccg acagcgagtc cagactcgcg accgccttcg ccagcacagg   43980
cgcggtgcgc agcgggccga tcaggacatt ggtgagcagc ccgatccggg aggtcgcccc   44040
ggccgccgcc ccagcgcca gcgggatc gtggcccgga taccaggc gctcggtggc   44100
cgcgagcgag gcgaatcccc gctcctcggc ccgccgcgcc caatcggtta tcaggcgccc   44160
gtccgcgccg ggcacggtgt cggcagagc aatgctgatc ttcattggtc tccccggggg   44220
ttcgcaggat ttccggtcga atgtgacagg ggattccggc acggccggcg tgattgcggc   44280
aggagttcac cagcggcccg gcgcggagaa atgcggcggc atttccacgg cccctgtcg   44340
gaccgccgga ccgccgtgta cgttttcgg aaagcaacgt cgtacggtgc gcacagcgag   44400
aggaatccgc gatgcccgct gccggaaaag tcgccgtgat aggactcgac tccgcgactc   44460
cgcagtacat gttcgaccgg ttcgccgagg acatgccggt gttcaccgcc ctcaggcgca   44520
```

```
agt ccctgtg   gggtccgatg   cgcagcatcg   acccgcccat   caccatgccc   gcctggtcct   44580
gcatgatgtc   cggccgctcg   cccggcgaac   tcggcgtcta   cggattccgc   gaccgcggcg   44640
cctacgacta   cgggccgttg   aagttcgcca   cctcccacag   catccaagcc   ccccggatct   44700
gggacgagat   gacggccgcc   gggcgctcca   gcgtggtcct   gggcgtcccc   ggcacctatc   44760
ctcccgcccc   catccgcggg   gccatggtct   cctgcttcct   ggctccctcc   acacagtcgc   44820
gctacacctc   cccgcccggc   ctcgccgacg   agctggagaa   gctcaccggc   ggctacgccc   44880
tggacgtgga   ggacttccgc   tccaccgacc   tggaacgcgt   atcccagcgc   gtcttcgaca   44940
tgagcgagca   gcgcttcgag   gtcgcgcgcc   acctggcgac   cacccaggag   tgggacttcc   45000
tctccttcgt   ggacatgggc   cccgaccgcc   tccaccacgg   cttctggaaa   tactgcgacc   45060
ccgaccaccc   gcgccacgag   ccgggcaacg   cctacgccgg   tctcttccgc   gactactacc   45120
gcgccctcga   ccggcacctc   ggccgcttcc   tggagagcct   gcccgagaac   acgaccgtcc   45180
tggtcgtctc   cgaccacgcc   gccagccga   tgtggggcgg   gctcttcgtc   aacgagtggc   45240
tgcgcaagga   gggttacctc   gtcctgaccg   aggagcccgc   cggacccacc   ccgtcgccc   45300
aggccgccgt   cgactggaag   cggaccaccg   cctgggccga   aggcggctac   tacggacgga   45360
tcttcctcaa   cgtcgagggc   cgggagccgc   agggcaccat   cccggccgcg   gagtacgaga   45420
gcacccgcga   cctcatcgcc   tccgccctgg   aagcgctgcc   cgacgaccag   gggcagccga   45480
tgggcacccg   cgccctgcgc   cccggcgagc   tctacggaga   ggtcaacggc   atcgcccccg   45540
acctcctggt   ctacgtcggc   aacctgcgct   ggcgggccct   ggccacccct   ggcatgggca   45600
agggcctcta   cacgacggag   aacgacaccg   gccctgacca   cgccaaccac   ggggacaccg   45660
gcatcttcgc   cctcagcgcc   cccggcatca   ccccggcg   cgcggacggc   ctgtcgctgt   45720
acgacgtggc   ccccaccctg   cgggaactgc   tgggtctcgc   gccgcagggc   tcccgcggct   45780
ccctcctcgg   ctgacatcac   ccgcccagca   gcgcgtaggg   agtgggcgg   gccggcaccc   45840
cgcccgctcc   cgcaccgcca   ccgtgcacca   cgtgcttgtg   gcggtaggcg   tccagctcgt   45900
tggtgagccg   gtcccagacg   gcggagcggg   gcccggctgt   gccgggcagc   tccaggtcga   45960
ccagccggta   gtcgttgatc   catacccggt   ccgcgcgcag   ccgctcggcc   accgcgcggg   46020
cccgcgcggg   atcggcggac   cacacccggg   cgctgagccg   gtagcgggag   ccgttggcga   46080
tgcgcaccgc   gtcgtcgtcg   acccggccc   ggacgaccgc   gagcaccggg   ccgaagatct   46140
cctcctgcgc   gacggcgtcg   tccgcgccga   ccgacgccag   caccgtgggc   aggaaatacg   46200
ccccggcgtc   cagcccgggc   ggcagcgtcgt   cgccgcggg   cgccgcgccg   ccgcacacga   46260
gctccgcgcc   ctgggagagc   ccgagttcgg   tgaagcgcct   ggccgtacgc   gcctggttgc   46320
gcgagaccag   cggccccagg   tcggtggccg   ggtccagcgg   atcaccgacg   cgcagccggc   46380
ccacccgttc   gctcagcagc   cgcaggaagt   cgtcgtggac   gtcggcgtgc   accaccgcgc   46440
gggtaccggc   catgcacacc   tgcccgttgt   gcaggaacgc   tccccacgtg   acgccggtga   46500
ccgcccggtc   cagatcggcg   tccgcgagca   cgatgttggg   ggacttgccc   ccaggtcca   46560
gccgggcgct   cgtccccgcc   gcggcggcac   cctcccgtac   ggcggccccg   gtctcgtccg   46620
agccggtgaa   cgccaccagg   tcgaccgcgg   gcgagcgcac   cagctgctcc   ccggcgaccc   46680
cgcccggccc   cgtgaccacg   ttgaccacgc   ccggcggcag   gccgcactcg   tggagcagct   46740
ccaccagtcg   cagcgtggag   agcgaggcga   acgaagccgg   tttgatcaca   caggtgttgc   46800
ccgcggcgat   ggcgggcgcg   atgcgccagg   ccgccagcag   cagcggcaga   ttccacggca   46860
cgatcgcggc   gacgaccccc   accggccgcc   acacgacgta   ggaacccgaa   ccgggcgcct   46920
ccggctgccg   ttcgggcacg   tgctccgccc   accacgcgct   ccactcgaag   gctgccgcgg   46980
cccccggcac   atcggccccg   agagccttgc   gcagcgtcga   gccgttgtcg   cgggcctcca   47040
actcggccag   cggctccgct   tcttcacgca   agcgctgtgc   ggccttgcgc   agcaggcccg   47100
cccgctcgcc   cggcgccatc   cgcggccacg   ggccctcgtc   gaaggcccgc   cgggcggcgg   47160
acaccgcccg   gcggacgtcc   tccgcgccgc   cgctgggaag   gtcggccagg   tggccgcgcg   47220
tggccggctc   gaaggtgcgc   aggacggcgc   cgtcgtgggc   ctgcacggcg   tgcccgtcga   47280
tgtacatcgg   gaaccgctcg   accgctctgt   ccaccggtc   catcgccttc   accttctcct   47340
tctgctgacc   cgtggggatg   cgcccggccg   ggcccgcccg   cggccgcggc   cgtaccggaa   47400
cacccgcccc   ggagcggccg   cgcccgcggt   caggccggca   ggggcgggat   gttggggttg   47460
aaccggaaga   cgttgcccgg   gtcgtactgc   gacttcaggg   cctggagccg   cgcgtagtcc   47520
tccggcgtgt   aggcgctgcg   ggtcgtctcc   ctcgatgtgt   tgtgacccgc   gaggaagttc   47580
aggcacaccc   cgggcgtcgt   ccacggccgc   atgctgtcga   cgaactcctg   ctgcgccgcg   47640
tccacggccg   ccaggtgtc   cgggtcgacc   agcgagccca   cgtaggcgtt   gaacaccgcc   47700
tccgggaagt   ggcccaccgc   gctcgggtgc   cggggcggcc   gggcgagggc   gccgccagg   47760
tgccgcagct   ccaccccgaa   cagcgcgtcc   gtgcccggcc   ccgcgagcct   gaggatctcg   47820
tcgacggcga   tctcgtccag   ctgccgaac   atgaccgttt   tgctgtgact   cgacaccggg   47880
gccggcggat   cgttgtggat   gatcccggcc   cgcgtgtacg   ggagcgtgtc   caccgtatcc   47940
atgacgaccg   tgccggcggc   ccggagctcg   gcgaaccggc   gctcaccctc   ctcggggtct   48000
cccagccagg   ccagccggat   gtgggtgacg   aaccggccgc   gcagcggtcc   gggcacccc   48060
tcggcatcgg   gatacgcggc   caggaacacc   gacgacgcca   tgtcctcggg   catccggggc   48120
gcccactgga   gataggtgtt   cagcacggcg   cgcgtggagc   cggcgtcgaa   gaacagccct   48180
ccgccgtaca   cctgggtgac   ggggaacagc   ccgacctcga   cggaggtgac   gatgccgagg   48240
```

```
ttc ccctgc  tgccgcgcac  gccccagaag  agatcggggt  gttcctcggc  ggagacctgg   48300
ag aaaccgcc  cgtcggccgt  caccaggtcg  agcgagacga  catggtcgcc  ggcgaacccg   48360
tacttccgcg  acagaagccc  gagcccgccg  ccgaggaggt  aggagaccgc  gccgacgaac   48420
ggcgccgagc  cgctcagcgg  tgcaagaccg  tgccgccgcc  cctcgtggat  cacctgctcc   48480
cagcgcacgc  ccgcctcgat  ccgggcggtc  cgggcccgcg  ggtcgaccct  gacgccggtc   48540
atccgccggg  tgctgatgag  gacgtcggtg  gccgccgagg  acttcccgtg  accggtggcc   48600
tggacggcga  tcccaaggcc  ccgggccctg  gcgaagcgca  cggcggcgat  gacatccgcg   48660
gcaccggtgg  cgacgacgac  gagggcgggg  cggtgttcca  cggacagttc  gaagccggag   48720
cgctcctcgt  cgtaccccctc  gtccccgggc  aggaggacgg  atccggcgac  ctgcgccgcg   48780
agctcttcgg  cggccgcggc  gccgagggcc  gcggacgtgt  ccgtcacgga  gtggctggct   48840
ggtttcaccg  aggaaccttt  ctggctggag  cttcgagaag  cgcgccgcgc  gtgcgcgggc   48900
agggccgcgg  ggctcgccgg  cccttggaac  ggagcggccc  ccgtcagttg  cgcgggccgg   48960
ggaccaccgg  cagtgaccgg  acgcccaggg  gcaggagttc  ggagctgtgc  tcgacctctt   49020
cgggaggcac  ggccagggcg  atgcggggga  aggccgccag  caggcggccg  atgccgacgg   49080
tcagttcggt  cacggccagc  ccggtcgcgg  ggcaggcgtg  ctgccggcg   ccgaacgcga   49140
tgccgcggtc  ggccacccgc  tcgatgtcga  gcacgtgggg  atcggcgaag  acctcggggt   49200
cgcgggaggc  cgccgagacc  agtggcagca  cggcgtcccc  ggcggcgacg  cgcctgccgg   49260
agagcaccac  gtcctcggtg  gcgacccgca  gcaggccgtc  gttgctggag  gggtagtagc   49320
gcagcaactc  ctgtacggca  gagggcagta  cggaggggtc  ctcgcgcagc  cgggccgcga   49380
ggccggggga  ggagagcacg  ccgaagaggt  gccgggccag  caggtcgcgg  atggtgatga   49440
agcccgagat  gatcaggccg  tggagcagca  ggcgccggtc  gtcgtcggtg  agctcctccg   49500
cgtccagcag  cgtgtcggtg  acgctgtcgc  ccggctcggc  cctgcgggcc  gcgagcagtt   49560
cgtccagcac  ctggccgagc  ctgccgcggg  cctccttcag  cgcctgctcg  gtggcaccgc   49620
gcggaagcag  cagcagctcg  acgtcggagg  tgacgtcctg  ccaccggtcc  ccgggcagcc   49680
cgaggaactc  ggctgtgacg  cggccggcga  agggcgcggt  gtacgccgcg  acgaggtcca   49740
ccgtgccgct  gccggcgggc  agcggtcca   gggccgcctc  ggcggccgcc  tcgatgcggg   49800
gtgcgaaccg  cgccgtgcgc  gaggaccga   acgcggccac  caccggaccg  cgcagccggc   49860
cgtgctccgg  cgggtcgagg  tccacgatgc  ccgaccctg   ggaccggcag  aagccgagc   49920
ccggcagcat  ggcggcgcga  tggcggctga  agcggccgtc  ggtgagcacc  gtgccgcacgt  49980
cctcgtgccg  ggtcaccagc  cagatgcgcg  agccgtccgc  caggcgcacc  tcggcgaccg   50040
ggtcatcggt  gagcagccgc  gcgtactcgg  gcggcaccgt  gccgccgggg  ccgggcggga   50100
agggaaaggc  gggcggggcg  gctgaggtca  tgcgccccgg  ctcctctcac  cggccggcgc   50160
gccggcgcgg  gcgtggcccg  gccaggtgaa  gtccttcgcc  aggacgcggt  tgtccagctg   50220
gtgttccacg  acgatgttgc  cgcagccgta  gtcgtcggcg  atgacctcga  cgtcctcggc   50280
ggacaccagg  tgtccggggt  cggccagcag  ggtcgccacg  cccttggcgg  gggccaggac   50340
ctccagggcg  aagccgcggg  ccacgtgctg  cggtgggtg   tgcgccgccg  cgatcaggaa   50400
ggtgtcgtcg  gggtcgcaga  tcagatgcca  cagcgcgcgg  gcctggagga  agcggcgcgg   50460
gcggtcggtg  aagcgccggg  aggagaccag  gaccggcccg  tccgcgcccc  tgcgggtgcc   50520
gagggcgacc  aggccccggt  ccatataggg  gacctgctcg  gtgcggtagc  ccatcagggg   50580
ggccgggtcg  aagggcgcgg  tgtcgtccag  acccgcccac  gcgcgcaccc  ggtgcgccac   50640
ctcgtagccg  aggtccagg   ggttgtcgag  tcgccccgga  gcaagaact   tctcgctcaa   50700
gtcggcgcag  tccttgcgca  gttccaccaa  ggcgggaggg  agcggggtat  ccgcgggcgc   50760
ggtgcccatc  agggtgcgga  cgcgcgcgat  ccactggag   tggtcggcta  tccgctcagg   50820
ccgcacccgg  ttgaagaagt  cactggcgag  cggttccgcc  aactgctcgg  cggccttgag   50880
gatgtccgcc  tcgtacggct  cggcctcggc  gtaggggtcc  aggcccagcc  gtgccgcgat   50940
gcggcagaag  gcggcctcgt  cctcgtcggt  ggcgcggacg  gcggcccact  cctcctggag   51000
cggggtgccg  gtgatgccct  ggtccgtgag  gcgctcggtc  accgcgtcga  cgaacgaggc   51060
cagtgtggcg  gtgaacgcgg  cgctctccac  acaggagttg  ccccggctcg  cgaagcggtt   51120
cccgggtcgt  acgtcgggc   ccatgtccgg  catccatacg  atccgggtct  cccggccctc   51180
gggcacgaag  agcatgtccg  ccagcggaa   ccgtcgcag   gcggcgcgca  ggatgtgacg   51240
gcgcgaacgc  atccaccacg  aaccgcggtt  gtcgcccaca  ccgtggcggt  aggcgaagcg   51300
cagctgggat  atctgggtgc  cgggccgcgc  gtcggccacc  agcgaccacc  agttgaaggc   51360
gatccactcg  gccaggggt   agagcgagcc  ggtcgtgtgc  tcccggaagg  tccctgccc   51420
gggctcctgg  acgagtgtga  cggtctcggc  gcccacggcg  atgcgcagcc  gggcccaggt   51480
cgcttgcagc  tcgcctccgc  cgccggccgg  ggcgtcgagc  caattccact  gcaattggaa   51540
ctcaggaagc  atggtccgcc  agcccttccg  gccattcgct  cgggtggagt  tcgtatccgg   51600
tgtattcgcc  cggcgcacgg  cccgtcagcc  ggaattccac  gacggagtca  ccggaccggt   51660
gccagacata  gcgcgggaag  ccgtcctgcc  agggaccgcc  gaggaatccg  gtgcggatcc   51720
ctgaacggag  ggtgcccagc  ggggcggcc   acagggaacc  gggcacggcg  agcagatcgg   51780
ccggggccgg  gccgtattcc  cggcgggcga  atgtcacccg  cccgcagagt  tcttcccgtt   51840
cgctgcggtc  gggcagtggc  gcgatcgcgc  gacgtggctc  gcggcggcgc  ccgggcgctc   51900
gtaggaccat  gatgtccgcc  tttcggggaa  cgtgccggtg  agctgggccg  gcggggcccg   51960
```

FIG. 21N

```
gacgcggcgt gcgtccgggc cccgcccagg gtgttacggg aggggcgcga agaggtccac   52020
cacgttgccg tcggggtcct tgacgatggc gtagcgctga ccccacacgg cgttccacgg   52080
cttgaggtgg ccctcgtagc cggcgtcgac gagctcggcg tacttcttgt ccacgctcgc   52140
ggtgtcgggg aactcgaacg cgatggcgaa gcggtggccg ccggtggggg cctgccactc   52200
ggggtcgtag ctgcgcaccg tctccacggt gtcccaggcg agccggatgc cgccgtcgag   52260
cacggcctcc gtgtgcggcg cggagtcggc ctcggcgggg atctcgacgc ccagcttccg   52320
gtagaactcc agcgacttgg ccatgtcctc gaccaccacg gcgaagaggg aaatccttgc   52380
tgacatgcgc gttcctttct tgcacttta aattggtctc cggtgccggg ccgtctgaat   52440
tctccggggc cggccggacc acgaagtccg aatgtgctgg acgcgccgta cgctagtgac   52500
tgcgcgctga ctttggccaa tcggggtatc ccccgccgga gtcaacgccg ctgacaggac   52560
aacgatttca ggacagcggc acgccgtccc agtcgttcgg cacgtcacgc ccgagcagag   52620
cgcatacggt cgcgggaata tcgacggggg cggcggtgcg ggtctgccgc gccccaccgg   52680
tgaagccggg gccgacggcc gaccagtagg actcccggcg gtgccagccg ctctgccagt   52740
cgcggtggac gtgcgaggcc cagtgcgggt cgcccagcgg aagatagcgc cagtccgccg   52800
gctccaggat gaggtcgggg gcgtgctggg tggcctcgcc gggatagacc tcctcccggc   52860
ggcgcaccgc gtcgaagaac agcctgccgg tacggggggtt cgccgctcc agcagcgcgg   52920
ccgcgacgtc ggtgcggacc ttctcgtagt cgcgctccgg gaccaggccg tgcttgtagc   52980
ggtcgcgcag gttgatgttc accccgtgcg tgccctgcac cgcctcgaag gccgcgctgc   53040
cggcccactc gacgcggccg tcctcggcgg tggccaggaa acccgcctgc tccatctcgt   53100
cgttgatgga acagtagttg cgcagcggcc cgaagcctat ctccgagaag gccacgacac   53160
tggtcgggtc gtcggccgcc cgcagggcgt cctggatgac ctggtcgcag gtgcggtagg   53220
cggcgaagac ggcgctctcc cgctcgtgct cgggggccgtg ctccagctcc tgccagtaga   53280
tgtgcgaaca gcggtcgatg ctcgtgaggt tgacgatcac gacatcggac tcctccagca   53340
gagccaatgc cgcgcgcccg cgctgcacgt ccgcctccag cagggaaggc agcagctcgt   53400
cgcggtcctg cccggtccag aagatcgaca cgtcgtggac cggacggatg cccttcttcg   53460
ccagggtgcg ctggaggctg cgcgggtggc aggcgtggag ggtggcatac atcggatagg   53520
tgatcaggga accgtcgaag ggctccgggg gatgggtgcc gaagaggcct atcgaggcga   53580
acctgacgcc ctggaacacc tcgtgctgcc acagcagtgg gtggcggcgg tgctcggggg   53640
tgaggacctg cggcgcgtac tccgggtcgt gacaggtcca gtaggagtag aagccgtggt   53700
ccgcggcgcg ccggccggtc aggacgctca gcaggcccgg cggttcgtag ggggtgccct   53760
cggcgtggag cggcccggaa gcccctgcg agcgcagggc ggcgaagccg ggcagcagcc   53820
cctgggcaca ccagcggtcg agcagctcgg gtgccgctcc ctcggtgatg acgacgacga   53880
cacgctggcg gattgtcacg tgcgactccc tcggggttgcg tggcagttgg catgccgtca   53940
tccgggaggc gccggaaagg ccgaggcgtt ccggcgccgg acaggcgtcg atcgtcggat   54000
caagctaaca gcgggacgag gactctctcc agacgacggt acggaggaaa ttgagagagg   54060
gctgagagag ggctgagaga gggcagaggc gggggagtgg cgtgggtca cacggtgcgc   54120
aggaggcgca gacgttcccg taccgccttg ggcagccccg ccaccacgcg atcgtacgaa   54180
tgctccacca tctcccgcag ctccccacg ggaaccgtgc cgttcaggac aaccgtgttc   54240
cagtggcgct tgttgacgtg gtagccgggc accaccgccg cgtactgctc gcgcaggtgc   54300
agcgccagat ccggttcgca cttcagcgtg acctgcgcg ggcggtcctc ggaggcgtcc   54360
tggagaatgg cgaagacctt cttctccacc ttgaagaccg cggctccggg ccgaacgcc   54420
tcgtcgtcca ccgcctccgg cagctccagc gcgaagtcgg agagttcctc tggtgtcatc   54480
gccggtcctt cttcctgcgg cacggcagcg agcggccgaa ccgcgtggtc atggggtcgg   54540
ccaacagact agaggcgcag gaggagttgc cgtgcggcag ggcgcggacg ctgatccacg   54600
atggccgaaa cactgcgggg agttccggtc gcggcgggac ggcgaccttg acgggcggtc   54660
ctgccattgg cacagtttgg ctggctccac acaggttttc ggtggaccgt tcgttcctct   54720
cccggtgctg cccggtcgcg gtaccggtgt ccgcgcgatc cgtgtgccgc ccgcgccgtc   54780
ccgaaccggc ccgtgcgccc actctcccgg ccctccgccg ccggtctccg taccgccgcc   54840
ccgcccttgc cggggcggcg ccgacgcccg caccccggcc ttggccctgc ccacggccgc   54900
atccgcgcac ccccctcacc ccggcgccgg ccatgcccccgtgccgcctg ccccccttga   54960
tgccctgtgg aggaaccccc gtatgaccgt ggagcagacc cccgagaatc ccgggaccgc   55020
ggcccgcgcc ccgcggaag agaccgtgaa cgacatcctg caaggggcgt ggaaggcccg   55080
cgccatccac gtggccgtcg aactcggcgt cccggaactg ctccaggagg cccccgcac   55140
cgcgaccgcc ctcgccgagg ccaccggcgc ccacgagcag accctgcgca gactgctccg   55200
actgctcgcc acggtgggcg tcttcgacga cctcggccac gacgacctgt cgcccagaa   55260
cgccctctcc gccgtcctgc tgcccgaccc cgcgagcccg gtcgccaccg acgcgcgctt   55320
ccaggcggcc ccctggcact ggcggggcctg ggaacagctc acgcacaggg tccgcaccgg   55380
tgaggcgtcc tttccttcga cgtggccaac ggcacctcgt tctggcagct caccccacgg   55440
gaccccaag gcgcgcgaac tgttcaaccg gccatgggg tcggtctccc tcaccgaggc   55500
cggacaggtc gccgcggcct acgacttctc cggcgccgcg accgccgtgg acatcggcgg   55560
cggccgcggc agcctcatgg cggccgtcct cgacgccttc cccggcctgc gcggaacccct   55620
gctggagcgc ccgcccgtcg ccgaggaggc ccgtgagctc ctcaccggcc gcggcctcgc   55680
```

FIG. 21O

```
ggaccggtgc gagatcctgc ccggcgactt cttcgagacc atccccgacg gcgccgacgt   55740
ctacctcatc aagcacgtgc tgcacgactg ggacgacgac gacgtcgtac gcatcctccg   55800
ccggatcgcc accgccatga agccggactc ccggctcctg gtcatcgaca acctcatcga   55860
cgagcggccc gccgcatcga cgctcttcgt cgacctgctg ctgctcgtcc tcgtcggcgg   55920
cgccgaacgc tcggagagcg aattcgccgc gctgctggag aagtcgggcc tgagggtgga   55980
gcgctcgctg ccctgcggcg ccggcccggt gcgcatcgtc gagatccgca gggcctgaaa   56040
ccgcccctcc tgaccgaagc cggccacagc tgaaggagca atgacaccat gacggtgctg   56100
ggtctgggtg gatccggaca tgactgggcc tcctgtgcca ccgacggccg acggctggtg   56160
gcgatcgacg aggagcggct ggtcgacagc aagtacgcc tgggagcgga cctcctggcg   56220
ggccacagcc ggcgcgccgt cctcgacgcc ctcgacgca gtgccgaggc cgtggaacac   56280
gtggtggcct gcgagctcgt accacgcccc ttctaccact cgttccgcag gcgcgtgacg   56340
gtcgtcaacc accatctcgc ccacgcctac agcgcgttcg gggcctccgg gatgacccgc   56400
gccgccgtac tggtctgcga caactccggc agcctggtga cgggcctgaa gtccggccca   56460
gggccgcgcg aggcggagac gatcagctgc tacaccgccg acgcctccgg gctgcgcctg   56520
gtcaaccggg tcgccgggac acacgccgtg gacgcctcct ccgagagcgc ctactaccag   56580
cccggcgaga ccgacaattc cctcggccac ttctaccgct cggccagcct cgcactcggc   56640
ctcgcctact ccggtcccaa gacccgctac cccgtcagcg aggacggcaa gaccatgggc   56700
ctcgcgccct acggcgacga ccgcttcgtc gacgaggtcg cggagctggt caccctgctg   56760
cccgagggcg gcgtgcagat ctcggcgagc aaggtgaacc acctcttcga acgcctcgtg   56820
gaatcgggtg agttcgagga ccgggcggcc ttggcctacg ccgcccagga gacgctggaa   56880
cgcgccctgc tgcactgcgc ccgcgacctg caccgccgca ccggcctgac ggacctgtgc   56940
atcgccggcg gcgtcggcct caacagcgtc gccaacggcc ggatcctgcg cgagaccccc   57000
ttcgagcggg tcttcgtcgt cccggccgcg gcgacaacg gatcagcct cggctgcgcc   57060
tactacggcc tccacgagct ggaggggcgc gcgccgtcgg agctccccgc cctcgacacc   57120
gcctacctcg gccccgacta ccccgccgag cgcgtcgacg cggcgctggc cggctcgggc   57180
ttcaccgtgg agaccccga cgacctgccc ggcagggtcg ccggcctgct cgccgaaggg   57240
aagatcatcg gctggttcga cggccgctcc gaattcgccc cgcgcgcact gggacaccgc   57300
agcatcctcg ccgcacccct ccccgcctcc gtgcgggacc acctcaacga caacgtcaaa   57360
caccgcgagt ggttccgccc ctacgccccc atcgtccgcg aggaccgggc ggcggactac   57420
ttcgacctcg tccagccctc cccgttcatg ctggtcgtcg cgcgcgtgac ccggcaggac   57480
gccatccccg ccgccaccca cgtggacggc accgcccggc tccagacgct gaacgccgca   57540
cagaacccga aggtctacga gctgctcggc aggttcgagg cgctcaccgg ctgcgccgtg   57600
ctgctcaaca cctccttcaa cgtcgccggc cagcccatcg tcgagacccc ggaggacgcc   57660
gtcgaggcgt tcgcgggcat gcgcctggac cacctcgtcg tggggaccg gctggcgacc   57720
aagccctgac agcacgccga ggcccgcgac cggcagggag gagagccaag cggtggacgt   57780
ccccgtgctc gtggtcggag gaggaccgac gggcttggcg atggcgctct tcctcgcacg   57840
ccacggcgtc ggctgcctgc tggtcgaacg gcggacgacc acctcgcccg tcccgcgcgc   57900
cacccacgtc agccgccgct ccatggaact cttccgcgag gcgggcctgg aggaggagat   57960
ccgccggggcc gggttcgagg tcgtgcgcga ggacgaccca cggctgcgga cccggcccga   58020
acgccacctg ccccgggtgg tcctgcaagc cgcctcgctc gccggccccg gcccggtggg   58080
ggtcctggag accggtgacg aggaactggc cgtacccggc ccctgcgcac ccttctggtg   58140
cggccaggac cggatggaac ccctgctcgc caaggccgcg gcgcgccacg gcgccgatgt   58200
gcgcttcggc cacgaactga ccggcctgtg gccgggggag gacagcacac gggcccgcgt   58260
ccggcagcg ggaacgggac ggacctacac cgtcgacgcc cgcttcgtca tcgccgccga   58320
cggggcgcgc ggcgagatcg ccgagcgcgt gggcatcgcg cgggagggcc tgggcacgcc   58380
cgcccaccgg gtgagcatcc tcttccgcgc cgacccgggg cgctgggccc gcgaccggcg   58440
gttcttcatg tgcatgatcc agaacccggg gttcgacggg gcggtgatgg agctcaacac   58500
cccgggccgc tggtgcgccg cggtggacta cgacccggcc cgcgccgaac ccgacggcac   58560
ctactccgca cgcacctgcc tcgacctggt ccgggccgcc gtcggtgacg accggagcga   58620
cgcggcggtc gacaccgtct tccactggaa ggcccggcac cgcatagcgg ccgcctaccg   58680
cagtggggcg gtgttcctca tcggcgacgc cgcccacctc cacccgccct ccggcggcta   58740
cggatccaac gtcggcttcc aggacgcgca caacctcgcc tggaagatcg ccgccgtgct   58800
cggcggctgg gccggaccgc ggctgctgga cacctacgac gaagagcgcc gccccgtggg   58860
aaaggcgacg gcggagcagt cgatgctcct cgacggcgtg ccaccggaac cactgggggg   58920
aagcgtcgtc cgctgcgatc cccgcaccct gatcatggga taccgctacc actccgccgc   58980
cgtcctcggc ccccgcacg gccccgcctt ccccgcggcc ttcaccctgc gcggagaccc   59040
gggcaccgg ctgccgcacg tatggctgcg tacggacgcg ggggaacgcg tctccacgct   59100
cgacctgtgc cacgggcact tgtcctgct ctccgccgac ccggtctggg cggcggccgc   59160
ggcgcgctcg gcgaaggaga cgggcgtacc gctgcgggc caccacctgg cggccaccgg   59220
aagcgaactc gccgacccct ccggcgagtt cccgcggagc tgcgggaccg ggcccgcggg   59280
ggccgtgctc gtacggccgg acggcatggt cgcctggcgc acggcccgcg ccgtgccccc   59340
ggaccccgga cagcgcgcagg acctggtcac ggcagcggtg agacgtgtcc tcgcactgcc   59400
```

FIG. 21P

```
ggagcgcgcg gcgccaccgg tgctcggtcc gccgcggttg tcacgcggtt cctatcggcg   59460
agtcgggagc gacgggtgaa gcctcattcc ttctgcacgt gctggccggg cgccaccgta   59520
tggctgacgg gcccaccggg cgcgggcaag acgacgatcg cccgcgcact ggcggagcgg   59580
ctgcgcgaac ggggccggcg cgtggaggtg ctcgacggcg acgcgacccg cgcgctcctg   59640
accgcgggct cctcgtggga ggaccgtggc accggcctcc agcgggtcgg cctgatggcc   59700
gaggtcctgg cgcgcaacgg catcgtcgtc ctcgtcccgg tgaccgcggc ccgcgcggac   59760
agccgcgaag ccgtacgcag acgccacgag cggtccggca ccgcgcacct ggaagtgcgg   59820
gtggtccggg acgcagtgcc tccgagcggg ctccccgcgc cgcccggccc agatctgcgg   59880
atcgcggcgc acgagcagag cgccgaggag tcggccgggg cactgcaccg gctcctggcg   59940
gagagggagc tggcgtgaac cccgggcgcg gtggagcgta cgccgcgggg cgcgacggga   60000
cccgcgggac gcgacgccct cacggtctgt cgcacctgga tctgctggag tcggagtcgg   60060
tccacatctt ccgtgaggtg gcgggcgagt cgagcggcc ggtgatcctc ttctccggcg   60120
gcaaggactc gatcgtcatg ctgcacctgg cgctgaagtc cttcgctccc gcacccgtgc   60180
cgttcgcgct gctgcacgtg gacaccggcc acaacttccc cgaggtgatc gcctaccggg   60240
accgcgtcgt ggcggcgctc ggtctgcggc tggaagtggc ctccgtgcag gacttcatcg   60300
acaacggcac cttgcgcgaa cgcccggacg gcacccgcaa tccgctgcag acggtgccac   60360
tgctggacgc gatcgggcgc caccgcttcg acgccgtctt cggcggcggc cgccgcgacg   60420
aggagaaggc ccgcgcgaag gagcgggtgt tctccctgcg cgacgagttc ggcggctggg   60480
acccgcgccg ccagcgcccc gaactgtggc ggctctacaa cggccgccac gcacccggcg   60540
agcacgtccg cgtcttcccc ctctccaact ggaccgagct cgacgtgtgg cagtacgtcg   60600
cccgcgagga gatcgaactc cccaccatct actacgccca cgagcgcgag gtcttccgcc   60660
gcggcggcat gtggctggca ccggggagt ggggcggccc acgcgagggg gaagcggtgg   60720
agaagcgacg ggtgcgctac cgcacggtgg gggacatgtc ctgcaccggc gcggtggact   60780
cggcggcggc caccgtgcc gacgtcgtcg ccgagatcgc cacgtcccgc ctcacggaac   60840
ggggcgcgac ccgggccgac gacaagctgc cggaagccgc gatggaggac cgcaagcgcg   60900
aggggtattt ctagcgcggc ggggccggtg cggcccacaa gcggaggact agtccctaag   60960
tatgaagtcc cctactccgt ttgtctgttg agggcagggg cgccgtctga ggatgatgca   61020
gtccatgtca cagttacttt ccgggaagga cggcgcccag gaggcgccaa gtcgcggcgg   61080
gtccacgtgg gtggcggtcc tcgccgcgtg cgtggggcag ttcgtggtgg tcctcgacgt   61140
gtccgtcatc aatgtcgcgc tgccgtcgat ccgttccggc ctcgacatcg gcgagacggg   61200
cctgcagtgg gtggtcaacg cctacgtcat cgccttcgcg ggcttcctgc tgctcggcgg   61260
ccgggcctcc gacctcttcg gccgcaaggc cgtgttcgtc ttcggcctcg ggtgttcac   61320
cgccgcgagc ctgctcggcg gcctcgcgca ggcgccgtgg atgctcatcg tcgcccgcgc   61380
cctgcaaggc atcggggcgg ccgtgctctc acccgccacc ctcgcgatcc tcaccaccac   61440
gttccccgag ggtccggcgc gcatcaaagc cgtcgcgatc tggacggccg tgggcacggg   61500
cggcggcgcg gccggcggcc tcatcggcgg cctgctcacc gactacctct cgtggcgctg   61560
ggtgttgctg atcaacgtgc cgctgggcct tgtcgtgatc gtcgcgaccg tcgcctggct   61620
ggccgagagc cgcacgcacc aggcacaccg acgccggctg gacctcccgg gagcggtgct   61680
ggtgaccctg ggcgtcggca gcctggccta cggcatccg cagagcgagg gccacggctg   61740
gggctcgccg cggacgctca ccttcctgat cgtcggtgtc gtggcgctcc tcgccttcgt   61800
cgccgtggag cagcgcacgc gcgagccgtt gatgccgctc ggtgtcttcc gggtgcgctc   61860
ggtgtcggcg gccaacgcca tcaccatcgt cagtggcatg ggcttctacg cgatgtggta   61920
cttcctctcg ctctacatgc agaacgtgct gaaatactcc gccgtacaga ccggcctggc   61980
cctgcttccc cacaccgcca ccatcatcct ctccgcgcag ttcgcacccc gcctgatgcg   62040
gtggatcaag gggcgcaccc tcctcgtgat cgcgggactg ctgaccgccg cgggcttcat   62100
ctggcagggg aacatggacg ccgacggctc cttcctggcg accctgctcg gcccgggaat   62160
cgtcttctcc ttcggcgcgg gcctgatgat gacgctcctc gcggtctccg ccacgacggg   62220
cgtggagctc tccgaatcgg gcctggtggc cggcctcgcc aacacctcgc gcaccatggg   62280
cggcgcgctc ggcctgtcgg tcctcgcgtc cgtcgccgcc cgccgcacgg ccgacgtggg   62340
gcccggcgcg gagggcctgg cctccggcta cggtcgggcg ttcgtcgtgt ccggggccat   62400
catcctcgtg agcatgctga tgatcccctt cctgcccaag ccccagcccc agaccccggc   62460
ggaatgacct gtgagcacgg acatacgagg aggcttcgtg gggcaggaca gccggccgcg   62520
gtggctcacc gacgaggaac aacgcgtgtg gcgcggctat ctgcgggcca ccaggctggt   62580
ggaggaccac ctggaccgcc gcctccagcg ggaagcggac atgccgcacc tctattacgg   62640
tcttctcgtc cagctctccg aggccccgcg ccggggatc cggatgaccg accttgcccg   62700
caacgcgaag atcacccgcc cgcggctctc gcacgcgatc acccgcctgg agaagctcgg   62760
ctgggtgcgc cgggaatcgt gccacggcga caggcgcggc cagaacgccg tcctcacgga   62820
agagggccgc gaggttctgg agaagtcggc gccgggccat gtcgccgctg tgcgcgcggc   62880
cgtcttcgac agcctcaccc cggaacaggt cgggcaactg gccggatct gccaggcgat   62940
agagaagggg ctggaccggg aaggcgcgga cctgccgtgg ctgcgctgag gcgggaagcc   63000
gtcgcgagcg cgcggggccg tcaggctctg acggccccg ccgcccgcgt acgggatcgg   63060
gccgaccgcg ccccggattc acgcgagtcc gggagcagac cggacgacac ggatattctg   63120
```

FIG. 21Q

```
gatgccgtgg aacgacacga cggggcaccg ggctggggct tcacccatac ccagtacagc 63180
gcggaccacg gtgaacgcgg cgccaccgc agggcgggg ccctgctctc cgcgcggccc 63240
ctgccgcaga accagcacat catgggctgg ggcgcggaga atcccgaacc ggcgcccgga 63300
cgctacgact tcgaggtcct cgacgagcgc gtcgcgcctga tgcgcgcgac ggggccacg 63360
cccgtcctga ccctgtgtgc cgcccccgac tggatgaagg gcggccggcc cggccgcacc 63420
gactggtcgc gactggagac cgcccccgac ccccggcact acgcggactt cgcccggctc 63480
gcgggcgtga tcgcccaacg ctaccccggac atcaggcact tcctcgtgtg aacgagctg 63540
aagggcttct acgacgagga caggcggcgc tgggattatg agggatacac ccggctgtac 63600
aacctcgtcc acgccgagct gaagcggcgg aacccgcgca atctggtggg cggcccctat 63660
gcggtggtcg accacgaccc gcccgccgag gacgcggcgc accgctcgcg cgaactgcgc 63720
ggtccctggg gcgagctgga ccagcgctcc gccgacgtca tccgctattg gaacgcccac 63780
aaggcgggcg cggacttcgt cgtcgtcgac gggtccagct acacccgcga gggccaccgg 63840
gcgattccgg acgagttcgc cgccaccgag aagttcgccg acgtcacccg ctgggtcagg 63900
agcgtgaccg gactcccggt gtggtgggcc gagtggtacg tcgagccgcc cgccgaggac 63960
gaccggccgg gcggccggga cggctggggc gaggggcacc gcaccgccgt gcaggccacc 64020
gcgatgatgc ggctggcgga gagccgcgcg tcggccgcct tctactggaa cccgcagcgg 64080
accgggaagg cgtgccccgg ctgcctgtgg cggacaccc acttgcgca cggggaggg 64140
gagttgccca tggcgggtct cctgagccgg ttcgctcgcg aattccctcc gggcaccgcc 64200
ttccggccgg tcgccgtcac ctgcgggagc ggtgacaggg tcgaggccct cgccgacgag 64260
gccgccgtgc tcgtcgtcaa caccgagtgc cggccggtgg ccgccagggt ggacgggcag 64320
gcgctgtccc tcgcgccgta cgaggtcgcc tggctgaccc gcccgtaatc cagtggggcg 64380
gcgcacgggc gcggacaggg aattgcggaa cagggaagtt cacgaataag gagaacgcgg 64440
gaaagcgctc gggcggagcg tgaaacccct gtcggcgctc acgatatcca cccagctgat 64500
ttgcaggtga acgggcggt cgcctcgacg gtgccgcccg tttcctgttg cccgaaaggg 64560
caatcgggca tcagcaggag agattgccgc ccggcgccac gccgaggatc ttggtgaatc 64620
gctggtagtt cgcgacgcgg ctctggacct gggcggggtt gtggccgtcg cactccaggg 64680
cgccgttgat gctgcggatg gtctgcccga agccgcggtg gttgaccatg gcctcgtgcg 64740
gggtcatggt gccggggccg cgctgggtgt tccagtacca caggccggtc ttccaggaga 64800
cggccgcgtc cttctgcacc agcgaggggt tgtggagcag gtcgatgccg agggcgtcac 64860
ccgccgcctt gtagttgaag ttccagctga tctggagcgg gccgcgaccg tagtaggcgg 64920
cctggccgtc cggacagccg tagggccggc tccggtcgca gtagtggggg tagttggcgg 64980
tgttctgctc cacgacatag accagtccgc cggtctcgtg ggcgacgttg gcgaggaagg 65040
cggcggcctc ctgcttccgg acctcggcgc tgccggtgcc cgcgaagccc gggtacgcct 65100
tgagcgcggc gaccaggccc ttgtacgtat agaacgcgtt ccgcttcggg aacatctgct 65160
tgaactgggc ctcgctcacg gggaatgcgg cggcctgcga ggtgccgccg tgcggtgcgg 65220
ccgcgctcgc cgtggtggcg ggggcgagga cggatatgcc gaccagtgcc agagcggccg 65280
gcagcagggc ggcgatgcga tttcttctca tggcggctcc cgtgggggaa agggtgagtg 65340
acgcccgccg acggtgaatc gggcccgttg ggcgccttcg cgtcatcgcg cagtgaataa 65400
ctccgtgag tttggtgtca atggcatgcg ccgtgtccgg ccgaaccagg tgcactgagc 65460
aatgagttca ggacaactgc ggccgatagg gcttgcggga gcaacgagga ccatgacctc 65520
atatgccgga agccggacac gtgccagaa atgccgctgt cctgtggctc cttgggtgac 65580
ctgtgaaacc cggctggctc atgaacgagc cgattgaacg agccgattga acaagccgat 65640
gaacaaggag agaacatgcg tggatcgaag gccctccgat acgcggcccc cgtcctggtc 65700
gccgccgcaa ccggcatcgc cctcgccgcg ggaccggcgg ccgccgtccc gatcggtcag 65760
tccgtgaacg gcaagatgac ctactacacc gaccagggct acggcgcctg cggcaccccc 65820
atcgacgcga actcccagga cctcgtcgcg gtcccgtcca cgtggtggac ctccgccaac 65880
cccaacaacg accagctctg ccagggcata tcggtggagg tcagctacaa cggcaggacc 65940
atcagagtgc cggtgcggga caagtgccct tcgtgcgacc ggacccacat cgacctcagc 66000
aggacggcct tccagaagct ggcgccgctc gacagggggt tggtcaacgg catcacctgg 66060
aagttcgtcc gctgacgcca cgccggggtc cccaaagccc ggaccccgg cgctccgcgc 66120
ccggcacgcc ggggnccgcc cggcgtgtcg gcgtgaggtt cgtcgccttc aagagtcata 66180
aagacaatcg cgactgttga cgttatgagt tcatcaaatt taaggtcgcg ggactcttgg 66240
aacagatcaa gacgacggag aacaatgacg tactccccg gcgcgcggcc gcgccggcc 66300
cggctgtccg cactgctgct cgcaggcgcg ctcgtcgcct cggtccgcc cgcggccgcc 66360
gcgcgagcgc cgcaaccccc caccgccgac cgccccgca ccgccgcctc ccccacaggc 66420
ggctgccgta cgggtgacgg ctggacactc gactccaccc gcatcgaccc cgacgacacc 66480
caccacgcct atgtcggcaa cggctacctg gggcagcgcg taccgcccaa cggcgccggc 66540
tacaccgaca gcgacaccaa gaccggctgg ccgctcttcg ctccggccta cgacggctcg 66600
ttcgtgtccg ggctctacgc gcacaacaag cagaccgccg ccgaccggca ggtgatcgcc 66660
gctctgccca cctggaccgg actggccgtc ggcaccggcg gcgagcacgg cgatatcttc 66720
aactcttcga cgaagtcggg ccggatttcc ggatatcacc agaccctctt ccagagctgc 66780
ggcatcgtcc gtaccgccct gacctggacc gccgccgacg gccgcaggac cgacctggtc 66840
```

FIG. 21R

```
tacgaggtgc tggccgaccg cgacgacccg cacacgggcg ccgtacggct gagcatgacg    66900
ccgcgctgga gcggcgaggc caccgtcacc gaccagctgg acggacgcgg cgcgcggcgc    66960
atgcggcaga ccggcggcgg cgaccgcacc ggtgggaccg gccgggacgg ccgcaccatg    67020
gacgtggcct tccgcaccga cggcacggac accgacggcg ccgtcgcctc caccctgagg    67080
gccgggcgcg gtgtgcacac gaccgggggac cgacgcgccg cggccgcgaa ggacttgagc    67140
gtgaaccagt ccctcacgtt ccccgtccgt gcgggccacg cgtacgaact caccaaatac    67200
gtgggtgtcg acaccgcgct caccctcgca cgcgccccgcg aggacgccac caccgcctcc    67260
ctgcgcgccg cccgccgcgg ctgggacggg ctgctgcgtg cccacaccgc cgcctgggcc    67320
cggctgtggc gctccgacat cgagctgccg ggacagcgcg acctccaggc gtgggtgcgt    67380
tccgcccagt acgggctgct gtccagcacc cggcaggggg catccaacag catcgccccg    67440
gccgggctga ccagcgacaa ctacgcgggc ctggtgttct gggacgccga gacctggatg    67500
tacccggccc tgctggccac cgcgccccaa ctcgccagga ccgtcgtcga ctaccgctac    67560
cgcaccctcg ccggagcgcg cgagaacgcc cacaagctcg gctaccaagg gctcttctac    67620
ccctggaaca gcggcagcga gggcgacctg gcccaggagt gccacagcgt cgacccgccc    67680
cactgccgca cccagatcca cctccagtcg gacatctccc tcgccacctg gcagttctac    67740
ctcgccaccg gcgacaccgc ctggctgcgc gagcgcggct ggccggtgat ggagggcatc    67800
gccgaattct gggccgggcg ggtcacccccc aacgccgacg gcagctactc catcaaggac    67860
accgccggcc ccgacgaata cagcaacggc gtcgacgacg cggtcttcac caacgccggt    67920
gccgccaccg ccctgcgcga cgccgcccgt gccgcgcggc tgctgggcga gcgcgccccg    67980
gcggagtgga cgacgatcgc cgaccggatc cgcatcccgt acgacgcgcg gcacaaggtc    68040
ttcgagcagt acgacggcta cccgggcagc aagatcaagc aggccgacac ggtgctgctg    68100
atgtaccccc tggagtggcc gatgtcccag gccgacgcgg cgcgcaccct cgactactac    68160
gcccggcgca ccgaccccga cggccccgcc atgacggact cggtcacgac catcgacgcc    68220
gcggccacgg gcgagccggg ctgctcggcg tacacctatc tccagcgttc cgtccggccc    68280
ttcgtgcgcg gtcctttcga ccagttctcg gaagcccgcg gcaccaaggc cggcggccgac    68340
gacccccctgg ccggctcgcc cgcccacgac ttcctcaccg gcaagggcgg cttcctccag    68400
atcttcacca acggcctgac cggcatgcgg atgcgcgagg accggctgca cctcgacccg    68460
atgctgcccc cgcagctcgg ccgcggcgtc accctgcgcg gcctgcactg gcagggccgc    68520
acgtacgaca tcgccatcgg cgcccacgag accaccgtgc ggctcaccgg gggtgcgccc    68580
atgaccctct acaccccgca gggcgagcac gtgctgacca aggcggcacc ggccgtgctc    68640
aagacccgcc gccccgacct cgctcccacc gacaacgtgg cccgctgcac caccgccggt    68700
gcctcctccg aggaacccgg tatgtacgcg gcagccgcgg tcgacggcaa ccccgccacc    68760
gcctgggtcc ccgacgggcc gaacggtgaa ctgaccaccg acctcggcaa gtccgtacgc    68820
gtcaccaagg ccacccccgt ctggagcggc ccggcaccgg cctcgtacag cgtccagctc    68880
tccctcgacg gccggcactg gcacgacgcg gtcgcgggcg gcgctccggt gtccgcgcgg    68940
tacgtacgcg tcgcgctacg cggtcaggcc gatgccaagt cccgtacggg catcgccgag    69000
ctgaccgtta cgtagggcac cagcagcccg cgcgcccggg ctggatgacg acgaggatcc    69060
gcgggacttc acccgcccctc ggccgacagg gacgtcctga cgagagcgag cacgtcgtcg    69120
tcgctcagcc ccagccgcgcg gggctcgccg accaggcgcc gggcctgcac ggtgagccgg    69180
gcgcgctcgg cggtcgaccc tccggtgacg accgcccgc gccccgacg cagttcgagg    69240
aggccctcct cgcgcagccg ttggtagcca cggagcacgc tgtgcatgtt gaccccgagc    69300
gacgcggcga atcgcgggc ggacggcagg cgctcgccgg agcgtacggt gccgtcggcg    69360
atggcaccac ggacgcatgc ggcgatctgg tcgcccaggg ggagggggga cgcggggtcg    69420
acgcggaaga gcacggtcac ccgcccgcgg aggtgcggcg ttcgcggtcg gcgagggtgt    69480
tgagcagcgc ggcggccgtg gcggcgtcgt cgacggtgac gacgaactcg ctgccggtgg    69540
tcagacggac gctgatggcg tcgccggaac gcagcacgac gccgctcgcc ccggaacgga    69600
cccggtagcc ccagccaccg aagtcccgca gaggcttgac cggacggtga ccggcttcgg    69660
cgatccgctg gagcggcacg ttgatgcgcg ccaggggac ggtcgagggc gtgacggtga    69720
gcccgcgccg gtcggcggtc acccggacac ccgtcagcag gtcatggcg gctccgatga    69780
ggaacagcga cagcgcggac agccatccgg cggcgacccc gacgacgacg ccgaggcga    69840
agaccaggac accggtgagg ggcagcaccc gggagcccgc cacccttgac cagccggcga    69900
tctcggagtc gccgagcgcg agacgcgagg catcggcgga cggcccggaa tcgctgtcgg    69960
ctccctggtc cttgccacag gccgccagcc caccgccgc gtagagcgca gcagccccga    70020
aagcgagcgc ggcctgcgcc ccgggcaagg tgacggaaga ggcgtcgtgg acaccggtgt    70080
tggccagcag cacgcggt gccagccatc cggtcagcac cgcgacggcg ccgccgatga    70140
cggccagcac gcgctgtccg ccgttgcccg gccgcgtgaa gtagacgagc gcgccgaaga    70200
ggacaccgtc gcccagcagc actccccacg cgaccgcgag gaaggagccc tgccccgaga    70260
agccgtcggc attccctccc ggcccgatgt gcgaggcgat ccgcccggc agccggtccc    70320
gcaccgagag gaacacccac aggacgacgg cagcgcagac cagaggcggc acgacggaga    70380
cggcaaggcg acggacgagg acggacgagg accgtgacag cggcatgaga gcaaacctcc    70440
acttgtttgc acactagtag aacaagtgga ggtgaactcg gcgaaggcgg ctgcctcttc    70500
ctgacgcgtt ccgaacgcca ccggagccgc cacgactgac ccagtgtcac cccgcgggag    70560
```

FIG. 21S

```
gcggaacgct tcagtccgtg ccgggagcgg cggccgcttc ccgtggtgcg actggtggtg   70620
tctgcgtggg gcggcgcatg agcggcaggc ggagccgccg gatgcccggc cccgagggag   70680
gtgccagtct gcgcgtggac ctgtggaaga cgagcaggct gacggcggcg gctccggcga   70740
accaggccag ttggacggcg aggtagccgg agacgggagc ggtcgagaag ccggccgcgg   70800
caccggtctg cagcgagccg taggagggga ggagcgtcac gaggccgccg ttggcggcgc   70860
cgccggtggt gacggggttc tgcaggcccg cgtcgagacc gctggtcatc acgatggcga   70920
acatcccctc gacgtcccgg cgcacgcaggg agccgaagac gatgccgatg gcgccgtagg   70980
tcagggacgc gcagaacagg gcggcgacga agaggaccgg ccggcggggc gaccagaagg   71040
cgtaggtgat ggcggtggcg tagacggcga cggtggcgga gatgagggtg agggcggtga   71100
gcttggcgag aaggaggtgg acgcgccggt agcccgccat ggacaggcgt cggtcgaagg   71160
ggccgctggt gaaggtcgcg gcgaacatca tgaagccgac gatcagggtg atggagttca   71220
gcgccccgac gatcgacgtg agttcgttgc cccgcgggtg gaggatctgc ccggtctcgt   71280
gcagcctgaa ggggatgggc gggtcttcga tgacgcagta ggccagcgtg atccacaccg   71340
ggatgaacgc ggcgatcagg cccatggcga gccggttgcg caggtgctcg accaaggcga   71400
accgggtggc ggtgacgtag aggggttgtgt ggttcatacc ggtgccgtcg tccttgagtg   71460
cagcagtccg ccgtcgaggt gccggagttc gtcgagccgt tcggcgtcgt aggccaggtg   71520
ggagacgacc agcacggacc gcccgcgttc gcgcagaccg gcggccaggc tccagaaccg   71580
ctggtgggtg tcccagtcga agccctggta gggctcgtcc aggaggagca ggtcagggtc   71640
gtgcatcagg gccagtgtga ggttgagctt ctgtttcgtg ccgccgctga gcacgctgac   71700
ccgctcgtcc ccgtagtcgg acagccggag cacgtccatg attctctcgg catggctgag   71760
ggtggcgagg ccgtacgcca cccggaaata ctccaggtgc tggcggacgg tgagagcctg   71820
gttcaggacg agatgctgcg ggcagtaacc gaaccggccg ccgtagtgga cctgcccgcg   71880
ctgcggccgc agctcaccgg cgaggatctt caggagcgtc gacttcccg cgccgttctc   71940
gcccacgacg ccggccagcg ttccggggcg cagggacaag tcgatgccgc gcagcaccct   72000
gcgggtgccg taggtgtggt ggacgtccct gacgtccagg agattccggg gcacggcttc   72060
ctctcctcag gcgacctggt cgcgccggac gaccgagagg gccagctcgt acaacaagtg   72120
gctgtggcct gccgacggca gcaggggctc gagcttgttc cacgcgtcgc tcaccaactg   72180
gtcggcttcc tccaggcagg ctctcaccgc tccgcaggcg ttcaggtccc ggcacacctc   72240
ggccaccgcc gtcgcgctgc ccgagccgtc cttgacctgc tgccagagct ggttcagccg   72300
ggctctgcgg cagccggacc acggcgtggg ccagtggcat ggtgaccttg ccgctccgca   72360
ggtcctcggt ggcctgcttc gtcggtgccc ccgcccgtgt gacaccgctc aggtcggcga   72420
cgtcgtcggc gatctggtag gcggtgccca ccgctgaacc gaaagccccc agtgctctcc   72480
gcagttccgg ctcggcaccc gtgacgaccc ctgctgcctc catggccgcc gagaccgggg   72540
ccccggactt caaccggtgt gtcagacgga ccagttccag cacagtgtgc cggtcgtcgc   72600
cggccacggc ctggtccatc tcttccggt gaccttggag atccagtgcc tgaccggcgt   72660
gagccgctcg cagcgcggcc agcccagtg cccgcaactc cccgcaccgc gaggcgtcgt   72720
cgggaaaggt gagctgaacg gcccgctccc agaggaaata ggcggccgta cccgcgttca   72780
ccgcagtcgg catgccgaac atggtgtgca cggccggttg tccgcggcgc agcggtgagg   72840
cgtcctggac gtcgtcgacg atgagggatc cggtgtggag cagctcactc gccgcgatca   72900
gcaggccgca ggattcgacg tcacctccca tcagaccgat ggcctcccag gccagcaccg   72960
gccgccagcg ctgtcctccg gcatcggtca gatgcggcag gggagagctc agggcccggt   73020
gcagccgctg ggcgacgacc ggcggcgtgc caggcccggt cgtcccggtg atgtggcccg   73080
gtggcagcca cgtggagcaa gcatctgccg acgcgttcgg gcacaggcgg tcgatgtgat   73140
ggttgatgcg ttcggccgtg cggtcgatgc gctgccggat gaagtccgcg ttcgccgcga   73200
aagtcgggga gatgtccctg gacagagga gggcgccggt catggagtgg tcagctttcg   73260
gtcaggggcg ggcgatggac gaggctccct catggggtcg ccggcccgat gccgcggagg   73320
gactgctcgg gcacggctcg cggagtgcgg cgatcatggt caggccgcgt ggcatcgcgg   73380
cgagttcgaa gccggagcgc accgtccggc ccggacgcgc cgtgcgtacg gtccgcgtgg   73440
cgaccagagt ggcgagcgcg acgggcacca tgacgtcggc caccgcggca ccagggcagt   73500
agcggggccc gagcgcatag gaagccagg cagcagggga gaccgagggc tgagcgtccg   73560
gcatccagcg cgtcggatcc aagacatcag gccgttcgaa gtgggcgggg tcacggctca   73620
tcgccccgag gtggaggaac accgtcgcct tcgcgggcag ccggtggccg cccagccacg   73680
tctcgcggcg cgtgcaacgc acaaggaccg ggaggccgtg aagccggatg acttccttga   73740
cgaaggcggc tgtccggggc aaccggttta ttccgacgcc ggcctgcgag tgcccaggc    73800
cgagtgccgc gtcggcctcc tcctgcaagg cctgttgatg gtgggggtgg cggcccagtt   73860
cgtagcaggc ccacgcgagt gtcgaggcgg tggcctcccc gccggtgaac agcagcgtgc   73920
gcacgtcctg caccgccgct tccgagggct cgcgccacgc ttgcttcagc agggagacca   73980
catcacaccc gtcctcagcc ggccgatggc gcgcaggac ttcccggggtg gcctcgtcca    74040
gcaccgcgag ggcacggcgg agcgcgcgtt gtcttggcac gggtacccaa ggcacgggg    74100
acaggagaaa ccgcaaggcc ccgacctgcg acagcgtggc atgcgccgcg gccagcgcgg   74160
tcagcgttcc gggcgagacc tcgctgcgca agacgcacct gacggcgaga tggaaagtga   74220
gccgggtcat ctcgtggctc atgtcgaccg gacggtccgc gggaagggtg gcgagcagac   74280
```

FIG. 21T

```
ttcgggtctc ggtccgcacg gacgccccga ggtccgccgg ccggggcacg gcgaacgcgg    74340
gcctcatcac cgcccgccgg tcacggtgga ccgttccctc ggtgctcagc agtccctctc    74400
ttacgatcac ccgcacatgg ggttccctgc cccagaacat gaaggtgtcc tcgtcgcgag    74460
cagcctgccg gatcagcgag gagtcattga gcaggtaccc gacgaacggg cccgccttca    74520
ccctgaccac aggccccgcc ttgccgagcc gggccgcgat ctccctcaga tccatcaaga    74580
accgcacgga gcgggcatgc ccgagcaacc gactgcagtc aggagccatc ggcacaacgg    74640
agtccgcctt cgaatctccg ttcatcaggc gtcctcccgc ccgcatgtca ccctctgtcc    74700
tcctgtgaac gaccaggagt gaggagtgtc acgcagagca tcacctgctg tatcggcagc    74760
aatgccgacc cgcaccgacg gctgggcggg gcgaccggga accgccttgc ggctacgccg    74820
tgctcgcgtg cctgaagcgc accgtcacat tcaccggtac ccacgacaga ggcgggttcg    74880
cggccacctg tatggacgcc cgctgaatgg ggacggagtg caggggtgc  tcgatggcgg    74940
tgccttcgcg gctcagcagg ccctgcctcg cggtttgagc gcaacgggcg gcagttcggg    75000
agcaggcagt cgggccccct cgtagccgtg cacctcgccg aagcgggagc cggtcgcccg    75060
agccgtcgcc gccgccggcc cgattcgcca tccggatgga agaggacacc gcgcagggac    75120
cgccgcccac ttcaccggaa tcctctccac cggaaaattt atccgcaaac ctgtcacatc    75180
ttcgacacat gaagcgtcag ggcggtgacg gcagttgaag ccgttgcccg acgacgccga    75240
aggagaccgt gggacagcta cgcacgtgcg ggccctggag cggtcggcca cgccgacagg    75300
aatcggcctt ccgccgctga tccggcctcc cagcgttcgc gaacacctct gccacacct    75360
cccgcgcggc ccccgcattc gagcggtcgg ctgacgacgc cctgcgacgc cgcgcacacc    75420
acccacgcac ctcgccacgc cgaaggctgc ccgaaaacaa gaagaccgag gaaagcacac    75480
atgaagatct ctcgaatagg ccgcgcgtca tccatcgccg ccctggtgac aaccgcactc    75540
gctttcacgg cagttggcac cgtcgctccc acggccgtcg ccgactcccg cgcggccgcc    75600
gcttccggga cgcagaatga ccacccgagc tcggggcagg gcacctccac ctctgagctc    75660
cggcgcaagg gcctggtccc gtcgagtctc gtggccaagc ccatcacccg cagcgagacc    75720
ctcagacgcg ccgccagctg gttcggcaag ggtctccact acagcgggga caacacctat    75780
cagggctggc gcacggactg ctccggcttc gtctccatgg cctggggact gcccggccg    75840
ggtgagacca ccgattcgtt cattcccggg ggcgtggccc acgaaatctc caaggacgaa    75900
ctgaagcccg gcgacgcgct caacaacaag gcgctcggca acgacggtca cgtcgtcctg    75960
ttcgagaagt gggccgattc ctcccagtcc tcctactggg gttatgagtt cagcagcagc    76020
ggtctgcacc accgtgtgat cccgtacgcc tacttctcca ggtccgagca gtaccgcccg    76080
atccgcttca acaccatcgt ggacgacgac acggccgcag ggcccgccga ggacaacgcc    76140
cgggtccagg gtgacttcga cggcgacggc cgcgacgacg tggcggtgct ctacgactac    76200
ggcaggaagg acgaccgcag tcgctcggcc ctgtggacgt caacagcaa  cggcagcgt    76260
ttcaacagtc ccaagcaggt gtgggacagc gggacgtcgg agagctggaa ctgggcctcc    76320
agcaagttga cggtcggtga cttcaacggc gacggcaagg ccgacatcgg cgtcctctac    76380
aacatgggcg cgaccgagga cggccgcaac cgcaccaagc tgttcgtgtt caccagcacc    76440
ggcagcggat tcgccgcccc ggtcaaggtc tgggacagca cgacgaccc  cgtgaagagc    76500
tggaactgga acgccagcaa gctcaccgtc ggcgacttca cggcgacgg  caaggccgac    76560
atcggggtgc tgtacgacta cggcaaggac gacgaccaca accggacagg gctctggacg    76620
ttcaccagca ccggcagcgg gttcaacagc ccgaagcagg tgtgggacag caacaacgac    76680
cccgtgaaga gctggaactg ggaagccagc aagcccgtct ccggggactt caacggcgac    76740
ggcaaggccg acatcggcgt cctctacgac tacggcaaga ccgactccgg cagccgcacc    76800
ggactctgga cgttcaacgg caatggcaac gggttcaaca gcccgaagca ggtgtgggac    76860
agcaacaacg accccgtgaa gagctggaac tgggaagccg gcaagcccgt ttccggcgac    76920
ttcaacggcg acggcaagga cgacatcggc gtcctctacg acatgggtcg caccgaggac    76980
ggccgcaacc gcaccaagct gttcaccttc accggcacgg cgaccggttt caacagcccg    77040
gtcaaggtgt gggacagcaa cgacgacccc gtgaagagct ggaacgcgtc cgcgagcaag    77100
cccgtcgcag gtgacttcaa cggcgacggc aaggcggaca tcggcgtcct ctacgactac    77160
ggcaagaccg actccggcaa ccgcagcgga ctgtggacct tcaccagcaa cggcagcggc    77220
agcgacagcc ccaagcttgg ctgggacagc agcgcggacc ccgtcaagag ctggaactgg    77280
agcgcgagca agctcggctg accggcttcg cccctcctca cctcaccgtt cgggagagtc    77340
accgcacatg cgaaccatac gaatacgaag aacgaacggc gtggccttcg ccgccgctgc    77400
cgccctgatg gccctcgtcg cctccggcac cgccacggtc caggccgcgc cctcgcacgc    77460
cggaccctcc ggcaccactc cgatcaccta ccgtggcctc accctcgaca taccctccgg    77520
gtggccggtc gtggacctgg agaaagaccc gcacacgtgt gtgcggttcg accgccacac    77580
ggtgtacttg ggccaccccg gcaccgaaca gtcctgcccc tcccatctgg tcgcggacaa    77640
gacggacgcc ctgatattgg agccgatcac cggagcgggc ggccaggacg cctcccacgc    77700
gctgcgcatc cctgccgggg ccccgatgcc gcacgagctg ccggtgacgt acgaccacga    77760
gacgaaggtc gccgtcgaag gcgccggagt catggtcacg tcctcctacg gcacgtccag    77820
tacaacggtc gccgccgtcc tcggctcgg  ccgcacggac gcgacagcca agccgacccc    77880
cctgcccggc aaggcgggca ggggcctcgc ggctccaccg gttgccgccg tcgcggccga    77940
caagggatac acagggctgg gcttcgagtc ctgcaccgcc ccttcgtccg ccgcgatgaa    78000
```

FIG. 21U

```
ggcatggaag gcctcgtcgc cctacggggc cgtcggcatc tacatcggcg gtcgcaagcg 78060
gggctgtgcg caaccgcagc tcaccggcga ctgggtgcgt cagcagaccg ccgacggctg 78120
gcacctgctg cctctcttcg tggacctcca ggccggcgac atctctccgg ccaccgcgga 78180
cgcgcagggc cgcgagtccg cggacgccgc cgtggcaag gcggcggacc tgggcctggg 78240
ccccgggacg gtcatctaca gcgacatgga gcactacgac agccgctcgt accgggcccg 78300
ggtcatcgac tacgtgtcgg ggtggaccag ccgcctccac gaacatggct accgctccgg 78360
tgtgtacgcg ggtgaaacga gcggcatccc ggacctcgcc tcggtggccg acgacaccaa 78420
ctacgcatca cccgacgtgc tgtggtcggc gaactggaac ctcaaggccg atgtgtcgga 78480
cgcgtcgatg ggacttccgg gccccggcta ctggcccaat gggcggcgca tccaccagta 78540
ccgcggccag gtgaacgaca cctacggcgg tgtcaccctc gccatcgacc gcgactacgt 78600
cgatgtcgcc gcggactcgg ccctgcccgc acccggcgga gaggacggtt cctcgcgcgt 78660
caagggcgac ttcgacggcg acggccgcga cgacgtggcc gtgctgtacg actacggcaa 78720
ggagggcggc gtcagccggt ccgcgctgtg gacgttcgcg ggaccggca gcggcttcgg 78780
cgccccgaag aaggtgtggg acagcggatc ggacagctgg agttggtcgg ccgccaagct 78840
gacggccggc gatttcaacg gagacggcaa ggccgacatc gcggtcctgt acgacatggg 78900
tcgcactgag gacggccgca accgcaccaa gttgtacgag ttcaccagca ccggcagcgg 78960
attcaacagc ccggtcaagg tctgggacag caacgacgac cccgtcaaga gctggaactg 79020
ggcctccagc aagctgaccg tcggcgactt cgacggcgac ggcaaggccg acatcgcggt 79080
tctgtacgac tacggcaggg acggcgaccg cagccgtacg ggcctgtgga ccttcaccag 79140
caccggtgcc gccttcaccg gccccaagct ggtgtgggac agcaacaacg acccggtcaa 79200
gagctggaac tggaacgcca gcaagcccac cgtcggcgac ttcaacggcg acggcaaggc 79260
cgacatcggc gtcctctacg acatggtcg caccgaggac ggccgcaacc gcaccaagct 79320
gttcaccttc accggcacgg cgaccggttc caacgacccg gtcaaggtgt gggacagcaa 79380
cgacgacccc gtgaagagct ggaactggga cgccgtcaag gtagtgggag gcgacttcaa 79440
cggcgacggc aagagcgaca tcggggtgtt gtacgactac ggcaaggacg gcgaccgcag 79500
ccgcaccgga ctgtggacct tcaccagcaa cggcagcggg ttcaacagcc gaagcaggt 79560
gtgggacagc agcaacgacc cggtgaagag ctggaactgg gccgcgagca agccggtcgc 79620
aggggacttc aacggcgacg gaaaaacgga tatcggcgtg ctctacgact acggcaggac 79680
cgattccggc aatcgcaccg gactgtggac cttcaccagc gacggcaccg gattcggtac 79740
accctcctg ggctgggaca gcgtgacgga tgccgtgaag agctggaact ggcgtgccag 79800
caaggtgagt tgacacccct cctgtgagac atggggcact cctcgacgcc cgtccggccc 79860
ggctgcggcc cggccggacg ggcccgtcat tcaatggaag gaagaagtgg atcccttgac 79920
gcgcaagacc cgcaccccc gcaagaaggg cagacgcgcg agcgcggcgg cgatgtcggc 79980
ctccggcatg ctgctcgcct tggtggccac cgccgccccc gtccccgccc aggcggcatc 80040
actcgccacc tgggaaaaga tggcccagtg cgagagcagc ggggactggg gatacaacca 80100
gccaccgtac tacggcggcc tgcaattcct ggagagtacg tgggtggcgt accacggaac 80160
ggactatgcg ccatacccct atcaggccac caaggaacag cagatccggg tcgcgcagcg 80220
gctcctcgac aatgagggcg cggctccctg gccgctactgc ggaaagaagg tggggctggc 80280
tgacgacgac gcacgcccct tccccgacgg gccggacgac gacgcctccg cccggatcaa 80340
cggtgacttc gacggcgacg gatgcgacga cgtggccgtg ctctatgact acggcaagga 80400
gggcggcgtc agccggtccg ggctgtggac gttctccggg agcggtaccg gcctcggcag 80460
cccgaagaag gtgtgggaca gcggatcggc cagctggagt tggtcggccg ccaaactggc 80520
cgtcggcgat ttcaacggcg acggcaaggc cgacatcgcg gtcctgtacg acatgggccg 80580
cactgaggac ggccgcaacc gcaccaagtt gtacgagttc accagcaccg gcagcggatt 80640
caacagcccg gtcaaggtct gggacagcaa cgacgacccc gtcaagagct ggaactggaa 80700
cgccggcaag ctcaccgtcg gcgacttcaa cggtgacggc aagaccgaca tcggcgtcct 80760
ctacgactcc ggcaagaccg actccggcaa ccgcaccgga ctgtggacct tcaccagcaa 80820
cggcactgga ttcaacagcc gaaacaggt gtgggacagc aagagcgacc cggtgaaaag 80880
ctggaactgg ccgcgagca agccggtcgc gggcgatttc aacggtgacg caagaccga 80940
tatcggggtg ctttacgact acggcaaaga tggcgaccgc agccgcaccg gactgtggac 81000
cttcaccagc acgggcagcg gattcaacag ccccaagcag acctgggaca gcgggtcgga 81060
aagctggaga tggtcggcgg ccaaggtggt cggcggcgac ttcaacggtg acggcaaggc 81120
cgacatcggg gtgctgtacg acctcggcag gaacggcgac cgcaaccgca ccgaactgtt 81180
cacgttcgcg ggcaacggca ccggcctcaa cacaccggcc aaggtgtggg acagccagga 81240
cgacagccgg gtgaagagct ggaactgggc cgcgagcaag ccggtcgcag gtgacttcaa 81300
cggcgacgga aagacggata tcggcgtcct ctacgactac ggccagacg actccggcaa 81360
ccgcaccggg ctgtggacct tcaccagcga cggcagtgga ttcgccggcc ccaagctcac 81420
ctgggacagc cggaccgacc cgtcaagag ctggaactgg aacatgagca agaccggctg 81480
agccattcat gccgtacaga agagaagagg aaggatgaaa taccgaccgg gaacactgct 81540
cacttccata acagtcttgt gtgccctgct cgttccggtg cgttcgcgg ctcaggcggc 81600
caggcccgag cagggacgtt ccgtggtggc gcggccgcc gtactggagc aaagtccgcc 81660
gacgctgctc gccgagccgg aaatgcgcgt cgtctcctgg aacatctgcg gtgaggcggg 81720
```

FIG. 21V

```
cggggtgcgc ggggagggcg gctactgccc ctaccgcaac gatccccagg cgaaagtcga   81780
ccagatcgcg caggtggtcg cggagcgcag tgccaatgtc gtcatgctcc aggaagtgtg   81840
cggcgaggcg cccggcagcc atatggagcg gctgcgcgcg gccctgggca gcggatggtc   81900
gatcgcgcac gccccggggg cccgcccgga cgacggaacc acgaactgcc ggggcgggct   81960
cagcggcata ttgggcgtgg ggatcgcggt gaagggcgc gtcaccgaca ccaccgcgac    82020
gaacaccgtg cccggggggcg gcggtgacaa gcagaccctg cccatcctct gtgtacgtgt   82080
cgagggctgg tcgtccagga tctgcaccac ccacatcctg tccgaccctg ccgatccgcg   82140
caggccgggg cagatccaga acgtcaagaa cgagatctgg ccggaccgct atcagctggt   82200
gctcggcggc gacttcaaca tgttccccga ctccgccggg ctcaagccga tctcggacga   82260
attcgacgag tgcgaccgcc gctcctacgg cgccggtgac atggtcaacg aggtcaccca   82320
tcactcctgg gagaaaaagg gcggacacat atggcgcaag cgtgaccaca tcttcgcctc   82380
gtggggagag tccgggagcc agttcacatc ctgcgaggtc gaccggaccc ggatggacac   82440
caccgagaac gcgcccgaaa gcgtccgcc aacgggtat tcggaccatg cgccgatcat    82500
cggctacctc aagccgccgc ggcacctgag cacgtccggg gacttcgacg gcgacggcaa   82560
ggccgacctc gcggtcctct acgggcaggg gaagaccccg gacggccaca accggtccag   82620
cctgtggatc tcaggcggtt ccggtaccgg agcggagacc ggattcgccg cgccgcgcga   82680
ggtctgggac agcggtgccg acagctggaa ctggtccgcg agcgcgctga cctccgggga   82740
cttcgacggc gacggcaaga ccgacatcgg cgtcctctac aactacggca gggacggcga   82800
ccgcaaccgc accgcgctgt ggaccttcaa ggggacatcg aacggcttcg aggcgcccg    82860
caaggtgtgg gacagccacg acgacacggc cgttcccagc tggaactggt ccacgagcaa   82920
gctcgtcgcg ggcgatttca acggcgacgg caaagcggac atcggcgtcc tgtacgacta   82980
cggcaggacc gcctccggca accgcaccgg actgtggacc ttcaccagca ccggcaccgg   83040
attcggcaag ccccacctgg cgtgggacag ctccaccgac ccggtgaaga gctggaactg   83100
ggccgcgagc aagccggtcg caggtgactt caacggcgat ggcaagaccg acatcggcgt   83160
cctctacgac tacggcaacc acaccgccct atggaccttc accagcaacg caccggatt   83220
cgccggcccc aagcaggcct gggacagcca accggagaac tggaactggt ccgccgccaa   83280
gccggtcgcc ggggacttcg acggcgacgg caggaccgac atcgcggtcc tgtacgacta   83340
cggcaggacc gcctccggca accgcaccgg actgtggacc ttcaccggca ccggcaccgg   83400
attcggcaag ccccacctgg cgtgggacag ctccaccgac ccggtgaaga gctggaactg   83460
ggccgcgagc gagccggtcg ctggtgactt caacggggac ggcagggccg acctcgcggt   83520
gatgtacgac tacgggaacg cgaccaacgg ccgcaaccgc accgcgctgt ggtccttcac   83580
cagccgcggc acggacttcg ccgccccgcg ggcgaactgg gacagcagca acgccgctga   83640
ccagctgaaa tcgggcgagc tgagggcggc tccgctcagc gggtccagt tctccatgat    83700
cggtccgtcg ccctccagac cggccgctct cccggtcagc gtcgcggcca gtgcgtcagc   83760
gtcgcgaccg agtccgtaac agcgcatccc ggcgatcgcg aagtacgcct ggtcgagcca   83820
gacgcgggcc gcgccagtgc tgccgcgcgg cgaagtacgg cgagctc                 83867
```

FIG. 21W

ORF1-9 SEQUENCE

```
ggatcccgat cgtctcggac atgaccggcg accttctcgg cgcgcgggag gcccaggacc      60
ccgcctactg ggtgtcccac atccgccgcg cggtgcgctt ccacgaccag atccgccgtc     120
tgcagcgcta cggggccggg gccttcgtcg aggtcggccc ggacacggtg ctcagctcgg     180
ccggccaggc gtgcctgacg gaccaggcgg gcaggagcgc gcccgtcctg gtgtccctcg     240
cgcacgccga gcgcgcggag gtgcccgcgc tcctgaccgc tctggccacc ctgcacaccc     300
gtggcgtggc cgtggactgg cgggcgtggt cggcgacgg gccgcgcgcg gccggcctgc     360
ccacatacgc gttccagaag cagcactact ggccgtcggg ccccaccggt tggcggtccg     420
ggcccgcccc cgtacccctg ccccaggccg aacggagga cgccgaaagg cccggtcgcg     480
ccgcggagtg gcgggcgctg ccgcccggtg agcggtacga cgcgctgctg cggatggtgc     540
gcggcgaagc cgccgccgtg atggggcacg ccggggccgga ggcggtggag ccggagcgcg     600
gcttcctcga ccacgcttc gactcggtga tggccgtgaa gctgcgcgac cgtctcgtgg     660
ccgggacggg gcgggagctg ccgacgaccc tgctgttcga ccaccccacg cccgcggccg     720
tcgccgacta ccctgctggcg gggacgggcg aggccgagac ggcgccgtcc gtgtccctgt     780
cggaccagct cgaccgcctg gaggccgacc tcgcgcggct gccggccgac gaccggcagc     840
gcgcccgcgt cgccgagcgg ctcaagggcc tgctcgcggt ccacgcgccg gaccggggcg     900
ccggggagcga ggacgcgccg gaccaggacg cgctggacac ggcgaccgac gacgagatgt     960
tcgagctgat cgagaaggaa ctccgccgtg gatgagacca acgagaccaa actccgcgag    1020
tacctgcggc tggtcacggc cgatctgcgg cgaacccgca ggcagttgga ggaggccgag    1080
gacgcggccc gcgagccgt cgcgatcgtg ggcatggcgt gccgcttccc cggggacgtg    1140
gcatcgccgg acgacctgtg gcagctggtc ccgagggcc gggacgccgt caccgagttc    1200
cccgccgacc ggggctggga cgtcgacgcc gtctacgacc ccgagccggg caccccgggc    1260
aggacgtacg cgcgccacgg cggcttcctc aaggacgccg ccggattcga cgccgccttc    1320
ttcggcatca cgccgcgcga ggcgctcgcc atggacccgc agcagcgcat gatcatggag    1380
gtctcctggg aggcgttcga gcaggcgggc ctcgacgcga ccaccctgcg gggcgaggac    1440
gtcggcgtct tcgtcggctc caacagcaac gactacctga tcaacgtgct cgacgcgcgg    1500
gacgtcgccg agggcttcat cgggaccggc aactccgtca gcatcctctc cggccgcgtc    1560
gcctacacct tcggcttcga gggcccggcc gtgtccgtcg acaccgcctg ctcctcctcg    1620
ctggtcgcgc tgcacctggc cgcgcagtcc ctgcggcagg gggagtgctc cctggcgctg    1680
gcgggcggcg cgacggtgat ggccacgccg accgccttca tcgagttcag ccgccagcgg    1740
ggcctggccc ccgacggccg ctgcaagtcc ttctcggcga ccgccgacgg caccacctgg    1800
tccgagggcg cggccgtgct gctgctggcc cggctctcgg acgcccgccg cctgggctac    1860
cccgtgcacg cggtcatccg gggcagcgcc gtcaaccagg acggcgcgag cgcggggcctg    1920
accgcgccca acggaccggc gcaacagcgg gtgatccggc aggcactggc caacgcacgg    1980
ctgacggccg acagcgtcga cgcggtcgag cacacggca ccggcacccc gctgggcgac    2040
ccgatcgagg cccaggccct cctcgccacc tacgggcggg cccgcggcga gggcaggccg    2100
ctgtggctgg gctcgctgaa gtcgaacctg gccacaccc agtccgcggc cggcgcgggc    2160
ggcgtcatca agatggtgat ggccatgcgg cacgggacgc tgcccgcac gctgcacctc    2220
acggagccca ccccgcgcgt cgactggtcc gccggtgacg tacggctgct gaccgaggcc    2280
caggactggc cggacaccgg acagccgcgc cgtgcggccg tctcgtcctt cggcgtcagc    2340
ggcaccaacg cccatgtgat cctggagggc ccgcccgccg aggaggcacc ggacgcgccg    2400
ctgccggacg tctcctcgca gccgcgggcc ccgctgccgt gggtcgtctc cggccgcagc    2460
gaggcggccg tccgagcgca ggccgagcgc ctggcgcccc acctgaccgc gcgcccgcac    2520
ctggcaccgg ccgacgtggc caccgcgctg ccaccacgc gggcggcctt cgaccaccgg    2580
gccgccgtcg tcggccggga ccgtgaggaa ctgctcgccg gcctcgcggc cctggccacc    2640
ggaacccgcg cgcccggcct ggtcaccggc cggaccccgc cgtccggcgg caaggccgcc    2700
ttcctcttca ccggacaggg cagccagcag cccggcatgg ccgcgaact ggcggctcac    2760
agcaccgtgt tcgccgacgc cctggacgag tctgcgccc agctcgaccg caccctcgac    2820
cggccgctgc gcaggtgct gttcgccgcg gacggcacgc ccgaggccgc cctgctcgac    2880
acgacggcct acacccagcc gcgctgttc gccgtcgagg tcgcgctgct gcggctgctg    2940
gaggactggg gcttgcggcc cggcatggtc gcgggccact cggtcggcga actgaccgcc    3000
gcctacgccg ccggggtctg gtcgctcgcc gacgcctgcg ccctggtcgc gcccgcggc    3060
cggctgaccc aggcactgcc gcgggcggc gccatggtcg ccgtgcaggc gaccgaggac    3120
gaggtgcgcg cccaactcgc cgacggccgc cccggcgtgg acatcgccgc cgtcaacgga    3180
ccggaagcgg tggtgctgtc cggcgacgag gccgccgtca ggacctggc gcgcgagtgg    3240
gccgcccggg gccgggagac caggaggctg cgggtcagcc acgccttcca ctccgcccac    3300
ctggacgcca tgaccgaggc gttccgcgag gtcgtccacg agggtgtccta cagcgcgccg    3360
tccctcccgg tggtctccac gctcaccggg gccccgtca ccgacgagct ccgcaggccg    3420
gaacactggg tgcggcacgt ccggggagacg gtgcgcttcc acgacgcggt ccgcgccctg    3480
cgcgaccgcg gggccaccgc gttcctggag gtcgggcccg gcggcgtgct gacggccgcg    3540
gcacgccgat gcctgcccga cgccgccccc gagacgttcg tccccgtgct gcggcgccgc    3600
```

FIG. 22A

```
aggcccgaac ccgagtccgt gctgacggcc gtcgcgcagg cccacacgat cggcctctcg  3660
ccggcgtggg accgcctgct gcccaaggcc cggacgcgcg tggacctgcc cacgtacgcc  3720
ttccagcgcg gccactactg gctggcgggc atggccggag cgggcaccgc gcggccggtg  3780
cggccggaag tgcaggagcc caccgccccc tccggtacgc cgccgctgtc gcgacggctg  3840
gccgacgcgt cggaggagga gcgcggccac ctgctgctga cgctggtacg cgagcagtcg  3900
gccaccgtga tgggcggcgt cgaccccgcg caggtcgaac ccgaccgccc cttcctggag  3960
ctcggcttcg actccctgat gggcgtcgag ctgcgcaccg cgctcgccgc cgactgcgca  4020
ctgcccctgc cgcccggcct gatcttcgac caccccacgc ccgccgccct ggccgccttc  4080
ctcggcgagc agctcgcggc ggcggcctcc ggcaccccca cggcggcggc accctcgccg  4140
tactccctgg aggcgctgta ccgcaacgcc aacaccctcg accggcccga ggacgcgctc  4200
gccctcacca aggccgcctc ccggctgcgc ccggtcttcg ccagcgtggc cgaggcgggg  4260
caggacccgg tcacggtgga gctggcacag gccaccggcc ttccgggcct gatctgctgc  4320
ccggcacccg tgccgctgta cggggcacag cagtacagcc ggctcgcagc cgccttccgc  4380
ggcacgcgcg gagtctcggc cctgctcgcc cccggcttct ccccgggcga actgctgccc  4440
gccgacttcg aggtgatgca ggacttcctc gccgagggg tccggcggca gaccgacggc  4500
gcgcccttcg tcctcctggg ccactcctcc ggggctggt tcgcctacag cctggcggcc  4560
cacctggcgc gcaccgggcc gcgcccggag gccgtcgtgc tgctggacac ctatcagctg  4620
cacgacccgg cgctgcaccg catgcagcgc gaactcgccc agggcgtcct ggaccgcgag  4680
gaggacttcg ggcgatgac ggacgtacgg ctgagtgcca tgggcaaata cttcgacttc  4740
ttcaccgact gggtggccga ggacgccggt gtcccgacgc tgctgctgcg ggcctcgag  4800
cctctgggcg aggtcgtcga gggccaggag tggcgctcca cctggccgtt cgacagcacg  4860
gtcctcgaca cggaaggcga ccacttcgcc atggtcaacg accacgcgcc gcggacggcc  4920
caggccgtga acggctggct gtcgggcctc accggcggaa ggggctgagc gccggtggag  4980
acacgcaacg ccgaacggcc gtggatacgc agcttccacc ccgctcccca ggcccctgtg  5040
cggctgctgt gcctgccgca cgccgggggc tccgcgagcg cctacttcgc gctgtcgagg  5100
gaactggcgc cccgggtgga ggtgtccgcg gtgcagtacc ccgggcggca ggaccggcgc  5160
gacgagccgc tgctggactc gatcgaggcc ctgcgcgacg gggtcgccga ggccctgacg  5220
ccctggctgg accggccggt cgccctcttc ggccacagca tgggcgccgt ggtggcctac  5280
gagctggcgc ggctgctgtg ccaggacgcg ggcgtgccgc tcacccacct cttcgtctcc  5340
ggacgccggg gatccgaccg aagtctccgt ccttgccgcc gtgttccgga attcaccgtg  5400
acaccgccgc gcggctcttc ttccgaagtc ctccagatcc ggcacgagtt tgtatccgaa  5460
cggggttctg cgtgcgaaat actctcttcg aattgggtga catacccccg atcggcaccg  5520
tacccgagca gatgtacgcc tcggtgatcc gacgggagcg ctacggacag ccccaccagg  5580
cgttccgcag cgaggtcgtg gacgtgccga aggtggggcc cggtcaggcg ctggtcctcg  5640
tgatggccgc gggcatcaac tacaacaacg tctgggcctc cctggggcag ccggtcgacg  5700
tgatctccgc gcggcagaag cagggccaca gcgaggactt ccacatcggc gggtccgagg  5760
gctccggcgt ggtgtgggcg gtggggagg cgtcaccca ggtcgcggtg ggcgacgaag  5820
tgatcctctc cggctgccag tggacggaga cggccgccga catccggctc ggcgccgacc  5880
ccatgacctc cggctcgcag tcggtgtggg gatacgaggg caactacggc tccttcgccc  5940
agttcgccct cgtcgacgac tatcagtgcc accccaagcc gcccggcctg acctgggagg  6000
aagccgcctg cttcctgctc accggggcca ccgcctaccg ccagctgtgc ggctggcagc  6060
cgcacgacgt gcggccgggc gacccggtcc tcatctgggg cggggccggc gggctcggct  6120
ccatggccat ccagatccgg gcgctggccc gcggcatccc cgtcgccgtg gtctccgacg  6180
aggagcgggc ccgctactgc cgggagctcg gcgcccaggg caccatcaac cgcctggact  6240
tcgaccactg gggacggctg cccgacatcg cgaccacga ggcgatgggc cgctggaccg  6300
agggtgtacg ggccttcggc cggcgcttct gggaggtgct gggcgagcgc aggtccccgc  6360
gcatcgtcct ggagcacagc ggccaggcca ccatccccac ctcgatgtac ctgtgcgaca  6420
acgcgggcat ggtcgtcatc tgcggcggca ccaccggcta caacgccgac atcgacctgc  6480
gcttcctgtg gatgcgtcag aagcgcttgc agggctcgca cttcgccaac ctgcggcagt  6540
gccgcgacgt catccacatg gtcgcgaacg ccagctcga cccgtgcctg tcgtggaccg  6600
gcggcttcga cgacatcggc aaggcacacc agctgatgca cgacaaccag cacccccagg  6660
gcaaccaggc cgtcctggtc aacgcgccgc ggaccggcct gaccaccttc gcctgaacca  6720
ccgccccggt gttccgacgt cttccccca cacttaccga ccaaggagag atcaccatgg  6780
acaagctcga catcctctgg agcgagcgcg agatccgtgc cgtgctgcag cgctactgcc  6840
gcgggctcga ccgcctcgac gaggaactgg tcaagtccgc ctaccacgag gacgcgcacg  6900
acgaccgcgg cgtcatccgc ggcaacgcac acgacttcgt caagcagatc gtcccgctcc  6960
tgcgcgacgc ctacaccggc accctgcaca ccctgcacgg cagcacgatc gagatcgacg  7020
gggatgccgc gggcggtgag tcctactgca ccgcctacca ctaccgcgag agcgacggca  7080
tcaagcgggt ggagcagttc gccggcgct acgtcgaccg cttgagcgg cgcgacggcg  7140
tctggaagat cgcccgccgg ctcgtgctga acgacttcag cctcgcccag gaggtgccgc  7200
tcgaccccgc cgaggcccag gccggcttca accctccca ccgcgacctc accgacgcca  7260
gctaccaggt gctgccgctg cgcggcccgg acgcccccac cctctgagcc gtccggccgc  7320
```

FIG. 22B

```
cccaactcgc cccacctcac caggagtcac caccgtgtcc gacaccgagc agcacgcgcc    7380
cacgctgccg cggcagcgca cctgccccttt ctcgccgccg cccgagctcg aggagctgcg    7440
gcgcaccgat cccatcagca ggatgcggtt cgccgacgac tccccgggat ggctgctgac    7500
ccgccacgcc gacgtccgcg ccgcgctggc cgaccccggc gtcagctcgc accccggcaa    7560
ggcaccccag ccctggcgca acctcgcccc cgagatgcgc gccgagcact acctgccggg    7620
cttcctgatc ttcatggacc cgccggacca cacccgctac cgccgcctgc tcaccaagtg    7680
gttcaccatg cgggccatcc gcaagctcga acccaggatc gagcagatcg tcaccgagac    7740
cctcgacgcc atggaggccc agggcggcac cgtcgacctg gtgcagtcct cgcgctgcc    7800
gatcccgctg ctggtcatct gcgagctgat gggcatccgc tacgaggagc gcgaggagtt    7860
catggacatg gtcctgcgac tccaggccct ggacgccacg cccgaggaac tcggggccct    7920
cggcgccagg atgaacgagt tcatgatgaa gctcgccgcc gccaagcgcg cgaaccccgg    7980
cgacgacctg ctcagccacc tcgcccacga ccccgacgcc gacccggcgc tcacggatct    8040
ggagatcgcc ggcatcggcg tgctgatgct catcgcgggg cacgagacct cggccaacat    8100
gctgggcgtc ggcacctaca ccctgctgga gaacgccgac cagtgggccc tgctccgtga    8160
cgacatcagc ctgatcgacc gggccgtcga ggagctgctg cgccaccaga ccatcgtcca    8220
gcagggcctg ccgcgcggcg tcacccggga catggagatc gccgggcacc aggtgaagac    8280
cggggagtcc ctgctggcct cgctgccgc cgccaaccgc gaccccgccg tcttccccga    8340
ccccgaccgc ctcgacatca cgcgcgagca caacccgcac ctcgccttcg gccacggcat    8400
ccacctctgc ctgggcatgg agctcgcccg ggtggagatg cgccaggcgt ggcgcggcct    8460
cgtcacgcgc ttccccggcc tgcgcatggc cgccgcgccc gaggacatcc gctggcgcga    8520
cgaccagatc gtctacggcg tgtacaacct cccggtgacc tgggacgagg ccaagtgacc    8580
ggccccgagg ccgcggtgcg cgggtgcccc ttcggccgg gcgaggcgcc cgcgtacccc    8640
ttccacgccc ccgaccgctc ggagcccgac ccgtactggg agccgctgcg ccgcgagcgg    8700
ccgctgcaac gcgtcacgct gccgtacggc ggcgaggcgt ggctcgccac ccgctatcag    8760
gacgtgcgcg cggtcttcgc cgaccgcagg ttctcccggc agctcgccgt cgcgccggc    8820
gctccgcgct tcctcccgca ccagccgccg ccggacgccg tcctgagcgt cgagggcccc    8880
gaccacgcgc ggctgcgccg gctggtcggg aaggtcttca cgccgcgccg cgtggaggac    8940
atgcgtccgc tcatccagcg caccgccgac ggactcctcg acgcgatgga ggagatgggg    9000
ccgccgcgg acctggtcga ggacttctcc ctgcccttcg ccgtgtccat gatctgcgag    9060
ctgctcggcg tgccgcccga ggaccgcaag cggttctgcg tctggtcgga cgcgctgctg    9120
acgaccaccg cgcacacccc cgcccaggtg cgcgactaca tgatgcagat gcacgactac    9180
ctcggcgggc tcgtcgcgca gcgccgggtg cggcccaccg cggacctgat cggctccctc    9240
gtgaccgcgc gcgacgagga ggacaagctc accgagggcg agctggtgcg gctggccgag    9300
gccatcctca tcgccggcta cgagacctcg gcgagccaga tccccaactt cctctacgtc    9360
ctcttccgcc acccgcagct gctggagcgg atcaggaacg accacgacct catccccgac    9420
gccgtcgagg aactgctgcg cttcgtgccc atcggcaccg tggacggctt tccccgtacg    9480
gccaccgagg acgtcgagct cggggggagtc ctggtcaggg ccggggagac ggtcgtgccg    9540
tcgatgggcg ccgccaaccg cgaccccgag ctgttcacgg accccgacga gctggacctc    9600
gcgcggcggc cgaatccgca cctgggcttc ggcgcgggac cgcaccactg cctgggcgcc    9660
caactggccc gggtggagct ccagatcacg ctcacgacgc tgttccgcag ataccccgc    9720
ctgcggctgg ccgtgccgga ggagagcctc tcgtggaagg aggggctgat ggtccgcggc    9780
atgcacacca tgccggtcac ctggtgagga caccggcgtc ctcctgacct tcccggcgtt    9840
ctcacgccgt cccggcagcc ttccttccga cacgagccca cagaggcgtga agcgaccgca    9900
atgagcacca tcgacgaatg ggaacacagc acgaaggagg cgggcatgga ccccgcggcc    9960
ctcagacgcc tgaccgatgt ggtgcgggcg agggggcggcc cggcgcagct gtgcgtcatg   10020
cggcggggca ccgtggtcct ggaccgctcg ttcggctgct cctccgactc cctcttcctc   10080
gtctacgcgg ccaccaagcc cgtcgccgcc ctcgccgtgc acgcgctcgc cgagcggggc   10140
ctgatcgggc tggaccggcc ggtggccgaa tactggccgc agttcgcccg gcacggcaag   10200
ggtgacgtga ccgtccgtca tgtcctccag caccgggccg gggtgccggt cggccggggc   10260
atcgtgcgca cgatgcgcac cgccggcgac tgggagcgct ccgtgcgcga ccttgagcag   10320
tcccggccca agtggcccgg cggcgaggtc gccgcctacc acttcatgag tttcggattc   10380
attctcggcg aactggtgca gcgcgtcacc gggcggtcgt tccgagattt cgtgacttcc   10440
gagctcttcg ccccacttgg gctgaatgat ttgcacatgg gattgcccgg cagtgcctgg   10500
ccccggcatg tgcccgcgcg ggccgcccac ccctccgaat ggcccaatca gtggatgagc   10560
aaccgccgcg gctaccgcca ggccgtcatt ccgtccgccg gtctttccgg aaccgccgca   10620
caaatggccc gcttttacca gatgcttatg gagggcggct cgctcgacgg catccgcgtg   10680
ctgcggcccg aaactgtgga ggaagccaga aaccgtcca atgacggcgg aatcgacgct   10740
tccctcaagc gtccggtccg ctggtccac ggattcatgc tcggtggtcc gggcccggac   10800
ccgcggggcc tgtccaatgt gctgggccgc acgagcgacc cgagcgcctt cgggcacgcg   10860
ggcaccacgt ccagcgtcgt gtgggccgac cccacgcgcg agctggtcct cgcctacctc   10920
tccaacatcc agcccgagtt cggagcgggt atcgagcggc tccgcgaggt cagtgacctc   10980
gcgctcggtg cctgcgaggc aggctgaccc gagccgtgcc gccacggccc ggcgcccgcc   11040
```

FIG. 22C

```
cgatccgatc gggtccggtg ggggccggcc gggtccgggc ggggacgcac ttcccccggc   11100
gtccccgccc gggccccggt gcgaaccggg cgcaaaggcg gccgatcgcc cggcgcggcc   11160
ggatgccccc gaacggtgtg aaacgttctt atcagcctct gaccagcacc gagtgatcta   11220
ctgcacagcc cgaggccgcg attccggcag tatcttgatc ttgacggggc accaatgcga   11280
gcgggctatt cgccgcggtt ttccctgacg tcggatgcag atgacaccgg aggagggcca   11340
gtgctgaatc tgcccaaagg aatggagcgc gcgcatccgc attctccgcc acaggtggga   11400
atactcggac ccttggaagt ccgctcggcc ggaggtgccg gaacgggagc cgcggtaagc   11460
ggtattcgcg tacgcacatt gcttgccgcg ttgactgccc gcctggggca ggcgatgtcg   11520
accgagcgca tcctcaaaga ggtctgggcc gacaacccgc ccgcgaccga tcgcaaggcg   11580
gtggccgtcg ccgtcctgcg gctgcggcgg gtcctcggcg acaacgaagg acggtggctg   11640
ctcacccgcc cctccggtta cgtcctggac atcccccggg accacctcga cgccgtacgc   11700
gcggagaccc tggtgcggga aggccgggcc gccctggccg ccggcgaccc acgcgtcgcg   11760
gcccgccacc tcacgcgcgc cctcgaccag tggcggggcg agccctacgc ggacgccaac   11820
gccatctcga ccgtgtccca gcgcatcacg gagctggaga acctcaggtc cgaggccgtc   11880
caggcgcaca tcgacgccag gctcgaactg ggtcaccacc aggaactggt cggcgaactc   11940
cgctcgctga ccgccgcgaa ccccctgcac gagccgcact ggctgcagct gatgctcgcc   12000
ctctaccgct ccggcaagca ggccgaggct ctcgccgcct atatgcagct gcggcaggcg   12060
ctggccgaga acctgggcat cgacccgggt cgtcagctcc aggaactgca cctgcggatc   12120
ctgcgcgccg acgcgggcct gctgacgggg tccggggcgg cggcaccggc cgagccactg   12180
ctcgtacggc agtcctgagg gctcacggcc acccgaagaa cgcgcggtag cacggaacct   12240
gctgctcca                                                          12249
```

FIG. 22D

ORF11-22 SEQUENCE

```
cccaggacct cgtcgcggtc ccggccgcgt ggtggacctc cgccaacccc aacaacgacc    60
agctctgcca gggcatatcg gtggaggtca gctacaacgg caggaccatc agagtgccgg   120
tgcgggacaa gtgcccttcg tgcgaccgga cccacatcga cctcagcagg acggccttcc   180
agaagctggc gccgctcgac aggggtgtgg tcaacggcat cacctggaag ttcgtccgct   240
gacgccacgc cggggtcccc aaagcccggg accccggcgc tccgcgcccg gcacgccggg   300
gnccgcccgg cgtgtcggcg tgaggttcgt cgccttcaag agtcataaag acaatcgcga   360
ctgttgacgt tatgagttca tcaaatttaa ggtcgcggga ctcttggaac agatcaagac   420
gacggagaac aatgacgtac tcccccggcg cgcggccgcg cccggcccgg ctgtccgcac   480
tgctgctcgc aggcgcgctc gtcgcctcgg tgccgccgc ggccgccgcg cgagcgccgc   540
aaccccccac cgccgaccgc ccccgcaccg ccgcctcccc cacaggcggc tgccgtacgg   600
gtgacggctg gacactcgac tccacccgca tcgacccga cgacacccac cacgcctatg   660
tcggcaacgg ctacctgggg cagcgcgtac cgcccaacgg cgccggctac accgacagcg   720
acaccaagac cggctggccg ctcttcgctc cggcctacga cggctcgttc gtgtccggc   780
tctacgcgca caacaagcag accgccgccg accggcaggt gatcgccgct ctgcccacct   840
ggaccggact ggccgtcggc accggcggcg agcacggcga tatcttcaac tcttcgacga   900
agtcgggccg gatttccgga tatcaccaga ccctcttcca gagctgcggc atcgtccgta   960
ccgccctgac ctggaccgcc gccgacggcc gcaggaccga cctggtctac gaggtgctgg  1020
ccgaccgcga cgacccgcac acgggcgccg tacggctgag catgacgccg cgctggagcg  1080
gcgaggccac cgtcaccgac cagctggacg gacgcggcgc gcggcgcatg cggcagaccg  1140
gcggcggcga ccgcaccggt gggaccggcc gggacggccg caccatggac gtggccttcc  1200
gcaccgacgg cacggacacc gacggcgccg tcgcctccac cctgagggcc gggcgcggtg  1260
tgcacacgac cggggaccga cgcgccgcgg ccgcgaagga cttgagcgtg aaccagtccc  1320
tcacgttccc cgtccgtgcg ggccacgcgt acgaactcac caaatacgtg ggtgtcgaca  1380
ccgcgctcac ctgcaccgcg ccccgcgagg acgccaccac cgcctccctg cgcgccgccc  1440
gccgcggctg ggacgggctg ctgcgtgccc acaccgccgc ctgggccgg ctgtggcgct  1500
ccgacatcga gctgccggga cagcgcgacc tccaggcgtg ggtgcgttcc gcccagtacg  1560
ggctgctgtc cagcacccgg caggggcat ccaacagcat cgccccggcc gggctgacca  1620
gcgacaacta cgcgggcctg gtgttctggg acgccgagac ctggatgtac ccggccctgc  1680
tggccaccgc gccccaactc gccaggaccg tcgtcgacta ccgctaccgc accctcgccg  1740
gagcgcgcga gaacgcccac aagctcggct accaagggct cttctacccc tggaacagcg  1800
gcagcgaggg cgacctggcc caggagtgcc acagcgtcga cccgccccac tgccgcaccc  1860
agatccacct ccagtcggac atctccctcg ccacctggca gttctacctc gccaccggcg  1920
acaccgcctg gctgcgcgag cgcggctggc cggtgatgga gggcatcgcc gaattctggg  1980
ccgggcgggt cacccccaac gccgacggca gctactccat caaggacacc gccggccccg  2040
acgaatacag caacggcgtc gacgacgcgg tcttcaccaa cgccggtgcc gccaccgccc  2100
tgcgcgacgc cgcccgtgcc gcgcggctgc tgggcgagcg cgccccggcg gagtggacga  2160
cgatcgccga ccggatccgc atcccgtacg acgcgcggca caaggtcttc gagcagtacg  2220
acggctaccc gggcagcaag atcaagcagg ccgacacggt gctgctgatg taccccctgg  2280
agtggccgat gtcccaggcc gacgcggcgc gcaccctcga ctactacgcc cggcgcaccg  2340
accccgacgg ccccgccatg acggactcgg tccacgccat cgacgccgcg ccacgggcg  2400
agccgggctg ctcggcgtac acctatctcc agcgttccgt ccggccctc gtgccgggtc  2460
ctttcgacca gttctcggaa gcccgcggca ccaaggccgg cgccgacgac ccctggccgg  2520
gctcgcccgc ccacgacttc ctcaccggca agggcggctt cctccagatc ttcaccaacg  2580
gcctgaccgg catgcggatg cgcgaggacc ggctgcacct cgacccgatg ctgccccgc  2640
agctcggccg cggcgtcacc ctgcgcggcc tgcactggca gggccgcacg tacgacatcg  2700
ccatcggcgc ccacgagacc accgtgcggc tcaccggggg tgcgcccatg accctctaca  2760
ccccgcaggg cgagcacgtg ctgaccaagg cggcaccggc cgtgctcaag cccgccgcc  2820
ccgacctcgc tcccaccgac aacgtggccc gctgcaccac cgccggtgcc cctccgagg  2880
aacccggtat gtacgcggca ccgcggtcg acggcaaccc cgccaccgcc tgggtccccg  2940
acgggccgaa cggtgaactg accaccgacc tcggcaagtc cgtacgcgtc accaaggcca  3000
ccccgtctg gagcggcccg gcaccggcct cgtacagcgt ccagctctcc ctcgacggcc  3060
ggcactggca cgacgcggtc gcgggcggcg ctccggtgtc cgcgcggtac gtacgcgtcg  3120
cgctacgcgg tcaggccgat gccaagtccc gtacgggcat cgccgagctg accgttacgt  3180
agggcaccag cagcccgcgc gcccgggctg gatgacgacg aggatccgcg ggacttcacc  3240
cgccctcggc cgacagggac gtcctgacga gagcgagcac gtcgtcgtcg ctcagcccca  3300
gcgcgcgggc gtcggcgacc aggcgcgggg cctgcacggt gagccgggcg cgctcggcgg  3360
tcgaccctcc ggtgacgacc gccccgcgcc ccggcgcag ttcgaggagg ccctcctcgc  3420
gcagccgttg gtagccacgg agcacggtgt gcatgttgac cccgagcgac gcggcgagat  3480
cgcgggcgga cggcaggcgc tcgccggagc gtacggtgcc gtcggcgatg caccacgga  3540
cgcatgcggc gatctggtcg cccaggggga ggggggacgc ggggtcgacg cggaagagca  3600
```

FIG. 23A

```
cggtcacccg cccgcggagg tgcggcgttc gcggtcggcg agggtgttga gcagcgcggc    3660
ggccgtggcg gcgtcgtcga cggtgacgac gaactcgctg ccggtggtca gacggacgct    3720
gatggcgtcg ccggaacgca gcacgacgcc gctcgccccg gaacggaccc ggtagcccca    3780
gccaccgaag tcccgcagag gcttgaccgg acggtgaccg gcttcggcga tccgctggag    3840
cggcacgttg atgcgcggcc aggggacggt cgagggcgtg acggtgagcc cgcgccggtc    3900
ggcggtcacc cggacacccg tcagcagggt catggcggct ccgatgagga acagcgacag    3960
cgcggacagc catccggcgg cgaccccgac gacgacgccg gaggcgaaga ccaggacacc    4020
ggtgaggggc agcacccggg agcccgccac ccttgaccag ccggcgatct cggagtcgcc    4080
gagcgcgaga cgcgaggcat cggcggacgg cccggaatcg ctgtcggctc cctggtcctt    4140
gccacaggcc gcccagccca ccgccgcgta gagcgcagca gccccgaaag cgagcgcggc    4200
ctgcgccccg ggcaaggtga cggaagaggc gtcgtggaca ccggtgttgg ccagcagcac    4260
ggcggtggcc agccatccgg tcagcaccgc gacggcgccg ccgatgacgg ccagcacgcg    4320
ctgtccgccg ttgcccggcc gcgtgaagta cgagcgcg ccgaagagga caccgtcgcc    4380
cagcagcact cccccacgcga cgccgaggaa ggagccctgc cccgagaagc cgtcggcatt    4440
ccctcccggc ccgatgtgcg aggcagatccg cccggggcagc cggtcccgca ccgagaggaa    4500
cacccacagg acgacggcag cgcagaccag aggcggcacg acggagacgg caaggcgacg    4560
gacgaggacg gacgaggacc gtgacagcgg catgagagca aacctccact tgtttgcaca    4620
ctagtagaac aagtggaggt gaactcggcg aaggcggctg cctcttcctg acgcgttccg    4680
aacgccaccg gagccgccac gactgaccca gtgtcacccc gcgggaggcg gaacgcttca    4740
gtccgtgccg ggagcggcgg ccgcttcccg tggtgcgact ggtggtgtct gcgtggggcg    4800
gcgcatgagc ggcaggcgga gccgccggat gcccggcccc gagggaggtg ccagtctgcg    4860
cgtggacctg tggaagacga gcaggctgac ggcggcggct ccggcgaacc aggccagttg    4920
gacggcgagg tagccggaga cgggagcggt cgagaagccg gccgcggcac cggtctgcag    4980
cgagccgtag gaggggagga gcgtcacgag gccgccgttg gcggcgccgc cggtggtgac    5040
ggggttctgc aggcccgcgt cgagaccgct ggtcatcacg atggcgaaca tccccctcgac    5100
gtcccggcgc agcagggagc cgaagacgat gccgatggcg ccgtaggtca gggacgcgca    5160
gaacagggcg gcgacgaaga ggaccggccg gcggggcgac cagaaggcgt aggtgatggc    5220
ggtggcgtag acggcgacgg tggcggagat gagggtgagg gcggtgagct ggcgagaag    5280
gaggtggacg cgccggtagc ccgccatgga caggcgtcgg tcgaaggggc cgctggtgaa    5340
ggtcgcggcg aacatcatga agccgacgat cagggtgatg gagttcagcg ccccgacgat    5400
cgacgtgagt tcgttgcccc gcgggtggga gatctgcccg gtctcgtgca gcctgaaggg    5460
gatggcgggg tcttcgatga cgcagtaggc cagcgtgatc cacaccggga tgaacgcggc    5520
gatcaggccc atggcgagcc ggttgcgcag gtgctcgacc aaggcgaacc gggtggcggt    5580
gacgtagagg gttgtgtggt tcataccggt gccgtcgtcc ttgagtgcag cagtccgccg    5640
tcgaggtgcc ggagttcgtc gagccgttcg gcgtcgtagg ccaggtggga gacgaccagc    5700
acggaccgcc cgcgttcgcg cagaccggcg gccaggctcc agaaccgctg gtgggtgtcc    5760
cagtcgaagc cctggtaggg ctcgtccagg aggagcaggt cagggtcgtg catcagggcc    5820
agtgtgaggt tgagcttctg tttcgtgccg ccgctgagca cgctgacccg ctcgtccccg    5880
tagtcggaca gccggagcac gtccatgatt ctctcggcat ggctgagggt ggcgaggccg    5940
tacgccaccc ggaaatactc caggtgctgg cggacggtga gagcctggtt caggacgaga    6000
tgctgcgggc agtaaccgaa ccggccgccg tagtggacct gcccgcgctg cggccgcagc    6060
tcaccggcga ggatcttcag gagcgtcgac ttccccgcgc cgttctcgcc cacgacgccg    6120
gccagcgttc cggggcgcag ggacaagtcg atgccgcgca gcaccctgcg ggtgccgtag    6180
gtgtggtgga cgtccctgac gtccaggaga ttccggggca cggcttcctc tcctcaggcg    6240
acctggtcgc gccggacgac cgagagggcc agctcgtaca acaagtggct gtggcctgcc    6300
gacggcagca ggggctcgag cttgttccac gcgtcgctca ccaactggtc ggcttcctcc    6360
aggcaggctc tcaccgctcc gcaggcgttc aggtcccggc acacctcggc caccgccgtc    6420
gcgctgcccg agccgtcctt gacctgctgc cagagctggt tcagccgggc tctgcggcag    6480
ccggaccacg gcgtgggcca gtggcatggt gaccttgccg ctccgcaggt cctcggtggc    6540
ctgcttcgtc ggtgccccg cccgtgtgac accgctcagg tcggcgcagt cgtcggcgat    6600
ctggtaggcg gtgcccaccg ctgaaccgaa agccccagt gctctccgca gttccggctc    6660
ggcacccgtg acgacccctg ctgcctccat ggccgccgag accggggccc cggacttcaa    6720
ccggtgtgtc agacggacca gttccagcac agtgtgccgg tcgtcgccgg ccacggcctg    6780
gtccatctct tcccggtgac cttggagatc cagtgcctga ccggcgtgag ccgctcgcag    6840
cgcggccaga cccagtgccc gcaactcccc gcaccgcgag cgtcgtcgg gaaaggtgag    6900
ctgaacggcc cgctcccaga ggaaataggc ggccgtaccc gcgttcaccg cagtcggcat    6960
gccgaacatg gtgtgcacgg ccggttgtcc gcggcgcagc ggtgaggcgt cctggacgtc    7020
gtcgacgatg agggatccgg tgtggagcag ctcactcgcc gcgatcagca ggccgcagga    7080
ttcgctgtca cctcccatca gaccgatggc ctcccaggcc agcaccggcc gccagcgctg    7140
tcctccggca tcggtcagat ggcggacggg agaggtcagg gcccggtgca ccgctgggc    7200
gacgaccggc ggcgtgccag gcccggtcgt cccggtgatg tggcccggtg cagccacgt    7260
ggagcaagca tctgccgacg cgttcgggca caggcggtcg atgtgatggt tgatgcgttc    7320
```

FIG. 23B

```
ggccgtgcgg tcgatgcgct gccggatgaa gtccgcgttc gccgcgaaag tcggggagat    7380
gtccctggga cagaggaggg cgccggtcat ggagtggtca gctttcggtc aggggcggc     7440
gatggacgag gctccctcat ggggtcgccg gcccgatgcc gcggagggac tgctcgggca    7500
cggctcgcgg agtgcggcga tcatggtcag gccgcgtggc atcgcggcga gttcgaagcc    7560
ggagcgcacc gtccggcccg gacgcgccgt gcgtacggtc cgcgtggcga ccagagtggc    7620
gagcgcgacg ggcaccatga cgtcggccac cgcggcacca gggcagtagc ggggcccgag    7680
cgcataggga agccaggcag caggggagac cgagggctga gcgtccggca tccagcgcgt    7740
cggatcgaag acatcaggcc gttcgaagtg ggcggggtca cggctcatcg ccccgaggtg    7800
gaggaacacc gtcgccttcg cgggcagccg gtggccgccc agccacgtct cgcggcgcgt    7860
gcaacgcaca aggacccgga ggccgtgaag ccggatgact tccttgacga aggcggctgt    7920
ccggggcaac cggtttattc cgaccgccgg ctgcgagtgc cccaggccga gtgccgcgtc    7980
ggcctcctcc tgcaaggcct gttgatggtg ggggtggcgg cccagttcgt agcaggccca    8040
cgcgagtgtc gaggcggtgg cctccccgcc ggtgaacagc agcgtgcgca cgtcctgcac    8100
cgccgcttcc gagggctcgc gccacgcttg cttcagcagg gagaccacat cacaccccgtc   8160
ctcagccggc cgatggcgcg cgaggacttc ccgggtggcc tcgtccagca ccgcgagggc    8220
acggcggagc gcgcgttgtc ttggcacggg tacccaaggc cacggggaca ggagaaaccg    8280
caaggccccg acctgcgaca gcgtggcatg cgccgcggcc agcgcggtca gcgttccggg    8340
cgagacctcg ctgcgcaaga cgcacctgac ggcgagatgg aaagtgagcc gggtcatctc    8400
gtggctcatg tcgaccggac ggtccgcggg aagggtggcg agcagacttc gggtctcggt    8460
ccgcacggac gccccgaggt ccgccggccg gggcacggcg aacgcgggcc tcatcaccgc    8520
ccgccggtca cggtggaccg ttcctcggt gctcagcagt ccctctctta cgatcacccg     8580
cacatggggt tccctgcccc agaacatgaa ggtgtcctcg tcgcgagcag cctgccggat    8640
cagcgaggag tcattgagca ggtacccgac gaacgggccc gccttcaccc tgaccacagg    8700
ccccgccttg ccgagccggg ccgcgatctc cctcagatcc atcaagaacc gcacggagcg    8760
ggcatgcccg agcaaccgac tgcagtcagg agccatcggc acaacggagt ccgccttcga    8820
atctccgttc atcaggcgtc ctcccgcccg catgtcaccc tctgtcctcc tgtgaacgac    8880
caggagtgag gagtgtcacg cagagcatca cctgctgtat cggcagcaat gccgacccgc    8940
accgacggct gggcggggcg accgggaacc gccttgcggc tacgccgtgc tcgcgtgcct    9000
gaagcgcacc gtcacattca ccggtaccca cgacagaggc gggttcgcgg ccacctgtat    9060
ggacgcccgc tgaatgggga cggagtgcag ggggtgctcg atggcggtgc cttcgcggct    9120
cagcaggccc tgcctcgcgg tttgagcgca acggcggca gttcgggagc aggcagtcgg     9180
gcccctcgt agccgtgcac ctcgccgaag cgggagccgg tcgcccgagc cgtcgccgcc    9240
gccggcccga ttcgccatcc ggatggaaga ggacaccgcg cagggaccgc cgcccacttc    9300
accggaatcc tctccaccgg aaaatttatc cgcaaacctg tcacatcttc gacacatgaa    9360
gcgtcagggc ggtgacggca gttgaagccg ttgcccgacg acgccgaagg agaccgtggg    9420
acagctacgc acgtgcgggc cctggagcgg tcggccacgc cgacaggaat cggccttccg    9480
ccgctgatcc ggcctccag cgttcgcgaa cacctcttgc cacacctccc gcgcggcccc     9540
cgcattcgag cggtcggctg acgacgccct gcgacgccgc gcacaccacc cacgcacctc    9600
gccacgccga aggctgcccg aaaacaagaa gaccgaggaa agcacacatg aagatctctc    9660
gaataggccg cgcgtcatcc atcgccgccc tggtgacaac cgcactcgct ttcacggcag    9720
ttggcaccgt cgctcccacg gccgtcgccg actcccgcgc ggccgccgct tccgggacgc    9780
agaatgacca cccgagctcg gggcagggca cctccacctc tgagctccgg cgcaagggcc    9840
tggtcccgtc gagtcgtg gccaagccca tcacccgcag cgagaccctc agacgcgccg     9900
ccagctggtt cggcaagggt ctccactaca gcggggacaa cacctatcag ggctggcgca    9960
cggactgctc cggcttcgtc tccatggcct gggggactgc cggcccgggt gagaccaccg   10020
attcgttcat tcccggggc gtggcccacg aaatctccaa ggacgaactg aagcccggcg    10080
acgcgctcaa caacaaggcg ctcggcaacg acggtcacgt cgtcctgttc gagaagtggg   10140
ccgattcctc ccagtcctcc tactggggtt atgagttcag cagcagcggt ctgcaccacc   10200
gtgtgatccc gtacgcctac ttctccaggt ccgagcagta ccgcccgatc cgcttcaaca   10260
ccatcgtgga cgacgacacg gccgcagggc ccgccgagga caacgcccgg gtccagggtg   10320
acttcgacgg cgacggccgc gacgacgtgg cggtgctcta cgactacggc aggaaggacg   10380
accgcagtcg ctcggccctg tggacgttca acagcaacgg cagcggtttc aacagtccca   10440
agcaggtgtg ggacagcggg acgtcggaga gctggaactg gcctccagc aagttgacgg    10500
tcggtgactt caacggcgac ggcaaggccg acatcggcgt cctctacaac atgggcgcga   10560
ccgaggacgg ccgcaaccgc accaagctgt tcgtgttcac cagcaccggc agcggattcg   10620
ccgccccggt caaggtctgg acagcaacg acgacccgt gaagagctgg aactggaacg     10680
ccagcaagct caccgtcggc gacttcaacg gcgacggcaa ggccgacatc ggggtgctgt   10740
acgactacgg caaggacgac gaccacaacc ggacagggct ctggacgttc accagcaccg   10800
gcagcgggtt caacagcccg aagcaggtgt gggacagcaa caacgacccc gtgaagagct   10860
ggaactggga agccagcaag cccgtctccg gggacttcaa cggcgacggc aaggccgaca   10920
tcggcgtcct ctacgactac ggcaagaccg actccggcag ccgcaccgga ctctggacgt   10980
tcaacggcaa tggcaacggg ttcaacagcc cgaagcaggt gtgggacagc aacaacgacc  11040
```

FIG. 23C

```
ccgtgaagag ctggaactgg gaagccggca agcccgtttc cggcgacttc aacggcgacg   11100
gcaagagcga catcggcgtc ctctacgaca tgggtcgcac cgaggacggc cgcaaccgca   11160
ccaagctgtt caccttcacc ggcacggcga ccggtttcaa cagcccggtc aaggtgtggg   11220
acagcaacga cgaccccgtg aagagctgga acgcgtccgc gagcaagccc gtcgcaggtg   11280
acttcaacgg cgacggcaag gcggacatcg gcgtcctcta cgactacggc aagaccgact   11340
ccggcaaccg cagcggactg tggaccttca ccagcaacgg cagcggcagc gacagcccca   11400
agcttggctg ggacagcagc gcggacgccc tcaagagctg gaactggagc gcgagcaagc   11460
tcggctgacc ggcttcgccc ctcctcacct caccgttcgg gagagtcacc gcacatgcga   11520
accatacgaa tacgaagaac gaacggcgtg gccttcgccg ccgctgccgc cctgatggcc   11580
ctcgtcgcct ccggcaccgc cacggtccag gccgcgccct cgcacgccgg accctccggc   11640
accactccga tcacctaccg tggcctcacc ctcgacatac cctccgggtg gccggtcgtg   11700
gacctggaga agacccgca cacgtgtgtg cggttcgacc gccacggt gtacttgggc   11760
caccccggca ccgaacagtc ctgcccctcc catctggtcg cggacaagac ggacgccctg   11820
atattggagc cgatcaccgg agcgggcggc caggacgcct cccacgcgct gcgcatccct   11880
gccggggccc cgatgccgca cgagctgccg gtgacgtacg accacgagac gaaggtcgcc   11940
gtcgaaggcg ccggagtcat ggtcacgtcc tcctacggca cgtccagtac aacggtcgcc   12000
gccgtcctcg gctcggcccg cacggacgcg acagccaagc cgacccccct gcccggcaag   12060
gcgggcaggg gcctcgcggc tccaccggtt gccgccgtcg cggccgacaa gggatacaca   12120
gggctgggct tcgagtcctg caccgcccct tcgtccgccg cgatgaaggc atggaaggcc   12180
tcgtcgccct acggggccgt cggcatctac atcggcggtc gcaagcgggg ctgtgcgcaa   12240
ccgcagctca ccggcgactg ggtgcgtcag cagaccgccg acggctggca cctgctgcct   12300
ctcttcgtgg acctccaggc cggcgacatc tctccggcca ccgcggacgc gcagggccgc   12360
gagtccgcgg acgccgccgt ggccaaggcg gcggacctgg gcctgggccc cgggacggtc   12420
atctacagcg acatggagca ctacgacagc cgctcgtacc gggcccgggt catcgactac   12480
gtgtcggggt ggaccagccg cctccacgaa catggctacc gctccggtgt gtacgcgggt   12540
gaaacgagcg gcatcccgga cctcgcctcg gtgccgacga acaccaacta cgcatcaccc   12600
gacgtgctgt ggtcggcgaa ctggaacctc aaggccgatg tgtcggacgc gtcgatggga   12660
cttccggggcc ccggctactg gcccaatggg cggcgcatcc accagtaccg cggccaggtg   12720
aacgacacct acggcggtgt caccctcgcc atcgaccgcg actacgtcga tgtcgccgcg   12780
gactcggccc tgcccgcacc cggcggagag gacggttcct cgcgcgtcaa gggcgacttc   12840
gacggcgacg gccgcgacga cgtggccgtg ctgtacgact acggcaagga gggcggcgtc   12900
agccggtccg cgctgtggac gttcgcgggg accggcagcg gcttcggcgc cccgaagaag   12960
gtgtgggaca gcggatcgga cagctggagt tggtcggccg ccaagctgac ggccggcgat   13020
ttcaacggag acggcaaggc cgacatcgcg gtcctgtacg acatgggtcg cactgaggac   13080
ggccgcaacc gcaccaagtt gtacgagttc accagcaccg cagcggatt caacagcccg   13140
gtcaaggtct gggacagcaa cgacgacccc gtcaagagct ggaactgggc ctccagcaag   13200
ctgaccgtcg gcgacttcga cggcgacggc aaggccgaca tcgcggttct gtacgactac   13260
ggcagggacg gcgaccgcag ccgtacgggc ctgtggacct tcaccagcac cggtgccgcc   13320
ttcaccggcc ccaagctggt gtgggacagc aacaacgacc cggtcaagag ctggaactgg   13380
aacgccagca agcccagcc cggcgacttc aacggcgacg gcaaggccga catcggcgtc   13440
ctctacgaca tgggtcgcac cgaggacggc cgcaaccgca ccaagctgtt caccttcacc   13500
ggcacggcga ccggtttcaa cagcccggtc aaggtgtggg acagcaacga cgaccccgtg   13560
aagagctgga actgggacgc cgtcaaggta gtgggaggcg acttcaacgg cgacggcaag   13620
agcgacatcg gggtgttgta cgactacggc aaggacggcg accgcagccg caccggactg   13680
tggaccttca ccagcaacgg cagcggggttc aacagcccga agcaggtgtg gacagcagc   13740
aacgacccgg tgaagagctg gaactgggcc gcgagcaagc cggtcgcagg ggacttcaac   13800
ggcgacggaa aacggatat cggcgtgctc tacgactacg gcaggaccga ttccggcaat   13860
cgcaccggac tgtggacctt caccagcgac ggcaccggat tcgtacacc cctcctgggc   13920
tgggacagcg tgacggatgc cgtgaagagc tggaactggc gtgccagcaa ggtgagttga   13980
cacccctcct gtgagacatg gggcactcct cgacgcccgt ccggcccggc tgcggcccgg   14040
ccggacgggc ccgtcattca atggaaggaa gaagtggatc ccttgacgcg caagacccgc   14100
acccccgca agaagggcag acgcgcgagc gcggcggcga tgtcggcctc cggcatgctg   14160
ctcgccttgg tggccaccgc cgccccgtc cccgcccagg cggcatcact cgccacctgg   14220
gaaaagatgg cccagtgcga gagcagcggg gactggggat acaaccagcc accgtactac   14280
ggcggcctgc aattcctgga gagtacgtgg gtggcgtacc acggaacgga ctatgcgcca   14340
taccccctatc aggccaccaa ggaacagcag atccgggtcg cgcagcggct cctcgacaat   14400
gagggcgcgg ctcctggcc gtactgcgga aagaaggtgg ggctggctga cgacgacgca   14460
cgcccctccc ccgacgcgcc ggacgacgcc gcctccgccc ggatcaacgg tgacttcgac   14520
ggcgacggat gcgacgacgt ggccgtgctc tatgactacg gcaaggaggg cggcgtcagc   14580
cggtccgggc tgtggacgtt ctccgggagc ggtaccggcc tcggcagccc gaagaaggtg   14640
tgggacagcg atcggccag ctggagttgg tcggccgcca aactggccgt cggcgatttc   14700
aacggcgacg gcaaggccga catcgcggtc ctgtacgaca tgggccgcac tgaggacggc   14760
```

FIG. 23D

```
cgcaaccgca ccaagttgta cgagttcacc agcaccggca gcggattcaa cagcccggtc  14820
aaggtctggg acagcaacga cgaccccgtc aagagctgga actggaacgc cggcaagctc  14880
accgtcggcg acttcaacgg tgacggcaag accgacatcg gcgtcctcta cgactccggc  14940
aagaccgact ccggcaaccg caccggactg tggaccttca ccagcaacgg cactggattc  15000
aacagcccga acaggtgtg ggacagcaag agcgacccgg tgaaaagctg gaactgggcc  15060
gcgagcaagc cggtcgcggg cgatttcaac ggtgacggca agaccgatat cggggtgctt  15120
tacgactacg gcaaagatgg cgaccgcagc cgcaccggac tgtggacctt caccagcacg  15180
ggcagcggat tcaacagccc caagcagacc tgggacagcg ggtcggaaag ctggagatgg  15240
tcggcggcca aggtggtcgg cggcgacttc aacggtgacg gcaaggccga catcggggtg  15300
ctgtacgacc tcggcaggaa cggcgaccgc aaccgcaccg aactgttcac gttcgcgggc  15360
aacggcaccg gcctcaacac accggccaag gtgtgggaca gccaggacga cagcgcggtg  15420
aagagctgga actgggccgc gagcaagccg gtcgcaggtg acttcaacgg cgacgaaaag  15480
acggatatcg gcgtcctcta cgactacggc cagaccgact ccggcaaccg caccgggctg  15540
tggaccttca ccagcgacgg cagtggattc gccgacccca agctcacctg ggacagccgg  15600
accgaccccg tcaagagctg gaactggaac atgagcaaga ccggctgagc cattcatgcc  15660
gtacagaaga gaagaggaag gatgaaatac cgaccgggaa cactgctcac ttccataaca  15720
gtcttgtgtg ccctgctcgt tccggtgcgt tcggcggctc aggcggccag gcccgagcag  15780
ggacgttccg tggtggccgc ggccgccgta ctggagcaaa gtccgccgac gctgctcgcc  15840
gagccggaaa tgcgcgtcgt ctcctggaac atctgcggtg aggcgggcgg ggtgcgcggg  15900
gagggcggct actgccccta ccgcaacgat ccccaggcga aagtcgacca gatcgcgcag  15960
gtggtcgcgg agcgcagtgc caatgtcgtc atgctccagg aagtgtgcgg cgaggcgccc  16020
ggcagccata tggagcggct gcgcgcggcc ctgggcagcg gatggtcgat cgcgcacgcc  16080
ccgggggccc gcccggacga cggaaccacg aactgccggg gcgggctcag cggcatattg  16140
ggcgtgggga tcgcggtgaa ggggcgcgtc accgacacca ccgcgacgaa caccgtgccc  16200
gggggcggcg gtgacaagca gaccctgccc atcctctgtg tacgtgtcga gggctggtcg  16260
tccaggatct gcaccaccca catcctgtcc gaccctgccg atccgcgcag gccggggcag  16320
atccagaacg tcaagaacga gatctggccg gaccgctatc agctggtgct cggcggcgac  16380
ttcaacatgt tccccgactc cgccgggctc aagccgatct cggacgaatt cgacgagtgc  16440
gaccgccgct cctacggcgc cggtgacatg gtcaacgagg tcacccatca ctcctgggag  16500
aaaaagggcg gacacatatg gcgcaagcgt gaccacatct tcgcctcgtg gggagagtcc  16560
gggagccagt tcacatcctg cgaggtcgac cggacccgga tggacaccac cgagaacgcg  16620
cccgaaagcg gtccgcccaa cgggtattcg gaccatgcgc cgatcatcgg ctacctcaag  16680
ccgccgcggc acctgagcac gtccggggac ttcgacggcg acggcaaggc cgacctcgcg  16740
gtcctctacg ggcagggaa gaccccggac ggccacaacc ggtccagcct gtggatctca  16800
ggcggttccg gtaccggagc ggagaccgga ttcgccgcgc cgcgcgaggt ctgggacagc  16860
ggtgccgaca gctggaactg gtccgcgagc gcgctgacct ccggggactt cgacggcgac  16920
ggcaagaccg acatcggcgt cctctacaac tacggcaggg acggcgaccg caaccgcacc  16980
gcgctgtgga ccttcaaggg gacatcgaac ggcttcgagg cgccccgcaa ggtgtgggac  17040
agccacgacg acacggccgt tcccagctgg aactggtcca cgagcaagct cgtcgcgggc  17100
gatttcaacg gcgacggcaa agcggacatc ggcgtcctgt acgactacgg caggaccgcc  17160
tccggcaacc gcaccggact gtggaccttc accagcaccg gcaccggatt cggcaagccc  17220
cacctggcgt gggacagctc caccgacccg gtgaagagct ggaactgggc cgcgagcaag  17280
ccggtcgcag gtgacttcaa cggcgatggc aagaccgaca tcggcgtcct ctacgactac  17340
ggcaaccaca ccgccctatg gaccttcacc agcaacggca ccggattcgc cggccccaag  17400
caggcctggg acagcggacc ggagaactgg aactggtccg ccgccaagcc ggtcgccggg  17460
gacttcgacg gcgacggcag gaccgacatc gcggtcctgt acgactacgg caggaccgcc  17520
tccggcaacc gcaccggact gtggaccttc accgcaccg gcaccggatt cggcaagccc  17580
cacctggcgt gggacagctc caccgacccg gtgaagagct ggaactgggc cgcgagcgag  17640
ccggtcgctg gtgacttcaa cggggacggc agggccgacc tcgcggtgat gtacgactac  17700
gggaacgcga ccaacggccg caaccgcacc gcgctgtggt ccttcaccag ccgcggcacg  17760
gacttcgccg ccccgcgggc gaactgggac agcagcaacg ccgctgacca gctgaaatcg  17820
ggcgagctga gggcggctcc gctcagcggg tcctagttct ccatgatcgg tccgtcgccc  17880
tccagaccgg ccgctctccc ggtcagcgtc gcggccagtg cgtcagcgtc gcgaccgagt  17940
ccgtaacagc gcatcccggc gatcgcgaag tacgccggt cgagccagac gcgggccgcg  18000
ccagtgctgc cgcgcggcga agtacggcga gctc                             18034
```

| Amino Acid | Codon |
|---|---|
| Phe | UUU, UUC |
| Ser | UCU, UCC, UCA, UCG, AGU, AGC |
| Tyr | UAU, UAC |
| Cys | UGU, UGC |
| Leu | UUA, UUG, CUU, CUC, CUA, CUG |
| Trp | UGG |
| Pro | CCU, CCC, CCA, CCG |
| His | CAU, CAC |
| Arg | CGU, CGC, CGA, CGG, AGA, AGG |
| Gln | CAA, CAG |
| Ile | AUU, AUC, AUA |
| Thr | ACU, ACC, ACA, ACG |
| Asn | AAU, AAC |
| Lys | AAA, AAG |
| Met | AUG |
| Val | GUU, GUC, GUA, GUG |
| Ala | GCU, GCC, GCA, GCG |
| Asp | GAU, GAC |
| Gly | GGU, GGC, GGA, GGG |
| Glu | GAA, GAG |

FIG. 24

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

FIG. 25

MC-BIOSYNTHETIC-GENE SEQUENCE

```
gtccgggccg gcggcaccgg ccgagccact gctcgtacgg cagtcctgag ggctcacggc    60
cacccgaaga acgcgcggta gcacggaacc tgctgctcca gcatatggat gccgtggtgc   120
acacggcgcc cggcggtggc ggccgcgctc agcagcgccg tctcgtgcgg cttcatgacg   180
acgtcgacca ccacggcatc cggtcgcacc ctcgcggggt cgaagggcag cgggtcctcg   240
gaacgcatgc ccagaggcgt cgcgttgacg gcgaaatcgg ccgcctccag atcgccgggc   300
cccagcgccc ggatcccgtc cggccggcgg gacccgagcc gcagcagcag cgcgtcgagc   360
tgggcgcggt cggtgtcgtg cacggacacc cgcgggcgt cggccatcag cagcgccgtg   420
gcgatcgcgc tgcccgcccc tccgcgccg accagtgcca catgcctgtc gcgcaccgtg   480
tgcccggccg cctgaagacc ctggacgaac ccgagcccgt cgaagttctc ggcgtaccag   540
cggccgtcgg gttcgcgccg catcgcgttg gccgtcccga tgagggcggc cgccggcccg   600
agcccgtccg cgagcccgca cagggccgcc ttgtgcggca cggtgaccag cagaccgtcc   660
agattgccga tccgcttgag ccccctcgacc acctcggcga gatcccgcgc ccggacgtgc   720
accggcacca ccacggcgtc cagaccgctt tcgctcagca ggggggttgag cagaccgggc   780
gccttgacct gggcgacggg atcacccagc accgcgtaca gccgcgtggc gcccgagaca   840
ccggccgccg gcccgaggaa ttccatcagc cgatcctctc tgtaccccg acggatgttg   900
ccctacggtg ctggagatgc tccacagctt tgccgtgacc gccggtcggc acaaccctgc   960
gtgcccctga cgcgccaggc cctccaggta gttgctcccg gcggatccg acagctcccg  1020
accggtcccg acggagggaa gaagccatca gatacctggg aatcgacgtc ggaggcacga  1080
aggtcgccct gcgggtgacg ggggacaccg acggtgcggg cggcggcgac gtgacgttcc  1140
gctggcccgc cgccggcgac gtcaccgcgg atctggacct gctcgccgcg cgggtccgcg  1200
gtcttctggg acaccgcgag gaccccctcg ccggggtcgg cgtggccatg cccgcgatct  1260
gcgacgcggc cgggacggtc cgcacgtggc cgggacggcc gagctgggcg ggcctgaacc  1320
tgacggccgc cttcgggcag ttgctgcccg gcaccccggt cgcctgcgcc gacgacggtg  1380
acctggccgc gctggccgga tcccgcgccg ccggctgccg gcatctgctg tacgtggggg  1440
tcggcacggg catcggcggc ggcatcgtcc atgagggccg cgcctggccg ggccccggac  1500
gcggctcgtg cgaggtcggc catgtcgtcg tcgaccgctc gggcccacgc tgcgactgcg  1560
ggcgcgccgg ctgcgtccag gcggtcgcgt cgggaccggc gaccctccgg cggggccgccg  1620
aacggcgcgg ccgggagacc ggcttcgacg aactggcctc cggggcgcgc ttgcacgccc  1680
cgtgggcgga agcggccgtc gacgagagcg ccgcggccct ggccaccgcc gtgaccggca  1740
tctgcgagct ggcccacccc gaactcgtcc tcgtcggcgg cgggttcgcg gcgggcgtgc  1800
cgggatacgt ggcctcggtg gcggcgcacg tcgagcggct gacccgcccg gaacggatc   1860
ccgtgcgggt gcgcccggcg gtgctcggcg ggcggtcctc cctgcacggc gcactgctgc  1920
tcgcgcggga ggcacacggg cggggaaacc ggccgccgga gagtgaccgt gtttcttccg  1980
atgtttcttc cgatgtttct ttcgggggag tgacagacag ggccgttggc cggtccgact  2040
gagcacaatc acaggtgatt tcgcccaggt tcaccacgcc tcgtgtgctc ggggtcggca  2100
gaaggagtca gagtcatgct cgacaggcgg agcgtcattc gcgtcggcgc cggggtggcg  2160
gcggccgccg ccgtggccgg tacggccgcc accggtgcgg cggccgtggg gctgccgggt  2220
gtacggggac gcgcggcgtc gcgcggggtc gactgggcct ccttacgccg tcatctgtcg  2280
ggcgagctcg tcctgccggc ggacaccgga tacgagcggg ccaggaagct ctacagcggc  2340
cagttcgacg gcatccgccc gcaggccgtc gcctactgcc ggaccgagga ggacgtgcgg  2400
acgaccctcg cgttcgccca ggaccacgcc ctgcccctca cccgcgcag tggcgggcac  2460
agcttcggcg gctactccac gaccgacgga atcgtcctgg acgtctccgg cttccacgcg  2520
gtgagcctca cccggaacac cgtcgtcatg ggcgcgggca cccagcaggt ggacgccctc  2580
accgccctgt cgccgcgcgg tgtcgccgtg gcgagcggca actgcgcggg cgtctgtccc  2640
ggcggcttcg tccagggcgg cggactgggc tggcagagcc gcaagttcgg catggcgtgc  2700
gaccggctcg tctccgcccg ggtcgtgctc gccgacggcc gcgccgtgac cgcctccgcc  2760
accgaacacc ccgacctttt ctgggcgatg cgcggcggag cggcggcaa cttcggcgtc  2820
gtcaccggct tcgagctgcg ccccaccgac gtcccctccg tcgtcagcta caacctcacc  2880
tggccgtggg agtcggcgcg gcgcgtcatc gaggcgtggc agcactggat catcgacggc  2940
ccccgcgacc tcggtgccgc gatggccgtg cagtggcccg acgccgggac cggcacgccg  3000
gtcgtggtcg tcaccggcgc ctggctgggc gcggccgacg cgctcacccc cgtgctggac  3060
tccctggtgg cctccgtggg cagcgcgccc gccacccgct cggccaaggc gctctcccag  3120
cacgacgcga tgatggcgca gtacggctgc gccgacctca cgcccgagca gtgccacacg  3180
gtcggctact cgcccgaggc gcgctgccc cggcagaact tctccatgga ccgcaaccgg  3240
ctcttctccc gggccatcgg gcaaggaggc gtcgagcgga tcctggaggc gttcgccgcc  3300
gacccgcgcg ccggacagtt ccgcttcctg agcttcttcg ccctcggcgg cgccgccaac  3360
cgccccgacc gcaccaccac cgcctacgtt caccgcgaca ccgagttcta cctcggtttc  3420
tcgatcgggc tgaacgaccc ggagtacacg gcggaggacg agaggctcgg ccgcgcctgg  3480
gccgcgcgag gactgcgcac gctcgatccc cactccaacg gcgagagcta ccagaacttc  3540
atcgacccgg agctcgacga ctggaagtcg gcctactacg ccgagaacta cgtgcgcctg  3600
```

FIG. 26A

```
gccgccgtca aggcggccta cgacccgcac cggctcttct ccttcgcgca ggccgtctga  3660
cctctcccga aagacccctg ccggcctgct cccctccgcg gctcctgtgg gcactggtgc  3720
gcccgcgcac ttctgtgtga ttgagtgaag tccgggcgtg cagagctcag ttgccgtgga  3780
gggggcgcca gttgcgagca tcagcggtgg agagggtgga gctgatccgc tggccggtgg  3840
agtccgagcg gcgggagcgc tgccgcgacc ggggcgtcat gcggatcctg gtgctggagg  3900
cggggccga ggcacccttg tgcgtggacc ccaaggagga ctgggtccgc gctcccgtca  3960
gcaccgacga cctgcgggcc cgcgtcgagg ccctgcgcct tcggggagcc gccgccgagt  4020
cccggcccga ggtcgacccg aacggagtgc tgcgtttccg gtggcgctcc gccctgctct  4080
cgcccaccga ggcccggctc gtcgcccggc tcgccgagtc ctatgccgag gtcgtcgccc  4140
gcgacgacct gctccgcccg ccccgggcc gtaccgtgcc gagccgtaac gcgctcgacc  4200
tccacatcat gcgatccga cggcgcctcg ccgcgctggg cctgagggtg cgcaccgtcc  4260
gggggcgtgg ctacgtcctg gagagcgcgg aaggagtctg accgacgggc gtggccgcgc  4320
accgcaccga ccgcccctac gagcgaggag cccgaagtgc agcagcctca tcacagccgc  4380
gtcgacgtgg aactgggcga gaggtcctac cccgtccacg tcggaccggg ggtccgccac  4440
ctcctgcccg gcatcgtcgc ctccctcggc gcgcaccgcg ccgccgtcgt gaccgcacgg  4500
cccccccgacc tggtgcccga tcccggcgtg cccgcgctga tcgtgcgggc acgtgacggc  4560
gagcggcaca agacgctcgc caccgtcgag gacctgtgcc gcaagttcac caccttcggc  4620
atcacgcgcc acgacgtcgt cgtctcctgc ggaggaggct cgacgaccga caccgtcggc  4680
ctggcggcgg cgctgcacca ccgtgggggtg ccggtggtgc acctgccgac caccctcctg  4740
gcccaggtgg acgcgagcgt cggcggcaag acggcggtca acctgcccga gggcaagaac  4800
ctcgtcggcg cctactggca gcccaaggcc gtgctgtgcg acaccacgta tctccagacg  4860
ctgccgccg aggagtgggt caacggctac ggcgagatag cgcgctgcca cttcatcggt  4920
gccggcgacc tccgcggcct cgccgtccac gaccaggtca ccgcgagcct gcggctgaag  4980
gcgtccgtcg tcgcggccga cgagcgggac accggcctgc ggcacatcct caactacggc  5040
catacgctgg gccacgcact ggagaccgcc accggcttcg ggctgcggca cggactcggc  5100
gtggcgatcg ggacggtctt cgcgggccgg ctcgcggagg cgctgggccg catcggcgcc  5160
gaccgcgcgc gggagcacac cgaggtcgtc cgccactacg gacttcccga cagcctcccg  5220
ggaaacaccg acatccggca gctcgtcgcg ctgatgaggc acgacaagaa ggccacgtcg  5280
ggactgacct tcgtgctcga cgggccttcc ggcgtggagc tggtgtccgg gatcccggag  5340
gacgtcgtcc tgcgtacgct cgcggcgatg ccgcgaggaa cggcctgacc gagtgttccg  5400
tcttccgagg ggaagtgacc gtttcgtgtc ggcagagctg tcagaaccgc tgaagaaggc  5460
cctggactcc ctggtgttcg gcgtcgtggc gacgaccgac cccgacggcc gcccgcacca  5520
gtcggtggtg tgggtccggc gcgagggctc cgacgtgctg ttctcgatca cgcgcggcag  5580
ccgcaaggag aggaacatcc tgcgcgaccc gcgtgtgagc gtgctgatca gcccggcgga  5640
ctcgccgtac acctacgccg cgatccgggg caccgcgcac ttcgaggacg tgccggaccc  5700
gggcgcgtac ctcgacacgt tctccataaa gtaccacggc gtgccctacc gggagtcgtt  5760
ccccgagccg ccggaggtga gcaccattct cgccgtccgg ctcgttccga cgtcggtcta  5820
cgagcagtgg tgagggcgta ggcgtcccga agccccggca gcgtcccgaa tgccgctgcc  5880
ggggcttccc gtgggagccc tacgccggtt tccgcgcggt gaccaccgag tagccgacct  5940
cctccaccga gcccatgcgg tcgatgccgt cgaccatgcg gtggaacgcc tcgtcgtcca  6000
tgtgggagcc gagctcgtcc ctggccgcac gcatcttcgc cgccaccgcc tcgtaggagg  6060
gccgcacctc gtccccgatg tcgaggaact ccaccacctc cagccccacc gaccgcatgc  6120
agtcctcgta cgcctcgcgg gtgaggacgg ggccctgctg gaagttgtcg ttggcggtgt  6180
cgacgatcgt cctggacgcg tcgctcaggg gccggcgcag cacgaagtcc gtcaccgtca  6240
cccgcgcc cgggcgcagc acccgggcga tctcggtgaa gacgtcggcc cgttccaggg  6300
cgtggcagat gctctcgatc gcgtaacagg gtcgaacga gccgtcggga aaggggagcg  6360
cgagcatgtc accgatgcgg aactcggtcg cctcgtcgcc ctccttctcg gcgagctgcc  6420
gcgacagacc cacctggtag gggttgatgg agaccccggt ggccgcacc ccgtgccggg  6480
cggcgatgcg caaggtggcc ttgccgttgc ccgacccac gtcgagcacc cgctccccgg  6540
gggcgaggcg caggcgctcc gagacgtagt cggtcagccg gtcgcctgcc tcttccaccg  6600
tcgtggggac gtcgggtccc gcccagtagc caccgtgcat gtagccgcct tccgcgtgca  6660
ccatcaagtc ggtgacgcgg ttgtagagtt cgaccatccg gtcggaggcg gacgcggttt  6720
ccgtcatgcc gctcactttc ccgggcgctg ggcgaccagc agcagatagc cgaactcctt  6780
gacgccgacg aggtcgccgg ggtcgaactg gttcaccatc tcctcgccga actgcgtctc  6840
cagcctctgc ttcgaggagt tgatgcgctc cgagagcagc ctgaaggtct tctccagggt  6900
ctggtcgctg atgtcgagga actcctccag ccacaggccc gcccccgca gcaggggagg  6960
gtacgcctcg gcgctgacca tggtcatcat gaagtcgtgg aggtagcgct ggacggcggc  7020
ccgcccctcg ggggcgaggg gggcccgctc gaagaagtcg gtgagcacca gacggccccc  7080
gggccgcagc accggccga cctgggcgag cacctgggcg cggtcgggca tgtggatgat  7140
cgattcgagg gcgatgacgg cgtcgaagct ctcgtcctcg aaggggaggt ccatcgcgtc  7200
ggcccgctgg aagcgcgccc ggtcggcgag cccggcctcc tcggccagcg cgttggcccg  7260
gacgacctgc tcatggctca ccagatgcc cgtgacatgc gctccgctga gccgggcgat  7320
```

FIG. 26B

```
gcgtacgccc ggggtcccca cgccgcagcc gaggtccagg acgcgggagc cggcgccgat     7380
gcgcagccgc tcggccatca tgtcggtgag ccggtcggtg gcctcggcca gcggcacctg     7440
gctgtcgggg gagtcccagt agccgaagtg caggttctcg ccgagggagg cggctcccag     7500
cgcggtgaac cggtcgtaga gcgcgcccac ttcctcggag gcgggtgagg gcatggggag     7560
ttcggacagc tcggagtgcg gcatggacga tccctctcgt gaaaggtcgg gggtgggtcg     7620
ggcagtcggt gtcaggagag acggaggtcc tggtagacgg cgtcggcgag gcggacgatg     7680
cgctcgcggt gccgttcgtg ctccaccttc ccgttgaggt ggagggcgac gacgagagcg     7740
gcgtccgggt cggcgaagac cacggcggtc cacagcccgt cgtgcccgaa ggaccggggg     7800
gaggcgtacg agccgaagct ggtgaaccgc ggatccagct gacggcattc gaggcggaac     7860
cccatgcccc agtcggcgtt gccgtagcgg tcctggaggc cggtgcggtg ccgggccgtg     7920
agggcggcga cggtgggcgg cgccaggacg cgcccgccgg gagcgtcccc gccgcgcagc     7980
agcatctcga agagcctgcc catgtcccgc agcgggccac gggtgttgac ccccgggatg     8040
cagcgtgtgg tggccgcctc cgtcgaccac cagtgggtgg gcagcgggcc gccctcgggg     8100
ttgctcacat ggatcagcgg cagctcgccc ccgagcgcgg cgaactcctc gcgatccagg     8160
tggacacggg tgccggacat gccgcacggc ccgaggatct cctcctggac gtacgcgcgg     8220
tactccctgc cgtcgacgac cggaaggatg cgcgccagga cgaaccaggc ccaccactgg     8280
ctgtagttga tgccgggcgt gcccccggga cgcggtgcca ccggcacctc gaaggcacgg     8340
cgcacacgct cctcgtccgg gccggccacg atgccgtgca gcgggtcgtc gccggtgggc     8400
agcgggcccg tatgcgtcag cagttccatc gaggtgatgg actccttgcc ccggttgccg     8460
aactccggca gatagtgcgc gacgggcaga tacgggtcgt acgctcccgc ctcccacagc     8520
cggcccaggg cgaccgacag cagtggcttg gcgcagcagt accacagggg cagcgaccgg     8580
tgggtcatcg ccaccccggg gcgggccagc cccaacccgg cgtccgccag agggactccg     8640
tcgcgggaga cgtagatctg cgcccccggg gtcgaggtgc cgacctcgcg ctccagctcc     8700
cgcatggtgc cgggaagcgc cgcacgggcg gccggacgg cctcggccgc gtcctcggtg      8760
ccgggcggcg gggccgcttc ccgcgccgtg gtaccgggcg tgcccctgag cgcggccaca     8820
tggcccgagg cgtcccgctc cagtgcggcg tcgatgaaga acagcaggct gaaattgccc     8880
tcggcccgta cgtcgccccg ctcgaatacg ccggtccgat cccgcgcggg gccgagcagc     8940
agggcgcggg cggcctccag gggaagccgg atccgcagtc ccggactctc accggccgcg     9000
gccgcgaggc cgagccgccc ggcgacgagg tccacctgga cgtcgacggc cggggttcg      9060
ccgggcggtg ggtcggtgag ctccaggcgg agcgcgaccg tgccgcgttc gcccacgggc     9120
gggcgttcga gcctcgcggc cccggcgagc caggccgtgg acaggaacgg cgcggtggac     9180
agggtgttca gcacgggctc actcctccgc ttccttggcg gcccccggcg ccacctgggg     9240
gacgacctcc tggaacagcc gctccaggct ggtggtggcc gggtagtcgc ggaaccacag     9300
cacgaactcc gccacgcccg cggcgaccag gcgccgggcg cgctcggtga gctgttccgg     9360
cgtcccgtac aggctgcgcc gcgccagcag gtcgggatgg tggctccaga acagcacctc     9420
gtgcggggtg gagagccagc ggtcgcgttc caggacggag tcgaagatcc ggcactccgc     9480
ggcccaggcg tgccggacgc cgtccggatc gagcccgagc tccgtgcgac ggcggcggaa     9540
cgcggtgacg gccgcggcga cctgagcggg ctcaccggtc cactggacat gagcgcactc     9600
ccgcacggtg gcgtcggcgg gccgcagcgc gccgctcccg cgtccccgg ccggggtgcg      9660
cagcgcgagg gggaggggct gctgccgtgg ggcgggcacg cagtgcgccg aagtgaggcg     9720
gatgtgttcc ccggtgaagg tgacgggctg tccgccccac agcgcgcgca gggcctcgac     9780
cgtctcgccg agagcccggt ggccggcggc ctcctcctcg tccgcctcca ggcccgtggg     9840
cacctcgcgc cccgtcgagt ggtgctccgg caggtactcg cgggccggga agccgagggt     9900
gagccggccg tcgcagacga cgtccaggct cgcggcccgc ttggcgatca gcgcggcgtt     9960
gcggaacggc ggggccgagg agagcagtcc cagatccaga ccgggcaccg cgcccgcgag    10020
ggccgccagc gccgtccagc cctcccagac cggctcgggc tcgcgccggg cagggtgtc    10080
ggtgcggtcc agcagccaga gggcgccacg gccgtgccgg tggacggtgc gggcggtctc    10140
caggaggagc cgccagccct cgcggccgcc cgtaccggcc agttcgaggt tggtgccctg    10200
cggggcgacg acgctccagc gcggggtcgc gggcgtcatg cgtggccgcc gctgcggacc    10260
agcgcgagca ggctctgcgg cttgtccagc aggaagtcgg ccgctcggc gcgcagttgg     10320
ccggccgcgc cctcgcccca ggtcgcgccc acggtggcgg tccggcggg cgggccgctg     10380
cggatgtcga tcaccgcgtc gccgaccatg accgcgtcct cgggcgccgc gtccagccgg    10440
cgcagtgcct cccgcacgat gtcggggtgc ggcttgggcc tcggcacctc gtcgctgccc    10500
accctcgt ccagcagggg cagcagcccg accgcctcca gcacgcgcgc cgcccgggag      10560
ccggacttgc cggtggcgat cgcggtgccg acgccgtccg cgcgcagctc gccagcaac     10620
tgcggcacgt ccgggtacac ctcgacgcgg tccatcagcc ggtggctctc ccggacgaac    10680
ggttcctcca tctcgccggg caggcccatc agccgcatga tgtccgggaa gtagcggccc    10740
tggtgcgtgc ggtactcctc gaagggcggc tcgcccggcc ccaccacttc gcggtaggcc    10800
acggcgaacg cctcgacgcat caccgcgaaa ctgtcgatga ggacgccgtc gaggtcgaag   10860
accacggtgg tgaaccggca cggagagcg gtggcgggcg cgtccgccgc ggcccgcgag     10920
gcgggcgggg ggttcagggg catggcagga gctccgtggg tagggacgtc ggggcccaga    10980
ccccggcgtg gctgacgact ttcgtgaagc ggcccgcgag ccggtggtag acggccccg     11040
```

FIG. 26C

```
gcgagctgtg cggcgggtgg gccgccgcgt ccagcccgcc ccaggcggcc atggccctca   11100
gcagcagcgg atcggccggc acccagcggc cgcccaccag gaactcggcc cagcagtgcg   11160
gtgtggagta cggcttggcc accagcagcc cgaaggagaa ccgcacgtcg agcccgcgcc   11220
gccggccctc cgccaccagc caggccgcgg cgccgccgca gtcggccatg tgcgtgctcc   11280
acaggaaccc cgggtccag cggatcgctt cgggcagcag gaagaagccg accggctcca    11340
gggtgcgcag caggtcgagg acggccgggg ggaagtccgg ccagtggccg cgcgaccgtg   11400
tgtacagccg cgccagcgtg gtctcccgcg gcgaagccgc ctccaccggg cggcgggcgc   11460
cgggcagcag cactccgtag cggcacgggc ccgcgtggcc gggcaccggg caggacgccg   11520
tgacgtcgac gcgccagccg gggctctccg cggccggagc ggtccgcagg gaaccggccc   11580
acgagcggat ggcccggcgc tgcaccgagg acaggccaag gtgcagggcc gcgttgccca   11640
ggtcgtagcc gtcgaagagg cgtcccgcgc cgcttccac gaagggcacg cccgcctcgc    11700
acagcgcgga cagcagctcc ggtccgatcc ggtgcagccg gcgcgcgctc tgctcgtcga   11760
cggtgaaacg gcggtgctcg tcgggcacga gcttcagacg ctccacgagc gcctggagct   11820
cctgggtgga gggggccgg gccggcaggt agacgctgat ctcctcaatc ctttcgccgg    11880
ggcgggcagc cggtgcggga cggccggggc ggccgccggt ggggtgccgg gtcagtcgat   11940
gtagcccaga gcctggaggc gggccgccac ctgctgctcg tcgctcgcgg tgtacgccgg   12000
ctcctgcggg cgcggcgcgt aggggagaa ggcgcgcagt gccgggcca cctcgtgcgc    12060
gaacagttcc atggactcga tgcggtgccg gtccgccagc tcgccgaagg tgaactcgcc   12120
cagcagcgtg tcgaaatggc cctccaggga cgcggccctg atccggtcgg ccacggtcgc   12180
cggcgagccg acgaagacga ggttgttctc cagcaggaag cgcaggtcgc cggagcccgc   12240
caggatgtcc gtcgtgctga gcctgctggg tggggcgtgc tgatcgcggg aacgggacac   12300
cgagccgtac cgcagcgtct tggtgaacgt ctcggtgatg tgcgcggccg cccgctcctc   12360
cgcctcggcg tccgtccggg ccacgtggac cagccgatgc tagccgatgc gcgggtcgct   12420
cgcgtggccg tggccgacgc accagtcgag gtagtccgg tagaccagcg ccatggaggc    12480
gcgcggcacg atcatcgtgg aactggtgtg ggcaccggcc tcgctgagat agcgcaaggt   12540
gttgcggttg tggtgggca cccacatcgg cgggtgcggg cgctgcaccg gcgggaagga    12600
cagggcgatg tcgcgcagcc ggtgcgcggg cccgtcgaag tcgaaggcgc cccgcgcggc   12660
gaacgcggca cgcagcagct ccagggcctc ccgggtcagg aggtgacggt tgtcgaaatc   12720
ggcgtcgaag ggcaggaagg ggtcacggct gacgcccgag gcgagcccca cctccagccg   12780
cccgcccagg agctggtcca gggtcgcgac ctcctcgacc aggtgcagcg ggtggcgcag   12840
cggcggcacc caccccatcg ggccgacccg gatgcgctcg gtgcgcagcg cggcgcccgt   12900
gcagaagacc gcgggcgagg gcatccagct ctcgtgcggc gtgcagtggt gctccaccga   12960
gaacgcgtag tcgaagccga gccggtcggc gtcctcgacc tcgcgccaca gctcttcgta   13020
gcgctcgccc ggcgtgatac cgggacgtcc ccagacatgg gagaaataag cgaatttcat   13080
tggcttcccc gggtgggcag gacacgtgga caactggacg tgctgggcgc cgcgtcgctc   13140
tgcggccggt gcaggggcga gggagggtcg acgccggcgg ccgaatagat gtggtcgatg   13200
caggaggcca ggatggtcac ttcggccatc gaccccctcgc ccagcccga caccgggccc   13260
tgcccgtcgg ccgagccgcc gagcctgcgg gcgagttcgt ccacctgccg ccggtactcc   13320
acgcccacgg gctcgtcggg cagcgcgacg gtctcctcca cccctgccg caggaccacg    13380
aggctcgact tctgtagccg gtgggggctg aagccgaagg tgccgcgcag cgtcgccacc   13440
ccctcggtgc cctccacggt gatcgtggtg acgtccagcg cctggtggga ggcccagcgt   13500
gtctccaggg agatgcccac gtcggtgtcg gtgacgagga agccgcgggc ggtgtcctcc   13560
accgtctccc cggggcctgg ccgcgccgtg ccggaggagc gccggctcca gtcggccgtg   13620
gcctcgcccc ggctcatcca gtccgcggac atcgtgctcg ccgcccggac cacgcgcggc   13680
cacccccagca ggtgcaggcc cacgtccagc aggtgccagc ccaggtcgag cagcgcgccg   13740
cccccggcga gccggcggtc gacgaaccac ccggtgcgct gcgggatgcc ggtggcccgg   13800
atccagctca gcccgacact gcgcacggtg cccagcgagg cagcagctc cgccaggcgg    13860
cagacatcgg tgcggtccg ggcggcgctc caggcgtaga gggtgatgtc cccgatgctg    13920
tcgccccgcg cctggtggtc cagggcgagc gcctgggcct cgaagagcgt gcggcacacc   13980
ggcttctcga cgaacaccgg cacgtccgc tccaggaggg ccttggccac ggggagatgg    14040
aggtggttgg gcagggcgat gatggccgcg tccacgcttc tgggggcgag ctcttccggt   14100
ctgctcagga cgcgggtccg cgcgccctcc ggcagggccg acctggccgc cacggggtcg   14160
tcgtccacga ggaagtcgac ccggaacgcc gggtgttccg ccagcagcgg cagccacacc   14220
ttgcgcgaga cccatcccgc gcccagcact gccatccgga ggggttcgcg agctgtcgtc   14280
ggcggtgtca cgacgggtgc cttctccgtg aaagtcatca gaagcgggca ccaccgtcga   14340
cgacgagcgt attgccgttg acgtacgagg ccgacggcga cagcaggaac gacaccgccg   14400
ccgcgaccte ctccggctca ccgagccgcc ccgccccgat gaactgcagg accagatcgc   14460
gctcggcctc cgagaagtcc atcacctcgg cgcggatcgc cccgggcgcg acgacgttga   14520
cggtgatgcc gtgcttgccg acctcacccg ccaccgacgc cgcccacggc tggagcgccc   14580
ccttggtggc ggcgtacgcg ctgtggccgg gcagcccgct ggtcccggcc cgggagccga   14640
agagcacgat ccgcccgtac ctggcgcgca tcatcggctt caggcacgcc ttggcgagac   14700
ccacggaacc ggccaggttg acccgcagca gcttctccag gctccgggcg tccgtggcca   14760
```

FIG. 26D

```
tcgcgagccg gcgcgtacgc aagcccgcag cagccacaca gccgtccacc cgcccgaacc   14820
gttcgacggc cgccgccacc agcgcgtcgg cgccctcggg ttcgctcagg tccgccgcca   14880
cgggcacgag ggtgccgccc tggcccctcca cctgctcccg cagcttgcgg atcgcctgct   14940
cgccgctgtg gtagccggcg acgacggtgg cgccgagcgc ggcgagctcc agcgcgcacg   15000
cgccgcctat ctgcccggac gcgcccgaga ccacgaccac gcggccgctc tgtcccaggc   15060
gctccgtggc ccggtcggtg acggtgctca tgaaccggcc tccttggcga tgatcagatg   15120
acaggggggac gcgtccagcg gcacgtgccg tgcgacctcc gccccctctt gcagcagccc   15180
ggcgatcagc tcgccggtgg ccggccacgc ggtcccgccg tgcgtgagcc agtccagagc   15240
cagttcgctc cccggcccgg acgccggcag gaagacgtcg tcgaccagca gccgcccgcc   15300
cggccgcagg gagccgagca gggcaccgag agcgctgccc ggcccgggc cgtgcacggc   15360
gttggcgacc acgcagaagt cggcgtagcc gacgggcagt tccgtcccca cggtcaccct   15420
gccctcctcg accgccgcgg cgacggccga ggagagcggc ccgctcagcc ggccgacggt   15480
gaccagatgg ccgctcgccc cggggtccga ggcgagcagg cgttccagat agcggcccgg   15540
gcccgcggtc acctccacca cccgggctcc cggcccgggc cgcaggagcc gcaggccgag   15600
cgcggcccgg gcccgtgcgc cggggccgtc catcgcgccc tggtacaggg cgacgagcgg   15660
accgaggctc tcgggggac gctcctcgaa gggacgccgc gccgtcccgc tccgggccac   15720
cgcgacgagc tcctcgcgcg tgaccagccc acgggagagg tgctcctcca gcgccacgaa   15780
cgcggccagc tccccggccc ggacccggtc cccgggctct tgcgccccgg tggtcagcac   15840
ccccagagcg gtggccgtgc gcagcagcca ctccagggca tccgcgtcgc acccccagctc   15900
cccggcgagg agagccgtgc cggcaccctg ggcgagtgcc tccagggcgc ccaagtcgtg   15960
cagcgcgaag agcacttcgg atgccttgta cgcccgggcg gcctccgccg cgctccgggt   16020
gaggcggtag acggacgccg cccgcacctt gcccgcggcg ttgaccggca ggctctcccg   16080
caggacgaac tcgtcgggca ccttgtgcgg ggccagctcc cggcgggcgt gctcgcgcag   16140
cgcctcgggg gtgagccccg gccccgccgc cgagacctcc gcgacgatcc cgtcctcgcc   16200
ccggtgccgc ccccgccggg cgccacccg cacattcacc acgtccggat gaccgcgcag   16260
cacctcctcg atctccagcg gggagaccca gcgcccgccc cggcggatcg cccggtcctc   16320
gcgtcccagg atgcgcaggc ccccgggcac ggccacgcg agatcgccga tggcgtacgg   16380
ccggccgtcg acccgtacgc tcagcagccc cggggtgccg gcggcggca ccacgccctc   16440
cgggccggtc agttcgcact ccaccccgg caggggagca ccggcgcaca agggctccag   16500
ccccgccggt ccggcgagca cggcgcccgt ctccgtggaa ccgtagttgc gggcgagacc   16560
ggtcccgaac gcctcggtga acgcgcggtc cagctgctcg tccaccggcc ccgcacccac   16620
catggccagc cggagaccgg gagcggcggg cgcccgcccg gccgctgctc cccgcagccg   16680
ccgggtcgcc agcagccggg ccacactggg caccagggcc accacggtcg caccaccgga   16740
cagctccgcg gcgatgcggc cgagggcggt cggcggtacg gggcgcagcg cggcacccgt   16800
cagcagtccg ccgaacagcc agcccagcgc gtacgcgtgg gacagcggca ccggcagcag   16860
cagggtgtcc tctcccgtca gcccgacccc gtcgcggtag cggcggccct ccgcgagcag   16920
gctctcctcg ctgcgggcga cgagcttgct cgcaccggtc gaccccgagg tcgggagcag   16980
cacggcgggc ggggcgccgg agggttctcc gggcgagccg gtcaacgtca ggcggaggcc   17040
gtcgccggtc ccggggacga ccagggacct gccgccccg cagcccgca gcagccgcgc   17100
ggtctcgggg ccgggggtgt cgggttcgag cagcagggc ctggcgccgg atgccagcag   17160
ggagaggaag gcgacgaccc accgcgggct gttgggcgcg cgcagggcca ccgcctcgcc   17220
ctccaccgcc tcggccttga gctgtgccgc ggccgtacgc acctgctcca gcagggagtt   17280
cacatcggtc ccgggcagcg gtatccgcc ggacggcagc cgttccaccg cgcccaggag   17340
ggtgtccgcc tcgtgaccgg tcgcctgttc agtcatgcc gccctggagg tagtcggcct   17400
tcgcgtcgct gagcatctgc cggatgcggg gcggggagta ggtgggagcg gcgcacagct   17460
cgtcgagggt gatctcgtcc tcgaagtaca tcgagagcgt gtcccaggc gtgaagcagc   17520
cgtggcacgc cttgagccgg ggcttggggg cgagcagggc acggtagagg ccgctggtgc   17580
ccaccgtgtc cagcatctcg ctccagtcgt cctccagggc gttgcccatg tcggagaacc   17640
agatgttggg gcagggcgtg acgacgccgt cgctgaagct ggagacgacc agccgcggca   17700
gatggcagcg gaaggtgcgg cggccctcgc ggtagaagct cgtcagccgg tcgaagtagg   17760
gccgcggcgg gaggacccgc gcgaactcgt cgtagcggtc gacgagttcc tggatgtggc   17820
cgaactgccc gggccgcacc ttgaagtcct ccgagtccgg gccccgcacc gggaagggga   17880
agtagacggg aggccgggag aatcccgaca gccactcggc gaacgcgcag acctccgtga   17940
cgctccggtc gttgagcact gaatagatct ccaccggcag ccccgagtcc aggatccggg   18000
cgatggcggc gacgaccttc tcgtgcaggc tcccggacgg cacacgatgg ctgttgccgt   18060
ggtggaggtg gctgtcgagg gagacctgga gcacgacgtt gccccacgag cggaaccgct   18120
ccaggtgctc ctcgcgcacc aggacaccgt tggtctggat gaccagcacg tcgtatttac   18180
gggcctcctg ctccaggaag tccatgatcc cccggaccag gaagatctcg cctccggtca   18240
ccttgagcag cggcaggccg aagcggtccc ggatccggtc ggcgaccttg tccatgcgct   18300
gccccagccc gctgtccttg gcgtagctgt cgcgccgcgg gggctcgaag atcagttgaa   18360
gggagtggcc ctccttgagg ttgctctgtc cggtgaggca gtaggtgcag ctgaggttgc   18420
aggagtcctc gttgatgacc aggtcgttgc cgatcagcgg cagcgtcgc ctggtgcccg   18480
```

FIG. 26E

```
cgtcgggggt ggctgtcggc gggtgggtgc tacgggacat gagtggcctc tctcgtggtg   18540
gggctgcgca cggcgtgggt cacggccccc tttccacggg tgccggccgg gcctcgcccc   18600
ggtcgtcctg gccgacgggc acccagtggc ggtcggcgtg gccgggccgg ccgggcccgc   18660
cgtgtgcgcg ggcgcgggcg aacagggcct cgcgcagggc ggccgcaccg ccgaagtggg   18720
cgctcgcctg gctggagtag tgaccggcgg cggtcagcca gcggtccacc gcctcggacg   18780
gcagccgttc cgtgcgcggc cgcaggttcg tgtggtcacg ttcgcgcagc cggtagggga   18840
agtcctcgta gaagacggta cgggcggggg acagggctc caccgcgccg cggaccaggc   18900
ggtggtcgac gtgccggccc gccgccaggg gaacgtggac gctcgacgcc cccgcgcaca   18960
gcggcagcag agccgcccgc acctcctcca gcagcgggag gtcggccggg tgccagggggc  19020
cgaagagccg gcgcgcgggaa gcgtagagat aggcgcccga ggccgtacgc agtgccgcgt   19080
cggtgaagcc cagcggcacg tggcgcacgc ccagttcggc acatgccgcc cggtcctcgg   19140
cccggcgcac cgcgggatcg gcggcgctcc gccacgactc gggcttcccg gccgcgggcc   19200
cggcgaagac cgtgacgacg gtcggccgcg ggccctcggc ggcccagcgc gccagccgcc   19260
cgcccaggga ccacacggcg tcgtccgcgt gcggggagag caccacggga ccgtacggcg   19320
cggtggccgg tgtgccgctc atcgcgccgc gtcccgtgcc ggtgcggcct cttcggccag   19380
gacggcgcgc acatacgcct ccggcgtgcc gtcgggcccg agcagggcct ccaaggcgcg   19440
taccgacggg tgcgggtggc cggcggagaa gtgcgtgagg ttgcggtggt gctgctccca   19500
gcggccgggg cgggcgtggc tgaggtgcac accgagggcg tcggggcga gggtcctgcg    19560
cagcccggcg gcgtgcaggc ggaagccgaa ctccaggtcc tcgcaccccc aggtgagccc    19620
gaactcctcg tcgaatccgc cggtatgctc ccatgcggcc ttgtcgaggg cggtgttcgc   19680
gccgatgaag ccgagccagg gggcgacgtc cggcagggag ccgccggcca tggcctccac   19740
ggcccgctcc agggcgttgg cgacgagccg ccggtgcggt tggcgccgct cggaggcggc   19800
cggggcagcg ggttcgagtc cggcgcgggc gcggcggacc tcggtcgggg cggccttctc   19860
gacagcggcg aggaaccgcg ccgcggtggg gagttcgcgc agccggccgt gggtgaaggc   19920
gtccggttcc gcggccgcgg cgtgtgcggc gaggaagccg ggccccacca ggacgtcgtc   19980
gtcgaggaag accagccggg gcgcgagggc gcgggccgcc cggcgttcc gggcggcggc    20040
ccgcccccgc agcggtcccc gcaccacgcg cagccgggaga aggccgctca tctcgcctgt   20100
cacggcgatc agttgatcac cggcgtcgcc cccgtcgttg tcgtcgacga cgaccacttc   20160
gaagggcggc gttcccgggg aggggccggc aaggcatgcg agggtcgcgc gcaggcgtgc   20220
cgcgggcccc cggctgggga cgacgacgct cagccgggggg gcggtggtgc cgttggggc   20280
ccgcatcggg tcagagcgcg ccgacgaggc cggagaagac ctccgccagc cggtccagcg   20340
tggtcacgtc ggcgagcagg acgcgatggt gcagccagag gcagtcgctg ccgatctcct   20400
ccgccacggg acagctcttg gccagctcct cggcgtccgc cggcgccggg ccgcgcgcga   20460
aaccctcggt gcggtagacc ggcgggaagc cgacgaacgc gggcactccc cgctcgacca   20520
gcgcgtccac cagcgcgagg cggcgccggg ccgagatgcc gggcagccgg accatggcca   20580
tgtagtggga gtggaggtcg ccgcgctcgt cgcgcccctg cggcaccacg ccgtcgatgg   20640
cggccagtgc cgtacgcagc tgggcccagc gctcctccct gatgcgcaac tgatccttca   20700
agcgcttcag ttgagcacgc aggacgctcg cggagaactc gttcatgcgg tagttggagc   20760
cctgcgtcag atggcggtag acgcggtccc cgggcgggcg ccgcagcag tgctggagga    20820
acgcctcgtg gaaggactcg tcgtccggca ggagcagggc gccgcctcg ccggcggtca    20880
tcagcttgcc gttctgaag ctgaaggcgg cgatcgagcc gagctcccg acccgcggc     20940
cctgccactg cgcgccgtgg gcgtgcgcgg cgtcctggag gaccggcacg cccgtcgcga   21000
cggagagctt ctccagggcg tccatgtcgg cgaactggcc cgccatgtgg accggcatga   21060
tcgctttggt gcgtggcgtc accagccgcc ccgccgcgtc ggcatcgagg cagtaggtgt   21120
cgggccgtac gtccgccggc accggcaccg ccgccatgcg ctgcacggcc agcgacgacg   21180
agatgaaggt gaacgcgggg acgatgacct cgtcaccggg gccgatcccc atgaccccca   21240
gggcgagttc cagggcgtgg gtgccgttcg tcgtggcgat cgcgtgcggg gcgccgtggt   21300
ggtcggcgaa ctcccgctcg aagagatcga cctcctgccc cgcgtcgcgc caccacccct   21360
tctggtccag ggcccgcagg agtccggcgc gctcctccgc gccgtgttgc ggccatgagg   21420
gaaaggacag gacgtcatca ccggacgtag gtgtcattga gcagcctttc ggtcctgcgg   21480
gtgcggcggc acggtcgact tcggggcgct gtacggcggg agggcgggtg tcgaggcctt   21540
tgccttcggt ggccgtggct tcacggcccg gttccgttgt gttcgccccg cgtcgggaag   21600
ggtggtgcgt gacccgacgg gaaacgccgt tcctcggggg cggcgggaaa tccggcccgc   21660
ggtgtgaggg gtggccggag cgggcatgtg atccggcccc cggtcatagg ccgggatcgg   21720
atgccagaca cgagcctcca tagggcagtt gccggagtca acaccttgc cgggaaggtc    21780
tgccccgacc gccggtcggc ggtggattct cgtcagcagg gtggttgagc agtgaaactg   21840
ccttattccc aagggaattg atccagttca ggggctgctc ggcgggcctg tcggcaacgt   21900
tatccggcgt cgaagtggct caaaccgcac ggctggaggg agcgggaagc gtcgcgtatg   21960
gtgggcgcga caccgtcctg gtatgtgctg tgtgcatggt tcattgagcc gaatcccact   22020
ccggccctcg gatccgggcg ccatacgatc accgttgtcc ggtctgtgga cgcaccggtg   22080
aggggctgtt acagtcctcg gatcatcgat gagcggcggc agtttctgcc tgcaatcgtg   22140
atgagttctc agagctggag gcaatttcgt gccaccctct ccccgcgccc tcgtcatcgg   22200
```

FIG. 26F

```
aatcgacgga ggcacattcg atacggtcga cccgctgatc gagtgcggtc tgctgcccca 22260
tatggcgaag ttgctgcgcg agagcgccag tgccgccacg gactgcacct ggcccgccca 22320
cacggcgccg gggtggagca cgttcgtctc cgccagcgat cccggcggtc acgggatcta 22380
tcagttctac gacacccagg acccggccta cggggcccgc gtcacgcgct ccggcgacct 22440
gggccggtcc tgcgcctggg actggctcgc cgcgcaggaa tattcgctgg gcctcatcaa 22500
catcccgatg tcgcacccgc cggccgacct ccccggctat caggtcacct ggccgctgga 22560
gcggacactc aagcactgcc gcccggattc cctgctgcgc gaactcgccc cggccaaggc 22620
ccatttccag tcggacctcg cgaccatgtt ccggggcgac atggcctatc tggaggaggc 22680
cgagcgcaat gtggcggcgc gggtccgctc cgtacggcat ctgatgagca cccggcccac 22740
cgatgtcgtg atggtcgtgc tcaccgaggc cgaccgggtc ggccaccact actggcacta 22800
cggcgacccc ggtcaccggg gccaccggcc cgccccggag ggcagcggct gggacgtcgc 22860
catgccccgg atctaccagg ccatcgacca cgcggtgggc gagctcctgg agctcgtgga 22920
cgaggacacc tccgtcgtgc tcgtctccga ccacggcctg ggcaccgggc gccacggcct 22980
gtcggtgcac accctcctgg aggaggccgg gctgctggcc accgcaccgg gggaggagcc 23040
gcaggacgcg cggcgagct ggttcgcggg caacggccgg cacgtcgact tccgccgcac 23100
cagcgtctac atgcccgtcc ccggcagcta cggcctcaac atcaacgtac gcggacgcca 23160
gcagcgcggc accgtcgcac cccgcgaccg cgaacgcgtc atggacgagg tcacgggcct 23220
gctctccggg ctgaccggcc ccgagggaca gcaggtcttc cgggccgtcc gcccgcgcga 23280
agaggcgtac ccagggccgc acaccggccg ggcacccgac ctcctcctcg tcccgcggga 23340
cgagaccgtc ctgccgtcc cgacctcgg cggtgacgtg tggcggccga gcgcgcagac 23400
cggcctgcac cgctaccgcg gcctgtgggc gcaccgctcg ccccgcgtcc gccccggccg 23460
cctgcccggc accgtcgcgc tcaccgacac cctgcccacc ctgctcaccg acctcggggc 23520
cgcatggccc agcgacatcc acggccgccc cgtgaccgcc gtcctcgacg acggcgtacg 23580
cgtcccgccc tccgaccccc gggtcgaggc caccggcacc ccggccacca cgatcccggc 23640
cgccgcttcg gccgctgatg ccgccgagga cgcgtacacc agcgaccgct tgcgcgaaat 23700
gggctacctg taagcaccgc cgggccgtac cggcgcttgt ccccaccgga gtcccgccgc 23760
tcgcggcggc gtggaggaga gaggtatttc tgccatggag accctgacga ccgacaagat 23820
caaggaccgg ctgccgaagg tgctcgtcga ttccctcgaa ctgtccctgg acccctcggc 23880
cgtacccgac gagggactcg tggagaagct gggcctggac tcgatcaaca ccatcgaatt 23940
cctcatctgg gtcgagagcg aattcggcat agagatcgcc gacgaggacc tgtcgatcaa 24000
gctcatcgac agtctcgacc tcctcgccgg ctatgtgtcc gagcgcgtga acggcgtcac 24060
cgcacccgcc gaatgacggc cgtgcgcgcg ctcgcctccg ggcccactcc ccgcagcgga 24120
aggacgtgag cacgatggac cggcacgccc tggtgatcgg gctcgacggc atgccgagga 24180
ccctgctgac ccgcctggcc ggcgacggga ccatgccgca caccgcggcg ctgctcgccg 24240
agggccactg cgcggaactg ctggcacccg taccggagat cagctccacc tcctgggcca 24300
ccttcctcac cggcaccaac ccgggccggc acggcatcta cggcttcacc gacctcgccc 24360
ccggcgacgg ctaccgcatc accttccccg gtgtgcggca gctgcgcgaa ccccgctgt 24420
gggaactcgc cgcccgcgcc ggccgcagga ccgtgtgcct gaacgtgccg ggcacctacc 24480
ccgcccccgc catcgacggc gtgctggtct ccggcttcgt cgcgcccgaa ctggagcgcg 24540
ccgtcagccc gccacggctg ctgccgctgc tgcgcggcct cgactacgaa ctcgacgtcg 24600
aggtcggcga cgtcgccgcc gacccggcc ccttcctcgg gcgggccgtc cgggccctgc 24660
gcgcccgcac ccgggcgatg gaacacctgc tgcgccagga gacctgggac ctcgcggtcg 24720
ccgtgctcac cgagaccgac cgcgtccacc acttcctgtg gcgcgcggtc gccgaccccg 24780
ccgaccccct ccacggggac gtcctcgcct tctaccgcct cgtggacgac tgcgtcgcca 24840
ccctggtgag caccctccca ccgggcgggg aactcttcct gatgagcgac cacggcttcg 24900
gacccgccgc ctgtcaggtc tatctgaacg cgtggctcag ggagtccggc tggctggccg 24960
ggctcgacgt ctgtccggac ctcaccgcgg tcgacgctcg cagcaccgcc ttcgcgctcg 25020
accccgcccg catccacctc aaccgcaaga gccgcttccc cggcggcggc ctgaccgacg 25080
cggaggcgga cgaggccgcc cacgagatcg cgcgcgagct gtccgccctg cgctgcgacg 25140
gcacccgcct gggccccgac gtcgacggac ccctgctcgt ccgcgacctc taccgcgctc 25200
aggagatcta ccacggcccg ctgttgggca acgccccga cctggtggcc gtaccggccc 25260
ccggggtgca gctgcgcggc ggctggggcg gcacgcacac cgtacgcaac gacatcctca 25320
ccggcaccca cacccgcgac gacgcggtct tctaccggcg cggcgcgccc gcgcccgccc 25380
ccggggcgga cgacggcccc ctcgacatga cggacgtcgc cccgaccgtc ctcgcctccc 25440
tgggcatcca ccccggcggg ctcgacggcg cggccgtact cggcaccacg gacccgcgt 25500
ccggtcacgg ccgcacggac ccccctctcg acatcaggga gctctgatga agcacgacct 25560
cggtctggca ccatcggcac ccaaaccggg aacactcgac ctgagcctgg acccacgcat 25620
cacggacccc gcttccttcc gggtcagttt cctgatcctc ctcgacggcg acctcgtgat 25680
gtcccccgaa caccctcggcg tcgcctacat ggccggtgtg ctgcgccata cgggcttcac 25740
cgcggagatc cggaggtgg agcacggcga cgaccaggcg ccgccaccg tcgaggcgct 25800
caaggagtac cggcccgacc tcgtctgctt caccctgatg agcctgaacc tgggcagctg 25860
tctgaccctg tgccggatgc tgcgggagga gctgccgggg acgacgatcg cctgcggcgg 25920
```

FIG. 26G

```
cc cagccggg accttcgcgg gcctggacgt cctgcggaac aaccccctgga ccgacgtcgt  25980
cgccgtgggg gagggcgagc ccaccatcct cgacctcgtc caacggctct acctcaagga  26040
gccgttgtcc gcctgcaagg ggatctgcta ccgcgacgag gacggcacac cgcgccagaa  26100
ccccgcccgc ccctgatcc acaacctgga ggacctcccc ttccccgccc gggaccagct  26160
gcgccagcac ggcgacaagc tggagtacgt ccgggtcagc accagccggg gctgcgtcgc  26220
caactgcgcc ttctgctccg ccccgcacct gaagaaccgc gtccaggcgg gcaaggcgtg  26280
gcgcggccgc gggccggaac agatcgtgga cgaggtcgcc gagatcgtcg aacgccacca  26340
gttccggacc ttcgacttcg tcgactccac cttcgaggac cccgacggcg gccgggtcgg  26400
caagaaacgg gtcgccgcca tcgcgaacgg catcctggag cgcggcctcg acatctacta  26460
caacgtctgc atgcgggccg agaactggca cgacacccccc gaggaccacg ccctgctcga  26520
cctgctggtc gcctcgggcc tggagaaggt caacgtcggc atcgaggccg caccgccga  26580
ggaactgctc ctctgggaga agcgcgccac cgtcgaggac aacgtcacca tcatcaggat  26640
gctgcgggaa cacggcatct atctcgccat gggattcatt cccttccacc cctacgcgac  26700
cctggagacc atcgtcacca acgcggcctt cctgcgcgac aattccggcc acaacctccg  26760
gcgcatgacc gaacgcctgg agatctaccc cggaacggcc atcgtcagcc gcatgcgggc  26820
cgacggactc ctcggcgaga gctatctcga agggctcgac ccctacggct acgcattcaa  26880
ggatccccgc gtcggacggc tcgccaagca tttcgcccag ctctacaaca acgacgacta  26940
ccaccggcac ggcgtcatca ccgagcagtc ctccgtcttc gccttcgaga cctacaacgt  27000
cgtactccag accttcatct cccggctgca ccgccggttc accaccctgc cggggggtgga  27060
cgaggtgatg gaggcattca aggcccgggt gcacgagatc cgccaggaga tgggccggca  27120
caactacggc ttcttcatgt ccaatgtcga ggcggtcatg aacgacaccc tcgacccgga  27180
gaagcagcgc cggcaggtgg tggacgtcga gcacttcttc cgcgaccgcc tcgatgtgtt  27240
gcgcagcgag caattcgcg tcggcaaggc cctcacccgg ctcggcgccc gggtgacgga  27300
ggtcagctcg accattccca aggagcgccc cggcggactg ccgcgccagt acacgggaga  27360
gggcagcggt gccacgtggt gagacgggaa ccgccgcggc gcgggtggcg gtctgcacgc  27420
tgagcagcag ggaactggtc ggcccgctgg cccggttgcc cggtgtggcg gccgcgggca  27480
cgctgatgac cgccaacctg ggcatcgagc aggtgatcaa ggccctgcgg tgcgaccgga  27540
cggtccgcgg cctgctcgtg tgcggccgcg actcaccccg cttccgcgcc ggccagagcc  27600
tgatcgccct cttccgccac ggcctgcgcc ccgaggacgg gcacatccgg ggagccaccg  27660
gctatctccc cgtcctgagg tcggtgacgg cgcgggagac cgaggaggta cgcgccgcg  27720
tcgagctggt ggacgcccgt ggcgagcgcg acgtcgagac gctgcgcgcc gaggtcgcgg  27780
cactcctcgc ccgcgtacgg cgcaccccgg ccctccccctc ccgcgagcac gacggcggcc  27840
aacccagctt cgtggagccg gacttcggac ggctgcatcc tgtcggccgc cgccgctccc  27900
tggacgcggg catcggcggg ttcgtgctca tcagcgtcga ccgtgagcac cggcggatcc  27960
tgctgcgcca ctacacctcc gatgtgcggc cccggcacga gatgtggggc acccgcgggg  28020
aggcgatgct gctcgggctg ctggaggccg cgtcatcga ggaccccgcc cacgccggat  28080
acctcggcgc cgaactggcc aaggccgaga cggcgctgcg gctcggcctg cactacgaac  28140
aggacctgcc cctgcgcccg ccgggcaggc cgcccggccc tgtgcggcgc cggaccgcga  28200
aggagcgaac gaccatggcg caagcacccg cgctggagga cttcctgcgt ctcgtgacga  28260
ggacgctggg ggccggaggac gccgtcctgg acctgcacac gccgctcggc gagcaactgg  28320
cggtggactc cgccccggctc atcgaactca ccgtcgtcct ggaggaggag ctcggcgcgg  28380
acctccccga cgacgccgac ctcgccaggg ccaccccccgc ggaactccac aaagcactcg  28440
tgggctgagg aggagaccga catgcgcagc gtgctgttgc tcaacggacc caacctgggg  28500
acgctcggca agcggcaacc ggagatctac ggaaccgaca ccctggccga gatcgaggcc  28560
gccgtggccg aggaggtggg agcgcgcggc tgggaggtgg tctccgaaca gcgcaacggc  28620
gaggggaac tggtcgatgt gctccagcgc cacgacgacg tggtggggcgc cgtggtcaac  28680
cccggcgccc tgatgatcgc cggctggtca ctgcgcacg cgctcgccga cttcgccccg  28740
ccctgggtgg aggtgcacct gagcaacgtg tggggacgcg aggcattccg gcacacctcc  28800
gtcacggccc cgctggcctc cggcgtcgtg atggggatgg gggcgctggg ctaccggctg  28860
gcagcgcgcg ccctcacccg gctggtcccc gaggactgac ggtgacccgg cccggcccgt  28920
acgcacctcc agatgggacc ggcccgcccg gcagggacgc cacctcggcg cccggcccgt  28980
acgcacgctc aggcgggcca cacccgcagc tcctccttga tcacctgagc gccggcctgg  29040
tcgcacgccc cgggcagcgg gcaggccgcc gggaggatcc gcacggtgaa cggcccctcg  29100
gtcaggccgc gccaggcggg gaccacggcg cgaccgcggt ccacctccgc ggacaccaag  29160
gccgtgaccg gacagggaaa ttgaccggag acctccccgc ccaccccttc gccgggcccg  29220
cggctgccga gccacagcag cacatgcacc ggcgggcgcg cggccgctc ggcggccgc  29280
agccgcgc ccagcccggc accggcacag accagcgccc acgcccgcc gtcccggcc  29340
gcctccgcga tcgcctcgac gccgtgctcc accaccagtt cgggggcgag cgcctgccgc  29400
cagccctccg cgtccgcgcc gtcgtcagcg cgaccagcc ggaccaccgg caccaccacg  29460
cctccggcgt tcccctcagc cgtacggac atccccagac cctctcttcc gtaccgtccc  29520
acccgcccctc gctctcccgc ccggcgccgc tacggcaggc cgtcggtcat cccgagggag  29580
aagtagttct cgtaccccag cagccggcgc agttcgggcg tcgcgcgggt ggcgacgtcc  29640
```

FIG. 26H

```
tcccgcagac cgagaagaa gttctgctgc tgccggacgt agccgcggca gtagtagttg    29700
aggatgccgt gccgcggccg gtcggtggtg ttggcgcccg tctggtgcca caggcgcccg    29760
tcgaagacca tcacgctccc ggccggcgcg cacacggcga ccgtctcggt gttcccctcg    29820
ccccggtcgt agtccggctg ccggcccagc agatggagc cgggcaccag gcgggtcgcg    29880
ccgttgtcct cggtgaagtc gtccagcatc cacatgctgt tggccaccag cggatacggg    29940
ggccacggcg ggcgggcgaa ggtctggtcc gcgtgcagat gcatccggga accgccgggg    30000
cccgcgatat tggcgtgcgt gctggagagc aggaagccga agcccaggat ctcctccatc    30060
aggagcatga cggtgggatc ctgcacgttc tgctcgaatt cctcgccctt gttcagcagg    30120
ctgaagacgc gttggttgcc gccgtcgtag agaaaggccg agccgttctc acgtcctgc    30180
tcggcgacct ccagcagccg ccctctgagc ttttcgaaga ccgcggccgg caaggggcac    30240
tcgatcaggc agtatccggc ttcgaccaga tcccgggagg ctttctcgac gtcattcgtc    30300
aaagtcgcat ccatatggcg aggctagcag ccgaaatctc ggccgcacca tagcgcgaaa    30360
acgccggtcc atgattttt cacgtgcggg aaggacggat tttccatggc acactcaccg    30420
cggcggccgg acggcccct ccgcatcggg gtctggctgg cccccagca cacctcggtg    30480
gccgaactgc gcgccgcctg gcgcgcggcc gactccctgg gcgtggactc gctgtggctg    30540
tgggaccact tcttcccgct caccggggac cccgacggca gccacttcga ggcctggacc    30600
ctgctggcgg ccatggccgc cgacaccggc gccgcccgcc tgggcaccct ggtgtccaac    30660
tacgcctacc gcaaccccga cctcctggcc gacatggccc gcacggtcga ccacatcggc    30720
gacggccgcc tgatcctcgg catgggcgcc ggctgggtcg aacgcgacct gaaggagtac    30780
ggctacccca cgcccggcgc gggggagcgg gtggacgggc tcatcgaggc ggtggagcgc    30840
gtcgaccgca gactcggccg gctgcgcccc gggccgctcg gcgacctccc cctgctcatc    30900
ggcggggacg ggcagcggcg cctgctgcgc ttcgccgccg aacgggccgc catctggaac    30960
accatggcct ggcgcttcgc cgagggcaat cgcgtgctgg acgagtggtg cgcgcgggtc    31020
ggccgcgacc cggcggagat cgagcgcagc gccttcgtca cccgcgacca gaccgacgag    31080
gagctgcgct gcctggtggc gacgggcgtc cagcacctga tcttccaggt cgggcacccc    31140
ttccgcttcg acggcgtgga gcgggccctg cgcttcgcgg gcggctggag caagggggtaa    31200
ggccagggcc cggacgcgcc ccgcgtcgcc actagagcaa cgcgtccgcc agccggtcca    31260
cttgggacag cgccgccgcc gtggggtgga ggacgacctc gtccaccccg ccgtcggcga    31320
gcgccgagac cgccgcgcgg agctgccccg cggtgcgcgg ggtcttcgcc acgaactcct    31380
ccgcctcctc gcccagcacc gcgaagtagt cccggacgaa ggccgccgac tcctgggcca    31440
cgtcctcgcc cagggtgtag cgcgccagcg ccaccacatg cggcgcccg gcgcgtcccg    31500
cctcgctcca ggcgcggcgc acccgttccg cgaccggcac gatccgctcc ggctccaggc    31560
cgggcgccgt ccagccgtcg gcccagcgcg ccacgcggcg cacggccgcg gcgctgaccc    31620
cgccgacgag gaccggcaca ccggggccct ccgcgcccgg ccgggcgccc cggccgagca    31680
gctccagctg ctcctcgaac gccgcgcgcc ggtcgtcgaa ggcgcggccg gcggcctcga    31740
agtcgtcctc gcgcacgccg ggcccgaccc ccagggtgaa ccgcccgccc gacagcgagt    31800
ccagactcgc gaccgccttc gccagcacag gcgcggtgcg cagcgggccg atcaggacat    31860
tggtgagcag cccgatccgg gaggtcgccc cggccgccgc cgccagcgcc agcagcggat    31920
cgtggcccgg ataccaggg cgctcggtgg ccgcgagcga ggcgaatccc cgctcctcgg    31980
cccgccgcgc caatcggtt atcaggcgcc cgtccgcgcc gggcacggtg ttcggcagag    32040
caatgctgat cttcattggt ctccccgggg gttcgcagga tttccggtcg aatgtgacag    32100
gggattccgg cacggccggc gtgattgcgg caggagttca ccagcggccc ggcgcggaga    32160
aatgcggcgg catttccacg gccccctgtc ggaccgccgg accgccgtgt acgtttttcg    32220
gaaagcaacg tcgtacggtg cgcacagcga gaggaatccg cgatgcccgc tgccggaaaa    32280
gtcgccgtga taggactcga ctccgcgact ccgcagtaca tgttcgaccg gttcgccgag    32340
gacatgccgg tgttcaccgc cctcaggcgc aagtccctgt ggggtccgat gcgcagcatc    32400
gacccgccca tcaccatgcc cgcctggtcc tgcatgatgt ccggccgctc gcccggcgaa    32460
ctcggcgtct acggattccg cgaccgcggc gcctacgact acggcgtgct gaagttcgcc    32520
acctcccaca gcatccaagc ccccggatc tgggacgaga tgacggccgc cgggcgctcc    32580
agcgtggtcc tgggcgtccc cggcacctat cctcccgccc catccgcgg ggccatggtc    32640
tcctgcttcc tggctccctc cacacagtcg cgctacacct ccccgcccgg cctcgccgac    32700
gagctggaga agctcaccgg cggctacgcc ctggacgtgg aggacttccg ctccaccgac    32760
ctgaacgcg tatccagcg cgtcttcgac atgagcgagc agcgcttcga ggtcgcgcgc    32820
cacctggcga ccacccagga gtgggacttc ctctccttcg tggacatggg ccccgaccgc    32880
ctccaccacg gcttctggaa atactgcgac cccgaccacc cgccacga gccgggcaac    32940
gcctacgccg gtctcttccg cgactactac cgcgccctcg accggcacct cggccgcttc    33000
ctggagagcc tgcccgagaa cacgaccgtc ctggtcgtct ccgaccacgg cgcccagccg    33060
atggtgggcg ggctcttcgt caacagtgg ctgcgcaagg agggttacct cgtcctgacc    33120
gaggagcccg ccggacccac ccccgtcgcc caggccgccg tcgactggaa gcggaccacc    33180
gcctgggcg aaggcggcta ctacggacgg atcttcctca cgtcgaggg ccgggagccg    33240
cagggcacca tcccggccgc ggagtacgag agcacccgcg acctcatcgc ctccgccctg    33300
gaagcgctgc ccgacgacca ggggcagccg atgggcaccc gcgccctgcg ccccggcgag    33360
```

FIG. 26I

```
ctctacggag aggtcaacgg catcgccccc gacctcctgg tctacgtcgg caacctgcgc  33420
tggcgggccc tggccaccct cggcatgggc aagggcctct acacgacgga gaacgacacc  33480
ggccctgacc acgccaacca cggggacacc ggcatcttcg ccctcagcgc ccccggcatc  33540
accccggcc gcgcggacgg cctgtcgctg tacgacgtgg ccccaccct gcgggaactg  33600
ctgggtctcg cgccgcaggg ctcccgcggc tccctcctcg gctgacatca cccgcccagc  33660
agcgcgtagg gagtgggcgg cgccggcacc ccgcccgctc ccgcaccgcc accgtgcacc  33720
acgtgcttgt ggcggtaggc gtccagctcg ttggtgagcc ggtcccagac ggcggagcgg  33780
ggcccggctg tgccgggcag ctccaggtcg accagccggt agtcgttgat ccatacccgg  33840
tccgcgcgca gccgctcggc caccgcgcgg gcccgcgcgg gatcggcgga ccacacccg  33900
gcgctgagcc ggtagcggga gccgttggcg atgcgcaccg cgtcgtcgtc ggacccggcc  33960
cggacgaccg cgagcaccgg gccgaagatc tcctcctgcg cgacggcgtc gtccgcgccg  34020
accgacgcca gcaccgtggg caggaaatac gccccggcgt ccagccgggg cggcagctcg  34080
tccgccgcgg gcgcccggcc gccgcacacg agctccgcgc cctgggagag cccgagttcg  34140
gtgaagcgcc tggccgtacg cgcctggttg cgcgagacca gcggcccag gtcggtggcc  34200
gggtccagcg gatcaccgac gcgcagccgg cccacccgtt cgctcagcag ccgcaggaag  34260
tcgtcgtgga cgtcggcgtg caccaccgcg cgggtaccgg ccatgcacac ctgcccgttg  34320
tgcaggaacg ctccccacgt gacgccggtg accgcccggt ccagatcggc gtccgcgagc  34380
acgatgttgg gggacttgcc ccccaggtcc agccgggcgc tcgtccccgc cgcggcggca  34440
ccctcccgta cggcggcccc ggtctcgtcc gagccggtga acgccaccag gtcgacgccg  34500
ggcgagcgca ccagctgctc cccggcgacc ccgcccggcc ccgtgaccac gttgaccacg  34560
cccggcggca ggccgcactc gtggagcagc tccaccagtc gcagcgtgga gagcgaggcg  34620
aacgaagccg gtttgatcac acaggtgttg cccgcggcga tggcgggcgc gatgcgccag  34680
gccgccagca gcagcggcag attccacggc acgatcgcgg cgacgacccc caccggccgc  34740
cacacgacgt aggaacccga accgggcgcc tccggctgcc gttcgggcac gtgctccgcc  34800
caccacgcgc tccactcgaa ggctgccgcg gccccggca catcggcccc gagagccttg  34860
cgcagctcg agccgttgtc gcgggcctcc aactcggcca gcggctccgc ttcttcacgc  34920
aagcgctgtg cggccttgcg cagcaggccc gcccgctcgc ccggcgccat ccgcggccac  34980
gggccctcgt cgaaggcccg ccgggcggcg gacaccgccc ggcggacgtc ctccgcgccg  35040
ccgctgggaa ggtcggccag gtggcgccgc gtggccggct cgaaggtgcg caggacggcg  35100
ccgtcgtggg cctgcacggc ctgccgtcg atgtacatcg ggaaccgctc gaccgctctg  35160
tccacccggt ccatcgcctt caccttctcc ttctgctgac ccgtggggat gcgcccggcc  35220
gggcccgccc gcggccgcgg ccgtaccgga acacccgccc cggagcggcc gcgcccgcgg  35280
tcaggccggc aggggcggga tgttggggtt gaaccggaag acgttgcccg ggtcgtactg  35340
cgacttcagg gcctggagcc gcgcgtagtc ctccggcgtg taggcgctgc gggtcgtctc  35400
cctcgatgtg ttgtgacccg cgaggaagtt caggcacacc ccgggcgtcg tccacggccg  35460
catgctgtcg acgaactcct gctgcgccgc gtccacggcc gccagggtgt ccgggtcgac  35520
cagcgagccc acgtaggcgt tgaacaccgc ctccgggaag tggcccaccg cgctcgggtg  35580
ccggggcggc cgggcgaggg cgccgcccag gtgccgcagc tccaccccga acagcgcgtc  35640
cgtgcccggc cccgcgagcc tgaggatctc gtcgacggcg atctcgtcca gctgcccgaa  35700
catgaccgtt ttgctgtgac tcgacaccgg ggccggcgga tcgttgtgga tgatcccggc  35760
ccgcgtgtac gggagcgtgt ccaccgtatc catgacgacc gtgccggcgg cccggagctc  35820
ggcgaaccgg cgctcaccct cctcggggtc tcccagccag gccagccgga tgtgggtgac  35880
gaaccggccg cgcagcggtc cgggcacccc ctcggcatcg ggatacgcgg ccaggaacac  35940
cgacgacgcc atgtcctccg gcatccgggg cgcccactgg agataggtgt tcagcacggc  36000
gcgcgtggag ccggcgtcga agaacgacc tccgccgtac acctgggtga cggggaacag  36060
cccgacctcg acggaggtga cgatgccgag gttccccctg ctgccgcgca cgccccagaa  36120
gagatcgggg tgttcctcgg cggagacctg gagaaaccgc ccgtcgccg tcaccaggtc  36180
gagcgagacg acatggtcgc cggcgaaccc gtacttccgc gacagaagcc cgagccgcc  36240
gccgaggagg taggagaccg cgccgacgaa cggcgccgag ccgctcagcg gtgcaagacc  36300
gtgcgccgcc gcctcgtgga tcacctgctc ccagcgcacg cccgcctcga tccggcggt  36360
ccgggccgc gggtcgaccc tgacgccggt catccgccgg gtgctgatga ggacgtcggt  36420
ggccgccgag gacttccgt gaccggtggc ctggacggcg atcccaaggc ccgggccct  36480
ggcgaagcgc acggcggcga tgacatccgc ggcaccggtg cgacgacga cgagggcggg  36540
gcggtgttcc acggacagtt cgaagccgga gcgctcctcg tcgtacccct cgtccccggg  36600
caggaggacg gatccggcga cctgcgccgc gagctcttcg gcggccgcgg gccgagggc  36660
cgcggacgtg tccgtcacgg agtggctggc tggtttcacc gaggaacctt tctggctgga  36720
gcttcgagaa gcgcgccgcg cgtgcgcggg cagggccgcg ggctcgccg gccttggaa  36780
cggagcgggc cccgtcagtt gcgcgggccg ggaccaccg gcagtgaccg gacgcccagg  36840
ggcaggagtt cggagctgtg ctcgacctct cgggaggca cggccagggc gatgcggggg  36900
aaggccgcca gcaggcggcc gatgccgacg gtcagttcgg tcacggccag cccggtcgcg  36960
gggcaggcgt gctgcccggc gccgaacgcg atgccgcggt cggccacccg ctcgatgtcg  37020
agcacgtggg gatcggcgaa gacctcgggg tcgcgggagg ccgccgagac cagtggcagc  37080
```

FIG. 26J

```
acggcgtccc cggcggcgac gcgcctgccg gagagcacca cgtcctcggt ggcgacccgc 37140
agcaggccgt cgttgctgga ggggtagtag cgcagcaact cctgtacggc agagggcagt 37200
acggaggggt cctcgcgcag ccgggccgcg aggccggggg aggagagcac gccgaagagg 37260
tgccgggcca gcaggtcgcg gatggtgatg aagcccgaga tgatcaggcc gtggagcagc 37320
aggcgccggt cgtcgtcggt gagctcctcc gcgtccagca gcgtgtcggt gacgctgtcg 37380
cccggctcgg ccctgcgggc cgcgagcagt tcgtccagca cctggccgag cctgccgcgg 37440
gcctccttca gcgcctgctc ggtggcaccg cgcggaagca gcagcagctc gacgtcggag 37500
gtgacgtcct gccaccggtc cccgggcagc ccgaggaact cggctgtgac gcggccggcg 37560
aagggcgcgg tgtacgccgc gacgaggtcc accgtgccgc tgccggcggg cagccggtcc 37620
agggccgcct cggcggccgc ctcgatgcgg ggtgcgaacc gcgccgtgcg cgaggcaccg 37680
aacgcggcca ccaccggacc gcgcagccgg ccgtgctccg gcgggtcgag gtccacgatg 37740
cccgagccct gggaccggcc gaagcccgag cccggcagca tggcggcgcg atggcggctg 37800
aagcggccgt cggtgagcac cgtgcgcacg tcctcgtgcc gggtcaccag ccagatgcgc 37860
gagccgtccg ccaggcgcac ctcggcgacc gggtcatcgg tgagcagccg cgcgtactcg 37920
ggcggcaccg tgccgccggg gccgggcggg aagggaaagg cgggcggggc ggctgaggtc 37980
atgcgccccg gctcctctca ccggccggcg cgccggcgcg ggcgtggccc ggccaggtga 38040
agtccttcgc caggacgcgg ttgtccagct ggtgttccac gacgatgttg ccgcagccgt 38100
agtcgtcggc gatgacctcg acgtcctcgg cggacaccag gtgtccgggg tcggccagca 38160
gggtcgccac gcccttggcg ggggccagga cctccagggc gaagccgcgg gccacgtgct 38220
ggcggtgggt gtgcgccgcc gcgatcagga aggtgtcgtc ggggtcgcag atcagatgcc 38280
acagcgcgcg ggcctggagg aagcggcgcg ggcggtcggt gaagcgccgg gaggagacca 38340
ggaccggccc gtccgcgccc ctgcgggtgc cgagggcgac caggccccgg tccatatagg 38400
ggacctgctc ggtgcggtag cccatcaggg gggccgggtc gaagggcgcg tgtcgtcca 38460
gacccgccca cgcgcgcacc cggtgcgcca cctcgtagcc gaggtcccag gggttgtcga 38520
gtcgcccccg agcgaagaac ttctcgctca agtcggcgca gtccttgcgc agttccacca 38580
aggcggggagg gagcgggta tccgcgggcg cggtgcccat cagggtgcgg acgcgcgcga 38640
tccactggag ctggtcggct atccgctcag gccgcacccc gttgaagaag tcactggcga 38700
gcggttccgc caactgctcg gcggccttga ggatgtccgc ctcgtacggc tcggcctcgg 38760
cgtaggggtc caggcccagc cgtgccgcga tgcggcagaa ggcggcctcg tcctcgtcgg 38820
tggcgcggac ggcggccac tcctcctgga gcggggtgcc ggtgatgccc tggtccgtga 38880
ggcgctcggt caccgcgtcg acgaacgagg ccagtgtggc ggtgaacgcg gcgctctcca 38940
cacaggagtt gccccggctc gcgaagcggt tcccgggtcg tacgtcgggg cccatgtccg 39000
gcatccatac gatccgggtc tccggccct cgggcacgaa gagcatgtcc ggccagcgga 39060
agccgtcgca ggcggcgcgc aggatgtgac ggcgcgaacg catccaccac gaaccgcggt 39120
tgtcgcccac accgtggcgg taggcgaagc gcagctggga tatctgggtg ccgggccgcg 39180
cgtcggccac cagcgaccac cagttgaagg cgatccactc ggccaggggg tagagcgagc 39240
cggtcgtgtg ctcccggaag gtccctgcc cgggctcctg gacgagtgtg acggtctcgg 39300
cgcccacggc gatgcgcagc cgggcccagg tcgcttgcag ctcgcctccg ccgccggccg 39360
gggcgtcgag ccaattccac tgcaattgga actcaggaag catggtccgc cagcccttcc 39420
ggccattcgc tcgggtggag ttcgtatccg gtgtattcgc ccggcgcacg gcccgtcagc 39480
cggaattcca cgacggagtc accggaccgg tgccagacat agcgcgggaa gccgtcctgc 39540
cagggaccgc cgaggaatcc ggtgcggatc cctgaacgga gggtgcccag cggggcggcc 39600
gacagggaac cgggcacggc gagcagatcg gccggggccg gccgtattc ccggcgggcg 39660
aatgtcaccc gcccgcagag ttcttcccgt tcgctgcggt cgggcagtgg cgcgatcgcg 39720
cgacgtggct cgcggcggcg cccgggcgct cgtaggacca tgatgtccgc ctttcgggga 39780
acgtgccggt gagctggcc ggcggggccc ggacgcggcg tgcgtccggg ccccgcccag 39840
ggtgttacgg gaggggcgcg aagaggtcca ccacgttgcc gtcggggtcc ttgacgatgg 39900
cgtagcgctg accccacacg gcgttccacg gcttgaggtg gccctcgtag ccggcgtcga 39960
cgagctcggc gtacttcttg tccacgctcg cggtgtcggg gaactcgaac gcgatggcga 40020
agcggtggcc gccggtgggg gcctgccact cggggtcgta gctgcgcacc gtctccacgg 40080
tgtcccaggc gagccggatg ccgccgtcga gcacggcctc cgtgtgcggc gcggagtcgg 40140
cctcggcggg gatctcgacg cccagcttcc ggtagaactc cagcgacttg gccatgtcct 40200
cgaccaccac ggcgaagagg gaaatccttg ctgacatgcg cgttccttc ttgcactttt 40260
aaattggtct ccggtgccgg gccgtctgaa ttctccgggg ccggccggac cacgaagtcc 40320
gaatgtgctg gacgcgccgt acgctagtga ctgcgcgctg actttggcca atcggggtat 40380
cccccgccgg agtcaacgcc gctgacagga caacgatttc aggacagcgg cacgccgtcc 40440
cagtcgttcg gcacgtcacg cccgagcaga gcgcatacgg tcgcgggaat atcgacgggg 40500
gcggcggtgc gggtctgccg cgccccaccg gtgaagccgg gccgacggc cgaccagtag 40560
gactccggc ggtgccagcc gctctgccag tcgcggtgga cgtgcgaggc ccagtgcggg 40620
tcgcccagcg gaagatagcg ccagtccgcc ggctccagga tgaggtcggg ggcgtgctgg 40680
gtggcctcgc cgggatagac ctcctcccgg cggcgcaccg cgtcgaagaa cagcctgccg 40740
gtacggggt tgcgccgctc cagcagcgcg gccgcgacgt cggtgcggac cttctcgtag 40800
```

FIG. 26K

```
tcgcgctccg ggaccaggcc gtgcttgtag cggtcgcgca ggttgatgtt cacccgtgc   40860
gtgccctgca ccgcctcgaa ggccgcgctg ccggcccact cgacgcggcc gtcctcggcg   40920
gtggccagga aacccgcctg ctccatctcg tcgttgatgg aacagtagtt gcgcagcggc   40980
ccgaagccta tctccgagaa ggccacgaca ctggtgcggt cgtcggccgc ccgcagggcg   41040
tcctggatga cctggtcgca ggtgcggtag gcggcgaaga cggcgctctc ccgctcgtgc   41100
tcggggccgt gctccagctc ctgccagtag atgtgcgaac agcggtcgat gctcgtgagg   41160
ttgacgatca cgacatcgga ctcctccagc agagccaatg ccgcgcgccc gcgctgcacg   41220
tccgcctcca gcaggaagg cagcagctcg tcgcggtcct gcccggtcca gaagatcgac   41280
acgtcgtgga ccggacggat gcccttcttc gccagggtgc gctggaggct gcgcgggtgg   41340
caggcgtgga gggtggcata catcggatag gtgatcaggg aaccgtcgaa gggctccggg   41400
ggatgggtgc cgaagaggcc tatcgaggcg aacctgacgg cctggaacac ctcgtgctgc   41460
cacagcagtg ggtggcggcg gtgctcgggg gtgaggacct gcggcgcgta ctccgggtcg   41520
tgacaggtcc agtaggagta gaagccgtgg tccgcggcgc gccggccggt caggacgctc   41580
agcaggcccg gcggttcgta gggggtgccc tcggcgtgga gcggcccgga agcccctgc    41640
gagcgcaggg cggcgaagcc gggcagcagc ccctgggcac accagcggtc gagcagctcg   41700
ggtgccgctc cctcggtgat gacgacgacg acacgctggc ggattgtcac gtgcgactcc   41760
ctcggggttgc gtggcagttg gcatgccgtc atccgggagg cgccggaaag gccgaggcgt   41820
tccggcgccg gacaggcgtc gatcgtcgga tcaagctaac agcgggacga ggactctctc   41880
cagacgacgg tacggaggaa attgagagag ggctgagaga gggctgagag agggcagagg   41940
cgggggagtg gcgtggggtc acacggtgcg caggaggcgc agacgttccc gtaccgcctt   42000
gggcagcccc gccaccacgc gatcgtacga atgctccacc atctcccgca gctcctccac   42060
gggaaccgtg ccgttcagga caaccgtgtt ccagtggcgc ttgttgacgt ggtagccggg   42120
caccaccgcc gcgtactgct cgcgcaggtg cagcgccaga tccggttcgc acttcagcgt   42180
gacctgcggc gggcggtcct cggaggcgtc ctggagaatg gcgaagacct tcttctccac   42240
cttgaagacc gcggctccgg ggccgaacgc ctcgtcgtcc accgcctccg gcagctccag   42300
cgcgaagtcg gagagttcct ctggtgtcat cgccggtcct tcttcctgcg gcacggcagc   42360
gagcggccga accgcgtggt catggggtcg gccaacagac tagaggcgca ggaggagttg   42420
ccgtgcggca gggcgcggac gctgatccac gatggccgaa acactgcggg gagttccggt   42480
cgcggcggga cggcgacctt gacgggcggt cctgccattg gcacagtttg gctggctcca   42540
cacaggtttt cggtggaccg ttcgttcctc tcccggtgct gcccggtcgc ggtaccggtg   42600
tccgcgcgat ccgtgtgccg cccgcgccgt cccgaaccgg cccgtgcgcc cactctcccg   42660
gccctccgcc gccggtctcc gtaccgccgc cccgcccttg ccggggcggc gccgacgccc   42720
gcaccccggc cttggccctg cccacggccg catccgcgca ccccctcac cccggcgccg    42780
gccatgcccc cgtgccgcct gccccccttg atgccctgtg gaggaacccc cgtatgaccg   42840
tggagcagac ccccgagaat cccgggaccg cggcccgcgc cgccgcggaa gagaccgtga   42900
acgacatcct gcaaggggcg tggaaggccg cgccatcca cgtggccgtc gaactcggcg    42960
tcccggaact gctccaggag ggccccgca ccgcgaccgc cctcgccgag gccaccggcg    43020
cccacgagca gaccctgcgc agactgctcc gactgctcgc cacggtgggc gtcttcgacg   43080
acctcggcca cgacgacctg ttcgcccaga acgccctctc cgccgtcctg ctgcccgacc   43140
ccgcgagccc ggtcgccacc gacgcgcgct tccaggcggc ccctggcac tggcgggcct    43200
gggaacagct cacgcacagc gtccgcaccg gtgaggcgtc ctttccttcg acgtggccaa   43260
cggcacctcg ttctggcagc tcacccacga gggaccccaa ggcgcgcgaa ctgttcaacc   43320
gcgccatggg gtcggtctcc ctaccgagg ccggacaggt cgccgcggcc tacgacttct    43380
ccggcgccgc gaccgccgtg gacatcggcg gcggccgcgg cagcctcatg gcggccgtcc   43440
tcgacgcctt ccccaccctg cgcggaaccc tgctggagcg cccgcccgtc gccgaggagg   43500
cccgtgagct cctcaccggc gcgggcctcg cggaccggtg cgagatcctg cccggcgact   43560
tcttcgagac catccccgac ggcgccgacg tctacctcat caagcacgtg ctgcacgact   43620
gggacgacga cgacgtcgta cgcatcctcc gccggatcgc caccgccatg aagccggact   43680
cccggctcct ggtcatcgac aacctcatcg acgagcggcc cgccgcatcg acgctcttcg   43740
tcgacctgct gctgctcgtc ctcgtcggcg gcgccgaacg ctcggagagc gaattcgccg   43800
cgctgctgga gaagtcgggc ctgagggtgg agcgctcgct gccctgcggc gccggcccgg   43860
tgcgcatcgt cgagatccgc agggcctgaa accgccctc ctgaccgaag ccggccacag    43920
ctgaaggagc aatgacacca tgacggtgct gggtctgggt ggatccggac atgactgggc   43980
ctcctgtgcc accgacggcc gacggctggt ggcgatcgac gaggagcggc tggtccgcag   44040
caagtacggc ctgggagcgg acctcctggc gggcacagc cggcgcgccg tcctcgacgc    44100
cctcggcacg agtgccgagg ccgtggaaca cgtggtggcc tgcgagctcg taccacgccc   44160
cttctaccac tcgttccgca ggcgcgtgac ggtcgtcaac caccatctcg cccacgccta   44220
cagcgcgttc ggggcctccg ggatgacccg cgccgcgta ctggtctgcg acaactccgg    44280
cagcctggtg acgggcctga gtccggccc agggccgcgc gaggcggaga cgatcagctg   44340
ctacaccgcc gacgcctccg ggctgcgcct ggtcaaccgg gtcgccggga cacgccgt    44400
ggacgcctcc tccgagagcg cctactacca gcccggcgag accgacaatt ccctcggcca   44460
cttctaccgc tcggccagcc tcgcactcgg cctcgcctac tccggtccca agacccgcta   44520
```

FIG. 26L

```
cc ccgtcagc gaggacggca agaccatggg cctcgcgccc tacggcgacg accgcttcgt  44580
cgacgaggtc gcggagctgg tcaccctgct gcccgagggc ggcgtgcaga tctcggcgag  44640
caaggtgaac cacctcttcg aacgcctcgt ggaatcgggt gagttcgagg accgggcggc  44700
cttggcctac gccgcccagg agacgctgga acgcgccctg ctgcactgcg cccgcgacct  44760
gcaccgccgc accggcctga cggacctgtg catcgccggc ggcgtcggcc tcaacagcgt  44820
cgccaacggc cggatcctgc gcgagacccc cttcgagcgg gtcttcgtcg tcccggccgc  44880
gggcgacaac gggatcagcc tcggctgcgc ctactacggc ctccacgagc tggaggggcg  44940
cgcgccgtcg gagctccccg ccctcgacac cgcctacctc gggcccgact accccgccga  45000
gcgcgtcgac gcggcgctgg ccggctcggg cttcaccgtg gagaccccg acgacctgcc  45060
cggcagggtc gccggcctgc tcgccgaagg gaagatcatc ggctggttcg acggccgctc  45120
cgaattcggc ccgcgcgcac tgggacaccg cagcatcctc gccgcaccct tccccgcctc  45180
cgtgcgggac cacctcaacg acaacgtcaa acaccgcgag tggttccgcc cctacgcccc  45240
catcgtccgc gaggaccggg cggcggacta cttcgacctc gtccagccct cccccgttcat  45300
gctggtcgtc gcgcgcgtga cccggcagga cgccatcccc gccgccaccc acgtggacgg  45360
caccgcccgg ctccagacgc tgaacgccgc acagaacccg aaggtctacg agctgctcgg  45420
caggttcgag gcgctcaccg gctgcgccgt gctgctcaac acctccttca acgtcgccgg  45480
ccagcccatc gtcgagaccc cggaggacgc cgtcgaggcg ttcgcgggca tgcgcctgga  45540
ccacctcgtc gtggggacc ggctggcgac caagccctga cagcacgccg aggcccgcga  45600
ccggcaggga ggagagccaa gcggtggacg tccccgtgct cgtggtcgga ggaggaccga  45660
cgggcttggc gatggcgctc ttcctcgcac gccacgacgt cggctgcctg ctggtcgaac  45720
ggcggacgac cacctcgccc gtcccgcgcg ccaccacgt cagccgccgc tccatggaac  45780
tcttccgcga ggcgggcctg gaggaggaga tccgccgggc cgggttcgag gtcgtgcgcg  45840
aggacgaccc acggctgcgg acccggcccg aacgccacct gccccgggtg gtcctgcaag  45900
ccgcctcgct cgccggcccc ggcccggtgg gggtcctgga gaccggtgac gaggaactgg  45960
ccgtacccgg ccccctgcgc a cccttctggt gcggccagga ccggatggaa cccctgctcg  46020
ccaaggccgc ggcgcgccac ggcgccgatg tgcgcttcgg ccacgaactg accggcctgt  46080
ggccggggga ggacagcaca cgggcccgcg tccgggcagc gggaacggga cggacctaca  46140
ccgtcgacgc ccgcttcgtc atcgccgccg acggggcgcg cggcgagatc gccgagcgcg  46200
tgggcatcgc gcgggagggc ctgggcacgg tcgcccaccg ggtgagcatc ctcttccgcg  46260
ccgacccggg gcgctgggcc cgcgaccggc ggttcttcat gtgcatgatc cagaacccgg  46320
ggttcgacgg ggcggtgatg gagctcaaca ccccggggccg ctggtgcgcc gcggtggact  46380
acgacccggc ccgcgccgaa cccgacggca cctactccgc acgcacctgc ctcgacctgg  46440
tccgggccgc cgtcggtgac gaccggagcg acgcggcggt cgacaccgtc ttccactgga  46500
aggcccggca ccgcatagcg gccgcctacc gcagtgggc ggtgttcctc atcggcgacg  46560
ccgcccacct ccacccgccc tccggcggct acggatccaa cgtcggcttc caggacgcgc  46620
acaacctcgc ctggaagatc gccgccgtgc tcggcggctg ggccggaccg cggctgctgg  46680
acacctacga cgaagagcgc cgccccgtgg gaaaggcgac ggcggagcag tcgatgctcc  46740
tcgacggcgt gccaccggaa ccactggggg gaagcgtcgt ccgctgcgat ccccgcaccc  46800
tgatcatggg ataccgctac cactccgccg ccgtcctcgg ccccccgcac ggccccgcct  46860
tccccgcggc cttcaccctg gcggagacc cgggcacccg gctgccgcac gtatggctgc  46920
gtacggacgc gggggaacgc gtctccacgc tcgacctgtg ccacgggac ttcgtcctgc  46980
tctccgccga cccggtctgg gcggcggccg cggcgcgctc ggcgaaggag acgggcgtac  47040
cgctgcgggg ccaccacctg gcggccaccg gaagcgaact cgccgacccc tccggcgagt  47100
tcccgcggag ctgcgggacc gggcccgcgg gggccgtgct cgtacggccg gacggcatgg  47160
tcgcctggcg cacggcccgc gccgtgcccc cggaccggga cagcgcgcag gacctggtca  47220
cggcagcggt gagacgtgtc ctcgcactgc cggagcgcgc ggcgccaccg gtgctcggtc  47280
cgccgcggtt gtcacgcggt cctatcggc gagtcgggag cgacgggtga agcctcattc  47340
cttctgcacg tgctggccgg gcgccaccgt atggctgacg ggcccaccgg gcgcgggcaa  47400
gacgacgatc gcccgcgcac tggcggagcg gctgcgcgaa cggggccggc gcgtggaggt  47460
gctcgacggc gacgcgaccc gcgcgctcct gaccgcgggc tcctcgtggg aggacgtgg  47520
caccggcctc cagcgggtcg gcctgatggc cgaggtcctg gcgcgcaacg gcatcgtcgt  47580
cctcgtcccg gtgaccgcgg cccgcgcgga cagccgcgaa gccgtacgca gcgccacga  47640
gcggtccggc accgcgcacc tggaagtgcg ggtggtccgg gacgcagtgc ctccgagcgg  47700
gctccccgcg ccgcccggcc cagatctgcg gatcgcggcg cacgagcaga gcgccgagga  47760
gtcggcgcgg gcactgcacc ggctcctggc ggagagggag ctggcgtgaa ccccgggcgc  47820
ggtggagcgt acgccgcggg gcgcgacggg accgcgggga cgcgacgccc tcacggtctg  47880
tcgcacctgg atctgctgga gtcggagtcg gtccacatct tccgtgaggt ggcgggcgag  47940
ttcgagcggc cggtgatcct cttctccggc ggcaaggact cgatcgtcat gctgcacctg  48000
gcgctgaagt ccttcgctcc cgcaccgtg ccgttcgcgc tgctgcacgt ggacaccggc  48060
cacaacttcc ccgaggtgat cgcctaccgg gaccgcgtcg tggcggcgct cggtctgcgg  48120
ctggaagtgg cctccgtgca ggacttcatc gacaacggca ccttgcgcga acgcccggac  48180
ggcacccgca atccgctgca gacggtgcca ctgctggacg cgatcgggcg ccaccgcttc  48240
```

FIG. 26M

```
ga cgccgtct tcggcggcgg ccgccgcgac gaggagaagg cccgcgcgaa ggagcgggtg   48300
ttctccctgc gcgacgagtt cggcggctgg gacccgcgcc gccagcgccc cgaactgtgg   48360
cggctctaca acggccgcca cgcacccggc gagcacgtcc gcgtcttccc cctctccaac   48420
tggaccgagc tcgacgtgtg gcagtacgtc gcccgcgagg agatcgaact ccccaccatc   48480
tactacgccc acgagcgcga ggtcttccgc cgcggcggca tgtggctggc accgggggag   48540
tggggcggcc cacgcagggg gaagcggtg gagaagcgac gggtgcgcta ccgcacggtg   48600
ggggacatgt cctgcaccgg cgcggtggac tcggcggcgg ccaccgtggc cgacgtcgtc   48660
gccgagatcg ccacgtcccg cctcacggaa cggggcgcga cccgggccga cgacaagctg   48720
tcggaagccg cgatggagga ccgcaagcgc gaggggtatt tctagcgcgg cggggccggt   48780
gcggcccaca agcggaggac tagtccctaa gtatgaagtc ccctactccg tttgtctgtt   48840
gagggcaggg gcgccgtctg aggatgatgc agtccatgtc acagttactt tccgggaagg   48900
acggcgccca ggaggcgcca agtcgcggcg ggtccacgtg ggtggcggtc ctcgccgcgt   48960
gcgtggggca gttcgtggtg gtcctcgacg tgtccgtcat caatgtcgcg ctgccgtcga   49020
tccgttccgg cctcgacatc ggcgagacgg gcctgcagtg ggtggtcaac gcctacgtca   49080
tcgccttcgc gggcttcctg ctgctcggcg gccgggcctc cgacctcttc ggccgcaagg   49140
ccgtgttcgt cttcggcctc ggggtgttca ccgccgcgag cctgctcggc ggcctcgcgc   49200
aggcgccgtg gatgctcatc gtcgcccgcg ccctgcaagg catcggggcg gccgtgctct   49260
cacccgccac cctcgcgatc ctcaccacca cgttccccga gggtccggcg cgcatcaaag   49320
ccgtcgcgat ctggacggcc gtgggcacgg gcggcggcgc ggccggcggc ctcatcggcg   49380
gcctgctcac cgactacctc tcgtggcgct gggtgttgct gatcaacgtg ccgctgggcc   49440
ttgtcgtgat cgtcgcgacc gtcgcctggc tggccgagag ccgcagcgac caggcacacc   49500
gacgccggct ggacctcccg ggagcggtgc tggtgaccct gggcgtcggc agcctggcct   49560
acggcatctc gcagagcgag ggccacggct ggggctcgcc gcggacgctc accttcctga   49620
tcgtcggtgt cgtggcgctc ctcgccttcg tcgccgtgga gcagcgcacg cgcgagccgt   49680
tgatgccgct cggtgtcttc cgggtgcgct cggtgtcggc ggccaacgcc atcaccatcg   49740
tcagtggcat gggcttctac gcgatgtggt acttcctctc gctctacatg cagaacgtgc   49800
tgaaatactc cgccgtacag accggcctgg ccctgcttcc ccacaccgcc accatcatcc   49860
tctccgcgca gttcgcaccc cgcctgatgc ggtggatcaa ggggcgcacc ctcctcgtga   49920
tcgcgggact gctgaccgcc gcgggcttca tctggcaggg gaacatggac gccgacggct   49980
ccttcctggc gaccctgctc ggcccgggaa tcgtcttctc cttcggcgcg ggcctgatga   50040
tgacgctcct cgcggtctcc gccacgacgg gcgtggagct ctccgaatcg ggcctggtgg   50100
ccggcctcgc caacacctcg cgcaccatgg gcggcgcgct cggcctgtcg gtcctcgcgt   50160
ccgtcgccgc ccgccgcacg gccgacgtgg ggccggcgc ggagggcctg gcctccggct   50220
acggtcgggc gttcgtcgtg tccggggcca tcatcctcgt gagcatgctg atgatcccct   50280
tcctgcccaa gccccagccc cagaccccgg cggaatgacc tgtgagcacg gacatacgag   50340
gaggcttcgt ggggcaggac agccggccgc ggtggctcac cgacgaggaa caacgcgtgt   50400
ggcgcggcta tctgcgggcc accaggctgg tggaggacca cctggaccgc cgcctccagc   50460
gggaagcgga catgccgcac ctctattacg gtcttctcgt ccagctctcc gaggccccgc   50520
gccggggat ccggatgacc gaccttgccc gcaacgcgaa gatcacccgc ccgcggctct   50580
cgcacgcgat cacccgcctg gagaagctcg gctgggtgcg ccgggaatcg tgccacggcg   50640
acaggcgcgg ccagaacgcc gtcctcacgg aagagggccg cgaggttctg gagaagtcgg   50700
cgccgggcca tgtcgccgct gtgcgcgcgg ccgtcttcga cagcctcacc ccggaacagg   50760
tcgggcaact gggccggatc tgccaggcga tagagaaggg gctggaccgg aaggcgcgg   50820
acctgccgtg gctgcgctga ggcgggaagc cgtcgcgagc gcgcggggcc gtcaggctct   50880
gacgccccc gccgcccgcg tacgggatcg ggccgaccgc gccccggatt cacgcgagtc   50940
cgggagcaga ccggacgaca cggatattct ggatgccgtg gaacgacacg acggggcacc   51000
gggctggggc ttcaccccata cccagtacag cgcggaccac ggtgaacgcg gcgccacccg   51060
caggccggg gccctgctct ccgtcgcggcc cctgccgcag aaccagcaca tcatgggctg   51120
gggcgcggag aatcccgaac cggcgcccgg acgctacgcc ttcgaggtcc tcgacagcg   51180
cgtcgccctg atgcgcgcga cggggccac gcccgtcctg accctgtgtg ccgccccccga   51240
ctggatgaag gcggccggc ccggccgcac cgactggtcg cgactggaga ccgccccga   51300
cccccggcac tacgcggact tcgcccggct cgcgggcgtg atcgcccaac gctacccgga   51360
catcaggcac ttcctcgtgt ggaacgagct gaagggcttc tacgacgagg acaggcggcg   51420
ctgggattat gagggataca cccggctgta caacctcgtc cacgccgagc tgaagcggcg   51480
gaacccgcgc aatctggtgg gcggcccta tgcggtggtc gaccacgacc cgcccgccga   51540
ggacgggcg gaccgctcgc gcgaactgcg cggtccctgg ggcgagctgg accagcgctc   51600
cgccgacgtc atccgctatt ggaacgccca caaggcgggc gcggacttcg tcgtcgtcga   51660
cgggtccagc tacacccgcg agggccaccg ggcgattccg gacgagttcg ccgccaccga   51720
gaagttcgcc gacgtcaccc gctgggtcag gagcgtgacc ggactcccgg tgtggtgggc   51780
cgagtggtac gtcgagccgc ccgccgagga cgaccggccg ggcggccggg acggctgggg   51840
cgaggggcac cgcaccgccg tgcaggccac cgcgatgatg cggctggcgg agagcggcgc   51900
gtcggccgcc ttctactgga acccgcagcg gaccgggaag gcgtgccccg gctgcctgtg   51960
```

FIG. 26N

```
gcggagcacc cacttgcgcg acgggggagg ggagttgccc atggcgggtc tcctgagccg    52020
gttcgctcgc gaattccctc cgggcaccgc cttccggccg gtcgccgtca cctgcgggag    52080
cggtgacagg gtcgaggccc tcgccgacga ggccgccgtg ctcgtcgtca acaccgagtg    52140
ccggccggtg gccgccaggg tggacgggca ggcgctgtcc ctcgcgccgt acgaggtgcg    52200
ctggctgacc cgcccgtaat ccagtggggc ggcgcacggg cgcggacagg gaattgcgga    52260
acagggaagt tcacgaataa ggagaacgcg ggaaagcgct cgggcggagc gtgaaacccc    52320
tgtcggcgct cacgatatcc acccagctga tttgcaggtg aaacgggcgg tcgcctcgac    52380
ggtgccgccc gtttcctgtt gcccgaaagg gcaatcgggc atcagcagga gagattgccg    52440
cccggcgcca cgccgaggat cttggtgaat cgctggtagt tcgcgacgcg gctctggacc    52500
tgggcggggt tgtggccgtc gcactccagg gcgccgttga tgctgcggat ggtctgcccg    52560
aagccgcggt ggttgaccat ggcctcgtgc ggggtcatgg tgccggggcc gcgctgggtg    52620
ttccagtacc acaggccggt cttccaggag acggccgcgt ccttctgcac cagcgagggg    52680
ttgtggagca ggtcgatgcc gagggcgtca cccgccgcct tgtagttgaa gttccagctg    52740
atctggagcg ggccgcgacc gtagtaggcg gcctggcctg ccggacagcc gtagggccgg    52800
ctccggtcgc agtagtgggg gtagttggcg gtgttctgct ccacgacata gaccagtccg    52860
ccggtctcgt gggcgacgtt ggcgaggaag gcggcggcct cctgcttccg gacctcggcg    52920
ctgccggtgc ccgcgaagcc cgggtacgcc ttgagcgcgg cgaccaggcc cttgtacgta    52980
tagaacgcgt tccgcttcgg gaacatctgc ttgaactggg cctcgctcac ggggaatgcg    53040
gcggcctgcg aggtgccgcc gtgcggtgcg gccgcgctcg ccgtggtggc ggggcgagg    53100
acggatatgc cgaccagtgc cagagcggcc ggcagcaggg cggcgatgcg atttcttctc    53160
atggcggctc ccgtggggga aagggtgagt gacgcccgcc gacggtgaat cgggccgtt    53220
gggcgccttc gcgtcatcgc gcagtgaata actcccgtga gtttggtgtc aatggcatgc    53280
gccgtgtccg gccgaaccag gtgcactgag caatgagttc aggacaactg cggccgatag    53340
ggcttgcggg agcaacgagg accatgacct catatgccgg aagccggaca cgtgccgaga    53400
aatgccgctg tcctgtggct ccttgggtga cctgtgaaac ccggctggct catgaacgag    53460
ccgattgaac gagccgattg aacaagccga tgaacaagga                          53500
```

FIG. 26O

SEQUENCE LISTING

<160> NUMBER OF SEQ ID NOS: 145

<210> SEQ ID NO 1
<211> LENGTH: 115
<212> TYPE: PRT
<213> ORGANISM: Streptomyces lavendulae

<400> SEQUENCE: 1

```
Arg Ile Gly Ala Gly Ser Arg Val Leu Asp Leu Gly Cys Gly Val Gly
 1               5                  10                  15

Thr Pro Gly Val Arg Ile Ala Arg Leu Ser Gly Ala His Val Thr Gly
            20                  25                  30

Ile Ser Val Ser His Glu Gln Val Val Arg Ala Asn Ala Leu Ala Glu
        35                  40                  45

Glu Ala Gly Leu Ala Asp Arg Ala Arg Phe Gln Arg Ala Asp Ala Met
    50                  55                  60

Asp Leu Pro Phe Glu Asp Glu Ser Phe Asp Ala Val Ile Ala Leu Glu
65                  70                  75                  80

Ser Ile Ile His Met Pro Asp Arg Ala Gln Val Leu Ala Gln Val Gly
                85                  90                  95

Arg Val Leu Arg Pro Gly Gly Arg Leu Val Leu Thr Asp Phe Phe Glu
               100                 105                 110

Arg Ala Pro
       115
```

<210> SEQ ID NO 2
<211> LENGTH: 114
<212> TYPE: PRT
<213> ORGANISM: Streptomyces lavendulae

<400> SEQUENCE: 2

```
Arg Leu Ala Pro Gly Glu Arg Val Leu Asp Val Gly Ser Gly Asn Gly
 1               5                  10                  15

Lys Ala Thr Leu Arg Ile Ala Ala Arg His Gly Val Arg Ala Thr Gly
            20                  25                  30

Val Ser Ile Asn Pro Tyr Gln Val Gly Leu Ser Arg Gln Leu Ala Glu
        35                  40                  45

Lys Glu Gly Asp Glu Ala Thr Glu Phe Arg Ile Gly Asp Met Leu Ala
    50                  55                  60

Leu Pro Phe Pro Asp Gly Ser Phe Asp Ala Cys Tyr Ala Ile Glu Ser
65                  70                  75                  80

Ile Cys His Ala Leu Glu Arg Ala Asp Val Phe Thr Glu Ile Ala Arg
                85                  90                  95

Val Leu Arg Pro Gly Gly Arg Val Thr Val Thr Asp Phe Val Leu Arg
               100                 105                 110

Arg Pro
```

<210> SEQ ID NO 3
<211> LENGTH: 115
<212> TYPE: PRT
<213> ORGANISM: Streptomyces lavendulae

<400> SEQUENCE: 3

```
Asp Phe Ser Gly Ala Ala Thr Ala Val Asp Ile Gly Gly Gly Arg Gly
 1               5                  10                  15

Ser Leu Met Ala Ala Val Leu Asp Ala Phe Pro Gly Leu Arg Gly Thr
```

-continued

```
                    20                  25                  30
Leu Leu Glu Arg Pro Pro Val Ala Glu Glu Ala Arg Glu Leu Leu Thr
                35                  40                  45
Gly Arg Gly Leu Ala Asp Arg Cys Glu Ile Leu Pro Gly Asp Phe Phe
         50                  55                  60
Glu Thr Ile Pro Asp Gly Ala Asp Val Tyr Leu Ile Lys His Val Leu
 65                  70                  75                  80
His Asp Trp Asp Asp Asp Val Val Arg Ile Leu Arg Arg Ile Ala
                 85                  90                  95
Thr Ala Met Lys Pro Asp Ser Arg Leu Val Ile Asp Asn Leu Ile
                100                 105                 110
Asp Glu Arg
        115

<210> SEQ ID NO 4
<211> LENGTH: 115
<212> TYPE: PRT
<213> ORGANISM: Streptomyces anulatus

<400> SEQUENCE: 4

Asp Phe Ser Ser Tyr Gly Thr Val Val Asp Ile Gly Gly Ala Asp Gly
  1               5                  10                  15
Ser Leu Leu Ala Ala Val Leu Ser Ala His Pro Gly Val Glu Gly Val
                 20                  25                  30
Val Phe Asp Ser Pro Glu Gly Ala Arg Asp Ala Ala Thr Leu Asp
                 35                  40                  45
Ala Ala Gly Val Gly Glu Arg Gly Arg Val Glu Thr Gly Asp Phe Phe
         50                  55                  60
Thr Arg Val Pro Gly Gly Gly Asp Leu Tyr Val Leu Lys Ser Ile Leu
 65                  70                  75                  80
His Asp Trp Ser Asp Ala Arg Ser Ala Asp Ile Leu Arg Thr Val Arg
                 85                  90                  95
Ala Ala Met Pro Ala His Ala Arg Leu Leu Val Val Glu Val Leu Leu
                100                 105                 110
Pro Asp Thr
        115

<210> SEQ ID NO 5
<211> LENGTH: 117
<212> TYPE: PRT
<213> ORGANISM: Streptomyces glaucescens

<400> SEQUENCE: 5

Gly Met Glu Arg Phe Ser Arg Ile Ala Asp Leu Gly Gly Gly Asp Gly
  1               5                  10                  15
Trp Phe Leu Ala Gln Ile Leu Arg Arg His Pro His Ala Thr Gly Leu
                 20                  25                  30
Leu Met Asp Leu Pro Arg Val Ala Ala Ser Ala Gly Pro Val Leu Glu
                 35                  40                  45
Glu Ala Lys Val Ala Asp Arg Val Thr Val Leu Pro Gly Asp Phe Phe
         50                  55                  60
Thr Asp Pro Val Pro Thr Gly Tyr Asp Ala Tyr Leu Phe Lys Gly Val
 65                  70                  75                  80
Leu His Asn Trp Ser Asp Glu Arg Ala Val Thr Val Leu Arg Arg Val
                 85                  90                  95
Arg Glu Ala Ile Gly Asp Asp Asp Ala Arg Leu Leu Ile Phe Asp Gln
```

```
                    100             105             110
Val Met Ala Pro Glu
            115

<210> SEQ ID NO 6
<211> LENGTH: 115
<212> TYPE: PRT
<213> ORGANISM: Amycolatopsis mediterranei

<400> SEQUENCE: 6

Pro Leu Arg Ala Gly Asp Arg Leu Leu Asp Ile Gly Cys Gly Asn Gly
 1               5                  10                  15

Glu Pro Ala Ile Arg Met Ala Thr Ala Asn Asp Val Met Val Thr Gly
            20                  25                  30

Ile Ser Ile Ser Glu Lys Gln Val Glu Arg Ala Asn Asp Arg Ala Tyr
        35                  40                  45

Lys Ala Asp Val Asp Asp Arg Val Val Phe Glu Tyr Ala Asp Ala Met
    50                  55                  60

Glu Leu Pro Tyr Pro Asp Ala Ser Phe Asp Val Val Trp Ala Leu Glu
65                  70                  75                  80

Ser Leu His His Met Pro Asp Arg Trp His Val Ile Arg Gln Ala Ala
                85                  90                  95

Arg Val Leu Arg Pro Gly Gly Arg Leu Ala Leu Gly Asp Phe Leu Leu
            100                 105                 110

Val Pro Ser
        115

<210> SEQ ID NO 7
<211> LENGTH: 116
<212> TYPE: PRT
<213> ORGANISM: Saccharopolyspora erythraea

<400> SEQUENCE: 7

Gly Ile Ser Glu Gly Asp Glu Val Leu Asp Val Gly Phe Gly Leu Gly
 1               5                  10                  15

Ala Gln Asp Phe Phe Trp Leu Glu Thr Arg Lys Pro Ala Arg Ile Val
            20                  25                  30

Gly Val Asp Leu Thr Pro Ser His Val Arg Ile Ala Ser Glu Arg Ala
        35                  40                  45

Glu Arg Glu Asn Val Gln Asp Arg Leu Gln Phe Lys Glu Gly Ser Ala
    50                  55                  60

Thr Asp Leu Pro Phe Gly Ala Glu Thr Phe Asp Arg Val Thr Ser Leu
65                  70                  75                  80

Glu Ser Ala Leu His Tyr Glu Pro Arg Thr Asp Phe Phe Lys Gly Ala
                85                  90                  95

Phe Glu Val Leu Lys Pro Gly Gly Val Leu Ala Ile Gly Asp Ile Ile
            100                 105                 110

Pro Leu Asp Leu
        115

<210> SEQ ID NO 8
<211> LENGTH: 120
<212> TYPE: PRT
<213> ORGANISM: Artificial Sequence
<220> FEATURE:
<223> OTHER INFORMATION: A consensus sequence
<220> FEATURE:
<221> NAME/KEY: SITE
<222> LOCATION: (1)...(120)
```

-continued

<223> OTHER INFORMATION: Where present in this sequence, Xaa represents
      an amino acid that varied between the sequences used
      to determine this consensus sequence.

<400> SEQUENCE: 8

Xaa Xaa Xaa Xaa Gly Xaa Arg Xaa Leu Asp Xaa Gly Xaa Gly Xaa Gly
 1               5                  10                  15

Xaa Xaa Xaa Ala Xaa Xaa Xaa Xaa Xaa Xaa Gly Xaa Xaa Xaa Thr
             20                  25                  30

Gly Xaa Xaa Xaa Xaa Pro Xaa Xaa Val Xaa Xaa Ala Xaa Xaa Xaa Ala
             35                  40                  45

Glu Xaa Ala Gly Val Xaa Asp Arg Xaa Xaa Phe Xaa Xaa Gly Asp Xaa
         50                  55                  60

Xaa Xaa Leu Pro Xaa Pro Asp Gly Xaa Phe Asp Xaa Val Tyr Xaa Leu
 65                  70                  75                  80

Glu Ser Xaa Leu His Xaa Xaa Xaa Arg Xaa Xaa Xaa Xaa Xaa Val Xaa
                 85                  90                  95

Arg Xaa Xaa Xaa Xaa Val Leu Xaa Pro Gly Xaa Gly Arg Leu Xaa Xaa
                100                 105                 110

Xaa Asp Xaa Xaa Xaa Xaa Xaa Xaa
            115                 120

<210> SEQ ID NO 9
<211> LENGTH: 3765
<212> TYPE: DNA
<213> ORGANISM: Streptomyces lavendulae

<400> SEQUENCE: 9
ggatccgagg gccggagtgg gattcggctc aatgaaccat gcacacagca cataccagga      60
cggtgtcgcg cccaccatac gcgacgcttc ccgctccctc cagccgtgcg gtttgagcca     120
cttcgacgcc ggataacgtt gccgacaggc ccgccgagca gcccctgaac tggatcaatt     180
cccttgggaa taaggcagtt tcactgctca accaccctgc tgacgagaat ccaccgccga     240
ccggcggtcg gggcagacct tcccggcaag ggtgttgact ccggcaactg ccctatggag     300
gctcgtgtct ggcatccgat cccggcctat gaccgggggc cggatcacat gcccgctccg     360
gccacccctc acaccgcggg ccggatttcc cgccgccccc gaggaacggc gtttcccgtc     420
gggtcacgca ccacccttcc cgacgcgggg cgaacacaac ggaaccgggc cgtgaagcca     480
cggccaccga aggcaaaggc ctcgacaccc gccctcccgc cgtacagcgc cccgaagtcg     540
accgtgccgc cgcacccgca ggaccgaaag gctgctcaat gacacctacg tccggtgatg     600
acgtcctgtc ctttccctca tggccgcaac acggcgcgga ggagcgcgcc ggactcctgc     660
gggccctgga ccagaagggg tggtggcgcg acgcggggca ggaggtcgat ctcttcgagc     720
gggagttcgc cgaccaccac ggcgccccgc acgcgatcgc cacgacgaac ggcacccacg     780
ccctggaact cgccctgggg gtcatgggga tcggccccgg tgacgaggtc atcgtccccg     840
cgttcacctt catctcgtcg tcgctggccg tgcagcgcat gggcgcggtg ccggtgccgg     900
cggacgtacg gcccgacacc tactgcctcg atgccgacgc ggcggcggcg ctggtgacgc     960
cacgcaccaa agcgatcatg ccggtccaca tggcgggcca gttcgccgac atggacgccc    1020
tggagaagct ctccgtcgcg acgggcgtgc cggtcctcca ggacgccgcg cacgcccacg    1080
gcgcgcagtg gcaggccgcc cgggtcgggg agctcggctc gatcgccgcc ttcagcttcc    1140
agaacggcaa gctgatgacc gccggcgagg gcggcgccct gctcctgccg gacgacgagt    1200
ccttccacga ggcgttcctc cagcactgct gcggccgccc gcccggggac cgcgtctacc    1260

```
gccatctgac gcagggctcc aactaccgca tgaacgagtt ctccgcgagc gtcctgcgtg    1320
ctcaactgaa gcgcttgaag gatcagttgc gcatcaggga ggagcgctgg gcccagctgc    1380
gtacggcact ggccgccatc gacggcgtgg tgccgcaggg gcgcgacgag cgcggcgacc    1440
tccactccca ctacatggcc atggtccggc tgcccggcat ctcggccggg cgccgcctcg    1500
cgctggtgga cgcgctggtc gagcggggag tgcccgcgtt cgtcggcttc ccgccggtct    1560
accgcaccga gggtttcgcg cgcggcccgg cgccggcgga cgccgaggag ctggccaaga    1620
gctgtcccgt ggcggaggag atcggcagcg actgcctctg gctgcaccat cgcgtcctgc    1680
tcgccgacgt gaccacgctg gaccggctgg cggaggtctt ctccggcctc gtcggcgcgc    1740
tctgacccga tgcgggcccc caacggcacc accgccccc ggctgagcgt cgtcgtcccc    1800
agccgggggc ccgcggcacg cctgcgcgcg accctcgcat gccttgccgg ccctccccg    1860 ggaacgccgc ccttcgaagt ggtcgtcgtc gacgacaacg acggggcga cgccggtgat    1920 caactgatcg ccgtgacagg cgagatgagc ggccttctcc cgctgcgcgt ggtgcgggga    1980
ccgctgcggg ggcgggccgc cgcccggaac gccggggcgg ccgcgcccct cgcgcccgg    2040 ctggtcttcc tcgacgacga cgtcctggtg gggcccggct tcctcgccgc acacgccgcg    2100
gccgcggaac cggacgcctt cacccacggc cggctgcgcg aactcccac gcggcgcgg    2160 ttcctcgccg ctgtcgagaa ggccgccccg accgaggtcc gccgcgcccg cgccggactc    2220
gaacccgctg ccccggccgc ctccgagcgg cgccaaccgc accggcggct cgtcgccaac    2280
gccctggagc gggccgtgga ggccatggcc ggcggctccc tgccggacgt cgcccctgg     2340 ctcggcttca tcggcgcgaa caccgccctc gacaaggccg catgggagca taccggcgga    2400
ttcgacgagg agttcgggct cacctggggg tgcgaggacc tggagttcgg cttccgcctg    2460
cacgccgccg ggctgcgcag gaccctcgcc cccgacgccc tcggtgtgca cctcagccac    2520
gcccgccccg gccgctggga gcagcaccac cgcaacctca cgcacttctc cgccggccac    2580
ccgcacccgt cggtacgcgc cttggaggcc ctgctcgggc ccgacggcac gccggaggcg    2640
tatgtgcgcg ccgtcctggc cgaagaggcc gcaccggcac gggacgcggc gcgatgagcg    2700
gcacaccggc caccgcgccg tacggtcccg tggtgctctc cccgcacgcg gacgacgccg    2760
tgtggtccct gggcgggcgg ctggcgcgct gggccgccga gggcccgcgg ccgaccgtcg    2820
tcacggtctt cgccgggccc gcggccggga agcccgagtc gtggcggagc gccgccgatc    2880
ccgcggtgcg ccgggccgag gaccggcggg catgtgccga actgggcgtg cgccacgtgc    2940 cgctggctt caccgacgcg gcactgcgta cggcctcggg cgcctatctc tacgcttccc    3000
cgcgccggct cttcggcccc tggcacccgg ccgacctccc gctgctggag gaggtgcggg    3060
cggctctgct gccgctgtgc gcgggggcgt cgagcgtcca cgttcccctg gcggcgggcc    3120
ggcacgtcga ccaccgcctg gtccgcgcg cggtggagcc cctgtccccc gcccgtaccg    3180
tcttctacga ggacttcccc taccggctgc gcgaacgtga ccacacgaac ctgcggccgc    3240
gcacggaacg gctgccgtcc gaggcggtgg accgctggct gaccgccgcc ggtcactact    3300
ccagccaggc gagcgcccac ttcggcggtg cggccgccct gcgcgaggcc ctgttcgccc    3360
gcgcccgcgc acacgcgggg cccggccggc ccggccacgc cgaccgccac tgggtgcccg    3420
tcggccagga cgaccggggc gaggcccggc cggcacccgt ggaaaggggg ccgtgaccca    3480
cgccgtcgcg agccccacca cgagagaggc cactcatgtc ccgtagcacc cacccgccga    3540
cagccacccc cgacgcgggc accaggcgac gcctgccgct gatcggcaac gacctggtca    3600
```

```
tcaacgagga ctcctgcaac ctcagctgca cctactgcct caccggacag agcaacctca   3660
aggagggcca ctcccttcaa ctgatcttcg agccccgcg gcgcgacagc tacgccaagg   3720
acagcgggct ggggcagcgc atggacaagg tcgccgaccg gatcc                  3765
```

<210> SEQ ID NO 10  
<211> LENGTH: 388  
<212> TYPE: PRT  
<213> ORGANISM: Streptomyces lavendulae

<400> SEQUENCE: 10

```
Met Thr Pro Thr Ser Gly Asp Asp Val Leu Ser Phe Pro Ser Trp Pro
  1               5                  10                  15

Gln His Gly Ala Glu Glu Arg Ala Gly Leu Leu Arg Ala Leu Asp Gln
                 20                  25                  30

Lys Gly Trp Trp Arg Asp Ala Gly Gln Glu Val Asp Leu Phe Glu Arg
             35                  40                  45

Glu Phe Ala Asp His His Gly Ala Pro His Ala Ile Ala Thr Thr Asn
         50                  55                  60

Gly Thr His Ala Leu Glu Leu Ala Leu Gly Val Met Gly Ile Gly Pro
 65                  70                  75                  80

Gly Asp Glu Val Ile Val Pro Ala Phe Thr Phe Ile Ser Ser Ser Leu
                 85                  90                  95

Ala Val Gln Arg Met Gly Ala Val Pro Val Pro Ala Asp Val Arg Pro
            100                 105                 110

Asp Thr Tyr Cys Leu Asp Ala Asp Ala Ala Ala Leu Val Thr Pro
            115                 120                 125

Arg Thr Lys Ala Ile Met Pro Val His Met Ala Gly Gln Phe Ala Asp
        130                 135                 140

Met Asp Ala Leu Glu Lys Leu Ser Val Ala Thr Gly Val Pro Val Leu
145                 150                 155                 160

Gln Asp Ala Ala His Ala His Gly Ala Gln Trp Gln Gly Arg Arg Val
                165                 170                 175

Gly Glu Leu Gly Ser Ile Ala Ala Phe Ser Phe Gln Asn Gly Lys Leu
            180                 185                 190

Met Thr Ala Gly Glu Gly Gly Ala Leu Leu Pro Asp Asp Glu Ser
        195                 200                 205

Phe His Glu Ala Phe Leu Gln His Cys Cys Gly Arg Pro Pro Gly Asp
    210                 215                 220

Arg Val Tyr Arg His Leu Thr Gln Gly Ser Asn Tyr Arg Met Asn Glu
225                 230                 235                 240

Phe Ser Ala Ser Val Leu Arg Ala Gln Leu Lys Arg Leu Lys Asp Gln
                245                 250                 255

Leu Arg Ile Arg Glu Glu Arg Trp Ala Gln Leu Arg Thr Ala Leu Ala
            260                 265                 270

Ala Ile Asp Gly Val Val Pro Gln Gly Arg Asp Glu Arg Gly Asp Leu
        275                 280                 285

His Ser His Tyr Met Ala Met Val Arg Leu Pro Gly Ile Ser Ala Arg
    290                 295                 300

Arg Arg Leu Ala Leu Val Asp Ala Leu Val Glu Arg Gly Val Pro Ala
305                 310                 315                 320

Phe Val Gly Phe Pro Pro Val Tyr Arg Thr Glu Gly Phe Ala Arg Gly
                325                 330                 335

Pro Ala Pro Ala Asp Ala Glu Glu Leu Ala Lys Ser Cys Pro Val Ala
            340                 345                 350
```

```
Glu Glu Ile Gly Ser Asp Cys Leu Trp Leu His His Arg Val Leu Leu
        355                 360                 365

Ala Asp Val Thr Thr Leu Asp Arg Leu Ala Glu Val Phe Ser Gly Leu
    370                 375                 380

Val Gly Ala Leu
385

<210> SEQ ID NO 11
<211> LENGTH: 272
<212> TYPE: PRT
<213> ORGANISM: Streptomyces lavendulae

<400> SEQUENCE: 11

Met Val Val Val Asp Asp Asn Asp Gly Gly Asp Ala Gly Asp Gln Leu
1               5                   10                  15

Ile Ala Val Thr Gly Glu Met Ser Gly Leu Leu Pro Leu Arg Val Val
            20                  25                  30

Arg Gly Pro Leu Arg Gly Arg Ala Ala Ala Arg Asn Ala Gly Ala Ala
        35                  40                  45

Ala Ala Leu Ala Pro Arg Leu Val Phe Leu Asp Asp Asp Val Leu Val
    50                  55                  60

Gly Pro Gly Phe Leu Ala Ala His Ala Ala Ala Ala Glu Pro Asp Ala
65                  70                  75                  80

Phe Thr His Gly Arg Leu Arg Glu Leu Pro Thr Ala Ala Arg Phe Leu
                85                  90                  95

Ala Ala Val Glu Lys Ala Ala Pro Thr Glu Val Arg Arg Ala Arg Ala
            100                 105                 110

Gly Leu Glu Pro Ala Ala Pro Ala Ala Ser Glu Arg Arg Gln Pro His
        115                 120                 125

Arg Arg Leu Val Ala Asn Ala Leu Glu Arg Ala Val Glu Ala Met Ala
    130                 135                 140

Gly Gly Ser Leu Pro Asp Val Ala Pro Trp Leu Gly Phe Ile Gly Ala
145                 150                 155                 160

Asn Thr Ala Leu Asp Lys Ala Ala Trp Glu His Thr Gly Gly Phe Asp
                165                 170                 175

Glu Glu Phe Gly Leu Thr Trp Gly Cys Glu Asp Leu Glu Phe Gly Phe
            180                 185                 190

Arg Leu His Ala Ala Gly Leu Arg Arg Thr Leu Ala Pro Asp Ala Leu
        195                 200                 205

Gly Val His Leu Ser His Ala Arg Pro Gly Arg Trp Glu Gln His His
    210                 215                 220

Arg Asn Leu Thr His Phe Ser Ala Gly His Pro His Pro Ser Val Arg
225                 230                 235                 240

Ala Leu Glu Ala Leu Leu Gly Pro Asp Gly Thr Pro Glu Ala Tyr Val
                245                 250                 255

Arg Ala Val Leu Ala Glu Glu Ala Ala Pro Ala Arg Asp Ala Ala Arg
            260                 265                 270

<210> SEQ ID NO 12
<211> LENGTH: 260
<212> TYPE: PRT
<213> ORGANISM: Streptomyces lavendulae

<400> SEQUENCE: 12

Met Ser Gly Thr Pro Ala Thr Ala Pro Tyr Gly Pro Val Val Leu Ser
1               5                   10                  15
```

```
Pro His Ala Asp Asp Ala Val Trp Ser Leu Gly Gly Arg Leu Ala Arg
             20                  25                  30

Trp Ala Ala Glu Gly Pro Arg Pro Thr Val Val Thr Val Phe Ala Gly
         35                  40                  45

Pro Ala Ala Gly Lys Pro Glu Ser Trp Arg Ser Ala Ala Asp Pro Ala
     50                  55                  60

Val Arg Arg Ala Glu Asp Arg Ala Ala Cys Ala Glu Leu Gly Val Arg
 65                  70                  75                  80

His Val Pro Leu Gly Phe Thr Asp Ala Ala Leu Arg Thr Ala Ser Gly
                 85                  90                  95

Ala Tyr Leu Tyr Ala Ser Pro Arg Arg Leu Phe Gly Pro Trp His Pro
            100                 105                 110

Ala Asp Leu Pro Leu Leu Glu Glu Val Arg Ala Ala Leu Leu Pro Leu
            115                 120                 125

Cys Ala Gly Ala Ser Ser Val His Val Pro Leu Ala Ala Gly Arg His
            130                 135                 140

Val Asp His Arg Leu Val Arg Gly Ala Val Glu Pro Leu Ser Pro Ala
145                 150                 155                 160

Arg Thr Val Phe Tyr Glu Asp Phe Pro Tyr Arg Leu Arg Glu Arg Asp
                165                 170                 175

His Thr Asn Leu Arg Pro Arg Thr Glu Arg Leu Pro Ser Glu Ala Val
            180                 185                 190

Asp Arg Trp Leu Thr Ala Ala Gly His Tyr Ser Ser Gln Ala Ser Ala
            195                 200                 205

His Phe Gly Gly Ala Ala Leu Arg Glu Ala Leu Phe Ala Arg Ala
            210                 215                 220

Arg Ala His Gly Gly Pro Gly Arg Pro Gly His Ala Asp Arg His Trp
225                 230                 235                 240

Val Pro Val Gly Gln Asp Asp Arg Gly Glu Ala Arg Pro Ala Pro Val
                245                 250                 255

Glu Arg Gly Pro
            260

<210> SEQ ID NO 13
<211> LENGTH: 386
<212> TYPE: PRT
<213> ORGANISM: Streptomyces collinus

<400> SEQUENCE: 13

Met Ser Ser Gly Val Gln Leu Gly Ser Ala Phe Arg Val Trp Pro Gln
  1               5                  10                  15

Tyr Asp Asp Ala Glu Arg Thr Gly Leu Ile Arg Ala Leu Glu Gln Gly
             20                  25                  30

Gln Trp Trp Arg Met Gly Gly Glu Val Glu Arg Phe Glu Arg Glu
         35                  40                  45

Phe Ala Glu Tyr His Gly Gly Glu His Ala Leu Ala Val Thr Asn Gly
     50                  55                  60

Thr His Ala Leu Glu Leu Ala Leu Glu Val Met Gly Val Gly Pro Gly
 65                  70                  75                  80

Thr Glu Val Ile Val Pro Ala Phe Thr Phe Ile Ser Ser Ser Gln Ala
                 85                  90                  95

Ala Gln Arg Leu Gly Ala Val Val Pro Val Asp Val Asp Pro Glu
            100                 105                 110

Thr Tyr Cys Ile Asp Pro Ala Glu Ala Ala Lys Ala Ile Thr Pro Arg
```

-continued

```
            115                 120                 125
Thr Arg Ala Ile Met Pro Val His Met Ala Gly Gln Leu Ala Asp Met
            130                 135                 140
Asp Ala Leu Glu Lys Val Ala Ala Asp Ser Gly Val Pro Leu Ile Gln
145                 150                 155                 160
Asp Ala Ala His Ala Gln Gly Ala Thr Trp Asn Gly Arg Arg Leu Gly
                165                 170                 175
Glu Leu Gly Ser Val Ala Ala Phe Ser Phe Gln Asn Gly Lys Leu Met
                180                 185                 190
Thr Ala Gly Glu Gly Gly Ala Val Leu Phe Pro Thr Ala Glu Met Ala
                195                 200                 205
Glu His Ala Phe Leu Arg His Ser Cys Gly Arg Pro Arg Asn Asp Arg
            210                 215                 220
Gly Tyr Phe His Arg Thr Ser Gly Ser Asn Phe Arg Leu Asn Glu Phe
225                 230                 235                 240
Ser Ala Ser Val Leu Arg Ala Gln Leu Ala Arg Leu Asp Gly Gln Ile
                245                 250                 255
Arg Thr Arg Glu Glu Arg Trp Pro Leu Leu Ser Ser Leu Leu Ala Glu
                260                 265                 270
Ile Pro Gly Val Val Pro Gln Arg Leu Asp Arg Arg Pro Asp Arg Asn
            275                 280                 285
Pro His Tyr Met Ala Met Phe Arg Val Pro Arg Ile Thr Glu Glu Arg
            290                 295                 300
Arg Ala Arg Val Val Asp Thr Leu Val Glu Arg Gly Val Pro Ala Phe
305                 310                 315                 320
Val Ala Phe Arg Ser Val Tyr Arg Thr Asp Ala Phe Trp Glu Met Gly
                325                 330                 335
Ala Pro Asp Leu Ser Val Asp Glu Leu Ala Arg Leu Pro Pro Leu Arg
                340                 345                 350
Gly Leu Thr Thr Asp Cys Leu Trp Leu His His Arg Thr Leu Leu Gly
                355                 360                 365
Thr Glu Glu Gln Met His Glu Val Ala Ala Val Ile Ala Asp Val Leu
            370                 375                 380
Gly Ser
385

<210> SEQ ID NO 14
<211> LENGTH: 388
<212> TYPE: PRT
<213> ORGANISM: Actinosynnema pretiosum

<400> SEQUENCE: 14

Met Gly Ser Ser Pro Asp Ala Gly Ile Asp Phe Pro Ala Trp Pro Gln
 1               5                  10                  15
His Asp Asp Ala Glu Arg Ala Ala Leu Leu Arg Ala Leu Asp Gln Gly
                20                  25                  30
Gln Trp Trp Arg Val Gly Gly Ser Glu Val Asp Glu Phe Glu Arg Glu
            35                  40                  45
Phe Ala Glu Tyr His Gly Ala Gly His Ala Leu Ala Val Thr Asn Gly
    50                  55                  60
Thr His Ala Leu Glu Leu Ala Leu Gln Val Leu Asp Val Gly Pro Gly
65                  70                  75                  80
Thr Glu Val Ile Val Pro Ala Phe Thr Phe Ile Ser Ser Ser Gln Ala
                85                  90                  95
```

-continued

```
Val Gln Arg Leu Gly Ala Val Ala Val Pro Val Asp Val Asp Pro Asp
                100                 105                 110

Thr Tyr Cys Leu Asp Val Ala Ala Glu Asp Ala Val Thr Ser Arg
        115                 120                 125

Thr Ser Ala Ile Met Pro Val His Met Ala Gly Gln Phe Ala Asp Met
    130                 135                 140

Asp Arg Leu Asp Lys Leu Ser Ala Ser Thr Gly Val Pro Val Val Gln
145                 150                 155                 160

Asp Ala Ala His Ala His Gly Ala His Trp Arg Gly Lys Arg Val Gly
                165                 170                 175

Glu Leu Gly Ser Ile Ala Thr Phe Ser Phe Gln Asn Gly Lys Leu Met
            180                 185                 190

Thr Ala Gly Glu Gly Gly Ala Val Leu Phe Ala Asp Gln Ala Gln Trp
        195                 200                 205

Glu Lys Ala Phe Val Leu His Ser Cys Gly Arg Pro Lys Gly Asp Arg
    210                 215                 220

Gly Tyr Phe His Leu Thr Ser Gly Ser Asn Phe Arg Met Asn Glu Phe
225                 230                 235                 240

Ser Ala Ala Val Leu Arg Ala Gln Leu Gly Arg Leu Asp Ser Gln Ile
                245                 250                 255

Ala Thr Arg Gln Ala Arg Trp Pro Val Leu Ser Ala Leu Leu Ala Gly
            260                 265                 270

Ile Asp Gly Val Val Pro Gln Thr Val Asp Pro Arg Ser Asp Arg Asn
        275                 280                 285

Pro Ser Tyr Met Ala Met Phe Arg Met Pro Gly Val Thr Glu Glu Arg
    290                 295                 300

Arg Asn Ala Val Val Asp Glu Leu Val Arg Arg Gly Ile Pro Ala Phe
305                 310                 315                 320

Met Ala Phe Arg Ala Val Tyr Arg Thr Gln Ala Phe Trp Glu Thr Gly
                325                 330                 335

Ala Pro Asp Leu Thr Pro Glu Glu Leu Ala Ala Arg Cys Pro Val Ser
            340                 345                 350

Glu Glu Ile Thr Arg Asp Cys Val Trp Leu His His Arg Val Leu Leu
        355                 360                 365

Gly Ala Glu Glu Gln Val Arg Arg Leu Ala Ala Val Val Ala Asp Val
    370                 375                 380

Val Ala Gly Ala
385

<210> SEQ ID NO 15
<211> LENGTH: 388
<212> TYPE: PRT
<213> ORGANISM: Amycolatopsis mediterranei

<400> SEQUENCE: 15

Met Asn Ala Arg Lys Ala Pro Glu Phe Pro Ala Trp Pro Gln Tyr Asp
1               5                   10                  15

Asp Ala Glu Arg Asn Gly Leu Val Arg Ala Leu Glu Gln Gly Gln Trp
                20                  25                  30

Trp Arg Met Gly Gly Asp Glu Val Asn Ser Phe Glu Arg Glu Phe Ala
            35                  40                  45

Ala His His Gly Ala Ala His Ala Leu Ala Val Thr Asn Gly Thr His
        50                  55                  60

Ala Leu Glu Leu Ala Leu Gln Val Met Gly Val Gly Pro Gly Thr Glu
65                  70                  75                  80
```

```
Val Ile Val Pro Ala Phe Thr Phe Ile Ser Ser Gln Ala Ala Gln
                85                  90                  95

Arg Leu Gly Ala Val Thr Val Pro Val Asp Val Asp Ala Ala Thr Tyr
            100                 105                 110

Asn Leu Asp Pro Glu Ala Val Ala Ala Val Thr Pro Arg Thr Lys
            115                 120                 125

Val Ile Met Pro Val His Met Ala Gly Leu Met Ala Asp Met Asp Ala
            130                 135                 140

Leu Ala Lys Ile Ser Ala Asp Thr Gly Val Pro Leu Leu Gln Asp Ala
145                 150                 155                 160

Ala His Ala His Gly Ala Arg Trp Gln Gly Lys Arg Val Gly Glu Leu
                165                 170                 175

Asp Ser Ile Ala Thr Phe Ser Phe Gln Asn Gly Lys Leu Met Thr Ala
            180                 185                 190

Gly Glu Gly Gly Ala Val Val Phe Pro Asp Gly Glu Thr Glu Lys Tyr
            195                 200                 205

Glu Thr Ala Phe Leu Arg His Ser Cys Gly Arg Pro Arg Asp Asp Arg
            210                 215                 220

Arg Tyr Phe His Lys Ile Ala Gly Ser Asn Met Arg Leu Asn Glu Phe
225                 230                 235                 240

Ser Ala Ser Val Leu Arg Ala Gln Leu Ala Arg Leu Asp Glu Gln Ile
                245                 250                 255

Ala Val Arg Asp Glu Pro Trp Thr Leu Leu Ser Arg Leu Leu Gly Ala
            260                 265                 270

Ile Asp Gly Val Val Pro Gln Gly Gly Asp Val Arg Ala Asp Arg Asn
            275                 280                 285

Ser His Tyr Met Ala Met Phe Arg Ile Pro Gly Leu Thr Glu Glu Arg
            290                 295                 300

Arg Asn Ala Leu Val Asp Arg Leu Val Glu Ala Gly Leu Pro Ala Phe
305                 310                 315                 320

Ala Ala Phe Arg Ala Ile Tyr Arg Thr Asp Ala Phe Trp Glu Leu Gly
                325                 330                 335

Ala Pro Asp Glu Ser Val Asp Ala Ile Ala Arg Arg Cys Pro Asn Thr
            340                 345                 350

Asp Ala Ile Ser Ser Asp Cys Val Trp Leu His His Arg Val Leu Leu
            355                 360                 365

Ala Gly Glu Pro Glu Leu His Ala Thr Ala Glu Ile Ile Ala Asp Ala
            370                 375                 380

Val Gly Arg Ala
385

<210> SEQ ID NO 16
<211> LENGTH: 1800
<212> TYPE: DNA
<213> ORGANISM: Streptomyces lavendulae

<400> SEQUENCE: 16
atggaggacc gcaagcgcga ggggtatttc tagcgcggcg gggccggtgc ggcccacaag    60
cggaggacta gtccctaagt atgaagtccc ctactccgtt tgtctgttga gggcaggggc   120
gccgtctgag gatgatgcag tccatgtcac agttactttc cgggaaggac ggcgcccagg   180
aggcgccaag tcgcggcggg tccacgtggg tggcggtcct cgccgcgtgc gtggggcagt   240
tcgtggtggt cctcgacgtg tccgtcatca atgtcgcgct gccgtcgatc cgttccggcc   300
```

-continued

```
tcgacatcgg cgagacgggc ctgcagtggg tggtcaacgc ctacgtcatc gccttcgcgg    360
gcttcctgct gctcggcggc cgggcctccg acctcttcgg ccgcaaggcc gtgttcgtct    420
tcggcctcgg ggtgttcacc gccgcgagcc tgctcggcgg cctcgcgcag cgccgtggaa    480
tgctcatcgt cgcccgcgcc ctgcaaggca tcggggcggc cgtgctctca cccgccaccc    540
tcgcgatcct caccaccacg ttccccgagg tccggcgcg catcaaagcc gtcgcgatct    600
ggacggccgt gggcacgggc ggcggcgcgg ccggcggcct catcggcggc ctgctcaccg    660
actacctctc gtggcgctgg gtgttgctga tcaacgtgcc gctgggcctt gtcgtgatcg    720
tcgcgaccgt cgcctggctg ccgagagcc gcagcgacca ggcacaccga cgccggctgg    780
acctcccggg agcggtgctg gtgaccctgg gcgtcggcag cctggcctac ggcatctcgc    840
agagcgaggg ccacggctgg ggctcgccgc ggacgctcac cttcctgatc gtcggtgtcg    900
tggcgctcct cgccttcgtc gccgtggagc agcgcacgcg cgagccgttg atgccgctcg    960
gtgtcttccg ggtgcgctcg gtgtcggcgg ccaacgccat caccatcgtc agtggcatgg    1020
gcttctacgc gatgtggtac ttcctctcgc tctacatgca gaacgtgctg aaatactccg    1080
ccgtacagac cggcctggcc ctgcttcccc acaccgccac catcatcctc tccgcgcagt    1140
tcgcaccccg cctgatgcgg tggatcaagg ggcgcaccct cctcgtgatc gcgggactgc    1200
tgaccgccgc gggcttcatc tggcagggga acatggacgc cgacggctcc ttcctggcga    1260
ccctgctcgg cccgggaatc gtcttctcct tcggcgcggg cctgatgatg acgctcctcg    1320
cggtctccgc cacgacgggc gtggagctct ccgaatcggg cctggtggcc ggcctcgcca    1380
acacctcgcg caccatgggc ggcgcgctcg gcctgtcggt cctcgcgtcc gtcgccgccc    1440
gccgcacggc cgacgtgggg cccggcgcgg agggcctggc ctccggctac ggtcgggcgt    1500
tcgtcgtgtc cggggccatc atcctcgtga gcatgctgat gatccccttc ctgcccaagc    1560
cccagcccca gacccccggcg gaatgacctg tgagcacgga catacgagga ggcttcgtgg    1620
ggcaggacag ccggccgcgg tggctcaccg acgaggaaca acgcgtgtgg cgcggctatc    1680
tgcgggccac caggctggtg gaggaccacc tggaccgccg cctccagcgg gaagcggaca    1740
tgccgcacct ctattacggt cttctcgtcc agctctccga ggccccgcgc cggggggatcc    1800
```

<210> SEQ ID NO 17
<211> LENGTH: 484
<212> TYPE: PRT
<213> ORGANISM: Streptomyces lavendulae

<400> SEQUENCE: 17

```
Met Met Gln Ser Met Ser Gln Leu Leu Ser Gly Lys Asp Gly Ala Gln
 1               5                  10                  15

Glu Ala Pro Ser Arg Gly Gly Ser Thr Trp Val Ala Val Leu Ala Ala
            20                  25                  30

Cys Val Gly Gln Phe Val Val Leu Asp Val Ser Val Ile Asn Val
            35                  40                  45

Ala Leu Pro Ser Ile Arg Ser Gly Leu Asp Ile Gly Glu Thr Gly Leu
        50                  55                  60

Gln Trp Val Val Asn Ala Tyr Val Ile Ala Phe Ala Gly Phe Leu Leu
 65                  70                  75                  80

Leu Gly Gly Arg Ala Ser Asp Leu Phe Gly Arg Lys Ala Val Phe Val
                85                  90                  95

Phe Gly Leu Gly Val Phe Thr Ala Ala Ser Leu Leu Gly Leu Ala
            100                 105                 110
```

```
Gln Ala Pro Trp Met Leu Ile Val Ala Arg Ala Leu Gln Gly Ile Gly
        115                 120                 125

Ala Ala Val Leu Ser Pro Ala Thr Leu Ala Ile Leu Thr Thr Thr Phe
130                 135                 140

Pro Glu Gly Pro Ala Arg Ile Lys Ala Val Ala Ile Trp Thr Ala Val
145                 150                 155                 160

Gly Thr Gly Gly Gly Ala Ala Gly Gly Leu Ile Gly Gly Leu Leu Thr
                165                 170                 175

Asp Tyr Leu Ser Trp Arg Trp Val Leu Leu Ile Asn Val Pro Leu Gly
                180                 185                 190

Leu Val Val Ile Val Ala Thr Val Ala Trp Leu Ala Glu Ser Arg Ser
        195                 200                 205

Asp Gln Ala His Arg Arg Leu Asp Leu Pro Gly Ala Val Leu Val
        210                 215                 220

Thr Leu Gly Val Gly Ser Leu Ala Tyr Gly Ile Ser Gln Ser Glu Gly
225                 230                 235                 240

His Gly Trp Gly Ser Pro Arg Thr Leu Thr Phe Leu Ile Val Gly Val
                245                 250                 255

Val Ala Leu Leu Ala Phe Val Ala Val Glu Gln Arg Thr Arg Glu Pro
            260                 265                 270

Leu Met Pro Leu Gly Val Phe Arg Val Arg Ser Val Ser Ala Ala Asn
        275                 280                 285

Ala Ile Thr Ile Val Ser Gly Met Gly Phe Tyr Ala Met Trp Tyr Phe
        290                 295                 300

Leu Ser Leu Tyr Met Gln Asn Val Leu Lys Tyr Ser Ala Val Gln Thr
305                 310                 315                 320

Gly Leu Ala Leu Leu Pro His Thr Ala Thr Ile Ile Leu Ser Ala Gln
                325                 330                 335

Phe Ala Pro Arg Leu Met Arg Trp Ile Lys Gly Arg Thr Leu Leu Val
            340                 345                 350

Ile Ala Gly Leu Leu Thr Ala Ala Gly Phe Ile Trp Gln Gly Asn Met
        355                 360                 365

Asp Ala Asp Gly Ser Phe Leu Ala Thr Leu Leu Gly Pro Gly Ile Val
        370                 375                 380

Phe Ser Phe Gly Ala Gly Leu Met Met Thr Leu Leu Ala Val Ser Ala
385                 390                 395                 400

Thr Thr Gly Val Glu Leu Ser Glu Ser Gly Leu Val Ala Gly Leu Ala
                405                 410                 415

Asn Thr Ser Arg Thr Met Gly Gly Ala Leu Gly Leu Ser Val Leu Ala
                420                 425                 430

Ser Val Ala Ala Arg Arg Thr Ala Asp Val Gly Pro Gly Ala Glu Gly
        435                 440                 445

Leu Ala Ser Gly Tyr Gly Arg Ala Phe Val Val Ser Gly Ala Ile Ile
        450                 455                 460

Leu Val Ser Met Leu Met Ile Pro Phe Leu Pro Lys Pro Gln Pro Gln
465                 470                 475                 480

Thr Pro Ala Glu

<210> SEQ ID NO 18
<211> LENGTH: 990
<212> TYPE: DNA
<213> ORGANISM: Streptomyces lavendulae

<400> SEQUENCE: 18
```

-continued

| | | |
|---|---|---|
| atcccgatcg tctcggacat gaccggcgac cttctcggcg cgcgggaggc ccaggacccc | 60 |
| gcctactggg tgtcccacat ccgccgcgcg gtgcgcttcc acgaccagat ccgccgtctg | 120 |
| cagcgctacg gggccggggc cttcgtcgag gtcggcccgg acacggtgct cagctcggcc | 180 |
| ggccaggcgt gcctgacgga ccaggcgggc aggagcgcgc ccgtcctggt gtccctcgcg | 240 |
| cacgccgagc gcgcggaggt gcccgcgctc ctgaccgctc tggccacccct gcacacccgt | 300 |
| ggcgtggccg tggactggcg ggcgtggttc ggcgacgggc cgcgcgcggc cggcctgccc | 360 |
| acatacgcgt tccagaagca gcactactgg ccgtcgggcc ccaccggttg gcggtccggg | 420 |
| cccgcccccg tacccctgcc ccaggccgga acggaggacg ccgaaaggcc cggtcgcgcc | 480 |
| gcggagtggc gggcgctgcc gcccggtgag cggtacgacg cgctgctgcg gatggtgcgc | 540 |
| ggcgaagccg ccgccgtgat ggggcacgcc gggccggagg cggtggagcc ggagcgcggc | 600 |
| ttcctcgacc acggcttcga ctcggtgatg gccgtgaagc tgcgcgaccg tctcgtggcc | 660 |
| gggacggggc gggagctgcc gacgaccctg ctgttcgacc accccacgcc cgcggccgtc | 720 |
| gccgactacc tgctggcggg gacgggcgag gccgagacgg cgccgtccgt gtccctgtcg | 780 |
| gaccagctcg accgcctgga ggccgacctc gcgcggctgc cggccgacga ccggcagcgc | 840 |
| gcccgcgtcg ccgagcggct caagggcctg ctcgcggtcc acgcgccgga ccggggcgcc | 900 |
| gggagcgagg acgcgccgga ccaggacgcg ctggacacgc cgaccgacga cgagatgttc | 960 |
| gagctgatcg agaaggaact ccgccgtgga | 990 |

<210> SEQ ID NO 19
<211> LENGTH: 3978
<212> TYPE: DNA
<213> ORGANISM: Streptomyces lavendulae

<400> SEQUENCE: 19

| | | |
|---|---|---|
| gtggatgaga ccaacgagac caaactccgc gagtacctgc ggctggtcac ggccgatctg | 60 |
| cggcgaaccc gcaggcagtt ggaggaggcc gaggacgcgg cccgcgagcc cgtcgcgatc | 120 |
| gtgggcatgg cgtgccgctt ccccggggac gtggcatcgc cggacgacct gtggcagctg | 180 |
| gtcgccgagg gccgggacgc cgtcaccgag ttccccgccg accggggctg ggacgtcgac | 240 |
| gccgtctacg accccgagcc gggcaccccg ggcaggacgt acgcgcgcca cggcggcttc | 300 |
| ctcaaggacg ccgccggatt cgacgccgcc ttcttcggca tcacgccgcg cgaggcgctc | 360 |
| gccatggacc gcagcagcg catgatcatg gaggtctcct gggaggcgtt cgagcaggcg | 420 |
| ggcctcgacg cgaccaccct gcggggcgag gacgtcggcg tcttcgtcgg ctccaacagc | 480 |
| aacgactacc tgatcaacgt gctcgacgcg cgggacgtcg ccgagggctt catcgggacc | 540 |
| ggcaactccg ccagcatcct ctccggccgc gtcgcctaca ccttcggctt cgagggcccg | 600 |
| gccgtgtccg tcgacaccgc ctgctcctcc tcgctggtcg cgctgcacct ggccgcgcag | 660 |
| tccctgcggc aggggagtg ctccctggcg ctggcgggcg gcgcgacggt gatggccacg | 720 |
| ccgaccgcct tcatcgagtt cagccgccag cggggcctgg ccccgacgg ccgctgcaag | 780 |
| tccttctcgg cgaccgccga cggcaccacc tggtccgagg gcgcggccgt gctgctgctg | 840 |
| gcccggctct cggacgcccg ccgcctgggc taccccgtgc acgcggtcat ccggggcagc | 900 |
| gccgtcaacc aggacggcgc gagcgcgggc ctgaccgcgc caacggacc ggcgcaacag | 960 |
| cgggtgatcc ggcaggcact ggccaacgca cggctgacgg ccgacagcgt cgacgcggtc | 1020 |
| gaggcacacg gcaccggcac cccgctgggc gacccgatcg aggcccaggc cctcctcgcc | 1080 |
| acctacgggc gggcccgcgg cgagggcagg ccgctgtggc tgggctcgct gaagtcgaac | 1140 |

-continued

```
ctgggccaca cccagtccgc ggccggcgcg ggcggcgtca tcaagatggt gatggccatg    1200
cggcacggga cgctgccccg cacgctgcac ctcacggagc ccaccccgcg cgtcgactgg    1260
tccgccggtg acgtacggct gctgaccgag gcccaggact ggccggacac cggacagccg    1320
cgccgtgcgg ccgtctcgtc cttcggcgtc agcggcacca acgcccatgt gatcctggag    1380
ggcccgcccg ccgaggaggc accggacgcg ccgctgccgg acgtctcctc gcagccgcgg    1440
ggcccgctgc cgtgggtcgt ctccggccgc agcgaggcgg ccgtccgagc gcaggccgag    1500
cgcctggcgg cccacctgac cgcgcgcccg cacctggcac cggccgacgt ggccaccgcg    1560
ctggccacca cgcgggcggc cttcgaccac cgggccgccg tcgtcggccg ggaccgtgag    1620
gaactgctcg ccgcctcgc ggccctggcc accggaaccc gcgcgcccgg cctggtcacc    1680
ggccggaccc cgccgtccgg cggcaaggcc gccttcctct tcaccggaca gggcagccag    1740
cagcccggca tgggccgcga actggcggct cacagcaccg tgttcgccga cgccctggac    1800
gaggtctgcg cccagctcga ccggcacctc gaccggccgc tgcgcgaggt gctgttcgcc    1860
gcggacggca cgcccgaggc cgccctgctc gacacgacgg cctacaccca gcccgcgctg    1920
ttcgccgtcg aggtcgcgct gctgcggctg ctggaggact ggggcttgcg gcccggcatg    1980
gtcgcgggcc actcggtcgg cgaactgacc gccgcctacg ccgccggggt ctggtcgctc    2040
gccgacgcct gcgccctggt cgccgcccgc ggccggctga cccaggcact gccgcgggc    2100 ggcgccatgg tcgccgtgca ggcgaccgag gacgaggtgc gcgcccaact cgccgacggc    2160
cgccccggcg tggacatcgc cgccgtcaac ggaccggaag cggtggtgct gtccggcgac    2220
gaggccgccg tcacggacct ggcgcgcgag tgggccgccc gcggccggga gaccaggagg    2280
ctgcgggtca gccacgcctt ccactccgcc cacctggacg ccatgaccga ggcgttcgcc    2340
gaggtcgcac gagggtgtc ctacagcgcg ccgtccctcc cggtggtctc cacgctcacc    2400
ggggcccccg tcaccgacga gctccgcagg ccggaacact gggtgcggca cgtccgggag    2460
acggtgcgct tccacgacgc ggtccgcgcc ctgcgcgacc gcggggccac cgcgttcctg    2520
gaggtcgggc cggcggcgt gctgacggcc gcggcacgcc gatgcctgcc cgacgccgcc    2580
cccgagacgt tcgtccccgt gctgcggcgc gcaggcccg aacccgagtc cgtgctgacg    2640
gccgtcgcgc aggcccacac gatcggcctc tcgccggcgt gggaccgcct gctgcccaag    2700
gcccggacgc gcgtggacct gcccacgtac gccttccagc gcggccacta ctggctggcg    2760
ggcatggccg gagcgggcac cgcgcggccg gtgcggccga aagtgcagga gcccaccgcc    2820
ccctccggta cgccgccgct gtcgcgacgg ctggccgacg cgtcggagga ggagcgcggc    2880
cacctgctgc tgacgctggt acgcgagcag tcggccaccg tgatgggcgg cgtcgacccc    2940
gcgcaggtcg aacccgaccg ccccttcctg gagctcggct tcgactccct gatgggcgtc    3000
gagctgcgca ccgcgctcgc cgccgactgc gcactgcccc tgccgcccgg cctgatcttc    3060
gaccacccca cgcccgccgc cctggccgcc ttcctcggcg agcagctcgc ggcggcggcc    3120
tccggcaccc ccacgcggc ggcacccctcg ccgtactccc tggaggcgct gtaccgcaac    3180
gccaacaccc tcgaccggcc cgaggacgcg ctcgccctca ccaaggccgc ctcccggctg    3240
cgcccggtct tcgccagcgt ggccgaggcg ggcaggacc cggtcacggt ggagctggca    3300
caggccaccg gccttccggg cctgatctgc tgcccggcac ccgtgccgct gtacggggca    3360
cagcagtaca gccggctcgc agccgccttc gcggcacgcg gcggagtctc ggccctgctc    3420 gccccccggct tctccccggg cgaactgctg cccgccgact tcgaggtgat gcaggacttc    3480
```

```
ctcgccgagg gggtccggcg gcagaccgac ggcgcgccct tcgtcctcct gggccactcc    3540
tccgggggct ggttcgccta cagcctggcg gcccacctgg cgcgcaccgg gccgcgcccg    3600
gaggccgtcg tgctgctgga cacctatcag ctgcacgacc cggcgctgca ccgcatgcag    3660
cgcgaactcg cccagggcgt cctggaccgc gaggaggact tcggggcgat gacggacgta    3720
cggctgagtg ccatgggcaa atacttcgac ttcttcaccg actgggtggc cgaggacgcc    3780
ggtgtcccga cgctgctgct gcgggcctcc gagcctctgg gcgaggtcgt cgagggccag    3840
gagtggcgct ccacctggcc gttcgacagc acggtcctcg acacggaagg cgaccacttc    3900
gccatggtca acgaccacgc gccgcggacg gcccaggccg tgaacggctg gctgtcgggc    3960
ctcaccggcg gaaggggc                                                 3978

<210> SEQ ID NO 20
<211> LENGTH: 570
<212> TYPE: DNA
<213> ORGANISM: Streptomyces lavendulae

<400> SEQUENCE: 20
gtggagacac gcaacgccga acggccgtgg atacgcagct ccacccccgc tccccaggcc      60
cctgtgcggc tgctgtgcct gccgcacgcc gggggctccg cgagcgccta cttcgcgctg     120
tcgagggaac tggcgccccg ggtggaggtg ctcgccgtgc agtaccccgg gcggcaggac     180
cggcgcgacg agccgctgct ggactcgatc gaggccctgc gcgacggggt cgccgaggcc     240
ctgacgccct ggctggaccg gccggtcgcc ctcttcggcc acagcatggg cgccgtggtg     300
gcctacgagc tggcgcggct gctgtgccag gacgcgggcg tgccgctcac ccacctcttc     360
gtctccggac gccgggatc cgaccgaagt ctccgtcctt gccgccgtgt tccggaattc     420
accgtgacac cgccgcgcgg ctcttcttcc gaagtcctcc agatccggca cgagtttgta     480
tccgaacggg gttctgcgtg cgaaatactc tcttcgaatt gggtgacata ccccgatcg      540 gcaccgtacc cgagcagatg tacgcctcgg                                     570

<210> SEQ ID NO 21
<211> LENGTH: 1245
<212> TYPE: DNA
<213> ORGANISM: Streptomyces lavendulae

<400> SEQUENCE: 21
gtgcgaaata ctctcttcga attgggtgac ataccccga tcggcaccgt acccgagcag      60
atgtacgcct cggtgatccg acgggagcgc tacggacagc cccaccaggc gttccgcagc    120
gaggtcgtgg acgtgccgaa ggtggggccc ggtcaggcgc tggtcctcgt gatggccgcg    180
ggcatcaact acaacaacgt ctgggcctcc ctggggcagc cggtcgacgt gatctccgcg    240
cggcagaagc agggccacag cgaggacttc cacatcggcg gtccgaggg ctccggcgtg    300 gtgtgggcgg tggggagggg cgtcacccag gtcgcggtgg gcgacgaagt gatcctctcc    360
ggctgccagt ggacggagac ggccgccgac atccggctcg cgccgacccc catgacctcc    420
ggctcgcagt cggtgtgggg atacgagggc aactacggct ccttcgccca gttcgccctc    480
gtcgacgact atcagtgcca ccccaagccg cccggcctga cctgggagga agccgcctgc    540
ttcctgctca ccggggccac cgcctaccgc cagctgtgcg gctggcagcc gcacgacgtg    600
cggccgggcg acccgtcct catctgggc ggggccggcg ggctcggctc catggccatc    660
cagatcaccc gggcgcgggg cggcatcccc gtcgccgtgg tctccgacga ggagcgggcc    720
cgctactgcc gggagctcgg cgcccagggc accatcaacc gcctggactt cgaccactgg    780
```

-continued

```
ggacggctgc ccgacatcgg cgaccacgag gcgatgggcc gctggaccga gggtgtacgg    840
gccttcggcc ggcgcttctg ggaggtgctg ggcgagcgca ggtccccgcg catcgtcctg    900
gagcacagcg gccaggccac catccccacc tcgatgtacc tgtgcgacaa cgcgggcatg    960
gtcgtcatct gcggcggcac caccggctac aacgccgaca tcgacctgcg cttcctgtgg   1020
atgcgtcaga gcgcttgca gggctcgcac ttcgccaacc tgcggcagtg ccgcgacgtc   1080
atccacatgg tcgcgaacgg ccagctcgac ccgtgcctgt cgtggaccgg cggcttcgac   1140
gacatcggca aggcacacca gctgatgcac gacaaccagc cccccaggg caaccaggcc   1200 gtcctggtca acgcgccgcg gaccggcctg accaccttcg cctga                  1245
```

<210> SEQ ID NO 22
<211> LENGTH: 1224
<212> TYPE: DNA
<213> ORGANISM: Streptomyces lavendulae

<400> SEQUENCE: 22

```
gtgtccgaca ccgagcagca cgcgcccacg ctgccgcggc agcgcacctg ccccttctcg    60
ccgccgcccg agctcgagga gctgcggcgc accgatccca tcagcaggat gcggttcgcc   120
gacgactccc cggatggct gctgaccgcc cacgccgacg tccgcgccgc gctggccgac   180
cccggcgtca gctcgcaccc cggcaaggca ccccagccct ggcgcaacct cgcccccgag   240
atgcgcgccg agcactacct gccgggcttc ctgatcttca tggacccgcc ggaccacacc   300
cgctaccgcc gcctgctcac caagtggttc accatgcggg ccatccgcaa gctcgaaccc   360
aggatcgagc agatcgtcac cgagaccctc gacgccatgg aggcccaggg cggcaccgtc   420
gacctggtgc agtccttcgc gctgccgatc ccgctgctgg tcatctgcga gctgatgggc   480
atccgctacg aggagcgcga ggagttcatg gacatggtcc tgcgactcca ggccctggac   540
gccacgcccg aggaactcgg ggccctcggc gccaggatga acgagttcat gatgaagctc   600
gccgccgcca agcgcgcgaa ccccggcgac gacctgctca gccacctcgc ccacgacccc   660
gacgccgacc cggcgctcac ggatctggag atcgccggca tcggcgtgct gatgctcatc   720
gcggggcacg agacctcggc caacatgctg ggcgtcggca cctacaccct gctggagaac   780
gccgaccagt gggccctgct ccgtgacgac atcagcctga tcgaccgggc cgtcgaggag   840
ctgctgcgcc accagaccat cgtccagcag ggcctgccgc gcggcgtcac ccgggacatg   900
gagatcgccg ggcaccaggt gaagaccggg gagtccctgc tggcctcgct gcccgccgcc   960
aaccgcgacc ccgccgtctt ccccgacccc gaccgcctcg acatcacgcg cgagcacaac  1020
ccgcacctcg ccttcggcca cggcatccac ctctgcctgg gcatggagct cgcccgggtg  1080
gagatgcgcc aggcgtggcg cggcctcgtc acgcgcttcc ccggcctgcg catggccgcc  1140
gcgcccgagg acatccgctg gcgcgacgac cagatcgtct acggcgtgta caacctcccg  1200
gtgacctggg acgaggccaa gtga                                         1224
```

<210> SEQ ID NO 23
<211> LENGTH: 531
<212> TYPE: DNA
<213> ORGANISM: Streptomyces lavendulae

<400> SEQUENCE: 23

```
atggacaagc tcgacatcct ctggagcgag cgcgagatcc gtgccgtgct gcagcgctac    60
tgccgcgggc tcgaccgcct cgacgaggaa ctggtcaagt ccgcctacca cgaggacgcg   120
```

-continued cacgacgacc gcggcgtcat ccgcggcaac gcacacgact tcgtcaagca gatcgtcccg    180
ctcctgcgcg acgcctacac cggcaccctg cacaccctgc acggcagcac gatcgagatc    240 gacgggatg ccgcgggcgt ggagtcctac tgcaccgcct accactaccg cgagagcgac    300
ggcatcaagc gggtggagca gttcgccggg cgctacgtcg accgcttcga gcggcgcgac    360
ggcgtctgga agatcgcccg ccggctcgtg ctgaacgact tcagcctcgc ccaggaggtg    420
ccgctcgacc ccgccgaggc ccaggccggc ttcaacccct cccaccgcga cctcaccgac    480
gccagctacc aggtgctgcc gctgcgcggc ccggacgccc ccaccctctg a             531

<210> SEQ ID NO 24
<211> LENGTH: 1233
<212> TYPE: DNA
<213> ORGANISM: Streptomyces lavendulae

<400> SEQUENCE: 24
gtgaccggcc ccgaggccgc ggtgcgcggg tgccccttcg gcgccggcga ggcgcccgcg     60
taccccttcc acgcccccga ccggctggag cccgacccgt actgggagcc gctgcgccgc    120
gagcggccgc tgcaacgcgt cacgctgccg tacgcggca aggcgtggct cgccacccgc     180
tatcaggacg tgcgcgcggt cttcgccgac cgcaggttct cccggcagct cgccgtcgcg    240
cccggcgctc cgcgcttcct cccgcaccag ccgccgccgg acgccgtcct gagcgtcgag    300
ggccccgacc acgcgcggct gcgccggctg gtcgggaagg tcttcacgcc gcgccgcgtg    360
gaggacatgc gtccgctcat ccagcgcacc gccgacggac tcctcgacgc gatggaggag    420
atggggccgc ccgcggacct ggtcgaggac ttctccctgc ccttcgccgt gtccatgatc    480
tgcgagctgc tcggcgtgcc gcccgaggac cgcaagcggt tctgcgtctg gtcggacgcg    540
ctgctgacga ccaccgcgca cacccccgcc caggtgcgcg actacatgat gcagatgcac    600
gactacctcg gcgggctcgt cgcgcagcgc cgggtgcggc ccaccgcgga cctgatcggc    660
tccctcgtga ccgcgcgcga cgaggaggac aagctcaccg agggcgagct ggtgcggctg    720
gccgaggcca tcctcatcgc cggctacgag acctcggcga ccagatccc caacttcctc    780 tacgtcctct tccgccaccc gcagctgctg gagcggatca ggaacgacca cgacctcatc    840
cccgacgccg tcgaggaact gctgcgcttc gtgcccatcg gcaccgtgga cggctttccc    900
cgtacggcca ccgaggacgt cgagctcggg ggagtcctgg tcagggccgg ggagacggtc    960
gtgccgtcga tggcgccgc caaccgcgac cccgagctgt tcacgacccc cgacgagctg   1020
gacctcgcgc ggcggccgaa tccgcacctg gcttcggcg cgggaccgca ccactgcctg   1080
ggcgcccaac tggcccgggt ggagctccag atcacgctca cgacgctgtt ccgcagatac   1140
ccccgcctgc ggctggccgt gccggaggag agcctctcgt ggaaggaggg gctgatggtc   1200
cgcggcatgc acaccatgcc ggtcacctgg tga                                1233

<210> SEQ ID NO 25
<211> LENGTH: 1107
<212> TYPE: DNA
<213> ORGANISM: Streptomyces lavendulae

<400> SEQUENCE: 25
atgagcacca tcgacgaatg ggaacacagc acgaaggagg cgggcatgga ccccgcggcc     60
ctcagacgcc tgaccgatgt ggtgcgggcg aggggcggcg cggcgcagct gtcgtcatg    120 cggcggggca ccgtggtcct ggaccgctcg ttcggctgct cctccgactc cctcttcctc    180
gtctacgcgg ccaccaagcc cgtcgccgcc ctcgccgtgc acgcgctcgc cgagcggggc    240

```
ctgatcgggc tggaccggcc ggtggccgaa tactggccgc agttcgcccg gcacggcaag      300
ggtgacgtga ccgtccgtca tgtcctccag caccgggccg gggtgccggt cggccggggc      360
atcgtgcgca cgatgcgcac cgccggcgac tgggagcgct ccgtgcgcga ccttgagcag      420
tcccggccca agtggcccgg cggcgaggtc gccgcctacc acttcatgag tttcggattc      480
attctcggcg aactggtgca gcgcgtcacc gggcggtcgt tccgagattt cgtgacttcc      540
gagctcttcg ccccacttgg gctgaatgat ttgcacatgg gattgccggg cagtgcctgg      600
ccccggcatg tgcccgcgcg ggccgcccac ccctccgaat ggcccaatca gtggatgagc      660
aaccgccgcg gctaccgcca ggccgtcatt ccgtccgccg gtctttccgg aaccgccgca      720
caaatggccc gcttttacca gatgcttatg gagggcggct cgctcgacgg catccgcgtg      780
ctgcggcccg aaactgtgga ggaagccaga aaccgtcca atgacggcgg aatcgacgct       840
tccctcaagc gtccggtccg ctggtccac ggattcatgc tcgtggtcc gggcccggac        900 ccgcgggggc tgtccaatgt gctgggccgc acgagcgacc cgagcgcctt cgggcacgcg      960
ggcaccacgt ccagcgtcgt gtgggccgac cccacgcgcg agctggtcct cgcctacctc     1020
tccaacatcc agcccgagtt cggagcgggt atcgagcggc tccgcgaggt cagtgacctc     1080
gcgctcggtg cctgcgaggc aggctga                                         1107

<210> SEQ ID NO 26
<211> LENGTH: 858
<212> TYPE: DNA
<213> ORGANISM: Streptomyces lavendulae

<400> SEQUENCE: 26
gtgctgaatc tgcccaaagg aatggagcgc gcgcatccgc attctccgcc acaggtggga       60
atactcggac ccttggaagt ccgctcggcc ggaggtgccg gaacgggagc gcggtaagc      120 ggtattcgcg tacgcacatt gcttgccgcg ttgactgccg gcctggggca ggcgatgtcg      180
accgagcgca tcctcaaaga ggtctgggcc gacaaccgc ccgcgaccga tcgcaaggcg       240
gtggccgtcg ccgtcctgcg gctgcggcgg gtcctcggcg acaacgaagg acggtggctg      300
ctcacccgcc cctccggtta cgtcctggac atcccccgg accacctcga cgccgtacgc      360
gcggagaccc tggtgcggga aggccgggcc gccctggccg ccggcgaccc acgcgtcgcg      420
gcccgccacc tcacgcgcgc cctcgaccag tggcggggcg agcccttacgc ggacgccaac    480 gccatctcga ccgtgtccca gcgcatcacg gagctggaga acctcaggtc cgaggccgtc      540
caggcgcaca tcgacgccag gctcgaactg ggtcaccacc aggaactggt cggcgaactc      600
cgctcgctga ccgccgcgaa cccctgcac gagccgcact ggctgcagct gatgctcgcc       660
ctctaccgct ccggcaagca ggccgaggct ctcgccgcct atatgcagct gcggcaggcg      720
ctggccgaga acctgggcat cgaccggggt cgtcagctcc aggaactgca cctgcggatc      780
ctgcgcgccg acgcgggcct gctgacgggg tccggggccgg cggcaccggc cgagccactg     840
ctcgtacggc agtcctga                                                    858

<210> SEQ ID NO 27
<211> LENGTH: 420
<212> TYPE: DNA
<213> ORGANISM: Streptomyces lavendulae

<400> SEQUENCE: 27
atgcgtggat cgaaggccct ccgatacgcg gcccccgtcc tggtcgccgc cgcaaccggc       60
```

-continued

| | |
|---|---|
| atcgccctcg ccgcgggacc ggcggccgcc gtcccgatcg gtcagtccgt gaacggcaag | 120 |
| atgacctact acaccgacca gggctacggc gcctgcggca cccccatcga cgcgaactcc | 180 |
| caggacctcg tcgcggtccc ggccgcgtgg tggacctccg ccaacccaa caacgaccag | 240 |
| ctctgccagg gcatatcggt ggaggtcagc tacaacggca ggaccatcag agtgccggtg | 300 |
| cgggacaagt gcccttcgtg cgaccggacc cacatcgacc tcagcaggac ggccttccag | 360 |
| aagctggcgc cgctcgacag gggtgtggtc aacggcatca cctggaagtt cgtccgctga | 420 |

<210> SEQ ID NO 28
<211> LENGTH: 2811
<212> TYPE: DNA
<213> ORGANISM: Streptomyces lavendulae

<400> SEQUENCE: 28

| | |
|---|---|
| atgagttcat caaatttaag gtcgcgggac tcttggaaca gatcaagacg acggagaaca | 60 |
| atgacgtact ccccggcgc gcggccgcgc ccggcccggc tgtccgcact gctgctcgca | 120 |
| ggcgcgctcg tcgcctcggt gccgcccgcg ccgccgcgc gagcgccgca accccccacc | 180 |
| gccgaccgcc cccgcaccgc cgcctccccc acaggcggct gccgtacggg tgacggctgg | 240 |
| acactcgact ccacccgcat cgaccccgac gacacccacc acgcctatgt cggcaacggc | 300 |
| tacctggggc agcgcgtacc gcccaacggc gccggctaca ccgacagcga caccaagacc | 360 |
| ggctggccgc tcttcgctcc ggcctacgac ggctcgttcg tgtccgggct ctacgcgcac | 420 |
| aacaagcaga ccgccgccga ccggcaggtg atcgccgctc tgcccacctg gaccggactg | 480 |
| gccgtcggca ccggcggcga gcacggcgat atcttcaact cttcgacgaa gtcgggccgg | 540 |
| atttccggat atcaccagac cctcttccag agctgcggca tcgtccgtac cgccctgacc | 600 |
| tggaccgccg ccgacggccg caggaccgac ctggtctacg aggtgctggc cgaccgcgac | 660 |
| gacccgcaca cgggcgccgt acggctgagc atgacgccgc gctggagcgg cgaggccacc | 720 |
| gtcaccgacc agctggacgg acgcggcgcg cggcgcatgc ggcagaccgg cggcggcgac | 780 |
| cgcaccggtg ggaccggccg ggacggccgc accatggacg tggccttccg caccgacggc | 840 |
| acggacaccg acggcgccgt cgcctccacc ctgagggccg ggcgcggtgt gcacacgacc | 900 |
| ggggaccgac gcgccgcggc cgcgaaggac ttgagcgtga accagtccct cacgttcccc | 960 |
| gtccgtgcgg gccacgcgta cgaactcacc aaatacgtgg gtgtcgacac cgcgctcacc | 1020 |
| tcgcacgcgc cccgcgagga cgccaccacc gcctccctgc gcgccgcccg ccgcggctgg | 1080 |
| gacgggctgc tgcgtgccca caccgccgcc tgggcccggc tgtggcgctc cgacatcgag | 1140 |
| ctgccgggac agcgcgacct ccaggcgtgg gtgcgttccg cccagtacgg gctgctgtcc | 1200 |
| agcacccggc aggggcatc caacagcatc gccccggccg ggctgaccag cgacaactac | 1260 |
| gcgggcctgg tgttctggga cgccgagacc tggatgtacc cggccctgct ggccaccgcg | 1320 |
| ccccaactcg ccaggaccgt cgtcgactac cgctaccgca ccctcgccgg agcgcgcgag | 1380 |
| aacgcccaca gctcggcta ccaagggctc ttctacccct ggaacagcgg cagcgagggc | 1440 |
| gacctggccc aggagtgcca cagcgtcgac ccgccccact gccgcaccca gatccacctc | 1500 |
| cagtcggaca tctccctcgc cacctggcag ttctacctcg ccaccggcga caccgcctgg | 1560 |
| ctgcgcgagc gcggctggcc ggtgatggag ggcatcgccg aattctgggc cggcgggtc | 1620 |
| accccccaacg ccgacggcag ctactccatc aaggacaccg ccggcccga cgaatacagc | 1680 |
| aacggcgtcg acgacgcgt cttcaccaac gccggtgccg ccaccgccct gcgcgacgcc | 1740 |
| gcccgtgccg cgcggctgct gggcgagcgc gccccggcgg agtggacgac gatcgccgac | 1800 |

```
cggatccgca tcccgtacga cgcgcggcac aaggtcttcg agcagtacga cggctacccg    1860
ggcagcaaga tcaagcaggc cgacacggtg ctgctgatgt acccccgga gtggccgatg    1920 tcccaggccg acgcggcgcg caccctcgac tactacgccc ggcgcaccga ccccgacggc    1980
cccgccatga cggactcggt ccacgccatc gacgccgcgg ccacgggcga gccgggctgc    2040
tcggcgtaca cctatctcca gcgttccgtc cggcccttcg tgcgcggtcc tttcgaccag    2100
ttctcggaag cccgcggcac caaggccggc gccgacgacc ccctggccgg ctcgcccgcc    2160
cacgacttcc tcaccggcaa gggcggcttc ctccagatct tcaccaacgg cctgaccggc    2220
atgcggatgc gcgaggaccg gctgcacctc gacccgatgc tgccccgca gctcggccgc    2280 ggcgtcaccc tgcgcggcct gcactggcag ggccgcacgt acgacatcgc catcggcgcc    2340
cacgagacca ccgtgcggct caccgggggt gcgcccatga ccctctacac cccgcagggc    2400
gagcacgtgc tgaccaaggc ggcaccggcc gtgctcaaga cccgccgccc cgacctcgct    2460
cccaccgaca acgtggcccg ctgcaccacc gccggtgcct cctccgagga acccggtatg    2520
tacgcggcag ccgcggtcga cggcaacccc gccaccgcct gggtccccga cgggccgaac    2580
ggtgaactga ccaccgacct cggcaagtcc gtacgcgtca ccaaggccac ccccgtctgg    2640
agcgccccgg caccggcctc gtacagcgtc cagctctccc tcgacggccg gcactggcac    2700
gacgcggtcg cgggcggcgc tccggtgtcc gcgcggtacg tacgcgtcgc gctacgcggt    2760
caggccgatg ccaagtcccg tacgggcatc gccgagctga ccgttacgta g            2811
```

<210> SEQ ID NO 29
<211> LENGTH: 813
<212> TYPE: DNA
<213> ORGANISM: Streptomyces lavendulae

<400> SEQUENCE: 29

```
atggaattcc tcgggccggc ggccggtgtc tcgggcgcca cgcggctgta cgcggtgctg      60
ggtgatcccg tcgcccaggt caaggcgccc ggtctgctca ccccctgct gagcgaaagc     120 ggtctggacg ccgtggtggt gccggtgcac gtccgggcgc gggatctcgc cgaggtggtc     180 gagggctca gcggatcgg caatctggac ggtctgctgg tcaccgtgcc gcacaaggcg      240
gccctgtgcg ggctcgcgga cgggctcggg ccggcggccg ccctcatcgg gacggccaac     300
gcgatgcggc gcgaacccga cggccgctgg tacgccgaga acttcgacgg gctcgggttc     360
gtccagggtc ttcaggcggc cgggcacacg gtgcgcgaca ggcatgtggc actggtcggc     420
gccggagggg cgggcagcgc gatcgccacg gcgctgctga tggccgacgc cgcgcgggtg     480
tccgtgcacg acaccgaccg cgcccagctc gacgcgctgc tgctgcggct cggtcccgc     540 cggccggacg ggatccgggc gctggggccc ggcgatctgg aggcggccga tttcgccgtc     600
aacgcgacgc ctctgggcat gcgttccgag gaccgctgc ccttcgaccc cgcgagggtg     660
cgaccggatg ccgtggtggt cgacgtcgtc atgaagccgc acgagacggc gctgctgagc     720
gcggccgcca ccgccgggcg ccgtgtgcac cacggcatcc atatgctgga gcagcaggtt     780
ccgtgctacc gcgcgttctt cgggtggccg tga                                 813
```

<210> SEQ ID NO 30
<211> LENGTH: 948
<212> TYPE: DNA
<213> ORGANISM: Streptomyces lavendulae

<400> SEQUENCE: 30

-continued

```
gtgacggggg acaccgacgg tgcgggcggc ggcgacgtga cgttccgctg gcccgccgcc      60
ggcgacgtca ccgcggatct ggacctgctc gccgcgcggg tccgcggtct tctgggacac     120
cgcgaggacc ccctcgccgg ggtcggcgtg gccatgcccg cgatctgcga cgcggccggg     180
acggtccgca cgtggccggg acggccgagc tgggcgggcc tgaacctgac ggccgccttc     240
gggcagttgc tgcccggcac cccggtcgcc tgcgccgacg acggtgacct ggccgcgctg     300
gcggagtccc gcgccgccgg ctgccggcat ctgctgtacg tgggggtcgg cacgggcatc     360
ggcggcggca tcgtccatga gggccgcgcc tggccgggcc ccggacgcgg ctcgtgcgag     420
gtcggccatg tcgtcgtcga ccgctcgggc ccacgctgcg actgcgggcg cgccggctgc     480
gtccaggcgg tcgcgtcggg accggcgacc ctccggcggg ccgccgaacg gcgcggccgg     540
gagaccggct cgacgaact ggcctccggg gcgcgcttgc acgcccgtg ggcggaagcg       600
gccgtcgacg agagcgccgc ggccctggcc accgccgtga ccggcatctg cgagctggcc     660
caccccgaac tcgtcctcgt cggcggcggg ttcgcggcgg gcgtgccggg atacgtggcc     720
tcggtggcgg cgcacgtcga gcggctgacc cgcccgggaa cggatcccgt gcgggtgcgc     780
ccggcggtgc tcggcgggcg gtcctccctg cacgcgcac tgctgctcgc gcgggaggca     840
cacgggcggg gaaaccggcc gccggagagt gaccgtgttt cttccgatgt ttcttccgat     900
gtttctttcg ggggagtgac agacagggcc gttggccggt ccgactga                 948
```

<210> SEQ ID NO 31
<211> LENGTH: 1545
<212> TYPE: DNA
<213> ORGANISM: Streptomyces lavendulae

<400> SEQUENCE: 31

```
atgctcgaca ggcggagcgt cattcgcgtc ggcgccgggg tggcggcggc cgccgccgtg      60
gccggtacgg ccgccaccgg tgcggcggcc gtggggctgc cgggtgtacg gggacgcgcg     120
gcgtcgcgcg gggtcgactg ggcctcctta cgccgtcatc tgtcgggcga gctcgtcctg     180
ccggcggaca ccggatacga gcgggccagg aagctctaca gcggccagtt cgacggcatc     240
cgcccgcagg ccgtcgccta ctgccggacc gaggaggacg tgcggacgac cctcgcgttc     300
gcccaggacc acgcgctgcc cctcaccccg cgcagtggcg ggcacagctt cggcggctac     360
tccacgaccg acggaatcgt cctggacgtc tccggcttcc acgcggtgag cctcacccgg     420
aacaccgtcg tcatgggcgc gggcacccag caggtgacg ccctcaccgc cctgtcgccg      480
cgcggtgtcg ccgtggcgag cggcaactgc gcgggcgtct gtcccggcgg cttcgtccag     540
ggcggcggac tgggctggca gagccgcaag ttcggcatgg cgtgcgaccg gctcgtctcc     600
gcccgggtcg tgctcgccga cggccgcgcc gtgaccgcct ccgccaccga caccccgac     660
cttttctggg cgatgcgcgg cggaggcggc ggcaacttcg cgtcgtcac cggcttcgag      720
ctgcgcccca ccgacgtccc ctccgtcgtc agctacaacc tcacctggcc gtgggagtcg     780
gcgcggcgcg tcatcgaggc gtggcagcac tggatcatcg acggccccg cgacctcggt      840
gccgcgatgg ccgtgcagtg gccccgacgcc gggaccggca cgccggtcgt ggtcgtcacc    900
ggcgcctggc tgggcgcggc cgacgcgctc acccccgtgc tggactccct ggtggcctcc    960
gtgggcagcg cgcccgccac ccgctcggcc aaggcgctct cccagcacga cgcgatgatg   1020
gcgcagtacg gctgcgccga cctcacgccc gagcagtgcc acacggtcgg ctactcgccc   1080
gaggccgcgc tgccccggca gaacttctcc atggaccgca accggctctt ctcccgggcc   1140
atcgggcaag gaggcgtcga gcggatcctg gaggcgttcg ccgccgaccc gcgcgccgga    1200
```

```
cagttccgct tcctgagctt cttcgccctc ggcggcgccg ccaaccgccc cgaccgcacc    1260
accaccgcct acgttcaccg cgacaccgag ttctacctcg gtttctcgat cgggctgaac    1320
gacccggagt acacggcgga ggacgagagg ctcgccgcg cctgggccgc gcgaggactg     1380
cgcacgctcg atccccactc caacggcgag agctaccaga acttcatcga cccggagctc    1440
gacgactgga agtcggccta ctacgccgag aactacgtgc gcctggccgc cgtcaaggcg    1500
gcctacgacc cgcaccggct cttctccttc gcgcaggccg tctga                   1545

<210> SEQ ID NO 32
<211> LENGTH: 495
<212> TYPE: DNA
<213> ORGANISM: Streptomyces lavendulae

<400> SEQUENCE: 32
gtggagaggg tggagctgat ccgctggccg gtggagtccg agcggcggga gcgctgccgc     60
gaccggggcg tcatgcggat cctggtgctg gaggcggggg ccgaggcacc cttgtgcgtg    120
gaccccaagg aggactgggt ccgcgctccc gtcagcaccg acgacctgcg ggcccgcgtc    180
gaggccctgc gccttcgggg agccgccgcc gagtcccggc ccgaggtcga cccgaacgga    240
gtgctgcgtt tccggtggcg ctccgccctg ctctcgccca ccgaggcccg gctcgtcgcc    300
cggctcgccg agtcctatgc cgaggtcgtc gcccgcgacg acctgctccg cccgccccg     360 ggccgtaccg tgccgagccg taacgcgctc gacctccaca tcatgcggat ccgacggcgc    420
ctcgccgcgc tgggcctgag ggtgcgcacc gtccgggggc gtggctacgt cctggagagc    480
gcggaaggag tctga                                                    495

<210> SEQ ID NO 33
<211> LENGTH: 1032
<212> TYPE: DNA
<213> ORGANISM: Streptomyces lavendulae

<400> SEQUENCE: 33
gtgcagcagc ctcatcacag ccgcgtcgac gtggaactgg gcgagaggtc ctaccccgtc     60
cacgtcggac cggggtccg ccacctcctg cccggcatcg tcgcctccct cggcgcgcac     120
cgcgccgccg tcgtgaccgc acggcccccc gacctggtgc ccgatcccgg cgtgcccgcg    180
ctgatcgtgc gggcacgtga cggcgagcgg cacaagacgc tcgccaccgt cgaggacctg    240
tgccgcaagt tcaccacctt cggcatcacg cgccacgacg tcgtcgtctc ctgcggagga    300
ggctcgacga ccgacaccgt cggcctggcg gcggcgctgc accaccgtgg ggtgccggtg    360
gtgcacctgc cgaccaccct cctggcccag gtggacgcga cgtcggcgg caagacggcg    420 gtcaacctgc ccgagggcaa gaacctcgtc ggcgcctact ggcagcccaa ggccgtgctg    480
tgcgacacca cgtatctcca cacgctgccc gccgaggagt gggtcaacgg ctacggcgag    540
atagcgcgct gccacttcat cggtgccggc gacctccgcg cctcgccgt ccacgaccag     600 gtcaccgcga gctgcggct gaaggcgtcc gtcgtcgcgg ccgacgagcg ggacaccggc    660
ctgcggcaca tcctcaacta cggccatacg ctgggccacg cactggagac cgccaccggc    720
ttcgggctgc ggcacggact cggcgtggcg atcgggacgg tcttcgcggg ccggctcgcg    780
gaggcgctgg ccgcatcgg cgccgaccgc gcgcgggagc acaccgaggt cgtccgccac    840
tacggacttc ccgacagcct cccggggaaac ccgacatca ccgagctcgt cgcgctgatg    900
aggcacgaca agaaggccac gtcgggactg accttcgtgc tcgacgggcc ttccggcgtg    960
```

-continued

```
gagctggtgt ccgggatccc ggaggacgtc gtcctgcgta cgctcgcggc gatgccgcga    1020
ggaacggcct ga                                                        1032
```

<210> SEQ ID NO 34
<211> LENGTH: 441
<212> TYPE: DNA
<213> ORGANISM: Streptomyces lavendulae

<400> SEQUENCE: 34

```
gtgttccgtc ttccgagggg aagtgaccgt ttcgtgtcgg cagagctgtc agaaccgctg      60
aagaaggccc tggactccct ggtgttcggc gtcgtggcga cgaccgaccc cgacggccgc     120
ccgcaccagt cggtggtgtg ggtccggcgc gagggctccg acgtgctgtt ctcgatcacg     180
cgcggcagcc gcaaggagag gaacatcctg cgcgacccgc gtgtgagcgt gctgatcagc     240
ccggcggact cgccgtacac ctacgccgcg atccggggca ccgcgcactt cgaggacgtg     300
ccggacccgg gcgcgtacct cgacacgttc tccataaagt accacggcgt gccctaccgg     360
gagtcgttcc ccgagccgcc ggaggtgagc accattctcg ccgtccggct cgttccgacg     420
tcggtctacg agcagtggtg a                                               441
```

<210> SEQ ID NO 35
<211> LENGTH: 828
<212> TYPE: DNA
<213> ORGANISM: Streptomyces lavendulae

<400> SEQUENCE: 35

```
atgacggaaa ccgcgtccgc ctccgaccgg atggtcgaac tctacaaccg cgtcaccgac      60
ttgatggtgc acgcggaagg cggctacatg cacggtggct actgggcggg acccgacgtc     120
cccacgacgg tggaagaggc aggcgaccgg ctgaccgact acgtctcgga gcgcctgcgc     180 ctcgccccg gggagcgggt gctcgacgtg gggtcgggca acggcaaggc caccttgcgc     240
atcgccgccc ggcacggggt gcgggccacc ggggtctcca tcaaccccta ccaggtgggt     300
ctgtcgcggc agctcgccga aggagggc gacgaggcga ccgagttccg catcggtgac     360
atgctcgcgc tccccttccc cgacggctcg ttcgacgcct gttacgcgat cgagagcatc     420
tgccacgccc tggaacgggc cgacgtcttc accgagatcg cccgggtgct cgcccgggc     480 ggccgggtga cggtgacgga cttcgtgctg cgccggcccc tgagcgacgc gtccaggacg     540
atcgtcgaca ccgccaacga caacttccag cagggccccg tcctcacccg cgaggcgtac     600
gaggactgca tgcggtcggt ggggctggag gtggtggagt tcctcgacat cggggacgag     660
gtgcggccct cctacgaggc ggtggcggcg aagatgcgtg cggccaggga cgagctcggc     720
tcccacatgg acgacgaggc gttccaccgc atggtcgacg gcatcgaccg catgggctcg     780
gtggaggagg tcggctactc ggtggtcacc gcgcggaaac cggcgtag                  828
```

<210> SEQ ID NO 36
<211> LENGTH: 852
<212> TYPE: DNA
<213> ORGANISM: Streptomyces lavendulae

<400> SEQUENCE: 36

```
atgccgcact ccgagctgtc cgaactcccc atgccctcac ccgcctccga ggaagtgggc      60
gcgctctacg accggttcac cgcgctggga gccgcctccc tcggcgagaa cctgcacttc     120
ggctactggg actcccccga cagccaggtg ccgctggccg aggccaccga ccggctcacc     180
gacatgatgg ccgagcggct gcgcatcggc gccggctccc cgtcctgga cctcggctgc     240
```

-continued

```
ggcgtgggga ccccgggcgt acgcatcgcc cggctcagcg gagcgcatgt cacgggcatc      300
tcggtgagcc atgagcaggt cgtccgggcc aacgcgctgg ccgaggaggc cgggctcgcc      360
gaccgggcgc gcttccagcg ggccgacgcg atggacctcc ccttcgagga cgagagcttc      420
gacgccgtca tcgccctcga atcgatcatc cacatgcccg accgcgccca ggtgctcgcc      480
caggtcggcc gggtgctgcg gcccggggc cgtctggtgc tcaccgactt cttcgagcgg      540
gcccccctcg cccccgaggg gcgggccgcc gtccagcgct acctccacga cttcatgatg      600
accatggtca gcgccgaggc gtaccctccc ctgctgcggg gggcgggcct gtggctggag      660
gagttcctcg acatcagcga ccagaccctg gagaagacct caggctgct ctcggagcgc       720 atcaactcct cgaagcagag gctggagacg cagttcggcg aggagatggt gaaccagttc      780
gaccccggcg acctcgtcgg cgtcaaggag ttcggctatc tgctgctggt cgcccagcgc      840
ccgggaaagt ga                                                          852

<210> SEQ ID NO 37
<211> LENGTH: 1563
<212> TYPE: DNA
<213> ORGANISM: Streptomyces lavendulae

<400> SEQUENCE: 37
gtgctgaaca ccctgtccac cgcgccgttc ctgtccacgg cctggctcgc cggggccgcg       60
aggctcgaac gccgcccgt gggcgaacgg ggcacggtcg cgctccgcct ggagctcacc       120
gacccaccgc ccggcgaacc cccggccgtc gacgtccagg tggacctcgt cgccgggcgg      180
ctcggcctcg cggccgcggc cggtgagagt ccgggactgc ggatccggct tcccctggag      240
gccgcccgcg ccctgctgct cggccccgcg cgggatcgga ccggcgtatt cgagcggggc      300
gacgtacggg ccgagggcaa tttcagcctg ctgttcttca tcgacgccgc actggagcgg      360
gacgcctcgg gccatgtggc cgcgctcagg ggcacgcccg gtaccacggc gcgggaagcg      420
gccccgccgc ccggcaccga ggacgcggcc gaggccgtcc ggcgcgcccg tgcggcgctt      480
cccggcacca tgcgggagct ggagcgcgag gtcggcacct cgaccccggg ggcgcagatc      540
tacgtctccc gcgacggagt ccctctggcg gacgccgggt tggggctggc ccgcccgggg      600
gtggcgatga cccaccggtc gctgcccctg tggtactgct gcgccaagcc actgctgtcg      660
gtcgccctgg gccggctgtg ggaggcggga gcgtacgacc cgtatctgcc cgtcgcgcac      720
tatctgccgg agttcggcaa ccggggcaag gagtccatca cctcgatgga actgctgacg      780
catacgggcc cgctgcccac cggcgacgac ccgctgcacg gcatcgtggc cggcccggac      840
gaggagcgtg tgcgccgtgc cttcgaggtg ccggtggcac cgcgtccggg gggcacgccc      900
ggcatcaact acagccagtg gtgggcctgg ttcgtcctgg cgcgcatcct tccggtcgtc      960
gacggcaggg agtaccgcgc gtacgtccag gaggagatcc tcgggccgtg cggcatgtcc     1020
ggcacccgtg tccacctgga tcgcgaggag ttcgccgcgc tcgggggcga gctgccgctg     1080
atccatgtga gcaaccccga gggcggcccg ctgcccaccc actggtggtc gacggaggcg     1140
gccaccacac gctgcatccc gggggtcaac acccgtggcc cgctgcggga catgggcagg     1200
ctcttcgaga tgctgctgcg cggcggggac gctcccggcg ggcgcgtcct ggcgccgccc     1260
accgtcgccg ccctcacggc ccggcaccgc accggcctcc aggaccgcta cggcaacgcc     1320
gactgggcga tggggttccg cctcgaatgc cgtcagctgg atccgcggtt caccagcttc     1380
ggctcgtacg cctcccccg gtccttcggg cacgacgggc tgtggaccgc cgtggtcttc     1440
```

| | |
|---|---|
| gccgacccgg acgccgctct cgtcgtcgcc ctccacctca acgggaaggt ggagcacgaa | 1500 |
| cggcaccgcg agcgcatcgt ccgcctcgcc gacgccgtct accaggacct ccgtctctcc | 1560 |
| tga | 1563 |

<210> SEQ ID NO 38
<211> LENGTH: 1041
<212> TYPE: DNA
<213> ORGANISM: Streptomyces lavendulae

<400> SEQUENCE: 38

| | |
|---|---|
| atgacgcccg cgaccccgcg ctggagcgtc gtcgccccgc agggcaccaa cctcgaactg | 60 |
| gccggtacgg gcggccgcga gggctggcgg ctcctcctgg agaccgcccg caccgtccac | 120 |
| cggcacggcc gtggcgccct ctggctgctg gaccgcaccg acaccctgcc ccggcgcgag | 180 |
| cccgagccgg tctgggaggg ctggacggcg ctggcggccc tcgcgggcgc ggtgccggt | 240 |
| ctggatctgg gactgctctc ctcggccccg ccgttccgca acgccgcgct gatcgccaag | 300 |
| cgggccgcga ccctggacgt cgtctgcgac ggccggctca ccctcggctt ccgcgcccgc | 360 |
| gagtacctgc cggagcacca ctcgacgggg cgcgaggtgc ccacgggcct ggaggcggac | 420 |
| gaggaggagg ccgccggcca ccgggctctc ggcgagacgg tcgaggccct gcgcgcgctg | 480 |
| tggggcggac agcccgtcac cttcaccggg gaacacatcc gcctcacttc ggcgcactgc | 540 |
| gtgcccgccc cacggcagca gcccctcccc ctcgcgctgc gcaccccggc cggggacgcc | 600 |
| gggagcggcc cgctgcggcc cgccgacgcc accgtgcggg agtgcgctca tgtccagtgg | 660 |
| accggtgagc ccgctcaggt cgccgcggcc gtcaccgcgt tccgccgccg tcgcacggag | 720 |
| ctcgggctcg atccggacgg cgtccggcac gcctgggccg cggagtgccg gatcttcgac | 780 |
| tccgtcctgg aacgcgaccg ctggctctcc accccgcacg aggtgctgtt ctggagccac | 840 |
| catcccgacc tgctggcgcg cgcagcctg tacgggacgc cggaacagct caccgagcgc | 900 |
| gcccggcgcc tggtcgccgc gggcgtggcg gagttcgtgc tgtggttccg cgactacccg | 960 |
| gccaccacca gcctggagcg gctgttccag gaggtcgtcc cccaggtggc gccggggcc | 1020 |
| gccaaggaag cggaggagtg a | 1041 |

<210> SEQ ID NO 39
<211> LENGTH: 708
<212> TYPE: DNA
<213> ORGANISM: Streptomyces lavendulae

<400> SEQUENCE: 39

| | |
|---|---|
| atgcccctga ccccccgcc cgcctcgcgg gccgcggcgg acgcgcccgc caccgctctc | 60 |
| ccgtgccggt tcaccaccgt ggtcttcgac ctcgacggcg tcctcatcga cagtttcgcg | 120 |
| gtgatgcgcg aggcgttcgc cgtggcctac cgcgaagtgg tggggccggg cgagccgccc | 180 |
| ttcgaggagt accgcacgca ccagggccgc tacttcccgg acatcatgcg gctgatgggc | 240 |
| ctgcccggcg agatggagga accgttcgtc cgggagagcc accggctgat ggaccgcgtc | 300 |
| gaggtgtacc cggacgtgcc gcagttgctg gcggagctgc gcgcggacgg cgtcggcacc | 360 |
| gcgatcgcca ccggcaagtc cggctcccgg gcgcgcgccg tgctggaggc ggtcgggctg | 420 |
| ctgcccctgc tggacgaggt ggtgggcagc gacgaggtgc gaggcccaa gccgcacccc | 480 |
| gacatcgtgc gggaggcact gcgccggctg acgcggcgc ccgaggacgc ggtcatggtc | 540 |
| ggcgacgcg tgatcgacat ccgcagcggc ccgccgccg gaccgccac cgtgggcgcg | 600 |
| acctggggcg agggcgcggc cggccaactg cgcgccgagc ggcccgactt cctgctggac | 660 |

| aagccgcaga gcctgctcgc gctggtccgc agcggcggcc acgcatga | 708 |

<210> SEQ ID NO 40
<211> LENGTH: 873
<212> TYPE: DNA
<213> ORGANISM: Streptomyces lavendulae

<400> SEQUENCE: 40

| gtggagcgtc tgaagctcgt gcccgacgag caccgccgtt tcaccgtcga cgagcagagc | 60 |
| gcgcgccggc tgcaccggat cggaccggag ctgctgtccg cgctgtgcga ggcgggcgtg | 120 |
| cccttcgtgg aagcggcgc gggacgcctc ttcgacggct acgacctggg caacgcggcc | 180 |
| ctgcaccttg gcctgtcctc ggtgcagcgc cgggccatcc gctcgtgggc cggttccctg | 240 |
| cggaccgcct cggccgcgga gagcccgcgc tggcgcgtcg acgtcacggc gtcctgcccg | 300 |
| gtgcccggcc acgcgggccc gtgccgctac ggagtgctgc tgcccggcgc ccgccgcccg | 360 |
| gtggaggcgg cttcgccgcg ggagaccacg ctggcgcggc tgtacacacg gtcgcgcggc | 420 |
| cactggccga acttcccccc ggccgtcctc gacctgctgc gcaccctgga gccggtcggc | 480 |
| ttcttcctgc tgcccgaagc gatccgctgg gacccggggt tcctgtggag cacgcacatg | 540 |
| gccgactgcg gcgcgccgc ggcctggctg gtggcggagg gccggcggcg cgggctcgac | 600 |
| gtgcggttct ccttcgggct gctggtggcc aagccgtact ccacaccgca ctgctgggcc | 660 |
| gagttcctgg tgggcggccg ctgggtgccg gccgatccgc tgctgctgag ggccatggcc | 720 |
| gcctggggcg ggctggacgc ggcggcccac ccgccgcaca gctcgccggg ggccgtctac | 780 |
| caccggctcg cgggccgctt cacgaaagtc gtcagccacg ccggggtctg ggccccgacg | 840 |
| tccctaccca cggagctcct gccatgcccc tga | 873 |

<210> SEQ ID NO 41
<211> LENGTH: 1149
<212> TYPE: DNA
<213> ORGANISM: Streptomyces lavendulae

<400> SEQUENCE: 41

| atgaaattcg cttatttctc ccatgtctgg ggacgtcccg gtatcacgcc gggcgagcgc | 60 |
| tacgaagagc tgtggcgcga ggtcgaggac gccgaccggc tcggcttcga ctacgcgttc | 120 |
| tcggtggagc accactgcac gccgcacgag agctggatgc cctcgcccgc ggtcttctgc | 180 |
| acgggcgccg cgctgcgcac cgagcgcatc cgggtcggcc cgatggggtg ggtgccgccg | 240 |
| ctgcgccacc cgctgcacct ggtcgaggag gtcgcgaccc tggaccagct cctgggcggg | 300 |
| cggctggagg tggggctcgc ctcgggcgtc agccgtgacc ccttcctgcc cttcgacgcc | 360 |
| gatttcgaca accgtcacct cctgacccgg gaggccctgg agctgctgcg tgccgcgttc | 420 |
| gccgcgcggg gcgccttcga cttcgacggg cccgcgcacc ggctgcgcga catcgccctg | 480 |
| tccttcccgc cggtgcagcg cccgcacccg ccgatgtggg tgcccaccac caaccgcaac | 540 |
| accttgcgct atctcagcga ggccggtgcc cacaccagtt ccacgatgat cgtgccgcgc | 600 |
| gcctccatgg cgctggtcta ccggcactac ctcgactggt ggcgcggcca cggccacgcg | 660 |
| agcgaccccgc gcatcggcta ctggacgctg gtccacgtgg cccggacgga cgccgaggcg | 720 |
| gaggagcggg cggccgcgca catcaccgag acgttcacca agacgctgcg gtacggctcg | 780 |
| gtgtcccgtt ccgcgatca gcacgcccca cccagcaggc tcagcacgac ggacatcctg | 840 |
| gcgggctccg gcgacctgcg cttcctgctg gagaacaacc tcgtcttcgt cggctcgccg | 900 |

-continued

| | |
|---|---|
| gcgaccgtgg ccgaccggat cagggccgcg tccctggagg gccatttcga cacgctgctg | 960 |
| ggcgagttca ccttcggcga gctggcggac cggcaccgca tcgagtccat ggaactgttc | 1020 |
| gcgcacgagg tggccccggc actgcgcgcc ttctccccct acgcgccgcg cccgcaggag | 1080 |
| ccggcgtaca ccgcgagcga cgagcagcag gtggcggccc gcctccaggc tctgggctac | 1140 |
| atcgactga | 1149 |

<210> SEQ ID NO 42
<211> LENGTH: 1215
<212> TYPE: DNA
<213> ORGANISM: Streptomyces lavendulae

<400> SEQUENCE: 42

| | |
|---|---|
| gtgacaccgc cgacgacagc tcgcgaaccc ctccggatgg cagtgctggg cgcgggatgg | 60 |
| gtctcgcgca aggtgtggct gccgctgctg cggaacaccc cggcgttccg ggtcgacttc | 120 |
| ctcgtggacg acgaccccgt ggcggccagg tcggccctgc cggagggcgc gcggacccgc | 180 |
| gtcctgagca gaccggaaga gctcgccccc agaagcgtgg acgcggccat catcgccctg | 240 |
| cccaaccacc tccatctccc cgtggccaag gccctcctgg agcgggacgt gccggtgttc | 300 |
| gtcgagaagc cggtgtgccg cacgctcttc gaggcccagg cgctcgccct ggaccaccag | 360 |
| gcgcggggcg acagcatcgg ggacatcacc ctctacgcct ggagcgccgc ccggcaccgc | 420 |
| accgatgtct gccgcctggc ggagctgctg ccctcgctgg caccgtgcg cagtgtcggg | 480 |
| ctgagctgga tccgggccac cggcatcccg cagcgcaccg gtggttcgt cgaccgccgg | 540 |
| ctcgccgggg gcggcgcgct gctcgacctg gctggcacc tgctggacgt gggcctgcac | 600 |
| ctgctggggt ggccgcgcgt ggtccgggcg gcgagcacga tgtccgcgga ctggatgagc | 660 |
| cggggcgagg ccacggccga ctggagccgg cgctcctccg gcacggcgcg gccaggcccc | 720 |
| ggggagacgt ggaggacac cgcccgcggc ttcctcgtca ccgacaccga cgtgggcatc | 780 |
| tccctggaga cacgctgggc ctcccaccag gcgctggacg tcaccacgat caccgtggag | 840 |
| ggcaccgagg gggtggcgac gctgcgcggc accttcggct tcagccccca ccggctacag | 900 |
| aagtcgagcc tcgtggtcct gcgccagggg gtggaggaga ccgtcgcgct gcccgacgag | 960 |
| cccgtgggcg tggagtaccg gcggcaggtg gacgaactcg cccgcaggct cggcggctcg | 1020 |
| gccgacgggc agggcccggt gtcgggcctg gcgaggggt cgatggccga agtgaccatc | 1080 |
| ctggcctcct gcatcgacca catctattcg gccgccggcg tcgaccctcc ctcgcccctg | 1140 |
| caccggccgc agagcgacgc ggcgcccagc acgtccagtt gtccacgtgt cctgcccacc | 1200 |
| cggggaagcc aatga | 1215 |

<210> SEQ ID NO 43
<211> LENGTH: 774
<212> TYPE: DNA
<213> ORGANISM: Streptomyces lavendulae

<400> SEQUENCE: 43

| | |
|---|---|
| atgagcaccg tcaccgaccg ggccacggag cgcctggaca gagcggccg cgtggtcgtg | 60 |
| gtctcgggcg cgtccgggca gataggcggc gcgtgcgcgc tggagctcgc cgcgctcggc | 120 |
| gccaccgtcg tcgccggcta ccacagcggc gagcaggcga tccgcaagct gcgggagcag | 180 |
| gtggagggcc agggcggcac cctcgtgccc gtgcggcgg acctgagcga acccgagggc | 240 |
| gccgacgcgc tggtggcggc ggccgtcgaa cggttcgggc gggtggacgg ctgtgtggct | 300 |
| gctgcgggct tgcgtacgcg ccggctcgcg atggccacgg acgcccggag cctggagaag | 360 |

```
ctgctgcggg tcaacctggc cggttccgtg gtctcgcca aggcgtgcct gaagccgatg    420
atgcgcgcca ggtacgggcg gatcgtgctc ttcggctccc gggccgggac cagcgggctg    480
cccggccaca gcgcgtacgc cgccaccaag ggggcgctcc agccgtgggc ggcgtcggtg    540
gcgggtgagg tcggcaagca cggcatcacc gtcaacgtcg tcgcgcccgg ggcgatccgc    600
gccgaggtga tggacttctc ggaggccgag cgcgatctgg tcctgcagtt catcggggcg    660
gggcggctcg gtgagccgga ggaggtcgcg gcggcggtgt cgttcctgct gtcgccgtcg    720
gcctcgtacg tcaacggcaa tacgctcgtc gtcgacggtg gtgcccgctt ctga          774

<210> SEQ ID NO 44
<211> LENGTH: 2124
<212> TYPE: DNA
<213> ORGANISM: Streptomyces lavendulae

<400> SEQUENCE: 44
gtggccctgc gcgcgcccaa cagcccgcgg tgggtcgtcg ccttcctctc cctgctggca     60
tccggcgcca ggcccctgct gctcgaaccc gacaccccg gccccgagac cgcgcggctg    120 ctgcggggctg ccggggggcgg caggtccctg gtcgtccccg ggaccggcga cggcctccgc    180
ctgacgttga ccggctcgcc cggagaaccc tccggcgccc cgcccgccgt gctgctcccg    240
acctcggggt cgaccggtgc gagcaagctc gtcgcccgca gcgaggagag cctgctcgcg    300
gagggccgcc gctaccgcga cggggtcggg ctgacgggag aggacaccct gctgctgccg    360
gtgccgctgt cccacgcgta cgcgctgggc tggctgttcg gcggactgct gacgggtgcc    420
gcgctgcgcc ccgtaccgcc gaccgccctc ggccgcatcg ccgcggagct gtccggtggt    480
gcgaccgtgg tggccctggt gcccagtgtg gcccggctgc tggcgacccg gcggctgcgg    540
ggagcagcgg ccgggcgggc gcccgccgct cccggtctcc ggctggccat ggtgggtgcg    600
gggccggtgg acgagcagct ggaccgcgcg ttcaccgagg cgttcgggac cggtctcgcc    660
cgcaactacg gttccacgga gacgggcgcc gtgctcgccg gaccggcggg gctggagccc    720
ttgtgcgccg gtgctccccct gccggggggtg gagtgcgaac tgaccggccc ggagggcgtg    780
gtgccgcccg ccggcacccc gggggctgctg agcgtacggg tcgacggccg gccgtacgcc    840
atgggcgatc tcgccgtggc cgtgcccggg ggcctgcgca tcctgggacg cgaggaccgg    900
gcgatccgcc gggggcgggcg ctgggtctcc ccgctggaga tcgaggaggt gctgcgcggt    960
catccggacg tggtgaatgt gcgggtgggc gcccggcggg ggcggcaccg gggcgaggac   1020
gggatcgtcg cggaggtctc ggcggcgggg ccggggctca cccccgaggc gctgcgcgag   1080
cacgcccgcc gggagctggc cccgcacaag gtgcccgacg agttcgtcct gcgggagagc   1140
ctgccggtca cgccgcgggg caaggtgcgg gcggcgtccg tctaccgcct cacccggagc   1200
gcggcggagg ccgcccgggc gtacaaggca tccgaagtgc tcttcgcgct gcacgacttg   1260
ggcgccctgg aggcactcgc ccagggtgcc ggcacggctc tcctcgccgg ggagctgggg   1320
tgcgacgcgg atgcccctgga gtggctgctg cgcacgccca ccgctctggg ggtgctgacc   1380
accggggcgc aagagcccgg ggaccgggtc cgggccgggg agctggccgc gttcgtggcg   1440
ctggaggagc acctctcccg tgggctggtc acgcgcgagg agtcgtcgc ggtggcccgg   1500 agcgggacgg cgcggcgtcc cttcgaggag cgtcccccccg agagcctcgg tccgctcgtc   1560
gccctgtacc agggcgcgat ggacggcccc ggcgcacggg cccgggccgc gctcggcctg   1620
cggctcctgc ggcccgggcc gggagcccgg gtggtggagg tgaccgcggg cccgggccgc   1680
```

```
                                              -continued tatctggaac gcctgctcgc ctcggacccc ggggcgagcg gccatctggt caccgtcggc    1740
cggctgagcg ggccgctctc ctcggccgtc gccgcggcgg tcgaggaggg cagggtgacc    1800
gtggggacgg aactgcccgt cggctacgcc gacttctgcg tggtcgccaa cgccgtgcac    1860
ggcccggggc cgggcagcgc tctcggtgcc ctgctcggct ccctgcggcc gggcgggcgg    1920
ctgctggtcg acgacgtctt cctgccggcg tccgggccgg ggagcgaact ggctctggac    1980
tggctcacgc acggcgggac cgcgtggccg gccaccggcg agctgatcgc cgggctgctg    2040
caagaggggg cggaggtcgc acggcacgtg ccgctggacg cgtcccgctg tcatctgatc    2100
atcgccaagg aggccggttc atga                                          2124

<210> SEQ ID NO 45
<211> LENGTH: 1152
<212> TYPE: DNA
<213> ORGANISM: Streptomyces lavendulae

<400> SEQUENCE: 45
atgtcccgta gcacccaccc gccgacagcc acccccgacg cgggcaccag gcgacgcctg      60
ccgctgatcg gcaacgacct ggtcatcaac gaggactcct gcaacctcag ctgcacctac     120
tgcctcaccg gacagagcaa cctcaaggag ggccactccc ttcaactgat cttcgagccc     180
ccgcggcgcg acagctacgc caaggacagc gggctggggc agcgcatgga caaggtcgcc     240
gaccggatcc gggaccgctt cggcctgccg ctgctcaagg tgaccggagg cgagatcttc     300
ctggtccggg ggatcatgga cttcctggag caggaggccc gtaaatacga cgtgctggtc     360
atccagacca acggtgtcct ggtgcgcgag gagcacctgg agcggttccg ctcgtggggc     420
aacgtcgtgc tccaggtctc cctcgacagc cacctccacc acggcaacag ccatcgtgtg     480
ccgtccggga gcctgcacga aaggtcgtc gccgccatcg cccggatcct ggactcgggg     540
ctgccggtgg agatctattc agtgctcaac gaccggagcg tcacggaggt ctgcgcgttc     600
gccgagtggc tgtcgggatt ctcccggcct cccgtctact tccccttccc ggtgcggggc     660
ccggactcga aggacttcaa ggtgcggccc ggcagttcg gccacatcca ggaactcgtc     720
gaccgctacg acgagttcgc gcgggtcctc ccgccgcggc cctacttcga ccggctgacg     780
agcttctacc gcgagggccg ccgcaccttc cgctgccatc tgccgcggct ggtcgtctcc     840
agcttcagcg acggcgtcgt cacgccctgc cccaacatct ggttctccga catgggcaac     900
gccctggagg acgactggag cgagatgctg gacacggtgg caccagcgg cctctaccgt     960 gccctgctcg cccccaagcc ccggctcaag gcgtgccacg gctgcttcac gccctgggac    1020
acgctctcga tgtacttcga ggacgagatc accctcgacg agctgtgcgc cgctcccacc    1080
tactccccgc cccgcatccg gcagatgctc agcgacgcga aggccgacta cctccagggc    1140
ggccatgact ga                                                       1152

<210> SEQ ID NO 46
<211> LENGTH: 21
<212> TYPE: DNA
<213> ORGANISM: Streptomyces lavendulae

<400> SEQUENCE: 46
ggcaaggcat gcgagggtcg c                                               21

<210> SEQ ID NO 47
<211> LENGTH: 30
<212> TYPE: DNA
<213> ORGANISM: Artificial Sequence
```

```
<220> FEATURE:
<223> OTHER INFORMATION: A primer

<400> SEQUENCE: 47
ttccagaacg gcgccctgat gaccgccggc                                       30

<210> SEQ ID NO 48
<211> LENGTH: 30
<212> TYPE: DNA
<213> ORGANISM: Artificial Sequence
<220> FEATURE:
<223> OTHER INFORMATION: A primer

<400> SEQUENCE: 48
gccggcggtc atcagggcgc cgttctggaa                                       30

<210> SEQ ID NO 49
<211> LENGTH: 1545
<212> TYPE: DNA
<213> ORGANISM: Streptomyces lavendulae

<400> SEQUENCE: 49
gtgccaccct ctccccgcgc cctcgtcatc ggaatcgacg gaggcacatt cgatacggtc       60
gacccgctga tcgagtgcgg tctgctgccc catatggcga agttgctgcg cgagagcgcc      120
agtgccgcca cggactgcac ctggcccgcc cacacggcgc cggggtggag cacgttcgtc      180
tccgccagcg atcccggcgg tcacgggatc tatcagttct acgacaccca ggacccggcc      240
tacggggccc gcgtcacgcg ctccggcgac ctgggccggt cctgcgcctg ggactggctc      300
gccgcgcagg aatattcgct gggcctcatc aacatcccga tgtcgcaccc gccggccgac      360
ctccccggct atcaggtcac ctggccgctg agcggacac tcaagcactg ccgcccggat      420
tccctgctgc gcgaactcgc cgcggccaag gcccatttcc agtcggacct cgcgaccatg      480
ttccggggcg acatggccta tctggaggag gccgagcgca atgtggcggc gcgggtccgc      540
tccgtacggc atctgatgag cacccggccc accgatgtcg tgatggtcgt gctcaccgag      600
gccgaccggg tcggccacca ctactggcac tacgcgacc ccggtcaccc gggccaccgg      660
cccgccccgg agggcagcgg ctgggacgtc gccatgcccc ggatctacca ggccatcgac      720
cacgcggtgg gcgagctcct ggagctcgtg gacgaggaca cctccgtcgt gctcgtctcc      780
gaccacggcc tgggcaccgg gcgccacggc ctgtcggtgc acaccctcct ggaggaggcc      840
gggctgctgg ccaccgcacc ggggaggag ccgcaggacg cggcggcgag ctggttcgcg      900
ggcaacggcc ggcacgtcga cttccgccgc accagcgtct acatgcccgt ccccggcagc      960
tacgcctca acatcaacgt acgcggacgc cagcagcgcg gcaccgtcgc accccgcgac     1020
cgcgaacgcg tcatggacga ggtcacgggc ctgctctccg ggctgaccgg ccccgaggga     1080
cagcaggtct tccgggccgt ccgcccgcgc gaagaggcgt acccagggcc gcacaccggc     1140
cgggcacccg acctcctcct cgtcccgcgg gacgagaccg tcctgcccgt ccccgacctc     1200
ggcggtgacg tgtggcggcc gagcgcgcag accggcctgc accgctaccg ggcctgtgg     1260
gcgcaccgct cgccccgcgt ccgccccggc cgcctgcccg caccgtcgc gctcaccgac     1320
accctgccca cctgctcac cgacctcggg gccgcatggc ccagcgacat ccacggccgc     1380
cccgtgaccg ccgtcctcga cgacggcgta ccgtcccgc cctccgaccc ccgggtcgag     1440
gccaccggca ccccggccac cacgatcccg gcgccgcctt cggccgctga tgccgccgag     1500
gacgcgtaca ccagcgaccg cttgcgcgaa atgggctacc tgtaa                     1545
```

<210> SEQ ID NO 50
<211> LENGTH: 282
<212> TYPE: DNA
<213> ORGANISM: Streptomyces lavendulae

<400> SEQUENCE: 50

| | | | | | |
|---|---|---|---|---|---|
| atggagaccc | tgacgaccga | caagatcaag | gaccggctgc | gcaaggtgct | cgtcgattcc | 60 |
| ctcgaactgt | ccctggaccc | tcggccgta | cccgacgagg | gactcgtgga | gaagctgggc | 120 |
| ctggactcga | tcaacaccat | cgaattcctc | atctgggtcg | agagcgaatt | cggcatagag | 180 |
| atcgccgacg | aggacctgtc | gatcaagctc | atcgacagtc | tcgacctcct | cgccggctat | 240 |
| gtgtccgagc | gcgtgaacgg | cgtcaccgca | cccgccgaat | ga | | 282 |

<210> SEQ ID NO 51
<211> LENGTH: 1413
<212> TYPE: DNA
<213> ORGANISM: Streptomyces lavendulae

<400> SEQUENCE: 51

| | | | | | |
|---|---|---|---|---|---|
| atggaccggc | acgccctggt | gatcgggctc | gacggcatgc | cgaggaccct | gctgacccgc | 60 |
| ctggccggcg | acgggaccat | gccgcacacc | gcggcgctgc | tcgccgaggg | ccactgcgcg | 120 |
| gaactgctgg | cacccgtacc | ggagatcagc | tccacctcct | gggccacctt | cctcaccggc | 180 |
| accaacccgg | gccggcacgg | catctacggc | ttcaccgacc | tcgcccccgg | cgacggctac | 240 |
| cgcatcacct | tccccggtgt | gcggcagctg | cgcgaacccc | cgctgtggga | actgccgcc | 300 |
| cgcgccggcc | gcaggaccgt | gtgcctgaac | gtgccgggca | cctacccgc | ccccgccatc | 360 |
| gacggcgtgc | tggtctccgg | cttcgtcgcg | cccgaactgg | agcgcgccgt | cagcccgcca | 420 |
| cggctgctgc | cgctgctgcg | cggcctcgac | tacgaactcg | acgtcgaggt | cggcgacgtc | 480 |
| gccgccgacc | cggccgcctt | cctcgggcgg | gccgtccggg | ccctgcgcgc | ccgcacccgg | 540 |
| gcgatggaac | acctgctgcg | ccaggagacc | tgggacctcg | cggtcgccgt | gctcaccgag | 600 |
| accgaccgcg | tccaccactt | cctgtggcgc | gcggtcgccg | accccgccga | ccccctccac | 660 |
| ggggacgtcc | tcgccttcta | ccgcctcgtg | gacgactgcg | tcgccaccct | ggtgagcacc | 720 |
| ctcccaccgg | gcgcgaact | cttcctgatg | agcgaccacg | gcttcggacc | cgccgcctgt | 780 |
| caggtctatc | tgaacgcgtg | gctcagggag | tccggctggc | tggccgggct | cgacgtctgt | 840 |
| ccggacctca | ccgcggtcga | cgctcgcagc | accgccttcg | cgctcgaccc | cgcccgcatc | 900 |
| cacctcaacc | gcaagagccg | cttccccggc | ggcggcctga | ccgacgcgga | ggcggacgag | 960 |
| gccgcccacg | agatcgcgcg | cgagctgtcc | gccctgcgct | gcgacggcac | ccgcctgggc | 1020 |
| cccgacgtcg | acggaccct | gctcgtccgc | gacctctacc | gcgctcagga | gatctaccac | 1080 |
| ggcccgctgt | tgggcaacgc | cccgacctg | gtggccgtac | cggcccccgg | ggtgcagctg | 1140 |
| cgcggcggct | ggggcggcac | gcacaccgta | cgcaacgaca | tcctcaccgg | cacccacacc | 1200 |
| cgcgacgacg | cggtcttcta | ccggcgcggc | gcgcccgcgc | ccgccccgg | ggcggacgac | 1260 |
| ggccccctcg | acatgacgga | cgtcgcccg | accgtcctcg | cctccctggg | catccacccc | 1320 |
| ggcgggctcg | acgcgcggc | cgtactcggc | accacgggac | ccgcgtccgg | tcacggccgc | 1380 |
| acggaccccc | ctctcgacat | cagggagctc | tga | | | 1413 |

<210> SEQ ID NO 52
<211> LENGTH: 1836
<212> TYPE: DNA
<213> ORGANISM: Streptomyces lavendulae

<400> SEQUENCE: 52

```
atgaagcacg acctcggtct ggcaccatcg gcacccaaac cgggaacact cgacctgagc      60
ctggacccac gcatcacgga ccccgcttcc ttccgggtca gtttcctgat cctcctcgac     120
ggcgacctcg tgatgtcccc cgaacacctc ggcgtcgcct acatggccgg tgtgctgcgc     180
catacgggct tcaccgcgga gatccgggag gtggagcacg cgacgacca ggcggccgcc      240
accgtcgagg cgctcaagga gtaccggccc gacctcgtct gcttcaccct gatgagcctg     300
aacctgggca gctgtctgac cctgtgccgg atgctgcggg aggagctgcc ggggacgacg     360
atcgcctgcg gcggcccagc cgggaccttc gcgggcctgg acgtcctgcg gaacaacccc     420
tggaccgacg tcgtcgccgt gggggagggc gagcccacca tcctcgacct cgtccaacgg     480
ctctacctca aggagccgtt gtccgcctgc aaggggatct gctaccgcga cgaggacggc     540
acaccgcgcc agaaccccgc ccgccccctg atccacaacc tggaggacct ccccttcccc     600
gcccgggacc agctgcgcca gcacggcgac aagctggagt acgtccgggt cagcaccagc     660
cggggctgcg tcgccaactg cgccttctgc tccgccccgc acctgaagaa ccgcgtccag     720
gcgggcaagg cgtggcgcgg ccgcgggccg gaacagatcg tggacgaggt cgccgagatc     780
gtcgaacgcc accagttccg gaccttcgac ttcgtcgact ccaccttcga ggaccccgac     840
ggcggccggg tcggcaagaa cgggtcgcc gccatcgcga acggcatcct ggagcgcggc      900
ctcgacatct actacaacgt ctgcatgcgg gccgagaact ggcacgacac ccccgaggac     960
cacgccctgc tcgacctgct ggtcgcctcg gcctggaga aggtcaacgt cggcatcgag     1020
gccggcaccg ccgaggaact gctcctctgg gagaagcgcg ccaccgtcga ggacaacgtc    1080
accatcatca ggatgctgcg ggaacacggc atctatctcg ccatgggatt cattcccttc    1140
caccccctacg cgaccctgga gaccatcgtc accaacgcgg ccttcctgcg cgacaattcc    1200
ggccacaacc tccggcgcat gaccgaacgc ctggagatct accccggaac ggccatcgtc    1260
agccgcatgc gggccgacgg actcctcggc gagagctatc tcgaagggct cgaccccctac   1320
ggctacgcat tcaaggatcc ccgcgtcgga cggctcgcca agcatttcgc ccagctctac    1380
aacaacgacg actaccaccg gcacggcgtc atcaccgagc agtcctccgt cttcgccttc    1440
gagacctaca acgtcgtact ccagaccttc atctcccggc tgcaccgccg gttcaccacc    1500
ctgccgggg tggacgaggt gatgaggca ttcaaggccc gggtgcacga gatccgccag      1560
gagatgggcc ggcacaacta cggcttcttc atgtccaatg tcgaggcggt catgaacgac    1620
accctcgacc cggagaagca cgccggcag gtggtggacg tcgagcactt cttccgcgac    1680
cgcctcgatg tgttgcgcag cgagcaattg cgcgtcggca aggccctcac ccggctcggc    1740
gcccgggtga cggaggtcag ctcgaccatt cccaaggagc gccccggcgg actgccgcgc    1800
cagtacacgg gagagggcag cggtgccacg tggtga                              1836
```

<210> SEQ ID NO 53
<211> LENGTH: 1080
<212> TYPE: DNA
<213> ORGANISM: Streptomyces lavendulae

<400> SEQUENCE: 53

```
gtgccacgtg gtgagacggg aaccgccgcg gcgcgggtgg cggtctgcac gctgagcagc      60
agggaactgg tcgcccgct ggccggttg ccggtgtgg cggccgcggg cacgctgatg         120
accgccaacc tgggcatcga gcaggtgatc aaggccctgc ggtgcgaccg gacggtccgc     180
```

-continued

```
ggcctgctcg tgtgcggccg cgactcaccc cgcttccgcg ccggccagag cctgatcgcc    240
ctcttccgcc acggcctgcg ccccgaggac gggcacatcc ggggagccac cggctatctc    300
cccgtcctga gtcggtgacg gcgcgggag accgaggagg tacgcgcccg cgtcgagctg    360
gtggacgccc gtggcgagcg cgacgtcgag acgctgcgcg ccgaggtcgc ggcactcctc    420
gcccgcgtac ggcgcacccc ggccctcccc tcccgcgagc acgacggcgg ccaacccagc    480
ttcgtggagc cggacttcgg acggctgcat cctgtcggcc gccgccgctc cctggacgcg    540
ggcatcggcg ggttcgtgct catcagcgtc gaccgtgagc accggcggat cctgctgcgc    600
cactacacct ccgatgtgcg gccccggcac gagatgtggg gcacccgcgg ggaggcgatg    660
ctgctcgggc tgctggaggc cggcgtcatc gaggaccccg cccacgccgg atacctcggc    720
gccgaactgg ccaaggccga cggcgctg cggctcggcc tgcactacga acaggacctg      780
cccctgcgcc cgccgggcag gccgcccggc cctgtgcggc gccggaccgc gaaggagcga    840
acgaccatgg cgcaagcacc cgcgctggag gacttcctgc gtctcgtgac gaggacgctg    900
ggggccgagg acgccgtcct ggacctgcac acgccgctcg gcgagcaact ggcggtggac    960
tccgcccggc tcatcgaact caccgtcgtc ctggaggagg agctcggcgc ggacctcccc   1020
gacgacgccg acctcgccag ggccacccc gcggaactcc acaaagcact cgtgggctga   1080
```

<210> SEQ ID NO 54
<211> LENGTH: 438
<212> TYPE: DNA
<213> ORGANISM: Streptomyces lavendulae

<400> SEQUENCE: 54

```
atgcgcagcg tgctgttgct caacggaccc aacctgggga cgctcggcaa gcggcaaccg     60
gagatctacg gaaccgacac cctggccgag atcgaggccg ccgtggccga ggaggtggga    120
gcgcgcggct gggaggtggt ctccgaacag cgcaacggca aggggggaact ggtcgatgtg    180 ctccagcgcc acgacgacgt ggtgggcgcc gtggtcaacc ccggcgccct gatgatcgcc    240
ggctggtcac tgcgcgacgc gctcgccgac ttcgccccgc cctgggtgga ggtgcacctg    300
agcaacgtgt ggggacgcga ggcattccgg cacacctccg tcacggcccc gctggcctcc    360
ggcgtcgtga tgggatggg ggcgctgggc taccggctgg cagcgcgcgc cctcacccgg    420
ctggtccccg aggactga                                                  438
```

<210> SEQ ID NO 55
<211> LENGTH: 534
<212> TYPE: DNA
<213> ORGANISM: Streptomyces lavendulae

<400> SEQUENCE: 55

```
gtgggacggt acggaagaga gggtctgggg atgtcgcgta cggctgaggg gaacgccgga     60
ggcgtggtgg tgccggtggt ccggctggtc gccgtgacga cgggccgga cgcggagggc    120 tggcggcagg cgctcgcccc cgaactggtg gtggagcacg cgtcgaggc gatcgcggag    180 gcggccgggg acggcgggcc gtgggcgctg gtctgtgccg gtgccgggct gggcgcggcg    240 ctgcggggccg ccgagcgggc cgcgcgcccg ccggtgcatg tgctgctgtg gctcggcagc    300
cgcgggcccg gcgaagggt gggcggggag gtctccggtc aatttccctg tccggtcacg    360
gccttggtgt ccgcggaggt ggaccgcggt cgcgccgtgg tccccgcctg gcgcggcctg    420
accgaggggc cgttcaccgt gcggatcctc ccggcggcct gcccgctgcc cggggcgtgc    480
gaccaggccg cgctcaggt gatcaaggag gagctgcggg tgtggcccgc ctga           534
```

<210> SEQ ID NO 56
<211> LENGTH: 765
<212> TYPE: DNA
<213> ORGANISM: Streptomyces lavendulae

<400> SEQUENCE: 56

| | | | | | |
|---|---|---|---|---|---|
| atggatgcga | ctttgacgaa | tgacgtcgag | aaagcctccc | gggatctggt | cgaagccgga | 60 |
| tactgcctga | tcgagtgccc | cttgccggcc | gcggtcttcg | aaaagctcag | agggcggctg | 120 |
| ctggaggtcg | ccgagcagga | gcgtgagaac | ggctcggcct | ttctctacga | cggcggcaac | 180 |
| caacgcgtct | tcagcctgct | gaacaagggc | gaggaattcg | agcagaacgt | gcaggatccc | 240 |
| accgtcatgc | tcctgatgga | ggagatcctg | ggcttcggct | tcctgctctc | cagcacgcac | 300 |
| gccaatatcg | cgggccccgg | cggttcccgg | atgcatctgc | acgcggacca | gaccttcgcc | 360 |
| cgcccgccgt | ggccccccgta | tccgctggtg | gccaacagca | tgtggatgct | ggacgacttc | 420 |
| accgaggaca | acggcgcgac | ccgcctggtg | cccggctccc | atctgctggg | ccggcagccg | 480 |
| gactacgacc | ggggcgaggg | gaacaccgag | acggtcgccg | tgtgcgcgcc | ggccgggagc | 540 |
| gtgatggtct | cgacgggcg | cctgtggcac | cagacgggcg | ccaacaccac | cgaccggccg | 600 |
| cggcacggca | tcctcaacta | ctactgccgc | ggctacgtcc | ggcagcagca | gaacttcttc | 660 |
| tcgggtctgc | gggaggacgt | cgccacccgc | gcgacgcccg | aactgcgccg | gctgctgggg | 720 |
| tacgagaact | acttctccct | cgggatgacc | gacggcctgc | cgtag | | 765 |

<210> SEQ ID NO 57
<211> LENGTH: 795
<212> TYPE: DNA
<213> ORGANISM: Streptomyces lavendulae

<400> SEQUENCE: 57

| | | | | | |
|---|---|---|---|---|---|
| atggcacact | caccgcggcg | gccggacggc | cccctccgca | tcggggtctg | gctggccccc | 60 |
| cagcacacct | cggtggccga | actgcgcgcc | gcctggcgcg | cggccgactc | cctgggcgtg | 120 |
| gactcgctgt | ggctgtggga | ccacttcttc | ccgctcaccg | gggaccccga | cggcagccac | 180 |
| ttcgaggcct | ggaccctgct | ggcggccatg | gccgccgaca | cccgcgccgc | ccgcctgggc | 240 |
| accctggtgt | ccaactacgc | ctaccgcaac | cccgacctcc | tggccgacat | ggcccgcacg | 300 |
| gtcgaccaca | tcggcgacgg | ccgcctgatc | ctcggcatgg | gcgccggctg | ggtcgaacgc | 360 |
| gacctgaagg | agtacggcta | ccccacgccc | ggcgcggggg | agcgggtgga | cgggctcatc | 420 |
| gaggcggtgg | agcgcgtcga | ccgcagactc | ggccggctgc | gccccgggcc | gctcggcgac | 480 |
| ctcccccctgc | tcatcggcgg | ggacgggcag | cggcgcctgc | tgcgcttcgc | cgccgaacgg | 540 |
| gccgccatct | ggaacaccat | ggcctggcgc | ttcgccgagg | gcaatcgcgt | gctggacgag | 600 |
| tggtgcgcgc | gggtcggccg | cgaccgcgcg | gagatcgagc | gcagcgcctt | cgtcacccgc | 660 |
| gaccagaccg | acgaggagct | gcgctgcctg | gtggcgacgg | gcgtccagca | cctgatcttc | 720 |
| caggtcgggc | accccttccg | cttcgacggc | gtggagcggg | ccctgcgctt | cgcgggcggc | 780 |
| tggagcaagg | ggtaa | | | | | 795 |

<210> SEQ ID NO 58
<211> LENGTH: 825
<212> TYPE: DNA
<213> ORGANISM: Streptomyces lavendulae

<400> SEQUENCE: 58

-continued

```
atgaagatca gcattgctct gccgaacacc gtgcccggcg cggacgggcg cctgataacc      60
gattgggcgc ggcgggccga ggagcgggga ttcgcctcgc tcgcggccac cgagcgcctg     120
gtgtatccgg gccacgatcc gctgctggcg ctggcggcgg cggccgggc gacctcccgg      180
atcgggctgc tcaccaatgt cctgatcggc ccgctgcgca ccgcgcctgt gctggcgaag     240
gcggtcgcga gtctggactc gctgtcgggc ggcggttca ccctggggt cgggcccggc       300
gtgcgcgagg acgacttcga ggccgccggc cgcgccttcg acaccggcg cgcggcgttc      360
gaggagcagc tggagctgct cggccgggc gcccggccgg gcgcggaggg ccccggtgtg      420
ccggtcctcg tcggcggggt cagcgcggcg gccgtgcgcc gcgtggcgcg ctgggccgac     480
ggctggacgg cgcccggcct ggagccggag cggatcgtgc cggtcgcgga acgggtgcgc     540
cgcgcctgga gcgaggcggg acgcgccggg gcgccgcatg tggtggcgct ggcgcgctac     600
accctgggcg aggacgtggc ccaggagtcg gcggccttcg tccgggacta cttcgcggtg     660
ctgggcgagg aggcggagga gttcgtggcg aagacccgc gcaccgcggg gcagctccgc      720
gcggcggtct cggcgctcgc cgacggcggg gtggacgagg tcgtcctcca ccccacggcg     780
gcggcgctgt cccaagtgga ccggctggcg gacgcgttgc tctag                    825
```

<210> SEQ ID NO 59
<211> LENGTH: 1383
<212> TYPE: DNA
<213> ORGANISM: Streptomyces lavendulae

<400> SEQUENCE: 59

```
atgcccgctg ccggaaaagt cgccgtgata ggactcgact ccgcgactcc gcagtacatg     60
ttcgaccggt tcgccgagga catgccggtg ttcaccgccc tcaggcgcaa gtccctgtgg    120
ggtccgatgc gcagcatcga cccgcccatc accatgcccg cctggtcctg catgatgtcc    180
ggccgctcgc ccgcgaact cggcgtctac ggattccgcg accgcggcgc ctacgactac     240
ggccgttga agttcgccac ctcccacagc atccaagccc ccggatctg gacgagatg      300
acggccgccg gcgctccag cgtggtcctg gcgtccccg gcacctatcc tcccgccccc     360
atccgcgggg ccatggtctc ctgcttcctg gctccctcca cacagtcgcg ctacacctcc    420
ccgcccggcc tcgccgacga gctggagaag ctcaccggcg gctacgccct ggacgtggag    480
gacttccgct ccaccgacct ggaacgcgta tcccagcgcg tcttcgacat gagcgagcag    540
cgcttcgagg tcgcgcgcca cctggcgacc acccaggagt gggacttcct ctccttcgtg    600
gacatgggcc ccgaccgcct ccaccacggc ttctggaaat actgcgaccc cgaccacccg    660
cgccacgagc cggcaacgc ctacgccggt ctcttccgcg actactaccg cgccctcgac    720
cggcacctcg gccgcttcct ggagagcctg cccgagaaca cgaccgtcct ggtcgtctcc    780
gaccacggcg cccagccgat ggtgggcggg ctcttcgtca acgagtggct cgcaaggag    840
ggttacctcg tcctgaccga ggagcccgcc ggacccaccc ccgtcgccca gccgccgtc    900
gactggaagc ggaccaccgc ctgggccgaa ggcggctact acggacggat cttcctcaac    960
gtcgagggcc gggagccgca ggcaccatc ccggccgcgg agtacgagag cacccgcgac   1020
ctcatcgcct ccgccctgga agcgctgccc gacgaccagg gcagccgat gggcacccgc    1080
gccctgcgcc cggcgagct ctacgagag gtcaacggca tcgcccccga cctcctggtc     1140
tacgtcggca acctgcgctg gcgggccctg gccaccctcg gcatgggcaa gggcctctac    1200
acgacggaga acgacaccgg ccctgaccac gccaaccacg ggacaccgg catcttcgcc    1260
ctcagcgccc ccggcatcac ccccggccgc gcggacggcc tgtcgctgta cgacgtggcc    1320
```
cccaccctgc gggaactgct gggtctcgcg ccgcagggct cccgcggctc cctcctcggc   1380
tga   1383

<210> SEQ ID NO 60
<211> LENGTH: 1536
<212> TYPE: DNA
<213> ORGANISM: Streptomyces lavendulae

<400> SEQUENCE: 60
gtgaaggcga tggaccgggt ggacagagcg gtcgagcggt tcccgatgta catcgacggg     60
caggccgtgc aggcccacga cggcgccgtc ctgcgcacct tcgagccggc cacgcggcgc    120
cacctggccg accttcccag cggcggcgcg gaggacgtcc gccgggcggt gtccgccgcc    180
cggcgggcct tcgacgaggg cccgtggccg cggatggcgc cgggcgagcg ggcgggcctg    240
ctgcgcaagg ccgcacagcg cttgcgtgaa gaagcggagc cgctggccga gttggaggcc    300
cgcgacaacg gctcgacgct gcgcaaggct ctcggggccg atgtgccggg ggccgcggca    360
gccttcgagt ggagcgcgtg gtgggcggag cacgtgcccg aacggcagcc ggaggcgccc    420
ggttcgggtt cctacgtcgt gtggcggccg gtgggggtcg tcgccgcgat cgtgccgtgg    480
aatctgccgc tgctgctggc ggcctggcgc atcgcgcccc ccatcgccgc gggcaacacc    540
tgtgtgatca aaccggcttc gttcgcctcg ctctccacgc tgcgactggt ggagctgctc    600
cacgagtgcg gcctgccgcc gggcgtggtc aacgtggtca cggggccggg cggggtcgcc    660
ggggagcagc tggtgcgctc gcccggcgtc gacctggtgg cgttcaccgg ctcggacgag    720
accggggccg ccgtacggga gggtgccgcc gcggcgggga cgagcgcccg gctgaacctg    780
gggggcaagt cccccaacat cgtgctcgcg gacgccgatc tggaccgggc ggtcaccggc    840
gtcacgtggg gagcgttcct gcacaacggg caggtgtgca tggccggtac ccgcgcggtg    900
gtgcacgccg acgtccacga cgacttcctg cggctgctga gcgaacgggt gggccggctg    960
cgcgtcggtg atccgctgga cccggccacc gacctgggc cgctggtctc gcgcaaccag   1020
gcgcgtacgg ccaggcgctt caccgaactc gggctctccc agggcgcgga gctcgtgtgc   1080
ggcggccggg cgcccgcggc ggacgagctg ccgcccgggc tggacgccgg ggcgtatttc   1140
ctgcccacgg tgctggcgtc ggtcggcgcg gacgacgccg tcgcgcagga ggagatcttc   1200
ggcccggtgc tcgcggtcgt ccgggccggg tccgacgacg acgcggtgcg catcgccaac   1260
ggctcccgct accggctcag cgccggggtg tggtccgccg atcccgcgcg ggcccgcgcg   1320
gtggccgagc ggctgcgcgc ggaccgggta tggatcaacg actaccggct ggtcgacctg   1380
gagctgcccg gcacagccgg gccccgctcc gccgtctggg accggctcac caacgagctg   1440
gacgcctacc gccacaagca cgtggtgcac ggtggcggtg cgggagcggg cggggtgccg   1500
gcgccgccca ctccctacgc gctgctgggc gggtga   1536

<210> SEQ ID NO 61
<211> LENGTH: 1419
<212> TYPE: DNA
<213> ORGANISM: Streptomyces lavendulae

<400> SEQUENCE: 61
gtgaaaccag ccagccactc cgtgacggac acgtccgcgg ccctcggcgc gcggccgcc     60 gaagagctcg cggcgcaggt cgccggatcc gtcctcctgc ccggggacga ggggtacgac    120
gaggagcgct ccggcttcga actgtccgtg gaacaccgcc ccgccctcgt cgtcgtcgcc    180

-continued

```
accggtgccg cggatgtcat cgccgccgtg cgcttcgcca gggcccgggg ccttgggatc      240
gccgtccagg ccaccggtca cgggaagtcc tcggcggcca ccgacgtcct catcagcacc      300
cggcggatga ccggcgtcag ggtcgacccg cgggcccgga ccgcccggat cgaggcgggc      360
gtgcgctggg agcaggtgat ccacgaggcg gcggcgcacg tcttgcacc gctgagcggc       420 tcggcgccgt tcgtcggcgc ggtctcctac ctcctcggcg cgggctcgg gcttctgtcg       480 cggaagtacg ggttcgccgg cgaccatgtc gtctcgctcg acctggtgac ggccgacggg      540
cggtttctcc aggtctccgc cgaggaacac cccgatctct tctggggcgt gcgcggcagc      600 aggggggaacc tcggcatcgt cacctccgtc gaggtcgggc tgttccccgt cacccaggtg     660
tacggcggag ggctgttctt cgacgccggc tccacgcgcg ccgtgctgaa cacctatctc      720
cagtgggcgc cccggatgcc cgaggacatg gcgtcgtcgg tgttcctggc cgcgtatccc     780
gatgccgagg gggtgcccgg accgctgcgc ggccggttcg tcacccacat ccggctggcc      840
tggctgggag accccgagga gggtgagcgc cggttcgccg agctccgggc cgccggcacg     900
gtcgtcatgg atacggtgga cacgctcccg tacacgcggg ccgggatcat ccacaacgat     960
ccgccggccc cggtgtcgag tcacagcaaa acggtcatgt tcgggcagct ggacgagatc     1020
gccgtcgacg agatcctcag gctcgcgggg ccgggcacgg acgcgctgtt cggggtggag    1080
ctgcggcacc tgggcggcgc cctcgcccgg ccgcccggg accgagcgc ggtggggccac      1140 ttcccggagg cggtgttcaa cgcctacgtg ggctcgctgg tcgacccgga caccctggcg     1200
gccgtggacg cggcgcagca ggagttcgtc gacagcatgg ggccgtggac gacgcccggg    1260
gtgtgcctga acttcctcgc gggtcacaac acatcgaggg agacgacccg cagcgcctac    1320
acgccggagg actacgcgcg gctccaggcc ctgaagtcgc agtacgaccc gggcaacgtc     1380
ttccggttca accccaacat cccgcccctg ccggcctga                            1419
```

<210> SEQ ID NO 62
<211> LENGTH: 1188
<212> TYPE: DNA
<213> ORGANISM: Streptomyces lavendulae

<400> SEQUENCE: 62

```
atgacctcag ccgccccgcc cgcctttccc ttccgcccg gccccggcgg cacggtgccg        60
cccgagtacg cgcggctgct caccgatgac ccggtcgccg aggtgcgcct ggcggacggc      120
tcgcgcatct ggctggtgac ccggcacgag gacgtgcgca cggtgctcac cgacggccgc     180
ttcagccgcc atcgcgccgc catgctgccg ggctcgggct tcggccggtc ccagggctcg      240
ggcatcgtgg acctcgaccc gccggagcac ggccggctgc gcggtccggt ggtggccgcg     300
ttcggtgcct cgcgcacggc gcggttcgca ccccgcatcg aggcggccgc cgaggcggcc      360
ctggaccggc tgcccgccgg cagcggcacg gtggacctcg tcgcggcgta caccgcgccc     420
ttcgccggcc gcgtcacagc cgagttcctc gggctgcccg ggaccggtg caggacgtc       480 acctccgacg tcgagctgct gctgcttccg cgcggtgcca ccgagcaggc gctgaaggag     540
gcccgcggca ggctcggcca ggtgctggac gaactgctcg cggcccgcag ggccgagccg     600
ggcgacagcg tcaccgacac gctgctggac gcggaggagc tcaccgacga cgaccggcgc    660
ctgctgctcc acgcctgat catctcgggc ttcatcacca tccgcgacct gctggcccgg     720
cacctcttcg gcgtgctctc ctccccggc ctcgcggccc ggctgcgcga ggaccccctcc    780 gtactgccct ctgccgtaca ggagttgctg cgctactacc cctccagcaa cgacggcctg     840
ctgcgggtcg ccaccgagga cgtggtgctc tccggcaggc gcgtcgccgc cggggacgcc    900
```

```
gtgctgccac tggtctcggc ggcctcccgc gaccccgagg tcttcgccga tccccacgtg    960
ctcgacatcg agcgggtggc cgaccgcggc atcgcgttcg cgccgggca gcacgcctgc   1020 cccgcgaccg ggctggccgt gaccgaactg accgtcggca tcgccgcct gctggcggcc   1080 ttcccccgca tcgccctggc cgtgcctccc gaagaggtcg agcacagctc cgaactcctg   1140
cccctgggcg tccggtcact gccggtggtc cccggcccgc gcaactga              1188
```

<210> SEQ ID NO 63
<211> LENGTH: 1425
<212> TYPE: DNA
<213> ORGANISM: Streptomyces lavendulae

<400> SEQUENCE: 63

```
atgcttcctg agttccaatt gcagtggaat tggctcgacg ccccggccgg cggcggaggc     60
gagctgcaag cgacctgggc ccggctgcgc atcgccgtgg cgccgagac cgtcacactc    120 gtccaggagc ccgggcaggg gaccttccgg gagcacacga ccggctcgct ctaccccctg    180
gccgagtgga tcgccttcaa ctggtggtcg ctggtggccg acgcgcggcc cggcacccag    240
atatcccagc tgcgcttcgc ctaccgccac ggtgtgggcg acaaccgcgg ttcgtggtgg    300
atgcgttcgc gccgtcacat cctgcgcgcc gcctgcgacg gcttccgctg gccggacatg    360
ctcttcgtgc ccgagggccg ggagacccgg atcgtatgga tgccggacat gggccccgac    420
gtacgacccg ggaaccgctt cgcgagccgg ggcaactcct gtgtggagag cgccgcgttc    480
accgccacac tggcctcgtt cgtcgacgcg gtgaccgagc gcctcacgga ccagggcatc    540
accggcaccc cgctccagga ggagtgggcc gccgtccgcg ccaccgacga ggacgaggcc    600
gccttctgcc gcatcgcggc acggctgggc ctggaccccct acgccgaggc cgagccgtac    660
gaggcggaca tcctcaaggc cgccgagcag ttggcggaac cgctcgccag tgacttcttc    720
aacggggtgc ggcctgagcg gatagccgac cagtccagt ggatcgcgcg cgtccgcacc    780
ctgatgggca ccgcgcccgc ggatacccgg ctccctcccg ccttggtgga actgcgcaag    840
gactgcgccg acttgagcga gaagttcttc gctccggggc gactcgacaa ccctggac    900 ctcggctacg aggtggcgca ccgggtgcgc cgtgggcgg tctggacga caccgcgccc    960 ttcgacccgg ccccctgat gggctaccgc accgagcagg tccctatat ggaccggggc   1020 ctggtcgccc tcggcacccg caggggcgcg gacgggccgg tcctggtctc ctcccgcgc   1080 ttcaccgacc gcccgcgccg cttcctccag gcccgcgcgc tgtggcatct gatctgcgac   1140
cccgacgaca ccttcctgat cgcggcggcg cacacccacc gccagcacgt ggcccgcggc   1200
ttcgccctgg aggtcctggc ccccgccaag ggcgtggcga ccctgctggc cgaccccgga   1260
cacctggtgt ccgccgagga cgtcgaggtc atcgccgacg actacggctg cggcaacatc   1320
gtcgtggaac accagctgga caaccgcgtc ctggcgaagg acttcacctg gccgggccac   1380
gcccgcgccg gcgcgccggc cggtgagagg agccggggcg catga                  1425
```

<210> SEQ ID NO 64
<211> LENGTH: 1332
<212> TYPE: DNA
<213> ORGANISM: Streptomyces lavendulae

<400> SEQUENCE: 64

```
gtgacaatcc gccagcgtgt cgtcgtcgtc atcaccgagg gagcggcacc cgagctgctc     60
gaccgctggt gtgcccaggg gctgctgccc ggcttcgccg ccctgcgctc gcagggggct    120
```

-continued

```
tccgggccgc tccacgccga gggcacccc  tacgaaccgc cgggcctgct gagcgtcctg    180
accggccggc gcgccgcgga ccacggcttc tactcctact ggacctgtca cgacccggag    240
tacgcgccgc aggtcctcac ccccgagcac cgccgccacc cactgctgtg gcagcacgag    300
gtgttccagg gcgtcaggtt cgcctcgata ggcctcttcg cacccatcc  cccggagccc    360 ttcgacggtt ccctgatcac ctatccgatg tatgccaccc tccacgcctg ccaccgcgc    420 agcctccagc gcaccctggc gaagaagggc atccgtccgg tccacgacgt gtcgatcttc    480
tggaccgggg aggaccgcga cgagctgctg ccttccctgc tggaggcgga cgtgcagcgc    540
gggcgcgcgg cattggctct gctggaggag tccgatgtcg tgatcgtcaa cctcacgagc    600
atcgaccgct gttcgcacat ctactggcag gagctggagc acggccccga gcacgagcgg    660
gagagcgccg tcttcgccgc ctaccgcacc tgcgaccagg tcatccagga cgccctgcgg    720
gcggccgacg accgcaccag tgtcgtggcc ttctcggaga taggcttcgg gccgctgcgc    780
aactactgtt ccatcaacga cgagatggag caggcgggtt tcctggccac cgccgaggac    840
ggccgcgtcg agtgggccgg cagcgcggcc ttcgaggcgg tgcagggcac gcacggggtg    900
aacatcaacc tgcgcgaccg ctacaagcac ggcctggtcc cggagcgcga ctacgagaag    960
gtccgcaccg acgtcgcggc cgcgctgctg gagcggcgca accccgtac  cggcaggctg    1020 ttcttcgacg cggtgcgccg ccgggaggag gtctatcccg gcgaggccac ccagcacgcc    1080
cccgacctca tcctggagcc ggcggactgg cgctatcttc cgctgggcga ccgcactgg    1140 gcctcgcacg tccaccgcga ctggcagagc ggctggcacc gccgggagtc ctactggtcg    1200
gccgtcggcc ccggcttcac cggtggggcg cggcagaccc gcaccgccgc ccccgtcgat    1260
attcccgcga ccgtatgcgc tctgctcggg cgtgacgtgc cgaacgactg ggacggcgtg    1320
ccgctgtcct ga                                                       1332
```

<210> SEQ ID NO 65
<211> LENGTH: 372
<212> TYPE: DNA
<213> ORGANISM: Streptomyces lavendulae

<400> SEQUENCE: 65

```
atgacaccag aggaactctc cgacttcgcg ctggagctgc cggaggcggt ggacgacgag     60
gcgttcggcc ccggagccgc ggtcttcaag gtggagaaga aggtcttcgc cattctccag    120
gacgcctccg aggaccgccc gccgcaggtc acgctgaagt gcgaaccgga tctggcgctg    180
cacctgcgcg agcagtacgc ggcggtggtg cccggctacc acgtcaacaa gcgccactgg    240
aacacggttg tcctgaacgg cacggttccc gtggaggagc tgcgggagat ggtgagcat    300 tcgtacgatc gcgtggtggc ggggctgccc aaggcggtac gggaacgtct gcgcctcctg    360
cgcaccgtgt ga                                                       372
```

<210> SEQ ID NO 66
<211> LENGTH: 1056
<212> TYPE: DNA
<213> ORGANISM: Streptomyces lavendulae

<400> SEQUENCE: 66

```
atgaccgtgg agcagacccc cgagaatccc gggaccgcgg cccgcgccgc cgcggaagag     60
accgtgaacg acatcctgca aggggcgtgg aaggcccgcg ccatccacgt ggccgtcgaa    120
ctcggcgtcc cggaactgct ccaggagggc ccccgcaccg cgaccgccct cgccgaggcc    180
accggcgccc acgagcagac cctgcgcaga ctgctccgac tgctcgccac ggtgggcgtc    240
```

```
ttcgacgacc tcggccacga cgacctgttc gcccagaacg ccctctccgc cgtcctgctg      300
cccgaccccg cgagcccggt cgccaccgac gcgcgcttcc aggcggcccc ctggcactgg      360
cgggcctggg aacagctcac gcacagcgtc cgcaccggtg aggcgtcctt tccttcgacg      420
tggccaacgg cacctcgttc tggcagctca cccacgaggg accccaaggc gcgcgaactg      480
ttcaaccgcg ccatggggtc ggtctccctc accgaggccg acaggtcgc cgcggcctac       540 gacttctccg gcgccgcgac cgccgtggac atcggcggcg gccgcggcag cctcatggcg      600
gccgtcctcg acgccttccc cggcctgcgc ggaaccctgc tggagcgccc gcccgtcgcc      660
gaggaggccc gtgagctcct caccggccgc ggcctcgcgg accggtgcga gatcctgccc      720
ggcgacttct tcgagaccat ccccgacggc gccgacgtct acctcatcaa gcacgtgctg      780
cacgactggg acgacgacga cgtcgtacgc atcctccgcc ggatcgccac cgccatgaag      840
ccggactccc ggctcctggt catcgacaac ctcatcgacg agcggcccgc cgcatcgacg      900
ctcttcgtcg acctgctgct gctcgtcctc gtcggcggcg ccgaacgctc ggagagcgaa      960
ttcgccgcgc tgctggagaa gtcgggcctg agggtggagc gctcgctgcc ctgcggcgcc     1020
ggcccggtgc gcatcgtcga gatccgcagg gcctga                               1056
```

```
<210> SEQ ID NO 67
<211> LENGTH: 1641
<212> TYPE: DNA
<213> ORGANISM: Streptomyces lavendulae

<400> SEQUENCE: 67
atgacggtgc tgggtctggg tggatccgga catgactggg cctcctgtgc caccgacggc       60
cgacggctgg tggcgatcga cgaggagcgg ctggtccgca gcaagtacgg cctgggagcg      120
gacctcctgg cgggccacag ccggcgcgcc gtcctcgacg ccctcggcac gagtgccgag      180
gccgtggaac acgtggtggc ctgcgagctc gtaccacgcc ccttctacca ctcgttccgc      240
aggcgcgtga cggtcgtcaa ccaccatctc gcccacgcct acagcgcgtt cggggcctcc      300
gggatgaccc gcgccgccgt actggtctgc gacaactccg gcagcctggt gacgggcctg      360
aagtccggcc cagggccgcg cgaggcggag acgatcagct gctacaccgc cgacgcctcc      420
gggctgcgcc tggtcaaccg ggtcgccggg acacacgccg tggacgcctc ctccgagagc      480
gcctactacc agcccggcga gaccgacaat tccctcggcc acttctaccg ctcggccagc      540
ctcgcactcg gcctcgccta ctccggtccc aagaccgct accccgtcag cgaggacggc       600
aagaccatgg gcctcgcgcc ctacggcgac gaccgcttcg tcgacgaggt cgcggagctg      660
gtcaccctgc tgcccgaggg cggcgtgcag atctcggcga gcaaggtgaa ccacctcttc      720
gaacgcctcg tggaatcggg tgagttcgag gaccgggcgg ccttggccta cgccgcccag      780
gagacgctgg aacgcgccct gctgcactgc gcccgcgacc tgcaccgccg caccggcctg      840
acggacctgt gcatcgccgg cggcgtcggc ctcaacagcg tcgccaacgg ccggatcctg      900
cgcgagaccc cttcgagcg gtcttcgtc gtcccggccg cgggcgacaa cgggatcagc       960
ctcggctgcg cctactacgg cctccacgag ctggagggc gcgcgccgtc ggagctcccc     1020
gccctcgaca ccgcctacct cgggcccgac taccccgccg agcgcgtcga cgcggcgctg     1080
gccggctcgg gcttcaccgt ggagaccccc gacgacctgc ccggcagggt cgccggcctg     1140
ctcgccgaag ggaagatcat cggctggttc gacggccgct ccgaattcgg cccgcgcgca     1200
ctgggacacc gcagcatcct cgccgcaccc ttccccgcct ccgtgcggga ccacctcaac     1260
```

-continued

```
gacaacgtca aacaccgcga gtggttccgc ccctacgccc ccatcgtccg cgaggaccgg    1320
gcggcggact acttcgacct cgtccagccc tccccgttca tgctggtcgt cgcgcgcgtg    1380
acccggcagg acgccatccc cgccgccacc cacgtggacg caccgcccg gctccagacg     1440 ctgaacgccg cacagaaccc gaaggtctac gagctgctcg gcaggttcga ggcgctcacc    1500
ggctgcgccg tgctgctcaa cacctccttc aacgtcgccg ccagcccat cgtcgagacc     1560 ccggaggacg ccgtcgaggc gttcgcgggc atgcgcctgg accacctcgt cgtgggggac    1620
cggctggcga ccaagccctg a                                              1641
```

<210> SEQ ID NO 68
<211> LENGTH: 1707
<212> TYPE: DNA
<213> ORGANISM: Streptomyces lavendulae

<400> SEQUENCE: 68

```
gtggacgtcc ccgtgctcgt ggtcggagga ggaccgacgg gcttggcgat ggcgctcttc     60
ctcgcacgcc acggcgtcgg ctgcctgctg gtcgaacggc ggacgaccac ctcgcccgtc    120
ccgcgcgcca cccacgtcag ccgccgctcc atggaactct ccgcgaggc gggcctggag     180 gaggagatcc gccgggccgg gttcgaggtc gtgcgcgagg acgacccacg gctgcggacc    240
cggcccgaac gccacctgcc ccgggtggtc ctgcaagccg cctcgctcgc cggccccggc    300
ccggtggggg tcctggagac cggtgacgag gaactggccg tacccggccc ctgcgcaccc    360
ttctggtgcg gccaggaccg gatggaaccc ctgctcgcca aggccgcggc gcgccacggc    420
gccgatgtgc gcttcggcca cgaactgacc ggcctgtggc cgggggagga cagcacacgg    480 gccccgcgtcc gggcagcggg aacgggacgg acctacaccg tcgacgcccg cttcgtcatc    540
gccgccgacg gggcgcgcgg cgagatcgcc gagcgcgtgg gcatcgcgcg ggagggcctg    600
ggcacggtcc ccaccgggt gagcatcctc ttccgcgccg acccggggcg ctgggcccgc     660
gaccggcggt tcttcatgtg catgatccag aacccggggt tcgacggggc ggtgatggag    720
ctcaacaccc cggccgctg gtgcgccgcg gtggactacg acccgcccg cgccgaaccc      780 gacggcacct actccgcacg cacctgcctc gacctggtcc gggccgccgt cggtgacgac    840
cggagcgacg cggcggtcga caccgtcttc cactggaagg cccggcaccg catagcggcc    900
gcctaccgca gtggggcggt gttcctcatc ggcgacgccg cccacctcca cccgccctcc    960
ggcggctacg gatccaacgt cggcttccag gacgcgcaca acctcgcctg gaagatcgcc   1020
gccgtgctcg gcggctgggc cggaccgcgg ctgctggaca cctacgacga agagcgccgc   1080
cccgtgggaa aggcgacggc ggagcagtcg atgctcctcg acggcgtgcc accggaacca   1140 ctgggggaa gcgtcgtccg ctgcgatccc cgcaccctga tcatgggata ccgctaccac   1200
tccgccgccg tcctcggccc cccgcacggc cccgccttcc ccgcggcctt cacccctgcgc   1260 ggagacccgg gcacccggct gccgcacgta tggctgcgta cggacgcggg ggaacgcgtc   1320
tccacgctcg acctgtgcca cgggcacttc gtcctgctct ccgccgaccc ggtctgggcg   1380
gcggccgcgg cgcgctcggc gaaggagacg ggcgtaccgc tgcggggcca ccacctggcg   1440
gccaccggaa gcgaactcgc cgaccctcc ggcgagttcc cgcggagctg cgggaccggg    1500
cccgcggggg ccgtgctcgt acggccggac ggcatggtcg cctggcgcac ggcccgcgcc   1560
gtgcccccgg acccggacag cgcgcaggac ctggtcacgg cagcggtgag acgtgtcctc   1620
gcactgccgg agcgcgcggc gccaccggtg ctcggtccgc cgcggttgtc acgcggttcc   1680
tatcggcgag tcgggagcga cgggtga                                      1707
```

<210> SEQ ID NO 69
<211> LENGTH: 483
<212> TYPE: DNA
<213> ORGANISM: Streptomyces lavendulae

<400> SEQUENCE: 69

```
gtgaagcctc attccttctg cacgtgctgg ccgggcgcca ccgtatggct gacgggccca      60
ccgggcgcgg gcaagacgac gatcgcccgc gcactggcgg agcggctgcg cgaacggggc     120
cggcgcgtgg aggtgctcga cggcgacgcg acccgcgcgc tcctgaccgc gggctcctcg     180
tgggaggacc gtggcaccgg cctccagcgg gtcggcctga tggccgaggt cctggcgcgc     240
aacggcatcg tcgtcctcgt cccggtgacc gcggcccgcg cggacagccg cgaagccgta     300
cgcagacgcc acgagcggtc cggcaccgcg cacctggaag tgcgggtggt ccgggacgca     360
gtgcctccga gcgggctccc ccgcgccgcc ggcccagatc tgcggatcgc ggcgcacgag     420
cagagcgccg aggagtcggc gcgggcactg caccggctcc tggcggagag ggagctggcg     480
tga                                                                   483
```

<210> SEQ ID NO 70
<211> LENGTH: 960
<212> TYPE: DNA
<213> ORGANISM: Streptomyces lavendulae

<400> SEQUENCE: 70

```
gtgaaccccg ggcgcggtgg agcgtacgcc gcggggcgcg acgggacccg cgggacgcga      60
cgccctcacg gtctgtcgca cctggatctg ctggagtcgg agtcggtcca catcttccgt     120
gaggtggcgg gcgagttcga gcggccggtg atcctcttct ccggcggcaa ggactcgatc     180
gtcatgctgc acctggcgct gaagtccttc gctcccgcac ccgtgccgtt cgcgctgctg     240
cacgtggaca ccggccacaa cttccccgag gtgatcgcct accgggaccg cgtcgtggcg     300
gcgctcggtc tgcggctgga agtggcctcc gtgcaggact tcatcgacaa cggcaccttg     360
cgcgaacgcc cggacggcac ccgcaatccg ctgcagacgg tgccactgct ggacgcgatc     420
gggcgccacc gcttcgacgc cgtcttcggc ggcggccgcc gcgacgagga gaaggcccgc     480
gcgaaggagc gggtgttctc cctgcgcgac gagttcggcg gctgggaccc cgccgccag     540
cgccccgaac tgtggcggct ctacaacggc cgccacgcac ccggcgagca cgtccgcgtc     600
ttccccctct ccaactggac cgagctcgac gtgtggcagt acgtcgcccg cgaggagatc     660
gaactcccca ccatctacta cgcccacgag cgcgaggtct ccgccgcgcg cggcatgtgg     720
ctggcaccgg gggagtgggg cggccacgc gagggggaag cggtggagaa cgacgggtg     780
cgctaccgca cggtggggga catgtcctgc accggcgcgg tggactcggc ggcggccacc     840
gtggccgacg tcgtcgccga gatcgccacg tcccgcctca cggaacgggg cgcgacccgg     900
gccgacgaca agctgtcgga agccgcgatg gaggaccgca agcgcgaggg gtatttctag     960
```

<210> SEQ ID NO 71
<211> LENGTH: 492
<212> TYPE: DNA
<213> ORGANISM: Streptomyces lavendulae

<400> SEQUENCE: 71

```
gtggggcagg acagccggcc gcggtggctc accgacgagg aacaacgcgt gtggcgcggc      60
tatctgcggg ccaccaggct ggtggaggac cacctggacc gccgcctcca gcgggaagcg     120
```

-continued

```
gacatgccgc acctctatta cggtcttctc gtccagctct ccgaggcccc gcgccggggg       180
atccggatga ccgaccttgc ccgcaacgcg aagatcaccc gcccgcggct ctcgcacgcg       240
atcacccgcc tggagaagct cggctgggtg cgccgggaat cgtgccacgg cgacaggcgc       300
ggccagaacg ccgtcctcac ggaagagggc gcgcgaggttc tggagaagtc ggcgccgggc      360
catgtcgccg ctgtgcgcgc ggccgtcttc gacagcctca ccccggaaca ggtcgggcaa      420
ctgggccgga tctgccaggc gatagagaag gggctggacc gggaaggcgc ggacctgccg       480
tggctgcgct ga                                                          492
```

<210> SEQ ID NO 72
<211> LENGTH: 1242
<212> TYPE: DNA
<213> ORGANISM: Streptomyces lavendulae

<400> SEQUENCE: 72

```
gtggaacgac acgacggggc accgggctgg ggcttcaccc atacccagta cagcgcggac       60
cacggtgaac gcggcgccac ccgcaggccc ggggccctgc tctccgcgcg gcccctgccg      120
cagaaccagc acatcatggg ctggggcgcg gagaatcccc aaccggcgcc cggacgctac      180
gacttcgagg tcctcgacga gcgcgtcgcc ctgatgcgcg cgacggggc cacgcccgtc      240 ctgaccctgt gtgccgcccc cgactggatg aagggcggcc ggcccggccg caccgactgg      300
tcgcgactgg agaccgcccc cgaccccccgg cactacgcgg acttcgcccg gctcgcgggc     360
gtgatcgccc aacgctaccc ggacatcagg cacttcctcg tgtggaacga gctgaagggc      420
ttctacgacg aggacaggcg gcgctgggat tatgagggat acacccggct gtacaacctc      480
gtccacgccc agctgaagcg gcggaacccc cgcaatctgg tgggcggccc ctatgcggtg      540
gtcgaccacg acccgcccgc cgaggacgcg gcggaccgct cgcgcgaact gcgcggtccc      600
tggggcgagc tggaccagcg ctccgccgac gtcatccgct attggaacgc ccacaaggcg      660
ggcgcggact tcgtcgtcgt cgacgggtcc agctacaccc gcgagggcca ccgggcgatt      720
ccggacgagt tcgccgccac cgagaagttc gccgacgtca cccgctgggt caggagcgtg      780
accggactcc cggtgtggtg ggccgagtgg tacgtcgagc cgcccgccga ggacgaccgg      840
ccgggcggcc gggacggctg gggcgagggg caccgcaccg ccgtgcaggc caccgcgatg      900
atgcggctgg cggagagcgg cgcgtcggcc gccttctact ggaacccgca gcggaccggg      960
aaggcgtgcc ccggctgcct gtggcggagc acccacttgc gcgacggggg aggggagttg     1020
cccatggcgg gtctcctgag ccggttcgct cgcgaattcc ctccgggcac cgccttccgg     1080
ccggtcgccc tcacctgcgg gagcggtgac agggtcgagg ccctcgccga cgaggccgcc     1140
gtgctcgtcg tcaacaccga gtgccggccg gtggccgcca gggtggacgg gcaggcgctg     1200
tccctcgcgc cgtacgaggt gcgctggctg acccgcccgt aa                        1242
```

<210> SEQ ID NO 73
<211> LENGTH: 816
<212> TYPE: DNA
<213> ORGANISM: Streptomyces lavendulae

<400> SEQUENCE: 73

```
atgacgcgaa ggcgcccaac gggcccgatt caccgtcggc gggcgtcact caccctttcc       60
cccacgggag ccgccatgag aagaaatcgc atcgccgccc tgctgccggc cgctctggca      120
ctggtcggca tatccgtcct cgcccccgcc accacgcgca gcgcggccgc accgcacggc      180
ggcacctcgc aggccgccgc attccccgtg agcgaggccc agttcaagca gatgttcccg      240
```

| | |
|---|---|
| aagcggaacg cgttctatac gtacaagggc ctggtcgccg cgctcaaggc gtacccgggc | 300 |
| ttcgcgggca ccggcagcgc cgaggtccgg aagcaggagg ccgccgcctt cctcgccaac | 360 |
| gtcgcccacg agaccggcgg actggtctat gtcgtggagc agaacaccgc caactacccc | 420 |
| cactactgcg accggagccg gcccgacggc tgtccggcag gccaggccgc ctactacgt | 480 |
| cgcggcccgc tccagatcag ctggaacttc aactacaagg cggcgggtga cgccctcggc | 540 |
| atcgacctgc tccacaaccc ctcgctggtg cagaaggacg cggccgtctc ctggaagacc | 600 |
| ggcctgtggt actggaacac ccagcgcggc cccggcacca tgaccccgca cgaggccatg | 660 |
| gtcaaccacc gcggcttcgg gcagaccatc cgcagcatca cggcgccct ggagtgcgac | 720 |
| ggccacaacc ccgcccaggt ccagagccgc gtcgcgaact accagcgatt caccaagatc | 780 |
| ctcggcgtgg cgccgggcgg caatctctcc tgctga | 816 |

<210> SEQ ID NO 74
<211> LENGTH: 12249
<212> TYPE: DNA
<213> ORGANISM: Streptomyces lavendulae

<400> SEQUENCE: 74

| | |
|---|---|
| ggatcccgat cgtctcggac atgaccggcg accttctcgg cgcgcgggag gcccaggacc | 60 |
| ccgcctactg ggtgtcccac atccgccgcg cggtgcgctt ccacgaccag atccgccgtc | 120 |
| tgcagcgcta cggggccggg gccttcgtcg aggtcggccc ggacacggtg ctcagctcgg | 180 |
| ccggccaggc gtgcctgacg gaccaggcgg gcaggagcgc gcccgtcctg gtgtccctcg | 240 |
| cgcacgccga gcgcgcggag gtgcccgcgc tcctgaccgc tctggccacc ctgcacaccc | 300 |
| gtggcgtggc cgtggactgg cgggcgtggt tcggcgacgg gccgcgcgcg gccggcctgc | 360 |
| ccacatacgc gttccagaag cagcactact ggccgtcggg ccccaccggt tggcggtccg | 420 |
| ggcccgcccc cgtaccctg ccccaggccg gaacggagga cgccgaaagg cccggtcgcg | 480 |
| ccgcggagtg gcgggcgctg ccgcccggtg agcggtacga cgcgctgctg cggatggtgc | 540 |
| gcggcgaagc cgccgccgtg atgggcacg ccgggccgga ggcggtggag ccggagcgcg | 600 |
| gcttcctcga ccacggcttc gactcggtga tggccgtgaa gctgcgcgac cgtctcgtgg | 660 |
| ccgggacggg gcgggagctg ccgacgaccc tgctgttcga ccaccccacg cccgcggccg | 720 |
| tcgccgacta cctgctggcg gggacgggcg aggccgagac ggcgccgtcc gtgtccctgt | 780 |
| cggaccagct cgaccgcctg gaggccgacc tcgcgcggct gccggccgac gaccggcagc | 840 |
| gcgcccgcgt cgccgagcgg ctcaagggcc tgctcgcggt ccacgcgccg gaccggggcg | 900 |
| ccgggagcga ggacgcgccg gaccaggacg cgctggacac ggcgaccgac gacgagatgt | 960 |
| tcgagctgat cgagaaggaa ctccgccgtg gatgagacca acgagaccaa actccgcgag | 1020 |
| tacctgcggc tggtcacggc cgatctgcgc cgaacccgca gcagttggga ggaggccgag | 1080 |
| gacgcggccc gcgagcccgt cgcgatcgtg ggcatggcgt gccgcttccc cggggacgtg | 1140 |
| gcatcgccgc acgacctgtg gcagctggtc gccgagggcc gggacgccgt caccgagttc | 1200 |
| cccgccgacc ggggctggga cgtcgacgcc gtctacgacc ccgagccggg cacccccggc | 1260 |
| aggacgtacg cgcgccacgg cggcttcctc aaggacgccg ccggattcga cgccgccttc | 1320 |
| ttcggcatca cgccgcgcga ggcgctcgcc atggacccgc agcagcgcat gatcatggag | 1380 |
| gtctcctggg aggcgttcga gcaggcgggc ctcgacgcga ccaccctgcg gggcgaggac | 1440 |
| gtcggcgtct tcgtcggctc caacagcaac gactacctga tcaacgtgct cgacgcgcgg | 1500 |

-continued

```
gacgtcgccg agggcttcat cgggaccggc aactccgcca gcatcctctc cggccgcgtc    1560
gcctacacct tcggcttcga gggcccggcc gtgtccgtcg acaccgcctg ctcctcctcg    1620
ctggtcgcgc tgcacctggc cgcgcagtcc ctgcggcagg gggagtgctc cctggcgctg    1680
gcgggcggcg cgacggtgat ggccacgccg accgccttca tcgagttcag ccgccagcgg    1740
ggcctggccc ccgacggccg ctgcaagtcc ttctcggcga ccgccgacgg caccacctgg    1800
tccgagggcg cggccgtgct gctgctggcc cggctctcgg acgcccgccg cctgggctac    1860
cccgtgcacg cggtcatccg gggcagcgcc gtcaaccagg acggcgcgag cgcgggcctg    1920
accgcgccca acggaccggc gcaacagcgg gtgatccggc aggcactggc caacgcacgg    1980
ctgacggccg acagcgtcga cgcggtcgag gcacacggca ccggcacccc gctgggcgac    2040
ccgatcgagg cccaggccct cctcgccacc tacgggcggg cccgcggcga gggcaggccg    2100
ctgtggctgg gctcgctgaa gtcgaacctg ggccacaccc agtccgcggc cggcgcgggc    2160
ggcgtcatca agatggtgat ggccatgcgg cacgggacgc tgccccgcac gctgcacctc    2220
acggagccca ccccgcgcgt cgactggtcc gccggtgacg tacggctgct gaccgaggcc    2280
caggactggc cggacaccgg acagccgcgc cgtgcgccg tctcgtcctt cggcgtcagc    2340
ggcaccaacg cccatgtgat cctggagggc ccgcccgccg aggaggcacc ggacgcgccg    2400
ctgccggacg tctcctcgca gccgcgggc ccgctgccgt gggtcgtctc cggccgcagc    2460
gaggcggccg tccgagcgca ggccgagcgc ctggcggccc acctgaccgc gcgcccgcac    2520
ctggcaccgc ccgacgtggc caccgcgctg ccaccacgc gggcggcctt cgaccaccgg    2580
gccgccgtcg tcggccggga ccgtgaggaa ctgctcgccg gcctcgcggc cctggccacc    2640
ggaacccgcg cgcccggcct ggtcaccggc cggacccgc cgtccggcgg caaggccgcc    2700
ttcctcttca ccggacaggg cagccagcag cccggcatgg gccgcgaact ggcggctcac    2760
agcaccgtgt tcgccgacgc cctggacgag gtctgcgccc agctcgaccg gcacctcgac    2820
cggccgctgc gcgaggtgct gttcgccgcg gacggcacgc ccgaggccgc cctgctcgac    2880
acgacggcct acacccagcc cgcgctgttc gccgtcgagg tcgcgctgct gcggctgctg    2940
gaggactggg gcttgcggcc cggcatggtc gcgggccact cggtcggcga actgaccgcc    3000
gcctacgccg ccgggggtctg gtcgctcgcc gacgcctgcg ccctggtcgc cgcccgcggc    3060
cggctgaccc aggcactgcc cgcgggcggc gccatggtcg ccgtgcaggc gaccgaggac    3120
gaggtgcgcg cccaactcgc cgacggccgc cccggcgtgg acatcgccgc cgtcaacgga    3180
ccggaagcgg tggtgctgtc cggcgacgag gccgccgtca cggacctggc gcgcgagtgg    3240
gccgcccgcg gccgggagac caggaggctg cgggtcagcc acgccttcca ctccgcccac    3300
ctggacgcca tgaccgaggc gttcgccgag gtcgcacgag gggtgtccta cagcgcgccg    3360
tccctcccgg tggtctccac gctcaccggg gcccccgtca ccgacgagct ccgcaggccg    3420
gaacactggg tgcggcacgt ccgggagacg gtgcgcttcc acgacgcggt ccgcgccctg    3480
cgcgaccgcg gggccaccgc gttcctggag gtcgggcccg gcggcgtgct gacggccgcg    3540
gcacgccgat gcctgcccga cgccgccccc gagacgttcg tccccgtgct gcggcgccgc    3600
aggcccgaac ccgagtccgt gctgacggcc gtcgcgcagg cccacacgat cggcctctcg    3660
ccggcgtggg accgcctgct gcccaaggcc cggacgcgcg tggacctgcc cacgtacgcc    3720
ttccagcgcg ccactactg gctggcgggc atggccggag cgggcaccgc gcggccggtg    3780
cggccggaag tgcaggagcc caccgccccc tccggtacgc cgccgctgtc cgacggctg    3840
gccgacgcgt cggaggagga gcgcggccac ctgctgctga cgctggtacg cgagcagtcg    3900
```

```
gccaccgtga tgggcggcgt cgaccccgcg caggtcgaac ccgaccgccc cttcctggag    3960
ctcggcttcg actccctgat gggcgtcgag ctgcgcaccg cgctcgccgc cgactgcgca    4020
ctgcccctgc cgcccggcct gatcttcgac cacccccacgc ccgccgccct ggccgccttc    4080
ctcggcgagc agctcgcggc ggcggcctcc ggcaccccca cggcggcggc accctcgccg    4140
tactccctgg aggcgctgta ccgcaacgcc aacaccctcg accggcccga ggacgcgctc    4200
gccctcacca aggccgcctc ccggctgcgc ccggtcttcg ccagcgtggc cgaggcgggg    4260
caggacccgg tcacggtgga gctggcacag gccaccggcc ttccgggcct gatctgctgc    4320
ccggcacccg tgccgctgta cggggcacag cagtacagcc ggctcgcagc cgccttccgc    4380
ggcacgcgcg gagtctcggc cctgctcgcc cccggcttct ccccgggcga actgctgccc    4440
gccgacttcg aggtgatgca ggacttcctc gccgaggggg tccggcggca gaccgacggc    4500
gcgcccttcg tcctcctggg ccactcctcc ggggctggt tcgcctacag cctggcggcc    4560
cacctggcgc gcaccgggcc gcgcccggag gccgtcgtgc tgctggacac ctatcagctg    4620
cacgacccgc cgctgcaccg catgcagcgc gaactcgccc agggcgtcct ggaccgcgag    4680
gaggacttcg gggcgatgac ggacgtacgg ctgagtgcca tgggcaaata cttcgacttc    4740
ttcaccgact gggtggccga ggacgccggt gtcccgacgc tgctgctgcg ggcctccgag    4800
cctctgggcg aggtcgtcga gggccaggag tggcgctcca cctggccgtt cgacagcacg    4860
gtcctcgaca cggaaggcga ccacttcgcc atggtcaacg accacgcgcc gcggacggcc    4920
caggccgtga acgctggct gtcgggcctc accggcggaa ggggctgagc gccggtggag    4980
acacgcaacg ccgaacggcc gtggatacgc agcttccacc ccgctcccca ggcccctgtg    5040
cggctgctgt gcctgccgca cgccggggc tccgcgagcg cctacttcgc gctgtcgagg    5100
gaactggcgc cccgggtgga ggtgctcgcc gtgcagtacc ccgggcggca ggaccggcgc    5160
gacgagccgc tgctggactc gatcgaggcc ctgcgcgacg gggtcgccga ggccctgacg    5220
ccctggctgg accggccggt cgccctcttc ggccacagca tgggcgccgt ggtggcctac    5280
gagctggcgc ggctgctgtg ccaggacgcg ggcgtgccgc tcacccacct cttcgtctcc    5340
ggacgccggg gatccgaccg aagtctccgt ccttgccgcc gtgttccgga attccaccgtg    5400 acaccgccgc gcggctcttc ttccgaagtc ctccagatcc ggcacgagtt tgtatccgaa    5460
cggggttctg cgtgcgaaat actctcttcg aattgggtga catacccccg atcggcaccg    5520
tacccgagca gatgtacgcc tcggtgatcc gacgggagcc ctacgacag ccccaccagg    5580 cgttccgcag cgaggtcgtg gacgtgccga aggtggggcc cggtcaggcg ctggtcctcg    5640
tgatggccgc gggcatcaac tacaacaacg tctgggcctc cctggggcag ccggtcgacg    5700
tgatctccgc gcggcagaag cagggccaca gcgaggactt ccacatcggc gggtccgagg    5760
gctccggcgt ggtgtgggcg gtgggggagg gcgtcaccca gtcgcggtg ggcgacgaag    5820 tgatcctctc cggctgccag tggacggaga cggccgccga catccggctc ggcgccgacc    5880
ccatgaccct cggctcgcag tcggtgtggg gatacgaggg caactacggc tccttcgccc    5940
agttcgccct cgtcgacgac tatcagtgcc accccaagcc gcccggcctg acctgggagg    6000
aagccgcctg cttcctgctc accggggcca ccgcctaccg ccagctgtgc ggctggcagc    6060
cgcacgacgt gcggccgggc gacccggtcc tcatctgggg cggggccggc gggctcggct    6120
ccatggccat ccagatcacc cgggcgcggg cggcatccc cgtcgccgtg gtctccgacg    6180
aggagcgggc ccgctactgc cgggagctcg gcgcccaggg caccatcaac cgcctggact    6240
```

-continued

```
tcgaccactg gggacggctg cccgacatcg gcgaccacga ggcgatgggc cgctggaccg   6300
agggtgtacg ggccttcggc cggcgcttct gggaggtgct gggcgagcgc aggtccccgc   6360
gcatcgtcct ggagcacagc ggccaggcca ccatccccac ctcgatgtac ctgtgcgaca   6420
acgcgggcat ggtcgtcatc tgcggcggca ccaccggcta caacgccgac atcgacctgc   6480
gcttcctgtg gatgcgtcag aagcgcttgc agggctcgca cttcgccaac ctgcggcagt   6540
gccgcgacgt catccacatg gtcgcgaacg gccagctcga cccgtgcctg tcgtggaccg   6600
gcggcttcga cgacatcggc aaggcacacc agctgatgca cgacaaccag cacccccagg   6660
gcaaccaggc cgtcctggtc aacgcgccgc ggaccggcct gaccaccttc gcctgaacca   6720 ccgcccggt gttccgacgt cttcccccca cacttaccga ccaaggagag atcaccatgg    6780
acaagctcga catcctctgg agcgagcgcg agatccgtgc cgtgctgcag cgctactgcc   6840
gcgggctcga ccgcctcgac gaggaactgg tcaagtccgc ctaccacgag gacgcgcacg   6900
acgaccgcgg cgtcatccgc ggcaacgcac acgacttcgt caagcagatc gtcccgctcc   6960
tgcgcgacgc ctacaccggc accctgcaca ccctgcacgg cagcacgatc gagatcgacg   7020
gggatgccgc gggcgtggag tcctactgca ccgcctacca ctaccgcgag agcgacggca   7080
tcaagcgggt ggagcagttc gccgggcgct acgtcgaccg cttcgagcgg cgcgacggcg   7140
tctggaagat cgcccgccgg ctcgtgctga acgacttcag cctcgcccag gaggtgccgc   7200
tcgaccccgc cgaggcccag gccggcttca acccctccca ccgcgacctc accgacgcca   7260
gctaccaggt gctgccgctg cgcggcccgg acgcccccac cctctgagcc gtccggccgc   7320
cccaactcgc cccacctcac caggagtcac caccgtgtcc gacaccgagc agcacgcgcc   7380
cacgctgccg cggcagcgca cctgcccctt ctcgccgccg cccgagctcg aggagctgcg   7440
gcgcaccgat cccatcagca ggatgcggtt cgccgacgac tccccgggat ggctgctgac   7500
ccgccacgcc gacgtccgcg ccgcgctggc cgaccccggc gtcagctcgc accccggcaa   7560
ggcaccccag ccctggcgca acctcgcccc cgagatgcgc gccgagcact acctgccggg   7620
cttcctgatc ttcatggacc cgccggacca caccgctac cgccgcctgc tcaccaagtg    7680
gttcaccatg cgggccatcc gcaagctcga acccaggatc gagcagatcg tcaccgagac   7740
cctcgacgcc atggaggccc agggcggcac cgtcgacctg gtgcagtcct cgcgctgcc    7800 gatcccgctg ctggtcatct gcgagctgat gggcatccgc tacgaggagc gcgaggagtt   7860
catggacatg gtcctgcgac tccaggccct ggacgccacg cccgaggaac tcggggccct   7920
cggcgccagg atgaacgagt tcatgatgaa gctcgccgcc gccaagcgcg cgaaccccgg   7980
cgacgacctg ctcagccacc tcgcccacga ccccgacgcc gacccggcgc tcacggatct   8040
ggagatcgcc ggcatcggcg tgctgatgct catcgcgggg cacgagacct cggccaacat   8100
gctgggcgtc ggcaccctaca ccctgctgga aacgccgac cagtgggccc tgctccgtga    8160
cgacatcagc ctgatcgacc gggccgtcga ggagctgctg cgccaccaga ccatcgtcca   8220
gcagggcctg ccgcgcggcg tcacccggga catgagatc gccgggcacc aggtgaagac     8280
cggggagtcc ctgctggcct cgctgcccgc cgccaaccgc gaccccgccg tcttccccga   8340
ccccgaccgc ctcgacatca cgcgcagca caacccgcac ctcgccttcg ccacggcat     8400 ccacctctgc ctgggcatgg agctcgcccg ggtggagatg cgccaggcgt ggcgcggcct   8460
cgtcacgcgc ttccccggcc tgcgcatggc cgccgcgccc gaggacatcc gctggcgcga   8520
cgaccagatc gtctacggcg tgtacaacct cccggtgacc tgggacgagg ccaagtgacc   8580
ggccccgagg ccgcggtgcg cgggtgcccc ttcggcgccg gcgaggcgcc cgcgtaccc    8640
```

-continued

```
ttccacgccc ccgaccggct ggagcccgac ccgtactggg agccgctgcg ccgcgagcgg      8700
ccgctgcaac gcgtcacgct gccgtacggc ggcgaggcgt ggctcgccac ccgctatcag      8760
gacgtgcgcg cggtcttcgc cgaccgcagg ttctcccggc agctcgccgt cgcgcccggc      8820
gctccgcgct tcctcccgca ccagccgccg ccggacgccg tcctgagcgt cgagggcccc      8880
gaccacgcgc ggctgcgccg gctggtcggg aaggtcttca cgccgcgccg cgtggaggac      8940
atgcgtccgc tcatccagcg caccgccgac ggactcctcg acgcgatgga ggagatgggg      9000
ccgcccgcgc acctggtcga ggacttctcc ctgcccttcg ccgtgtccat gatctgcgag      9060
ctgctcggcg tgccgcccga ggaccgcaag cggttctgcg tctggtcgga cgcgctgctg      9120
acgaccaccg cgcacacccc cgcccaggtg cgcgactaca tgatgcagat gcacgactac      9180
ctcggcgggc tcgtcgcgca gcgccgggtg cggcccaccg cggacctgat cggctccctc      9240
gtgaccgcgc gcgacgagga ggacaagctc accgagggca gctggtgcg gctggccgag      9300 gccatcctca tcgccggcta cgagacctcg gcgagccaga tccccaactt cctctacgtc      9360
ctcttccgcc acccgcagct gctggagcgg atcaggaacg accacgacct catccccgac      9420
gccgtcgagg aactgctgcg cttcgtgccc atcggcaccg tggacggctt tccccgtacg      9480
gccaccgagg acgtcgagct cggggggagtc ctggtcaggg ccggggagac ggtcgtgccg      9540
tcgatgggcg ccgccaaccg cgaccccgag ctgttcacgg accccgacga gctggacctc      9600
gcgcggcggc cgaatccgca cctgggcttc ggcgcgggac cgcaccactg cctgggcgcc      9660
caactggccc gggtggagct ccagatcacg ctcacgacgc tgttccgcag ataccccgc      9720 ctgcggctgg ccgtgccgga ggagagcctc tcgtggaagg aggggctgat ggtccgcggc      9780
atgcacacca tgccggtcac ctggtgagga caccggcgtc ctcctgacct tcccggcgtt      9840
ctcacgccgt cccggcagcc ttccttccga cacgagcgca cagagggtga agcgaccgca      9900
atgagcacca tcgacgaatg ggaacacagc acgaaggagg cgggcatgga ccccgcggcc      9960
ctcagacgcc tgaccgatgt ggtgcgggcg aggggcggcg cggcgcagct gtgcgtcatg      10020
cggcggggca ccgtggtcct ggaccgctcg ttcggctgct cctccgactc cctcttcctc      10080
gtctacgcgg ccaccaagcc cgtcgccgcc ctcgccgtgc acgcgctcgc cgagcggggc      10140
ctgatcgggc tggaccggcc ggtggccgaa tactggccgc agttcgcccg gcacggcaag      10200
ggtgacgtga ccgtccgtca tgtcctccag caccgggccg gggtgccggt cggccgggc      10260 atcgtgcgca cgatgcgcac cgccggcgac tgggagcgct ccgtgcgcga ccttgagcag      10320
tcccggccca gtggcccgg cggcgaggtc gccgcctacc acttcatgag tttcggattc      10380
attctcggcg aactggtgca gcgcgtcacc gggcggtcgt tccagatttt cgtgacttcc      10440
gagctcttcg ccccacttgg gctgaatgat ttgcacatgg gattgcccgg cagtgcctgg      10500
ccccggcatg tgcccgcgcg ggccgcccac ccctccgaat ggcccaatca gtggatgagc      10560
aaccgccgcg ctaccgcca ggccgtcatt ccgtccgccg gtctttccgg aaccgccgca      10620
caaatgcccg gctttacca gatgcttatg gagggcggct cgctcgacgg catccgcgtg      10680
ctgcggcccg aaactgtgga ggaagccaga aaaccgtcca atgacggcgg aatcgacgct      10740
tccctcaagc gtccggtccg ctggtccac ggattcatgc tcgtggtcc gggcccggac      10800 ccgcgggggc tgtccaatgt gctgggccgc acgagcgacc cgagcgcctt cgggcacgcg      10860
ggcaccacgt ccagcgtcgt gtgggccgac cccacgcgcg agctggtcct cgcctacctc      10920
tccaacatcc agcccgagtt cggagcgggt atcgagcggc tccgcgaggt cagtgacctc      10980
```

-continued

```
gcgctcggtg cctgcgaggc aggctgaccc gagccgtgcc gccacggccc ggcgcccgcc    11040
cgatccgatc gggtccggtg ggggccggcc gggtccgggc ggggacgcac ttcccccggc    11100
gtccccgccc gggcccccggt gcgaaccggg cgcaaaggcg gccgatcgcc cggcgcggcc   11160
ggatgccccc gaacggtgtg aaacgttctt atcagcctct gaccagcacc gagtgatcta    11220
ctgcacagcc cgaggccgcg attccggcag tatcttgatc ttgacggggc accaatgcga    11280
gcgggctatt cgccgcggtt ttccctgacg tcggatgcag atgacaccgg aggagggcca    11340
gtgctgaatc tgcccaaagg aatggagcgc gcgcatccgc attctccgcc acaggtggga    11400
atactcggac ccttggaagt ccgctcggcc ggaggtgccg gaacgggagc cgcggtaagc    11460
ggtattcgcg tacgcacatt gcttgccgcg ttgactgccc gcctggggca ggcgatgtcg    11520
accgagcgca tcctcaaaga ggtctgggcc gacaacccgc ccgcgaccga tcgcaaggcg    11580
gtggccgtcg ccgtcctgcg gctgcggcgg gtcctcggcg acaacgaagg acggtggctg    11640
ctcacccgcc cctccggtta cgtcctggac atccccccgg accacctcga cgccgtacgc    11700
gcggagaccc tggtgcggga aggccgggcc gccctggccg ccggcgaccc acgcgtcgcg    11760
gcccgccacc tcacgcgcgc cctcgaccag tggcggggcg agccctacgc ggacgccaac    11820
gccatctcga ccgtgtccca gcgcatcacg gagctggaga acctcaggtc cgaggccgtc    11880
caggcgcaca tcgacgccag gctcgaactg ggtcaccacc aggaactggt cggcgaactc    11940
cgctcgctga ccgccgcgaa ccccctgcac gagccgcact ggctgcagct gatgctcgcc    12000
ctctaccgct ccggcaagca ggccgaggct ctcgccgcct atatgcagct gcggcaggcg    12060
ctggccgaga acctgggcat cgacccgggt cgtcagctcc aggaactgca cctgcggatc    12120
ctgcgcgccg acgcgggcct gctgacgggg tccgggccgg cggcaccggc cgagccactg    12180
ctcgtacggc agtcctgagg gctcacggcc acccgaagaa cgcgcggtag cacggaacct    12240
gctgctcca                                                           12249
```

<210> SEQ ID NO 75
<211> LENGTH: 18034
<212> TYPE: DNA
<213> ORGANISM: Streptomyces lavendulae
<220> FEATURE:
<221> NAME/KEY: unsure
<222> LOCATION: (302)...(302)
<223> OTHER INFORMATION: n is a or t or g or c

<400> SEQUENCE: 75

```
cccaggacct cgtcgcggtc ccggccgcgt ggtggacctc cgccaacccc aacaacgacc      60
agctctgcca gggcatatcg gtggaggtca gctacaacgg caggaccatc agagtgccgg     120
tgcgggacaa gtgcccttcg tgcgaccgga cccacatcga cctcagcagg acggccttcc     180
agaagctggc gccgctcgac agggggtgtgg tcaacggcat cacctggaag ttcgtccgct     240
gacgccacgc cggggtcccc aaagcccggg acccggcgc tccgcgcccg gcacgccggg      300
gnccgcccgg cgtgtcggcg tgaggttcgt cgccttcaag agtcataaag acaatcgcga     360
ctgttgacgt tatgagttca tcaaatttaa ggtcgcggga ctcttggaac agatcaagac     420
gacggagaac aatgacgtac tcccccggcg cgcggccgcg cccggccggg ctgtccgcac     480
tgctgctcgc aggcgcgctc gtcgcctcgg tgccgccgc ggccgccgcg cgagcgccgc     540
aaccccccac cgccgaccgc ccccgcaccg ccgcctcccc cacaggcggc tgccgtacgg     600
gtgacggctg gacactcgac tccacccgca tcgacccga cgacacccac cacgcctatg      660
tcggcaacgg ctacctgggg cagcgcgtac cgcccaacgg cgccggctac accgacagcg     720
```

-continued

```
acaccaagac cggctggccg ctcttcgctc cggcctacga cggctcgttc gtgtccgggc      780
tctacgcgca caacaagcag accgccgccg accggcaggt gatcgccgct ctgcccacct      840
ggaccggact ggccgtcggc accggcggcg agcacgcgca tatcttcaac tcttcgacga      900
agtcgggccg gatttccgga tatcaccaga ccctcttcca gagctgcggc atcgtccgta      960
ccgccctgac ctggaccgcc gccgacggcc gcaggaccga cctggtctac gaggtgctgg     1020
ccgaccgcga cgaccgcac acgggcgccg tacggctgag catgacgccg cgctggagcg     1080
gcgaggccac cgtcaccgac cagctggacg gacgcggcgc gcggcgcatg cggcagaccg     1140
gcggcggcga ccgcaccggt gggaccggcc gggacggccg caccatggac gtggccttcc     1200
gcaccgacgg cacggacacc gacggcgccg tcgcctccac cctgagggcc gggcgcggtg     1260
tgcacacgac cggggaccga cgcgccgcgg ccgcgaagga cttgagcgtg aaccagtccc     1320
tcacgttccc cgtccgtgcg ggccacgcgt acgaactcac caaatacgtg ggtgtcgaca     1380
ccgcgctcac ctcgcacgcg ccccgcgagg acgccaccac cgcctccctg cgcgccgccc     1440
gccgcggctg ggacgggctg ctgcgtgccc acaccgccgc ctgggcccgg ctgtggcgct     1500
ccgacatcga gctgccggga cagcgcgacc tccaggcgtg ggtgcgttcc gcccagtacg     1560
ggctgctgtc cagcacccgg caggggcat ccaacagcat cgccccggcc gggctgacca     1620
gcgacaacta cgcgggcctg gtgttctggg acgccgagac ctggatgtac ccggccctgc     1680
tggccaccgc gccccaactc gccaggaccg tcgtcgacta ccgctaccgc accctcgccg     1740
gagcgcgcga gaacgcccac aagctcggct accaagggct cttctacccc tggaacagcg     1800
gcagcgaggg cgacctggcc caggagtgcc acagcgtcga cccgcccac tgccgcaccc     1860
agatccacct ccagtcggac atctccctcg ccacctggca gttctacctc gccaccggcg     1920
acaccgcctg gctgcgcgag cgcggctggc cggtgatgga gggcatcgcc gaattctggg     1980
ccgggcgggt caccccaac gccgacggca gctactccat caaggacacc gccggccccg     2040
acgaatacag caacgcgtc gacgacgcgg tcttccaccaa cgccggtgcc gccaccgccc     2100
tgcgcgacgc cgcccgtgcc gcgcggctgc tgggcgagcg cgccccggcg gagtggacga     2160
cgatcgccga ccggatccgc atcccgtacg acgcgcggca caggtcttc gagcagtacg     2220
acggctaccc gggcagcaag atcaagcagg ccgacacggt gctgctgatg taccccctgg     2280
agtggccgat gtcccaggcc gacgcggcgc gcaccctcga ctactacgcc cggcgcaccg     2340
acccgacgg ccccgccatg acggactcgg tccacgccat cgacgccgcg ccacgggcg     2400
agccgggctg ctcggcgtac acctatctcc agcgttccgt ccggcccttc gtgcgcggtc     2460
ctttcgacca gttctcggaa gcccgcgca ccaaggccgg cgccgacgac ccctggccg     2520
gctcgcccgc ccacgacttc ctcaccggca agggcggctt cctccagatc ttcaccaacg     2580
gcctgaccgg catgcggatg cgcgaggacc ggctgcacct cgacccgatg ctgccccgc     2640
agctcggccg cggcgtcacc ctgcgcggcc tgcactggca gggccgcacg tacgacatcg     2700
ccatcggcgc ccacgagacc accgtgcggc tcaccggggg tgcgcccatg accctctaca     2760
ccccgcaggg cgagcacgtg ctgaccaagg cggcaccggc cgtgctcaag acccgccgcc     2820
ccgacctcgc tccaccgac aacgtggccc gctgcaccac cgccggtgcc tcctccgagg     2880
aacccggtat gtacgcggca ccgcggtcg acggcaaccc cgccaccgcc tgggtccccg     2940
acgggccgaa cggtgaactg accaccgacc tcggcaagtc cgtacgcgtc accaaggcca     3000
ccccgtctg gagcggcccg gcaccggcct cgtacagcgt ccagctctcc ctcgacggcc     3060
```

-continued

```
ggcactggca cgacgcggtc gcgggcggcg ctccggtgtc cgcgcggtac gtacgcgtcg    3120
cgctacgcgg tcaggccgat gccaagtccc gtacgggcat cgccgagctg accgttacgt    3180
agggcaccag cagcccgcgc gcccgggctg atgacgacg aggatccgcg ggacttcacc      3240
cgccctcggc cgacagggac gtcctgacga gagcgagcac gtcgtcgtcg ctcagcccca    3300
gcgcgcgggc gtcggcgacc aggcgccggg cctgcacggt gagccgggcg cgctcggcgg    3360
tcgaccctcc ggtgacgacc gccccgcgcc cccggcgcag ttcgaggagg ccctcctcgc    3420
gcagccgttg gtagccacgg agcacggtgt gcatgttgac cccgagcgac gcggcgagat    3480
cgcgggcgga cggcaggcgc tcgccggagc gtacggtgcc gtcggcgatg gcaccacgga    3540
cgcatgcggc gatctggtcg cccaggggga gggggacgc ggggtcgacg cggaagagca     3600
cggtcacccg cccgcggagg tgcggcgttc gcggtcggcg agggtgttga gcagcgcggc    3660
ggccgtggcg gcgtcgtcga cggtgacgac gaactcgctg ccggtggtca gacggacgct    3720
gatggcgtcg ccggaacgca gcacgacgcc gctcgccccg gaacggaccc ggtagcccca    3780
gccaccgaag tcccgcagag gcttgaccgg acggtgaccg gcttcggcga tccgctggag    3840
cggcacgttg atgcgcggcc aggggacggt cgagggcgtg acggtgagcc cgcgccggtc    3900
ggcggtcacc cggacacccg tcagcagggt catggcggct ccgatgagga acagcgacag    3960
cgcggacagc catccggcgg cgaccccgac gacgacgccg gaggcgaaga ccaggacacc    4020
ggtgaggggc agcacccggg agcccgccac ccttgaccag ccggcgatct cggagtcgcc    4080
gagcgcgaga cgcgaggcat cggcggacgg cccggaatcg ctgtcggctc cctggtcctt    4140
gccacaggcc gcccagccca ccgccgcgta gagcgcagca gccccgaaag cgagcgcggc    4200
ctgcgccccg gcaaggtga cggaagaggc gtcgtgggaca ccgtgttgg ccagcagcac     4260
ggcggtggcc agccatccgg tcagcaccgc gacggcgccg ccgatgacgg ccagcacgcg    4320
ctgtccgccg ttgcccggcc gcgtgaagta gacgagcgcg ccgaagagga caccgtcgcc    4380
cagcagcact ccccacgcga cgccgaggaa ggagccctgc cccgagaagc cgtcggcatt    4440
ccctcccggc ccgatgtgcg aggcgatccg cccgggcagc cggtcccgca ccgagaggaa    4500
cacccacagg acgacggcag cgcagaccag aggcggcacg acggagacgg caaggcgacg    4560
gacgaggacg gacgaggacc gtgacagcgg catgagagca aacctccact tgtttgcaca    4620
ctagtagaac aagtggaggt gaactcggcg aaggcggctg cctcttcctg acgcgttccg    4680
aacgccaccg gagccgccac gactgaccca gtgtcacccc gcgggaggcg gaacgcttca    4740
gtccgtgccg ggagcggcgg ccgcttcccg tggtgcgact ggtggtgtct gcgtggggcg    4800
gcgcatgagc ggcaggcgga gccgccggat gcccggcccc gagggaggtg ccagtctgcg    4860
cgtggacctg tggaagacga gcaggctgac ggcggcggct ccggcgaacc aggccagttg    4920
gacggcgagg tagccggaga cgggagcggt cgagaagccg gccgcggcac cggtctgcag    4980
cgagccgtag gagggagga gcgtcacgag gccgccgttg gcggcgccgc cggtggtgac    5040
ggggttctgc aggcccgcgt cgagaccgct ggtcatcacg atggcgaaca tcccctcgac    5100
gtcccggcgc agcaggagc cgaagacgat gccgatggcc ccgtaggtca gggacgcgca     5160
gaacagggcg gcgacgaaga ggaccggccg gcgggggcgac cagaaggcgt aggtgatggc    5220
ggtggcgtag acgcgacgg tggcggagat gagggtgagg gcggtgagct tggcgagaag     5280
gaggtggacg cgccggtagc ccgccatgga caggcgtcgg tcgaaggggc cgctggtgaa    5340
ggtcgcggcg aacatcatga agccgacgat cagggtgatg gagttcagcg ccccgacgat    5400
cgacgtgagt tcgttgcccc gcgggtggag gatctgcccg gtctcgtgca gcctgaaggg    5460
```

-continued

```
gatgggcggg tcttcgatga cgcagtaggc cagcgtgatc cacaccggga tgaacgcggc    5520
gatcaggccc atggcgagcc ggttgcgcag gtgctcgacc aaggcgaacc gggtggcggt    5580
gacgtagagg gttgtgtggt tcataccggt gccgtcgtcc ttgagtgcag cagtccgccg    5640
tcgaggtgcc ggagttcgtc gagccgttcg gcgtcgtagg ccaggtggga gacgaccagc    5700
acggaccgcc cgcgttcgcg cagaccggcg gccaggctcc agaaccgctg gtgggtgtcc    5760
cagtcgaagc cctggtaggg ctcgtccagg aggagcaggt cagggtcgtg catcagggcc    5820
agtgtgaggt tgagcttctg tttcgtgccg ccgctgagca cgctgacccg ctcgtccccg    5880
tagtcggaca gccggagcac gtccatgatt ctctcggcat ggctgagggt ggcgaggccg    5940
tacgccaccc ggaaatactc caggtgctgg cggacggtga gagcctggtt caggacgaga    6000
tgctgcgggc agtaaccgaa ccggccgccg tagtggacct gccgcgcctg cggccgcagc    6060
tcaccggcga ggatcttcag gagcgtcgac ttccccgcgc cgttctcgcc cacgacgccg    6120
gccagcgttc cggggcgcag ggacaagtcg atgccgcgca gcaccctgcg ggtgccgtag    6180
gtgtggtgga cgtccctgac gtccaggaga ttccgggcca cggcttcctc tcctcaggcg    6240
acctggtcgc gccggacgac cgagagggcc agctcgtaca caagtggct gtggcctgcc    6300 gacggcagca ggggctcgag cttgttccac gcgtcgctca ccaactggtc ggcttcctcc    6360
aggcaggctc tcaccgctcc gcaggcgttc aggtcccggc acacctcggc caccgccgtc    6420
gcgctgcccg agccgtcctt gacctgctgc cagagctggt tcagccgggc tctgcggcag    6480
ccggaccacg gcgtgggcca gtggcatggt gaccttgccg ctccgcaggt cctcggtggc    6540
ctgcttcgtc ggtgccccg cccgtgtgac accgctcagg tcggcgacgt cgtcggcgat    6600
ctggtaggcg gtgcccaccg ctgaaccgaa agccccagt gctctccgca gttccggctc    6660
ggcacccgtg acgaccctg ctgcctccat ggccgccgag accggggccc cggacttcaa    6720
ccggtgtgtc agacggacca gttccagcac agtgtgccgg tcgtcgccgg ccacggcctg    6780
gtccatctct tcccggtgac cttggagatc cagtgcctga ccggcgtgag ccgctcgcag    6840
cgcggccaga cccagtgccc gcaactcccc gcaccgcgag gcgtcgtcgg gaaaggtgag    6900
ctgaacggcc cgctcccaga ggaaataggc ggccgtaccc gcgttcaccg cagtcggcat    6960
gccgaacatg gtgtgcacgg ccggttgtcc gcggcgcagc ggtgaggcgt cctggacgtc    7020
gtcgacgatg agggatccgg tgtggagcag ctcactcgcc gcgatcagca ggccgcagga    7080
ttcgctgtca cctcccatca gaccgatggc ctcccaggcc agcaccggcc gccagcgctg    7140
tcctccggca tcggtcagat ggcggacggg agaggtcagg gcccggtgca gccgctgggc    7200
gacgaccggc ggcgtgccag gcccggtcgt cccggtgatg tggcccggtg gcagccacgt    7260
ggagcaagca tctgccgacg cgttcgggca caggcggtcg atgtgatggt tgatgcgttc    7320
ggccgtgcgg tcgatgcgct gccggatgaa gtccgcgttc gccgcgaaag tcggggagat    7380
gtccctggga cagaggaggg cgccggtcat ggagtggtca gctttcggtc aggggcgggc    7440
gatggacgag gctccctcat ggggtcgccg gcccgatgcc gcggagggac tgctcgggca    7500
cggctcgcgg agtgcggcga tcatggtcag gccgcgtggc atcgcggcga gttcgaagcc    7560
ggagcgcacc gtccggcccg gacgcgccgt gcgtacggtc cgcgtggcga ccagagtggc    7620
gagcgcgacg ggcaccatga cgtcggccac cgcggcacca gggcagtagc ggggcccgag    7680
cgcataggga agccaggcag caggggagac cgagggctga gcgtccggca tccagcgcgt    7740
cggatcgaag acatcaggcc gttcgaagtg ggcggggtca cggctcatcg ccccgaggtg    7800
```

-continued

```
gaggaacacc gtcgccttcg cgggcagccg gtggccgccc agccacgtct cgcggcgcgt    7860
gcaacgcaca aggaccggga ggccgtgaag ccggatgact tccttgacga aggcggctgt    7920
ccggggcaac cggtttattc cgacgccggc ctgcgagtgc cccaggccga gtgccgcgtc    7980
ggcctcctcc tgcaaggcct gttgatggtg ggggtggcgg cccagttcgt agcaggccca    8040
cgcgagtgtc gaggcggtgg cctccccgcc ggtgaacagc agcgtgcgca cgtcctgcac    8100
cgccgcttcc gagggctcgc gccacgcttg cttcagcagg gagaccacat cacacccgtc    8160
ctcagccggc cgatggcgcg cgaggacttc ccgggtggcc tcgtccagca ccgcgagggc    8220
acggcggagc gcgcgttgtc ttggcacggg tacccaaggc cacggggaca ggagaaaccg    8280
caaggccccg acctgcgaca gcgtggcatg cgccgcggcc agcgcggtca gcgttccggg    8340
cgagacctcg ctgcgcaaga cgcacctgac ggcgagatgg aaagtgagcc gggtcatctc    8400
gtggctcatg tcgaccggac ggtccgcggg aagggtggcg agcagacttc gggtctcggt    8460
ccgcacggac gccccgaggt ccgccggccg gggcacggcg aacgcgggcc tcatcaccgc    8520
ccgccggtca cggtggaccg ttccctcggt gctcagcagt ccctctctta cgatcacccg    8580
cacatgggt tccctgcccc agaacatgaa ggtgtcctcg tcgcgagcag cctgccggat    8640
cagcgaggag tcattgagca ggtacccgac gaacgggccc gccttcaccc tgaccacagg    8700
ccccgccttg ccgagccggg ccgcgatctc cctcagatcc atcaagaacc gcacggagcg    8760
ggcatgcccg agcaaccgac tgcagtcagg agccatcggc acaacggagt ccgccttcga    8820
atctccgttc atcaggcgtc ctcccgcccg catgtcaccc tctgtcctcc tgtgaacgac    8880
caggagtgag gagtgtcacg cagagcatca cctgctgtat cggcagcaat gccgacccgc    8940
accgacggct gggcggggcg accgggaacc gccttgcgcg tacgccgtgc tcgcgtgcct    9000
gaagcgcacc gtcacattca ccggtaccca cgacagaggc gggttcgcgg ccacctgtat    9060
ggacgcccg tgaatgggga cggagtgcag ggggtgctcg atggcggtgc cttcgcggct    9120
cagcaggccc tgcctcgcgg tttgagcgca acgggcggca gttcgggagc aggcagtcgg    9180
gccccctcgt agccgtgcac ctcgccgaag cgggagccgg tcgcccgagc cgtcgccgcc    9240
gccggcccga ttcgccatcc ggatggaaga ggacaccgcg cagggaccgc cgcccacttc    9300
accggaatcc tctccaccgg aaaatttatc cgcaaacctg tcacatcttc gacacatgaa    9360
gcgtcagggc ggtgacggca gttgaagccg ttgcccgacg acgccgaagg agaccgtggg    9420
acagctacgc acgtgcgggc cctggagcgg tcggccacgc cgacaggaat cggccttccg    9480
ccgctgatcc ggcctcccag cgttcgcgaa cacctcttgc cacacctccc gcgcggcccc    9540
cgcattcgag cggtcggctg acgacgccct cgcgacgccgc gcacaccacc cacgcacctc    9600
gccacgccga aggctgcccg aaaacaagaa gaccgaggaa agcacacatg aagatctctc    9660
gaataggccg cgcgtcatcc atcgccgccc tggtgacaac cgcactcgct ttcacggcag    9720
ttggcaccgt cgctcccacg gccgtcgccg actcccgcgc ggccgccgct tccgggacgc    9780
agaatgacca cccgagctcg gggcagggca cctccacctc tgagctccgg cgcaagggcc    9840
tggtcccgtc gagtctcgtg gccaagccca tcacccgcag cgagaccctc agacgcgccg    9900
ccagctggtt cggcaagggt ctccactaca gcggggacaa cacctatcag ggctggcgca    9960
cggactgctc cggcttcgtc tccatggcct ggggactgcc cggcccgggt gagaccaccg    10020
attcgttcat tccgggggc gtggcccacg aaatctccaa ggacgaactg aagcccggcc    10080
acgcgctcaa caacaaggcg ctcggcaacg acggtcacgt cgtcctgttc gagaagtggg    10140
ccgattcctc ccagtcctcc tactgggggtt atgagttcag cagcagcggt ctgcaccacc    10200
```

```
gtgtgatccc gtacgcctac ttctccaggt ccgagcagta ccgcccgatc cgcttcaaca    10260
ccatcgtgga cgacgacacg gccgcagggc ccgccgagga caacgcccgg gtccagggtg    10320
acttcgacgg cgacggccgc gacgacgtgg cggtgctcta cgactacggc aggaaggacg    10380
accgcagtcg ctcggccctg tggacgttca acagcaacgg cagcggtttc aacagtccca    10440
agcaggtgtg ggacagcggg acgtcggaga gctggaactg ggcctccagc aagttgacgg    10500
tcggtgactt caacggcgac ggcaaggccg acatcggcgt cctctacaac atgggcgcga    10560
ccgaggacgg ccgcaaccgc accaagctgt tcgtgttcac cagcaccggc agcggattcg    10620
ccgccccggt caaggtctgg gacagcaacg acgacccccgt gaagagctgg aactggaacg    10680
ccagcaagct caccgtcggc gacttcaacg gcgacgcaa ggccgacatc ggggtgctgt    10740
acgactacgg caaggacgac gaccacaacc ggacagggct ctggacgttc accagcaccg    10800
gcagcgggtt caacagcccg aagcaggtgt gggacagcaa caacgacccc gtgaagagct    10860
ggaactggga agccagcaag cccgtctccg gggacttcaa cggcgacggc aaggccgaca    10920
tcggcgtcct ctacgactac ggcaagaccg actccggcag ccgcaccgga ctctggacgt    10980
tcaacggcaa tggcaacggg ttcaacagcc cgaagcaggt gtgggacagc aacaacgacc    11040
ccgtgaagag ctgaactgg gaagccggca agcccgtttc cggcgacttc aacggcgacg    11100
gcaagagcga catcggcgtc ctctacgaca tgggtcgcac cgaggacggc cgcaaccgca    11160
ccaagctgtt caccttcacc ggcacggcga ccggtttcaa cagcccggtc aaggtgtggg    11220
acagcaacga cgacccccgtg aagagctgga acgcgtccgc gagcaagccc gtcgcaggtg    11280
acttcaacgg cgacgcaag gcggacatcg gcgtcctcta cgactacggc aagaccgact    11340
ccggcaaccg cagcggactg tggaccttca ccagcaacgg cagcggcagc gacagcccca    11400
agcttggctg ggacagcagc gcggaccccg tcaagagctg gaactggagc gcgagcaagc    11460
tcggctgacc ggcttcgccc ctcctcacct caccgttcgg gagagtcacc gcacatgcga    11520
accatacgaa tacgaagaac gaacggcgtg gccttcgccg ccgctgccgc cctgatggcc    11580
ctcgtcgcct ccggcaccgc cacggtccag gccgcgccct cgcacgccgg accctccggc    11640
accactccga tcacctaccg tggcctcacc ctcgacatac cctccgggtg gccggtcgtg    11700
gacctggaga aagacccgca cacgtgtgtg cggttcgacc gccacacggt gtacttgggc    11760
caccccggca ccgaacagtc ctgccccctcc catctggtcg cggacaagac ggacgccctg    11820
atattggagc cgatcaccgg agcgggcggc caggacgcct cccacgcgct cgcatcccct    11880 gccgggccc cgatgccgca cgagctgccg gtgacgtacg accacgagac gaaggtcgcc    11940
gtcgaaggcg ccggagtcat ggtcacgtcc tcctacggca cgtccagtac aacggtcgcc    12000
gccgtcctcg gctcggcccg cacggacgcg acagccaagc cgaccccccct gcccggcaag    12060 gcgggcaggg gcctcgcggc tccaccggtt gccgccgtcg cggccgacaa gggatacaca    12120
gggctgggct tcgagtcctg caccgcccct tcgtccgccg cgatgaaggc atggaaggcc    12180
tcgtcgccct acgggccgt cggcatctac atcggcggtc gcaagcgggg ctgtgcgcaa    12240
ccgcagctca ccggcgactg ggtgcgtcag cagaccgccg acggctggca cctgctgcct    12300
ctcttcgtgg acctccaggc cggcgacatc tctccggcca ccgcggacgc gcagggccgc    12360
gagtccgcgg acgccgccgt ggccaaggcg gcggacctgg gcctgggccc cgggacggtc    12420
atctacagcg acatggagca ctacgacagc cgctcgtacc gggcccgggt catcgactac    12480
gtgtcggggt ggaccagccg cctccacgaa catggctacc gctccggtgt gtacgcgggt    12540
```

-continued

```
gaaacgagcg gcatcccgga cctcgcctcg gtggccgacg acaccaacta cgcatcaccc    12600
gacgtgctgt ggtcggcgaa ctggaacctc aaggccgatg tgtcggacgc gtcgatggga    12660
cttccgggcc ccggctactg gcccaatggg cggcgcatcc accagtaccg cggccaggtg    12720
aacgacacct acggcggtgt caccctcgcc atcgaccgcg actacgtcga tgtcgccgcg    12780
gactcggccc tgcccgcacc cggcggagag gacggttcct cgcgcgtcaa gggcgacttc    12840
gacggcgacg gccgcgacga cgtggccgtg ctgtacgact acggcaagga gggcggcgtc    12900
agccggtccg cgctgtggac gttcgcgggg accggcagcg gcttcggcgc cccgaagaag    12960
gtgtgggaca gcggatcgga cagctggagt tggtcggccg ccaagctgac ggccggcgat    13020
ttcaacggag acggcaaggc cgacatcgcg gtcctgtacg acatgggtcg cactgaggac    13080
ggccgcaacc gcaccaagtt gtacgagttc accagcaccg gcagcggatt caacagcccg    13140
gtcaaggtct gggacagcaa cgacgacccc gtcaagagct ggaactgggc ctccagcaag    13200
ctgaccgtcg gcgacttcga cggcgacggc aaggccgaca tcgcggttct gtacgactac    13260
ggcagggacg gcgaccgcag ccgtacgggc ctgtggacct tcaccagcac cggtgccgcc    13320
ttcaccggcc ccaagctggt gtgggacagc aacaacgacc cggtcaagag ctggaactgg    13380
aacgccagca gcccaccgt cggcgacttc aacggcgacg gcaaggccga catcggcgtc    13440
ctctacgaca tgggtcgcac cgaggacggc cgcaaccgca ccaagctgtt caccttcacc    13500
ggcacggcga ccggtttcaa cagcccggtc aaggtgtggg acagcaacga cgaccccgtg    13560
aagagctgga actgggacgc cgtcaaggta gtgggaggca cttcaacgg cgacggcaag    13620 agcgacatcg gggtgttgta cgactacggc aaggacggcg accgcagccg caccggactg    13680
tggaccttca ccagcaacgg cagcgggttc aacagcccga gcaggtgtg ggacagcagc    13740 aacgacccgg tgaagagctg gaactgggcc gcgagcaagc cggtcgcagg ggacttcaac    13800
ggcgacggaa aaacgcgatat cggcgtgctc tacgactacg gcaggaccga ttccggcaat    13860
cgcaccggac tgtggacctt caccagcgac ggcaccggat tcggtacacc cctcctgggc    13920
tgggacagcg tgacggatgc cgtgaagagc tggaactggc gtgccagcaa ggtgagttga    13980 caccctcct gtgagacatg gggcactcct cgacgcccgt ccggcccggc tgcggcccgg    14040
ccggacgggc ccgtcattca atggaaggaa gaagtggatc ccttgacgcg caagacccgc    14100 acccccgca agaagggcag acgcgcgagc gcggcggcga tgtcggcctc cggcatgctg    14160
ctcgccttgg tggccaccgc cgccccgtc cccgcccagg cggcatcact cgccacctgg    14220
gaaaagatgg cccagtgcga gagcagcggg gactgggat acaaccagcc accgtactac    14280
ggcggcctgc aattcctgga gagtacgtgg gtggcgtacc acggaacgga ctatgcgcca    14340 taccccctatc aggccaccaa ggaacagcag atccgggtcg cgcagcggct cctcgacaat    14400
gagggcgcgc tccctggcc gtactgcgga agaaggtgg ggctggctga cgacgacgca    14460
cgccccttcc ccgacgcgcc ggacgacgac gcctccgccc ggatcaacgg tgacttcgac    14520
ggcgacggat gcgacgacgt ggccgtgctc tatgactacg gcaaggaggg cggcgtcagc    14580
cggtccgggc tgtggacgtt ctccgggagc ggtaccggcc tcggcagccc gaagaaggtg    14640
tgggacagcg gatcggccag ctggagttgg tcggccgcca aactggccgt cggcgatttc    14700 aacgcgacg gcaaggccga catcgcgtc ctgtacgaca tgggccgcac tgaggacggc    14760
cgcaaccgca ccaagttgta cgagttcacc agcaccggca gcggattcaa cagcccggtc    14820
aaggtctggg acagcaacga cgaccccgtc aagagctgga actggaacgc cggcaagctc    14880
accgtcggcg acttcaacgg tgacggcaag accgacatcg cgtcctcta cgactccggc    14940
```

```
aagaccgact ccggcaaccg caccggactg tggaccttca ccagcaacgg cactggattc   15000
aacagcccga aacaggtgtg ggacagcaag agcgacccgg tgaaaagctg gaactgggcc   15060
gcgagcaagc cggtcgcggg cgatttcaac ggtgacggca agaccgatat cggggtgctt   15120
tacgactacg gcaaagatgg cgaccgcagc cgcaccggac tgtggacctt caccagcacg   15180
ggcagcggat tcaacagccc caagcagacc tgggacagcg gtcggaaag ctggagatgg    15240 tcggcggcca aggtggtcgg cggcgacttc aacggtgacg gcaaggccga catcggggtg   15300
ctgtacgacc tcggcaggaa cggcgaccgc aaccgcaccg aactgttcac gttcgcgggc   15360
aacggcaccg gcctcaacac accggccaag gtgtgggaca gccaggacga cagcgcggtg   15420
aagagctgga actgggccgc gagcaagccg gtcgcaggtg acttcaacgg cgacggaaag   15480
acggatatcg gcgtcctcta cgactacggc cagaccgact ccggcaaccg caccgggctg   15540
tggaccttca ccagcgacgg cagtggattc gccggcccca agctcacctg ggacagccgg   15600
accgaccccg tcaagagctg gaactggaac atgagcaaga ccggctgagc cattcatgcc   15660
gtacagaaga gaagaggaag gatgaaatac cgaccgggaa cactgctcac ttccataaca   15720
gtcttgtgtg ccctgctcgt tccggtgcgt tcggcggctc aggcggccag gcccgagcag   15780
ggacgttccg tggtggccgc ggccgccgta ctggagcaaa gtccgccgac gctgctcgcc   15840
gagccggaaa tgcgcgtcgt ctcctggaac atctgcggtg aggcgggcgg ggtgcgcggg   15900
gagggcggct actgccccta ccgcaacgat ccccaggcga aagtcgacca gatcgcgcag   15960
gtggtcgcgg agcgcagtgc caatgtcgtc atgctccagg aagtgtgcgg cgaggcgccc   16020
ggcagccata tggagcggct gcgcgcggcc ctgggcagcg gatggtcgat cgcgcacgcc   16080 ccggggccc gcccggacga cggaaccacg aactgccggg gcgggctcag cggcatattg    16140
ggcgtgggga tcgcggtgaa ggggcgcgtc accgacacca ccgcgacgaa caccgtgccc   16200
gggggcggcg gtgacaagca gaccctgccc atcctctgtg tacgtgtcga gggctggtcg   16260
tccaggatct gcaccaccca catcctgtcc gaccctgccg atccgcgcag gccggggcag   16320
atccagaacg tcaagaacga gatctggccg gaccgctatc agctggtgct cggcggcgac   16380
ttcaacatgt tccccgactc cgccgggctc aagccgatct cggacgaatt cgacgagtgc   16440
gaccgccgct cctacggcgc cggtgacatg gtcaacgagg tcacccatca ctcctgggag   16500
aaaaagggcg gacacatatg cgcaagcgt gaccacatct tcgcctcgtg gggagagtcc    16560
gggagccagt tcacatcctg cgaggtcgac cggacccgga tggacaccac cgagaacgcg   16620
cccgaaagcg gtccgcccaa cgggtattcg gaccatgcgc cgatcatcgg ctacctcaag   16680
ccgccgcggc acctgagcac gtccggggac ttcgacggcg acggcaaggc cgacctcgcg   16740
gtcctctacg gcaggggaa gaccccggac ggccacaacc ggtccagcct gtggatctca    16800
ggcggttccg gtaccggagc ggagaccgga ttcgccgcgc cgcgcgaggt ctgggacagc   16860
ggtgccgaca gctggaactg gtccgcgagc gcgctgacct ccggggactt cgacggcgac   16920
ggcaagaccg acatcggcgt cctctacaac tacgcaggg acggcgaccg caaccgcacc    16980
gcgctgtgga ccttcaaggg gacatcgaac ggcttcgagg cgccccgcaa ggtgtgggac   17040
agccacgacg acacggccgt tcccagctgg aactggtcca cgagcaagct cgtcgcgggc   17100
gatttcaacg gcgacggcaa agcggacatc ggcgtcctgt acgactacgg caggaccgcc   17160
tccggcaacc gcaccggact gtggaccttc accagcaccg gcaccggatt cggcaagccc   17220
cacctggcgt gggacagctc caccgacccg gtgaagagct ggaactgggc cgcgagcaag   17280
```

-continued

| | |
|---|---:|
| ccggtcgcag gtgacttcaa cggcgatggc aagaccgaca tcggcgtcct ctacgactac | 17340 |
| ggcaaccaca ccgccctatg gaccttcacc agcaacggca ccggattcgc cggccccaag | 17400 |
| caggcctggg acagcggacc ggagaactgg aactggtccg ccgccaagcc ggtcgccggg | 17460 |
| gacttcgacg gcgacggcag gaccgacatc gcggtcctgt acgactacgg caggaccgcc | 17520 |
| tccggcaacc gcaccggact gtggaccttc accggcaccg gcaccggatt cggcaagccc | 17580 |
| cacctggcgt gggacagctc caccgacccg gtgaagagct ggaactgggc cgcgagcgag | 17640 |
| ccggtcgctg gtgacttcaa cggggacggc agggccgacc tcgcggtgat gtacgactac | 17700 |
| gggaacgcga ccaacggccg caaccgcacc gcgctgtggt ccttcaccag ccgcggcacg | 17760 |
| gacttcgccg ccccgcgggc gaactgggac agcagcaacg ccgctgacca gctgaaatcg | 17820 |
| ggcgagctga gggcggctcc gctcagcggg tcctagttct ccatgatcgg tccgtcgccc | 17880 |
| tccagaccgg ccgctctccc ggtcagcgtc cggccagtg cgtcagcgtc gcgaccgagt | 17940 |
| ccgtaacagc gcatcccggc gatcgcgaag tacgcctggt cgagccagac gcgggccgcg | 18000 |
| ccagtgctgc cgcgcggcga agtacggcga gctc | 18034 |

<210> SEQ ID NO 76
<211> LENGTH: 53500
<212> TYPE: DNA
<213> ORGANISM: Streptomyces lavendulae

<400> SEQUENCE: 76

| | |
|---|---:|
| gtccgggccg gcggcaccgg ccgagccact gctcgtacgg cagtcctgag ggctcacggc | 60 |
| cacccgaaga acgcgcggta gcacggaacc tgctgctcca gcatatggat gccgtggtgc | 120 |
| acacggcgcc cggcggtggc ggccgcgctc agcagcgccc tctcgtgcgg cttcatgacg | 180 |
| acgtcgacca ccacggcatc cggtcgcacc ctcgcggggt cgaagggcag cgggtcctcg | 240 |
| gaacgcatgc ccagaggcgt cgcgttgacg gcgaaatcgg ccgcctccag atcgccgggc | 300 |
| cccagcgccc ggatcccgtc cggccggcgg gacccgagcc gcagcagcag cgcgtcgagc | 360 |
| tgggcgcggt cggtgtcgtg cacggacacc cgcgcggcgt cggccatcag cagcgccgtg | 420 |
| gcgatcgcgc tgcccgcccc tccggcgccg accagtgcca catgcctgtc gcgcaccgtg | 480 |
| tgcccggccg cctgaagacc ctggacgaac ccgagcccgt cgaagttctc ggcgtaccag | 540 |
| cggccgtcgg gttcgcgccg catcgcgttg gccgtcccga tgagggcggc cgccggcccg | 600 |
| agcccgtccg cgagcccgca cagggccgcc ttgtgcggca cggtgaccag cagaccgtcc | 660 |
| agattgccga tccgcttgag cccctcgacc acctcggcga gatcccgcgc ccggacgtgc | 720 |
| accggcacca ccacggcgtc cagaccgctt tcgctcagca gggggttgag cagaccgggc | 780 |
| gccttgacct gggcgacggg atcacccagc accgcgtaca gccgcgtggc gcccgagaca | 840 |
| ccggccgccg gcccgaggaa ttccatcagc cgatcctctc tgtaccccg acggatgttg | 900 |
| ccctacggtg ctggagatgc tccacagctt tgccgtgacc gccggtcggc acaaccctgc | 960 |
| gtgcccctga cgcgccaggc cctccaggta gttgctcccg gcggatcccg acagctcccg | 1020 |
| accggtcccg acgagggaa gaagccatca gatacctggg aatcgacgtc ggaggcacga | 1080 |
| aggtcgccct gcgggtgacg ggggacaccg acggtgcggg cggcggcgac gtgacgttcc | 1140 |
| gctggcccgc cgccggcgac gtcaccgcgg atctggacct gctcgccgcg cgggtccgcg | 1200 |
| gtcttctggg acaccgcgag gaccccctcg ccggggtcgg cgtggccatg cccgcgatct | 1260 |
| gcgacgcggc cgggacggtc cgcacgtggc cgggacggc gagctgggcg ggcctgaacc | 1320 |
| tgacggccgc cttcgggcag ttgctgcccg gcaccccggt cgcctgcgcc gacgacggtg | 1380 |

```
acctggccgc gctggcggag tcccgcgccg ccggctgccg gcatctgctg tacgtggggg    1440
tcggcacggg catcggcggc ggcatcgtcc atgagggccg cgcctggccg ggccccggac    1500
gcggctcgtg cgaggtcggc catgtcgtcg tcgaccgctc gggcccacgc tgcgactgcg    1560
ggcgcgccgg ctgcgtccag gcggtcgcgt cgggaccggc gaccctccgg cgggccgccg    1620
aacggcgcgg ccgggagacc ggcttcgacg aactggcctc cggggcgcgc ttgcacgccc    1680
cgtgggcgga agcggccgtc gacgagagcg ccgcggccct ggccaccgcc gtgaccggca    1740
tctgcgagct ggcccacccc gaactcgtcc tcgtcggcgg cgggttcgcg gcgggcgtgc    1800
cgggatacgt ggcctcggtg gcggcgcacg tcgagcggct gacccgcccg ggaacggatc    1860
ccgtgcgggt gcgcccggcg gtgctcggcg ggcggtcctc cctgcacggc gcactgctgc    1920
tcgcgcggga ggcacacggg cggggaaacc ggccgccgga gagtgaccgt gtttcttccg    1980
atgtttcttc cgatgtttct ttcggggag tgacagacag ggccgttggc cggtccgact    2040
gagcacaatc acaggtgatt tcgcccaggt tcaccacgcc tcgtgtgctc ggggtcggca    2100
gaaggagtca gagtcatgct cgacaggcgg agcgtcattc gcgtcggcgc cggggtggcg    2160
gcggccgccg ccgtggccgg tacggccgcc accggtgcgg cggccgtggg gctgccgggt    2220
gtacggggac gcgcggcgtc gcgcggggtc gactgggcct ccttacgccg tcatctgtcg    2280
ggcgagctcg tcctgccggc ggacaccgga tacgagcggg ccaggaagct ctacagcggc    2340
cagttcgacg gcatccgccc gcaggccgtc gcctactgcc ggaccgagga ggacgtgcgg    2400
acgaccctcg cgttcgccca ggaccacgcg ctgcccctca ccccgcgcag tggcgggcac    2460
agcttcggcg gctactccac gaccgacgga atcgtcctgg acgtctccgg cttccacgcg    2520
gtgagcctca cccggaacac cgtcgtcatg ggcgcgggca cccagcaggt ggacgccctc    2580
accgccctgt cgccgcgcgg tgtcgccgtg gcgagcggca actgcgcggg cgtctgtccc    2640
ggcggcttcg tccagggcgg cggactgggc tggcagagcc gcaagttcgg catggcgtgc    2700
gaccggctcg tctccgcccg ggtcgtgctc gccgacggcc gcgccgtgac cgcctccgcc    2760
accgaacacc ccgacctttt ctgggcgatg cgcggcggag gcggcggcaa cttcggcgtc    2820
gtcaccggct tcgagctgcg ccccaccgac gtccctccg tcgtcagcta caacctcacc    2880
tggccgtggg agtcggcgcg gcgcgtcatc gaggcgtggc agcactggat catcgacggc    2940
ccccgcgacc tcggtgccgc gatggccgtg cagtggcccg acgccgggac cggcacgccg    3000
gtcgtggtcg tcaccggcgc ctggctgggc gcggccgacg cgctcacccc cgtgctggac    3060
tccctggtgg cctccgtggg cagcgcgccc gccacccgct cggccaaggc gctctcccag    3120
cacgacgcga tgatggcgca gtacggctgc gccgacctca cgcccgagca gtgccacacg    3180
gtcggctact cgcccgaggc cgcgctgccc cggcagaact tctccatgga ccgcaaccgg    3240
ctcttctccc gggccatcgg gcaaggaggc gtcgagcgga tcctggaggc gttcgccgcc    3300
gacccgcgcg ccggacagtt ccgcttcctg agcttcttcg ccctcggcgg cgccgccaac    3360
cgccccgacc gcaccaccac cgcctacgtt caccgcgaca ccgagttcta cctcggtttc    3420
tcgatcgggc tgaacgaccc ggagtacacg gcggaggacg agaggctcgg ccgcgcctgg    3480
gccgcgcgag gactgcgcac gctcgatccc cactccaacg gcgagagcta ccagaacttc    3540
atcgacccgg agctcgacga ctggaagtcg gcctactacg ccgagaacta cgtgcgcctg    3600
gccgccgtca aggcggccta cgacccgcac cggctcttct ccttcgcgca ggccgtctga    3660
cctctcccga aagacccctg ccggcctgct cccctccgcg gctcctgtgg gcactggtgc    3720
```

-continued

```
gcccgcgcac ttctgtgtga ttgagtgaag tccgggcgtg cagagctcag ttgccgtgga   3780
gggggcgcca gttgcgagca tcagcggtgg agagggtgga gctgatccgc tggccggtgg   3840
agtccgagcg gcgggagcgc tgccgcgacc ggggcgtcat gcggatcctg gtgctggagg   3900
cgggggccga ggcacccttg tgcgtggacc ccaaggagga ctgggtccgc gctcccgtca   3960
gcaccgacga cctgcgggcc cgcgtcgagg ccctgcgcct tcggggagcc gccgccgagt   4020
cccggcccga ggtcgacccg aacggagtgc tgcgtttccg gtggcgctcc gccctgctct   4080
cgcccaccga ggcccggctc gtcgcccggc tcgccgagtc ctatgccgag gtcgtcgccc   4140
gcgacgacct gctccgcccg ccccgggcc gtaccgtgcc gagccgtaac gcgctcgacc   4200
tccacatcat gcggatccga cggcgcctcg ccgcgctggg cctgagggtg cgcaccgtcc   4260
gggggcgtgg ctacgtcctg gagagcgcgg aaggagtctg accgacgggc gtggccgcgc   4320
accgcaccga ccgcccctac gagcgaggag cccgaagtgc agcagcctca tcacagccgc   4380
gtcgacgtgg aactgggcga gaggtcctac cccgtccacg tcggaccggg ggtccgccac   4440
ctcctgcccg gcatcgtcgc ctccctcggc gcgcaccgcg ccgccgtcgt gaccgcacgg   4500
cccccgacc tggtgcccga tcccggcgtg cccgcgctga tcgtgcgggc acgtgacggc   4560
gagcggcaca agacgctcgc caccgtcgag gacctgtgcc gcaagttcac caccttcggc   4620
atcacgcgcc acgacgtcgt cgtctcctgc ggaggaggct cgacgaccga caccgtcggc   4680
ctggcggcgg cgctgcacca ccgtggggtg ccggtggtgc acctgccgac caccctcctg   4740
gcccaggtgg acgcgagcgt cggcggcaag acggcggtca acctgcccga gggcaagaac   4800
ctcgtcggcg cctactggca gcccaaggcc gtgctgtgcg acaccacgta tctccagacg   4860
ctgcccgccg aggagtgggt caacggctac ggcgagatag cgcgctgcca cttcatcggt   4920
gccggcgacc tccgcggcct cgccgtccac gaccaggtca ccgcgagcct gcggctgaag   4980
gcgtccgtcg tcgcggccga cgagcgggac accggcctgc ggcacatcct caactacggc   5040
catacgctgg gccacgcact ggagaccgcc accggcttcg ggctgcggca cggactcggc   5100
gtggcgatcg ggacggtctt cgcgggccgg ctcgcgagg cgctgggccg catcggcgcc   5160
gaccgcgcgc gggagcacac cgaggtcgtc cgccactacg gacttcccga cagcctcccg   5220
ggaaacaccg acatcaccga gctcgtcgcg ctgatgaggc acgacaagaa ggccacgtcg   5280
ggactgacct tcgtgctcga cgggccttcc ggcgtggagc tggtgtccgg gatcccggag   5340
gacgtcgtcc tgcgtacgct cgcggcgatg ccgcgaggaa cggcctgacc gagtgttccg   5400
tcttccgagg ggaagtgacc gtttcgtgtc ggcagagctg tcagaaccgc tgaagaaggc   5460
cctggactcc ctggtgttcg gcgtcgtggc gacgaccgac cccgacgcc gcccgcacca   5520
gtcggtggtg tgggtccggc gcgagggctc cgacgtgctg ttctcgatca cgcgcggcag   5580
ccgcaaggag aggaacatcc tgcgcgaccc gcgtgtgagc gtgctgatca gcccggcgga   5640
ctcgccgtac acctacgccg cgatccgggg caccgcgcac ttcgaggacg tgccggaccc   5700
gggcgcgtac ctcgacacgt tctccataaa gtaccacggc gtgccctacc gggagtcgtt   5760
ccccgagccg ccggaggtga gcaccattct cgccgtccgg ctcgttccga cgtcggtcta   5820
cgagcagtgg tgagggcgta ggcgtcccga agccccggca gcgtcccgaa tgccgctgcc   5880
ggggcttccc gtgggagccc tacgccggtt tccgcgcggt gaccaccgag tagccgacct   5940
cctccaccga gcccatgcgg tcgatgccgt cgaccatgcg gtggaacgcc tcgtcgtcca   6000
tgtgggagcc gagctcgtcc ctggccgcac gcatcttcgc cgccaccgcc tcgtaggagg   6060
gccgcacctc gtccccgatg tcgaggaact ccaccacctc cagccccacc gaccgcatgc   6120
```

```
agtcctcgta cgcctcgcgg gtgaggacgg ggccctgctg gaagttgtcg ttggcggtgt    6180
cgacgatcgt cctggacgcg tcgctcaggg gccggcgcag cacgaagtcc gtcaccgtca    6240
cccggccgcc cgggcgcagc acccgggcga tctcggtgaa gacgtcggcc cgttccaggg    6300
cgtggcagat gctctcgatc gcgtaacagg cgtcgaacga gccgtcggga aaggggagcg    6360
cgagcatgtc accgatgcgg aactcggtcg cctcgtcgcc ctccttctcg gcgagctgcc    6420
gcgacagacc cacctggtag gggttgatgg agaccccggt ggcccgcacc ccgtgccggg    6480
cggcgatgcg caaggtggcc ttgccgttgc ccgaccccac gtcgagcacc cgctccccgg    6540
gggcgaggcg caggcgctcc gagacgtagt cggtcagccg gtcgcctgcc tcttccaccg    6600
tcgtggggac gtcgggtccc gcccagtagc caccgtgcat gtagccgcct ccgcgtgca    6660 ccatcaagtc ggtgacgcgg ttgtagagtt cgaccatccg gtcggaggcg gacgcggttt    6720
ccgtcatgcc gctcactttc ccgggcgctg gcgaccagc agcagatagc cgaactcctt    6780
gacgccgacg aggtcgccgg ggtcgaactg gttcaccatc tcctcgccga actgcgtctc    6840
cagcctctgc ttcgaggagt tgatgcgctc cgagagcagc ctgaaggtct tctccagggt    6900
ctggtcgctg atgtcgagga actcctccag ccacaggccc gcccccgca gcaggggagg    6960 gtacgcctcg gcgctgacca tggtcatcat gaagtcgtgg aggtagcgct ggacggcggc    7020
ccgcccctcg ggggcgaggg gggcccgctc gaagaagtcg gtgagcacca gacggccccc    7080
gggccgcagc accggccga cctgggcgag cacctgggcg cggtcgggca tgtggatgat    7140
cgattcgagg gcgatgacgg cgtcgaagct ctcgtcctcg aagggaggt ccatcgcgtc    7200 ggcccgctgg aagcgcgccc ggtcggcgag cccggcctcc tcggccagcg cgttggcccg    7260
gacgacctgc tcatggctca ccgagatgcc cgtgacatgc gctccgctga gccgggcgat    7320
gcgtacgccc ggggtcccca cgccgcagcc gaggtccagg acgcgggagc cggcgccgat    7380
gcgcagccgc tcggccatca tgtcggtgag ccggtcggtg gcctcggcca gcggcacctg    7440
gctgtcgggg gagtcccagt agccgaagtc caggttctcg ccgagggagg cggctcccag    7500
cgcggtgaac cggtcgtaga gcgcgcccac ttcctcggag gcgggtgagg gcatggggag    7560
ttcggacagc tcggagtgcg gcatggacga tccctctcgt gaaaggtcgg gggtgggtcg    7620
ggcagtcggt gtcaggagag acggaggtcc tggtagacgg cgtcggcgag gcggacgatg    7680
cgctcgcggt gccgttcgtg ctccaccttc ccgttgaggt ggagggcgac gacgagagcg    7740
gcgtccgggt cggcgaagac cacggcggtc cacagcccgt cgtgcccgaa ggaccggggg    7800
gaggcgtacg agccgaagct ggtgaaccgc ggatccagct gacggcattc gaggcggaac    7860
cccatgcccc agtcggcgtt gccgtagcgg tcctggaggc cggtgcggtg ccgggccgtg    7920
agggcggcga cggtgggcgg cgccaggacg cgcccgccgg gagcgtcccc gccgcgcagc    7980
agcatctcga agagcctgcc catgtcccgc agcgggccac gggtgttgac ccccgggatg    8040
cagcgtgtgg tggccgcctc cgtcgaccac cagtgggtgg gcagcgggcc gccctcgggg    8100
ttgctcacat ggatcagcgg cagctcgccc cgagcgcgg cgaactcctc gcgatccagg    8160
tggacacggg tgccggacat gccgcacggc ccgaggatct cctcctggac gtacgcgcgg    8220
tactccctgc cgtcgacgac cggaaggatg cgcgccagga cgaaccaggc ccaccactgg    8280
ctgtagttga tgccgggcgt gccccccgga cgcggtgcca ccggcacctc gaaggcacgg    8340
cgcacacgct cctcgtccgg gccggccacg atgccgtgca gcgggtcgtc gccggtgggc    8400
agcgggcccg tatgcgtcag cagttccatc gaggtgatgg actccttgcc ccggttgccg    8460
```

```
aactccggca gatagtgcgc gacgggcaga tacgggtcgt acgctcccgc ctcccacagc    8520
cggcccaggg cgaccgacag cagtggcttg gcgcagcagt accacagggg cagcgaccgg    8580
tgggtcatcg ccaccccggg gcgggccagc cccaacccgg cgtccgccag agggactccg    8640
tcgcgggaga cgtagatctg cgcccccggg gtcgaggtgc cgacctcgcg ctccagctcc    8700
cgcatggtgc cgggaagcgc cgcacgggcg cgccggacgg cctcggccgc gtcctcggtg    8760
ccgggcggcg gggccgcttc ccgcgccgtg gtaccgggcg tgccctgag cgcggccaca     8820 tggcccgagg cgtcccgctc cagtgcggcg tcgatgaaga acagcaggct gaaattgccc    8880
tcggcccgta cgtcgccccg ctcgaatacg ccggtccgat cccgcgcggg gccgagcagc    8940
agggcgcggg cggcctccag gggaagccgg atccgcagtc ccggactctc accggccgcg    9000
gccgcgaggc cgagccgccc ggcgacgagg tccacctgga cgtcgacggc cggggttcg    9060 ccgggcggtg ggtcggtgag ctccaggcgg agcgcgaccg tgccgcgttc gcccacgggc    9120
gggcgttcga gcctcgcggc cccggcgagc caggccgtgg acaggaacgg cgcggtggac    9180 aggtgttca gcacgggctc actcctccgc ttccttggcg gccccggcg ccacctgggg     9240 gacgacctcc tggaacagcc gctccaggct ggtggtggcc gggtagtcgc ggaaccacag    9300
cacgaactcc gccacgcccg cggcgaccag gcgccgggcg cgctcggtga gctgttccgg    9360
cgtcccgtac aggctgcgcc gcgccagcag gtcgggatgg tggctccaga acagcacctc    9420
gtgcggggtg gagagccagc ggtcgcgttc caggacggag tcgaagatcc ggcactccgc    9480
ggcccaggcg tgccggacgc cgtccggatc gagcccgagc tccgtgcgac ggcggcggaa    9540
cgcggtgacg gccgcggcga cctgagcggg ctcaccggtc cactggacat gagcgcactc    9600
ccgcacggtg gcgtcggcgg gccgcagcgc gccgctcccg gcgtccccgg ccggggtgcg    9660
cagcgcgagg gggaggggct gctgccgtgg ggcgggcacg cagtgcgccg aagtgaggcg    9720
gatgtgttcc ccggtgaagg tgacgggctg tccgccccac agcgcgcgca gggcctcgac    9780
cgtctcgccg agagcccggt ggccggcggc ctcctcctcg tccgcctcca ggcccgtggg    9840
cacctcgcgc cccgtcgagt ggtgctccgg caggtactcg cgggccggga agccgagggt    9900
gagccggccg tcgcagacga cgtccagggt cgcggcccgc ttggcgatca gcgcggcgtt    9960
gcggaacggc ggggccgagg agagcagtcc cagatccaga ccgggcaccg cgcccgcgag    10020
ggccgccagc gccgtccagc cctcccagac cggctcgggc tcgcgccggg gcagggtgtc    10080
ggtgcggtcc agcagccaga gggcgccacg gccgtgccgg tggacggtgc gggcggtctc    10140
caggaggagc cgccagccct cgcggccgcc cgtaccggcc agttcgaggt tggtgccctg    10200
cggggcgacg acgctccagc gcggggtcgc gggcgtcatg cgtggccgcc gctgcggacc    10260
agcgcgagca ggctctgcgg cttgtccagc aggaagtcgg gccgctcggc gcgcagttgg    10320
ccggccgcgc cctcgcccca gtcgcgcgcc acggtggcgg tccgcgcggc gcggccgctg    10380
cggatgtcga tcaccgcgtc gccgaccatg accgcgtcct cgggcgccgc gtccagccgg    10440
cgcagtgcct cccgcacgat gtcggggtgc ggcttgggcc tcggcacctc gtcgctgccc    10500
accacctcgt ccagcagggg cagcagcccg accgcctcca gcacgcgcgc gcccgggag    10560 ccggacttgc cggtggcgat cgcggtgccg acgccgtccg cgcgcagctc cgccagcaac    10620
tgcggcacgt ccgggtacac ctcgacgcgg tccatcagcc ggtggctctc ccggacgaac    10680
ggttcctcca tctcgccggg caggcccatc agccgcatga tgtccgggaa gtagcggccc    10740
tggtgcgtgc ggtactcctc gaagggcggc tcgcccggcc ccaccacttc gcggtaggcc    10800
acggcgaacg cctcgcgcat caccgcgaaa ctgtcgatga ggacgccgtc gaggtcgaag    10860
```

```
accacggtgg tgaaccggca cgggagagcg gtggcgggcg cgtccgccgc ggcccgcgag   10920
gcgggcgggg ggttcagggg catggcagga gctccgtggg tagggacgtc ggggcccaga   10980
ccccggcgtg gctgacgact ttcgtgaagc ggcccgcgag ccggtggtag acggcccccg   11040
gcgagctgtg cggcgggtgg gccgccgcgt ccagcccgcc ccaggcggcc atggccctca   11100
gcagcagcgg atcggccggc acccagcggc cgcccaccag gaactcggcc cagcagtgcg   11160
gtgtggagta cggcttggcc accagcagcc cgaaggagaa ccgcacgtcg agcccgcgcc   11220
gccggccctc cgccaccagc caggccgcgg cgccgccgca gtcggccatg tgcgtgctcc   11280
acaggaaccc cgggtcccag cggatcgctt cgggcagcag gaagaagccg accggctcca   11340
gggtgcgcag caggtcgagg acggccgggg ggaagtccgg ccagtggccg cgcgaccgtg   11400
tgtacagccg cgccagcgtg gtctcccgcg gcgaagccgc ctccaccggg cggcgggcgc   11460
cgggcagcag cactccgtag cggcacgggc ccgcgtggcc gggcaccggg caggacgccg   11520
tgacgtcgac gcgccagcgc gggctctccg cggccgaggc ggtccgcagg gaaccggccc   11580
acgagcggat ggcccggcgc tgcaccgagg acaggccaag gtgcagggcc gcgttgccca   11640
ggtcgtagcc gtcgaagagg cgtcccgcgc cgcttcccac gaagggcacg cccgcctcgc   11700
acagcgcgga cagcagctcc ggtccgatcc ggtgcagccg gcgcgcgctc tgctcgtcga   11760
cggtgaaacg gcggtgctcg tcgggcacga gcttcagacg ctccacgagc gcctggagct   11820
cctgggtgga ggggggccgg gccggcaggt agacgctgat ctcctcaatc ctttcgccgg   11880
ggcgggcagc cggtgcggga cggccggggc ggccgccggt ggggtgccgg gtcagtcgat   11940
gtagcccaga gcctggaggc gggccgccac ctgctgctcg tcgctcgcgg tgtacgccgg   12000
ctcctgcggg cgcggcgcgt agggggagaa ggcgcgcagt gccggggcca cctcgtgcgc   12060
gaacagttcc atggactcga tgcggtgccg gtccgccagc tcgccgaagg tgaactcgcc   12120
cagcagcgtg tcgaaatggc cctccaggga cgcggccctg atccggtcgg ccacggtcgc   12180
cggcgagccg acgaagacga ggttgttctc cagcaggaag cgcaggtcgc cggagcccgc   12240
caggatgtcc gtcgtgctga gcctgctggg tggggcgtgc tgatcgcggg aacgggacac   12300
cgagccgtac cgcagcgtct tggtgaacgt ctcggtgatg tgcgcggccg cccgctcctc   12360
cgcctcggcg tccgtccggg ccacgtggac cagcgtccag tagccgatgc gcgggtcgct   12420
cgcgtggccg tggccgcgcc accagtcgag gtagtgccgg tagaccagcg ccatggaggc   12480
gcgcggcacg atcatcgtgg aactggtgtg ggcaccggcc tcgctgagat agcgcaaggt   12540
gttgcggttg gtggtgggca cccacatcgg cgggtgcggg cgctgcaccg gcgggaagga   12600
cagggcgatg tcgcgcagcc ggtgcgcggg cccgtcgaag tcgaaggcgc cccgcgcggc   12660
gaacgcggca cgcagcagct ccagggcctc ccgggtcagg aggtgacggt tgtcgaaatc   12720
ggcgtcgaag ggcaggaagg ggtcacggct gacgcccgag gcgagcccca cctccagccg   12780
cccgcccagg agctggtcca gggtcgcgac ctcctcgacc aggtgcagcg ggtggcgcag   12840
cggcggcacc caccccatcg ggccgacccg gatgcgctcg gtgcgcagcg cggcgcccgt   12900
gcagaagacc gcgggcgagg gcatccagct ctcgtgcggc gtgcagtggt gctccaccga   12960
gaacgcgtag tcgaagccga gccggtcggc gtcctcgacc tcgcgccaca gctcttcgta   13020
gcgctcgccc ggcgtgatac cgggacgtcc ccagacatgg agaaataag cgaatttcat   13080
tggcttcccc gggtgggcag gacacgtgga caactgacg tgctgggcgc cgcgtcgctc   13140
tgcggccggt gcaggggcga gggagggtcg acgccggcgg ccgaatagat gtggtcgatg   13200
```

```
caggaggcca ggatggtcac ttcggccatc gacccctcgc ccaggcccga caccgggccc   13260
tgcccgtcgg ccgagccgcc gagcctgcgg gcgagttcgt ccacctgccg ccggtactcc   13320
acgcccacgg gctcgtcggg cagcgcgacg gtctcctcca ccccctggcg caggaccacg   13380
aggctcgact tctgtagccg gtgggggctg aagccgaagg tgccgcgcag cgtcgccacc   13440
ccctcggtgc cctccacggt gatcgtggtg acgtccagcg cctggtggga ggcccagcgt   13500
gtctccaggg agatgcccac gtcggtgtcg gtgacgagga agccgcgggc ggtgtcctcc   13560
accgtctccc cggggcctgg ccgcgccgtg ccggaggagc gccggctcca gtcggccgtg   13620
gcctcgcccc ggctcatcca gtccgcggac atcgtgctcg ccgcccggac cacgcgcggc   13680 cacccccagca ggtgcaggcc cacgtccagc aggtgccagc ccaggtcgag cagcgcgccg   13740
cccccggcga gccggcggtc gacgaaccac ccggtgcgct gcgggatgcc ggtggcccgg   13800
atccagctca gcccgacact gcgcacggtg cccagcgagg gcagcagctc cgccaggcgg   13860
cagacatcgg tgcggtgccg ggcggcgctc caggcgtaga gggtgatgtc cccgatgctg   13920 tcgcccccgcg cctggtggtc cagggcgagc gcctgggcct cgaagagcgt gcggcacacc   13980
ggcttctcga cgaacaccgg cacgtcccgc tccaggaggg ccttggccac ggggagatgg   14040
aggtggttgg gcagggcgat gatggccgcg tccacgcttc tggggcgag ctcttccggt   14100 ctgctcagga cgcgggtccg cgcgcccctcc ggcagggcc acctggccgc cacggggtcg   14160
tcgtccacga ggaagtcgac ccggaacgcc gggtgttccg ccagcagcgg cagccacacc   14220
ttgcgcgaga cccatcccgc gcccagcact gccatccgga ggggttcgcg agctgtcgtc   14280
ggcggtgtca cgacgggtgc cttctccgtg aaagtcatca gaagcgggca ccaccgtcga   14340
cgacgagcgt attgccgttg acgtacgagg ccgacggcga cagcaggaac gacaccgccg   14400
ccgcgaccct ctccggctca ccgagccgcc ccgccccgat gaactgcagg accagatcgc   14460
gctcggcctc cgagaagtcc atcacctcgg cgcggatcgc cccgggcgcg acgacgttga   14520
cggtgatgcc gtgcttgccg acctcacccg ccaccgacgc cgcccacggc tggagcgccc   14580
ccttggtggc ggcgtacgcg ctgtggccgg gcagcccgct ggtcccggcc cgggagccga   14640
agagcacgat ccgcccgtac ctggcgcgca tcatcggctt caggcacgcc ttggcgagac   14700
ccacggaacc ggccaggttg acccgcagca gcttctccag gctccgggcg tccgtggcca   14760
tcgcgagccg gcgcgtacgc aagcccgcag cagccacaca gccgtccacc cgcccgaacc   14820
gttcgacggc cgccgccacc agcgcgtcgg cgccctcggg ttcgctcagg tccgccgcca   14880
cgggcacgag ggtgccgccc tggccctcca cctgctcccg cagcttgcgg atcgcctgct   14940
cgccgctgtg gtagccggcg acgacggtgg cgccgagcgc ggcgagctcc agcgcgcacg   15000
cgccgcctat ctgcccggac gcgcccgaga ccacgaccac gcggccgctc tgtcccaggc   15060
gctccgtggc ccggtcggtg acggtgctca tgaaccggcc tccttggcga tgatcagatg   15120 acaggggac gcgtccagcg gcacgtgccg tgcgacctcc gcccctctt gcagcagccc   15180 ggcgatcagc tcgccggtgg ccggccacgc ggtcccgccg tgcgtgagcc agtccagagc   15240
cagttcgctc cccggcccgg acgccggcag gaagacgtcg tcgaccagca gccgcccgcc   15300
cggccgcagg gagccgagca gggcaccgag agcgctgccc ggccccgggc cgtgcacggc   15360
gttggcgacc acgcagaagt cggcgtagcc gacgggcagt tccgtcccca cggtcaccct   15420
gccctcctcg accgccgcgg cgacggccga ggagagcggc ccgctcagcc ggccgacggt   15480
gaccagatgg ccgtcgcccc cggggtccga ggcgagcagg cgttccagat agcggcccgg   15540
gcccgcggtc acctccacca cccgggctcc cggcccgggc cgcaggagcc gcaggccgag   15600
```

-continued

```
cgcggcccgg gcccgtgcgc cggggccgtc catcgcgccc tggtacaggg cgacgagcgg    15660
accgaggctc tcgggggac gctcctcgaa gggacgccgc gccgtcccgc tccgggccac     15720
cgcgacgagc tcctcgcgcg tgaccagccc acgggagagg tgctcctcca gcgccacgaa    15780
cgcggccagc tccccggccc ggacccggtc ccgggctct tgcgcccgg tggtcagcac      15840 ccccagagcg gtggccgtgc gcagcagcca ctccagggca tccgcgtcgc accccagctc    15900
cccggcgagg agagccgtgc cggcaccctg ggcgagtgcc tccagggcgc ccaagtcgtg    15960
cagcgcgaag agcacttcgg atgccttgta cgcccgggcg gcctccgccg cgctccgggt    16020
gaggcggtag acggacgccg cccgcacctt gcccgcggcg ttgaccggca ggctctcccg    16080
caggacgaac tcgtcgggca ccttgtgcgg ggccagctcc cggcgggcgt gctcgcgcag    16140
cgcctcgggg gtgagccccg gccccgccgc cgagacctcc gcgacgatcc cgtcctcgcc    16200
ccggtgccgc ccccgccggg cgcccacccg cacattcacc acgtccggat gaccgcgcag    16260
cacctcctcg atctccagcg gggagaccca gcgcccgccc cggcggatcg cccggtcctc    16320
gcgtcccagg atgcgcaggc ccccgggcac ggccacggcg agatcgccca tggcgtacgg    16380
ccggccgtcg acccgtacgc tcagcagccc cggggtgccg gcgggcggca ccacgccctc    16440
cgggccggtc agttcgcact ccaccccccgg caggggagca ccggcgcaca agggctccag   16500
ccccgccggt ccggcgagca cggcgcccgt ctccgtggaa ccgtagttgc gggcgagacc    16560
ggtcccgaac gcctcggtga acgcgcggtc cagctgctcg tccaccggcc ccgcacccac    16620
catggccagc cggagaccgg gagcggcggg cgcccgcccg gccgctgctc cccgcagccg    16680
ccgggtcgcc agcagccggg ccacactggg caccagggcc accacggtcg caccaccgga    16740
cagctccgcg gcgatgcggc cgagggcggt cggcggtacg gggcgcagcg cggcacccgt    16800
cagcagtccg ccgaacagcc agcccagcgc gtacgcgtgg gacagcggca ccggcagcag    16860
cagggtgtcc tctcccgtca gcccgacccc gtcgcggtag cggcggccct ccgcgagcag    16920
gctctcctcg ctgcgggcga cgagcttgct cgcaccggtc gaccccgagg tcgggagcag    16980
cacggcgggc ggggcgccgg agggttctcc gggcgagccg gtcaacgtca ggcggaggcc    17040
gtcgccggtc ccggggacga ccagggacct gccgccccg gcagcccgca gcagccgcgc     17100
ggtctcgggg ccggggggtgt cgggttcgag cagcagggc ctggcgccgg atgccagcag    17160
ggagaggaag gcgacgaccc accgcgggct gttgggcgcg cgcagggcca ccgcctcgcc    17220
ctccaccgcc tcggccttga gctgtgccgc ggccgtacgc acctgctcca gcaggagtt    17280 cacatcggtc ccgggcagcg gtatccggcc ggacggcagc cgttccaccg cgcccaggag    17340
ggtgtccgcc tcgtgaccgg tcgcctgttc agtcatggcc gccctggagg tagtcggcct    17400
tcgcgtcgct gagcatctgc cggatgcggg gcggggagta ggtgggagcg cgcacagct    17460 cgtcgagggt gatctcgtcc tcgaagtaca tcgagagcgt gtcccagggc gtgaagcagc    17520
cgtggcacgc cttgagccgg ggcttggggg cgagcagggc acggtagagg ccgctggtgc    17580
ccaccgtgtc cagcatctcg ctccagtcgt cctccagggc gttgcccatg tcggagaacc    17640
agatgttggg gcagggcgtg acgacgccgt cgctgaagct ggagacgacc agccgcggca    17700
gatggcagcg gaaggtgcgg cggccctcgc ggtagaagct cgtcagccgg tcgaagtagg    17760
gccgcggcgg gaggacccgc gcgaactcgt cgtagcggtc gacgagttcc tggatgtggc    17820
cgaactgccc gggccgcacc ttgaagtcct ccgagtccgg gccccgcacc gggaagggga    17880
agtagacggg aggccgggag aatcccgaca gccactcggc gaacgcgcag acctccgtga    17940
```

```
cgctccggtc gttgagcact gaatagatct ccaccggcag ccccgagtcc aggatccggg   18000
cgatggcggc gacgaccttc tcgtgcaggc tcccggacgg cacacgatgg ctgttgccgt   18060
ggtggaggtg gctgtcgagg gagacctgga gcacgacgtt gccccacgag cggaaccgct   18120
ccaggtgctc ctcgcgcacc aggacaccgt tggtctggat gaccagcacg tcgtatttac   18180
gggcctcctg ctccaggaag tccatgatcc cccggaccag gaagatctcg cctccggtca   18240
ccttgagcag cggcaggccg aagcggtccc ggatccggtc ggcgaccttg tccatgcgct   18300
gccccagccc gctgtccttg gcgtagctgt cgcgccgcgg gggctcgaag atcagttgaa   18360
gggagtggcc ctccttgagg ttgctctgtc cggtgaggca gtaggtgcag ctgaggttgc   18420
aggagtcctc gttgatgacc aggtcgttgc cgatcagcgg caggcgtcgc ctggtgcccg   18480 cgtcggggt ggctgtcggc gggtgggtgc tacgggacat gagtggcctc tctcgtggtg   18540
gggctgcgca cggcgtgggt cacggccccc tttccacggg tgccggccgg gcctcgcccc   18600
ggtcgtcctg gccgacgggc acccagtggc ggtcggcgtg gccgggccgg ccgggcccgc   18660
cgtgtgcgcg ggcgcgggcg aacagggcct cgccgcaggg c ggccgcaccg ccgaagtggg   18720
cgctcgcctg gctggagtag tgaccggcgg cggtcagcca gcggtccacc gcctcggacg   18780
gcagccgttc cgtgcgcggc cgcaggttcg tgtggtcacg ttcgcgcagc cggtagggga   18840
agtcctcgta gaagacggta cgggcggggg acagggctc caccgcgccg cggaccaggc   18900
ggtggtcgac gtgccggccc gccgccaggg gaacgtggac gctcgacgcc cccgcgcaca   18960
gcggcagcag agccgcccgc acctcctcca gcagcggag g tcggccggg tgccaggggc   19020 cgaagagccg gcgcgcggga a gcgtagagat aggcgcccga ggccgtacgc agtgccgcgt   19080
cggtgaagcc cagcggcacg tggcgcacgc ccagttcggc acatgccgcc cggtcctcgg   19140
cccggcgcac cgcgggatcg gcggcgctcc gccacgactc gggcttcccg gccgcgggcc   19200
cggcgaagac cgtgacgacg tcggccgcg ggccctcggc ggcccagcgc gccagccgcc   19260
cgcccaggga ccacacggcg tcgtccgcgt gcggggagag caccacggga ccgtacggcg   19320
cggtggccgg tgtgccgctc atcgcgccgc gtcccgtgcc ggtgcggcct cttcggccag   19380
gacggcgcgc acatacgcct ccggcgtgcc gtcgggcccg agcagggcct ccaaggcgcg   19440
taccgacggg tgcgggtggc cggcggagaa gtgcgtgagg ttgcggtggt gctgctccca   19500
gcggccgggg cgggcgtggc tgaggtgcac accgagggcg tcggggcga gggtcctgcg   19560 cagcccggcg gcgtgcaggc ggaagccgaa ctccaggtcc tcgcacccc c aggtgagccc   19620 gaactcctcg tcgaatccgc cggtatgctc ccatgcggcc ttgtcgaggg cggtgttcgc   19680
gccgatgaag ccgagccagg gggcgacgtc cggcaggag ccgccggcca tggcctccac   19740
ggcccgctcc agggcgttgg cgacgagccg ccggtgcggt tggcgccgct cggaggcggc   19800
cggggcagcg ggttcgagtc cggcgcgggc gcggcggacc tcggtcgggg cggccttctc   19860
gacagcggcg aggaaccgcg ccgcggtggg gagttcgcgc agccggccgt gggtgaaggc   19920
gtccggttcc gcgccgcgg cgtgtgcgg g gaggaagccg ggcccacca ggacgtcgtc   19980 gtcgaggaag accagccggg gcgcgagggc gcggccgcc ccggcgttcc gggcggcggc   20040
ccgcccccgc agcggtcccc gcaccacgcg cagcgggaga aggccgctca tctcgcctgt   20100
cacggcgatc agttgatcac cggcgtcgcc cccgtcgttg tcgtcgacga cgaccacttc   20160
gaagggcggc gttccggggg agggg ccggc aaggcatgcg agggtcgcgc gcaggcgtgc   20220
cgcgggcccc cggctgggga cgacgacgct cagccggggg gcggtggtgc cgttgggggc   20280
ccgcatcggg tcagagcgcg ccgacgaggc cggagaagac ctccgccagc cggtccagcg   20340
```

```
tggtcacgtc ggcgagcagg acgcgatggt gcagccagag gcagtcgctg ccgatctcct   20400
ccgccacggg acagctcttg gccagctcct cggcgtccgc cggcgccggg ccgcgcgcga   20460
aaccctcggt gcggtagacc ggcgggaagc cgacgaacgc gggcactccc cgctcgacca   20520
gcgcgtccac cagcgcgagg cggcgccggg ccgagatgcc gggcagccgg accatggcca   20580
tgtagtggga gtggaggtcg ccgcgctcgt cgcgccctg cggcaccacg ccgtcgatgg    20640
cggccagtgc cgtacgcagc tgggcccagc gctcctccct gatgcgcaac tgatccttca   20700
agcgcttcag ttgagcacgc aggacgctcg cggagaactc gttcatgcgg tagttggagc   20760
cctgcgtcag atggcggtag acgcggtccc cgggcgggcg ccgcagcag tgctggagga    20820 acgcctcgtg gaaggactcg tcgtccggca ggagcagggc ccgccctcg ccggcggtca    20880 tcagcttgcc gttctggaag ctgaaggcgg cgatcgagcc gagctccccg accggcggc    20940 cctgccactg cgcgccgtgg gcgtgcgcgg cgtcctggag gaccggcacg cccgtcgcga   21000
cggagagctt ctccagggcg tccatgtcgg cgaactggcc cgccatgtgg accggcatga   21060
tcgctttggt gcgtggcgtc accagcgccg ccgccgcgtc ggcatcgagg cagtaggtgt   21120
cgggccgtac gtccgccggc accggcaccg cgcccatgcg ctgcacggcc agcgacgacg   21180
agatgaaggt gaacgcgggg acgatgacct cgtcaccggg gccgatcccc atgaccccca   21240
gggcgagttc cagggcgtgg gtgccgttcg tcgtggcgat cgcgtgcggg gcgccgtggt   21300
ggtcggcgaa ctcccgctcg aagagatcga cctcctgccc cgcgtcgcgc caccacccct   21360
tctggtccag ggcccgcagg agtccggcgc gctcctccgc gccgtgttgc ggccatgagg   21420
gaaaggacag gacgtcatca ccggacgtag gtgtcattga gcagccttc ggtcctgcgg    21480 gtgcggcggc acgtcgact tcggggcgct gtacggcggg agggcgggtg tcgaggcctt    21540
tgccttcggt ggccgtggct tcacggcccg gttccgttgt gttcgccccg cgtcgggaag   21600
ggtggtgcgt gacccgacgg gaaacgccgt tcctcggggg cggcgggaaa tccggcccgc   21660
ggtgtgaggg gtggccggag cgggcatgtg atccggcccc cggtcatagg ccgggatcgg   21720
atgccagaca cgagcctcca tagggcagtt gccggagtca acacccttgc cgggaaggtc   21780
tgccccgacc gccggtcggc ggtggattct cgtcagcagg gtggttgagc agtgaaactg   21840
ccttattccc aagggaattg atccagttca ggggctgctc ggcgggcctg tcggcaacgt   21900
tatccggcgt cgaagtggct caaaccgcac ggctggaggg agcgggaagc gtcgcgtatg   21960
gtgggcgcga caccgtcctg gtatgtgctg tgtgcatggt tcattgagcc gaatcccact   22020
ccggccctcg gatccgggcg ccatacgatc accgttgtcc ggtctgtgga cgcaccggtg   22080
aggggctgtt acagtcctcg gatcatcgat gagcggcggc agtttctgcc tgcaatcgtg   22140
atgagttctc agagctggag gcaatttcgt gccaccctct ccccgcgccc tcgtcatcgg   22200
aatcgacgga ggcacattcg atacggtcga cccgctgatc gagtgcggtc tgctgcccca   22260
tatggcgaag ttgctgcgcg agagcgccag tgccgccacg gactgcacct ggcccgccca   22320
cacggcgccg gggtggagca cgttcgtctc cgccagcgat cccggcggtc acgggatcta   22380
tcagttctac gacacccagg acccggccta cggggcccgc gtcacgcgct ccggcgacct   22440
gggccggtcc tgcgcctggg actggctcgc cgcgcaggaa tattcgctgg gcctcatcaa   22500
catcccgatg tcgcacccgc cggccgacct ccccggctat caggtcacct ggccgctgga   22560
gcggacactc aagcactgcc gcccggattc cctgctgcgc gaactcgccg cggccaaggc   22620
ccatttccag tcggacctcg cgaccatgtt ccggggcgac atggcctatc tggaggaggc   22680
```

-continued

```
cgagcgcaat gtggcggcgc gggtccgctc cgtacggcat ctgatgagca cccggcccac   22740
cgatgtcgtg atggtcgtgc tcaccgaggc cgaccgggtc ggccaccact actggcacta   22800
cggcgacccc ggtcacccgg gccaccggcc cgccccggag ggcagcggct gggacgtcgc   22860
catgccccgg atctaccagg ccatcgacca cgcggtgggc gagctcctgg agctcgtgga   22920
cgaggacacc tccgtcgtgc tcgtctccga ccacggcctg gcaccgggc gccacggcct   22980 gtcggtgcac accctcctgg aggaggccgg gctgctggcc accgcaccgg gggaggagcc   23040
gcaggacgcg gcggcgagct ggttcgcggg caacggccgg cacgtcgact ccgccgcac   23100 cagcgtctac atgcccgtcc ccggcagcta cggcctcaac atcaacgtac gcggacgcca   23160
gcagcgcggc accgtcgcac cccgcgaccg gaacgcgtc atggacgagg tcacgggcct   23220
gctctccggg ctgaccggcc cgagggaca gcaggtcttc cgggccgtcc gcccgcgcga   23280
agaggcgtac ccagggccgc acaccggccg gcacccgac ctcctcctcg tcccgcggga   23340
cgagaccgtc ctgcccgtcc ccgacctcgg cggtgacgtg tggcggccga gcgcgcagac   23400
cggcctgcac cgctaccgcg gcctgtgggc gcaccgctcg ccccgcgtcc gccccggccg   23460
cctgcccggc accgtcgcgc tcaccgacac cctgcccacc ctgctcaccg acctcggggc   23520
cgcatggccc agcgacatcc acggccgccc cgtgaccgcc gtcctcgacg acggcgtacg   23580
cgtcccgccc tccgacccc gggtcgaggc caccggcacc ccggccacca cgatcccggc   23640
cgccgcttcg gccgctgatg ccgccgagga cgcgtacacc agcgaccgct tgcgcgaaat   23700
gggctacctg taagcaccgc cgggccgtac cggcgcttgt ccccaccgga gtcccgccgc   23760
tcgcggcggc gtggaggaga gaggtatttc tgccatggag accctgacga ccgacaagat   23820
caaggaccgg ctgcgcaagg tgctcgtcga ttccctcgaa ctgtccctgg acccctcggc   23880
cgtacccgac gagggactcg tggagaagct gggcctggac tcgatcaaca ccatcgaatt   23940
cctcatctgg gtcgagagcg aattcggcat agagatcgcc gacgaggacc tgtcgatcaa   24000
gctcatcgac agtctcgacc tcctcgccgg ctatgtgtcc gagcgcgtga acggcgtcac   24060
cgcacccgcc gaatgacggc cgtgcgcgcg ctcgcctccg ggcccactcc ccgcagcgga   24120
aggacgtgag cacgatggac cggcacgccc tggtgatcgg gctcgacggc atgccgagga   24180
ccctgctgac ccgcctggcc ggcgacggga ccatgccgca caccgcggcg ctgctcgccg   24240
agggccactg cgcggaactg ctggcacccg taccggagat cagctccacc tcctgggcca   24300
ccttcctcac cggcaccaac ccgggccggc acggcatcta cggcttcacc gacctcgccc   24360
ccggcgacgg ctaccgcatc accttccccg gtgtgcggca gctgcgcgaa ccccgctgt   24420 gggaactcgc cgcccgcgcc ggccgcagga ccgtgtgcct gaacgtgccg ggcacctacc   24480
ccgcccccgc catcgacggc gtgctggtct ccggcttcgt cgcgcccgaa ctggagcgcg   24540
ccgtcagccc gccacggctg ctgccgctgc tgcgcggcct cgactacgaa ctcgacgtcg   24600
aggtcggcga cgtcgccgcc gacccggccg ccttcctcgg gcgggccgtc cgggccctgc   24660
gcgcccgcac ccggccgatg gaacaccctgc tgcgccagga cctgggac ctcgcggtcg   24720 ccgtgctcac cgagaccgac cgcgtccacc acttcctgtg gcgcgcggtc gccgacccg   24780 ccgacccct ccacgggac gtcctcgcct tctaccgcct cgtggacgac tgcgtcgcca   24840
ccctggtgag caccctccca ccgggcggcg aactcttcct gatgagcgac cacggcttcg   24900
gacccgccgc ctgtcaggtc tatctgaacg cgtggctcag ggagtccggc tggctggcca   24960
ggctcgacgt ctgtccggac ctcaccgcgg tcgacgctcg cagcaccgcc ttcgcgctcg   25020
accccgcccg catccacctc aaccgcaaga gccgcttccc cggcggcggc ctgaccgacg   25080
```

-continued

```
cggaggcgga cgaggccgcc cacgagatcg cgcgcgagct gtccgccctg cgctgcgacg    25140
gcacccgcct gggccccgac gtcgacggac ccctgctcgt ccgcgacctc taccgcgctc    25200
aggagatcta ccacggcccg ctgttgggca acgcccccga cctggtggcc gtaccggccc    25260
ccggggtgca gctgcgcggc ggctgggcg gcacgcacac cgtacgcaac gacatcctca    25320
ccggcaccca caccgcgac gacgcggtct tctaccggcg cggcgcgccc cgcccgccc    25380 ccggggcgga cgacggcccc ctcgacatga cggacgtcgc cccgaccgtc ctcgcctccc    25440
tgggcatcca ccccggcggg ctcgacgcg cggccgtact cggcaccacg ggacccgcgt    25500
ccggtcacgg ccgcacggac cccctctcg acatcaggga gctctgatga agcacgacct    25560
cggtctggca ccatcggcac ccaaaccggg aacactcgac ctgagcctgg acccacgcat    25620
cacggacccc gcttccttcc gggtcagttt cctgatcctc ctcgacggcg acctcgtgat    25680
gtcccccgaa cacctcggcg tcgcctacat ggccggtgtg ctgcgccata cgggcttcac    25740
cgcggagatc cggaggtgg agcacggcga cgaccaggcg gccgccaccg tcgaggcgct    25800
caaggagtac cggcccgacc tcgtctgctt caccctgatg agcctgaacc tgggcagctg    25860
tctgaccctg tgccggatgc tgcgggagga gctgccgggg acgacgatcg cctgcggcgg    25920
cccagccggg accttcgcgg gcctggacgt cctgcggaac aaccctgga ccgacgtcgt    25980 cgccgtgggg gagggcgagc ccaccatcct cgacctcgtc caacggctct acctcaagga    26040
gccgttgtcc gcctgcaagg ggatctgcta ccgcgacgag gacggcacac cgcgccagaa    26100
ccccgcccgc cccctgatcc acaacctgga ggacctcccc ttccccgccc gggaccagct    26160
gcgccagcac ggcgacaagc tggagtacgt ccgggtcagc accagccggg gctgcgtcgc    26220
caactgcgcc ttctgctccg ccccgcacct gaagaaccgc gtccaggcgg gcaaggcgtg    26280
gcgcggccgc gggccggaac agatcgtgga cgaggtcgcc gagatcgtcg aacgccacca    26340
gttccggacc ttcgacttcg tcgactccac cttcgaggac cccgacggcg gccgggtcgg    26400
caagaaacgg gtcgccgcca tcgcgaacgg catcctggag cgcggcctcg acatctacta    26460
caacgtctgc atgcgggccg agaactggca cgacaccccc gaggaccacg ccctgctcga    26520
cctgctggtc gcctcgggcc tggagaaggt caacgtcggc atcgaggccg caccgccga    26580 ggaactgctc ctctgggaga gcgcgccac cgtcgaggac aacgtcacca tcatcaggat    26640
gctgcgggaa cacggcatct atctcgccat gggattcatt cccttccacc cctacgcgac    26700
cctggagacc atcgtcacca acgcggcctt cctgcgcgac aattccggcc acaacctccg    26760
gcgcatgacc gaacgcctgg agatctaccc cggaacggcc atcgtcagcc gcatgcgggc    26820
cgacggactc ctcggcgaga gctatctcga agggctcgac ccctacggct acgcattcaa    26880
ggatccccgc gtcggacggc tcgccaagca tttcgcccag ctctacaaca acgacgacta    26940
ccaccggcac ggcgtcatca ccgagcagtc ctccgtcttc gccttcgaga cctacaacgt    27000
cgtactccag accttcatct cccggctgca ccgccggttc accaccctgc cggggtgga    27060 cgaggtgatg gaggcattca aggcccgggt gcacgagatc cgccaggaga tgggccggca    27120
caactacggc ttcttcatgt ccaatgtcga ggcggtcatg aacgacaccc tcgacccgga    27180
gaagcagcgc cggcaggtgg tggacgtcga gcacttcttc cgcgaccgcc tcgatgtgtt    27240
gcgcagcgag caattgcgcg tcggcaaggc cctcacccgg ctcggcgccc gggtgacgga    27300
ggtcagctcg accattccca aggagcgccc cggcggactg ccgcgccagt acacgggaga    27360
gggcagcggt gccacgtggt gagacgggaa ccgccgcggc gcgggtggcg gtctgcacgc    27420
```

```
tgagcagcag ggaactggtc ggcccgctgg cccggttgcc cggtgtggcg gccgcgggca    27480
cgctgatgac cgccaacctg ggcatcgagc aggtgatcaa ggccctgcgg tgcgaccgga    27540
cggtccgcgg cctgctcgtg tgcggccgcg actcaccccg cttccgcgcc ggccagagcc    27600
tgatcgccct cttccgccac ggcctgcgcc ccgaggacgg cacatccgg ggagccaccg     27660 gctatctccc cgtcctgagg tcggtgacga cgcgggagac cgaggaggta cgcgcccgcg    27720
tcgagctggt ggacgcccgt ggcgagcgcg acgtcgagac gctgcgcgcc gaggtcgcgg    27780
cactcctcgc ccgcgtacgg cgcacccgg  ccctcccctc ccgcgagcac gacggcggcc    27840
aacccagctt cgtggagccg gacttcggac ggctgcatcc tgtcggccgc cgccgctccc    27900
tggacgcggg catcggcggg ttcgtgctca tcagcgtcga ccgtgagcac cggcggatcc    27960
tgctgcgcca ctacacctcc gatgtgcggc cccggcacga gatgtggggc accgcggggg   28020
aggcgatgct gctcgggctg ctggaggccg gcgtcatcga ggaccccgcc cacgccggat    28080
acctcggcgc cgaactggcc aaggccgaga cggcgctgcg gctcggcctg cactacgaac    28140
aggacctgcc cctgcgcccg ccgggcaggc cgcccgcccc tgtgcggcgc cggaccgcga    28200
aggagcgaac gaccatggcg caagcacccg cgctggagga cttcctgcgt ctcgtgacga    28260
ggacgctggg ggccgaggac gccgtcctgg acctgcacac gccgctcggc gagcaactgg    28320
cggtggactc cgcccggctc atcgaactca ccgtcgtcct ggaggaggag ctcggcgcgg    28380
acctccccga cgacgccgac ctcgccaggg ccaccccgc ggaactccac aaagcactcg     28440
tgggctgagg aggagaccga catgcgcagc gtgctgttgc tcaacggacc caacctgggg    28500
acgctcggca gcggcaacc ggagatctac ggaaccgaca ccctggccga gatcgaggcc     28560
gccgtggccg aggaggtggg agcgcgcggc tgggaggtgg tctccgaaca gcgcaacggc    28620 gaggggggaac tggtcgatgt gctccagcgc cacgacgacg tggtgggcgc cgtggtcaac    28680
cccggcgccc tgatgatcgc cggctggtca ctgcgcgacg cgctcgccga cttcgccccg    28740
ccctgggtgg aggtgcacct gagcaacgtg tggggacgcg aggcattccg gcacacctcc    28800
gtcacggccc cgctggcctc cggcgtcgtg atggggatgg gggcgctggg ctaccggctg    28860
gcagcgcgcg ccctcacccg gctggtcccc gaggactgac ggtgacccgg cccggcccgt    28920
acgcacctcc agatgggacc ggcccgcccg gcagggacgc cacctcggcg cccggcccgt    28980
acgcacgctc aggcgggcca cacccgcagc tcctccttga tcacctgagc gccggcctgg    29040
tcgcacgccc cggcagcgg gcaggccgcc gggaggatcc gcacggtgaa cggcccctcg     29100
gtcaggccgc gccaggcggg gaccacggcg cgaccgcggt ccacctccgc ggacaccaag    29160
gccgtgaccg gacagggaaa ttgaccggag acctccccgc ccaccccttc gccgggcccg    29220
cggctgccga gccacagcag cacatgcacc ggcgggcgcg cggcccgctc ggcggcccgc    29280
agcgccgcgc ccagcccggc accggcacag accagcgccc acggcccgcc gtccccggcc    29340
gcctccgcga tcgcctcgac gccgtgctcc accaccagtt cggggggcgag cgcctgccgc    29400 cagccctccg cgtccggccc gtccgtcacg gcgaccagcc ggaccaccgg caccaccacg    29460
cctccggcgt tccctcagc cgtacgcgac atccccagac cctctcttcc gtaccgtccc     29520
acccgccctc gctctcccgc ccggcgccgc tacggcaggc cgtcggtcat cccgagggag    29580
aagtagttct cgtaccccag cagccggcgc agttcgggcg tcgcgcgggt ggcgacgtcc    29640
tcccgcagac ccgagaagaa gttctgctgc tgccggacgt agccgcggca gtagtagttg    29700
aggatgccgt gccgcggccg gtcggtggtg ttggcgcccg tctggtgcca caggcgcccg    29760
tcgaagacca tcacgctccc ggccggcgcg cacacggcga ccgtctcggt gttccctcg    29820
```

```
ccccggtcgt agtccggctg ccggcccagc agatgggagc cgggcaccag gcgggtcgcg    29880
ccgttgtcct cggtgaagtc gtccagcatc cacatgctgt tggccaccag cggatacggg    29940
ggccacggcg ggcgggcgaa ggtctggtcc gcgtgcagat gcatccggga accgccgggg    30000
cccgcgatat tggcgtgcgt gctggagagc aggaagccga agcccaggat ctcctccatc    30060
aggagcatga cggtgggatc ctgcacgttc tgctcgaatt cctcgccctt gttcagcagg    30120
ctgaagacgc gttggttgcc gccgtcgtag agaaaggccg agccgttctc acgctcctgc    30180
tcggcgacct ccagcagccg ccctctgagc ttttcgaaga ccgcggccgg caaggggcac    30240
tcgatcaggc agtatccggc ttcgaccaga tcccggagg ctttctcgac gtcattcgtc     30300
aaagtcgcat ccatatggcg aggctagcag ccgaaatctc ggccgcacca tagcgcgaaa    30360
acgccggtcc atgatttttt cacgtgcggg aaggacggat tttccatggc acactcaccg    30420
cggcggccga acgcccccct ccgcatcggg gtctggctgg cccccagca cacctcggtg     30480
gccgaactgc gcgccgcctg gcgcgcggcc gactccctgg gcgtggactc gctgtggctg    30540
tgggaccact tcttcccgct caccggggac cccgacggca gccacttcga ggcctggacc    30600
ctgctggcgg ccatggccgc cgacacccgc gccgcccgcc tgggcaccct ggtgtccaac    30660
tacgcctacc gcaaccccga cctcctggcc gacatggccc gcacggtcga ccacatcggc    30720
gacggccgcc tgatcctcgg catgggcgcc ggctgggtcg aacgcgacct gaaggagtac    30780
ggctacccca cgcccggcgc gggggagcgg gtggacgggc tcatcgaggc ggtggagcgc    30840
gtcgaccgca gactcggccg gctgcgcccc gggccgctcg gcgacctccc cctgctcatc    30900
ggcggggacg ggcagcggcg cctgctgcgc ttcgccgccg aacgggccgc catctggaac    30960
accatggcct ggcgcttcgc cgagggcaat cgcgtgctgg acgagtggtg cgcgcgggtc    31020
ggccgcgacc cggcggagat cgagcgcagc gccttcgtca cccgcgacca gaccgacgag    31080
gagctgcgct gcctggtggc gacgggcgtc cagcacctga tcttccaggt cgggcacccc    31140
ttccgcttcg acgcgtgga gcgggccctg cgcttcgcgg gcggctggag caaggggtaa     31200
ggccagggcc cggacgcgcc ccgcgtcgcc actagagcaa cgcgtccgcc agccggtcca    31260
cttgggacag cgccgccgcc gtggggtgga ggacgacctc gtccaccccg ccgtcggcga    31320
gcgccgagac cgccgcgcgg agctgccccg cggtgcgcgg ggtcttcgcc acgaactcct    31380
ccgcctcctc gcccagcacc gcgaagtagt cccggacgaa ggccgccgac tcctgggcca    31440
cgtcctcgcc caggtgtag cgcgccagcg ccaccacatg cggcgcccg gcgcgtcccg      31500
cctcgctcca ggcgcggcgc acccgttccg cgaccggcac gatccgctcc ggctccaggc    31560
cgggcgccgt ccagccgtcg gcccagcgcg ccacgcggcg cacggccgcc gcgctgaccc    31620
cgccgacgag gaccggcaca ccggggcct ccgcgcccgg ccgggcgccc cggccgagca     31680
gctccagctg ctcctcgaac gccgcgcgcc ggtcgtcgaa ggcgcggccg gcggcctcga    31740
agtcgtcctc gcgcacgccg ggcccgaccc ccaggtgaa ccgcccgccc gacagcgagt     31800
ccagactcgc gaccgccttc gccagcacag gcgcggtgcg cagcgggccg atcaggacat    31860
tggtgagcag cccgatccgg gaggtcgccc cggccgccgc cgccagcgcc agcagcggat    31920
cgtggcccga atacaccagg cgctcggtgg ccgcgagcga ggcgaatccc cgctcctcgg    31980
cccgccgcgc ccaatcggtt atcaggcgcc cgtccgcgcc gggcacggtg ttcggcagag    32040
caatgctgat cttcattggt ctccccgggg gttcgcagga tttccggtcg aatgtgacag    32100
gggattccgg cacggccggc gtgattgcgg caggagttca ccagcggccc ggcgcggaga    32160
```

```
aatgcggcgg catttccacg gcccctgtc ggaccgccgg accgccgtgt acgttttcg    32220 gaaagcaacg tcgtacggtg cgcacagcga gaggaatccg cgatgccgc tgccggaaaa    32280 gtcgccgtga taggactcga ctccgcgact ccgcagtaca tgttcgaccg gttcgccgag    32340
gacatgccgg tgttcaccgc cctcaggcgc aagtccctgt ggggtccgat gcgcagcatc    32400
gacccgccca tcaccatgcc cgcctggtcc tgcatgatgt ccggccgctc gcccggcgaa    32460
ctcggcgtct acggattccg cgaccgcggc gcctacgact acgggccgtt gaagttcgcc    32520
acctcccaca gcatccaagc cccccggatc tgggacgaga tgacgccgc cgggcgctcc    32580 agcgtggtcc tgggcgtccc cggcacctat cctccccgccc ccatccgcgg ggccatggtc    32640
tcctgcttcc tggctccctc cacacagtcg cgctacacct ccccgccccgg cctcgccgac    32700 gagctggaga agctcaccgg cggctacgcc ctggacgtgg aggacttccg ctccaccgac    32760
ctggaacgcg tatcccagcg cgtcttcgac atgagcgagc agcgcttcga ggtcgcgcgc    32820
cacctggcga ccacccagga gtgggacttc ctctccttcg tggacatggg ccccgaccgc    32880
ctccaccacg gcttctggaa atactgcgac cccgaccacc cgcgccacga gccgggcaac    32940
gcctacgccg gtctcttccg cgactactac gcgccctcg accggcacct cggccgcttc    33000
ctggagagcc tgcccgagaa cacgaccgtc ctggtcgtct ccgaccacgg cgcccagccg    33060
atggtgggcg ggctcttcgt caacgagtgg ctgcgcaagg agggttacct cgtcctgacc    33120
gaggagcccg ccggacccac ccccgtcgcc caggccgccg tcgactggaa gcggaccacc    33180
gcctgggccg aaggcggcta ctacgacgga atcttcctca acgtcgaggg ccgggagccg    33240
cagggcacca tcccggccgc ggagtacgag agcacccgcg acctcatcgc ctccgccctg    33300
gaagcgctgc ccgacgacca ggggcagccg atgggcaccc cgcgccctgcg ccccggcgag    33360 ctctacggag aggtcaacgg catcgccccc gacctcctgg tctacgtcgg caacctgcgc    33420
tggcgggccc tggccaccct cggcatgggc aagggcctct acacgacgga gaacgacacc    33480
ggccctgacc acgccaacca cggggacacc ggcatcttcg ccctcagcgc cccggcatc    33540 accccccggcc gcgcggacgg cctgtcgctg tacgacgtgg ccccacccct gcgggaactg    33600
ctgggtctcg cgccgcaggg ctcccgcggc tccctcctcg gctgacatca cccgcccagc    33660
agcgcgtagg gagtgggcgg cgccggcacc ccgcccgctc ccgcaccgcc accgtgcacc    33720
acgtgcttgt ggcggtaggc gtccagctcg ttggtgagcc ggtcccagac ggcggagcgg    33780
ggcccggctg tgccgggcag ctccaggtcg accagccggt agtcgttgat ccatacccgg    33840
tccgcgcgca gccgctcggc caccgcgcgg gccgcgcgg gatcggcgga ccacaccccg    33900
gcgctgagcc ggtagcggga gccgttggcg atgcgcaccg cgtcgtcgtc ggacccggcc    33960
cggacgaccg cgagcaccgg gccgaagatc tcctcctgcg cgacggcgtc gtccgcgccg    34020
accgacgcca gcaccgtggg caggaaatac gccccgcgt ccagcccggg cggcagctcg    34080
tccgccgcgg gcgcccggcc gccgcacacg agctccgcgc cctgggagag cccgagttcg    34140
gtgaagcgcc tggccgtacg cgcctggttg cgcgagacca gcggcccag tcggtggcc    34200 gggtccagcg gatcaccgac gcgcagccgg cccacccgtt cgctcagcag ccgcaggaag    34260
tcgtcgtgga cgtcggcgtg caccaccgcg cgggtaccgg ccatgcacac ctgcccgttg    34320
tgcaggaacg ctccccacgt gacgccggtg accgccggt ccagatcggc gtccgcgagc    34380
acgatgttgg gggacttgcc ccccaggtcc agcgggcgc tcgtcccgc cgcggcggca    34440 ccctcccgta cggcggcccc ggtctcgtcc gagcggtga acgccaccag gtcgacgccg    34500
ggcgagcgca ccagctgctc cccggcgacc ccgcccggcc ccgtgaccac gttgaccacg    34560
```

```
cccggcggca ggccgcactc gtggagcagc tccaccagtc gcagcgtgga gagcgaggcg   34620
aacgaagccg gtttgatcac acaggtgttg cccgcggcga tggcgggcgc gatgcgccag   34680
gccgccagca gcagcggcag attccacggc acgatcgcgg cgacgacccc caccggccgc   34740
cacacgacgt aggaacccga accgggcgcc tccggctgcc gttcgggcac gtgctccgcc   34800
caccacgcgc tccactcgaa ggctgccgcg gcccccggca catcggcccc gagagccttg   34860
cgcagcgtcg agccgttgtc gcgggcctcc aactcggcca cggctccgc ttcttcacgc    34920 aagcgctgtg cggccttgcg cagcaggccc gcccgctcgc ccggcgccat ccgcggccac   34980
gggccctcgt cgaaggcccg ccggggcggcg gacaccgccc ggcggacgtc ctccgcgccg   35040
ccgctgggaa ggtcggccag gtggcgccgc gtggccggct cgaaggtgcg caggacggcg   35100
ccgtcgtggg cctgcacggc ctgcccgtcg atgtacatcg gaaccgctc gaccgctctg    35160 tccaccggt ccatcgcctt caccttctcc ttctgctgac ccgtggggat gcgcccggcc    35220
gggcccgccc gcggccgcgg ccgtaccgga cacccgccc cggagcggcc gcgcccgcgg    35280
tcaggccggc aggggcggga tgttgggggtt gaaccggaag acgttgcccg ggtcgtactg   35340
cgacttcagg gcctggagcc gcgcgtagtc ctccggcgtg taggcgctgc gggtcgtctc   35400
cctcgatgtg ttgtgacccg cgaggaagtt caggcacacc ccgggcgtcg tccacggccg   35460
catgctgtcg acgaactcct gctgcgccgc gtccacggcc gccagggtgt ccgggtcgac   35520
cagcgagccc acgtaggcgt tgaacaccgc ctccgggaag tggcccaccg cgctcgggtg   35580
ccggggcggc cgggcgaggg cgccgcccag gtgccgcagc tccaccccga acagcgcgtc   35640
cgtgcccggc cccgcgagcc tgaggatctc gtcgacggcg atctcgtcca gctgcccgaa   35700
catgaccgtt ttgctgtgac tcgacaccgg ggccggcgga tcgttgtgga tgatcccggc   35760
ccgcgtgtac gggagcgtgt ccaccgtatc catgacgacc gtgccggcgg cccggagctc   35820
ggcgaaccgg cgctcaccct cctcggggtc tcccagccag gccagccgga tgtgggtgac   35880
gaaccggccg cgcagcggtc cgggcacccc ctcggcatcg ggatacgcgg ccaggaacac   35940
cgacgacgcc atgtcctcgg gcatccgggg cgcccactgg agataggtgt tcagcacggc   36000
gcgcgtggag ccggcgtcga agaacagccc tccgccgtac acctgggtga cggggaacag   36060
cccgacctcg acggaggtga cgatgccgag gttccccctg ctgccgcgca cgccccagaa   36120
gagatcgggg tgttcctcgg cggagacctg gagaaaccgc ccgtcggccg tcaccaggtc   36180
gagcgagacg acatggtcgc cggcgaaccc gtacttccgc gacagaagcc cgagcccgcc   36240
gccgaggagg taggagaccg cgccgacgaa cggcgccgag ccgctcagcg gtgcaagacc   36300
gtgcgccgcc gcctcgtgga tcacctgctc ccagcgcacg cccgcctcga tccggcggt    36360 ccgggcccgc gggtcgaccc tgacgccggt catccgccgg gtgctgatga ggacgtcggt   36420
ggccgccgag gacttcccgt gaccggtggc ctggacggca tcccaaggc cccgggccct    36480 ggcgaagcgc acggcggcga tgacatccgc ggcaccggtg cgacgacga cgagggcggg   36540 gcggtgttcc acggacagtt cgaagccgga gcgctcctcg tcgtacccct cgtccccggg   36600
caggaggacg gatccggcga cctgcgccgc gagctcttcg gcggccgcgg cgccgagggc   36660
cgcggacgtg tccgtcacgg agtggctggc tggtttcacc gaggaacctt tctggctgga   36720
gcttcgagaa gcgcgccgcg cgtgcgcggg cagggccgcg gggctcgccg gcccttggaa   36780
cggagcgggc cccgtcagtt gcgcgggccg ggaccaccg gcagtgaccg gacgcccagg    36840
ggcaggagtt cggagctgtg ctcgacctct tcgggaggca cggccagggc gatgcggggg   36900
```

-continued

```
aaggccgcca gcaggcggcc gatgccgacg gtcagttcgg tcacggccag cccggtcgcg    36960
gggcaggcgt gctgcccggc gccgaacgcg atgccgcggt cggccacccg ctcgatgtcg    37020
agcacgtggg gatcggcgaa gacctcgggg tcgcgggagg ccgccgagac cagtggcagc    37080
acggcgtccc cggcggcgac gcgcctgccg gagagcacca cgtcctcggt ggcgacccgc    37140
agcaggccgt cgttgctgga ggggtagtag cgcagcaact cctgtacggc agagggcagt    37200 acggagpggt cctcgcgcag ccgggccgcg aggccggggg aggagagcac gccgaagagg    37260
tgccgggcca gcaggtcgcg gatggtgatg aagcccgaga tgatcaggcc gtggagcagc    37320
aggcgccggt cgtcgtcggt gagctcctcc gcgtccagca gcgtgtcggt gacgctgtcg    37380
cccggctcgg ccctgcgggc cgcgagcagt tcgtccagca cctggccgag cctgccgcgg    37440
gcctccttca gcgcctgctc ggtggcaccg cgcggaagca gcagcagctc gacgtcggag    37500
gtgacgtcct gccaccggtc cccgggcagc ccgaggaact cggctgtgac gcggccggcg    37560
aagggcgcgg tgtacgccgc gacgaggtcc accgtgccgc tgccggcggg cagccggtcc    37620
agggccgcct cggcggccgc ctcgatgcgg ggtgcgaacc gcgccgtgcg cgaggcaccg    37680
aacgcggcca ccaccggacc gcgcagccgg ccgtgctccg gcgggtcgag gtccacgatg    37740
cccgagccct gggaccggcc gaagcccgag cccggcagca tggcggcgcg atggcggctg    37800
aagcggccgt cggtgagcac cgtgcgcacg tcctcgtgcc gggtcaccag ccagatgcgc    37860
gagccgtccg ccaggcgcac ctcggcgacc gggtcatcgg tgagcagccg cgcgtactcg    37920
ggcggcaccg tgccgccggg gccgggcggg aagggaaagg cgggcggggc ggctgaggtc    37980
atgcgccccg gctcctctca ccggccggcg cgccggcgcg ggcgtggccc ggccaggtga    38040
agtccttcgc caggacgcgg ttgtccagct ggtgttccac gacgatgttg ccgcagccgt    38100
agtcgtcggc gatgacctcg acgtcctcgg cggacaccag gtgtccgggg tcggccagca    38160
gggtcgccac gcccttggcg ggggccagga cctccaggge gaagccgcgg gccacgtgct    38220
ggcggtgggt gtgcgccgcc gcgatcagga aggtgtcgtc ggggtcgcag atcagatgcc    38280
acagcgcgcg ggcctggagg aagcggcgcg ggcggtcggt gaagccggg gaggagacca    38340 ggaccggccc gtccgcgccc ctgcgggtgc cgagggcgac caggccccgg tccatatagg    38400
ggacctgctc ggtgcggtag cccatcaggg gggccgggtc gaagggcgcg gtgtcgtcca    38460
gacccgccca cgcgcgcacc cggtgcgcca cctcgtagcc gaggtcccag gggttgtcga    38520
gtcgccccgg agcgaagaac ttctcgctca agtcggcgca gtccttgcgc agttccacca    38580
aggcgggagg gagcggggta ccgcggggcg cggtgcccat caggtgcgg acgcgcgcga    38640 tccactggag ctggtcggct atccgctcag gccgcacccc gttgaagaag tcactggcga    38700
gcggttccgc caactgctcg gcggccttga ggatgtccgc ctcgtacggc tcggcctcgg    38760
cgtaggggtc caggcccagc cgtgccgcga tgcggcagaa gcggcctcg tcctcgtcgg    38820 tggcgcggac ggcggcccac tcctcctgga gcggggtgcc ggtgatgccc tggtccgtga    38880
ggcgctcggt caccgcgtcg acgaacgagg ccagtgtggc ggtgaacgcg cgctctcca    38940 cacaggagtt gccccggctc gcgaagcggt tcccgggtcg tacgtcgggg cccatgtccg    39000
gcatccatac gatccgggtc tcccggccct cgggcacgaa gagcatgtcc ggccagcgga    39060
agccgtcgca ggcggcgcgc aggatgtgac ggcgcgaacg catccaccac gaaccgcggt    39120
tgtcgcccac accgtggcgg taggcgaagc gcagctggga tatctgggtg ccgggccgcg    39180
cgtcggccac cagcgaccac cagttgaagg cgatccactc ggccagggg tagagcgagc    39240 cggtcgtgtg ctcccggaag gtccctgcc cgggctcctg gacgagtgtg acggtctcgg    39300
```

```
cgcccacggc gatgcgcagc cgggcccagg tcgcttgcag ctcgcctccg ccgccggccg   39360
gggcgtcgag ccaattccac tgcaattgga actcaggaag catggtccgc cagcccttcc   39420
ggccattcgc tcgggtggag ttcgtatccg gtgtattcgc ccggcgcacg gcccgtcagc   39480
cggaattcca cgacggagtc accgaccgg tgccagacat agcgcgggaa gccgtcctgc   39540
cagggaccgc cgaggaatcc ggtgcggatc cctgaacgga gggtgcccag cggggcggcc   39600
gacagggaac cgggcacggc gagcagatcg gccggggccg ggccgtattc ccggcgggcg   39660
aatgtcaccc gcccgcagag ttcttcccgt tcgctgcggt cgggcagtgg cgcgatcgcg   39720
cgacgtggct cgcggcggcg cccgggcgct cgtaggacca tgatgtccgc ctttcgggga   39780
acgtgccggt gagctgggcc ggcggggccc ggacgcggcg tgcgtccggg ccccgcccag   39840
ggtgttacgg gaggggcgcg aagaggtcca ccacgttgcc gtcggggtcc ttgacgatgg   39900
cgtagcgctg accccacacg gcgttccacg gcttgaggtg gccctcgtag ccggcgtcga   39960
cgagctcggc gtacttcttg tccacgctcg cggtgtcggg gaactcgaac gcgatggcga   40020
agcggtggcc gccggtgggg gcctgccact cggggtcgta gctgcgcacc gtctccacgg   40080
tgtcccaggc gagccggatg ccgccgtcga gcacggcctc cgtgtgcggc gcggagtcgg   40140
cctcggcggg gatctcgacg cccagcttcc ggtagaactc cagcgacttg gccatgtcct   40200
cgaccaccac ggcgaagagg gaaatccttg ctgacatgcg cgttcctttc ttgcacttt   40260 aaattggtct ccggtgccgg gccgtctgaa ttctccgggg ccggccggac cacgaagtcc   40320
gaatgtgctg gacgcgccgt acgctagtga ctgcgcgctg actttggcca atcggggtat   40380
cccccgccgg agtcaacgcc gctgacagga caacgatttc aggacagcgg cacgccgtcc   40440
cagtcgttcg gcacgtcacg cccgagcaga gcgcatacgg tcgcgggaat atcgacgggg   40500
gcggcggtgc gggtctgccg cgccccaccg gtgaagccgg ggccgacggc cgaccagtag   40560
gactcccggc ggtgccagcc gctctgccag tcgcggtgga cgtgcgaggc ccagtgcggg   40620
tcgcccagcg gaagatagcg ccagtccgcc ggctccagga tgaggtcggg ggcgtgctgg   40680
gtggcctcgc cgggatagac ctcctcccgg cggcgcaccg cgtcgaagaa cagcctgccg   40740
gtacgggggt tgcgccgctc cagcagcgcg gccgcgacgt cggtgcggac cttctcgtag   40800
tcgcgctccg ggaccaggcc gtgcttgtag cggtcgcgca ggttgatgtt caccccgtgc   40860
gtgccctgca ccgcctcgaa ggccgcgctg ccggcccact cgacgcggcc gtcctcggcg   40920
gtggccagga aacccgcctg ctccatctcg tcgttgatgg aacagtagtt gcgcagcggc   40980
ccgaagccta tctccgagaa ggccacgaca ctggtgcggt cgtcggccgc ccgcagggcg   41040
tcctggatga cctggtcgca ggtgcggtag gcggcgaaga cggcgctctc ccgctcgtgc   41100
tcggggccgt gctccagctc ctgccagtag atgtgcgaac agcggtcgat gctcgtgagg   41160
ttgacgatca cgacatcgga ctcctccagc agagccaatg ccgcgcgccc cgctgcacg   41220 tccgcctcca gcagggaagg cagcagctcg tcgcggtcct gcccggtcca aagatcgac   41280 acgtcgtgga ccgacggat gcccttcttc gccaggtgc gctggaggct gcgcgggtgg   41340
caggcgtgga gggtggcata catcggatag gtgatcaggg aaccgtcgaa gggctccggg   41400
ggatgggtgc cgaagaggcc tatcgaggcg aacctgacgc cctggaacac ctcgtgctgc   41460
cacagcagtg ggtggcggcg gtgctcgggg gtgaggacct gcggcgcgta ctccgggtcg   41520
tgacaggtcc agtaggagta gaagccgtgg tccgcgcgcg gccggccggt caggacgctc   41580
agcaggcccg gcggttcgta gggggtgccc tcggcgtgga gcggcccgga agcccctgc   41640
```

```
gagcgcaggg cggcgaagcc gggcagcagc ccctgggcac accagcggtc gagcagctcg    41700
ggtgccgctc cctcggtgat gacgacgacg acacgctggc ggattgtcac gtgcgactcc    41760 ctcggttgc gtggcagttg gcatgccgtc atccggagg cgccggaaag gccgaggcgt      41820
tccggcgccg gacaggcgtc gatcgtcgga tcaagctaac agcgggacga ggactctctc    41880
cagacgacgg tacggaggaa attgagagag ggctgagaga gggctgagag agggcagagg    41940
cgggggagtg gcgtggggtc acacggtgcg caggaggcgc agacgttccc gtaccgcctt    42000
gggcagcccc gccaccacgc gatcgtacga atgctccacc atctcccgca gctcctccac    42060
gggaaccgtg ccgttcagga caaccgtgtt ccagtggcgc ttgttgacgt ggtagccggg    42120
caccaccgcc gcgtactgct cgcgcaggtg cagcgccaga tccggttcgc acttcagcgt    42180
gacctgcggc gggcggtcct cggaggcgtc ctggagaatg gcgaagacct tcttctccac    42240
cttgaagacc gcggctccgg ggccgaacgc ctcgtcgtcc accgcctccg gcagctccag    42300
cgcgaagtcg gagagttcct ctggtgtcat cgccggtcct tcttcctgcg gcacggcagc    42360
gagcggccga accgcgtggt catggggtcg gccaacagac tagaggcgca ggaggagttg    42420
ccgtgcggca gggcgcggac gctgatccac gatggccgaa acactgcggg gagttccggt    42480
cgcggcggga cggcgacctt gacgggcggt cctgccattg gcacagtttg gctggctcca    42540
cacaggtttt cggtggaccg ttcgttcctc tcccggtgct gccggtcgc ggtaccggtg     42600 tccgcgcgat ccgtgtgccg cccgcgccgt cccgaaccgg cccgtgcgcc cactctcccg    42660
gccctccgcc gccggtctcc gtaccgccgc cccgcccttg ccggggcggc gccgacgccc    42720
gcaccccggc cttggccctg cccacggccg catccgcgca ccccctcac cccggcgccg     42780 gccatgcccc cgtgccgcct gccccccttg atgcccgtgt gaggaacccc cgtatgaccg    42840
tggagcagac ccccgagaat cccgggaccg cggcccgcgc cgccgcggaa gagaccgtga    42900
acgacatcct gcaaggggcg tggaaggccc gcgccatcca cgtggccgtc gaactcggcg    42960
tcccggaact gctccaggag ggcccccgca ccgcgaccgc cctcgccgag gccaccggcg    43020
cccacgagca gaccctgcgc agactgctcc gactgctcgc cacggtgggc gtcttcgacg    43080
acctcggcca cgacgacctg ttcgcccaga acgccctctc cgccgtcctg ctgcccgacc    43140
ccgcgagccc ggtcgccacc gacgcgcgct tccaggcggc cccctggcac tggcgggcct    43200
gggaacagct cacgcacagc gtccgcaccg gtgaggcgtc cttttccttcg acgtggccaa    43260 cggcacctcg ttctggcagc tcacccacga gggaccccaa ggcgcgcgaa ctgttcaacc    43320
gcgccatggg gtcggtctcc ctcaccgagg ccggacaggt cgccgcggcc tacgacttct    43380
ccggcgccgc gaccgccgtg gacatcggcg gcggccgcgg cagcctcatg gcggccgtcc    43440
tcgacgcctt ccccggcctg cgcggaaccc tgctggagcg cccgcccgtc gccgaggagg    43500
cccgtgagct cctcaccggc cgcggcctcg cggaccggtg cgagatcctg cccggcgact    43560
tcttcgagac catccccgac ggcgccgacg tctacctcat caagcacgtg ctgcacgact    43620
gggacgacga cgacgtcgta cgcatcctcc gccggatcgc caccgccatg aagccggact    43680
cccggctcct ggtcatcgac aacctcatcg acgagcggcc cgccgcatcg acgctcttcg    43740
tcgacctgct gctgctcgtc ctcgtcggcg gcgccgaacg ctcggagagc gaattcgccg    43800
cgctgctgga gaagtcgggc ctgagggtgg agcgctcgct gccctgcggc gccggcccgg    43860
tgcgcatcgt cgagatccgc agggcctgaa accgcccctc ctgaccgaag ccggccacag    43920
ctgaaggagc aatgacacca tgacggtgct gggtctgggg ggatccggac atgactgggc    43980
ctcctgtgcc accgacggcc gacggctggt ggcgatcgac gaggagcggc tggtccgcag    44040
```

```
caagtacggc ctgggagcgg acctcctggc gggccacagc cggcgcgccg tcctcgacgc   44100
cctcggcacg agtgccgagg ccgtggaaca cgtggtggcc tgcgagctcg taccacgccc   44160
cttctaccac tcgttccgca ggcgcgtgac ggtcgtcaac caccatctcg cccacgccta   44220
cagcgcgttc ggggcctccg ggatgacccg cgccgccgta ctggtctgcg acaactccgg   44280
cagcctggtg acgggcctga agtccggccc agggccgcg gaggcggaga cgatcagctg    44340
ctacaccgcc gacgcctccg ggctgcgcct ggtcaaccgg gtcgccggga cacacgccgt   44400
ggacgcctcc tccgagagcg cctactacca gcccggcgag accgacaatt ccctcggcca   44460
cttctaccgc tcggccagcc tcgcactcgg cctcgcctac tccggtccca agacccgcta   44520
ccccgtcagc gaggacggca agaccatggg cctcgcgccc tacggcgacg accgcttcgt   44580
cgacgaggtc gcggagctgg tcaccctgct gcccgagggc ggcgtgcaga tctcggcgag   44640
caaggtgaac cacctcttcg aacgcctcgt ggaatcgggt gagttcgagg accgggcggc   44700
cttggcctac gccgcccagg agacgctgga acgcgccctg ctgcactgcg cccgcgacct   44760
gcaccgccgc accggcctga cggacctgtg catcgccggc ggcgtcggcc tcaacagcgt   44820
cgccaacggc cggatcctgc gcgagacccc cttcgagcgg gtcttcgtcg tcccggccgc   44880
gggcgacaac gggatcagcc tcggctgcgc ctactacggc ctccacgagc tggagggcg    44940 cgcgccgtcg gagctccccg ccctcgacac cgcctacctc gggcccgact accccgccga   45000
gcgcgtcgac gcggcgctgg ccggctcggg cttcaccgtg gagacccccg acgacctgcc   45060
cggcagggtc gccggcctgc tcgccgaagg gaagatcatc ggctggttcg acggccgctc   45120
cgaattcggc ccgcgcgcac tgggacaccg cagcatcctc gccgcaccct tccccgcctc   45180
cgtgcgggac cacctcaacg acaacgtcaa acaccgcgag tggttccgcc cctacgcccc   45240
catcgtccgc gaggacgggc cggcggacta cttcgacctc gtccagccct ccccgttcat   45300
gctggtcgtc gcgcgcgtga cccggcagga cgccatcccc gccgccaccc acgtggacgg   45360
caccgcccgg ctccagacgc tgaacgccgc acagaacccg aaggtctacg agctgctcgg   45420
caggttcgag gcgctcaccg gctgcgccgt gctgctcaac acctccttca cgtcgccgg    45480 ccagcccatc gtcgagaccc cggaggacgc cgtcgaggcg ttcgcgggca tgcgcctgga   45540
ccacctcgtc gtgggggacc ggctggcgac caagccctga cagcacgccg aggcccgcga   45600
ccggcaggga ggagagccaa gcggtggacg tccccgtgct cgtggtcgga ggaggaccga   45660
cgggcttggc gatggcgctc ttcctcgcac gccacgcgcg cggctgcctg ctggtcgaac   45720
ggcggacgac cacctcgccc gtcccgcgcg ccacccacgt cagccgccgc tccatggaac   45780
tcttccgcga ggcgggcctg gaggaggaga tccgccgggc cgggttcgag gtcgtgcgcg   45840
aggacgaccc acggctgcgg acccggcccg aacgccacct gccccgggtg gtcctgcaag   45900
ccgcctcgct cgccggcccc ggcccggtgg gggtcctgga gaccggtgac gaggaactgg   45960
ccgtacccgg ccctgcgca cccttctggt gcggccagga ccggatggaa cccctgctcg    46020
ccaaggccgc ggcgcgccac ggcgccgatg tgcgcttcgg ccacgaactg accggccgt    46080 ggccggggga ggacagcaca cgggcccgcg tccgggcagc gggaacggga cggacctaca   46140
ccgtcgacgc ccgcttcgtc atcgccgccg acggggcgcg cggcgagatc gccgagcgcg   46200
tgggcatcgc gcgggagggc ctgggcacgg tcgcccaccg ggtgagcatc ctcttccgcg   46260
ccgacccggg cgctgggcc cgcgaccggc ggttcttcat gtgcatgatc cagaaccggg    46320
ggttcgacgg ggcggtgatg gagctcaaca ccccggggcc ctggtgcgcc gcggtggact   46380
```

-continued

```
acgacccggc cgcgccgaa cccgacggca cctactccgc acgcacctgc ctcgacctgg   46440
tccgggccgc cgtcggtgac gaccggagcg acgcggcggt cgacaccgtc ttccactgga   46500
aggcccggca ccgcatagcg gccgcctacc gcagtggggc ggtgttcctc atcggcgacg   46560
ccgcccacct ccacccgccc tccggcggct acggatccaa cgtcggcttc caggacgcgc   46620
acaacctcgc ctggaagatc gccgccgtgc tcggcggctg ggccggaccg cggctgctgg   46680
acacctacga cgaagagcgc cgccccgtgg gaaaggcgac ggcggagcag tcgatgctcc   46740
tcgacgcgcg tgccaccggaa ccactggggg gaagcgtcgt ccgctgcgat ccccgcaccc   46800
tgatcatggg ataccgctac cactccgccg ccgtcctcgg cccccgcac ggccccgcct   46860
tccccgcggc cttcaccctg cgcggagacc cgggcacccg gctgccgcac gtatggctgc   46920
gtacggacgc gggggaacgc gtctccacgc tcgacctgtg ccacgggcac ttcgtcctgc   46980
tctccgccga cccggtctgg gcggcggccg cggcgcgctc ggcgaaggag acgggcgtac   47040
cgctgcgggg ccaccacctg cgcggccaccg gaagcgaact cgccgacccc tccggcgagt   47100
tcccgcggag ctgcgggacc gggcccgcgg gggccgtgct cgtacggccg gacggcatgg   47160
tcgcctggcg cacggcccgc gccgtgcccc cggacccgga cagcgcgcag gacctggtca   47220
cggcagcggt gagacgtgtc ctcgcactgc cggagcgcgc ggcgccaccg gtgctcggtc   47280
cgccgcggtt gtcacgcggt tcctatcggc gagtcggag cgacgggtga agcctcattc   47340
cttctgcacg tgctggccgg gcgccaccgt atggctgacg ggcccaccgg gcgcgggcaa   47400
gacgacgatc gcccgcgcac tggcggagcg gctgcgcgaa cggggccggc gcgtggaggt   47460
gctcgacggc gacgcgaccc gcgcgctcct gaccgcgggc tcctcgtggg aggaccgtgg   47520
caccggcctc cagcgggtcg gcctgatggc cgaggtcctg gcgcgcaacg gcatcgtcgt   47580
cctcgtcccg gtgaccgcgg cccgcgcgga cagccgcgaa gccgtacgca gacgccacga   47640
gcggtccggc accgcgcacc tggaagtgcg ggtggtccgg gacgcagtgc ctccgagcgg   47700
gctcccgcg ccgcccggcc cagatctgcg gatcgcggcg cacgagcaga gcgccgagga   47760
gtcggcgcgg gcactgcacc ggctcctggc ggagagggag ctggcgtgaa ccccgggcgc   47820
ggtggagcgt acgccgcggg gcgcgacggg accgcggga cgcgacgccc tcacggtctg   47880
tcgcacctgc atctgctgga gtcggagtcg gtccacatct tccgtgaggt ggcgggcgag   47940
ttcgagcggc cggtgatcct cttctccggc ggcaaggact cgatcgtcat gctgcacctg   48000
gcgctgaagt ccttcgctcc cgcacccgtg ccgttcgcgc tgctgcacgt ggacaccggc   48060
cacaacttcc ccgaggtgat cgcctaccgg gaccgcgtcg tggcggcgct cggtctgcgg   48120
ctggaagtgg cctccgtgca ggacttcatc gacaacggca ccttgcgcga acgcccggac   48180
ggcacccgca atccgctgca gacggtgcca ctgctggacg cgatcgggcg ccaccgcttc   48240
gacgccgtct tcgcggcgg ccgccgcgac gaggagaagg cccgcgcgaa ggagcgggtg   48300
ttctccctgc gcgacgagtt cggcggctgg gacccgcgcc gccagcgccc cgaactgtgg   48360
cggctctaca cgccgcca cgcacccggc gagcacgtcc gcgtcttccc cctctccaac   48420
tggaccgagc tcgacgtgtg gcagtacgtc gcccgcgagg agatcgaact ccccaccatc   48480
tactacgccc acgagcgcga ggtcttccgc cgcggcggca tgtggctggc accgggggag   48540
tggggcggcc cacgcgaggg ggaagcggtg gagaagcgac gggtgcgcta ccgcacggtg   48600
ggggacatgt cctgcaccgg cgcggtggac tcgcggcgg ccaccgtggc cgacgtcgtc   48660
gccgagatcg ccacgtcccg cctcacgaaa cggggcgcga cccgggccga cgacaagctg   48720
tcggaagccg cgatggagga ccgcaagcgc gagggtatt tctagcgcgg cggggccggt   48780
```

```
gcggcccaca agcggaggac tagtccctaa gtatgaagtc ccctactccg tttgtctgtt   48840
gagggcaggg gcgccgtctg aggatgatgc agtccatgtc acagttactt tccgggaagg   48900
acggcgccca ggaggcgcca agtcgcggcg ggtccacgtg ggtggcggtc ctcgccgcgt   48960
gcgtggggca gttcgtggtg gtcctcgacg tgtccgtcat caatgtcgcg ctgccgtcga   49020
tccgttccgg cctcgacatc ggcgagacgg gcctgcagtg ggtggtcaac gcctacgtca   49080
tcgccttcgc gggcttcctg ctgctcggcg gccgggcctc cgacctcttc ggccgcaagg   49140
ccgtgttcgt cttcggcctc ggggtgttca ccgccgcgag cctgctcggc ggcctcgcgc   49200
aggcgccgtg gatgctcatc gtcgcccgcg ccctgcaagg catcggggcg gccgtgctct   49260
cacccgccac cctcgcgatc ctcaccacca cgttccccga gggtccggcg cgcatcaaag   49320
ccgtcgcgat ctggacggcc gtgggcacgg gcggcggcgc ggccggcggc ctcatcggcg   49380
gcctgctcac cgactacctc tcgtggcgct gggtgttgct gatcaacgtg ccgctgggcc   49440
ttgtcgtgat cgtcgcgacc gtcgcctggc tggccgagag ccgcagcgac caggcacacc   49500
gacgccggct ggacctcccg ggagcggtgc tggtgaccct gggcgtcggc agcctggcct   49560
acggcatctc gcagagcgag ggccacggct ggggctcgcc gcggacgctc accttcctga   49620
tcgtcggtgt cgtggcgctc ctcgccttcg tcgccgtgga gcagcgcacg cgcgagccgt   49680
tgatgccgct cggtgtcttc cgggtgcgct cggtgtcggc ggccaacgcc atcaccatcg   49740
tcagtggcat gggcttctac gcgatgtggt acttcctctc gctctacatg cagaacgtgc   49800
tgaaatactc cgccgtacag accggcctgg ccctgcttcc ccacaccgcc accatcatcc   49860
tctccgcgca gttcgcaccc cgcctgatgc ggtggatcaa ggggcgcacc ctcctcgtga   49920
tcgcgggact gctgaccgcc gcgggcttca tctggcaggg gaacatggac gccgacggct   49980
ccttcctggc gaccctgctc ggcccgggaa tcgtcttctc cttcggcgcg ggcctgatga   50040
tgacgctcct cgcggtctcc gccacgacgg gcgtggagct ctccgaatcg ggcctggtgg   50100
ccggcctcgc caacacctcg cgcaccatgg gcggcgcgct cggcctgtcg gtcctcgcgt   50160
ccgtcgccgc ccgccgcacg gccgacgtgg ggcccggcgc ggagggcctg gcctccggct   50220
acggtcgggc gttcgtcgtg tccggggcca tcatcctcgt gagcatgctg atgatcccct   50280
tcctgcccaa gccccagccc cagacccggg cggaatgacc tgtgagcacg gacatacgag   50340
gaggcttcgt ggggcaggac agccggccgc ggtggctcac cgacgaggaa caacgcgtgt   50400
ggcgcggcta tctgcgggcc accaggctgg tggaggacca cctggaccgc cgcctccagc   50460
gggaagcgga catgccgcac ctctattacg gtcttctcgt ccagctctcc gaggccccgc   50520
gccgggggat ccggatgacc gaccttgccc gcaacgcgaa gatcacccgc ccgcggctct   50580
cgcacgcgat cacccgcctg gagaagctcg gctgggtgcg ccgggaatcg tgccacggcg   50640
acaggcgcgc ccagaacgcc gtcctcacgg aagagggccg cgaggttctg gagaagtcgg   50700
cgccgggcca tgtcgccgct gtgcgcgcgg ccgtcttcga cagcctcacc ccggaacagg   50760
tcgggcaact gggccggatc tgccaggcga tagagaaggg gctggaccgg gaaggcgcgg   50820
acctgccgtg gctgcgctga ggcgggaagc cgtcgcgagc gcgcggggcc gtcaggctct   50880 gacgccccc gccgccgcg tacgggatcg ggccgaccgc gccccggatt cacgcgagtc   50940
cgggagcaga ccggacgaca cggatattct ggatgccgtg gaacgacacg acgggcacc   51000 gggctggggc ttcacccata cccagtacag cgcggaccac ggtgaacgcg gcgccacccg   51060
cagggccggg gccctgctct ccgcgcggcc cctgccgcag aaccagcaca tcatgggctg   51120
```

```
gggcgcggag aatcccgaac cggcgcccgg acgctacgac ttcgaggtcc tcgacgagcg   51180
cgtcgccctg atgcgcgcga cgggggccac gcccgtcctg accctgtgtg ccgccccga   51240 ctggatgaag gcggccggc ccggccgcac cgactggtcg cgactggaga ccgccccga   51300 cccccggcac tacgcggact tcgcccggct cgcgggcgtg atcgcccaac gctacccgga   51360
catcaggcac ttcctcgtgt ggaacgagct gaagggcttc tacgacgagg acaggcggcg   51420
ctgggattat gagggataca cccggctgta caacctcgtc cacgccgagc tgaagcggcg   51480
gaacccgcgc aatctggtgg gcggcccta tgccgtggtc gaccacgacc cgcccgccga   51540
ggacgcggcg gaccgctcgc gcgaactgcg cggtccctgg ggcgagctgg accagcgctc   51600
cgccgacgtc atccgctatt ggaacgccca caaggcgggc gcggacttcg tcgtcgtcga   51660
cgggtccagc tacacccgcg agggccaccg ggcgattccg gacgagttcg ccgccaccga   51720
gaagttcgcc gacgtcaccc gctgggtcag gagcgtgacc ggactcccgg tgtggtgggc   51780
cgagtggtac gtcgagccgc ccgccgagga cgaccggccg ggcggccggg acggctgggg   51840
cgaggggcac cgcaccgccg tgcaggccac cgcgatgatg cggctggcgg agagcggcgc   51900
gtcggccgcc ttctactgga acccgcagcg gaccgggaag gcgtgccccg gctgcctgtg   51960
gcggagcacc cacttgcgcg acgggggagg ggagttgccc atggcgggtc tcctgagccg   52020
gttcgctcgc gaattccctc cgggcaccgc cttccggccg gtcgccgtca cctgcgggag   52080
cggtgacagg gtcgaggccc tcgccgacga ggccgccgtg ctcgtcgtca acaccgagtg   52140
ccggccggtg gccgccaggg tggacgggca ggcgctgtcc ctcgcgccgt acgaggtgcg   52200
ctggctgacc cgcccgtaat ccagtggggc ggcgcacggg cgcggacagg gaattgcgga   52260
acagggaagt tcacgaataa ggagaacgcg ggaaagcgct cgggcggagc gtgaaacccc   52320
tgtcggcgct cacgatatcc acccagctga tttgcaggtg aaacgggcgg tcgcctcgac   52380
ggtgccgccc gtttcctgtt gcccgaaagg gcaatcgggc atcagcagga gagattgccg   52440
cccggcgcca cgccgaggat cttggtgaat cgctggtagt tcgcgacgcg gctctggacc   52500
tgggcggggt tgtggccgtc gcactccagg gcgccgttga tgctgcggat ggtctgcccg   52560
aagccgcggt ggttgaccat ggcctcgtgc ggggtcatgg tgccggggcc gcgctgggtg   52620
ttccagtacc acaggccggt cttccaggag acggccgcgt ccttctgcac cagcgagggg   52680
ttgtggagca ggtcgatgcc gagggcgtca cccgccgcct tgtagttgaa gttccagctg   52740
atctggagcg ggccgcgacc gtagtaggcg gcctggcctg ccggacagcc gtaggccgcg   52800
ctccggtcgc agtagtgggg gtagttggcg gtgttctgct ccacgacata gaccagtccg   52860
ccggtctcgt gggcgacgtt ggcgaggaag gcggcggcct cctgcttccg gacctcggcg   52920
ctgccggtgc ccgcgaagcc cgggtacgcc ttgagcgcgg cgaccaggcc cttgtacgta   52980
tagaacgcgt tccgcttcgg gaacatctgc ttgaactggg cctcgctcac ggggaatgcg   53040
gcggcctgcg aggtgccgcc gtgcggtgcg gccgcgctcg ccgtggtggc gggggcgagg   53100
acggatatgc cgaccagtgc cagagcggcc ggcagcaggg cggcgatgcg atttcttctc   53160
atggcggctc ccgtggggga aagggtgagt gacgcccgcc gacggtgaat cgggcccgtt   53220
gggcgccttc gcgtcatcgc gcagtgaata actcccgtga gtttggtgtc aatggcatgc   53280
gccgtgtccg gccgaaccag gtgcactgag caatgagttc aggacaactg cggccgatag   53340
ggcttgcggg agcaacgagg accatgacct catatgccgg aagccggaca cgtgccgaga   53400
aatgccgctg tcctgtggct ccttgggtga cctgtgaaac ccggctggct catgaacgag   53460
ccgattgaac gagccgattg aacaagccga tgaacaagga                         53500
```

<210> SEQ ID NO 77
<211> LENGTH:
<212> TYPE:
<213> ORGANISM:

<400> SEQUENCE: 77

This Sequence is intentionally skipped

<210> SEQ ID NO 78
<211> LENGTH:
<212> TYPE:
<213> ORGANISM:

<400> SEQUENCE: 78

This Sequence is intentionally skipped

<210> SEQ ID NO 79
<211> LENGTH: 621
<212> TYPE: DNA
<213> ORGANISM: Streptomyces lavendulae

<400> SEQUENCE: 79

```
gtgccccgga atctcctgga cgtcagggac gtccaccaca cctacggcac ccgcagggtg      60
ctgcgcggca tcgacttgtc cctgcgcccc ggaacgctgg ccggcgtcgt gggcgagaac     120
ggcgcgggga agtcgacgct cctgaagatc ctcgccggtg agctgcggcc gcagcgcggg     180
caggtccact acggcggccg gttcggttac tgcccgcagc atctcgtcct gaaccaggct     240
ctcaccgtcc gccagcacct ggagtatttc cgggtggcgt acggcctcgc caccctcagc     300
catgccgaga gaatcatgga cgtgctccgg ctgtccgact acggggacga gcgggtcagc     360
gtgctcagcg gcggcacgaa acagaagctc aacctcacac tggccctgat gcacgaccct     420
gacctgctcc tcctggacga gccctaccag ggcttcgact gggacaccca ccagcggttc     480
tggagcctgg ccgccggtct gcgcgaacgc gggcggtccg tgctggtcgt ctcccacctg     540
gcctacgacg ccgaacggct cgacgaactc cggcacctcg acggcggact gctgcactca     600
aggacgacgg caccggtatg a                                                621
```

<210> SEQ ID NO 80
<211> LENGTH: 1350
<212> TYPE: DNA
<213> ORGANISM: Streptomyces lavendulae

<400> SEQUENCE: 80

```
atgaccggcg ccctcctctg tcccagggac atctccccga ctttcgcggc gaacgcggac      60
ttcatccggc agcgcatcga ccgcacggcc gaacgcatca accatcacat cgaccgcctg     120
tgcccgaacg cgtcggcaga tgcttgctcc acgtggctgc caccgggcca catcaccggg     180
acgaccgggc ctggcacgcc gccggtcgtc gcccagcggc tgcaccgggc cctgacctct     240
cccgtccgcc atctgaccga tgccggagga cagcgctggc ggccggtgct ggcctgggag     300
gccatcggtc tgatgggagg tgacagcgaa tcctgcggcc tgctgatcgc ggcgagtgag     360
ctgctccaca ccggatccct catcgtcgac gacgtccagg acgcctcacc gctgcgccgc     420
ggacaaccgg ccgtgcacac catgttcggc atgccgactg cggtgaacgc gggtacggcc     480
gcctatttcc tctgggagcg ggccgttcag ctcacctttc ccgacgacgc ctcgcggtgc     540
ggggagttgc gggcactggg tctggccgcg ctgcgagcgg ctcacgccgg tcaggcactg     600
```

-continued

```
gatctccaag gtcaccggga agagatggac caggccgtgg ccggcgacga ccggcacact    660
gtgctggaac tggtccgtct gacacaccgg ttgaagtccg ggccccggt ctcggcggcc     720 atggaggcag caggggtcgt cacgggtgcc gagccggaac tgcggagagc actgggggct    780
ttcggttcag cggtgggcac cgcctaccag atcgccgacg acgtcgccga cctgagcggt    840
gtcacacggg cggggcacc gacgaagcag gccaccgagg acctgcggag cggcaaggtc    900
accatgccac tggcccacgc cgtggtccgg ctgccgcaga gcccggctga accagctctg   960
gcagcaggtc aaggacggct cgggcagcgc gacggcggtg gccgaggtgt gccgggacct  1020
gaacgcctgc ggagcggtga gagcctgcct ggaggaagcc gaccagttgg tgagcgacgc  1080
gtggaacaag ctcgagcccc tgctgccgtc ggcaggccac agccacttgt tgtacgagct  1140
ggccctctcg gtcgtccggc gcgaccaggt cgcctgagga gaggaagccg tgccccggaa  1200
tctcctggac gtcagggacg tccaccacac ctacggcacc cgcagggtgc tgcgcggcat  1260
cgacttgtcc ctgcgccccg gaacgctggc cggcgtcgtg ggcgagaacg cgcgggggaa  1320
gtcgacgctc ctgaagatcc tcgccggtga                                    1350
```

<210> SEQ ID NO 81
<211> LENGTH: 1425
<212> TYPE: DNA
<213> ORGANISM: Streptomyces lavendulae

<400> SEQUENCE: 81

```
atgcgggcgg gaggacgcct gatgaacgga gattcgaagg cggactccgt tgtgccgatg     60
gctcctgact gcagtcggtt gctcgggcat gcccgctccg tgcggttctt gatggatctg    120
agggagatcg cggcccggct cggcaaggcg gggcctgtgg tcagggtgaa ggcgggcccg    180
ttcgtcgggt acctgctcaa tgactcctcg ctgatccggc aggctgctcg cgacgaggac    240
accttcatgt tctggggcag ggaacccat gtgcgggtga tcgtaagaga gggactgctg    300
agcaccgagg gaacggtcca ccgtgaccgg cgggcggtga tgaggcccgc gttcgccgtg    360
ccccggccgg cggacctcgg ggcgtccgtg cggaccgaga cccgaagtct gctcgccacc    420
cttcccgcgg accgtccggt cgacatgagc cacgagatga cccggctcac tttccatctc    480
gccgtcaggt gcgtcttgcg cagcgaggtc tcgcccggaa cgctgaccgc gctggccgcg    540
gcgcatgcca cgctgtcgca ggtcggggcc ttgcggtttc tcctgtcccc gtggccttgg    600
gtacccgtgc caagacaacg cgcgctccgc cgtgccctcg cggtgctgga cgaggccacc    660
cgggaagtcc tcgcgcgcca tcggccggct gaggacgggt gtgatgtggt ctccctgctg    720
aagcaagcgt ggcgcgagcc ctcggaagcg cggtgcagg acgtgcgcac gctgctgttc    780
accggcgggg aggccaccgc ctcgacactc gcgtgggcct gctacgaact gggccgccac    840
ccccaccatc aacaggcctt gcaggaggag gccgacgcgg cactcggcct ggggcactcg    900
caggccggcg tcggaataaa ccggttgccc cggacagccg ccttcgtcaa ggaagtcatc    960
cggcttcacg gcctcccggt ccttgtgcgt tgcacgcgcc gcgagacgtg gctgggcggc   1020
caccggctgc ccgcgaaggc gacggtgttc ctccacctcg gggcgatgag ccgtgaccc   1080 gcccacttcg aacggcctga tgtcttcgat ccgacgcgct ggatgccgga cgctcagccc   1140
tcggtctccc ctgctgcctg gcttccctat gcgctcgggc cccgctactg ccctggtgcc  1200
gcggtggccg acgtcatggt gcccgtcgcg ctcgccactc tggtcgccac gcggaccgta  1260
cgcacggcgc gtcggggccg gacggtgcgc tccggcttcg aactcgccgc gatgccacgc  1320
ggcctgacca tgatcgccgc actccgcgag ccgtgcccga gcagtccctc cgcggcatcg  1380
```

-continued ggccggcgac cccatgaggg agcctcgtcc atcgcccgcc cctga    1425

<210> SEQ ID NO 82
<211> LENGTH: 1821
<212> TYPE: DNA
<213> ORGANISM: Streptomyces lavendulae

<400> SEQUENCE: 82
atgaagatct ctcgaatagg ccgcgcgtca tccatcgccg ccctggtgac aaccgcactc    60
gctttcacgg cagttggcac cgtcgctccc acggccgtcg ccgactcccg cgcggccgcc   120
gcttccggga cgcagaatga ccacccgagc tcggggcagg gcacctccac ctctgagctc   180
cggcgcaagg gcctggtccc gtcgagtctc gtggccaagc ccatcacccg cagcgagacc   240
ctcagacgcg ccgccagctg gttcggcaag gtctccact acagcgggga caacacctat   300
cagggctggc gcacggactg ctccggcttc gtctccatgg cctggggact gcccggcccg   360
ggtgagacca ccgattcgtt cattcccggg ggcgtggccc acgaaatctc caaggacgaa   420
ctgaagcccg cgacgcgct caacaacaag gcgctcggca cgacggtca cgtcgtcctg   480
ttcgagaagt gggccgattc ctcccagtcc tcctactggg gttatgagtt cagcagcagc   540
ggtctgcacc accgtgtgat cccgtacgcc tacttctcca gtccgagca gtaccgcccg   600
atccgcttca acaccatcgt ggacgacgac acggccgcag gcccgccga ggacaacgcc   660
cgggtccagg tgacttcga cggcgacggc cgcgacgacg tggcggtgct ctacgactac   720
ggcaggaagg acgaccgcag tcgctcggcc ctgtggacgt tcaacagcaa cggcagcggt   780
ttcaacagtc ccaagcaggt gtgggacagc gggacgtcgg agagctggaa ctgggcctcc   840
agcaagttga cggtcggtga cttcaacggc gacggcaagg ccgacatcgg cgtcctctac   900
aacatgggcg cgaccgagga cggccgcaac cgcaccaagc tgttcgtgtt caccagcacc   960
ggcagcggat cgccgcccc ggtcaaggtc tgggacagca acgacgaccc cgtgaagagc  1020
tggaactgga acgccagcaa gctccaccgt ggcgacttca cggcgacgg caaggccgac  1080
atcggggtgc tgtacgacta cggcaaggac gacgaccaca accggacagg gctctggacg  1140
ttcaccagca ccggcagcgg gttcaacagc ccgaagcagg tgtgggacag caacaacgac  1200
cccgtgaaga gctggaactg ggaagccagc aagcccgtct ccggggactt caacggcgac  1260
ggcaaggccg acatcggcgt cctctacgac tacggcaaga ccgactccgg cagccgcacc  1320
ggactctgga cgttcaacgg caatggcaac gggttcaaca gcccgaagca ggtgtgggac  1380
agcaacaacg accccgtgaa gagctggaac tgggaagccg gcaagcccgt tccggcgac  1440
ttcaacggcg acggcaagag cgacatcggc gtcctctacg acatgggtcg caccgaggac  1500
ggccgcaacc gcaccaagct gttcaccttc accggcacgg cgaccggttt caacagcccg  1560
gtcaaggtgt gggacagcaa cgacgacccc gtgaagagct ggaacgcgtc cgcgagcaag  1620
cccgtcgcag gtgacttcaa cggcgacggc aaggcggaca tcggcgtcct ctacgactac  1680
ggcaagaccg actccggcaa ccgcagcgga ctgtggacct tcaccagcaa cggcagcggc  1740
agcgacagcc ccaagcttgg ctgggacagc agcgcggacc ccgtcaagag ctggaactgg  1800
agcgcgagca agctcggctg a                                            1821

<210> SEQ ID NO 83
<211> LENGTH: 2466
<212> TYPE: DNA
<213> ORGANISM: Streptomyces lavendulae -continued

```
<400> SEQUENCE: 83
atgcgaacca tacgaatacg aagaacgaac ggcgtggcct tcgccgccgc tgccgccctg      60
atggccctcg tcgcctccgg caccgccacg gtccaggccg cgccctcgca cgccggaccc     120
tccggcacca ctccgatcac ctaccgtggc ctcaccctcg acatacctc cggtggccg       180
gtcgtggacc tggagaaaga cccgcacacg tgtgtgcgt tcgaccgcca cacggtgtac      240
ttgggccacc ccggcaccga acagtcctgc ccctcccatc tggtcgcgga caagacggac     300
gccctgatat tggagccgat caccggagcg ggcggccagg acgcctccca cgcgctgcgc     360
atccctgccg ggccccgat gccgcacgag ctgccggtga cgtacgacca cgagacgaag      420
gtcgccgtcg aaggcgccgg agtcatggtc acgtcctcct acggcacgtc cagtacaacg     480
gtcgccgccg tcctcggctc ggcccgcacg gacgcgacag ccaagccgac cccctgccc     540
ggcaaggcgg cagggcct cgcggctcca ccggttgccg ccgtcgcggc cgacaaggga       600
tacacagggc tgggcttcga gtcctgcacc gcccttcgt ccgccgcgat gaaggcatgg      660
aaggcctcgt cgccctacgg ggccgtcgg atctacatcg gcgtcgcaa gcggggctgt       720
gcgcaaccgc agctcaccgg cgactgggtg cgtcagcaga ccgccgacgg ctggcacctg     780
ctgcctctct tcgtggacct ccaggccggc gacatctctc cggccaccgc ggacgcgcag     840
ggccgcgagt ccgcggacgc cgccgtggcc aaggcggcgg acctgggcct gggccccggg     900
acggtcatct acagcgacat ggagcactac gacagccgct cgtaccgggc ccgggtcatc     960
gactacgtgt cggggtggac cagccgcctc cacgaacatg ctaccgctc cggtgtgtac    1020
gcgggtgaaa cgagcggcat cccggacctc gcctcggtgg ccgacgacac caactacgca    1080
tcacccgacg tgctgtggtc ggcgaactgg aacctcaagg ccgatgtgtc ggacgcgtcg    1140
atgggacttc cgggccccgg ctactggccc aatgggcggc gcatccacca gtaccgcggc    1200
caggtgaaca cacctacgg cggtgtcacc ctcgccatcg accgcgacta cgtcgatgtc    1260
gccgcggact cggccctgcc cgcacccggc ggagaggacg gttcctcgcg cgtcaagggc    1320
gacttcgacg gcgacggccg cgacgacgtg gccgtgctgt acgactacgg caaggagggc    1380
ggcgtcagcc ggtccgcgct gtggacgttc gcggggaccg gcagcggctt cggcgccccg    1440
aagaaggtgt gggacagcgg atcggacagc tggagttggt cggccgccaa gctgacggcc    1500
ggcgatttca cggagacgg caaggccgac atcgcggtcc tgtacgacat gggtcgcact     1560
gaggacggcc gcaaccgcac caagttgtac gagttcacca gcaccggcag cggattcaac    1620
agcccggtca aggtctggga cagcaacgac gaccccgtca agagctggaa ctgggcctcc    1680
agcaagctga ccgtcggcga cttcgacggc gacggcaagg ccgacatcgc ggttctgtac    1740
gactacggca gggacggcga ccgcagccgt acgggcctgt ggaccttcac cagcaccggt    1800
gccgccttca ccgcccccaa gctggtgtgg acagcaaca acgacccggt caagagctgg    1860
aactggaacg ccagcaagcc caccgtcggc gacttcaacg gcgacggcaa ggccgacatc    1920
ggcgtcctct acgacatggg tcgcaccgag acggccgca accgcaccaa gctgttcacc    1980
ttcaccggca cggcgaccgg tttcaacagc ccggtcaagg tgtgggacag caacgacgac    2040
cccgtgaaga gctggaactg gacgccgtc aaggtagtgg aggcgacttc aacggcgac     2100
ggcaagagcg acatcggggt gttgtacgac tacgcaagg acggcgaccg cagccgcacc    2160
ggactgtgga ccttcaccag caacggcagc gggttcaaca gcccgaagca ggtgtgggac    2220
agcagcaacg acccggtgaa gagctggaac tgggccgcga gcaagccggt cgcaggggac    2280
ttcaacggcg acggaaaaac ggatatcggc gtgctctacg actacggcag gaccgattcc    2340
```

```
ggcaatcgca ccggactgtg gaccttcacc agcgacggca ccggattcgg tacaccctc    2400 ctgggctggg acagcgtgac ggatgccgtg aagagctgga actggcgtgc cagcaaggtg    2460
agttga                                                              2466

<210> SEQ ID NO 84
<211> LENGTH: 1575
<212> TYPE: DNA
<213> ORGANISM: Streptomyces lavendulae

<400> SEQUENCE: 84
gtggatccct tgacgcgcaa gacccgcacc ccccgcaaga agggcagacg cgcgagcgcg      60
gcggcgatgt cggcctccgg catgctgctc gccttggtgg ccaccgccgc ccccgtcccc     120
gcccaggcgg catcactcgc cacctgggaa aagatggccc agtgcgagag cagcggggac     180
tggggataca accagccacc gtactacggc ggcctgcaat tcctggagag tacgtgggtg     240
gcgtaccacg gaacggacta tgcgccatac ccctatcagg ccaccaagga acagcagatc     300
cgggtcgcgc agcggctcct cgacaatgag gcgcgggctc cctggccgta ctgcggaaag     360
aaggtggggc tggctgacga cgacgcacgc cccttccccg acgcgccgga cgacgacgcc     420
tccgcccgga tcaacggtga cttcgacggc gacggatgcg acgacgtggc cgtgctctat     480
gactacggca aggagggcgg cgtcagccgg tccgggctgt ggacgttctc cgggagcggt     540
accggcctcg gcagcccgaa gaaggtgtgg gacagcggat cggccagctg gagttggtcg     600
gccgccaaac tggccgtcgg cgatttcaac ggcgacggca aggccgacat cgcggtcctg     660
tacgacatgg gccgcactga ggacggccgc aaccgcacca agttgtacga gttcaccagc     720
accggcagcg gattcaacag cccggtcaag gtctgggaca gcaacgacga ccccgtcaag     780
agctggaact ggaacgccgg caagctcacc gtcggcgact caacggtga cggcaagacc     840 gacatcggcg tcctctacga ctccggcaag accgactccg gcaaccgcac cggactgtgg     900
accttcacca gcaacggcac tggattcaac agcccgaaac aggtgtggga cagcaagagc     960
gacccggtga aaagctggaa ctgggccgcg agcaagccgg tcgcgggcga tttcaacggt    1020
gacggcaaga ccgatatcgg ggtgctttac gactacggca agatggcga ccgcagccgc    1080 accggactgt ggaccttcac cagcacgggc agcggattca acagcccaa gcagacctgg    1140 gacagcgggt cggaaaagctg gagatggtcg gcggccaagg tggtcggcgg cgacttcaac    1200
ggtgacggca aggccgacat cggggtgctg tacgacctcg gcaggaacgg cgaccgcaac    1260
cgcaccgaac tgttcacgtt cgcgggcaac ggcaccggcc tcaacacacc ggccaaggtg    1320
tgggacagcc aggacgacag cgcggtgaag agctggaact gggccgcgag caagccggtc    1380
gcaggtgact tcaacggcga cggaaagacg gatatcggcg tcctctacga ctacggccag    1440
accgactccg gcaaccgcac cggctgtgg accttcacca gcgacggcag tggattcgcc    1500
ggcccccaag ctcacctggga cagccggacc gaccccgtca gagctggaa ctggaacatg    1560 agcaagaccg gctga                                                    1575

<210> SEQ ID NO 85
<211> LENGTH: 2175
<212> TYPE: DNA
<213> ORGANISM: Streptomyces lavendulae

<400> SEQUENCE: 85
atgaaatacc gaccgggaac actgctcact tccataacag tcttgtgtgc cctgctcgtt      60
```

-continued

```
ccggtgcgtt cggcggctca ggcggccagg cccgagcagg gacgttccgt ggtggccgcg    120
gccgccgtac tggagcaaag tccgccgacg ctgctcgccg agccggaaat gcgcgtcgtc    180
tcctggaaca tctgcggtga ggcgggcggg gtgcgcgggg agggcggcta ctgcccctac    240
cgcaacgatc cccaggcgaa agtcgaccag atcgcgcagg tggtcgcgga gcgcagtgcc    300
aatgtcgtca tgctccagga agtgtgcggc gaggcgcccg gcagccatat ggagcggctg    360
cgcgcggccc tgggcagcgg atggtcgatc gcgcacgccc cggggcccg cccggacgac     420 ggaaccacga actgccgggg cgggctcagc ggcatattgg gcgtggggat cgcggtgaag    480
gggcgcgtca ccgacaccac cgcgacgaac accgtgcccg gggcggcgg tgacaagcag     540 accctgccca tcctctgtgt acgtgtcgag ggctggtcgt ccaggatctg caccacccac    600
atcctgtccg accctgccga tccgcgcagg ccggggcaga tccagaacgt caagaacgag    660
atctggccgg accgctatca gctggtgctc ggcggcgact tcaacatgtt ccccgactcc    720
gccgggctca agccgatctc ggacgaattc gacgagtgcg accgccgctc ctacggcgcc    780
ggtgacatgg tcaacgaggt cacccatcac tcctgggaga aaagggcgg acacatatgg     840 cgcaagcgtg accacatctt cgcctcgtgg ggagagtccg ggagccagtt cacatcctgc    900
gaggtcgacc ggacccggat ggacaccacc gagaacgcgc ccgaaagcgg tccgcccaac    960
gggtattcgg accatgcgcc gatcatcggc tacctcaagc cgccgcggca cctgagcacg   1020
tccggggact cgacggcga cggcaaggcc gacctcgcgg tcctctacgg caggggaag     1080 accccggacg gccacaaccg gtccagcctg tggatctcag gcggttccgg taccggagcg   1140
gagaccggat tcgccgcgcc gcgcgaggtc tgggacagcg gtgccgacag ctggaactgg   1200
tccgcgagcg cgctgacctc cggggacttc gacggcgacg caagaccga catcggcgtc    1260 ctctacaact acggcaggga cggcgaccgc aaccgcaccg cgctgtggac cttcaagggg   1320
acatcgaacg gcttcgaggc gccccgcaag gtgtgggaca ccacgacga cacggccgtt    1380 cccagctgga actggtccac gagcaagctc gtcgcgggcg atttcaacgg cgacggcaaa   1440
gcggacatcg cgtcctgta cgactacggc aggaccgcct ccggcaaccg caccggactg     1500
tggaccttca ccagcaccgg caccggattc ggcaagcccc acctggcgtg ggacagctcc   1560
accgacccgt gaagagctg gaactgggcc gcgagcaagc cggtcgcagg tgacttcaac    1620
ggcgatggca agaccgacat cggcgtcctc tacgactacg gcaaccacac cgccctatgg   1680
accttcacca gcaacggcac cggattcgcc ggccccaagc aggcctggga cagcggaccg   1740
gagaactgga actggtccgc cgccaagccg gtcgccgggg acttcgacgg cgacggcagg   1800
accgacatcg cggtcctgta cgactacggc aggaccgcct ccggcaaccg caccggactg   1860
tggaccttca ccggcaccgg caccggattc ggcaagcccc acctggcgtg ggacagctcc   1920
accgacccgt gaagagctg gaactgggcc gcgagcgagc cggtcgctgg tgacttcaac    1980
ggggacggca gggccgacct cgcggtgatg tacgactacg gaacgcgac caacggccgc    2040 aaccgcaccg cgctgtggtc cttcaccagc cgcggcacgg acttcgccgc cccgcgggcg   2100
aactgggaca gcagcaacgc cgctgaccag ctgaaatcgg gcgagctgag ggcggctccg   2160
ctcagcgggt cctag                                                    2175
```

<210> SEQ ID NO 86
<211> LENGTH: 27
<212> TYPE: DNA
<213> ORGANISM: Artificial Sequence
<220> FEATURE:
<223> OTHER INFORMATION: A primer

```
<400> SEQUENCE: 86
tcagaattcg gatccgaggg ccggagt                                      27

<210> SEQ ID NO 87
<211> LENGTH: 18
<212> TYPE: DNA
<213> ORGANISM: Streptomyces lavendulae

<400> SEQUENCE: 87
acctactgcc tcgatgcc                                                18

<210> SEQ ID NO 88
<211> LENGTH: 15
<212> TYPE: DNA
<213> ORGANISM: Streptomyces lavendulae

<400> SEQUENCE: 88
ctgatccttc aagcg                                                   15

<210> SEQ ID NO 89
<211> LENGTH: 20
<212> TYPE: DNA
<213> ORGANISM: Amycolatopsis mediterranei

<400> SEQUENCE: 89
gcgtccgtgc tgcgcgcgca                                              20

<210> SEQ ID NO 90
<211> LENGTH: 20
<212> TYPE: DNA
<213> ORGANISM: Amycolatopsis mediterranei

<400> SEQUENCE: 90
tgcgcgcgca gcacggacgc                                              20

<210> SEQ ID NO 91
<211> LENGTH: 6
<212> TYPE: DNA
<213> ORGANISM: Streptomyces lavendulae

<400> SEQUENCE: 91 gaaagg                                                              6

<210> SEQ ID NO 92
<211> LENGTH: 80
<212> TYPE: PRT
<213> ORGANISM: Artificial Sequence
<220> FEATURE:
<223> OTHER INFORMATION: A conserved motif
<220> FEATURE:
<221> NAME/KEY: SITE
<222> LOCATION: (1)...(80)
<223> OTHER INFORMATION: Where present in this sequence, Xaa represents
      variable amino acid.

<400> SEQUENCE: 92

Gly Xaa Xaa Xaa Asp Xaa Xaa Xaa Xaa Xaa Xaa Ala Xaa Xaa Xaa
 1               5                  10                  15

Xaa Xaa Xaa Xaa Xaa Glu Asp Xaa Xaa Xaa Xaa Xaa Xaa Xaa Xaa
                20                  25                  30

Xaa Xaa Xaa Xaa Xaa Gly Xaa Xaa Xaa Xaa Xaa Xaa Xaa Xaa Xaa
                35                  40                  45
```

```
Xaa Xaa Xaa Lys Xaa Xaa Xaa Gly Glu Gly Gly Xaa Xaa Xaa Xaa
    50              55              60

Xaa Xaa Xaa Xaa Xaa Xaa Xaa Xaa Xaa Xaa Xaa Xaa Xaa Xaa Gly
65              70              75              80
```

<210> SEQ ID NO 93
<211> LENGTH: 6
<212> TYPE: DNA
<213> ORGANISM: Streptomyces lavendulae

<400> SEQUENCE: 93 ggaacg                                                                6

<210> SEQ ID NO 94
<211> LENGTH: 30
<212> TYPE: DNA
<213> ORGANISM: Artificial Sequence
<220> FEATURE:
<223> OTHER INFORMATION: A primer

<400> SEQUENCE: 94
gggaattcca tatgatgcag tccatgtcac                                       30

<210> SEQ ID NO 95
<211> LENGTH: 30
<212> TYPE: DNA
<213> ORGANISM: Artificial Sequence
<220> FEATURE:
<223> OTHER INFORMATION: A primer

<400> SEQUENCE: 95
gggaattcaa gctttcattc cgccggggtc                                       30

<210> SEQ ID NO 96
<211> LENGTH: 18331
<212> TYPE: DNA
<213> ORGANISM: Streptomyces lavendulae

<400> SEQUENCE: 96
ggatcccgat cgtctcggac atgaccggcg accttctcgg cgcgcgggag gcccaggacc      60
ccgcctactg ggtgtcccac atccgccgcg cggtgcgctt ccacgaccag atccgccgtc     120
tgcagcgcta cggggccggg gccttcgtcg aggtcggccc ggacacggtg ctcagctcgg     180
ccggccaggc gtgcctgacg gaccaggcgg gcaggagcgc gcccgtcctg gtgtccctcg     240
cgcacgccga gcgcgcggag gtgcccgcgc tcctgaccgc tctggccacc ctgcacaccc     300
gtggcgtggc cgtggactgg cgggcgtggt tcggcgacgg gccgcgcgcg gcggcctgc      360
ccacatacgc gttccagaag cagcactact ggccgtcggg cccaccggt tggcggtccg      420
ggcccgcccc cgtaccctg ccccaggccg gaacggagga cgccgaaagg cccggtcgcg      480
ccgcggagtg gcgggcgctg ccgcccggtg agcggtacga cgcgctgctg cggatggtgc     540
gcggcgaagc cgccgccgtg atggggcacg ccgggccgga ggcggtggag ccggagcgcg     600
gcttcctcga ccacggcttc gactcggtga tggccgtgaa gctgcgcgac cgtctcgtgg     660
ccgggacggg gcgggagctg ccgacgaccc tgctgttcga ccaccccacg cccgcggccg     720
tcgccgacta cctgctggcg gggacgggcg aggccgagac ggcgccgtcc gtgtccctgt     780
cggaccagct cgaccgcctg gaggccgacc tcgcgcggct gccggccgac gaccggcagc     840
gcgcccgcgt cgccgagcgg ctcaaggcc tgctcgcggt ccacgcgccg gaccggggcg     900
ccgggagcga ggacgcgccg gaccaggacg cgctggacac ggcgaccgac gacgagatgt     960
```

```
tcgagctgat cgagaaggaa ctccgccgtg gatgagacca acgagaccaa actccgcgag     1020
tacctgcggc tggtcacggc cgatctgcgg cgaacccgca ggcagttgga ggaggccgag     1080
gacgcggccc gcgagcccgt cgcgatcgtg ggcatggcgt gccgcttccc cggggacgtg     1140
gcatcgccgg acgacctgtg gcagctggtc gccgagggcc gggacgccgt caccgagttc     1200
cccgccgacc ggggctggga cgtcgacgcc gtctacgacc ccgagccggg caccccgggc     1260
aggacgtacg cgcgccacgg cggcttcctc aaggacgccg ccggattcga cgccgccttc     1320
ttcggcatca cgccgcgcga ggcgctcgcc atggacccgc agcagcgcat gatcatggag     1380
gtctcctggg aggcgttcga gcaggcgggc ctcgacgcga ccaccctgcg gggcgaggac     1440
gtcggcgtct tcgtcggctc caacagcaac gactacctga tcaacgtgct cgacgcgcgg     1500
gacgtcgccg agggcttcat cgggaccggc aactccgcca gcatcctctc cggccgcgtc     1560
gcctacacct tcggcttcga gggcccgccc gtgtccgtcg acaccgcctg ctcctcctcg     1620
ctggtcgcgc tgcacctggc cgcgcagtcc ctgcggcagg gggagtgctc cctggcgctg     1680
gcgggcggcg cgacggtgat ggccacgccg accgccttca tcgagttcag ccgccagcgg     1740
ggcctggccc ccgacggccg ctgcaagtcc ttctcggcga ccgccgacgg caccacctgg     1800
tccgagggcg cggccgtgct gctgctggcc ggctctcgg acgcccgccg cctgggctac     1860
cccgtgcacg cggtcatccg gggcagcgcc gtcaaccagg acggcgcgag cgcgggcctg     1920
accgcgccca acgaccggc gcaacagcgg gtgatccggc aggcactggc caacgcacgg     1980
ctgacggccg acagcgtcga cgcggtcgag gcacacggca ccggcacccc gctgggcgac     2040
ccgatcgagg cccaggccct cctcgccacc tacgggcggg cccgcggcga gggcaggccg     2100
ctgtggctgg gctcgctgaa gtcgaacctg gccacaccc agtccgcggc cggcgcgggc     2160
ggcgtcatca agatggtgat ggccatgcgg cacgggacgc tgccccgcac gctgcacctc     2220
acggagccca ccccgcgcgt cgactggtcc gccggtgacg tacggctgct gaccgaggcc     2280
caggactggc cggacaccgg acagccgcgc cgtgcggccg tctcgtcctt cggcgtcagc     2340
ggcaccaacg cccatgtgat cctggagggc ccgcccgccg aggaggcacc ggacgcgccg     2400
ctgccggacg tctcctcgca gccgcggggc ccgctgccgt gggtcgtctc cggccgcagc     2460
gaggcggccg tccgagcgca ggccgagcgc ctggcggccc acctgaccgc gcgcccgcac     2520
ctggcaccgg ccgacgtggc caccgcgctg ccaccacgc gggcggcctt cgaccaccgg     2580
gccgccgtcg tcggccggga ccgtgaggaa ctgctcgccg gcctcgcggc cctggccacc     2640
ggaacccgcg cgcccggcct ggtcaccggc cggaccccgc cgtccggcgg caaggccgcc     2700
ttcctcttca ccggacaggg cagccagcag cccggcatgg gccgcgaact ggcggctcac     2760
agcaccgtgt tcgccgacgc cctggacgag gtctgcgccc agctcgaccg gcacctcgac     2820
cggccgctgc gcgaggtgct gttcgccgcg gacggcacgc ccgaggccgc cctgctcgac     2880
acgacggcct acacccagcc cgcgctgttc gccgtcgagg tcgcgctgct gcggctgctg     2940
gaggactggg gcttgcggcc cggcatggtc gcgggccact cggtcggcga actgaccgcc     3000
gcctacgccg ccggggtctg gtcgctcgcc gacgcctgcg ccctggtcgc cgcccgcggc     3060
cggctgaccg aggcactgcc gcgggcggc gccatggtcg ccgtgcaggc gaccgaggac     3120
gaggtgcgcg cccaactcgc cgacggccgc cccggcgtgg acatcgccgc cgtcaacgga     3180
ccggaagcgg tggtgctgtc cggcgacgag ccgccgtca cggacctggc gcgcgagtgg     3240
gccgcccgcg gccgggagac caggaggctg cgggtcagcc acgccttcca ctccgcccac     3300
```

-continued

```
ctggacgcca tgaccgaggc gttcgccgag gtcgcacgag gggtgtccta cagcgcgccg    3360
tccctcccgg tggtctccac gctcaccggg gcccccgtca ccgacgagct ccgcaggccg    3420
gaacactggg tgcggcacgt ccgggagacg gtgcgcttcc acgacgcggt ccgcgccctg    3480
cgcgaccgcg gggccaccgc gttcctggag gtcgggcccg gcggcgtgct gacggccgcg    3540
gcacgccgat gcctgcccga cgccgccccc gagacgttcg tccccgtgct gcggcgccgc    3600
aggcccgaac ccgagtccgt gctgacggcc gtcgcgcagg cccacacgat cggcctctcg    3660
ccggcgtggg accgcctgct gcccaaggcc cggacgcgcg tggacctgcc cacgtacgcc    3720
ttccagcgcg gccactactg gctggcgggc atggccggag cgggcaccgc gcggccggtg    3780
cggccggaag tgcaggagcc caccgccccc tccggtacgc cgccgctgtc gcgacggctg    3840
gccgacgcgt cggaggagga gcgcggccac ctgctgctga cgctggtacg cgagcagtcg    3900
gccaccgtga tgggcggcgt cgaccccgcg caggtcgaac ccgaccgccc cttcctggag    3960
ctcggcttcg actccctgat gggcgtcgag ctgcgcaccg cgctcgccgc cgactgcgca    4020
ctgcccctgc cgcccggcct gatcttcgac caccccacgc ccgccgccct ggccgccttc    4080
ctcggcgagc agctcgcggc ggcggcctcc ggcaccccca cggcggcggc accctcgccg    4140
tactccctgg aggcgctgta ccgcaacgcc aacaccctcg accggcccga ggacgcgctc    4200
gccctcacca aggccgcctc ccggctgcgc ccggtcttcg ccagcgtggc cgaggcgggg    4260
caggacccgg tcacggtgga gctggcacag gccaccggcc ttcgggcct gatctgctgc    4320
ccggcacccg tgccgctgta cggggcacag cagtacagcc ggctcgcagc cgccttccgc    4380
ggcacgcgcg gagtctcggc cctgctcgcc cccggcttct ccccgggcga actgctgccc    4440
gccgacttcg aggtgatgca ggacttcctc gccgaggggg tccggcggca gaccgacggc    4500
gcgcccttcg tcctcctggg ccactcctcc ggggctggt tcgcctacag cctggcggcc    4560
cacctggcgc gcaccgggcc gcgcccgag gccgtcgtgc tgctggacac ctatcagctg    4620
cacgacccgg cgctgcaccg catgcagcgc gaactcgccc agggcgtcct ggaccgcgag    4680
gaggacttcg gggcgatgac ggacgtacgg ctgagtgcca tgggcaaata cttcgacttc    4740
ttcaccgact gggtggccga ggacgccggt gtcccgacgc tgctgctgcg ggcctccgag    4800
cctctgggcg aggtcgtcga gggccaggag tggcgctcca cctggccgtt cgacagcacg    4860
gtcctcgaca cggaaggcga ccacttcgcc atggtcaacg accacgcgcc gcggacggcc    4920
caggccgtga acggctggct gtcgggcctc accggcggaa ggggctgagc gccggtggag    4980
acacgcaacg ccgaacggcc gtggatacgc agcttccacc ccgctcccca ggccctgtg    5040
cggctgctgt gcctgccgca cgccggggc tccgcgagcg cctacttcgc gctgtcgagg    5100
gaactggcgc cccgggtgga ggtgctcgcc gtgcagtacc ccgggcggca ggaccggcgc    5160
gacgagccgc tgctggactc gatcgaggcc ctgcgcgacg ggtcgccga ggccctgacg    5220
ccctggctgg accggccggt cgccctcttc ggccacagca tgggcgccgt ggtggcctac    5280
gagctggcgc ggctgctgtg ccaggacgcg gcgtgccgc tcacccacct cttcgtctcc    5340
ggacgccggg gatccgaccg aagtctccgt ccttgccgcc gtgttccgga attcaccgtg    5400
acaccgccgc gcggctcttc ttccgaagtc ctccagatcc ggcacgagtt tgtatccgaa    5460
cggggttctg cgtgcgaaat actctcttcg aattgggtga catacccccg atcggcaccg    5520
tacccgagca gatgtacgcc tcggtgatcc gacgggagcg ctacgacag ccccaccagg    5580
cgttccgcag cgaggtcgtg gacgtgccga aggtggggcc cggtcaggcg ctggtcctcg    5640
tgatggccgc gggcatcaac tacaacaacg tctgggcctc cctggggcag ccggtcgacg    5700
```

```
tgatctccgc gcggcagaag cagggccaca gcgaggactt ccacatcggc gggtccgagg    5760
gctccggcgt ggtgtgggcg gtgggggagg gcgtcaccca ggtcgcggtg ggcgacgaag    5820
tgatcctctc cggctgccag tggacggaga cggccgccga catccggctc ggcgccgacc    5880
ccatgacctc cggctcgcag tcggtgtggg gatacgaggg caactacggc tccttcgccc    5940
agttcgccct cgtcgacgac tatcagtgcc accccaagcc gccggcctg acctgggagg     6000 aagccgcctg cttcctgctc accggggcca ccgcctaccg ccagctgtgc ggctggcagc    6060
cgcacgacgt gcggccgggc gacccggtcc tcatctgggg cggggccggc gggctcggct    6120
ccatggccat ccagatcacc cgggcgcggg gcggcatccc cgtcgccgtg gtctccgacg    6180
aggagcgggc ccgctactgc cgggagctcg gcgcccaggg caccatcaac cgcctggact    6240
tcgaccactg gggacggctg cccgacatcg gcgaccacga ggcgatgggc cgctggaccg    6300 aggtgtacg ggccttcggc cggcgcttct gggaggtgct gggcgagcgc aggtccccgc     6360
gcatcgtcct ggagcacagc ggccaggcca ccatcccac ctcgatgtac ctgtgcgaca     6420
acgcgggcat ggtcgtcatc tgcggcggca ccaccggcta caacgccgac atcgacctgc    6480
gcttcctgtg gatgcgtcag aagcgcttgc agggctcgca cttcgccaac ctgcggcagt    6540
gccgcgacgt catccacatg gtcgcgaacg gccagctcga cccgtgcctg tcgtggaccg    6600
gcggcttcga cgacatcggc aaggcacacc agctgatgca cgacaaccag cacccccagg    6660
gcaaccaggc cgtcctggtc aacgcgccgc ggaccggcct gaccaccttc gcctgaacca    6720 ccgcccggt gttccgacgt cttccccca cacttaccga ccaaggagag atcaccatgg      6780
acaagctcga catcctctgg agcgagcgcg agatccgtgc cgtgctgcag cgctactgcc    6840
gcgggctcga ccgcctcgac gaggaactgg tcaagtccgc ctaccacgag gacgcgcacg    6900
acgaccgcgg cgtcatccgc ggcaacgcac acgacttcgt caagcagatc gtcccgctcc    6960
tgcgcgacgc ctacaccggc accctgcaca ccctgcacgg cagcacgatc gagatcgacg    7020
gggatgccgc gggcgtggag tcctactgca ccgcctacca ctaccgcgag agcgacggca    7080
tcaagcgggt ggagcagttc gccgggcgct acgtcgaccg cttcgagcgg cgcgacggcg    7140
tctggaagat cgcccgccgg ctcgtgctga acgacttcag cctcgcccag gaggtgccgc    7200
tcgaccccgc cgaggcccag gccggcttca accctccca ccgcgacctc accgacgcca     7260
gctaccaggt gctgccgctg cgcggcccgg acgcccccac cctctgagcc gtccggccgc    7320
cccaactcgc cccacctcac caggagtcac caccgtgtcc gacaccgagc agcacgcgcc    7380
cacgctgccg cggcagcgca cctgcccctt ctcgccgccg cccgagctcg aggagctgcg    7440
gcgcaccgat cccatcagca ggatgcggtt cgccgacgac tcccccggat ggctgctgac    7500
ccgccacgcc gacgtccgcg ccgcgctggc cgaccccggc gtcagctcgc accccggcaa    7560 ggcacccag cctggcgca acctcgcccc cgagatcgcc gccgagcact acctgccggg      7620
cttcctgatc ttcatggacc cgccggacca caccgctac cgccgcctgc tcaccaagtg     7680
gttcaccatg cgggccatcc gcaagctcga acccaggatc gagcagatcg tcaccgagac    7740
cctcgacgcc atggaggccc agggcggcac cgtcgacctg gtgcagtcct tcgcgctgcc    7800
gatcccgctc ctggtcatct gcgagctgat gggcatccgc tacgaggagc gcgaggagtt    7860
catggacatg gtcctgcgac tccaggccct ggacgccacg cccgaggaac tcggggccct    7920
cggcgccagg atgaacgagt tcatgatgaa gctcgccgcc gccaagcgcg cgaacccccgg   7980 cgacgacctg ctcagccacc tcgcccacga ccccgacgcc gacccggcgc tcacggatct    8040
```

```
ggagatcgcc ggcatcggcg tgctgatgct catcgcgggg cacgagacct cggccaacat    8100
gctgggcgtc ggcacctaca ccctgctgga gaacgccgac cagtgggccc tgctccgtga    8160
cgacatcagc ctgatcgacc gggccgtcga ggagctgctg cgccaccaga ccatcgtcca    8220
gcagggcctg ccgcgcggcg tcacccggga catggagatc gccgggcacc aggtgaagac    8280
cggggagtcc ctgctggcct cgctgcccgc cgccaaccgc gaccccgccg tcttccccga    8340
ccccgaccgc ctcgacatca cgcgcgagca caacccgcac ctcgccttcg gccacggcat    8400
ccacctctgc ctgggcatgg agctcgcccg ggtggagatg cgccaggcgt ggcgcggcct    8460
cgtcacgcgc ttccccggcc tgcgcatggc cgccgcgccc gaggacatcc gctggcgcga    8520
cgaccagatc gtctacggcg tgtacaacct cccggtgacc tgggacgagg ccaagtgacc    8580
ggccccgagg ccgcggtgcg cgggtgcccc ttcggcgccg gcgaggcgcc cgcgtacccc    8640
ttccacgccc ccgaccggct ggagcccgac ccgtactggg agccgctgcg ccgcgagcgg    8700
ccgctgcaac gcgtcacgct gccgtacggc ggcgaggcgt ggctcgccac ccgctatcag    8760
gacgtgcgcg cggtcttcgc cgaccgcagg ttctcccggc agctcgccgt cgcgcccggc    8820
gctccgcgct tcctcccgca ccagccgccg ccggacgccg tcctgagcgt cgagggcccc    8880
gaccacgcgc ggctgcgccg gctggtcggg aaggtcttca cgccgcgccg cgtggaggac    8940
atgcgtccgc tcatccagcg caccgccgac ggactcctcg acgcgatgga ggagatgggg    9000
ccgcccgcgg acctggtcga ggacttctcc ctgcccttcg ccgtgtccat gatctgcgag    9060
ctgctcggcg tgccgcccga ggaccgcaag cggttctgcg tctggtcgga cgcgctgctg    9120
acgaccaccg cgcacacccc cgcccaggtg cgcgactaca tgatgcagat gcacgactac    9180
ctcggcgggc tcgtcgcgca gcgccgggtg cggcccaccg cggacctgat cggctccctc    9240
gtgaccgcgc gcgacgagga ggacaagctc accgagggcg agctggtgcg gctggccgag    9300
gccatcctca tcgccggcta cgagacctcg gcgagccaga tccccaactt cctctacgtc    9360
ctcttccgcc accgcagct gctggagcgg atcaggaacg accacgacct catccccgac    9420
gccgtcgagg aactgctgcg cttcgtgccc atcggcaccg tggacggctt ccccgtacg    9480
gccaccgagg acgtcgagct cgggggagtc ctggtcaggg ccggggagac ggtcgtgccg    9540
tcgatgggcg ccgccaaccg cgaccccgag ctgttcacgg accccgacga gctggacctc    9600
gcgcggcggc cgaatccgca cctgggcttc ggcgcgggac cgcaccactg cctgggcgcc    9660
caactggccc gggtggagct ccagatcacg ctcacgacgc tgttccgcag ataccccgc    9720
ctgcggctgg ccgtgccgga ggagagcctc tcgtggaagg aggggctgat ggtccgcggc    9780
atgcacacca tgccggtcac ctggtgagga caccggcgtc ctcctgacct tcccggcgtt    9840
ctcacgccgt cccggcagcc ttccttccga cacgagcgca cagagggtga agcgaccgca    9900
atgagcacca tcgacgaatg ggaacacagc acgaaggagg cgggcatgga ccccgcggcc    9960
ctcagacgcc tgaccgatgt ggtgcgggcg aggggcggcg cggcgcagct gtgcgtcatg   10020
cggcggggca ccgtggtcct ggaccgctcg ttcggctgct cctccgactc cctcttcctc   10080
gtctacgcgg ccaccaagcc cgtcgccgcc ctcgccgtgc acgcgctcgc cgagcggggc   10140
ctgatcgggc tggaccggcc ggtggccgaa tactggccgc agttcgcccg gcacggcaag   10200
ggtgacgtga ccgtccgtca tgtcctccag caccgggccg ggtgccggt cggccggggc   10260
atcgtgcgca cgatgcgcac cgccggcgac tgggagcgct ccgtgcgcga ccttgagcag   10320
tcccggccca agtggcccgg cggcgaggtc gccgcctacc acttcatgag tttcggattc   10380
attctcggcg aactggtgca gcgcgtcacc gggcggtcgt tccgagattt cgtgacttcc   10440
```

```
gagctcttcg ccccacttgg gctgaatgat ttgcacatgg gattgcccgg cagtgcctgg   10500
ccccggcatg tgcccgcgcg ggccgcccac ccctccgaat ggcccaatca gtggatgagc   10560
aaccgccgcg gctaccgcca ggccgtcatt ccgtccgccg gtctttccgg aaccgccgca   10620
caaatggccc gcttttacca gatgcttatg gagggcggct cgctcgacgg catccgcgtg   10680
ctgcggcccg aaactgtgga ggaagccaga aaaccgtcca atgacggcgg aatcgacgct   10740
tccctcaagc gtccggtccg ctggtccac ggattcatgc tcggtggtcc gggcccggac   10800
ccgcggggc tgtccaatgt gctgggccgc acgagcgacc cgagcgcctt cgggcacgcg   10860
ggcaccacgt ccagcgtcgt gtgggccgac cccacgcgcg agctggtcct cgcctacctc   10920
tccaacatcc agcccgagtt cggagcgggt atcgagcggc tccgcgaggt cagtgacctc   10980
gcgctcggtg cctgcgaggc aggctgaccc gagccgtgcc gccacggccc ggcgcccgcc   11040
cgatccgatc gggtccggtg ggggccggcc gggtccgggc ggggacgcac ttccccggc    11100
gtccccgccc gggccccggt gcgaaccggg cgcaaaggcg gccgatcgcc cggcgcggcc   11160
ggatgccccc gaacgtgtgt gaaacgttctt atcagcctct gaccagcacc gagtgatcta   11220
ctgcacagcc cgaggccgcg attccggcag tatcttgatc ttgacggggc accaatgcga   11280
gcgggctatt cgccgcggtt ttccctgacg tcggatgcag atgacaccgg aggagggcca   11340
gtgctgaatc tgcccaaagg aatggagcgc gcgcatccgc attctccgcc acaggtggga   11400
atactcggac ccttggaagt ccgctcggcc ggaggtgccg gaacgggagc gcggtaagc    11460
ggtattcgcg tacgcacatt gcttgccgcg ttgactgccc gcctggggca ggcgatgtcg   11520
accgagcgca tcctcaaaga ggtctgggcc gacaacccgc ccgcgaccga tcgcaaggcg   11580
gtggccgtcg ccgtcctgcg gctgcggcgg gtcctcggcg acaacgaagg acggtggctg   11640
ctcaccgcc cctccggtta cgtcctggac atcccccgg accacctcga cgccgtacgc    11700
gcggagaccc tggtgcggga aggccgggcc gccctggccg ccggcgaccc acgcgtcgcg   11760
gcccgccacc tcacgcgcgc cctcgaccag tggcggggcg agcccctacgc ggacgccaac   11820
gccatctcga ccgtgtccca gcgcatcacg gagctggaga acctcaggtc cgaggccgtc   11880
caggcgcaca tcgacgccag gctcgaactg ggtcaccacc aggaactggt cggcgaactc   11940
cgctcgctga ccgccgcgaa ccccctgcac gagccgcact ggctgcagct gatgctcgcc   12000
ctctaccgct ccggcaagca ggccgaggct ctcgccgcct atatgcagct gcggcaggcg   12060
ctggccgaga acctgggcat cgacccgggt cgtcagctcc aggaactgca cctgcggatc   12120
ctgcgcgccg acgcgggcct gctgacgggg tccgggccgg cggcaccggc cgagccactg   12180
ctcgtacggc agtcctgagg gctcacgcc acccgaagaa cgcgcggtag cacggaacct   12240
gctgctccag catatggatg ccgtggtgca cacggcgccc ggcggtggcg gccgcgctca   12300
gcagcgccgt ctcgtgcggc ttcatgacga cgtcgaccac cacggcatcc ggtcgcaccc    12360
tcgcggggtc gaagggcagc gggtcctcgg aacgcatgcc cagaggcgtc gcgttgacgg   12420
cgaaatcggc cgcctccaga tcgccgggcc ccagcgcccg gatcccgtcc ggccggcggg   12480
acccgagccg cagcagcagc gcgtcgagct gggcgcggtc ggtgtcgtgc acggacaccc   12540
gcgcggcgtc ggccatcagc agcgccgtgg cgatcgcgct gcccgcccct ccggcgccga   12600
ccagtgccac atgcctgtcg cgcaccgtgt gcccggccgc ctgaagaccc tggacgaacc   12660
cgagcccgtc gaagttctcg gcgtaccagc ggccgtcggg ttcgcgccgc atcgcgttgg   12720
ccgtcccgat gagggcggcc gccggcccga gcccgtccgc gagcccgcac agggccgcct   12780
```

-continued

```
tgtgcggcac ggtgaccagc agaccgtcca gattgccgat ccgcttgagc ccctcgacca    12840
cctcggcgag atcccgcgcc cggacgtgca ccggcaccac cacggcgtcc agaccgcttt    12900
cgctcagcag ggggttgagc agaccgggcg ccttgacctg ggcgacggga tcacccagca    12960
ccgcgtacag ccgcgtggcg cccgagacac cggccgccgg cccgaggaat tccatcagcc    13020
gatcctctct gtaccccga cggatgttgc cctacggtgc tggagatgct ccacagcttt     13080
gccgtgaccg ccggtcggca caaccctgcg tgccctgac gcgccaggcc ctccaggtag     13140
ttgctcccgg cggatcccga cagctcccga ccggtcccga cggagggaag aagccatcag    13200
atacctggga atcgacgtcg gaggcacgaa ggtcgccctg cgggtgacgg gggacaccga    13260
cggtgcgggc ggcggcgacg tgacgttccg ctggcccgcc gccggcgacg tcaccgcgga    13320
tctggacctg ctcgccgcgc gggtccgcgg tcttctggga caccgcgagg accccctcgc    13380
cggggtcggc gtggccatgc ccgcgatctg cgacgcggcc gggacggtcc gcacgtggcc    13440
gggacggccg agctgggcgg gcctgaacct gacgccgcc ttcgggcagt tgctgcccgg     13500 cacccggtc gcctgcgccg acgacggtga cctggccgcg ctggcggagt cccgcgccgc     13560
cggctgccgg catctgctgt acgtgggggt cggcacgggc atcggcggcg catcgtcca    13620 tgagggccgc gcctggccgg gccccggacg cggtcgtgc gaggtcggcc atgtcgtcgt     13680
cgaccgctcg ggcccacgct gcgactgcgg gcgcgccggc tgcgtccagg cggtcgcgtc    13740
gggaccggcg accctccggc gggccgccga acgcgcgcc cgggagaccg gcttcgacga     13800
actggcctcc ggggcgcgct tgcacgcccc gtgggcggaa gcggccgtcg acgagagcgc    13860
cgcggccctg gccaccgccg tgaccggcat ctgcgagctg gcccaccccg aactcgtcct    13920 cgtcggcgg gggttcgcgg cgggcgtgcc gggatacgtg gcctcggtgg cggcgcacgt     13980
cgagcggctg accgcccgg gaacggatcc cgtgcgggtg cgcccggcgg tgctcggcgg     14040
gcggtcctcc ctgcacggcg cactgctgct cgcgcgggag gcacacgggc ggggaaaccg    14100
gccgccggag agtgaccgtg tttcttccga tgtttcttcc gatgtttctt tcggggagt     14160 gacagacagg gccgttggcc ggtccgactg agcacaatca caggtgatt cgcccaggtt     14220 caccacgcct cgtgtgctcg gggtcggcag aaggagtcag agtcatgctc gacaggcgga    14280
gcgtcattcg cgtcggcgcc ggggtggcgg cggccgccgc cgtggccggt acggccgcca    14340
ccggtgcggc ggccgtgggg ctgccgggtg tacggggacg cgcggcgtcg cgcggggtcg    14400
actgggcctc cttacgccgt catctgtcgg gcgagctcgt cctgccggcg acaccggat    14460 acgagcgggc caggaagctc tacagcggcc agttcgacgg catccgcccg caggccgtcg    14520
cctactgccg gaccgaggag gacgtgcgga cgaccctcgc gttcgcccag gaccacgcgc    14580
tgcccctcac cccgcgcagt ggcgggcaca gcttcggcgg ctactccacg accgacggaa    14640
tcgtcctgga cgtctccggc ttccacgcgg tgagcctcac ccggaacacc gtcgtcatgg    14700
gcgcgggcac ccagcaggtg gacgccctca ccgccctgtc gccgcgcggt gtcgccgtgg    14760
cgagcggcaa ctgcgcgggc gtctgtcccg gcggcttcgt ccaggcggc ggactgggct     14820 ggcagagccg caagttcggc atggcgtgcg accggctcgt ctccgcccgg gtcgtgctcg    14880
ccgacgcgcc cgccgtgacc gcctccgcca ccgaacaccc cgacctttc tgggcgatgc     14940 gcggcggagg cggcggcaac ttcggcgtcg tcaccggctt cgagctgcgc cccaccgacg    15000 tccctccgt cgtcagctac aacctcacct ggcgtggga gtcggcgcgg cgcgtcatcg      15060
aggcgtggca gcactggatc atcgacggcc cccgcgacct cggtgccgcg atggccgtgc    15120
agtggcccga cgccgggacc ggcacgccgg tcgtggtcgt caccggcgcc tggctgggcg    15180
```

```
cggccgacgc gctcaccccc gtgctggact ccctggtggc ctccgtgggc agcgcgcccg   15240
ccacccgctc ggccaaggcg ctctcccagc acgacgcgat gatggcgcag tacggctgcg   15300
ccgacctcac gcccgagcag tgccacacgg tcggctactc gcccgaggcc gcgctgcccc   15360
ggcagaactt ctccatggac cgcaaccggc tcttctcccg ggccatcggg caaggaggcg   15420
tcgagcggat cctggaggcg ttcgccgccg acccgcgcgc cggacagttc cgcttcctga   15480
gcttcttcgc cctcggcggc gccgccaacc gccccgaccg caccaccacc gcctacgttc   15540
accgcgacac cgagttctac ctcggtttct cgatcgggct gaacgacccg gagtacacgg   15600
cggaggacga gaggctcggc cgcgcctggg ccgcgcgagg actgcgcacg ctcgatcccc   15660
actccaacgg cgagagctac cagaacttca tcgacccgga gctcgacgac tggaagtcgg   15720
cctactacgc cgagaactac gtgcgcctgg ccgccgtcaa gcggcctac gacccgcacc   15780 ggctcttctc cttcgcgcag gccgtctgac ctctcccgaa agaccctgc cggcctgctc   15840 ccctccgcgg ctcctgtggg cactggtgcg cccgcgcact tctgtgtgat tgagtgaagt   15900
ccgggcgtgc agagctcagt tgccgtggag ggggcgccag ttgcgagcat cagcggtgga   15960
gagggtggag ctgatccgct ggccggtgga gtccgagcgg cgggagcgct gccgcgaccg   16020
gggcgtcatg cggatcctgg tgctggaggc ggggccgag gcaccttgt gcgtggaccc   16080 caaggaggac tgggtccgcg ctcccgtcag caccgacgac ctgcgggccc cgtcgaggc   16140 cctgcgcctt cggggagccg ccgccgagtc ccggcccgag gtcgacccga acggagtgct   16200
gcgtttccgg tggcgctccg ccctgctctc gcccaccgag gcccggctcg tcgcccggct   16260
cgccgagtcc tatgccgagg tcgtcgcccg cgacgacctg ctccgcccgc ccccgggccg   16320
taccgtgccg agccgtaacg cgctcgacct ccacatcatg cggatccgac ggcgcctcgc   16380
cgcgctgggc ctgagggtgc gcaccgtccg ggggcgtggc tacgtcctgg agagcgcgga   16440
aggagtctga ccgacgggcg tggccgcgca ccgcaccgac cgcccctacg agcgaggagc   16500
ccgaagtgca gcagcctcat cacagccgcg tcgacgtgga actgggcgag aggtcctacc   16560
ccgtccacgt cggaccgggg gtccgccacc tcctgcccgg catcgtcgcc tccctcggcg   16620
cgcaccgcgc cgccgtcgtg accgcacggc ccccgacct ggtgcccgat ccggcgtgc   16680 ccgcgctgat cgtgcgggca cgtgacggcg agcggcacaa gacgctcgcc accgtcgagg   16740
acctgtgccg caagttcacc accttcggca tcacgcgcca cgacgtcgtc gtctcctgcg   16800
gaggaggctc gacgaccgac accgtcggcc tggcggcggc gctgcaccac cgtggggtgc   16860
cggtggtgca cctgccgacc accctcctgg cccaggtgga cgcgagcgtc ggcggcaaga   16920
cggcggtcaa cctgcccgag ggcaagaacc tcgtcggcgc ctactggcag cccaaggccg   16980
tgctgtgcga caccacgtat ctccagacgc tgcccgccga ggagtgggtc aacggctacg   17040
gcgagatagc gcgctgccac ttcatcggtg ccggcgacct ccgcggcctc gccgtccacg   17100
accaggtcac cgcgagcctg cggctgaagg cgtccgtcgt cgcggccgac gagcgggaca   17160
ccggcctgcg gcacatcctc aactacggcc atacgctggg ccacgcactg gagaccgcca   17220
ccggcttcgg gctgcggcac ggactcggcg tggcgatcgg gacggtcttc gcgggccggc   17280
tcgcggaggc gctgggccgc atcggcgcc accgcgcgcg ggagcacacc gaggtcgtcc   17340
gccactacgg acttcccgac agcctcccgg gaaacaccga catcaccgag ctcgtcgcgc   17400
tgatgaggca cgacaagaag gccacgtcgg gactgacctt cgtgctcgac gggccttccg   17460
gcgtggagct ggtgtccggg atcccggagg acgtcgtcct gcgtacgctc gcggcgatgc   17520
```

-continued

```
cgcgaggaac ggcctgaccg agtgttccgt cttccgaggg gaagtgaccg tttcgtgtcg      17580
gcagagctgt cagaaccgct gaagaaggcc ctggactccc tggtgttcgg cgtcgtggcg      17640
acgaccgacc ccgacggccg cccgcaccag tcggtggtgt gggtccggcg cgagggctcc      17700
gacgtgctgt tctcgatcac gcgcggcagc cgcaaggaga ggaacatcct gcgcgacccg      17760
cgtgtgagcg tgctgatcag cccggcggac tcgccgtaca cctacgccgc gatccggggc      17820
accgcgcact tcgaggacgt gccggacccg ggcgcgtacc tcgacacgtt ctccataaag      17880
taccacggcg tgccctaccg ggagtcgttc cccgagccgc cggaggtgag caccattctc      17940
gccgtccggc tcgttccgac gtcggtctac gagcagtggt gagggcgtag gcgtcccgaa      18000
gccccggcag cgtcccgaat gccgctgccg gggcttcccg tgggagccct acgccggttt      18060
ccgcgcggtg accaccgagt agccgacctc ctccaccgag cccatgcggt cgatgccgtc      18120
gaccatgcgg tggaacgcct cgtcgtccat gtgggagccg agctcgtccc tggccgcacg      18180
catcttcgcc gccaccgcct cgtaggaggg ccgcacctcg tccccgatgt cgaggaactc      18240
caccacctcc agccccaccg accgcatgca gtcctcgtac gcctcgcggg tgaggacggg      18300
gccctgctgg aagttgtcgt tggcggtgtc g                                    18331
```

<210> SEQ ID NO 97
<211> LENGTH: 1167
<212> TYPE: DNA
<213> ORGANISM: Streptomyces lavendulae

<400> SEQUENCE: 97

```
atgacaccta cgtccggtga tgacgtcctg tcctttccct catggccgca acacggcgcg        60
gaggagcgcg ccggactcct gcgggccctg gaccagaagg ggtggtggcg cgacgcgggg      120
caggaggtcg atctcttcga gcgggagttc gccgaccacc acggcgcccc gcacgcgatc      180
gccacgacga acggcaccca cgccctggaa ctcgccctgg gggtcatggg gatcggcccc      240
ggtgacgagg tcatcgtccc cgcgttcacc ttcatctcgt cgtcgctggc cgtgcagcgc      300 atgggcgcg tgccggtgcc ggcggacgta cggcccgaca cctactgcct cgatgccgac      360
gcggcggcgg cgctggtgac gccacgcacc aaagcgatca tgccggtcca catggcgggc      420
cagttcgccg acatggacgc cctggagaag ctctccgtcg cgacgggcgt gccggtcctc      480
caggacgccg cgcacgccca cggcgcgcag tggcagggcc gccgggtcgg ggagctcggc      540
tcgatcgccg ccttcagctt ccagaacggc aagctgatga ccgccggcga gggcggcgcc      600
ctgctcctgc cggacgacga gtccttccac gaggcgttcc tccagcactg ctgcggccgc      660
ccgcccgggg accgcgtcta ccgccatctg acgcagggct ccaactaccg catgaacgag      720
ttctccgcga gcgtcctgcg tgctcaactg aagcgcttga aggatcagtt gcgcatcagg      780
gaggagcgct gggcccagct gcgtacggca ctggccgcca tcgacggcgt ggtgccgcag      840
gggcgcgacg agcgcggcga cctccactcc cactacatgg ccatggtccg gctgcccggc      900
atctcggccc ggcgccgcct cgcgctggtg gacgcgctgg tcgagcgggg agtgcccgcg      960
ttcgtcggct tcccgccggt ctaccgcacc gagggtttcg cgcgcggccc ggcgccggcg     1020
gacgccgagg agctggccaa gagctgtccc gtgcggagg agatcggcag cgactgcctc     1080
tggctgcacc atcgcgtcct gctcgccgac gtgaccacgc tggaccggct ggcggaggtc     1140
ttctccggcc tcgtcggcgc gctctga                                        1167
```

<210> SEQ ID NO 98
<211> LENGTH: 819

```
<212> TYPE: DNA
<213> ORGANISM: Streptomyces lavendulae

<400> SEQUENCE: 98
gtggtcgtcg tcgacgacaa cgacggggc gacgccggtg atcaactgat cgccgtgaca      60
ggcgagatga gcggccttct cccgctgcgc gtggtgcggg gaccgctgcg ggggcgggcc    120
gccgcccgga acgccgggc ggccgcgcc ctcgcgcccc ggctggtctt cctcgacgac      180
gacgtcctgg tggggcccgg cttcctcgcc gcacacgccg cggccgcgga accggacgcc    240
ttcacccacg gccggctgcg cgaactcccc accgcggcgc ggttcctcgc cgctgtcgag    300
aaggccgccc cgaccgaggt ccgccgcgcc cgcgccggac tcgaacccgc tgccccggcc    360
gcctccgagc ggcgccaacc gcaccggcgg ctcgtcgcca acgccctgga gcgggccgtg    420
gaggccatgg ccggcggctc cctgccggac gtcgccccct ggctcggctt catcggcgcg    480
aacaccgccc tcgacaaggc cgcatgggag cataccggcg gattcgacga ggagttcggg    540
ctcacctggg ggtgcgagga cctggagttc ggcttccgcc tgcacgccgc cgggctgcgc    600
aggaccctcg cccccgacgc cctcggtgtg cacctcagcc acgcccgccc cggccgctgg    660
gagcagcacc accgcaacct cacgcacttc tccgccggcc acccgcaccc gtcggtacgc    720
gccttggagg ccctgctcgg gcccgacggc acgccggagg cgtatgtgcg cgccgtcctg    780
gccgaagagg ccgcaccggc acgggacgcg gcgcgatga                           819

<210> SEQ ID NO 99
<211> LENGTH: 783
<212> TYPE: DNA
<213> ORGANISM: Streptomyces lavendulae

<400> SEQUENCE: 99
atgagcggca caccggccac cgcgccgtac ggtcccgtgg tgctctcccc gcacgcggac     60
gacgccgtgt ggtccctggg cgggcggctg gcgcgctggg ccgccgaggg cccgcggccg    120
accgtcgtca cggtcttcgc cgggcccgcg gccgggaagc ccgagtcgtg gcggagcgcc    180
gccgatcccg cggtgcgccg ggccgaggac cgggcggcat gtgccgaact gggcgtgcgc    240
cacgtgccgc tgggcttcac cgacgcggca ctgcgtacgg cctcgggcgc ctatctctac    300
gcttccccgc gccggctctt cggcccctgg caccggccg acctcccgct gctggaggag    360
gtgcgggcgg ctctgctgcc gctgtgcgcg ggggcgtcga gcgtccacgt tcccctggcg    420
gcgggccggc acgtcgacca ccgcctggtc cgcggcgcg tggagcccct gtcccccgcc    480
cgtaccgtct tctacgagga cttcccctac cggctgcgcg aacgtgacca cacgaacctg    540
cggccgcgca cggaacggct gccgtccgag gcggtggacc gctggctgac cgccgccggt    600
cactactcca gccaggcgag cgcccacttc ggcggtgcgg ccgccctgcg cgaggccctg    660
ttcgcccgcg cccgcgcaca cggcgggccc ggccggcccg ccacgccga ccgccactgg    720
gtgcccgtcg gccaggacga ccggggcgag gcccggccgg cacccgtgga aaggggccg     780
tga                                                                  783

<210> SEQ ID NO 100
<211> LENGTH: 383
<212> TYPE: PRT
<213> ORGANISM: Streptomyces lavendulae

<400> SEQUENCE: 100

Met Ser Arg Ser Thr His Pro Pro Thr Ala Thr Pro Asp Ala Gly Thr
  1               5                  10                  15
```

```
Arg Arg Arg Leu Pro Leu Ile Gly Asn Asp Leu Val Ile Asn Glu Asp
             20                  25                  30

Ser Cys Asn Leu Ser Cys Thr Tyr Cys Leu Thr Gly Gln Ser Asn Leu
             35                  40                  45

Lys Glu Gly His Ser Leu Gln Leu Ile Phe Glu Pro Pro Arg Arg Asp
         50                  55                  60

Ser Tyr Ala Lys Asp Ser Gly Leu Gly Gln Arg Met Asp Lys Val Ala
 65                  70                  75                  80

Asp Arg Ile Arg Asp Arg Phe Gly Leu Pro Leu Leu Lys Val Thr Gly
                 85                  90                  95

Gly Glu Ile Phe Leu Val Arg Gly Ile Met Asp Phe Leu Glu Gln Glu
            100                 105                 110

Ala Arg Lys Tyr Asp Val Leu Val Ile Gln Thr Asn Gly Val Leu Val
            115                 120                 125

Arg Glu Glu His Leu Glu Arg Phe Arg Ser Trp Gly Asn Val Val Leu
            130                 135                 140

Gln Val Ser Leu Asp Ser His Leu His His Gly Asn Ser His Arg Val
145                 150                 155                 160

Pro Ser Gly Ser Leu His Glu Lys Val Val Ala Ala Ile Ala Arg Ile
            165                 170                 175

Leu Asp Ser Gly Leu Pro Val Glu Ile Tyr Ser Val Leu Asn Asp Arg
            180                 185                 190

Ser Val Thr Glu Val Cys Ala Phe Ala Glu Trp Leu Ser Gly Phe Ser
            195                 200                 205

Arg Pro Pro Val Tyr Phe Pro Phe Pro Val Arg Gly Pro Asp Ser Glu
            210                 215                 220

Asp Phe Lys Val Arg Pro Gly Gln Phe Gly His Ile Gln Glu Leu Val
225                 230                 235                 240

Asp Arg Tyr Asp Glu Phe Ala Arg Val Leu Pro Pro Arg Pro Tyr Phe
                245                 250                 255

Asp Arg Leu Thr Ser Phe Tyr Arg Glu Gly Arg Arg Thr Phe Arg Cys
            260                 265                 270

His Leu Pro Arg Leu Val Val Ser Ser Phe Ser Asp Gly Val Val Thr
            275                 280                 285

Pro Cys Pro Asn Ile Trp Phe Ser Asp Met Gly Asn Ala Leu Glu Asp
            290                 295                 300

Asp Trp Ser Glu Met Leu Asp Thr Val Gly Thr Ser Gly Leu Tyr Arg
305                 310                 315                 320

Ala Leu Leu Ala Pro Lys Pro Arg Leu Lys Ala Cys His Gly Cys Phe
                325                 330                 335

Thr Pro Trp Asp Thr Leu Ser Met Tyr Phe Glu Asp Glu Ile Thr Leu
            340                 345                 350

Asp Glu Leu Cys Ala Ala Pro Thr Tyr Ser Pro Pro Arg Ile Arg Gln
            355                 360                 365

Met Leu Ser Asp Ala Lys Ala Asp Tyr Leu Gln Gly Gly His Asp
            370                 375                 380

<210> SEQ ID NO 101
<211> LENGTH: 707
<212> TYPE: PRT
<213> ORGANISM: Streptomyces lavendulae

<400> SEQUENCE: 101

Met Ala Leu Arg Ala Pro Asn Ser Pro Arg Trp Val Val Ala Phe Leu
```

```
  1               5                   10                  15
Ser Leu Leu Ala Ser Gly Ala Arg Pro Leu Leu Glu Pro Asp Thr
                20                  25              30
Pro Gly Pro Glu Thr Ala Arg Leu Leu Arg Ala Gly Gly Arg
            35                  40              45
Ser Leu Val Val Pro Gly Thr Gly Asp Gly Leu Arg Leu Thr Leu Thr
    50                  55                  60
Gly Ser Pro Gly Glu Pro Ser Gly Ala Pro Pro Ala Val Leu Leu Pro
65              70                  75                      80
Thr Ser Gly Ser Thr Gly Ala Ser Lys Leu Val Ala Arg Ser Glu Glu
                85                  90                  95
Ser Leu Leu Ala Glu Gly Arg Arg Tyr Arg Asp Gly Val Gly Leu Thr
                100                 105             110
Gly Glu Asp Thr Leu Leu Pro Val Pro Leu Ser His Ala Tyr Ala
            115                 120             125
Leu Gly Trp Leu Phe Gly Gly Leu Leu Thr Gly Ala Ala Leu Arg Pro
    130                 135             140
Val Pro Pro Thr Ala Leu Gly Arg Ile Ala Ala Glu Leu Ser Gly Gly
145             150                 155                     160
Ala Thr Val Val Ala Leu Val Pro Ser Val Ala Arg Leu Leu Ala Thr
                165                 170                 175
Arg Arg Leu Arg Gly Ala Ala Gly Arg Ala Pro Ala Ala Pro Gly
            180                 185             190
Leu Arg Leu Ala Met Val Gly Ala Gly Pro Val Asp Glu Gln Leu Asp
    195                 200                 205
Arg Ala Phe Thr Glu Ala Phe Gly Thr Gly Leu Ala Arg Asn Tyr Gly
    210                 215                 220
Ser Thr Glu Thr Gly Ala Val Leu Ala Gly Pro Ala Gly Leu Glu Pro
225                 230                 235                 240
Leu Cys Ala Gly Ala Pro Leu Pro Gly Val Glu Cys Glu Leu Thr Gly
            245                 250                 255
Pro Glu Gly Val Val Pro Pro Ala Gly Thr Pro Gly Leu Leu Ser Val
            260                 265                 270
Arg Val Asp Gly Arg Pro Tyr Ala Met Gly Asp Leu Ala Val Ala Val
    275                 280                 285
Pro Gly Gly Leu Arg Ile Leu Gly Arg Glu Asp Arg Ala Ile Arg Arg
290                 295                 300
Gly Gly Arg Trp Val Ser Pro Leu Glu Ile Glu Val Leu Arg Gly
305             310                 315                     320
His Pro Asp Val Val Asn Val Arg Val Gly Ala Arg Gly Arg His
                325                 330             335
Arg Gly Glu Asp Gly Ile Val Ala Glu Val Ser Ala Ala Gly Pro Gly
            340                 345             350
Leu Thr Pro Glu Ala Leu Arg Glu His Ala Arg Arg Glu Leu Ala Pro
        355                 360             365
His Lys Val Pro Asp Glu Phe Val Leu Arg Glu Ser Leu Pro Val Asn
    370                 375             380
Ala Ala Gly Lys Val Arg Ala Ala Ser Val Tyr Arg Leu Thr Arg Ser
385             390                 395                     400
Ala Ala Glu Ala Ala Arg Ala Tyr Lys Ala Ser Glu Val Leu Phe Ala
            405                 410                 415
Leu His Asp Leu Gly Ala Leu Glu Ala Leu Ala Gln Gly Ala Gly Thr
        420                 425             430
```

```
Ala Leu Leu Ala Gly Glu Leu Gly Cys Asp Ala Asp Ala Leu Glu Trp
            435                 440                 445

Leu Leu Arg Thr Ala Thr Ala Leu Gly Val Leu Thr Thr Gly Ala Gln
        450                 455                 460

Glu Pro Gly Asp Arg Val Arg Ala Gly Glu Leu Ala Ala Phe Val Ala
465                 470                 475                 480

Leu Glu Glu His Leu Ser Arg Gly Leu Val Thr Arg Glu Glu Leu Val
                485                 490                 495

Ala Val Ala Arg Ser Gly Thr Ala Arg Arg Pro Phe Glu Glu Arg Pro
            500                 505                 510

Pro Glu Ser Leu Gly Pro Leu Val Ala Leu Tyr Gln Gly Ala Met Asp
        515                 520                 525

Gly Pro Gly Ala Arg Ala Arg Ala Ala Leu Gly Leu Arg Leu Leu Arg
    530                 535                 540

Pro Gly Pro Gly Ala Arg Val Val Glu Val Thr Ala Gly Pro Gly Arg
545                 550                 555                 560

Tyr Leu Glu Arg Leu Leu Ala Ser Asp Pro Gly Ala Ser Gly His Leu
                565                 570                 575

Val Thr Val Gly Arg Leu Ser Gly Pro Leu Ser Ser Ala Val Ala Ala
            580                 585                 590

Ala Val Glu Glu Gly Arg Val Thr Val Gly Thr Glu Leu Pro Val Gly
        595                 600                 605

Tyr Ala Asp Phe Cys Val Val Ala Asn Ala Val His Gly Pro Gly Pro
    610                 615                 620

Gly Ser Ala Leu Gly Ala Leu Leu Gly Ser Leu Arg Pro Gly Gly Arg
625                 630                 635                 640

Leu Leu Val Asp Asp Val Phe Leu Pro Ala Ser Gly Pro Gly Ser Glu
                645                 650                 655

Leu Ala Leu Asp Trp Leu Thr His Gly Gly Thr Ala Trp Pro Ala Thr
            660                 665                 670

Gly Glu Leu Ile Ala Gly Leu Leu Gln Glu Gly Ala Glu Val Ala Arg
        675                 680                 685

His Val Pro Leu Asp Ala Ser Pro Cys His Leu Ile Ile Ala Lys Glu
    690                 695                 700

Ala Gly Ser
705

<210> SEQ ID NO 102
<211> LENGTH: 257
<212> TYPE: PRT
<213> ORGANISM: Streptomyces lavendulae

<400> SEQUENCE: 102

Met Ser Thr Val Thr Asp Arg Ala Thr Glu Arg Leu Gly Gln Ser Gly
  1               5                  10                  15

Arg Val Val Val Ser Gly Ala Ser Gly Gln Ile Gly Gly Ala Cys
             20                  25                  30

Ala Leu Glu Leu Ala Ala Leu Gly Ala Thr Val Val Ala Gly Tyr His
         35                  40                  45

Ser Gly Glu Gln Ala Ile Arg Lys Leu Arg Glu Gln Val Glu Gly Gln
     50                  55                  60

Gly Gly Thr Leu Val Pro Val Ala Ala Asp Leu Ser Glu Pro Glu Gly
 65                  70                  75                  80

Ala Asp Ala Leu Val Ala Ala Ala Val Glu Arg Phe Gly Arg Val Asp
```

```
                    85                  90                  95
Gly Cys Val Ala Ala Gly Leu Arg Thr Arg Leu Ala Met Ala
                100                 105                 110

Thr Asp Ala Arg Ser Leu Glu Lys Leu Leu Arg Val Asn Leu Ala Gly
            115                 120                 125

Ser Val Gly Leu Ala Lys Ala Cys Leu Lys Pro Met Met Arg Ala Arg
    130                 135                 140

Tyr Gly Arg Ile Val Leu Phe Gly Ser Arg Ala Gly Thr Ser Gly Leu
145                 150                 155                 160

Pro Gly His Ser Ala Tyr Ala Ala Thr Lys Gly Ala Leu Gln Pro Trp
                165                 170                 175

Ala Ala Ser Val Ala Gly Glu Val Gly Lys His Gly Ile Thr Val Asn
            180                 185                 190

Val Val Ala Pro Gly Ala Ile Arg Ala Glu Val Met Asp Phe Ser Glu
        195                 200                 205

Ala Glu Arg Asp Leu Val Leu Gln Phe Ile Gly Ala Gly Arg Leu Gly
    210                 215                 220

Glu Pro Glu Glu Val Ala Ala Ala Val Ser Phe Leu Leu Ser Pro Ser
225                 230                 235                 240

Ala Ser Tyr Val Asn Gly Asn Thr Leu Val Val Asp Gly Gly Ala Arg
                245                 250                 255

Phe

<210> SEQ ID NO 103
<211> LENGTH: 404
<212> TYPE: PRT
<213> ORGANISM: Streptomyces lavendulae

<400> SEQUENCE: 103

Met Thr Pro Pro Thr Ala Arg Glu Pro Leu Arg Met Ala Val Leu
  1               5                  10                  15

Gly Ala Gly Trp Val Ser Arg Lys Val Trp Leu Pro Leu Leu Ala Glu
             20                  25                  30

His Pro Ala Phe Arg Val Asp Phe Leu Val Asp Asp Pro Val Ala
         35                  40                  45

Ala Arg Ser Ala Leu Pro Glu Gly Ala Arg Thr Arg Val Leu Ser Arg
     50                  55                  60

Pro Glu Glu Leu Ala Pro Arg Ser Val Asp Ala Ala Ile Ile Ala Leu
65                   70                  75                  80

Pro Asn His Leu His Leu Pro Val Ala Lys Ala Leu Leu Glu Arg Asp
                 85                  90                  95

Val Pro Val Phe Val Glu Lys Pro Val Cys Arg Thr Leu Phe Glu Ala
             100                 105                 110

Gln Ala Leu Ala Leu Asp His Gln Ala Arg Gly Asp Ser Ile Gly Asp
         115                 120                 125

Ile Thr Leu Tyr Ala Trp Ser Ala Ala Arg His Arg Thr Asp Val Cys
     130                 135                 140

Arg Leu Ala Glu Leu Leu Pro Ser Leu Gly Thr Val Arg Ser Val Gly
145                 150                 155                 160

Leu Ser Trp Ile Arg Ala Thr Gly Ile Pro Gln Arg Thr Gly Trp Phe
                165                 170                 175

Val Asp Arg Arg Leu Ala Gly Gly Ala Leu Leu Asp Leu Gly Trp
            180                 185                 190

His Leu Leu Asp Val Gly Leu His Leu Leu Gly Trp Pro Arg Val Val
```

```
                195                 200                     205
Arg Ala Ala Ser Thr Met Ser Ala Asp Trp Met Ser Arg Gly Glu Ala
            210                 215                 220

Thr Ala Asp Trp Ser Arg Arg Ser Ser Gly Thr Ala Arg Pro Gly Pro
225                 230                 235                 240

Gly Glu Thr Val Glu Asp Thr Ala Arg Gly Phe Leu Val Thr Asp Thr
                245                 250                 255

Asp Val Gly Ile Ser Leu Glu Thr Arg Trp Ala Ser His Gln Ala Leu
            260                 265                 270

Asp Val Thr Thr Ile Thr Val Glu Gly Thr Glu Gly Val Ala Thr Leu
        275                 280                 285

Arg Gly Thr Phe Gly Phe Ser Pro His Arg Leu Gln Lys Ser Ser Leu
        290                 295                 300

Val Val Leu Arg Gln Gly Val Glu Glu Thr Val Ala Leu Pro Asp Glu
305                 310                 315                 320

Pro Val Gly Val Glu Tyr Arg Arg Gln Val Asp Glu Leu Ala Arg Arg
                325                 330                 335

Leu Gly Gly Ser Ala Asp Gly Gln Gly Pro Val Ser Gly Leu Gly Glu
            340                 345                 350

Gly Ser Met Ala Glu Val Thr Ile Leu Ala Ser Cys Ile Asp His Ile
        355                 360                 365

Tyr Ser Ala Ala Gly Val Asp Pro Pro Ser Pro Leu His Arg Pro Gln
370                 375                 380

Ser Asp Ala Ala Pro Ser Thr Ser Ser Cys Pro Arg Val Leu Pro Thr
385                 390                 395                 400

Arg Gly Ser Gln

<210> SEQ ID NO 104
<211> LENGTH: 382
<212> TYPE: PRT
<213> ORGANISM: Streptomyces lavendulae

<400> SEQUENCE: 104

Met Lys Phe Ala Tyr Phe Ser His Val Trp Gly Arg Pro Gly Ile Thr
1               5                   10                  15

Pro Gly Glu Arg Tyr Glu Glu Leu Trp Arg Glu Val Glu Asp Ala Asp
            20                  25                  30

Arg Leu Gly Phe Asp Tyr Ala Phe Ser Val Glu His His Cys Thr Pro
        35                  40                  45

His Glu Ser Trp Met Pro Ser Pro Ala Val Phe Cys Thr Gly Ala Ala
    50                  55                  60

Leu Arg Thr Glu Arg Ile Arg Val Gly Pro Met Gly Trp Val Pro Pro
65                  70                  75                  80

Leu Arg His Pro Leu His Leu Val Glu Glu Val Ala Thr Leu Asp Gln
                85                  90                  95

Leu Leu Gly Gly Arg Leu Glu Val Gly Leu Ala Ser Gly Val Ser Arg
            100                 105                 110

Asp Pro Phe Leu Pro Phe Asp Ala Asp Phe Asp Asn Arg His Leu Leu
        115                 120                 125

Thr Arg Glu Ala Leu Glu Leu Leu Arg Ala Ala Phe Ala Ala Arg Gly
    130                 135                 140

Ala Phe Asp Phe Asp Gly Pro Ala His Arg Leu Arg Asp Ile Ala Leu
145                 150                 155                 160

Ser Phe Pro Pro Val Gln Arg Pro His Pro Pro Met Trp Val Pro Thr
```

```
                          165                 170                 175
        Thr Asn Arg Asn Thr Leu Arg Tyr Leu Ser Glu Ala Gly Ala His Thr
                        180                 185                 190

Ser Ser Thr Met Ile Val Pro Arg Ala Ser Met Ala Leu Val Tyr Arg
                        195                 200                 205

His Tyr Leu Asp Trp Trp Arg Gly His Gly His Ala Ser Asp Pro Arg
                        210                 215                 220

Ile Gly Tyr Trp Thr Leu Val His Val Ala Arg Thr Asp Ala Glu Ala
        225                 230                 235                 240

Glu Glu Arg Ala Ala Ala His Ile Thr Glu Thr Phe Thr Lys Thr Leu
                        245                 250                 255

Arg Tyr Gly Ser Val Ser Arg Ser Arg Asp Gln His Ala Pro Pro Ser
                        260                 265                 270

Arg Leu Ser Thr Thr Asp Ile Leu Ala Gly Ser Gly Asp Leu Arg Phe
                        275                 280                 285

Leu Leu Glu Asn Asn Leu Val Phe Val Gly Ser Pro Ala Thr Val Ala
                        290                 295                 300

Asp Arg Ile Arg Ala Ala Ser Leu Glu Gly His Phe Asp Thr Leu Leu
        305                 310                 315                 320

Gly Glu Phe Thr Phe Gly Glu Leu Ala Asp Arg His Arg Ile Glu Ser
                        325                 330                 335

Met Glu Leu Phe Ala His Glu Val Ala Pro Ala Leu Arg Ala Phe Ser
                        340                 345                 350

Pro Tyr Ala Pro Arg Pro Gln Glu Pro Ala Tyr Thr Ala Ser Asp Glu
                        355                 360                 365

Gln Gln Val Ala Arg Leu Gln Ala Leu Gly Tyr Ile Asp
                        370                 375                 380

<210> SEQ ID NO 105
<211> LENGTH: 290
<212> TYPE: PRT
<213> ORGANISM: Streptomyces lavendulae

<400> SEQUENCE: 105

Met Glu Arg Leu Lys Leu Val Pro Asp Glu His Arg Arg Phe Thr Val
        1               5                   10                  15

Asp Glu Gln Ser Ala Arg Arg Leu His Arg Ile Gly Pro Glu Leu Leu
                        20                  25                  30

Ser Ala Leu Cys Glu Ala Gly Val Pro Phe Val Gly Ser Gly Ala Gly
                        35                  40                  45

Arg Leu Phe Asp Gly Tyr Asp Leu Gly Asn Ala Ala Leu His Leu Gly
                        50                  55                  60

Leu Ser Ser Val Gln Arg Arg Ala Ile Arg Ser Trp Ala Gly Ser Leu
        65                  70                  75                  80

Arg Thr Ala Ser Ala Ala Glu Ser Pro Arg Trp Arg Val Asp Val Thr
                        85                  90                  95

Ala Ser Cys Pro Val Pro Gly His Ala Gly Pro Cys Arg Tyr Gly Val
                        100                 105                 110

Leu Leu Pro Gly Ala Arg Arg Pro Val Glu Ala Ala Ser Pro Arg Glu
                        115                 120                 125

Thr Thr Leu Ala Arg Leu Tyr Thr Arg Ser Arg Gly His Trp Pro Asp
                        130                 135                 140

Phe Pro Pro Ala Val Leu Asp Leu Leu Arg Thr Leu Glu Pro Val Gly
        145                 150                 155                 160
```

-continued

```
Phe Phe Leu Leu Pro Glu Ala Ile Arg Trp Asp Pro Gly Phe Leu Trp
                165                 170                 175

Ser Thr His Met Ala Asp Cys Gly Ala Ala Ala Trp Leu Val Ala
            180                 185                 190

Glu Gly Arg Arg Gly Leu Asp Val Arg Phe Ser Phe Gly Leu Leu
            195                 200                 205

Val Ala Lys Pro Tyr Ser Thr Pro His Cys Trp Ala Glu Phe Leu Val
    210                 215                 220

Gly Gly Arg Trp Val Pro Ala Asp Pro Leu Leu Arg Ala Met Ala
225                 230                 235                 240

Ala Trp Gly Gly Leu Asp Ala Ala His Pro Pro His Ser Ser Pro
                245                 250                 255

Gly Ala Val Tyr His Arg Leu Ala Gly Arg Phe Thr Lys Val Val Ser
                260                 265                 270

His Ala Gly Val Trp Ala Pro Thr Ser Leu Pro Thr Glu Leu Leu Pro
            275                 280                 285

Cys Pro
    290

<210> SEQ ID NO 106
<211> LENGTH: 235
<212> TYPE: PRT
<213> ORGANISM: Streptomyces lavendulae

<400> SEQUENCE: 106

Met Pro Leu Asn Pro Pro Ala Ser Arg Ala Ala Asp Ala Pro
1               5                   10                  15

Ala Thr Ala Leu Pro Cys Arg Phe Thr Thr Val Val Phe Asp Leu Asp
            20                  25                  30

Gly Val Leu Ile Asp Ser Phe Ala Val Met Arg Glu Ala Phe Ala Val
            35                  40                  45

Ala Tyr Arg Glu Val Val Gly Pro Gly Glu Pro Pro Phe Glu Glu Tyr
    50                  55                  60

Arg Thr His Gln Gly Arg Tyr Phe Pro Asp Ile Met Arg Leu Met Gly
65                  70                  75                  80

Leu Pro Gly Glu Met Glu Glu Pro Phe Val Arg Glu Ser His Arg Leu
                85                  90                  95

Met Asp Arg Val Glu Val Tyr Pro Asp Val Pro Gln Leu Leu Ala Glu
            100                 105                 110

Leu Arg Ala Asp Gly Val Gly Thr Ala Ile Ala Thr Gly Lys Ser Gly
            115                 120                 125

Ser Arg Ala Arg Ala Val Leu Glu Ala Val Gly Leu Leu Pro Leu Leu
    130                 135                 140

Asp Glu Val Val Gly Ser Asp Glu Val Pro Arg Pro Lys Pro His Pro
145                 150                 155                 160

Asp Ile Val Arg Glu Ala Leu Arg Arg Leu Asp Ala Ala Pro Glu Asp
                165                 170                 175

Ala Val Met Val Gly Asp Ala Val Ile Asp Ile Arg Ser Gly Arg Ala
            180                 185                 190

Ala Gly Thr Ala Thr Val Gly Ala Thr Trp Gly Glu Gly Ala Ala Gly
            195                 200                 205

Gln Leu Arg Ala Glu Arg Pro Asp Phe Leu Leu Asp Lys Pro Gln Ser
    210                 215                 220

Leu Leu Ala Leu Val Arg Ser Gly Gly His Ala
225                 230                 235
```

<210> SEQ ID NO 107
<211> LENGTH: 346
<212> TYPE: PRT
<213> ORGANISM: Streptomyces lavendulae

<400> SEQUENCE: 107

Met Thr Pro Ala Thr Pro Arg Trp Ser Val Val Ala Pro Gln Gly Thr
1               5                   10                  15

Asn Leu Glu Leu Ala Gly Thr Gly Arg Glu Gly Trp Arg Leu Leu
            20                  25                  30

Leu Glu Thr Ala Arg Thr Val His Arg His Gly Arg Gly Ala Leu Trp
        35                  40                  45

Leu Leu Asp Arg Thr Asp Thr Leu Pro Arg Arg Glu Pro Glu Pro Val
    50                  55                  60

Trp Glu Gly Trp Thr Ala Leu Ala Ala Leu Ala Gly Ala Val Pro Gly
65                  70                  75                  80

Leu Asp Leu Gly Leu Leu Ser Ser Ala Pro Pro Phe Arg Asn Ala Ala
                85                  90                  95

Leu Ile Ala Lys Arg Ala Ala Thr Leu Asp Val Val Cys Asp Gly Arg
            100                 105                 110

Leu Thr Leu Gly Phe Pro Ala Arg Glu Tyr Leu Pro Glu His His Ser
        115                 120                 125

Thr Gly Arg Glu Val Pro Thr Gly Leu Glu Ala Asp Glu Glu Glu Ala
    130                 135                 140

Ala Gly His Arg Ala Leu Gly Glu Thr Val Glu Ala Leu Arg Ala Leu
145                 150                 155                 160

Trp Gly Gly Gln Pro Val Thr Phe Thr Gly Glu His Ile Arg Leu Thr
                165                 170                 175

Ser Ala His Cys Val Pro Ala Pro Arg Gln Gln Pro Leu Pro Leu Ala
            180                 185                 190

Leu Arg Thr Pro Ala Gly Asp Ala Gly Ser Gly Ala Leu Arg Pro Ala
        195                 200                 205

Asp Ala Thr Val Arg Glu Cys Ala His Val Gln Trp Thr Gly Glu Pro
    210                 215                 220

Ala Gln Val Ala Ala Val Thr Ala Phe Arg Arg Arg Thr Glu
225                 230                 235                 240

Leu Gly Leu Asp Pro Asp Gly Val Arg His Ala Trp Ala Ala Glu Cys
                245                 250                 255

Arg Ile Phe Asp Ser Val Leu Glu Arg Asp Arg Trp Leu Ser Thr Pro
            260                 265                 270

His Glu Val Leu Phe Trp Ser His His Pro Asp Leu Leu Ala Arg Arg
        275                 280                 285

Ser Leu Tyr Gly Thr Pro Glu Gln Leu Thr Glu Arg Ala Arg Arg Leu
    290                 295                 300

Val Ala Ala Gly Val Ala Glu Phe Val Leu Trp Phe Arg Asp Tyr Pro
305                 310                 315                 320

Ala Thr Thr Ser Leu Glu Arg Leu Phe Gln Glu Val Val Pro Gln Val
                325                 330                 335

Ala Pro Gly Ala Ala Lys Glu Ala Glu Glu
            340                 345

<210> SEQ ID NO 108
<211> LENGTH: 520
<212> TYPE: PRT

-continued

<213> ORGANISM: Streptomyces lavendulae

<400> SEQUENCE: 108

```
Met Leu Asn Thr Leu Ser Thr Ala Pro Phe Leu Ser Thr Ala Trp Leu
  1               5                  10                  15

Ala Gly Ala Ala Arg Leu Glu Arg Pro Pro Val Gly Glu Arg Gly Thr
             20                  25                  30

Val Ala Leu Arg Leu Glu Leu Thr Asp Pro Pro Gly Glu Pro Pro
         35                  40                  45

Ala Val Asp Val Gln Val Asp Leu Val Ala Gly Arg Leu Gly Leu Ala
     50                  55                  60

Ala Ala Ala Gly Glu Ser Pro Gly Leu Arg Ile Arg Leu Pro Leu Glu
 65                  70                  75                  80

Ala Ala Arg Ala Leu Leu Leu Gly Pro Ala Arg Asp Arg Thr Gly Val
                 85                  90                  95

Phe Glu Arg Gly Asp Val Arg Ala Glu Gly Asn Phe Ser Leu Leu Phe
            100                 105                 110

Phe Ile Asp Ala Ala Leu Glu Arg Asp Ala Ser Gly His Val Ala Ala
            115                 120                 125

Leu Arg Gly Thr Pro Gly Thr Thr Ala Arg Glu Ala Ala Pro Pro Pro
    130                 135                 140

Gly Thr Glu Asp Ala Ala Glu Ala Val Arg Arg Ala Arg Ala Ala Leu
145                 150                 155                 160

Pro Gly Thr Met Arg Glu Leu Glu Arg Glu Val Gly Thr Ser Thr Pro
                165                 170                 175

Gly Ala Gln Ile Tyr Val Ser Arg Asp Gly Val Pro Leu Ala Asp Ala
            180                 185                 190

Gly Leu Gly Leu Ala Arg Pro Gly Val Ala Met Thr His Arg Ser Leu
        195                 200                 205

Pro Leu Trp Tyr Cys Cys Ala Lys Pro Leu Leu Ser Val Ala Leu Gly
    210                 215                 220

Arg Leu Trp Glu Ala Gly Ala Tyr Asp Pro Tyr Leu Pro Val Ala His
225                 230                 235                 240

Tyr Leu Pro Glu Phe Gly Asn Arg Gly Lys Glu Ser Ile Thr Ser Met
                245                 250                 255

Glu Leu Leu Thr His Thr Gly Pro Leu Pro Thr Gly Asp Asp Pro Leu
            260                 265                 270

His Gly Ile Val Ala Gly Pro Asp Glu Glu Arg Val Arg Arg Ala Phe
        275                 280                 285

Glu Val Pro Val Ala Pro Arg Pro Gly Thr Pro Gly Ile Asn Tyr
    290                 295                 300

Ser Gln Trp Trp Ala Trp Phe Val Leu Ala Arg Ile Leu Pro Val Val
305                 310                 315                 320

Asp Gly Arg Glu Tyr Arg Ala Tyr Val Gln Glu Ile Leu Gly Pro
                325                 330                 335

Cys Gly Met Ser Gly Thr Arg Val His Leu Asp Arg Glu Glu Phe Ala
            340                 345                 350

Ala Leu Gly Gly Glu Leu Pro Leu Ile His Val Ser Asn Pro Glu Gly
        355                 360                 365

Gly Pro Leu Pro Thr His Trp Trp Ser Thr Glu Ala Ala Thr Thr Arg
    370                 375                 380

Cys Ile Pro Gly Val Asn Thr Arg Gly Pro Leu Arg Asp Met Gly Arg
385                 390                 395                 400
```

-continued

Leu Phe Glu Met Leu Leu Arg Gly Gly Asp Ala Pro Gly Gly Arg Val
                405                 410                 415

Leu Ala Pro Pro Thr Val Ala Ala Leu Thr Ala Arg His Arg Thr Gly
            420                 425                 430

Leu Gln Asp Arg Tyr Gly Asn Ala Asp Trp Gly Met Gly Phe Arg Leu
            435                 440                 445

Glu Cys Arg Gln Leu Asp Pro Arg Phe Thr Ser Phe Gly Ser Tyr Ala
    450                 455                 460

Ser Pro Arg Ser Phe Gly His Asp Gly Leu Trp Thr Ala Val Val Phe
465                 470                 475                 480

Ala Asp Pro Asp Ala Ala Leu Val Val Ala Leu His Leu Asn Gly Lys
            485                 490                 495

Val Glu His Glu Arg His Arg Glu Arg Ile Val Arg Leu Ala Asp Ala
            500                 505                 510

Val Tyr Gln Asp Leu Arg Leu Ser
        515                 520

<210> SEQ ID NO 109
<211> LENGTH: 283
<212> TYPE: PRT
<213> ORGANISM: Streptomyces lavendulae

<400> SEQUENCE: 109

Met Pro His Ser Glu Leu Ser Glu Leu Pro Met Pro Ser Pro Ala Ser
1               5                   10                  15

Glu Glu Val Gly Ala Leu Tyr Asp Arg Phe Thr Ala Leu Gly Ala Ala
            20                  25                  30

Ser Leu Gly Glu Asn Leu His Phe Gly Tyr Trp Asp Ser Pro Asp Ser
        35                  40                  45

Gln Val Pro Leu Ala Glu Ala Thr Asp Arg Leu Thr Asp Met Met Ala
    50                  55                  60

Glu Arg Leu Arg Ile Gly Ala Gly Ser Arg Val Leu Asp Leu Gly Cys
65                  70                  75                  80

Gly Val Gly Thr Pro Gly Val Arg Ile Ala Arg Leu Ser Gly Ala His
                85                  90                  95

Val Thr Gly Ile Ser Val Ser His Glu Gln Val Val Arg Ala Asn Ala
            100                 105                 110

Leu Ala Glu Glu Ala Gly Leu Ala Asp Arg Ala Arg Phe Gln Arg Ala
        115                 120                 125

Asp Ala Met Asp Leu Pro Phe Glu Asp Glu Ser Phe Asp Ala Val Ile
130                 135                 140

Ala Leu Glu Ser Ile Ile His Met Pro Asp Arg Ala Gln Val Leu Ala
145                 150                 155                 160

Gln Val Gly Arg Val Leu Arg Pro Gly Gly Arg Leu Val Leu Thr Asp
                165                 170                 175

Phe Phe Glu Arg Ala Pro Leu Ala Pro Glu Gly Arg Ala Ala Val Gln
            180                 185                 190

Arg Tyr Leu His Asp Phe Met Met Thr Met Val Ser Ala Glu Ala Tyr
        195                 200                 205

Pro Pro Leu Leu Arg Gly Ala Gly Leu Trp Leu Glu Glu Phe Leu Asp
    210                 215                 220

Ile Ser Asp Gln Thr Leu Glu Lys Thr Phe Arg Leu Leu Ser Glu Arg
225                 230                 235                 240

Ile Asn Ser Ser Lys Gln Arg Leu Glu Thr Gln Phe Gly Glu Glu Met
                245                 250                 255

-continued

```
Val Asn Gln Phe Asp Pro Gly Asp Leu Val Gly Val Lys Glu Phe Gly
            260                 265                 270
Tyr Leu Leu Val Ala Gln Arg Pro Gly Lys
        275                 280

<210> SEQ ID NO 110
<211> LENGTH: 275
<212> TYPE: PRT
<213> ORGANISM: Streptomyces lavendulae

<400> SEQUENCE: 110

Met Thr Glu Thr Ala Ser Ala Ser Asp Arg Met Val Glu Leu Tyr Asn
  1               5                  10                  15
Arg Val Thr Asp Leu Met Val His Ala Glu Gly Gly Tyr Met His Gly
                 20                  25                  30
Gly Tyr Trp Ala Gly Pro Asp Val Pro Thr Thr Val Glu Glu Ala Gly
             35                  40                  45
Asp Arg Leu Thr Asp Tyr Val Ser Glu Arg Leu Arg Leu Ala Pro Gly
         50                  55                  60
Glu Arg Val Leu Asp Val Gly Ser Gly Asn Gly Lys Ala Thr Leu Arg
 65                  70                  75                  80
Ile Ala Ala Arg His Gly Val Arg Ala Thr Gly Val Ser Ile Asn Pro
                 85                  90                  95
Tyr Gln Val Gly Leu Ser Arg Gln Leu Ala Glu Lys Glu Gly Asp Glu
                100                 105                 110
Ala Thr Glu Phe Arg Ile Gly Asp Met Leu Ala Leu Pro Phe Pro Asp
            115                 120                 125
Gly Ser Phe Asp Ala Cys Tyr Ala Ile Glu Ser Ile Cys His Ala Leu
        130                 135                 140
Glu Arg Ala Asp Val Phe Thr Glu Ile Ala Arg Val Leu Arg Pro Gly
145                 150                 155                 160
Gly Arg Val Thr Val Thr Asp Phe Val Leu Arg Arg Pro Leu Ser Asp
                165                 170                 175
Ala Ser Arg Thr Ile Val Asp Thr Ala Asn Asp Asn Phe Gln Gln Gly
            180                 185                 190
Pro Val Leu Thr Arg Glu Ala Tyr Glu Asp Cys Met Arg Ser Val Gly
        195                 200                 205
Leu Glu Val Val Glu Phe Leu Asp Ile Gly Asp Glu Val Arg Pro Ser
    210                 215                 220
Tyr Glu Ala Val Ala Ala Lys Met Arg Ala Ala Arg Asp Glu Leu Gly
225                 230                 235                 240
Ser His Met Asp Asp Glu Ala Phe His Arg Met Val Asp Gly Ile Asp
                245                 250                 255
Arg Met Gly Ser Val Glu Glu Val Gly Tyr Ser Val Val Thr Ala Arg
            260                 265                 270
Lys Pro Ala
        275

<210> SEQ ID NO 111
<211> LENGTH: 146
<212> TYPE: PRT
<213> ORGANISM: Streptomyces lavendulae

<400> SEQUENCE: 111

Met Phe Arg Leu Pro Arg Gly Ser Asp Arg Phe Val Ser Ala Glu Leu
  1               5                  10                  15
```

```
Ser Glu Pro Leu Lys Lys Ala Leu Asp Ser Leu Val Phe Gly Val Val
            20                  25                  30

Ala Thr Thr Asp Pro Asp Gly Arg Pro His Gln Ser Val Val Trp Val
            35                  40                  45

Arg Arg Glu Gly Ser Asp Val Leu Phe Ser Ile Thr Arg Gly Ser Arg
 50                      55                  60

Lys Glu Arg Asn Ile Leu Arg Asp Pro Arg Val Ser Val Leu Ile Ser
 65                  70                  75                  80

Pro Ala Asp Ser Pro Tyr Thr Tyr Ala Ala Ile Arg Gly Thr Ala His
                 85                  90                  95

Phe Glu Asp Val Pro Asp Pro Gly Ala Tyr Leu Asp Thr Phe Ser Ile
            100                 105                 110

Lys Tyr His Gly Val Pro Tyr Arg Glu Ser Phe Pro Glu Pro Pro Glu
            115                 120                 125

Val Ser Thr Ile Leu Ala Val Arg Leu Val Pro Thr Ser Val Tyr Glu
            130                 135                 140

Gln Trp
145

<210> SEQ ID NO 112
<211> LENGTH: 343
<212> TYPE: PRT
<213> ORGANISM: Streptomyces lavendulae

<400> SEQUENCE: 112

Met Gln Gln Pro His His Ser Arg Val Asp Val Glu Leu Gly Glu Arg
 1               5                  10                  15

Ser Tyr Pro Val His Val Gly Pro Val Arg His Leu Leu Pro Gly
            20                  25                  30

Ile Val Ala Ser Leu Gly Ala His Arg Ala Ala Val Thr Ala Arg
            35                  40                  45

Pro Pro Asp Leu Val Pro Asp Pro Gly Val Pro Ala Leu Ile Val Arg
 50                      55                  60

Ala Arg Asp Gly Glu Arg His Lys Thr Leu Ala Thr Val Glu Asp Leu
 65                  70                  75                  80

Cys Arg Lys Phe Thr Thr Phe Gly Ile Thr Arg His Asp Val Val Val
                 85                  90                  95

Ser Cys Gly Gly Gly Ser Thr Thr Asp Thr Val Gly Leu Ala Ala Ala
            100                 105                 110

Leu His His Arg Gly Val Pro Val His Leu Pro Thr Thr Leu Leu
            115                 120                 125

Ala Gln Val Asp Ala Ser Val Gly Gly Lys Thr Ala Val Asn Leu Pro
130                      135                 140

Glu Gly Lys Asn Leu Val Gly Ala Tyr Trp Gln Pro Lys Ala Val Leu
145                 150                 155                 160

Cys Asp Thr Thr Tyr Leu Gln Thr Leu Pro Ala Glu Glu Trp Val Asn
                165                 170                 175

Gly Tyr Gly Glu Ile Ala Arg Cys His Phe Ile Gly Ala Gly Asp Leu
            180                 185                 190

Arg Gly Leu Ala Val His Asp Gln Val Thr Ala Ser Leu Arg Leu Lys
            195                 200                 205

Ala Ser Val Val Ala Ala Asp Glu Arg Asp Thr Gly Leu Arg His Ile
210                      215                 220

Leu Asn Tyr Gly His Thr Leu Gly His Ala Leu Glu Thr Ala Thr Gly
```

-continued

```
               225                 230                 235                 240

Phe Gly Leu Arg His Gly Leu Gly Val Ala Ile Gly Thr Val Phe Ala
                245                 250                 255

Gly Arg Leu Ala Glu Ala Leu Gly Arg Ile Gly Ala Asp Arg Ala Arg
                260                 265                 270

Glu His Thr Glu Val Val Arg His Tyr Gly Leu Pro Asp Ser Leu Pro
                275                 280                 285

Gly Asn Thr Asp Ile Thr Glu Leu Val Ala Leu Met Arg His Asp Lys
                290                 295                 300

Lys Ala Thr Ser Gly Leu Thr Phe Val Leu Asp Gly Pro Ser Gly Val
305                 310                 315                 320

Glu Leu Val Ser Gly Ile Pro Glu Asp Val Val Leu Arg Thr Leu Ala
                325                 330                 335

Ala Met Pro Arg Gly Thr Ala
                340

<210> SEQ ID NO 113
<211> LENGTH: 164
<212> TYPE: PRT
<213> ORGANISM: Streptomyces lavendulae

<400> SEQUENCE: 113

Met Glu Arg Val Glu Leu Ile Arg Trp Pro Val Glu Ser Glu Arg Arg
1               5                   10                  15

Glu Arg Cys Arg Asp Arg Gly Val Met Arg Ile Leu Val Leu Glu Ala
                20                  25                  30

Gly Ala Glu Ala Pro Leu Cys Val Asp Pro Lys Glu Asp Trp Val Arg
                35                  40                  45

Ala Pro Val Ser Thr Asp Asp Leu Arg Ala Arg Val Glu Ala Leu Arg
            50                  55                  60

Leu Arg Gly Ala Ala Ala Glu Ser Arg Pro Glu Val Asp Pro Asn Gly
65              70                  75                  80

Val Leu Arg Phe Arg Trp Arg Ser Ala Leu Leu Ser Pro Thr Glu Ala
                85                  90                  95

Arg Leu Val Ala Arg Leu Ala Glu Ser Tyr Ala Glu Val Val Ala Arg
                100                 105                 110

Asp Asp Leu Leu Arg Pro Pro Gly Arg Thr Val Pro Ser Arg Asn
            115                 120                 125

Ala Leu Asp Leu His Ile Met Arg Ile Arg Arg Leu Ala Ala Leu
            130                 135                 140

Gly Leu Arg Val Arg Thr Val Arg Gly Arg Gly Tyr Val Leu Glu Ser
145                 150                 155                 160

Ala Glu Gly Val

<210> SEQ ID NO 114
<211> LENGTH: 514
<212> TYPE: PRT
<213> ORGANISM: Streptomyces lavendulae

<400> SEQUENCE: 114

Met Leu Asp Arg Arg Ser Val Ile Arg Val Gly Ala Gly Val Ala Ala
1               5                   10                  15

Ala Ala Ala Val Ala Gly Thr Ala Ala Thr Gly Ala Ala Ala Val Gly
                20                  25                  30

Leu Pro Gly Val Arg Gly Arg Ala Ala Ser Arg Gly Val Asp Trp Ala
                35                  40                  45
```

-continued

```
Ser Leu Arg Arg His Leu Ser Gly Glu Leu Val Leu Pro Ala Asp Thr
 50                  55                  60
Gly Tyr Glu Arg Ala Arg Lys Leu Tyr Ser Gly Gln Phe Asp Gly Ile
 65                  70                  75                  80
Arg Pro Gln Ala Val Ala Tyr Cys Arg Thr Glu Glu Asp Val Arg Thr
                 85                  90                  95
Thr Leu Ala Phe Ala Gln Asp His Ala Leu Pro Leu Thr Pro Arg Ser
                100                 105                 110
Gly Gly His Ser Phe Gly Gly Tyr Ser Thr Thr Asp Gly Ile Val Leu
            115                 120                 125
Asp Val Ser Gly Phe His Ala Val Ser Leu Thr Arg Asn Thr Val Val
130                 135                 140
Met Gly Ala Gly Thr Gln Gln Val Asp Ala Leu Thr Ala Leu Ser Pro
145                 150                 155                 160
Arg Gly Val Ala Val Ala Ser Gly Asn Cys Ala Gly Val Cys Pro Gly
                165                 170                 175
Gly Phe Val Gln Gly Gly Leu Gly Trp Gln Ser Arg Lys Phe Gly
            180                 185                 190
Met Ala Cys Asp Arg Leu Val Ser Ala Arg Val Leu Ala Asp Gly
            195                 200                 205
Arg Ala Val Thr Ala Ser Ala Thr Glu His Pro Asp Leu Phe Trp Ala
210                 215                 220
Met Arg Gly Gly Gly Gly Asn Phe Gly Val Val Thr Gly Phe Glu
225                 230                 235                 240
Leu Arg Pro Thr Asp Val Pro Ser Val Val Ser Tyr Asn Leu Thr Trp
                245                 250                 255
Pro Trp Glu Ser Ala Arg Arg Val Ile Glu Ala Trp Gln His Trp Ile
            260                 265                 270
Ile Asp Gly Pro Arg Asp Leu Gly Ala Ala Met Ala Val Gln Trp Pro
            275                 280                 285
Asp Ala Gly Thr Gly Thr Pro Val Val Val Thr Gly Ala Trp Leu
            290                 295                 300
Gly Ala Ala Asp Ala Leu Thr Pro Val Leu Asp Ser Leu Val Ala Ser
305                 310                 315                 320
Val Gly Ser Ala Pro Ala Thr Arg Ser Ala Lys Ala Leu Ser Gln His
                325                 330                 335
Asp Ala Met Met Ala Gln Tyr Gly Cys Ala Asp Leu Thr Pro Glu Gln
            340                 345                 350
Cys His Thr Val Gly Tyr Ser Pro Glu Ala Ala Leu Pro Arg Gln Asn
            355                 360                 365
Phe Ser Met Asp Arg Asn Arg Leu Phe Ser Arg Ala Ile Gly Gln Gly
370                 375                 380
Gly Val Glu Arg Ile Leu Glu Ala Phe Ala Ala Asp Pro Arg Ala Gly
385                 390                 395                 400
Gln Phe Arg Phe Leu Ser Phe Ala Leu Gly Gly Ala Ala Asn Arg
                405                 410                 415
Pro Asp Arg Thr Thr Thr Ala Tyr Val His Arg Asp Thr Glu Phe Tyr
                420                 425                 430
Leu Gly Phe Ser Ile Gly Leu Asn Asp Pro Glu Tyr Thr Ala Glu Asp
            435                 440                 445
Glu Arg Leu Gly Arg Ala Trp Ala Ala Arg Gly Leu Arg Thr Leu Asp
450                 455                 460
```

-continued

```
Pro His Ser Asn Gly Glu Ser Tyr Gln Asn Phe Ile Asp Pro Glu Leu
465                 470                 475                 480

Asp Asp Trp Lys Ser Ala Tyr Tyr Ala Glu Asn Tyr Val Arg Leu Ala
            485                 490                 495

Ala Val Lys Ala Ala Tyr Asp Pro His Arg Leu Phe Ser Phe Ala Gln
            500                 505                 510

Ala Val

<210> SEQ ID NO 115
<211> LENGTH: 315
<212> TYPE: PRT
<213> ORGANISM: Streptomyces lavendulae

<400> SEQUENCE: 115

Met Thr Gly Asp Thr Asp Gly Ala Gly Gly Asp Val Thr Phe Arg
1               5                   10                  15

Trp Pro Ala Ala Gly Asp Val Thr Ala Asp Leu Asp Leu Leu Ala Ala
            20                  25                  30

Arg Val Arg Gly Leu Leu Gly His Arg Glu Asp Pro Leu Ala Gly Val
        35                  40                  45

Gly Val Ala Met Pro Ala Ile Cys Asp Ala Ala Gly Thr Val Arg Thr
    50                  55                  60

Trp Pro Gly Arg Pro Ser Trp Ala Gly Leu Asn Leu Thr Ala Ala Phe
65                  70                  75                  80

Gly Gln Leu Leu Pro Gly Thr Pro Val Ala Cys Ala Asp Asp Gly Asp
                85                  90                  95

Leu Ala Ala Leu Ala Glu Ser Arg Ala Ala Gly Cys Arg His Leu Leu
            100                 105                 110

Tyr Val Gly Val Gly Thr Gly Ile Gly Gly Gly Ile Val His Glu Gly
        115                 120                 125

Arg Ala Trp Pro Gly Pro Gly Arg Gly Ser Cys Glu Val Gly His Val
    130                 135                 140

Val Val Asp Arg Ser Gly Pro Arg Cys Asp Cys Gly Arg Ala Gly Cys
145                 150                 155                 160

Val Gln Ala Val Ala Ser Gly Pro Ala Thr Leu Arg Arg Ala Ala Glu
                165                 170                 175

Arg Arg Gly Arg Glu Thr Gly Phe Asp Glu Leu Ala Ser Gly Ala Arg
            180                 185                 190

Leu His Ala Pro Trp Ala Glu Ala Val Asp Glu Ser Ala Ala Ala
        195                 200                 205

Leu Ala Thr Ala Val Thr Gly Ile Cys Glu Leu Ala His Pro Glu Leu
    210                 215                 220

Val Leu Val Gly Gly Phe Ala Ala Gly Val Pro Gly Tyr Val Ala
225                 230                 235                 240

Ser Val Ala Ala His Val Glu Arg Leu Thr Arg Pro Gly Thr Asp Pro
                245                 250                 255

Val Arg Val Arg Pro Ala Val Leu Gly Gly Arg Ser Ser Leu His Gly
            260                 265                 270

Ala Leu Leu Leu Ala Arg Glu Ala His Gly Arg Gly Asn Arg Pro Pro
        275                 280                 285

Glu Ser Asp Arg Val Ser Ser Asp Val Ser Asp Val Ser Phe Gly
    290                 295                 300

Gly Val Thr Asp Arg Ala Val Gly Arg Ser Asp
305                 310                 315
```

-continued

```
<210> SEQ ID NO 116
<211> LENGTH: 514
<212> TYPE: PRT
<213> ORGANISM: Streptomyces lavendulae

<400> SEQUENCE: 116

Met Pro Ser Pro Arg Ala Leu Val Ile Gly Ile Asp Gly Gly Thr
 1               5                  10                  15

Phe Asp Thr Val Asp Pro Leu Ile Glu Cys Gly Leu Leu Pro His Met
                20                  25                  30

Ala Lys Leu Leu Arg Glu Ser Ala Ser Ala Ala Thr Asp Cys Thr Trp
                35                  40                  45

Pro Ala His Thr Ala Pro Gly Trp Ser Thr Phe Val Ser Ala Ser Asp
        50                  55                  60

Pro Gly Gly His Gly Ile Tyr Gln Phe Tyr Asp Thr Gln Asp Pro Ala
65                  70                  75                  80

Tyr Gly Ala Arg Val Thr Arg Ser Gly Asp Leu Gly Arg Ser Cys Ala
                    85                  90                  95

Trp Asp Trp Leu Ala Ala Gln Glu Tyr Ser Leu Gly Leu Ile Asn Ile
                    100                 105                 110

Pro Met Ser His Pro Pro Ala Asp Leu Pro Gly Tyr Gln Val Thr Trp
                    115                 120                 125

Pro Leu Glu Arg Thr Leu Lys His Cys Arg Pro Asp Ser Leu Leu Arg
            130                 135                 140

Glu Leu Ala Ala Ala Lys Ala His Phe Gln Ser Asp Leu Ala Thr Met
145                 150                 155                 160

Phe Arg Gly Asp Met Ala Tyr Leu Glu Glu Ala Glu Arg Asn Val Ala
                    165                 170                 175

Ala Arg Val Arg Ser Val Arg His Leu Met Ser Thr Arg Pro Thr Asp
                    180                 185                 190

Val Val Met Val Val Leu Thr Glu Ala Asp Arg Val Gly His His Tyr
                    195                 200                 205

Trp His Tyr Gly Asp Pro Gly His Pro Gly His Arg Pro Ala Pro Glu
            210                 215                 220

Gly Ser Gly Trp Asp Val Ala Met Pro Arg Ile Tyr Gln Ala Ile Asp
225                 230                 235                 240

His Ala Val Gly Glu Leu Leu Glu Leu Val Asp Glu Asp Thr Ser Val
                    245                 250                 255

Val Leu Val Ser Asp His Gly Leu Gly Thr Gly Arg His Gly Leu Ser
                    260                 265                 270

Val His Thr Leu Leu Glu Glu Ala Gly Leu Leu Ala Thr Ala Pro Gly
            275                 280                 285

Glu Glu Pro Gln Asp Ala Ala Ala Ser Trp Phe Ala Gly Asn Gly Arg
        290                 295                 300

His Val Asp Phe Arg Arg Thr Ser Val Tyr Met Pro Val Pro Gly Ser
305                 310                 315                 320

Tyr Gly Leu Asn Ile Asn Val Arg Gly Arg Gln Arg Gly Thr Val
                    325                 330                 335

Ala Pro Arg Asp Arg Glu Arg Val Met Asp Glu Val Thr Gly Leu Leu
            340                 345                 350

Ser Gly Leu Thr Gly Pro Glu Gly Gln Gln Val Phe Arg Ala Val Arg
                355                 360                 365

Pro Arg Glu Glu Ala Tyr Pro Gly Pro His Thr Gly Arg Ala Pro Asp
            370                 375                 380
```

```
Leu Leu Leu Val Pro Arg Asp Glu Thr Val Leu Pro Val Pro Asp Leu
385                 390                 395                 400

Gly Gly Asp Val Trp Arg Pro Ser Ala Gln Thr Gly Leu His Arg Tyr
            405                 410                 415

Arg Gly Leu Trp Ala His Arg Ser Pro Arg Val Arg Pro Gly Arg Leu
            420                 425                 430

Pro Gly Thr Val Ala Leu Thr Asp Thr Leu Pro Thr Leu Leu Thr Asp
            435                 440                 445

Leu Gly Ala Ala Trp Pro Ser Asp Ile His Gly Arg Pro Val Thr Ala
        450                 455                 460

Val Leu Asp Asp Gly Val Arg Val Pro Pro Ser Asp Pro Arg Val Glu
465                 470                 475                 480

Ala Thr Gly Thr Pro Ala Thr Thr Ile Pro Ala Ala Ser Ala Ala
                485                 490                 495

Asp Ala Ala Glu Asp Ala Tyr Thr Ser Asp Arg Leu Arg Glu Met Gly
            500                 505                 510

Tyr Leu

<210> SEQ ID NO 117
<211> LENGTH: 93
<212> TYPE: PRT
<213> ORGANISM: Streptomyces lavendulae

<400> SEQUENCE: 117

Met Glu Thr Leu Thr Thr Asp Lys Ile Lys Asp Arg Leu Arg Lys Val
1               5                   10                  15

Leu Val Asp Ser Leu Glu Leu Ser Leu Asp Pro Ser Ala Val Pro Asp
            20                  25                  30

Glu Gly Leu Val Glu Lys Leu Gly Leu Asp Ser Ile Asn Thr Ile Glu
        35                  40                  45

Phe Leu Ile Trp Val Glu Ser Glu Phe Gly Ile Glu Ile Ala Asp Glu
    50                  55                  60

Asp Leu Ser Ile Lys Leu Ile Asp Ser Leu Asp Leu Leu Ala Gly Tyr
65                  70                  75                  80

Val Ser Glu Arg Val Asn Gly Val Thr Ala Pro Ala Glu
                85                  90

<210> SEQ ID NO 118
<211> LENGTH: 470
<212> TYPE: PRT
<213> ORGANISM: Streptomyces lavendulae

<400> SEQUENCE: 118

Met Asp Arg His Ala Leu Val Ile Gly Leu Asp Gly Met Pro Arg Thr
1               5                   10                  15

Leu Leu Thr Arg Leu Ala Gly Asp Gly Thr Met Pro His Thr Ala Ala
            20                  25                  30

Leu Leu Ala Glu Gly His Cys Ala Glu Leu Leu Ala Pro Val Pro Glu
        35                  40                  45

Ile Ser Ser Thr Ser Trp Ala Thr Phe Leu Thr Gly Thr Asn Pro Gly
    50                  55                  60

Arg His Gly Ile Tyr Gly Phe Thr Asp Leu Ala Pro Gly Asp Gly Tyr
65                  70                  75                  80

Arg Ile Thr Phe Pro Gly Val Arg Gln Leu Arg Glu Pro Pro Leu Trp
                85                  90                  95
```

```
Glu Leu Ala Ala Arg Ala Gly Arg Arg Thr Val Cys Leu Asn Val Pro
             100                 105                 110

Gly Thr Tyr Pro Ala Pro Ala Ile Asp Gly Val Leu Val Ser Gly Phe
        115                 120                 125

Val Ala Pro Glu Leu Glu Arg Ala Val Ser Pro Pro Arg Leu Leu Pro
    130                 135                 140

Leu Leu Arg Gly Leu Asp Tyr Glu Leu Asp Val Glu Val Gly Asp Val
145                 150                 155                 160

Ala Ala Asp Pro Ala Ala Phe Leu Gly Arg Ala Val Arg Ala Leu Arg
                165                 170                 175

Ala Arg Thr Arg Ala Met Glu His Leu Leu Arg Gln Glu Thr Trp Asp
            180                 185                 190

Leu Ala Val Ala Val Leu Thr Glu Thr Asp Arg Val His His Phe Leu
        195                 200                 205

Trp Arg Ala Val Ala Asp Pro Ala Asp Pro Leu His Gly Asp Val Leu
    210                 215                 220

Ala Phe Tyr Arg Leu Val Asp Asp Cys Val Ala Thr Leu Val Ser Thr
225                 230                 235                 240

Leu Pro Pro Gly Gly Glu Leu Phe Leu Met Ser Asp His Gly Phe Gly
                245                 250                 255

Pro Ala Ala Cys Gln Val Tyr Leu Asn Ala Trp Leu Arg Glu Ser Gly
            260                 265                 270

Trp Leu Ala Gly Leu Asp Val Cys Pro Asp Leu Thr Ala Val Asp Ala
        275                 280                 285

Arg Ser Thr Ala Phe Ala Leu Asp Pro Ala Arg Ile His Leu Asn Arg
    290                 295                 300

Lys Ser Arg Phe Pro Gly Gly Leu Thr Asp Ala Glu Ala Asp Glu
305                 310                 315                 320

Ala Ala His Glu Ile Ala Arg Glu Leu Ser Ala Leu Arg Cys Asp Gly
                325                 330                 335

Thr Arg Leu Gly Pro Asp Val Asp Gly Pro Leu Leu Val Arg Asp Leu
            340                 345                 350

Tyr Arg Ala Gln Glu Ile Tyr His Gly Pro Leu Leu Gly Asn Ala Pro
        355                 360                 365

Asp Leu Val Ala Val Pro Ala Pro Gly Val Gln Leu Arg Gly Gly Trp
    370                 375                 380

Gly Gly Thr His Thr Val Arg Asn Asp Ile Leu Thr Gly Thr His Thr
385                 390                 395                 400

Arg Asp Asp Ala Val Phe Tyr Arg Arg Gly Ala Pro Ala Pro Ala Pro
                405                 410                 415

Gly Ala Asp Asp Gly Pro Leu Asp Met Thr Asp Val Ala Pro Thr Val
            420                 425                 430

Leu Ala Ser Leu Gly Ile His Pro Gly Gly Leu Asp Gly Ala Ala Val
        435                 440                 445

Leu Gly Thr Thr Gly Pro Ala Ser Gly His Gly Arg Thr Asp Pro Pro
    450                 455                 460

Leu Asp Ile Arg Glu Leu
465                 470

<210> SEQ ID NO 119
<211> LENGTH: 611
<212> TYPE: PRT
<213> ORGANISM: Streptomyces lavendulae

<400> SEQUENCE: 119
```

```
Met Lys His Asp Leu Gly Leu Ala Pro Ser Ala Pro Lys Pro Gly Thr
 1               5                  10                 15

Leu Asp Leu Ser Leu Asp Pro Arg Ile Thr Asp Pro Ala Ser Phe Arg
            20                  25                  30

Val Ser Phe Leu Ile Leu Asp Gly Asp Leu Val Met Ser Pro Glu
            35                  40                  45

His Leu Gly Val Ala Tyr Met Ala Gly Val Leu Arg His Thr Gly Phe
    50                  55                  60

Thr Ala Glu Ile Arg Glu Val Glu His Gly Asp Asp Gln Ala Ala Ala
 65              70                  75                  80

Thr Val Glu Ala Leu Lys Glu Tyr Arg Pro Asp Leu Val Cys Phe Thr
                85                  90                  95

Leu Met Ser Leu Asn Leu Gly Ser Cys Leu Thr Leu Cys Arg Met Leu
            100                 105                 110

Arg Glu Glu Leu Pro Gly Thr Thr Ile Ala Cys Gly Gly Pro Ala Gly
            115                 120                 125

Thr Phe Ala Gly Leu Asp Val Leu Arg Asn Asn Pro Trp Thr Asp Val
        130                 135                 140

Val Ala Val Gly Glu Gly Glu Pro Thr Ile Leu Asp Leu Val Gln Arg
145                 150                 155                 160

Leu Tyr Leu Lys Glu Pro Leu Ser Ala Cys Lys Gly Ile Cys Tyr Arg
                165                 170                 175

Asp Glu Asp Gly Thr Pro Arg Gln Asn Pro Ala Arg Pro Leu Ile His
            180                 185                 190

Asn Leu Glu Asp Leu Pro Phe Pro Ala Arg Asp Gln Leu Arg Gln His
        195                 200                 205

Gly Asp Lys Leu Glu Tyr Val Arg Val Ser Thr Ser Arg Gly Cys Val
    210                 215                 220

Ala Asn Cys Ala Phe Cys Ser Ala Pro His Leu Lys Asn Arg Val Gln
225                 230                 235                 240

Ala Gly Lys Ala Trp Arg Gly Arg Gly Pro Glu Gln Ile Val Asp Glu
                245                 250                 255

Val Ala Glu Ile Val Glu Arg His Gln Phe Arg Thr Phe Asp Phe Val
            260                 265                 270

Asp Ser Thr Phe Glu Asp Pro Asp Gly Gly Arg Val Gly Lys Lys Arg
        275                 280                 285

Val Ala Ala Ile Ala Asn Gly Ile Leu Glu Arg Gly Leu Asp Ile Tyr
        290                 295                 300

Tyr Asn Val Cys Met Arg Ala Glu Asn Trp His Asp Thr Pro Glu Asp
305                 310                 315                 320

His Ala Leu Leu Asp Leu Leu Val Ala Ser Gly Leu Glu Lys Val Asn
                325                 330                 335

Val Gly Ile Glu Ala Gly Thr Ala Glu Glu Leu Leu Leu Trp Glu Lys
            340                 345                 350

Arg Ala Thr Val Glu Asp Asn Val Thr Ile Ile Arg Met Leu Arg Glu
        355                 360                 365

His Gly Ile Tyr Leu Ala Met Gly Phe Ile Pro Phe His Pro Tyr Ala
    370                 375                 380

Thr Leu Glu Thr Ile Val Thr Asn Ala Ala Phe Leu Arg Asp Asn Ser
385                 390                 395                 400

Gly His Asn Leu Arg Arg Met Thr Glu Arg Leu Glu Ile Tyr Pro Gly
                405                 410                 415
```

```
Thr Ala Ile Val Ser Arg Met Arg Ala Asp Gly Leu Leu Gly Glu Ser
                420                 425                 430

Tyr Leu Glu Gly Leu Asp Pro Tyr Gly Tyr Ala Phe Lys Asp Pro Arg
            435                 440                 445

Val Gly Arg Leu Ala Lys His Phe Ala Gln Leu Tyr Asn Asn Asp Asp
        450                 455                 460

Tyr His Arg His Gly Val Ile Thr Glu Gln Ser Ser Val Phe Ala Phe
465                 470                 475                 480

Glu Thr Tyr Asn Val Val Leu Gln Thr Phe Ile Ser Arg Leu His Arg
                485                 490                 495

Arg Phe Thr Thr Leu Pro Gly Val Asp Glu Val Met Glu Ala Phe Lys
            500                 505                 510

Ala Arg Val His Glu Ile Arg Gln Glu Met Gly Arg His Asn Tyr Gly
        515                 520                 525

Phe Phe Met Ser Asn Val Glu Ala Val Met Asn Asp Thr Leu Asp Pro
    530                 535                 540

Glu Lys Gln Arg Arg Gln Val Val Asp Val Glu His Phe Phe Arg Asp
545                 550                 555                 560

Arg Leu Asp Val Leu Arg Ser Glu Gln Leu Arg Val Gly Lys Ala Leu
                565                 570                 575

Thr Arg Leu Gly Ala Arg Val Thr Glu Val Ser Ser Thr Ile Pro Lys
            580                 585                 590

Glu Arg Pro Gly Gly Leu Pro Arg Gln Tyr Thr Gly Glu Gly Ser Gly
        595                 600                 605

Ala Thr Trp
    610

<210> SEQ ID NO 120
<211> LENGTH: 359
<212> TYPE: PRT
<213> ORGANISM: Streptomyces lavendulae

<400> SEQUENCE: 120

Met Pro Arg Gly Glu Thr Gly Thr Ala Ala Ala Arg Val Ala Val Cys
1               5                   10                  15

Thr Leu Ser Ser Arg Glu Leu Val Gly Pro Leu Ala Arg Leu Pro Gly
                20                  25                  30

Val Ala Ala Gly Thr Leu Met Thr Ala Asn Leu Gly Ile Glu Gln
            35                  40                  45

Val Ile Lys Ala Leu Arg Cys Asp Arg Thr Val Arg Gly Leu Leu Val
    50                  55                  60

Cys Gly Arg Asp Ser Pro Arg Phe Arg Ala Gly Gln Ser Leu Ile Ala
65                  70                  75                  80

Leu Phe Arg His Gly Leu Arg Pro Glu Asp Gly His Ile Arg Gly Ala
                85                  90                  95

Thr Gly Tyr Leu Pro Val Leu Arg Ser Val Thr Ala Arg Glu Thr Glu
            100                 105                 110

Glu Val Arg Ala Arg Val Glu Leu Val Asp Ala Arg Gly Glu Arg Asp
        115                 120                 125

Val Glu Thr Leu Arg Ala Glu Val Ala Ala Leu Leu Ala Arg Val Arg
    130                 135                 140

Arg Thr Pro Ala Leu Pro Ser Arg Glu His Asp Gly Gly Gln Pro Ser
145                 150                 155                 160

Phe Val Glu Pro Asp Phe Gly Arg Leu His Pro Val Gly Arg Arg Arg
                165                 170                 175
```

```
Ser Leu Asp Ala Gly Ile Gly Gly Phe Val Leu Ile Ser Val Asp Arg
            180                 185                 190

Glu His Arg Arg Ile Leu Leu Arg His Tyr Thr Ser Asp Val Arg Pro
            195                 200                 205

Arg His Glu Met Trp Gly Thr Arg Gly Glu Ala Met Leu Leu Gly Leu
            210                 215                 220

Leu Glu Ala Gly Val Ile Glu Asp Pro Ala His Ala Gly Tyr Leu Gly
225                 230                 235                 240

Ala Glu Leu Ala Lys Ala Glu Thr Ala Leu Arg Leu Gly Leu His Tyr
                245                 250                 255

Glu Gln Asp Leu Pro Leu Arg Pro Pro Gly Arg Pro Pro Gly Pro Val
            260                 265                 270

Arg Arg Arg Thr Ala Lys Glu Arg Thr Thr Met Ala Gln Ala Pro Ala
            275                 280                 285

Leu Glu Asp Phe Leu Arg Leu Val Thr Arg Thr Leu Gly Ala Glu Asp
            290                 295                 300

Ala Val Leu Asp Leu His Thr Pro Leu Gly Glu Gln Leu Ala Val Asp
305                 310                 315                 320

Ser Ala Arg Leu Ile Glu Leu Thr Val Val Leu Glu Glu Leu Gly
                325                 330                 335

Ala Asp Leu Pro Asp Asp Ala Asp Leu Ala Arg Ala Thr Pro Ala Glu
                340                 345                 350

Leu His Lys Ala Leu Val Gly
                355

<210> SEQ ID NO 121
<211> LENGTH: 145
<212> TYPE: PRT
<213> ORGANISM: Streptomyces lavendulae

<400> SEQUENCE: 121

Met Arg Ser Val Leu Leu Asn Gly Pro Asn Leu Gly Thr Leu Gly
1               5                   10                  15

Lys Arg Gln Pro Glu Ile Tyr Gly Thr Asp Thr Leu Ala Glu Ile Glu
            20                  25                  30

Ala Ala Val Ala Glu Glu Val Gly Ala Arg Gly Trp Glu Val Val Ser
            35                  40                  45

Glu Gln Arg Asn Gly Glu Gly Glu Leu Val Asp Val Leu Gln Arg His
        50                  55                  60

Asp Asp Val Val Gly Ala Val Asn Pro Gly Ala Leu Met Ile Ala
65                  70                  75                  80

Gly Trp Ser Leu Arg Asp Ala Leu Ala Asp Phe Ala Pro Pro Trp Val
                85                  90                  95

Glu Val His Leu Ser Asn Val Trp Gly Arg Glu Ala Phe Arg His Thr
            100                 105                 110

Ser Val Thr Ala Pro Leu Ala Ser Gly Val Val Met Gly Met Gly Ala
            115                 120                 125

Leu Gly Tyr Arg Leu Ala Ala Arg Ala Leu Thr Arg Leu Val Pro Glu
        130                 135                 140

Asp
145

<210> SEQ ID NO 122
<211> LENGTH: 177
<212> TYPE: PRT
```

<213> ORGANISM: Streptomyces lavendulae

<400> SEQUENCE: 122

```
Met Gly Arg Tyr Gly Arg Glu Gly Leu Gly Met Ser Arg Thr Ala Glu
 1               5                  10                  15

Gly Asn Ala Gly Gly Val Val Pro Val Arg Leu Val Ala Val
            20                  25                  30

Thr Asp Gly Pro Asp Ala Glu Gly Trp Arg Gln Ala Leu Ala Pro Glu
            35                  40                  45

Leu Val Val Glu His Gly Val Glu Ala Ile Ala Glu Ala Ala Gly Asp
    50                  55                  60

Gly Gly Pro Trp Ala Leu Val Cys Ala Gly Ala Gly Leu Gly Ala Ala
65                  70                  75                  80

Leu Arg Ala Ala Glu Arg Ala Ala Arg Pro Val His Val Leu Leu
                85                  90                  95

Trp Leu Gly Ser Arg Gly Pro Gly Glu Gly Val Gly Gly Glu Val Ser
                100                 105                 110

Gly Gln Phe Pro Cys Pro Val Thr Ala Leu Val Ser Ala Glu Val Asp
            115                 120                 125

Arg Gly Arg Ala Val Val Pro Ala Trp Arg Gly Leu Thr Glu Gly Pro
            130                 135                 140

Phe Thr Val Arg Ile Leu Pro Ala Ala Cys Pro Leu Pro Gly Ala Cys
145                 150                 155                 160

Asp Gln Ala Gly Ala Gln Val Ile Lys Glu Glu Leu Arg Val Trp Pro
                165                 170                 175

Ala
```

<210> SEQ ID NO 123
<211> LENGTH: 254
<212> TYPE: PRT
<213> ORGANISM: Streptomyces lavendulae

<400> SEQUENCE: 123

```
Met Asp Ala Thr Leu Thr Asn Asp Val Glu Lys Ala Ser Arg Asp Leu
 1               5                  10                  15

Val Glu Ala Gly Tyr Cys Leu Ile Glu Cys Pro Leu Pro Ala Ala Val
            20                  25                  30

Phe Glu Lys Leu Arg Gly Arg Leu Leu Glu Val Ala Glu Gln Glu Arg
            35                  40                  45

Glu Asn Gly Ser Ala Phe Leu Tyr Asp Gly Gly Asn Gln Arg Val Phe
    50                  55                  60

Ser Leu Leu Asn Lys Gly Glu Glu Phe Glu Gln Asn Val Gln Asp Pro
65                  70                  75                  80

Thr Val Met Leu Leu Met Glu Glu Ile Leu Gly Phe Gly Phe Leu Leu
                85                  90                  95

Ser Ser Thr His Ala Asn Ile Ala Gly Pro Gly Gly Ser Arg Met His
                100                 105                 110

Leu His Ala Asp Gln Thr Phe Ala Arg Pro Pro Trp Pro Pro Tyr Pro
            115                 120                 125

Leu Val Ala Asn Ser Met Trp Met Leu Asp Asp Phe Thr Glu Asp Asn
            130                 135                 140

Gly Ala Thr Arg Leu Val Pro Gly Ser His Leu Leu Gly Arg Gln Pro
145                 150                 155                 160

Asp Tyr Asp Arg Gly Glu Gly Asn Thr Glu Thr Val Ala Val Cys Ala
                165                 170                 175
```

```
Pro Ala Gly Ser Val Met Val Phe Asp Gly Arg Leu Trp His Gln Thr
            180                 185                 190
Gly Ala Asn Thr Thr Asp Arg Pro Arg His Gly Ile Leu Asn Tyr Tyr
        195                 200                 205
Cys Arg Gly Tyr Val Arg Gln Gln Asn Phe Phe Ser Gly Leu Arg
    210                 215                 220
Glu Asp Val Ala Thr Arg Ala Thr Pro Glu Leu Arg Arg Leu Leu Gly
225                 230                 235                 240
Tyr Glu Asn Tyr Phe Ser Leu Gly Met Thr Asp Gly Leu Pro
                245                 250

<210> SEQ ID NO 124
<211> LENGTH: 264
<212> TYPE: PRT
<213> ORGANISM: Streptomyces lavendulae

<400> SEQUENCE: 124

Met Ala His Ser Pro Arg Arg Pro Asp Gly Pro Leu Arg Ile Gly Val
1               5                   10                  15
Trp Leu Ala Pro Gln His Thr Ser Val Ala Glu Leu Arg Ala Ala Trp
            20                  25                  30
Arg Ala Ala Asp Ser Leu Gly Val Asp Ser Leu Trp Leu Trp Asp His
        35                  40                  45
Phe Phe Pro Leu Thr Gly Asp Pro Asp Gly Ser His Phe Glu Ala Trp
    50                  55                  60
Thr Leu Leu Ala Ala Met Ala Ala Asp Thr Arg Ala Ala Arg Leu Gly
65                  70                  75                  80
Thr Leu Val Ser Asn Tyr Ala Tyr Arg Asn Pro Asp Leu Leu Ala Asp
                85                  90                  95
Met Ala Arg Thr Val Asp His Ile Gly Asp Gly Arg Leu Ile Leu Gly
            100                 105                 110
Met Gly Ala Gly Trp Val Glu Arg Asp Leu Lys Glu Tyr Gly Tyr Pro
        115                 120                 125
Thr Pro Gly Ala Gly Glu Arg Val Asp Gly Leu Ile Glu Ala Val Glu
    130                 135                 140
Arg Val Asp Arg Arg Leu Gly Arg Leu Arg Pro Gly Pro Leu Gly Asp
145                 150                 155                 160
Leu Pro Leu Leu Ile Gly Gly Asp Gly Gln Arg Arg Leu Leu Arg Phe
                165                 170                 175
Ala Ala Glu Arg Ala Ala Ile Trp Asn Thr Met Ala Trp Arg Phe Ala
            180                 185                 190
Glu Gly Asn Arg Val Leu Asp Glu Trp Cys Ala Arg Val Gly Arg Asp
        195                 200                 205
Pro Ala Glu Ile Glu Arg Ser Ala Phe Val Thr Arg Asp Gln Thr Asp
    210                 215                 220
Glu Glu Leu Arg Cys Leu Val Ala Thr Gly Val Gln His Leu Ile Phe
225                 230                 235                 240
Gln Val Gly His Pro Phe Arg Phe Asp Gly Val Glu Arg Ala Leu Arg
                245                 250                 255
Phe Ala Gly Gly Trp Ser Lys Gly
            260

<210> SEQ ID NO 125
<211> LENGTH: 274
<212> TYPE: PRT
```

<213> ORGANISM: Streptomyces lavendulae

<400> SEQUENCE: 125

Met Lys Ile Ser Ile Ala Leu Pro Asn Thr Val Pro Gly Ala Asp Gly
1               5                   10                  15

Arg Leu Ile Thr Asp Trp Ala Arg Arg Ala Glu Glu Arg Gly Phe Ala
            20                  25                  30

Ser Leu Ala Ala Thr Glu Arg Leu Val Tyr Pro Gly His Asp Pro Leu
        35                  40                  45

Leu Ala Leu Ala Ala Ala Ala Gly Ala Thr Ser Arg Ile Gly Leu Leu
    50                  55                  60

Thr Asn Val Leu Ile Gly Pro Leu Arg Thr Ala Pro Val Leu Ala Lys
65                  70                  75                  80

Ala Val Ala Ser Leu Asp Ser Leu Ser Gly Gly Arg Phe Thr Leu Gly
                85                  90                  95

Val Gly Pro Gly Val Arg Glu Asp Asp Phe Glu Ala Ala Gly Arg Ala
            100                 105                 110

Phe Asp Asp Arg Arg Ala Ala Phe Glu Glu Gln Leu Glu Leu Leu Gly
        115                 120                 125

Arg Gly Ala Arg Pro Gly Ala Glu Gly Pro Gly Val Pro Val Leu Val
    130                 135                 140

Gly Gly Val Ser Ala Ala Ala Val Arg Arg Val Ala Arg Trp Ala Asp
145                 150                 155                 160

Gly Trp Thr Ala Pro Gly Leu Glu Pro Glu Arg Ile Val Pro Val Ala
                165                 170                 175

Glu Arg Val Arg Arg Ala Trp Ser Glu Ala Gly Arg Ala Gly Ala Pro
            180                 185                 190

His Val Val Ala Leu Ala Arg Tyr Thr Leu Gly Glu Asp Val Ala Gln
        195                 200                 205

Glu Ser Ala Ala Phe Val Arg Asp Tyr Phe Ala Val Leu Gly Glu Glu
    210                 215                 220

Ala Glu Glu Phe Val Ala Lys Thr Pro Arg Thr Ala Gly Gln Leu Arg
225                 230                 235                 240

Ala Ala Val Ser Ala Leu Ala Asp Gly Gly Val Asp Glu Val Val Leu
                245                 250                 255

His Pro Thr Ala Ala Ala Leu Ser Gln Val Asp Arg Leu Ala Asp Ala
            260                 265                 270

Leu Leu

<210> SEQ ID NO 126
<211> LENGTH: 460
<212> TYPE: PRT
<213> ORGANISM: Streptomyces lavendulae

<400> SEQUENCE: 126

Met Pro Ala Ala Gly Lys Val Ala Val Ile Gly Leu Asp Ser Ala Thr
1               5                   10                  15

Pro Gln Tyr Met Phe Asp Arg Phe Ala Glu Asp Met Pro Val Phe Thr
            20                  25                  30

Ala Leu Arg Arg Lys Ser Leu Trp Gly Pro Met Arg Ser Ile Asp Pro
        35                  40                  45

Pro Ile Thr Met Pro Ala Trp Ser Cys Met Met Ser Gly Arg Ser Pro
    50                  55                  60

Gly Glu Leu Gly Val Tyr Gly Phe Arg Asp Arg Gly Ala Tyr Asp Tyr
65                  70                  75                  80

```
Gly Pro Leu Lys Phe Ala Thr Ser His Ser Ile Gln Ala Pro Arg Ile
                 85                  90                  95

Trp Asp Glu Met Thr Ala Ala Gly Arg Ser Ser Val Val Leu Gly Val
            100                 105                 110

Pro Gly Thr Tyr Pro Pro Ala Pro Ile Arg Gly Ala Met Val Ser Cys
        115                 120                 125

Phe Leu Ala Pro Ser Thr Gln Ser Arg Tyr Thr Ser Pro Pro Gly Leu
    130                 135                 140

Ala Asp Glu Leu Glu Lys Leu Thr Gly Gly Tyr Ala Leu Asp Val Glu
145                 150                 155                 160

Asp Phe Arg Ser Thr Asp Leu Glu Arg Val Ser Gln Arg Val Phe Asp
                165                 170                 175

Met Ser Glu Gln Arg Phe Glu Val Ala Arg His Leu Ala Thr Thr Gln
            180                 185                 190

Glu Trp Asp Phe Leu Ser Phe Val Asp Met Gly Pro Asp Arg Leu His
        195                 200                 205

His Gly Phe Trp Lys Tyr Cys Asp Pro Asp His Pro Arg His Glu Pro
    210                 215                 220

Gly Asn Ala Tyr Ala Gly Leu Phe Arg Asp Tyr Tyr Arg Ala Leu Asp
225                 230                 235                 240

Arg His Leu Gly Arg Phe Leu Glu Ser Leu Pro Glu Asn Thr Thr Val
                245                 250                 255

Leu Val Val Ser Asp His Gly Ala Gln Pro Met Val Gly Gly Leu Phe
            260                 265                 270

Val Asn Glu Trp Leu Arg Lys Glu Gly Tyr Leu Val Leu Thr Glu Glu
        275                 280                 285

Pro Ala Gly Pro Thr Pro Val Ala Gln Ala Ala Val Asp Trp Lys Arg
    290                 295                 300

Thr Thr Ala Trp Ala Glu Gly Gly Tyr Tyr Gly Arg Ile Phe Leu Asn
305                 310                 315                 320

Val Glu Gly Arg Glu Pro Gln Gly Thr Ile Pro Ala Ala Glu Tyr Glu
                325                 330                 335

Ser Thr Arg Asp Leu Ile Ala Ser Ala Leu Glu Ala Leu Pro Asp Asp
            340                 345                 350

Gln Gly Gln Pro Met Gly Thr Arg Ala Leu Arg Pro Gly Glu Leu Tyr
        355                 360                 365

Gly Glu Val Asn Gly Ile Ala Pro Asp Leu Leu Val Tyr Val Gly Asn
    370                 375                 380

Leu Arg Trp Arg Ala Leu Ala Thr Leu Gly Met Gly Lys Gly Leu Tyr
385                 390                 395                 400

Thr Thr Glu Asn Asp Thr Gly Pro Asp His Ala Asn His Gly Asp Thr
                405                 410                 415

Gly Ile Phe Ala Leu Ser Ala Pro Gly Ile Thr Pro Gly Arg Ala Asp
            420                 425                 430

Gly Leu Ser Leu Tyr Asp Val Ala Pro Thr Leu Arg Glu Leu Leu Gly
        435                 440                 445

Leu Ala Pro Gln Gly Ser Arg Gly Ser Leu Leu Gly
    450                 455                 460

<210> SEQ ID NO 127
<211> LENGTH: 511
<212> TYPE: PRT
<213> ORGANISM: Streptomyces lavendulae
```

-continued

```
<400> SEQUENCE: 127

Met Lys Ala Met Asp Arg Val Asp Arg Ala Val Glu Arg Phe Pro Met
  1               5                  10                  15

Tyr Ile Asp Gly Gln Ala Val Gln Ala His Asp Gly Ala Val Leu Arg
             20                  25                  30

Thr Phe Glu Pro Ala Thr Arg Arg His Leu Ala Asp Leu Pro Ser Gly
         35                  40                  45

Gly Ala Glu Asp Val Arg Arg Ala Val Ser Ala Ala Arg Arg Ala Phe
 50                  55                  60

Asp Glu Gly Pro Trp Pro Arg Met Ala Pro Gly Glu Arg Ala Gly Leu
 65                  70                  75                  80

Leu Arg Lys Ala Ala Gln Arg Leu Arg Glu Glu Ala Glu Pro Leu Ala
                 85                  90                  95

Glu Leu Glu Ala Arg Asp Asn Gly Ser Thr Leu Arg Lys Ala Leu Gly
            100                 105                 110

Ala Asp Val Pro Gly Ala Ala Ala Phe Glu Trp Ser Ala Trp Trp
            115                 120                 125

Ala Glu His Val Pro Glu Arg Gln Pro Glu Ala Pro Gly Ser Gly Ser
130                 135                 140

Tyr Val Val Trp Arg Pro Val Gly Val Val Ala Ala Ile Val Pro Trp
145                 150                 155                 160

Asn Leu Pro Leu Leu Leu Ala Ala Trp Arg Ile Ala Pro Ala Ile Ala
                165                 170                 175

Ala Gly Asn Thr Cys Val Ile Lys Pro Ala Ser Phe Ala Ser Leu Ser
            180                 185                 190

Thr Leu Arg Leu Val Glu Leu Leu His Glu Cys Gly Leu Pro Pro Gly
        195                 200                 205

Val Val Asn Val Val Thr Gly Pro Gly Gly Val Ala Gly Glu Gln Leu
210                 215                 220

Val Arg Ser Pro Gly Val Asp Leu Val Ala Phe Thr Gly Ser Asp Glu
225                 230                 235                 240

Thr Gly Ala Ala Val Arg Glu Gly Ala Ala Ala Gly Thr Ser Ala
                245                 250                 255

Arg Leu Asp Leu Gly Gly Lys Ser Pro Asn Ile Val Leu Ala Asp Ala
            260                 265                 270

Asp Leu Asp Arg Ala Val Thr Gly Val Thr Trp Gly Ala Phe Leu His
        275                 280                 285

Asn Gly Gln Val Cys Met Ala Gly Thr Arg Ala Val Val His Ala Asp
290                 295                 300

Val His Asp Asp Phe Leu Arg Leu Leu Ser Glu Arg Val Gly Arg Leu
305                 310                 315                 320

Arg Val Gly Asp Pro Leu Asp Pro Ala Thr Asp Leu Gly Pro Leu Val
                325                 330                 335

Ser Arg Asn Gln Ala Arg Thr Ala Arg Arg Phe Thr Glu Leu Gly Leu
            340                 345                 350

Ser Gln Gly Ala Glu Leu Val Cys Gly Gly Arg Ala Pro Ala Ala Asp
        355                 360                 365

Glu Leu Pro Pro Gly Leu Asp Ala Gly Ala Tyr Phe Leu Pro Thr Val
    370                 375                 380

Leu Ala Ser Val Gly Ala Asp Ala Val Ala Gln Glu Glu Ile Phe
385                 390                 395                 400

Gly Pro Val Leu Ala Val Val Arg Ala Gly Ser Asp Asp Asp Ala Val
                405                 410                 415
```

```
Arg Ile Ala Asn Gly Ser Arg Tyr Arg Leu Ser Ala Gly Val Trp Ser
            420                 425                 430

Ala Asp Pro Ala Arg Ala Arg Ala Val Ala Glu Arg Leu Arg Ala Asp
            435                 440                 445

Arg Val Trp Ile Asn Asp Tyr Arg Leu Val Asp Leu Glu Leu Pro Gly
            450                 455                 460

Thr Ala Gly Pro Arg Ser Ala Val Trp Asp Arg Leu Thr Asn Glu Leu
465                 470                 475                 480

Asp Ala Tyr Arg His Lys His Val Val His Gly Gly Ala Gly Ala
            485                 490                 495

Gly Gly Val Pro Ala Pro Pro Thr Pro Tyr Ala Leu Leu Gly Gly
            500                 505                 510

<210> SEQ ID NO 128
<211> LENGTH: 472
<212> TYPE: PRT
<213> ORGANISM: Streptomyces lavendulae

<400> SEQUENCE: 128

Met Lys Pro Ala Ser His Ser Val Thr Asp Thr Ser Ala Ala Leu Gly
1               5                   10                  15

Ala Ala Ala Ala Glu Glu Leu Ala Ala Gln Val Ala Gly Ser Val Leu
            20                  25                  30

Leu Pro Gly Asp Glu Gly Tyr Asp Glu Glu Arg Ser Gly Phe Glu Leu
            35                  40                  45

Ser Val Glu His Arg Pro Ala Leu Val Val Ala Thr Gly Ala Ala
            50                  55                  60

Asp Val Ile Ala Ala Val Arg Phe Ala Arg Ala Arg Gly Leu Gly Ile
65                  70                  75                  80

Ala Val Gln Ala Thr Gly His Gly Lys Ser Ala Ala Thr Asp Val
            85                  90                  95

Leu Ile Ser Thr Arg Arg Met Thr Gly Val Arg Val Asp Pro Arg Ala
            100                 105                 110

Arg Thr Ala Arg Ile Glu Ala Gly Val Arg Trp Glu Gln Val Ile His
            115                 120                 125

Glu Ala Ala Ala His Gly Leu Ala Pro Leu Ser Gly Ser Ala Pro Phe
            130                 135                 140

Val Gly Ala Val Ser Tyr Leu Leu Gly Gly Leu Gly Leu Leu Ser
145                 150                 155                 160

Arg Lys Tyr Gly Phe Ala Gly Asp His Val Val Ser Leu Asp Leu Val
            165                 170                 175

Thr Ala Asp Gly Arg Phe Leu Gln Val Ser Ala Glu Glu His Pro Asp
            180                 185                 190

Leu Phe Trp Gly Val Arg Gly Ser Arg Gly Asn Leu Gly Ile Val Thr
            195                 200                 205

Ser Val Glu Val Gly Leu Phe Pro Val Thr Gln Val Tyr Gly Gly Gly
            210                 215                 220

Leu Phe Phe Asp Ala Gly Ser Thr Arg Ala Val Leu Asn Thr Tyr Leu
225                 230                 235                 240

Gln Trp Ala Pro Arg Met Pro Glu Asp Met Ala Ser Ser Val Phe Leu
            245                 250                 255

Ala Ala Tyr Pro Asp Ala Glu Gly Val Pro Gly Pro Leu Arg Gly Arg
            260                 265                 270

Phe Val Thr His Ile Arg Leu Ala Trp Leu Gly Asp Pro Glu Glu Gly
```

-continued

```
                275                 280                 285
Glu Arg Arg Phe Ala Glu Leu Arg Ala Gly Thr Val Met Asp
            290                 295                 300

Thr Val Asp Thr Leu Pro Tyr Thr Arg Ala Gly Ile Ile His Asn Asp
305                 310                 315                 320

Pro Pro Ala Pro Val Ser Ser His Ser Lys Thr Val Met Phe Gly Gln
                325                 330                 335

Leu Asp Glu Ile Ala Val Asp Glu Ile Leu Arg Leu Ala Gly Pro Gly
                340                 345                 350

Thr Asp Ala Leu Phe Gly Val Glu Leu Arg His Leu Gly Gly Ala Leu
                355                 360                 365

Ala Arg Pro Pro Arg His Pro Ser Ala Val Gly His Phe Pro Glu Ala
370                 375                 380

Val Phe Asn Ala Tyr Val Gly Ser Leu Val Asp Pro Asp Thr Leu Ala
385                 390                 395                 400

Ala Val Asp Ala Ala Gln Gln Glu Phe Val Asp Ser Met Arg Pro Trp
                405                 410                 415

Thr Thr Pro Gly Val Cys Leu Asn Phe Leu Ala Gly His Asn Thr Ser
                420                 425                 430

Arg Glu Thr Thr Arg Ser Ala Tyr Thr Pro Glu Asp Tyr Ala Arg Leu
                435                 440                 445

Gln Ala Leu Lys Ser Gln Tyr Asp Pro Gly Asn Val Phe Arg Phe Asn
450                 455                 460

Pro Asn Ile Pro Pro Leu Pro Ala
465                 470
```

<210> SEQ ID NO 129
<211> LENGTH: 395
<212> TYPE: PRT
<213> ORGANISM: Streptomyces lavendulae

<400> SEQUENCE: 129

```
Met Thr Ser Ala Ala Pro Pro Phe Pro Phe Pro Pro Gly Pro Gly
1               5                   10                  15

Gly Thr Val Pro Pro Glu Tyr Ala Arg Leu Leu Thr Asp Asp Pro Val
                20                  25                  30

Ala Glu Val Arg Leu Ala Asp Gly Ser Arg Ile Trp Leu Val Thr Arg
            35                  40                  45

His Glu Asp Val Arg Thr Val Leu Thr Asp Gly Arg Phe Ser Arg His
        50                  55                  60

Arg Ala Ala Met Leu Pro Gly Ser Gly Phe Gly Arg Ser Gln Gly Ser
65                  70                  75                  80

Gly Ile Val Asp Leu Asp Pro Glu His Gly Arg Leu Arg Gly Pro
                85                  90                  95

Val Val Ala Ala Phe Gly Ala Ser Arg Thr Ala Arg Phe Ala Pro Arg
            100                 105                 110

Ile Glu Ala Ala Glu Ala Ala Leu Asp Arg Leu Pro Ala Gly Ser
        115                 120                 125

Gly Thr Val Asp Leu Val Ala Ala Tyr Thr Ala Pro Phe Ala Gly Arg
    130                 135                 140

Val Thr Ala Glu Phe Leu Gly Leu Pro Gly Asp Arg Trp Gln Asp Val
145                 150                 155                 160

Thr Ser Asp Val Glu Leu Leu Leu Leu Pro Arg Gly Ala Thr Glu Gln
                165                 170                 175
```

```
Ala Leu Lys Glu Ala Arg Gly Arg Leu Gly Gln Val Leu Asp Glu Leu
            180                 185                 190

Leu Ala Ala Arg Arg Ala Glu Pro Gly Asp Ser Val Thr Asp Thr Leu
            195                 200                 205

Leu Asp Ala Glu Glu Leu Thr Asp Asp Arg Arg Leu Leu Leu His
210                 215                 220

Gly Leu Ile Ile Ser Gly Phe Ile Thr Ile Arg Asp Leu Leu Ala Arg
225                 230                 235                 240

His Leu Phe Gly Val Leu Ser Ser Pro Gly Leu Ala Ala Arg Leu Arg
            245                 250                 255

Glu Asp Pro Ser Val Leu Pro Ser Ala Val Gln Glu Leu Leu Arg Tyr
            260                 265                 270

Tyr Pro Ser Ser Asn Asp Gly Leu Leu Arg Val Ala Thr Glu Asp Val
            275                 280                 285

Val Leu Ser Gly Arg Arg Val Ala Ala Gly Asp Ala Val Leu Pro Leu
            290                 295                 300

Val Ser Ala Ala Ser Arg Asp Pro Glu Val Phe Ala Asp Pro His Val
305                 310                 315                 320

Leu Asp Ile Glu Arg Val Ala Asp Arg Gly Ile Ala Phe Gly Ala Gly
            325                 330                 335

Gln His Ala Cys Pro Ala Thr Gly Leu Ala Val Thr Glu Leu Thr Val
            340                 345                 350

Gly Ile Gly Arg Leu Leu Ala Ala Phe Pro Arg Ile Ala Leu Ala Val
            355                 360                 365

Pro Pro Glu Glu Val Glu His Ser Ser Glu Leu Leu Pro Leu Gly Val
            370                 375                 380

Arg Ser Leu Pro Val Val Pro Gly Pro Arg Asn
385                 390                 395

<210> SEQ ID NO 130
<211> LENGTH: 474
<212> TYPE: PRT
<213> ORGANISM: Streptomyces lavendulae

<400> SEQUENCE: 130

Met Leu Pro Glu Phe Gln Leu Gln Trp Asn Trp Leu Asp Ala Pro Ala
1               5                   10                  15

Gly Gly Gly Gly Glu Leu Gln Ala Thr Trp Ala Arg Leu Arg Ile Ala
            20                  25                  30

Val Gly Ala Glu Thr Val Thr Leu Val Gln Glu Pro Gly Gln Gly Thr
            35                  40                  45

Phe Arg Glu His Thr Thr Gly Ser Leu Tyr Pro Leu Ala Glu Trp Ile
        50                  55                  60

Ala Phe Asn Trp Trp Ser Leu Val Ala Asp Ala Arg Pro Gly Thr Gln
65                  70                  75                  80

Ile Ser Gln Leu Arg Phe Ala Tyr Arg His Gly Val Gly Asp Asn Arg
                85                  90                  95

Gly Ser Trp Trp Met Arg Ser Arg His Ile Leu Arg Ala Ala Cys
            100                 105                 110

Asp Gly Phe Arg Trp Pro Asp Met Leu Phe Val Pro Glu Gly Arg Glu
            115                 120                 125

Thr Arg Ile Val Trp Met Pro Asp Met Gly Pro Asp Val Arg Pro Gly
        130                 135                 140

Asn Arg Phe Ala Ser Arg Gly Asn Ser Cys Val Glu Ser Ala Ala Phe
145                 150                 155                 160
```

```
Thr Ala Thr Leu Ala Ser Phe Val Asp Ala Val Thr Glu Arg Leu Thr
                165                 170                 175
Asp Gln Gly Ile Thr Gly Thr Pro Leu Gln Glu Glu Trp Ala Ala Val
            180                 185                 190
Arg Ala Thr Asp Glu Asp Glu Ala Ala Phe Cys Arg Ile Ala Ala Arg
        195                 200                 205
Leu Gly Leu Asp Pro Tyr Ala Glu Ala Glu Pro Tyr Glu Ala Asp Ile
    210                 215                 220
Leu Lys Ala Ala Glu Gln Leu Ala Glu Pro Leu Ala Ser Asp Phe Phe
225                 230                 235                 240
Asn Gly Val Arg Pro Glu Arg Ile Ala Asp Gln Leu Gln Trp Ile Ala
                245                 250                 255
Arg Val Arg Thr Leu Met Gly Thr Ala Pro Ala Asp Thr Pro Leu Pro
            260                 265                 270
Pro Ala Leu Val Glu Leu Arg Lys Asp Cys Ala Asp Leu Ser Glu Lys
        275                 280                 285
Phe Phe Ala Pro Gly Arg Leu Asp Asn Pro Trp Asp Leu Gly Tyr Glu
    290                 295                 300
Val Ala His Arg Val Arg Ala Trp Ala Gly Leu Asp Asp Thr Ala Pro
305                 310                 315                 320
Phe Asp Pro Ala Pro Leu Met Gly Tyr Arg Thr Glu Gln Val Pro Tyr
                325                 330                 335
Met Asp Arg Gly Leu Val Ala Leu Gly Thr Arg Gly Ala Asp Gly
            340                 345                 350
Pro Val Leu Val Ser Ser Arg Arg Phe Thr Asp Arg Pro Arg Phe
        355                 360                 365
Leu Gln Ala Arg Ala Leu Trp His Leu Ile Cys Asp Pro Asp Asp Thr
    370                 375                 380
Phe Leu Ile Ala Ala His Thr His Arg Gln His Val Ala Arg Gly
385                 390                 395                 400
Phe Ala Leu Glu Val Leu Ala Pro Ala Lys Gly Val Ala Thr Leu Leu
                405                 410                 415
Ala Asp Pro Gly His Leu Val Ser Ala Glu Asp Val Glu Val Ile Ala
            420                 425                 430
Asp Asp Tyr Gly Cys Gly Asn Ile Val Val Glu His Gln Leu Asp Asn
        435                 440                 445
Arg Val Leu Ala Lys Asp Phe Thr Trp Pro Gly His Ala Arg Ala Gly
    450                 455                 460
Ala Pro Ala Gly Glu Arg Ser Arg Gly Ala
465                 470

<210> SEQ ID NO 131
<211> LENGTH: 443
<212> TYPE: PRT
<213> ORGANISM: Streptomyces lavendulae

<400> SEQUENCE: 131

Met Thr Ile Arg Gln Arg Val Val Val Ile Thr Glu Gly Ala Ala
1               5                   10                  15
Pro Glu Leu Leu Asp Arg Trp Cys Ala Gln Gly Leu Leu Pro Gly Phe
                20                  25                  30
Ala Ala Leu Arg Ser Gln Gly Ala Ser Gly Pro Leu His Ala Glu Gly
            35                  40                  45
Thr Pro Tyr Glu Pro Pro Gly Leu Leu Ser Val Leu Thr Gly Arg Arg
```

```
                50                    55                    60
Ala Ala Asp His Gly Phe Tyr Ser Tyr Trp Thr Cys His Asp Pro Glu
 65                      70                  75                  80

Tyr Ala Pro Gln Val Leu Thr Pro Glu His Arg Arg His Pro Leu Leu
                     85                  90                  95

Trp Gln His Glu Val Phe Gln Gly Val Arg Phe Ala Ser Ile Gly Leu
                    100                 105                 110

Phe Gly Thr His Pro Pro Glu Pro Phe Asp Gly Ser Leu Ile Thr Tyr
                    115                 120                 125

Pro Met Tyr Ala Thr Leu His Ala Cys His Pro Arg Ser Leu Gln Arg
                130                 135                 140

Thr Leu Ala Lys Lys Gly Ile Arg Pro Val His Asp Val Ser Ile Phe
145                 150                 155                 160

Trp Thr Gly Gln Asp Arg Asp Glu Leu Leu Pro Ser Leu Leu Glu Ala
                    165                 170                 175

Asp Val Gln Arg Gly Arg Ala Ala Leu Ala Leu Leu Glu Glu Ser Asp
                    180                 185                 190

Val Val Ile Val Asn Leu Thr Ser Ile Asp Arg Cys Ser His Ile Tyr
                    195                 200                 205

Trp Gln Glu Leu Glu His Gly Pro Glu His Glu Arg Glu Ser Ala Val
                    210                 215                 220

Phe Ala Ala Tyr Arg Thr Cys Asp Gln Val Ile Gln Asp Ala Leu Arg
225                 230                 235                 240

Ala Ala Asp Asp Arg Thr Ser Val Val Ala Phe Ser Glu Ile Gly Phe
                    245                 250                 255

Gly Pro Leu Arg Asn Tyr Cys Ser Ile Asn Asp Glu Met Glu Gln Ala
                    260                 265                 270

Gly Phe Leu Ala Thr Ala Glu Asp Gly Arg Val Glu Trp Ala Gly Ser
                    275                 280                 285

Ala Ala Phe Glu Ala Val Gln Gly Thr His Gly Val Asn Ile Asn Leu
                    290                 295                 300

Arg Asp Arg Tyr Lys His Gly Leu Val Pro Glu Arg Asp Tyr Glu Lys
305                 310                 315                 320

Val Arg Thr Asp Val Ala Ala Leu Leu Glu Arg Arg Asn Pro Arg
                    325                 330                 335

Thr Gly Arg Leu Phe Phe Asp Ala Val Arg Arg Glu Glu Val Tyr
                    340                 345                 350

Pro Gly Glu Ala Thr Gln His Ala Pro Asp Leu Ile Leu Glu Pro Ala
                    355                 360                 365

Asp Trp Arg Tyr Leu Pro Leu Gly Asp Pro His Trp Ala Ser His Val
                    370                 375                 380

His Arg Asp Trp Gln Ser Gly Trp His Arg Arg Glu Ser Tyr Trp Ser
385                 390                 395                 400

Ala Val Gly Pro Gly Phe Thr Gly Gly Ala Arg Gln Thr Arg Thr Ala
                    405                 410                 415

Ala Pro Val Asp Ile Pro Ala Thr Val Cys Ala Leu Leu Gly Arg Asp
                    420                 425                 430

Val Pro Asn Asp Trp Asp Gly Val Pro Leu Ser
                    435                 440

<210> SEQ ID NO 132
<211> LENGTH: 123
<212> TYPE: PRT
<213> ORGANISM: Streptomyces lavendulae
```

```
<400> SEQUENCE: 132

Met Thr Pro Glu Glu Leu Ser Asp Phe Ala Leu Glu Leu Pro Glu Ala
 1               5                  10                  15
Val Asp Asp Glu Ala Phe Gly Pro Gly Ala Ala Val Phe Lys Val Glu
                20                  25                  30
Lys Lys Val Phe Ala Ile Leu Gln Asp Ala Ser Glu Asp Arg Pro Pro
            35                  40                  45
Gln Val Thr Leu Lys Cys Glu Pro Asp Leu Ala Leu His Leu Arg Glu
        50                  55                  60
Gln Tyr Ala Ala Val Pro Gly Tyr His Val Asn Lys Arg His Trp
 65                 70                  75                  80
Asn Thr Val Val Leu Asn Gly Thr Val Pro Val Glu Glu Leu Arg Glu
                85                  90                  95
Met Val Glu His Ser Tyr Asp Arg Val Val Ala Gly Leu Pro Lys Ala
                100                 105                 110
Val Arg Glu Arg Leu Arg Leu Leu Arg Thr Val
            115                 120

<210> SEQ ID NO 133
<211> LENGTH: 351
<212> TYPE: PRT
<213> ORGANISM: Streptomyces lavendulae

<400> SEQUENCE: 133

Met Thr Val Glu Gln Thr Pro Glu Asn Pro Gly Thr Ala Ala Arg Ala
 1               5                  10                  15
Ala Ala Glu Glu Thr Val Asn Asp Ile Leu Gln Gly Ala Trp Lys Ala
                20                  25                  30
Arg Ala Ile His Val Ala Val Glu Leu Gly Val Pro Glu Leu Leu Gln
            35                  40                  45
Glu Gly Pro Arg Thr Ala Thr Ala Leu Ala Glu Ala Thr Gly Ala His
        50                  55                  60
Glu Gln Thr Leu Arg Arg Leu Leu Arg Leu Leu Ala Thr Val Gly Val
 65                 70                  75                  80
Phe Asp Asp Leu Gly His Asp Asp Leu Phe Ala Gln Asn Ala Leu Ser
                85                  90                  95
Ala Val Leu Leu Pro Asp Pro Ala Ser Pro Val Ala Thr Asp Ala Arg
                100                 105                 110
Phe Gln Ala Ala Pro Trp His Trp Arg Ala Trp Glu Gln Leu Thr His
            115                 120                 125
Ser Val Arg Thr Gly Glu Ala Ser Phe Pro Ser Thr Trp Pro Thr Ala
        130                 135                 140
Pro Arg Ser Gly Ser Ser Pro Thr Arg Asp Pro Lys Ala Arg Glu Leu
145                 150                 155                 160
Phe Asn Arg Ala Met Gly Ser Val Ser Leu Thr Glu Ala Gly Gln Val
                165                 170                 175
Ala Ala Ala Tyr Asp Phe Ser Gly Ala Ala Thr Ala Val Asp Ile Gly
                180                 185                 190
Gly Gly Arg Gly Ser Leu Met Ala Ala Val Leu Asp Ala Phe Pro Gly
            195                 200                 205
Leu Arg Gly Thr Leu Leu Glu Arg Pro Pro Val Ala Glu Glu Ala Arg
        210                 215                 220
Glu Leu Leu Thr Gly Arg Gly Leu Ala Asp Arg Cys Glu Ile Leu Pro
225                 230                 235                 240
```

Gly Asp Phe Phe Glu Thr Ile Pro Asp Gly Ala Asp Val Tyr Leu Ile
                245                 250                 255

Lys His Val Leu His Asp Trp Asp Asp Asp Val Val Arg Ile Leu
            260                 265                 270

Arg Arg Ile Ala Thr Ala Met Lys Pro Asp Ser Arg Leu Leu Val Ile
            275                 280                 285

Asp Asn Leu Ile Asp Glu Arg Pro Ala Ala Ser Thr Leu Phe Val Asp
        290                 295                 300

Leu Leu Leu Leu Val Leu Val Gly Gly Ala Glu Arg Ser Glu Ser Glu
305                 310                 315                 320

Phe Ala Ala Leu Leu Glu Lys Ser Gly Leu Arg Val Glu Arg Ser Leu
                325                 330                 335

Pro Cys Gly Ala Gly Pro Val Arg Ile Val Glu Ile Arg Arg Ala
                340                 345                 350

<210> SEQ ID NO 134
<211> LENGTH: 546
<212> TYPE: PRT
<213> ORGANISM: Streptomyces lavendulae

<400> SEQUENCE: 134

Met Thr Val Leu Gly Leu Gly Gly Ser Gly His Asp Trp Ala Ser Cys
1               5                   10                  15

Ala Thr Asp Gly Arg Arg Leu Val Ala Ile Asp Glu Glu Arg Leu Val
            20                  25                  30

Arg Ser Lys Tyr Gly Leu Gly Ala Asp Leu Leu Ala Gly His Ser Arg
        35                  40                  45

Arg Ala Val Leu Asp Ala Leu Gly Thr Ser Ala Glu Ala Val Glu His
    50                  55                  60

Val Val Ala Cys Glu Leu Val Pro Arg Pro Phe Tyr His Ser Phe Arg
65                  70                  75                  80

Arg Arg Val Thr Val Val Asn His His Leu Ala His Ala Tyr Ser Ala
                85                  90                  95

Phe Gly Ala Ser Gly Met Thr Arg Ala Ala Val Leu Val Cys Asp Asn
                100                 105                 110

Ser Gly Ser Leu Val Thr Gly Leu Lys Ser Gly Pro Gly Pro Arg Glu
            115                 120                 125

Ala Glu Thr Ile Ser Cys Tyr Thr Ala Asp Ala Ser Gly Leu Arg Leu
        130                 135                 140

Val Asn Arg Val Ala Gly Thr His Ala Val Asp Ala Ser Ser Glu Ser
145                 150                 155                 160

Ala Tyr Tyr Gln Pro Gly Glu Thr Asp Asn Ser Leu Gly His Phe Tyr
                165                 170                 175

Arg Ser Ala Ser Leu Ala Leu Gly Leu Ala Tyr Ser Gly Pro Lys Thr
            180                 185                 190

Arg Tyr Pro Val Ser Glu Asp Gly Lys Thr Met Gly Leu Ala Pro Tyr
        195                 200                 205

Gly Asp Asp Arg Phe Val Asp Glu Val Ala Glu Leu Val Thr Leu Leu
    210                 215                 220

Pro Glu Gly Gly Val Gln Ile Ser Ala Ser Lys Val Asn His Leu Phe
225                 230                 235                 240

Glu Arg Leu Val Glu Ser Gly Glu Phe Glu Asp Arg Ala Ala Leu Ala
                245                 250                 255

Tyr Ala Ala Gln Glu Thr Leu Glu Arg Ala Leu Leu His Cys Ala Arg

```
                    260                 265                 270
Asp Leu His Arg Arg Thr Gly Leu Thr Asp Leu Cys Ile Ala Gly Gly
                275                 280                 285

Val Gly Leu Asn Ser Val Ala Asn Gly Arg Ile Leu Arg Glu Thr Pro
            290                 295                 300

Phe Glu Arg Val Phe Val Val Pro Ala Ala Gly Asp Asn Gly Ile Ser
305                 310                 315                 320

Leu Gly Cys Ala Tyr Tyr Gly Leu His Glu Leu Glu Gly Arg Ala Pro
                325                 330                 335

Ser Glu Leu Pro Ala Leu Asp Thr Ala Tyr Leu Gly Pro Asp Tyr Pro
            340                 345                 350

Ala Glu Arg Val Asp Ala Ala Leu Ala Gly Ser Gly Phe Thr Val Glu
                355                 360                 365

Thr Pro Asp Asp Leu Pro Gly Arg Val Ala Gly Leu Leu Ala Glu Gly
            370                 375                 380

Lys Ile Ile Gly Trp Phe Asp Gly Arg Ser Glu Phe Gly Pro Arg Ala
385                 390                 395                 400

Leu Gly His Arg Ser Ile Leu Ala Ala Pro Phe Pro Ala Ser Val Arg
                405                 410                 415

Asp His Leu Asn Asp Asn Val Lys His Arg Glu Trp Phe Arg Pro Tyr
            420                 425                 430

Ala Pro Ile Val Arg Glu Asp Arg Ala Ala Asp Tyr Phe Asp Leu Val
                435                 440                 445

Gln Pro Ser Pro Phe Met Leu Val Ala Arg Val Thr Arg Gln Asp
            450                 455                 460

Ala Ile Pro Ala Ala Thr His Val Asp Gly Thr Ala Arg Leu Gln Thr
465                 470                 475                 480

Leu Asn Ala Ala Gln Asn Pro Lys Val Tyr Glu Leu Leu Gly Arg Phe
                485                 490                 495

Glu Ala Leu Thr Gly Cys Ala Val Leu Leu Asn Thr Ser Phe Asn Val
            500                 505                 510

Ala Gly Gln Pro Ile Val Glu Thr Pro Glu Asp Ala Val Glu Ala Phe
                515                 520                 525

Ala Gly Met Arg Leu Asp His Leu Val Val Gly Asp Arg Leu Ala Thr
            530                 535                 540

Lys Pro
545

<210> SEQ ID NO 135
<211> LENGTH: 568
<212> TYPE: PRT
<213> ORGANISM: Streptomyces lavendulae

<400> SEQUENCE: 135

Met Asp Val Pro Val Leu Val Gly Gly Pro Thr Gly Leu Ala
1               5                   10                  15

Met Ala Leu Phe Leu Ala Arg His Gly Val Gly Cys Leu Leu Val Glu
                20                  25                  30

Arg Arg Thr Thr Thr Ser Pro Val Pro Arg Ala Thr His Val Ser Arg
            35                  40                  45

Arg Ser Met Glu Leu Phe Arg Glu Ala Gly Leu Glu Glu Ile Arg
        50                  55                  60

Arg Ala Gly Phe Glu Val Val Arg Glu Asp Asp Pro Arg Leu Arg Thr
65                  70                  75                  80
```

```
Arg Pro Glu Arg His Leu Pro Arg Val Val Gln Ala Ala Ser Leu
            85                  90                  95

Ala Gly Pro Gly Pro Val Gly Val Leu Glu Thr Gly Asp Glu Glu Leu
            100                 105                 110

Ala Val Pro Gly Pro Cys Ala Pro Phe Trp Cys Gly Gln Asp Arg Met
            115                 120                 125

Glu Pro Leu Leu Ala Lys Ala Ala Arg His Gly Ala Asp Val Arg
130                 135                 140

Phe Gly His Glu Leu Thr Gly Leu Trp Pro Gly Glu Asp Ser Thr Arg
145                 150                 155                 160

Ala Arg Val Arg Ala Ala Gly Thr Gly Arg Thr Tyr Thr Val Asp Ala
            165                 170                 175

Arg Phe Val Ile Ala Ala Asp Gly Ala Arg Gly Glu Ile Ala Glu Arg
            180                 185                 190

Val Gly Ile Ala Arg Glu Gly Leu Gly Thr Val Ala His Arg Val Ser
            195                 200                 205

Ile Leu Phe Arg Ala Asp Pro Gly Arg Trp Ala Arg Asp Arg Arg Phe
            210                 215                 220

Phe Met Cys Met Ile Gln Asn Pro Gly Phe Asp Gly Ala Val Met Glu
225                 230                 235                 240

Leu Asn Thr Pro Gly Arg Trp Cys Ala Ala Val Asp Tyr Asp Pro Ala
            245                 250                 255

Arg Ala Glu Pro Asp Gly Thr Tyr Ser Ala Arg Thr Cys Leu Asp Leu
            260                 265                 270

Val Arg Ala Ala Val Gly Asp Asp Arg Ser Asp Ala Ala Val Asp Thr
            275                 280                 285

Val Phe His Trp Lys Ala Arg His Arg Ile Ala Ala Ala Tyr Arg Ser
            290                 295                 300

Gly Ala Val Phe Leu Ile Gly Asp Ala Ala His Leu His Pro Pro Ser
305                 310                 315                 320

Gly Gly Tyr Gly Ser Asn Val Gly Phe Gln Asp Ala His Asn Leu Ala
            325                 330                 335

Trp Lys Ile Ala Ala Val Leu Gly Gly Trp Ala Gly Pro Arg Leu Leu
            340                 345                 350

Asp Thr Tyr Asp Glu Glu Arg Arg Pro Val Gly Lys Ala Thr Ala Glu
            355                 360                 365

Gln Ser Met Leu Leu Asp Gly Val Pro Pro Glu Pro Leu Gly Gly Ser
            370                 375                 380

Val Val Arg Cys Asp Pro Arg Thr Leu Ile Met Gly Tyr Arg Tyr His
385                 390                 395                 400

Ser Ala Ala Val Leu Gly Pro Pro His Gly Pro Ala Phe Pro Ala Ala
            405                 410                 415

Phe Thr Leu Arg Gly Asp Pro Gly Thr Arg Leu Pro His Val Trp Leu
            420                 425                 430

Arg Thr Asp Ala Gly Glu Arg Val Ser Thr Leu Asp Leu Cys His Gly
            435                 440                 445

His Phe Val Leu Leu Ser Ala Asp Pro Val Trp Ala Ala Ala Ala Ala
450                 455                 460

Arg Ser Ala Lys Glu Thr Gly Val Pro Leu Arg Gly His His Leu Ala
465                 470                 475                 480

Ala Thr Gly Ser Glu Leu Ala Asp Pro Ser Gly Glu Phe Pro Arg Ser
            485                 490                 495

Cys Gly Thr Gly Pro Ala Gly Ala Val Leu Val Arg Pro Asp Gly Met
```

-continued

```
                    500                 505                 510
Val Ala Trp Arg Thr Ala Arg Ala Val Pro Pro Asp Pro Asp Ser Ala
                515                 520                 525

Gln Asp Leu Val Thr Ala Ala Val Arg Arg Val Leu Ala Leu Pro Glu
    530                 535                 540

Arg Ala Ala Pro Pro Val Leu Gly Pro Pro Arg Leu Ser Arg Gly Ser
545                 550                 555                 560

Tyr Arg Arg Val Gly Ser Asp Gly
                565

<210> SEQ ID NO 136
<211> LENGTH: 160
<212> TYPE: PRT
<213> ORGANISM: Streptomyces lavendulae

<400> SEQUENCE: 136

Met Lys Pro His Ser Phe Cys Thr Cys Trp Pro Gly Ala Thr Val Trp
1               5                   10                  15

Leu Thr Gly Pro Pro Gly Ala Gly Lys Thr Thr Ile Ala Arg Ala Leu
            20                  25                  30

Ala Glu Arg Leu Arg Glu Arg Gly Arg Val Glu Val Leu Asp Gly
        35                  40                  45

Asp Ala Thr Arg Ala Leu Leu Thr Ala Gly Ser Ser Trp Glu Asp Arg
    50                  55                  60

Gly Thr Gly Leu Gln Arg Val Gly Leu Met Ala Glu Val Leu Ala Arg
65                  70                  75                  80

Asn Gly Ile Val Val Leu Val Pro Val Thr Ala Ala Arg Ala Asp Ser
                85                  90                  95

Arg Glu Ala Val Arg Arg His Glu Arg Ser Gly Thr Ala His Leu
            100                 105                 110

Glu Val Arg Val Arg Asp Ala Val Pro Pro Ser Gly Leu Pro Ala
        115                 120                 125

Pro Pro Gly Pro Asp Leu Arg Ile Ala Ala His Glu Gln Ser Ala Glu
    130                 135                 140

Glu Ser Ala Arg Ala Leu His Arg Leu Leu Ala Glu Arg Glu Leu Ala
145                 150                 155                 160

<210> SEQ ID NO 137
<211> LENGTH: 319
<212> TYPE: PRT
<213> ORGANISM: Streptomyces lavendulae

<400> SEQUENCE: 137

Met Asn Pro Gly Arg Gly Gly Ala Tyr Ala Ala Gly Arg Asp Gly Thr
1               5                   10                  15

Arg Gly Thr Arg Arg Pro His Gly Leu Ser His Leu Asp Leu Leu Glu
            20                  25                  30

Ser Glu Ser Val His Ile Phe Arg Glu Val Ala Gly Glu Phe Glu Arg
        35                  40                  45

Pro Val Ile Leu Phe Ser Gly Lys Asp Ser Ile Val Met Leu His
    50                  55                  60

Leu Ala Leu Lys Ser Phe Ala Pro Ala Pro Val Pro Phe Ala Leu Leu
65                  70                  75                  80

His Val Asp Thr Gly His Asn Phe Pro Glu Val Ile Ala Tyr Arg Asp
                85                  90                  95

Arg Val Val Ala Ala Leu Gly Leu Arg Leu Glu Val Ala Ser Val Gln
```

```
                    100                 105                 110
Asp Phe Ile Asp Asn Gly Thr Leu Arg Glu Arg Pro Asp Gly Thr Arg
            115                 120                 125

Asn Pro Leu Gln Thr Val Pro Leu Leu Asp Ala Ile Gly Arg His Arg
    130                 135                 140

Phe Asp Ala Val Phe Gly Gly Arg Arg Asp Glu Glu Lys Ala Arg
145                 150                 155                 160

Ala Lys Glu Arg Val Phe Ser Leu Arg Asp Glu Phe Gly Gly Trp Asp
                165                 170                 175

Pro Arg Arg Gln Arg Pro Glu Leu Trp Arg Leu Tyr Asn Gly Arg His
            180                 185                 190

Ala Pro Gly Glu His Val Arg Val Phe Pro Leu Ser Asn Trp Thr Glu
        195                 200                 205

Leu Asp Val Trp Gln Tyr Val Ala Arg Glu Glu Ile Glu Leu Pro Thr
    210                 215                 220

Ile Tyr Tyr Ala His Glu Arg Glu Val Phe Arg Arg Gly Gly Met Trp
225                 230                 235                 240

Leu Ala Pro Gly Glu Trp Gly Gly Pro Arg Glu Gly Glu Ala Val Glu
                245                 250                 255

Lys Arg Arg Val Arg Tyr Arg Thr Val Gly Asp Met Ser Cys Thr Gly
            260                 265                 270

Ala Val Asp Ser Ala Ala Ala Thr Val Ala Asp Val Val Ala Glu Ile
        275                 280                 285

Ala Thr Ser Arg Leu Thr Glu Arg Gly Ala Thr Arg Ala Asp Asp Lys
    290                 295                 300

Leu Ser Glu Ala Ala Met Glu Asp Arg Lys Arg Glu Gly Tyr Phe
305                 310                 315

<210> SEQ ID NO 138
<211> LENGTH: 163
<212> TYPE: PRT
<213> ORGANISM: Streptomyces lavendulae

<400> SEQUENCE: 138

Met Gly Gln Asp Ser Arg Pro Arg Trp Leu Thr Asp Glu Glu Gln Arg
1               5                   10                  15

Val Trp Arg Gly Tyr Leu Arg Ala Thr Arg Leu Val Glu Asp His Leu
            20                  25                  30

Asp Arg Arg Leu Gln Arg Glu Ala Asp Met Pro His Leu Tyr Tyr Gly
        35                  40                  45

Leu Leu Val Gln Leu Ser Glu Ala Pro Arg Arg Gly Ile Arg Met Thr
    50                  55                  60

Asp Leu Ala Arg Asn Ala Lys Ile Thr Arg Pro Arg Leu Ser His Ala
65                  70                  75                  80

Ile Thr Arg Leu Glu Lys Leu Gly Trp Val Arg Arg Glu Ser Cys His
                85                  90                  95

Gly Asp Arg Arg Gly Gln Asn Ala Val Leu Thr Glu Glu Gly Arg Glu
            100                 105                 110

Val Leu Glu Lys Ser Ala Pro Gly His Val Ala Ala Val Arg Ala Ala
        115                 120                 125

Val Phe Asp Ser Leu Thr Pro Glu Gln Val Gly Gln Leu Gly Arg Ile
    130                 135                 140

Cys Gln Ala Ile Glu Lys Gly Leu Asp Arg Glu Gly Ala Asp Leu Pro
145                 150                 155                 160
```

Trp Leu Arg

<210> SEQ ID NO 139
<211> LENGTH: 413
<212> TYPE: PRT
<213> ORGANISM: Streptomyces lavendulae

<400> SEQUENCE: 139

```
Met Glu Arg His Asp Gly Ala Pro Gly Trp Gly Phe Thr His Thr Gln
  1               5                  10                  15

Tyr Ser Ala Asp His Gly Glu Arg Gly Ala Thr Arg Arg Ala Gly Ala
             20                  25                  30

Leu Leu Ser Ala Arg Pro Leu Pro Gln Asn Gln His Ile Met Gly Trp
         35                  40                  45

Gly Ala Glu Asn Pro Glu Pro Ala Pro Gly Arg Tyr Asp Phe Glu Val
     50                  55                  60

Leu Asp Glu Arg Val Ala Leu Met Arg Ala Thr Gly Ala Thr Pro Val
 65                  70                  75                  80

Leu Thr Leu Cys Ala Ala Pro Asp Trp Met Lys Gly Arg Gly Arg Pro Gly
                 85                  90                  95

Arg Thr Asp Trp Ser Arg Leu Glu Thr Ala Pro Asp Pro Arg His Tyr
                100                 105                 110

Ala Asp Phe Ala Arg Leu Ala Gly Val Ile Ala Gln Arg Tyr Pro Asp
            115                 120                 125

Ile Arg His Phe Leu Val Trp Asn Glu Leu Lys Gly Phe Tyr Asp Glu
        130                 135                 140

Asp Arg Arg Arg Trp Asp Tyr Glu Gly Tyr Thr Arg Leu Tyr Asn Leu
145                 150                 155                 160

Val His Ala Glu Leu Lys Arg Arg Asn Pro Arg Asn Leu Val Gly Gly
                165                 170                 175

Pro Tyr Ala Val Val Asp His Asp Pro Ala Glu Asp Ala Ala Asp
            180                 185                 190

Arg Ser Arg Glu Leu Arg Gly Pro Trp Gly Glu Leu Asp Gln Arg Ser
        195                 200                 205

Ala Asp Val Ile Arg Tyr Trp Asn Ala His Lys Ala Gly Ala Asp Phe
    210                 215                 220

Val Val Val Asp Gly Ser Ser Tyr Thr Arg Glu Gly His Arg Ala Ile
225                 230                 235                 240

Pro Asp Glu Phe Ala Ala Thr Glu Lys Phe Ala Asp Val Thr Arg Trp
                245                 250                 255

Val Arg Ser Val Thr Gly Leu Pro Val Trp Trp Ala Glu Trp Tyr Val
            260                 265                 270

Glu Pro Pro Ala Glu Asp Asp Arg Pro Gly Gly Arg Asp Gly Trp Gly
        275                 280                 285

Glu Gly His Arg Thr Ala Val Gln Ala Thr Ala Met Met Arg Leu Ala
    290                 295                 300

Glu Ser Gly Ala Ser Ala Ala Phe Tyr Trp Asn Pro Gln Arg Thr Gly
305                 310                 315                 320

Lys Ala Cys Pro Gly Cys Leu Trp Arg Ser Thr His Leu Arg Asp Gly
                325                 330                 335

Gly Gly Glu Leu Pro Met Ala Gly Leu Leu Ser Arg Phe Ala Arg Glu
            340                 345                 350

Phe Pro Pro Gly Thr Ala Phe Arg Pro Val Ala Val Thr Cys Gly Ser
        355                 360                 365
```

-continued

Gly Asp Arg Val Glu Ala Leu Ala Asp Glu Ala Ala Val Leu Val Val
    370                 375                 380

Asn Thr Glu Cys Arg Pro Val Ala Ala Arg Val Asp Gly Gln Ala Leu
385                 390                 395                 400

Ser Leu Ala Pro Tyr Glu Val Arg Trp Leu Thr Arg Pro
                405                 410

<210> SEQ ID NO 140
<211> LENGTH: 270
<212> TYPE: PRT
<213> ORGANISM: Streptomyces lavendulae

<400> SEQUENCE: 140

Met Glu Phe Leu Gly Pro Ala Ala Gly Val Ser Gly Ala Thr Arg Leu
1               5                   10                  15

Tyr Ala Val Leu Gly Asp Pro Val Ala Gln Val Lys Ala Pro Gly Leu
            20                  25                  30

Leu Asn Pro Leu Leu Ser Glu Ser Gly Leu Asp Ala Val Val Val Pro
        35                  40                  45

Val His Val Arg Ala Arg Asp Leu Ala Glu Val Val Glu Gly Leu Lys
50                  55                  60

Arg Ile Gly Asn Leu Asp Gly Leu Leu Val Thr Val Pro His Lys Ala
65                  70                  75                  80

Ala Leu Cys Gly Leu Ala Asp Gly Leu Gly Pro Ala Ala Leu Ile
            85                  90                  95

Gly Thr Ala Asn Ala Met Arg Arg Glu Pro Asp Gly Arg Trp Tyr Ala
            100                 105                 110

Glu Asn Phe Asp Gly Leu Gly Phe Val Gln Gly Leu Gln Ala Ala Gly
            115                 120                 125

His Thr Val Arg Asp Arg His Val Ala Leu Val Gly Ala Gly Gly Ala
130                 135                 140

Gly Ser Ala Ile Ala Thr Ala Leu Leu Met Ala Asp Ala Ala Arg Val
145                 150                 155                 160

Ser Val His Asp Thr Asp Arg Ala Gln Leu Asp Ala Leu Leu Leu Arg
                165                 170                 175

Leu Gly Ser Arg Arg Pro Asp Gly Ile Arg Ala Leu Gly Pro Gly Asp
            180                 185                 190

Leu Glu Ala Ala Asp Phe Ala Val Asn Ala Thr Pro Leu Gly Met Arg
        195                 200                 205

Ser Glu Asp Pro Leu Pro Phe Asp Pro Ala Arg Val Arg Pro Asp Ala
210                 215                 220

Val Val Val Asp Val Val Met Lys Pro His Glu Thr Ala Leu Leu Ser
225                 230                 235                 240

Ala Ala Ala Thr Ala Gly Arg Arg Val His His Gly Ile His Met Leu
                245                 250                 255

Glu Gln Gln Val Pro Cys Tyr Arg Ala Phe Phe Gly Trp Pro
            260                 265                 270

<210> SEQ ID NO 141
<211> LENGTH: 271
<212> TYPE: PRT
<213> ORGANISM: Streptomyces lavendulae

<400> SEQUENCE: 141

Met Thr Arg Arg Arg Pro Thr Gly Pro Ile His Arg Arg Arg Ala Ser
1               5                   10                  15

-continued

```
Leu Thr Leu Ser Pro Thr Gly Ala Ala Met Arg Arg Asn Arg Ile Ala
            20                  25                  30

Ala Leu Leu Pro Ala Ala Leu Ala Leu Val Gly Ile Ser Val Leu Ala
            35                  40                  45

Pro Ala Thr Thr Ala Ser Ala Ala Ala Pro His Gly Gly Thr Ser Gln
 50                  55                  60

Ala Ala Ala Phe Pro Val Ser Glu Ala Gln Phe Lys Gln Met Phe Pro
 65                  70                  75                   80

Lys Arg Asn Ala Phe Tyr Thr Tyr Lys Gly Leu Val Ala Ala Leu Lys
                 85                  90                  95

Ala Tyr Pro Gly Phe Ala Gly Thr Gly Ser Ala Glu Val Arg Lys Gln
            100                 105                 110

Glu Ala Ala Phe Leu Ala Asn Val Ala His Glu Thr Gly Gly Leu
            115                 120                 125

Val Tyr Val Val Glu Gln Asn Thr Ala Asn Tyr Pro His Tyr Cys Asp
130                 135                 140

Arg Ser Arg Pro Tyr Gly Cys Pro Ala Gly Gln Ala Ala Tyr Tyr Gly
145                 150                 155                 160

Arg Gly Pro Leu Gln Ile Ser Trp Asn Phe Asn Tyr Lys Ala Ala Gly
                165                 170                 175

Asp Ala Leu Gly Ile Asp Leu Leu His Asn Pro Ser Leu Val Gln Lys
            180                 185                 190

Asp Ala Ala Val Ser Trp Lys Thr Gly Leu Trp Tyr Trp Asn Thr Gln
            195                 200                 205

Arg Gly Pro Gly Thr Met Thr Pro His Glu Ala Met Val Asn His Arg
210                 215                 220

Gly Phe Gly Gln Thr Ile Arg Ser Ile Asn Gly Ala Leu Glu Cys Asp
225                 230                 235                 240

Gly His Asn Pro Ala Gln Val Gln Ser Arg Val Ala Asn Tyr Gln Arg
                245                 250                 255

Phe Thr Lys Ile Leu Gly Val Ala Pro Gly Gly Asn Leu Ser Cys
            260                 265                 270
```

<210> SEQ ID NO 142
<211> LENGTH: 391
<212> TYPE: PRT
<213> ORGANISM: Artificial Sequence
<220> FEATURE:
<223> OTHER INFORMATION: A consensus sequence
<220> FEATURE:
<221> NAME/KEY: SITE
<222> LOCATION: (1)...(391)
<223> OTHER INFORMATION: Where present in this sequence, Xaa represents
      an amino acid that varied between the sequences used
      to generate this consensus sequence.

<400> SEQUENCE: 142

```
Met Xaa Xaa Xaa Xaa Xaa Xaa Xaa Xaa Xaa Phe Pro Xaa Trp Pro
 1               5                  10                  15

Gln Xaa Asp Asp Ala Glu Arg Xaa Gly Leu Xaa Arg Ala Leu Xaa Gln
            20                  25                  30

Gly Gln Trp Trp Arg Xaa Gly Gly Xaa Glu Val Xaa Xaa Phe Glu Arg
            35                  40                  45

Glu Phe Ala Xaa Xaa His Gly Ala Xaa His Ala Leu Ala Val Thr Asn
 50                  55                  60

Gly Thr His Ala Leu Glu Leu Ala Leu Xaa Val Met Gly Val Gly Pro
 65                  70                  75                   80
```

```
Gly Thr Glu Val Ile Val Pro Ala Phe Thr Phe Ile Ser Ser Ser Gln
                85                  90                  95

Ala Xaa Gln Arg Leu Gly Ala Val Xaa Val Pro Val Asp Val Asp Pro
            100                 105                 110

Xaa Thr Tyr Cys Leu Asp Xaa Xaa Ala Ala Ala Xaa Ala Val Thr Pro
        115                 120                 125

Arg Thr Xaa Ala Ile Met Pro Val His Met Ala Gly Gln Xaa Ala Asp
    130                 135                 140

Met Asp Ala Leu Xaa Lys Xaa Ser Ala Xaa Thr Gly Val Pro Xaa Xaa
145                 150                 155                 160

Gln Asp Ala Ala His Ala His Gly Ala Xaa Trp Xaa Gly Xaa Arg Val
                165                 170                 175

Gly Glu Leu Gly Ser Ile Ala Xaa Phe Ser Phe Gln Asn Gly Lys Leu
            180                 185                 190

Met Thr Ala Gly Glu Gly Gly Ala Val Leu Phe Pro Asp Xaa Glu Xaa
        195                 200                 205

Xaa Xaa Xaa Glu Xaa Ala Phe Leu Xaa His Ser Cys Gly Arg Pro Xaa
    210                 215                 220

Xaa Asp Arg Xaa Tyr Phe His Xaa Thr Xaa Gly Ser Asn Xaa Arg Xaa
225                 230                 235                 240

Asn Glu Phe Ser Ala Ser Val Leu Arg Ala Gln Leu Xaa Arg Leu Asp
                245                 250                 255

Xaa Gln Ile Xaa Xaa Arg Xaa Glu Arg Trp Xaa Xaa Leu Ser Xaa Leu
            260                 265                 270

Leu Ala Xaa Ile Asp Gly Val Val Pro Gln Xaa Xaa Asp Xaa Arg Xaa
        275                 280                 285

Asp Arg Asn Xaa His Tyr Met Ala Met Phe Arg Xaa Pro Gly Xaa Thr
    290                 295                 300

Glu Glu Arg Arg Xaa Ala Xaa Val Asp Xaa Leu Val Glu Arg Gly Xaa
305                 310                 315                 320

Pro Ala Phe Xaa Ala Phe Arg Xaa Val Tyr Arg Thr Xaa Ala Phe Trp
                325                 330                 335

Glu Xaa Gly Ala Pro Asp Xaa Xaa Xaa Glu Leu Ala Xaa Arg Cys
            340                 345                 350

Pro Xaa Xaa Xaa Xaa Ile Xaa Xaa Asp Cys Xaa Trp Leu His His Arg
        355                 360                 365

Val Leu Leu Xaa Xaa Glu Xaa Xaa Xaa Xaa Xaa Ala Xaa Val Xaa
370                 375                 380

Ala Asp Xaa Val Xaa Xaa Xaa
385                 390

<210> SEQ ID NO 143
<211> LENGTH: 393
<212> TYPE: DNA
<213> ORGANISM: Streptomyces lavendulae

<400> SEQUENCE: 143
atgtcagcaa ggatttccct cttcgccgtg gtggtcgagg acatggccaa gtcgctggag      60
ttctaccgga agctgggcgt cgagatcccc gccgaggccg actccgcgcc gcacacggag     120
gccgtgctcg acggcggcat ccggctcgcc tgggacaccg tggagacggt gcgcagctac     180
gaccccgagt ggcaggcccc caccggcggc accgcttcg ccatcgcgtt cgagttcccc     240
gacaccgcga gcgtggacaa gaagtacgcc gagctcgtcg acgccggcta cgagggccac     300
ctcaagccgt ggaacgccgt gtgggtcag cgctacgcca tcgtcaagga ccccgacggc     360
```

```
aacgtggtgg acctcttcgc gcccctcccg taa                                393

<210> SEQ ID NO 144
<211> LENGTH: 16
<212> TYPE: PRT
<213> ORGANISM: Artificial Sequence
<220> FEATURE:
<223> OTHER INFORMATION: A motif
<220> FEATURE:
<221> NAME/KEY: SITE
<222> LOCATION: (1)...(16)
<223> OTHER INFORMATION: Where present in this sequence, Xaa represents
      an amino acid that varied in this motif.

<400> SEQUENCE: 144

Val Xaa Gly Xaa Leu Xaa Asp Xaa Xaa Gly Arg Lys Xaa Xaa Xaa Leu
 1               5                  10                  15

<210> SEQ ID NO 145
<211> LENGTH: 11
<212> TYPE: PRT
<213> ORGANISM: Artificial Sequence
<220> FEATURE:
<223> OTHER INFORMATION: A motif
<220> FEATURE:
<221> NAME/KEY: SITE
<222> LOCATION: (1)...(11)
<223> OTHER INFORMATION: Where present in this sequence, Xaa represents
      an amino acid that varied in this conserved motif.

<400> SEQUENCE: 145

Leu Asp Xaa Thr Val Xaa Asn Val Ala Leu Pro
 1               5                  10
```

MITOMYCIN BIOSYNTHETIC GENE CLUSTER

CROSS-REFERENCE TO RELATED APPLICATIONS

This application is a continuation-in-part application of U.S. application Ser. No. 08/624,447, filed Aug. 19, 1996, which is a national stage filing of PCT/US94/11279, filed on Oct. 6, 1994, which is a continuation-in-part application of U.S. application Ser. No. 08/133,963, filed on Oct. 7, 1993, now abandoned.

BACKGROUND OF THE INVENTION

Streptomyces are filamentous Gram-positive soil bacteria with a nucleotide base composition greater than 70 mole % G+C (Stackebrandt and Woese, 1981). They produce a wide array of biologically active compounds including over two thirds of the commercially important natural product metabolites (Alderson et al., 1993; Bevax, 1998). Genetic information accumulated over the past 15 years has demonstrated that genes encoding enzymes for natural product assembly are clustered on the Streptomyces genome (Martin, 1992). In addition, one or more pathway-specific transcriptional regulatory genes, and at least one resistance gene are typically found within the antibiotic biosynthetic gene cluster (Chater, 1992). Heterologous hybridization with gene probes based on highly conserved biosynthetic enzyme amino acid sequences has been useful to clone antibiotic biosynthetic genes (Hopwood, 1997; Seno and Baltz, 1989; Turgay and Marahiel, 1994).

The mitomycins are a group of natural products that contain a variety of functional groups, including aminobenzoquinone and aziridine ring systems. One representative of the family, mitomycin C (MC), was the first recognized bioreductive alkylating agent. In particular, since its discovery and demonstration of anticancer activity in the 1960s, many aspects of the chemistry and biology of MC have been investigated. This has provided detailed information on its unprecedented molecular mechanism, unique biological and pharmacological properties, drug resistance, and bioactive analogues (Hata et al., 1956; Verweij, 1997). MC is regarded as the prototype natural product alkylating agent whose activity is dependent on the reductive activation (either chemically, such as low pH, or enzymatically, such as DT-diaphorase, NADH cytochrome c reductase) (Boxer, 1997; Cummings et al., 1998). Activated MC crosslinks double-stranded DNA, which in turn induces diverse biological effects including selective inhibition of DNA synthesis, mutagenesis, induction of DNA repair (SOS response), sister chromatid exchange, signal transduction, and induction of apoptosis (Tomasz and Palem, 1997). Tumor hypoxia and the increased expression of bioreductive enzymes in malignant cells create a selective environment for drug activation and make MC an attractive agent for anti-tumor therapy (Spanswick et al., 1998). MC has become one of the most effective antitumor drugs against non-small cell lung carcinoma and other soft tumors, as well as a clinically important component of combination cancer chemotherapy and radiotherapy of solid tumors (Henderson, 1993).

In addition to its biological and pharmacological importance, MC is prominent because its molecular mechanism represents a model for structurally related antitumor antibiotics such as porfiromycin (Pan and Iracki, 1988), mitiromycin (Wakaki et al., 1958), FR66979 (Paz and Hopkins, 1997), FR900482 (Williams et al., 1997), FK973 (Hirai et al., 1994), and FK317 (Naoe et al., 1998), as well as structurally unrelated bioreductive agents such as EO9 (Smitskampwilms et al., 1996), and tirapazamine (Evans et al., 1998). Numerous MC derivatives have been synthesized and tested for enhanced activities, including the recently identified selective protein tyrosine kinase inhibitor, 1a-docosahexaenoyl MC (Kasai and Arai, 1995; Shikano et al., 1998).

*Streptomyces lavendulae* produces MC. The molecule has an unusual structure comprised of aziridine, pyrrolizidine, pyrrolo-(1,2a)-indole, and amino-methylbenzoquinone rings to give the mitosane nucleus (Webb et al., 1962). The mitosane core of MC was shown to be derived from the junction of an amino-methylbenzoquinone ($mC_7N$ unit) and hexosamine ($C_6N$ unit) (Hornemann, 1981). The $C_6N$ unit consists of carbons 1, 2, 3, 9, 9a, 10, with the aziridine nitrogen derived intact from D-glucosamine (Hornemann et al., 1974).

The $mC_7N$ unit in MC and the ansamycins is derived from 3-amino-5-hydroxybenzoic acid (AHBA) (Becker et al., 1983; Kibby and Richards, 1981). AHBA was first shown to be incorporated into the ansamycin antibiotic actamycin (Kibby et al., 1980). Subsequently, it was confirmed as an efficient precursor for rifamycin (Becker et al., 1983; Kibby and Rickards, 1981; Ghilsalba and Neuesch, 1981), geldanamycin (Potgieter, 1983), ansamitocin (Hatano et al., 1982), ansatrienin (Wu et al., 1987), streptovaricin (Staley and Rinehart, 1991) and naphthomycin A (Lee et al., 1994). Anderson et al. (1980) demonstrated that [carboxy-$^{13}$C] AHBA could be efficiently and specifically incorporated into the C-6 methyl group of porfiromycin, which contains the same mitosane core as MC. Incorporation experiments with radiolabeled precursors have demonstrated that the mitosane core of MC was derived from the junction of AHBA and D-glucosamine (Anderson et al., 1980; Hornemann, 1981).

Meanwhile the O— and N— (but not C—) methyl groups were shown to be derived from L-methionine, while the C-10 carbamoyl group came from L-arginine or L-citrulline (Bezanson and Vining, 1971; Hornemann and Eggert, 1975; Hornemann et al., 1974). [$^{14}$C]-labeled precursor feeding studies with D-glucose, pyruvate and D-erythrose indicated that de novo biosynthesis of AHBA resulted directly from the shikimate pathway. However, no incorporation into the $mC_7N$ unit of either MC (Hornemann, 1981) or the ansamycin antibiotics (Chiao et al., 1998) was found from labeling studies with shikimic acid, the shikimate precursor 3-dehydroquinic acid, or the shikimate derived amino acids. These results led to the hypothesis of a modified shikimate pathway, in which a 3-deoxy-D-arabino-heptulosonic acid-7-phosphate (DAHP) synthase-like enzyme catalyzes the conversion to 3,4-dideoxy-4-amino-D-arabino-heptulosonic acid-7-phosphate (amino-DAHP), to give the ammoniated shikimate pathway (Kim et al., 1992). Floss (1997) provided strong support for this new variant of the shikimate pathway by showing that aminoDAHP, 5-deoxy-5-amino-3-dehydroquinic acid (aminoDHQ), and 5-deoxy-5-amino-3-dehydroshikimic acid (aminoDHS) could be efficiently converted into AHBA by a cell-free extract of *Amycolatopsis mediterranei* (rifamycin producer), in contrast to the normal shikimate pathway intermediate DAHP which was not converted (Kim et al., 1992; Kim et al., 1996). Recently, the AHBA synthase (rifK) gene from *A. mediterranei* has been cloned, sequenced and functionally characterized (Kim et al., 1998).

Little is known regarding the details of the convergent assembly of MC from AHBA and D-glucosamine in *S. lavendulae*, i.e., whether its de novo biosynthesis is related to the primary metabolic shikimate pathway, an important route in microorganisms and plants for aromatic amino acid biosynthesis (Floss, 1997). In addition, it is unclear how *S. lavendulae* resists the activity of MC since the preferred MC alkylation sites in DNA are guanine and cytosine, and MC-induced cell death can result from a single crosslink per genome (Tomasz, 1995).

Thus, there is a continuing need for the identification and isolation of antibiotic biosynthetic genes, including genes which confer resistance to antibiotics or result in enhanced production of antibiotics.

SUMMARY OF THE INVENTION

The present invention provides an isolated and purified nucleic acid molecule, e.g., DNA, comprising a gene cluster for mitomycin, a variant or a fragment thereof (the mit/mmc gene cluster). As described hereinbelow, the *S. lavendulae* mitomycin gene cluster includes the mitomycin biosynthetic gene cluster comprising 47 mitomycin biosynthetic genes spanning 55 kb of contiguous DNA. The biosynthetic portion of the gene cluster includes genes that encode polypeptides involved in the generation of biosynthetic precursors, mitosane ring system assembly and functionalization (e.g., methylation, hydroxylation, aminotransfer, carbamoylation, and carbonyl reduction), a mitomycin resistance gene which is different than mrd and the unlinked mcr, as well as several regulatory genes. Gene disruption was employed to further characterize some of the genes. Fourteen of 22 gene disruption mutants affected mitomycin biosynthesis, resulting in abrogation or overexpression of drug production, e.g., targeted genetic disruption of a mitomycin pathway regulator (e.g., mmcW) led to a substantial increase in drug production. It is preferred that the isolated and purified nucleic acid molecule of the invention is nucleic acid from Streptomyces spp., such as *Streptomyces lavendulae* (e.g., B19/ATCC 27422, NRRL 2564, KY681, ATCC 27423, or PB1000), *Streptomyces caespitosus, Streptomyces verticillatus*, and *Streptomyces sandaensis* (FERM-P7654), although isolated and purified nucleic acid molecules from other organisms which produce mitomycin or biological or functional equivalents thereof are also within the scope of the invention. The nucleic acid molecules of the invention are double-stranded or single-stranded.

As described hereinbelow, a 3.8 kb BamHI fragment from the *S. lavendulae* genome was isolated which comprises three open reading frames (ORFs). One of the ORFs (mitA) showed high similarity to previously identified AHBA synthase genes (Kim et al., 1998), while another (mitB) showed sequence similarity to several prokaryotic and eukaryotic glycosyltransferases. Nucleotide sequence analysis showed that mitA encodes a 388 amino acid protein that has 71% identity (80% similarity) with the rifamycin AHBA synthase from *Amycolatopsis mediterranei*, as well as with two additional AHBA synthases from related ansamycin antibiotic-producing microorganisms. Gene disruption and site-directed mutagenesis of the *S. lavendulae* chromosomal copy of mitA completely blocked the production of MC. The function of mitA was confirmed by complementation of a *S. lavendulae* strain containing a K191A mutation in MitA with 3-amino-5-hydroxybenzoic acid, i.e., MC production was restored when the mitA mutant strain was cultured in the presence of exogenous 3-amino-5-hydroxybenzoic acid. mitB encodes a 272 amino acid protein.

Seven gene products (aminoDHQ synthase (MitP), aminoquinate dehydrogenase (MitT), aminoDHQ dehydratase (MmcF), AHBA synthase (MitA), oxidoreductase (MitG), phosphatase (MitJ), and kinase (MitS)) are likely responsible for assembly of the intermediate 3-amino-5-hydroxybenzoic acid (AHBA) through a variant of the shikimate pathway. However, the gene encoding aminoDAHP synthase, the first presumed enzyme involved in AHBA biosynthesis from phosphoenol pyruvate (PEP) and erythrose 4-phosphate (E4P), is not linked within the mitomycin biosynthetic gene cluster.

A mitomycin resistance determinant (mct) encodes a membrane-associated protein involved in excretion of mitomycin from cells. Disruption of mct by insertional inactivation resulted in a *S. lavendulae* mutant strain that was considerably more sensitive to MC. Expression of mct in *E. coli* conferred a 5-fold increase in cellular resistance to MC, led to the synthesis of a membrane associated protein, and correlated with reduced intracellular accumulation of drug. Co-expression of mct and mrd in *E. coli* resulted in a 150-fold increase in resistance, as well as reduced intracellular accumulation of MC. The results establish that MRD maintains a high affinity for MC and may serve as the primary receptor (participating as an accessory component in a drug export system) for subsequent transport by MCT.

The cloned mitomycin biosynthetic genes are useful to elucidate the molecular basis for the biosynthesis of the mitosane ring system, as well as to engineer the biosynthesis of novel natural products. Moreover, genetic engineering or overexpression of the transport, resistance and regulatory proteins may lead to higher titers of mitomycin compounds from production cultures.

Preferably, the isolated nucleic acid molecule comprising the gene cluster includes a nucleic acid sequence comprising SEQ ID NO:96 or SEQ ID NO:76, a variant or a fragment thereof, e.g., a nucleic acid molecule that hybridizes under moderate, or more preferably stringent, hybridization conditions to SEQ ID NO:96, SEQ ID NO:76 or a fragment thereof. Moderate and stringent hybridization conditions are well known to the art, see, for example sections 9.47–9.51 of Sambrook et al. (*Molecular Cloning: A Laboratory Manual*, Cold Spring Harbor Laboratory, Cold Spring Harbor, N.Y. (1989). For example, stringent conditions are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% sodium dodecylsulfate (SDS), and 10% dextran sulfate at 42° C., with washes at 42° C. in 0.2×SSC and 0.1% SDS.

A preferred nucleic molecule of the invention comprises a nucleic acid sequence encoding a polypeptide including, but not limited to, MitA (e.g., SEQ ID NO:10 encoded by SEQ ID NO:97), MitB (e.g., SEQ ID NO:11 encoded by SEQ ID NO:98), MitC (e.g., SEQ ID NO:12 encoded by SEQ ID NO:99), MitD (e.g., SEQ ID NO:100 encoded by SEQ ID NO:45), MitE (e.g., SEQ ID NO:101 encoded by SEQ ID NO:44), MitF (e.g., SEQ ID NO:102 encoded by SEQ ID NO:43), MitG (e.g., SEQ ID NO:103 encoded by SEQ ID NO:42), MitH (e.g., SEQ ID NO:104 encoded by SEQ ID NO:41), MitI (e.g., SEQ ID NO:105 encoded by SEQ ID NO:40), MitJ (e.g., SEQ ID NO:106 encoded by SEQ ID NO:39), MitK (e.g., SEQ ID NO:107 encoded by SEQ ID NO:38), MitL (e.g., SEQ ID NO:108 encoded by SEQ ID NO:37), MitM (e.g., SEQ ID NO:109 encoded by SEQ ID NO:36), MitN (e.g., SEQ ID NO:110 encoded by SEQ ID NO:35), MitO (e.g., SEQ ID NO:111 encoded by SEQ ID NO:34), MitP (e.g., SEQ ID NO:112 encoded by SEQ ID NO:33), MitQ (e.g., SEQ ID NO:113 encoded by SEQ ID NO:32), MitR (e.g., SEQ ID NO:114 encoded by SEQ ID NO:31), MitS (e.g., SEQ ID NO:115 encoded by SEQ ID NO:30), MitT (e.g., SEQ ID NO:140 encoded by SEQ ID NO:29), MmcA (SEQ ID NO:116 encoded by SEQ ID NO:49), MmcB (SEQ ID NO:117 encoded by SEQ ID NO:50), MmcC (SEQ ID NO:118 encoded by SEQ ID NO:51), MmcD (SEQ ID NO:119 encoded by SEQ ID NO:52), MmcE (SEQ ID NO:120 encoded by SEQ ID NO:53), MmcF (SEQ ID NO:121 encoded by SEQ ID NO:54), MmcG (SEQ ID NO:122 encoded by SEQ ID NO:55), MmcH (SEQ ID NO:123 encoded by SEQ ID NO:56), MmcI (SEQ ID NO:124 encoded by SEQ ID NO:57), MmcJ (SEQ ID NO:125 encoded by SEQ ID NO:58), MmcK (SEQ ID NO:126 encoded by SEQ ID NO:59), MmcL (SEQ ID NO:127 encoded by SEQ ID NO:60), MmcM (SEQ ID NO:128 encoded by SEQ ID NO:61), MmcN (SEQ ID NO:129 encoded by SEQ ID NO:62), MmcO (SEQ ID NO:130 encoded by SEQ ID NO:63), MmcP (SEQ ID NO:131 encoded by SEQ ID NO:64), MmcQ (SEQ ID NO:132 encoded by SEQ ID NO:65), MmcR (SEQ ID NO:133 encoded by SEQ ID NO:66), MmcS (SEQ ID NO:134 encoded by SEQ ID NO:67), MmcT (SEQ ID NO:135 encoded by SEQ ID NO:68), MmcU (SEQ ID NO:136 encoded by SEQ ID NO:69), MmcV (SEQ ID NO:137 encoded by SEQ ID NO:70), MmcW (SEQ ID NO:138 encoded by SEQ ID NO:71), MmcX (SEQ ID NO:139 encoded by SEQ ID NO:72), MmcY (SEQ ID NO:141 encoded by SEQ ID NO:73), Mct (SEQ ID NO:17 encoded by SEQ ID NO:16), a variant or a fragment thereof, e.g., a nucleic acid molecule that hybridizes under moderate, or more preferably stringent, hybridization conditions to at least one of the nucleic acid sequences identified hereinabove.

The invention further provides an isolated and purified nucleic acid molecule which is linked to a mitomycin biosynthetic gene cluster and which encodes polyketide biosynthetic enzymes, a variant or a fragment thereof. Preferably, the nucleic acid molecule of this embodiment of the invention comprises at least one, preferably at least five, and more preferably at least nine, open reading frames. More preferably, the nucleic acid molecule hybridizes under moderate, or more preferably stringent, hybridization conditions to SEQ ID NO:74, or a portion thereof.

The invention also provides an isolated and purified nucleic acid molecule which is linked to a mitomycin biosynthetic gene cluster and which encodes sugar biosynthetic enzymes, a variant or a fragment thereof. Preferably, the nucleic acid molecule of this embodiment of the invention comprises at least one, preferably at least five, more preferably at least nine, and even more preferably at least twelve, open reading frames. Preferably, the nucleic acid molecule of the invention hybridizes under moderate, or more preferably stringent, hybridization conditions to SEQ ID NO:75, or a portion thereof.

The invention also provides a variant polypeptide having at least about 80%, more preferably at least about 90%, and even more preferably at least about 95%, but less than 100%, contiguous amino acid sequence identity to a polypeptide having an amino acid sequence encoded by SEQ ID NO:76, or a fragment thereof. A preferred variant polypeptide includes a variant polypeptide or fragment thereof having at least about 1%, more preferably at least about 10%, and even more preferably at least about 50%, the activity of the polypeptide having the amino acid sequence comprising SEQ ID NO:10–12, 17 or 100–141. Thus, for example, the activity of a polypeptide having SEQ ID NO:98 can be compared to a variant of SEQ ID NO:98 having at least one amino acid substitution, insertion, or deletion relative to SEQ ID NO:98.

A variant nucleic acid sequence of the invention has at least about 80%, more preferably at least about 90%, and even more preferably at least about 95%, but less than 100%, contiguous nucleic acid sequence identity to a nucleic acid sequence comprising SEQ ID NO:76, or a fragment thereof. The amino acid and/or nucleic acid similarity (or homology) of two sequences may be determined manually or using algorithms well known to the art.

The invention also provides probes and primers comprising at least a portion of the nucleic acid molecules of the invention. The probes or primers of the invention are preferably detectably labeled or have a binding site for a detectable label. Preferably, the probes or primers of the invention are at least about 7, more preferably at least about 15, contiguous nucleotides bases having at least about 80% identity, more preferably at least about 90% identity, to the isolated nucleic acid molecules of the invention. Such probes or primers are useful to detect, quantify, isolate and/or amplify DNA strands with complementary to sequences related to the mitomycin biosynthetic gene cluster, sequences related to those encoding the polyketide biosynthetic enzymes linked to the mitomycin biosynthetic gene cluster, sequences related to those encoding sugar biosynthetic enzymes linked to the mitomycin biosynthetic gene cluster, a variant or a fragment thereof Also provided is an expression cassette comprising a nucleic acid molecule comprising at least a portion of a mitomycin biosynthetic gene cluster, a nucleic acid molecule which is linked to a mitomycin biosynthetic gene cluster and which encodes polyketide biosynthetic enzymes, a nucleic acid molecule which is linked to a mitomycin biosynthetic gene cluster and which encodes sugar biosynthetic enzymes, a variant or fragment thereof, operably linked to a promoter functional in a host cell. Host cells that have been modified genetically, i.e., recombinant host cells, include host cells comprising an expression cassette, e.g., an expression cassette of the invention, or host cells in which the genome has been genetically manipulated, e.g., by deletion of a portion of, replacement of a portion of, or by disruption of, the host chromosome, so as to reduce or eliminate the expression of a particular mitomycin biosynthetic gene, polyketide biosynthetic gene or a sugar biosynthetic gene of the invention.

One embodiment of the invention is a recombinant host cell, e.g., a bacterial cell, in which a portion of a nucleic acid sequence comprising the mitomycin gene cluster, i.e., the endogenous or native genomic sequence, is disrupted or replaced, for example, by an insertion with heterologous. sequences or substituted with a variant nucleic acid sequence of the invention, preferably so as to result in altered mitomycin synthesis, such as an increase in mitomycin synthesis, and/or production of a novel compound. For example, the invention includes a recombinant host cell in which the mmcW gene is disrupted, for example, by replacement with a selectable marker gene, so as to yield a recombinant host cell having an increase in mitomycin production.

Another embodiment of the invention is a recombinant host cell, the genome of which is augmented by an expression cassette, e.g., via an extrachromosomal element such as a plasmid or by stable integration of the cassette into the host chromosome. Thus, the genome of the recombinant host cell is augmented with at least one mitomycin biosynthetic gene, polyketide biosynthetic gene or a sugar biosynthetic gene of the invention so as to yield an altered level of mitomycin and/or a novel compound(s) relative to the corresponding non-recombinant host cell.

Alternatively, the genome of a recombinant host cell is augmented with a non-mitomycin biosynthetic gene and, optionally, at least one mitomycin biosynthetic gene, polyketide biosynthetic gene or a sugar biosynthetic gene of the invention so as to yield an altered level of mitomycin and/or a novel compound(s) relative to the corresponding non-recombinant host cell. For example, the recombinant host cell may be augmented with pika (see U.S. application Ser. No. 09/105,537, filed Jun. 26, 1998, the disclosure of which is incorporated by reference herein) and pikA expressed in an amount effective to yield a novel compound (s).

Host cells useful to prepare the recombinant host cells of the invention include cells which do not express or do not comprise nucleic acid corresponding to the nucleic acid molecules of the invention, e.g., mitomycin biosynthetic genes, as well as cells which naturally produce mitomycin.

Thus, the invention also provides isolated and purified polypeptides encoded by a nucleic acid molecule of the invention. Preferably, the polypeptide of the invention is obtained from recombinant host cells, e.g., the genome of which is augmented by a nucleic acid molecule of the invention. In addition, expression cassettes and host cells comprising antisense sequences of at least a portion of the mitomycin biosynthetic gene cluster of the invention are envisioned.

In another embodiment of the invention, the isolated and purified nucleic acid molecule which is linked to a mitomycin biosynthetic gene cluster and which encodes polyketide biosynthetic enzymes, e.g., a polyketide synthase, is useful in methods to prepare recombinant polyhydroxyalkanoate monomer synthases and polymers.

Thus, the present invention provides a method of preparing a polyhydroxyalkanoate synthase. The method comprises introducing an expression cassette into a host cell. The expression cassette comprises a DNA molecule encoding a polyketide synthase, operably linked to a promoter functional in the host cell. The DNA molecule is preferably obtained from a mitomycin-producing organism, e.g., a Streptomyces spp. such as S. lavendulae. The DNA molecule encoding the polyketide synthase is then expressed in the cell. Thus, another embodiment of the invention provides a purified recombinant polyketide isolated from a host cell which expresses the synthase.

Another embodiment of the invention is a method of preparing a polyhydroxyalkanoate polymer. The method comprises introducing a first expression cassette and a second expression cassette into a host cell. The first expression cassette comprises a DNA segment encoding a fatty acid synthase in which the dehydrase activity has been inactivated that is operably linked to a promoter functional in the host cell, e.g., an insect cell. The inactivation preferably is via a mutation in the catalytic site of the dehydrase. The second expression cassette comprises a DNA segment encoding a polyketide synthase that is preferably obtained from a mitomycin-producing organism operably linked to a promoter functional in the host cell. The expression cassettes may be on the same or separate molecules. The DNA segments in the expression cassettes are expressed in the cell so as to yield a polyhydroxyalkanoate polymer.

The present invention also. provides an expression cassette comprising a nucleic acid molecule encoding a polyhydroxyalkanoate monomer synthase operably linked to a promoter functional in a host cell. The nucleic acid molecule comprises a plurality of DNA segments. Thus, the nucleic acid molecule comprises at least a first and a second DNA segment. The first DNA segment encodes a first module and the second DNA segment encodes a second module, wherein the DNA segments together encode a polyhydroxyalkanoate monomer synthase. No more than one DNA segment is derived from the eryA gene cluster of *Saccharopolyspora erythraea*. It is also preferred that the first DNA segment comprises a module from a mitomycin-producing organism, e.g., Streptomyces spp. The nucleic acid molecule may optionally further comprise a third DNA segment encoding a polyhydroxyalkanoate synthase. Alternatively, a second nucleic acid molecule encoding a polyhydroxyalkanoate synthase may be introduced into the host cell.

Also provided is an isolated and purified DNA molecule. The DNA molecule comprises a plurality of DNA segments. Thus, the DNA molecule comprises at least a first and a second DNA segment. The first DNA segment encodes a first module and the second DNA segment encodes a second module. Together the DNA segments encode a recombinant polyhydroxyalkanoate monomer synthase. It is preferred that no more than one DNA segment is derived from the eryA gene cluster of *Saccharopolyspora erythraea*. Also, it is preferred that no more than one module is derived from the gene cluster from *Streptomyces hygroscopicus* that encodes rapamycin or the gene cluster that encodes spiramycin. A preferred embodiment of the invention employs a first DNA segment comprising a module from a mitomycin-producing organism. A further preferred embodiment of the isolated DNA molecule of the invention includes a DNA segment encoding a polyhydroxyalkanoate synthase.

Further provided is a method of preparing a polyhydroxyalkanoate polymer. The method comprises introducing a first DNA molecule and a second DNA molecule into a host cell. The first DNA molecule comprises a DNA segment encoding a recombinant polyhydroxyalkanoate monomer synthase. The recombinant polyhydroxyalkanoate monomer synthase comprises a plurality of modules. Thus, the monomer synthase comprises at least a first module and a second module. The first DNA molecule is operably linked to a promoter functional in a host cell. The second DNA molecule comprises a DNA segment encoding a polyhydroxyalkanoate synthase operably linked to a promoter functional in the host cell. It is preferred that at least one module is from a mitomycin-producing organism. The DNAs encoding the recombinant polyhydroxyalkanoate monomer synthase and polyhydroxyalkanoate synthase are expressed in the host cell so as to generate a polyhydroxyalkanoate polymer.

Yet another embodiment of the invention is an isolated and purified DNA molecule. The DNA molecule comprises a plurality of DNA segments. That is, the DNA molecule comprises at least a first and a second DNA segment. The first DNA segment encodes a fatty acid synthase and the second DNA segment encodes a module of a polyketide synthase. A preferred embodiment of the invention employs a second DNA segment comprising a module of a polyketide synthase from a mitomycin-producing organism such as Streptomyces.

Also provided is a method of providing a polyhydroxyalkanoate monomer synthase. The method comprises introducing an expression cassette into a host cell. The expression cassette comprises a DNA molecule encoding a polyhydroxyalkanoate monomer synthase operably linked to a promoter functional in the host cell. The monomer synthase comprises a plurality of modules. Thus, the monomer synthase comprises at least a first and second module which together encode the monomer synthase. A preferred embodiment of the invention employs a module from a mitomycin-producing organism. Optionally, the expression cassette further comprises a second DNA molecule encoding a polyhydroxyalkanoate synthase.

The invention also provides an isolated and purified DNA molecule comprising a first DNA segment encoding a first module and a second DNA segment encoding a second module, wherein the DNA segments together encode a recombinant polyhydroxyalkanoate monomer synthase. Preferably, at least one DNA segment is derived from DNA which is linked to the mitomycin gene cluster of *S. lavendulae*. Also preferably, no more than one DNA segment is derived from the eryA gene cluster of *Saccharopolyspora erythraea*. In one embodiment of the invention, the 3' most DNA segment of the isolated DNA molecule of the invention encodes a thioesterase II. Also provided is an expression cassette comprising a nucleic acid molecule encoding the polyhydroxyalkanoate monomer synthase operably linked to a promoter functional in a host cell.

Yet another embodiment of the invention is a method of providing a polyhydroxyalkanoate monomer. The method comprises introducing into a host cell a DNA molecule comprising a DNA segment encoding a recombinant polyhydroxyalkanoate monomer synthase operably linked to a promoter functional in the host cell. Preferably, the second DNA molecule is derived from DNA which is linked to the mitomycin gene cluster. The recombinant polyhydroxyalkanoate monomer synthase comprises a first module and a second module, wherein at least one DNA segment is derived from DNA which is linked to a mitomycin gene. cluster, e.g., the mitomycin gene cluster of *S. lavendulae*. The DNA encoding the recombinant polyhydroxyalkanoate monomer synthase is then expressed in the host cell so as to generate a polyhydroxyalkanoate monomer. Optionally, a second DNA molecule may be introduced into the host cell. The second DNA molecule comprises a DNA segment encoding a polyhydroxyalkanoate synthase operably linked to a promoter functional in the host cell. The two DNA molecules are expressed in the host cell so as to generate a polyhydroxyalkanoate polymer.

Another embodiment of the invention is an isolated and purified DNA molecule comprising a first DNA segment encoding a fatty acid synthase and a second DNA segment encoding a module from the DNA which is linked to the mitomycin gene cluster of *S. lavendulae*. Such a DNA molecule can be employed in a method of providing a polyhydroxyalkanoate monomer. Thus, a DNA molecule comprising a first DNA segment encoding a fatty acid synthase and a second DNA segment encoding a polyketide synthase is introduced into a host cell. The first DNA segment is 5' to the second DNA segment and the first DNA segment is operably linked to a promoter functional in the host cell. The first DNA segment is linked to the second DNA segment so that the linked DNA segments express a fusion protein. The DNA molecule is expressed in the host cell so as to generate a polyhydroxyalkanoate monomer.

Further provided is a method of providing a polyhydroxyalkanoate monomer synthase. The method comprises introducing an expression cassette comprising a DNA molecule encoding a polyhydroxyalkanoate synthase operably linked to a promoter functional in a host cell. The DNA molecule comprises a first DNA segment encoding a first module and a second DNA segment encoding a second module wherein the DNA segments together encode a polyhydroxyalkanoate monomer synthase. At least one DNA segment is derived from DNA which is linked to the mitomycin gene cluster of *S. lavendulae*. The DNA molecule is expressed in the host cell. Optionally, the DNA molecule further comprises a DNA segment encoding a polyhydroxyalkanoate synthase. Alternatively, a second, separate DNA molecule encoding a polyhydroxyalkanoate synthase is introduced into the host cell.

Thus, the invention provides an isolated and purified DNA molecule comprising a first DNA segment encoding a first module and a second DNA segment encoding a second module, wherein the DNA segments together encode a recombinant polyhydroxyalkanoate monomer synthase, and wherein at least one DNA segment is derived from the mit/mmc gene cluster of *S. lavendulae*. Preferably, no more than one DNA segment is derived from the eryA gene cluster of *Saccharopolyspora erythraea*. In one embodiment of the invention, the 3' most DNA segment of the isolated DNA molecule of the invention encodes a thioesterase II. Also provided is an expression cassette comprising a nucleic acid molecule encoding the polyhydroxyalkanoate monomer synthase operably linked to a promoter functional in a host cell.

Yet another embodiment of the invention is a method of providing a polyhydroxyalkanoate monomer. The method comprises introducing into a host cell a DNA molecule comprising a DNA segment encoding a recombinant polyhydroxyalkanoate monomer synthase operably linked to a promoter functional in the host cell. The recombinant polyhydroxyalkanoate monomer synthase comprises a first module and a second module, wherein at least one DNA segment is derived from the mit/mmc gene cluster of *S. lavendulae*. The DNA encoding the recombinant polyhydroxyalkanoate monomer synthase is then expressed in the host cell so as to generate a polyhydroxyalkanoate monomer. Optionally, a a second DNA molecule may be introduced into the host cell. The second DNA molecule comprises a DNA segment encoding a polyhydroxyalkanoate synthase operably linked to a promoter functional in the host cell. The two DNA molecules are expressed in the host cell so as to generate a polyhydroxyalkanoate polymer.

Another embodiment of the invention is an isolated and purified DNA molecule comprising a first DNA segment encoding a fatty acid synthase and a second DNA segment encoding a module from the mit/mmc gene cluster of *S. lavendulae*. Such a DNA molecule can be employed in a method of providing a polyhydroxyalkanoate monomer. Thus, a DNA molecule comprising a first DNA segment encoding a fatty acid synthase and a second DNA segment encoding a polyketide synthase is introduced into a host cell. The first DNA segment is 5' to the second DNA segment and the first DNA segment is operably linked to a promoter functional in the host cell. The first DNA segment is linked to the second DNA segment so that the linked DNA segments express a fusion protein. The DNA molecule is expressed in the host cell so as to generate a polyhydroxyalkanoate monomer.

Further provided is a method of providing a polyhydroxyalkanoate monomer synthase. The method comprises introducing an expression cassette comprising a DNA molecule encoding a polyhydroxyalkanoate synthase operably linked to a promoter functional in a host cell. The DNA molecule comprises a first DNA segment encoding a first module and a second DNA segment encoding a second module wherein the DNA segments together encode a polyhydroxyalkanoate monomer synthase. At least one DNA segment is derived from the mit/mmc gene cluster of S. lavendulae. The DNA molecule is expressed in the host cell. Optionally, the DNA molecule further comprises a DNA segment encoding a polyhydroxyalkanoate synthase. Alternatively, a second, separate DNA molecule encoding a polyhydroxyalkanoate synthase is introduced into the host cell.

Also provided is a method for directing the biosynthesis of specific sugar-modified polyketides by genetic manipulation of a polyketide-producing microorganism. The method comprises introducing into a polyketide-producing microorganism a DNA sequence encoding enzymes in sugar biosynthesis, e.g., a DNA sequence comprising SEQ ID NO:75, a variant or fragment thereof, so as to yield a microorganism. that produces specific sugar-modified polyketides. Alternatively, an anti-sense DNA sequence of the invention may be employed. Then the sugar-modified polyketides are isolated from the microorganism. It is preferred that the DNA sequence is modified so as to result in the inactivation of at least one enzymatic activity in sugar biosynthesis or in the attachment of the sugar to a polyketide Thus, the modules encoded by the nucleic acid segments of the invention may be employed in the methods described hereinabove to prepare polyhydroxyalkanoates of varied chain length or having various side chain substitutions.

The compounds produced by the recombinant host cells of the invention are preferably biologically active agents such as antibiotics, anti-inflammatory agents, anti-cancer agents, antibiotics, immune-enhancers, immunosuppressants, agents to treat asthma, chronic obstructive pulmonary disease as well as other diseases involving respiratory inflammation, or cholesterol-lowering agents; or as crop protection agents (e.g., fungicides or insecticides), as well as biopolymers, e.g., in packaging or biomedical applications, or to engineer PHA monomer synthases. Methods employing these compounds, e.g., to treat a mammal, e.g., a human, bird or fish in need of such therapy, are also envisioned.

BRIEF DESCRIPTION OF THE FIGURES

FIG. 3. The three SAM dependent methyltransferase conserved motifs can be found in MitM (SEQ ID NO:1), MitN (SEQ ID NO:2), and MmcR (SEQ ID NO:3). DmpM (SEQ ID NO:4; Kim et al., 1998), TcmN (SEQ ID NO:5; Shikano et al., 1998), ORF14 (SEQ ID NO:6; August et. al., 1998), EryG (SEQ ID NO:7; Hardwick and Pelham, 1994) are O-methyltransferases for puromycin, tetracenomycin C, rifamycin, and erythromycin biosynthesis, respectively. Consen=consensus sequence (SEQ ID NO:8).

FIG. 5. MC genes and deduced enzyme functions.

FIG. 6. Bacterial strains and plasmids. Strains DH5α and DH5αF' are available from Gibco BRL (Gaithersburg, Md.), ATCC 27643and NRRL 2564are available from the American Type Culture Collection, and strain S17-1 is described in Hidaka et al. (1995). Plasmids pNJ1, pUC119, pKC 1139, pDHS3001pKN108, and pFD666 are described in Kuzuyama et al. (1995), Madduri et al. (1993), Boxer (1997), Kagan and Clarke (1994), Kim et al. (1998), and Coque et al. (1995), respectively.

FIG. 9. Nucleotide sequence of the 3.8 kb DNA fragment containing mitABC (SEQ ID NO:9). The deduced gene products are indicated in the one-letter code under the DNA sequence (SEQ ID NO:10, MitA; SEQ ID NO:11, MitB; SEQ ID NO:12, MitC). Possible ribosome binding sites are marked in the boxed regions. The presumed translational start site and direction of transcription for each ORF is indicated by an arrow and marked accordingly.

FIG. 10. Alignment of MitA with three other AHBA synthases. The deduced amino acid sequence comparison from AHBAS genes derived from Streptomyces lavendulae (SEQ ID NO:10). Streptomyces collinus (Z54208; SEQ ID NO:13), Actinosynnema pretiosum (139657; SEQ ID NO:14), and Amycolatopsis mediterranei (139657; SEQ ID NO:15) is shown with the conserved lysine in the PLP-binding motif underlined. Consensus (SEQ ID NO:142.

*dulae*. One mg of crude extract injected, 1 μg of MC injected as standard. B) *Bacillus subtilis* bioassay of mitomycin C production in mitA disruption mutant strain of *S. lavendulae*. Filter discs: 1) 100 μg injection of wild-type—collected 12.5–13.5 minutes; 2) 100 μg injection of mitA (ahbas) disruption mutant—collected 12.5–13.5 minutes; 3) 100 μg injection of W. T. containing vector—collected 12.5–13.5 minutes; 4) One μg of mitomycin C collected from HPLC from 12.5–13.5 minutes; 5) Tris buffer negative control; 6) methanol solvent negative control.

FIG. 14. Strains and plasmids employed in Example 3. BL21 (DE3) and pET17b are available from Novagen (Madison, Wis.). pDHS7006 is described in Sheldon et al. (1997).

Figure 15:
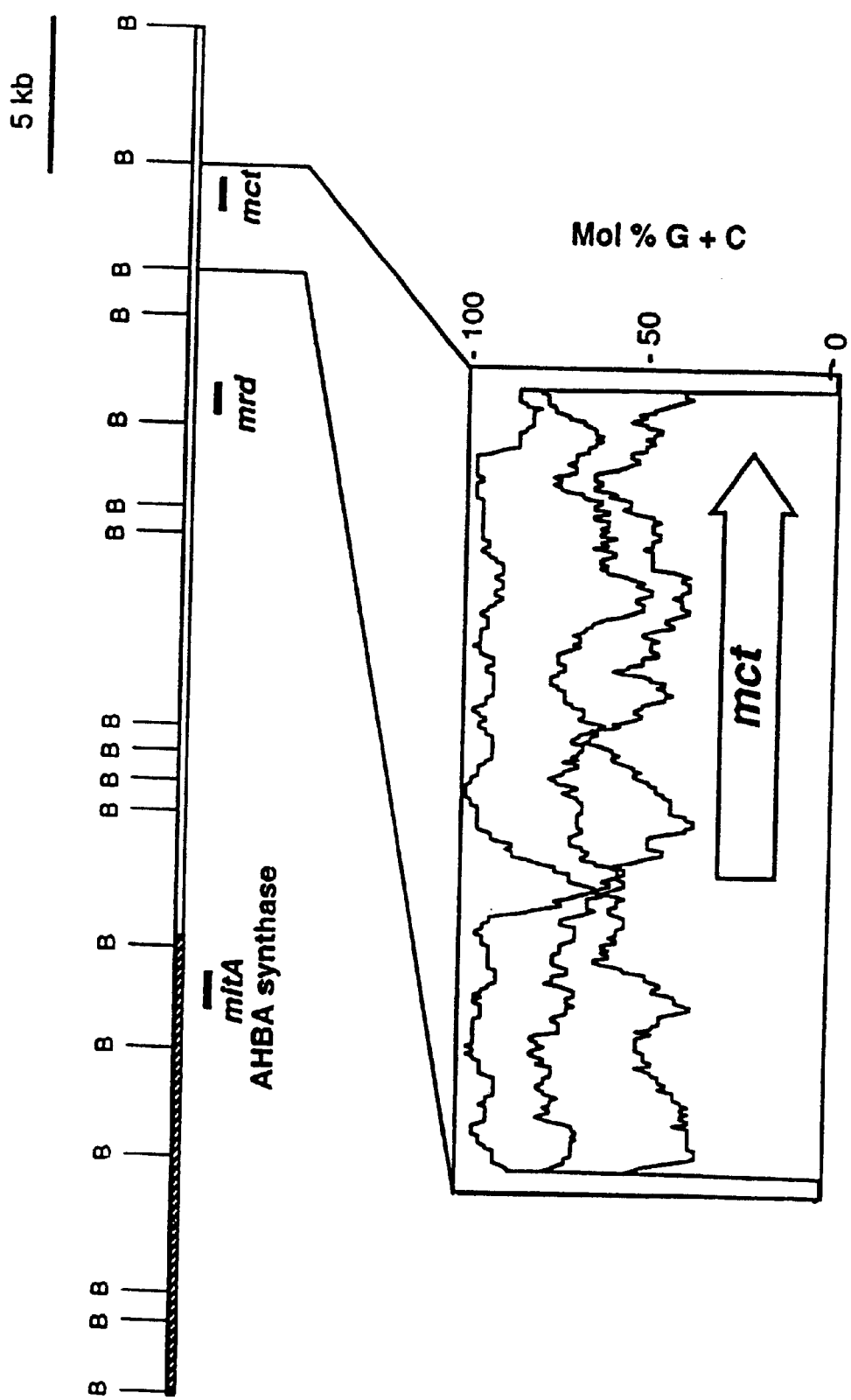

FIG. 15. Genetic map showing the physical linkage of the mct and mrd genes within the MC biosynthetic gene cluster. The expanded box shows the line plot of the mct ORF.

FIG. 16. The nucleotide sequence of mct (SEQ ID NO:16). The deduced amino acid sequence of mct is indicated under the nucleotide sequence with the one letter designation (SEQ ID NO:17). A conserved motif characteristic of 14 TMS proteins is boxed while the invariant beta-turn motif is denoted with a dashed underline. The putative ribosome binding site is marked with a solid underline.

FIG. 17. Dot matrix alignment of the deduced amino acid sequence of mct with other actinomycete antibiotic efflux proteins. Comparable parameters were utilized in generating the alignments.

Figure 18A:
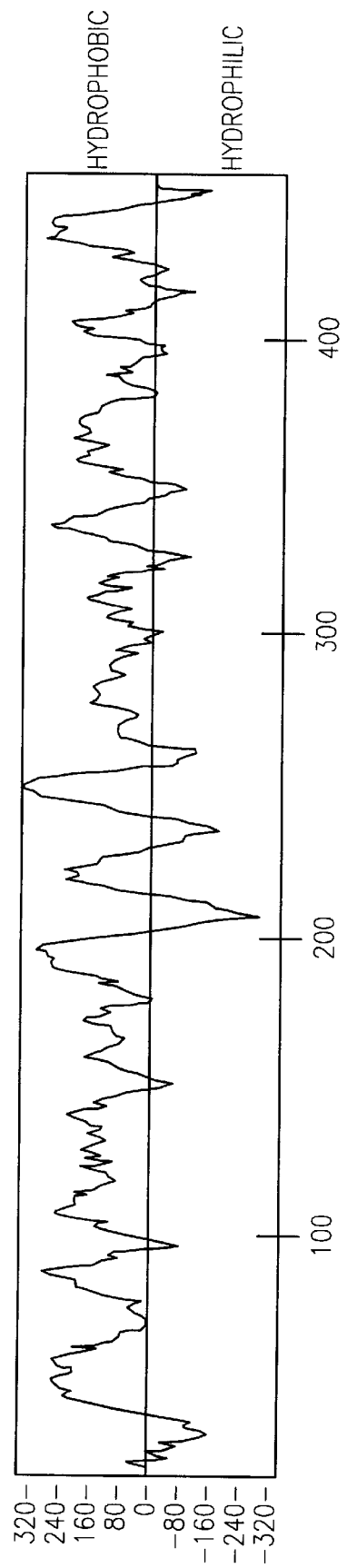
Figure 18B:
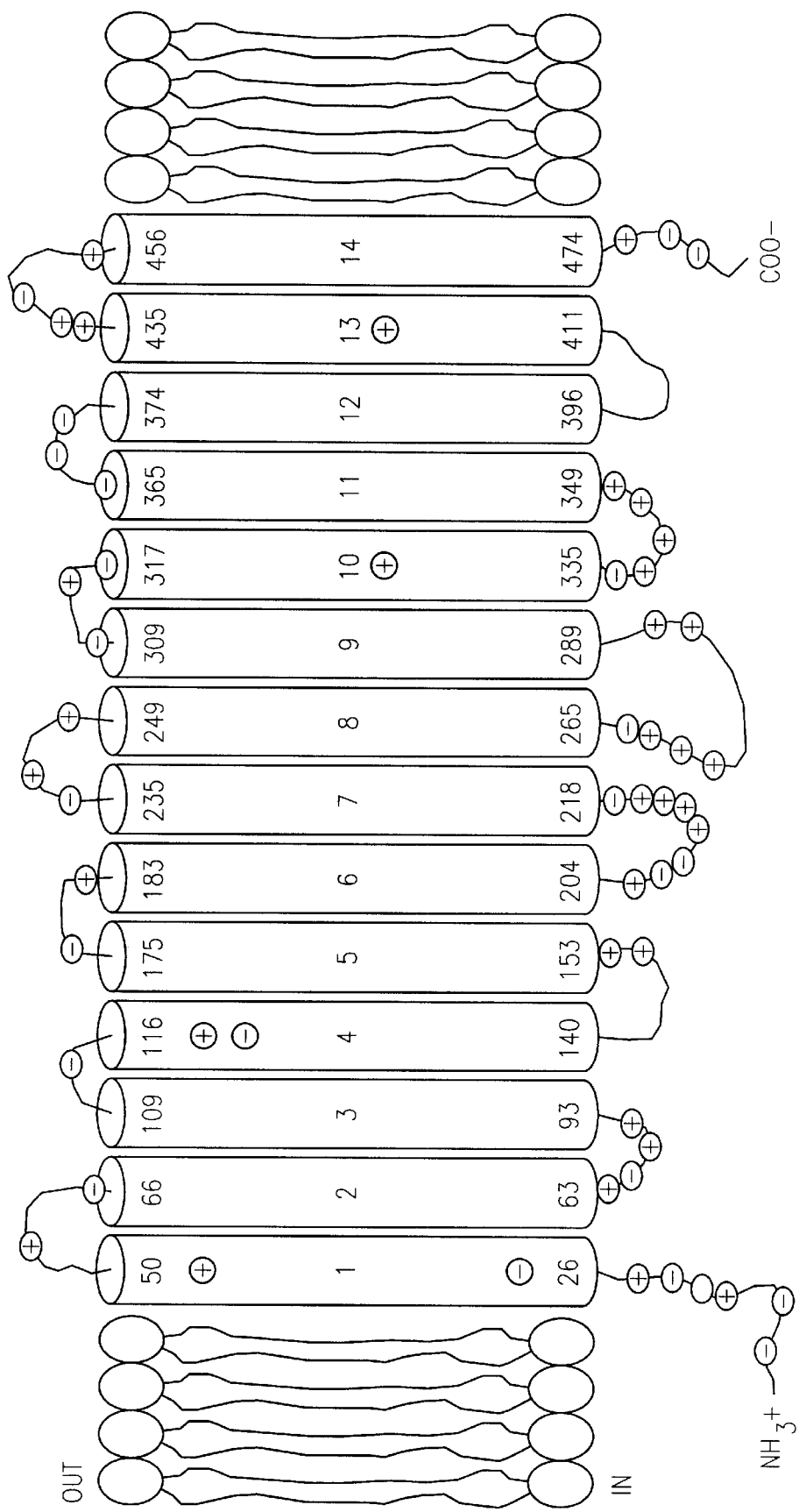

FIG. 18. Hydropathy analysis of the deduced amino acid sequence of MC-translocase. A) Hydropathy plot obtained from prediction of Kyte and Doolittle (1982). B) Schematic representation of MC-translocase protein topology. The transmembrane spanning regions are marked (1–14). The initial and final amino acid positions of each transmembrane domain are indicated by small numbers. The relative position of positively (H, R, K) and negatively (D, Q) charged amino acids are indicated by a plus and minus, respectively.

Figure 19A:
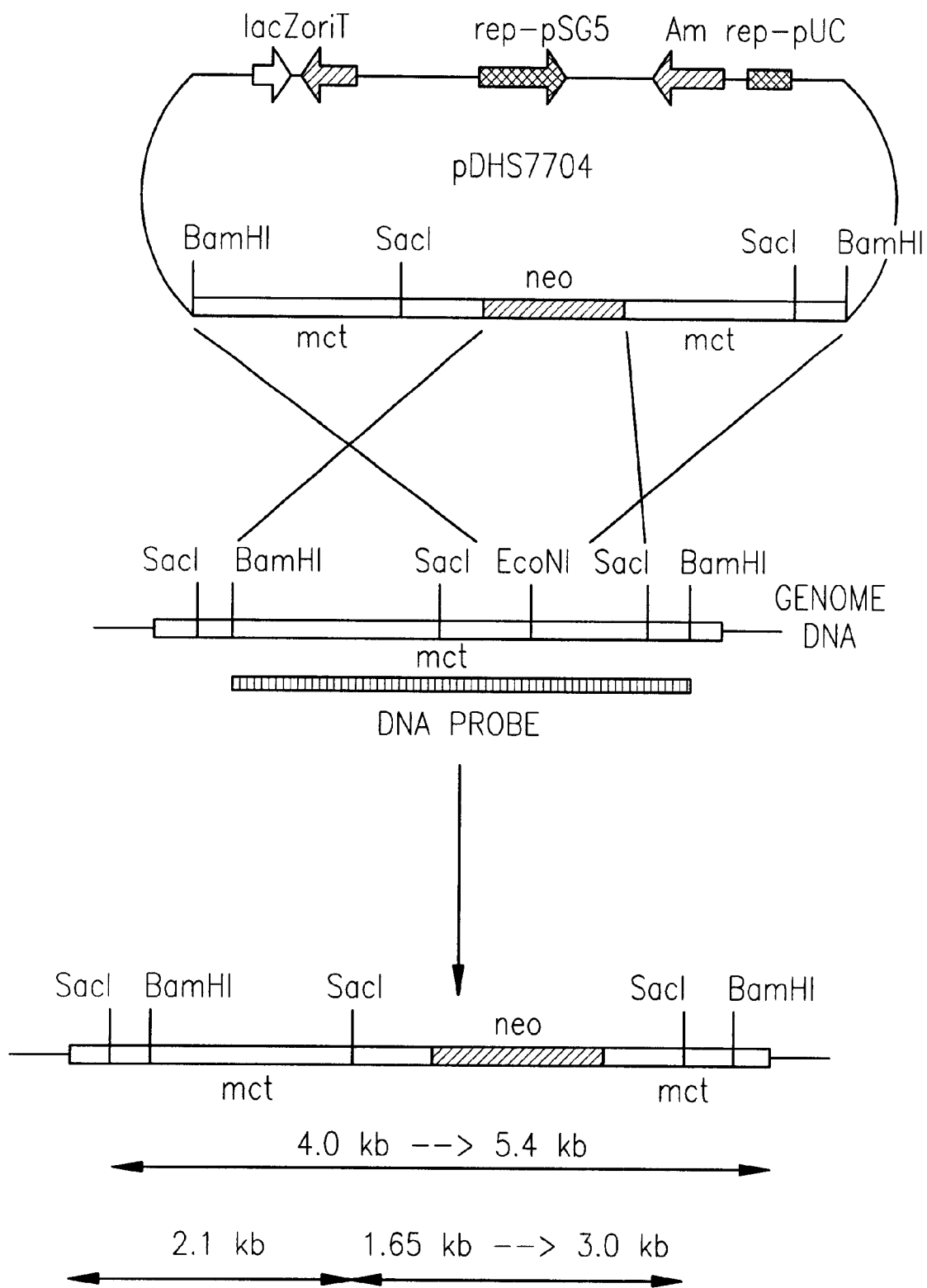
Figure 19B:
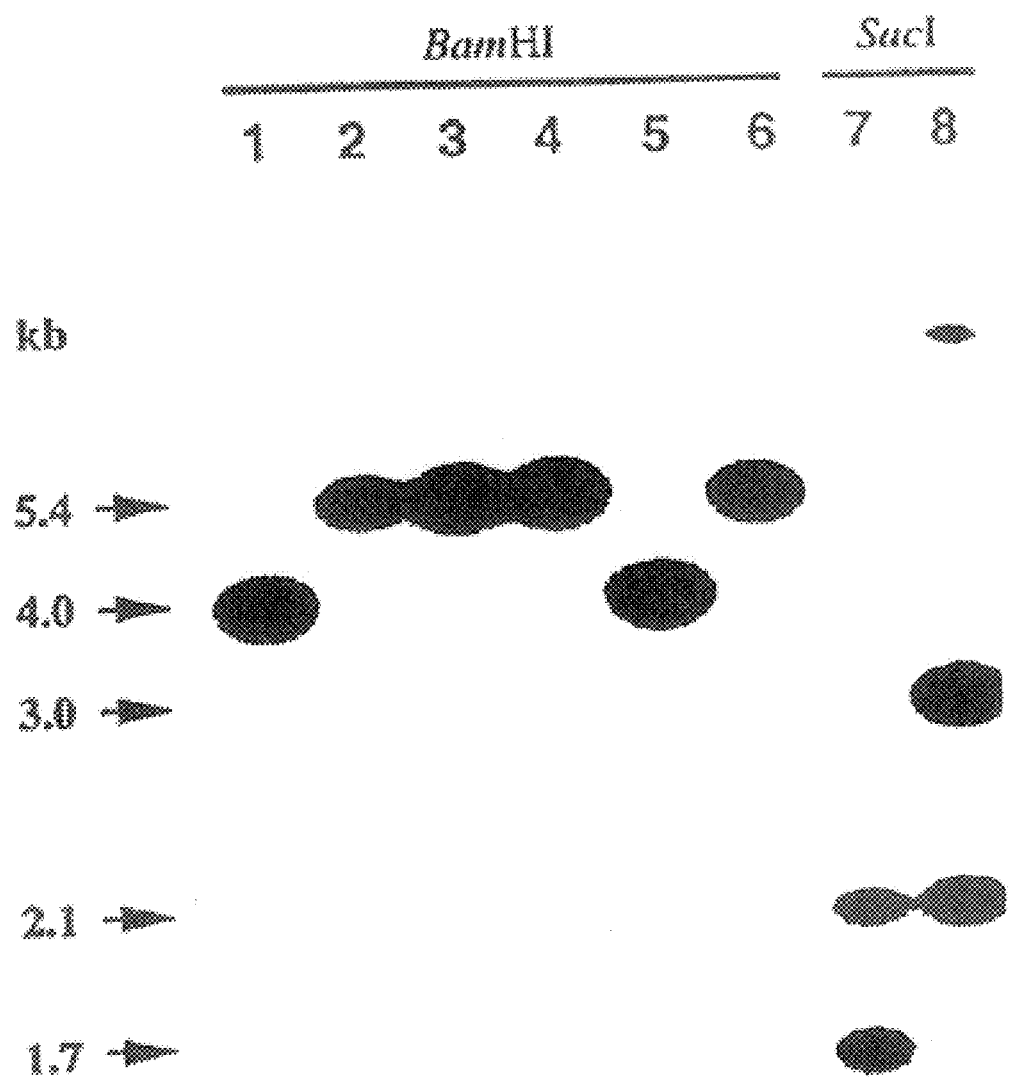

FIG. 19. Creation of the mct disruption mutant. A) The chromosomal mct gene (black bar) was disrupted by inserting a neomycin resistance marker (shaded) within the gene. Following double crossover recombination, specific restriction bands are predicted to be shifted in the mct mutant genome compared to the wild-type strain. B) Southern blot analysis of the mct mutant. As expected, when probed with the 4.0 kb BamHI insert from pDHS7661, the 4.0 kb BamHI hybridization band in wild-type *S. lavendulae* was shifted to 5.4 kb in mct knockouts, while a 1.65 kb SacI hybridization band was shifted to 3.0 kb in size. Lane 1 and 5: wild-type genomic DNA digested with BamHI. Lane 2, 3, 4, and 6: Four double crossover colonies genomic DNA digested with BamHI. Lane 7: wild-type genomic DNA digested with SstI. Lane 8: double crossover clone 6 genomic DNA digested with SstI.

Figure 20:
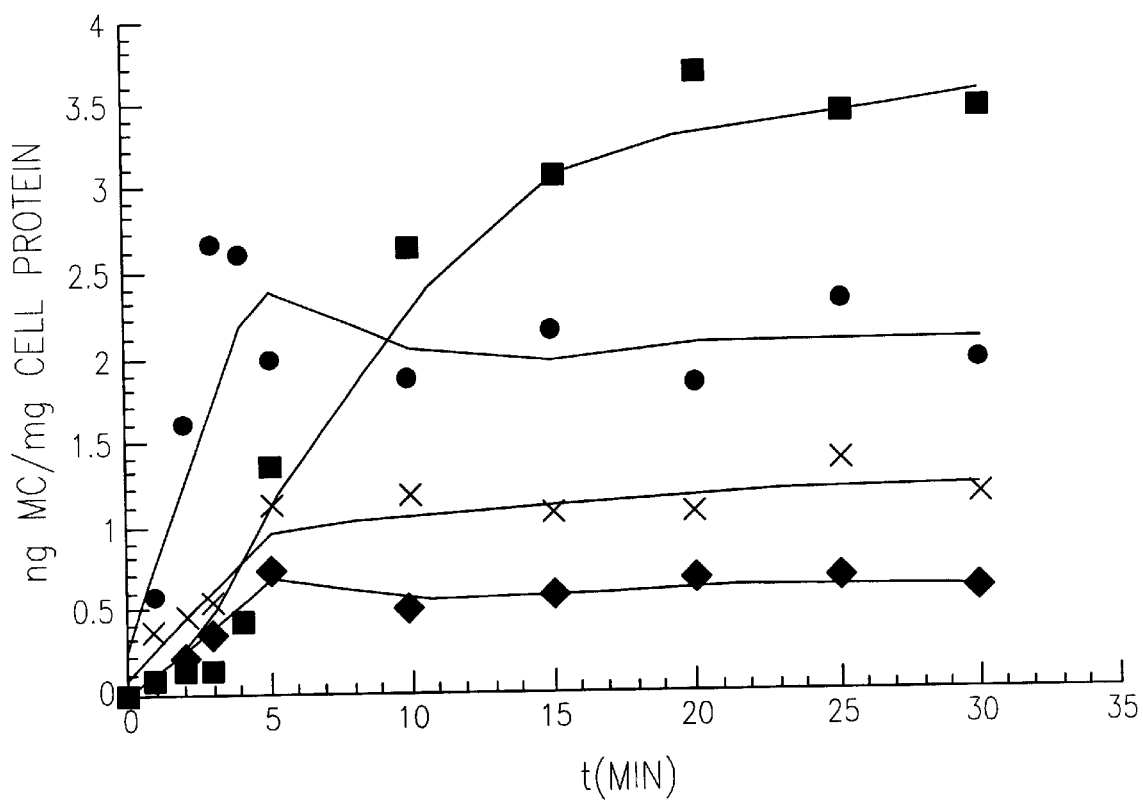

FIG. 20. MC uptake analysis of strains PJS100, PJS102, and PJS103. BL21(DE3)::pET17b vector control strain, (●); strain PJS100,(■); strain PJS102, (♦); strain PJS103, (x).

FIG. 21. Complete nucleotide sequence of the mitomycin gene cluster (SEQ ID NO:96).

FIG. 22. Complete nucleotide sequence of ORFs 1–9 (SEQ ID NO:74).

FIG. 23. Complete nucleotide sequence of ORFs 11–22 (SEQ ID NO:75).

FIG. 24. Codons for various amino acids.

FIG. 25. Exemplary amino acid substitutions.

FIG. 26. Complete nucleotide sequence of the mitomycin biosynthetic genes (SEQ ID NO:76).

DETAILED DESCRIPTION OF THE INVENTION

Definitions

As used herein, a "Type I polyketide synthase" is a single polypeptide with a single set of iteratively used active sites. This is in contrast to a Type II polyketide synthase which employs active sites on a series of polypeptides.

As used herein, a "linker region" is an amino acid sequence present in a multifunctional protein which is less well conserved in an amino acid sequence than an amino acid sequence with catalytic activity.

As used herein, an "extender unit" catalytic or enzymatic domain is an acyl transferase in a module that catalyzes chain elongation by adding 2–4 carbon units to an acyl chain and is located carboxy-terminal to another acyl transferase. For example, an extender unit with methylmalonylCoA specificity adds acyl groups to a methylmalonylCoA molecule.

As used herein, a "polyhydroxyalkanoate" or "PHA" polymer includes, but is not limited to, linked units of related, preferably heterologous, hydroxyalkanoates such as 3-hydroxybutyrate, 3-hydroxyvalerate, 3-hydroxycaproate, 3-hydroxyheptanoate, 3-hydroxyhexanoate, 3-hydroxyoctanoate, 3-hydroxyundecanoate, and 3-hydroxydodecanoate, and their 4-hydroxy and 5-hydroxy counterparts.

As used herein, a "recombinant" nucleic acid or protein molecule is a molecule where the nucleic acid molecule which encodes the protein has been modified in vitro, so that its sequence is not naturally occurring, or corresponds to naturally occurring sequences that are not positioned as they would be positioned in a genome which has not been modified.

As used herein, a "multifunctional protein" is one where two or more enzymatic activities are present on a single polypeptide.

As used herein, a "module" is one of a series of repeated units in a multifunctional protein, such as a Type I polyketide synthase or a fatty acid synthase.

As used herein, a "premature termination product" is a product which is produced by a recombinant multifunctional protein which is different than the product produced by the non-recombinant multifunctional protein. In general, the product produced by the recombinant multifunctional protein has fewer acyl groups.

As used herein, a DNA that is "derived from" a gene cluster is a DNA that has been isolated and purified in vitro from genomic DNA, or synthetically prepared on the basis of the sequence of genomic DNA.

An "antibiotic" as used herein is a substance produced by a microorganism which, either naturally or with limited chemical modification, will inhibit the growth of or kill another microorganism or eukaryotic cell.

An "antibiotic biosynthetic gene" is a nucleic acid, e.g.; DNA, segment or sequence that encodes an enzymatic activity which is necessary for an enzymatic reaction in the process of converting primary metabolites into antibiotics.

An "antibiotic biosynthetic pathway" includes the entire set of antibiotic biosynthetic genes necessary for the process of converting primary metabolites into antibiotics. These genes can be isolated by methods well known to the art, e.g., see U.S. Pat. No. 4,935,340.

Antibiotic-producing organisms include any organism, including, but not limited to, Actinoplanes, Actinomadura, Bacillus, Cephalosporium, Micromonospora, Penicillium, Nocardia, and Streptomyces, which either produces an antibiotic or contains genes which, if expressed, would produce an antibiotic.

The term "polyketide" as used herein refers to a large and diverse class of natural products, including but not limited to antibiotic, antifungal, anticancer, and anti-helminthic compounds.

The term "polyketide-producing microorganism" as used herein includes any microorganism that can produce a polyketide naturally or after being suitably engineered (i.e., genetically). Examples of actinomycetes that naturally produce polyketides include but are not limited to *Micromonospora rosaria, Micromonospora megalomicea, Saccharopolyspora erythraea, Streptomyces antibioticus, Streptomyces albereticuli, Streptomyces ambofaciens, Streptomyces avermitilis, Streptomycesfradiae, Streptomyces griseus, Streptomyces hydroscopicus, Streptomyces tsukulubaensis, Streptomyces mycarofasciens, Streptomyces platenesis, Streptomyces violaceoniger, Streptomyces violaceoniger, Streptomyces thermotolerans, Streptomyces rimosus, Streptomyces peucetius, Streptomyces coelicolor, Streptomyces glaucescens, Streptomyces roseofulvus, Streptomyces cinnamonensis, Streptomyces curacoi*, and *Amycolatopsis mediterranei* (see Hopwood, D. A. and Sherman, D. H., *Annu. Rev. Genet.*, 24:37–66 (1990), incorporated herein by reference). Other examples of polyketide-producing microorganisms that produce polyketides naturally include various Actinomadura, Dactylosporangium and Nocardia strains.

The term "glycosylated polyketide" refers to any polyketide that contains one or more sugar residues.

The term "glycosylation-modified polyketide" refers to a polyketide having a changed glycosylation pattern or configuration relative to that particular polyketide's unmodified or native state.

The term "sugar biosynthesis genes" as used herein refers to nucleic acid sequences from organisms such as *S. lavendulae* that encode sugar biosynthesis enzymes and is intended to include sequences of DNA from other polyketide-producing microorganisms which are identical or analogous to those obtained from *S. lavendulae*.

The term "sugar biosynthesis enzymes" as used herein refers to polypeptides which are involved in the biosynthesis and/or attachment of polyketide-associated sugars and their derivatives and intermediates.

The term "polyketide-associated sugar" refers to a sugar that is known to attach to polyketides or that can be attached to polyketides by the processes described herein.

The term "sugar derivative" refers to a sugar which is naturally associated with a polyketide but which is altered relative to the unmodified or native.

The term "sugar intermediate" refers to an intermediate compound produced in a sugar biosynthesis pathway.

A "recombinant" host cell of the invention has a genome that has been manipulated in vitro so as to alter, e.g., decrease or disrupt, or, alternatively, increase, the function or activity of at least one gene, e.g., in the mitomycin biosynthetic gene cluster, of the invention.

As used herein, the "mit/mmc" or "mitomycin" gene cluster includes sequences encoding enzymes for mitosane precursor formation, mitosane ring assembly, regulation of mitomycin biosynthesis, functionalization, and resistance to mitomycin, as well as closely linked sequences encoding polyketide and sugar biosynthetic enzymes.

As used herein, the terms "isolated and/or purified" refer to in vitro isolation of a RNA, DNA or polypeptide molecule from its natural cellular environment, and from association with other components of the cell, such as nucleic acid or polypeptide, so that is can be sequenced, replicated and/or expressed. Moreover, the nucleic acid may encode more than one polypeptide. For example, "an isolated DNA molecule encoding an AHBA synthase" is RNA or DNA containing greater than 7, preferably 15, and more preferably 20 or more sequential nucleotide bases that preferably encode a biologically active polypeptide, or a fragment or variant thereof, that is complementary to the non-coding, or complementary to the coding strand, of an AHBA synthase RNA, or hybridizes to the RNA or DNA encoding the AHBA synthase and remains stably bound under low, moderate, or stringent conditions, as defined by methods well known to the art, e.g., in Sambrook et al., supra.

An antibiotic resistance-conferring gene is a nucleic acid segment that encodes an enzymatic or other activity which alone or in combination with other gene products, confers resistance to an antibiotic.

As used herein, "mitomycin" includes, but is not limited to, mitomycin A, mitomycin B, mitomycin C, porfiromycin, mitiromycin, mitomycin D, mitomycin E, mitomycin F, mitomycin G, mitomycin H, mitomycin I, mitomycin J, mitomycin L, mitomycin M, mitomycin K, albomitomycin A, isomitomycin A, KW2149, KW2149 metabolites such as M-16 and M-18, FR66979, FK973, FK317, and FR900482, as well as structural or functional equivalents thereof ("analogs"), or derivatives thereof.

As used herein, the term "derivative" means that a particular compound produced by a host cell of the invention or prepared in vitro using polypeptides encoded by the nucleic acid molecules of the invention, is modified so that it comprises other moieties, e.g., peptide or polypeptide molecules, such as antibodies or fragments thereof, nucleic acid molecules, sugars, lipids, fats, a detectable signal molecule such as a radioisotope, e.g., gamma emitters, small chemicals, metals, salts, synthetic polymers, e.g., polylactide and polyglycolide, surfactants and glycosaminoglycans, which are covalently or non-covalently attached or linked to the compound.

It will be appreciated by those skilled in the art that each atom of the compounds of the invention having a chiral center may exist in and be isolated in optically active and racemic forms. Some compounds may exhibit polymorphism. It is to be understood that the present invention encompasses any racemic, optically active, polymorphic or stereoisomeric form, or mixtures thereof, of a compound of the invention, which possess the useful properties described herein, it being well known in the art how to prepare optically active forms (for example, by resolution of the racemic form by recrystallization techniques, by synthesis from optically active starting materials, by chiral synthesis, or by chromatographic separation using a chiral stationary phase) and how to determine activity using the standard tests described herein, or using other similar tests which are well known in the art.

The term "sequence homology" or "sequence identity" means the proportion of base matches between two nucleic acid sequences or the proportion amino acid matches between two amino acid sequences. When sequence homology is expressed as a percentage, e.g., 50%, the percentage denotes the proportion of matches over the length of sequence that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and more preferably not less than 19 matches out of 20 possible base pair matches (95%).

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, 1972, volume 5, National Biomedical Research Foundation, pp. 101–110, and Supplement 2 this volume, pp. 1–10. The two sequences or parts thereof are more preferably homologous if their amino acids are greater than or equal to 50% identical when optimally aligned using the ALIGN program.

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc; Natl. Acad. Sci. (U.S.A.)* 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 20–50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two peptide sequences, when optimally aligned, such as by the programs GAP or BESTFIT using default gap weights, share at least about 80 percent sequence identity, preferably at least about 90 percent sequence identity, more preferably at least about 95 percent sequence identity, and most preferably at least about 99 percent sequence identity.

In accordance with the present invention, there is provided a purified and isolated nucleic acid molecule which encodes the entire pathway for the biosynthesis of mitomycin, as well as polyketide biosynthetic and sugar biosynthetic genes that are linked to the mitomycin biosynthetic genes. Desirably, the nucleic acid molecule is a DNA isolated from Streptomyces spp. The present invention further includes isolated and purified DNA sequences which hybridize under standard or stringent conditions to the the nucleic acid molecules of the invention. It should be understood to those skilled in the art that the invention also encompasses the purified and isolated polypeptides which may be encoded by the sequences of the nucleic acid molecules of this invention.

The invention described herein can be used for the production of mitomycin, analogs or derivatives thereof, or novel compounds. Commercial chemical syntheses of mitomycin are not feasible. The gene cluster described herein contains all the genes required for the production of the mitosane group of antibiotics, compounds which are clinically prescribed antitumor compounds employed in the treatment of a wide variety of cancers including non-small cell lung cancer, metastatic breast cancer, esophageal, gastric, pancreatic, and anal canal carcinomas. Thus, the isolation and characterization of this gene cluster allows for the selective production of mitomycin antibiotics, the overproduction or under production of particular compounds, e.g., overproduction of certain mitomycin antibiotics, and the production of novel compounds, e.g., mitomycin-derived compounds as well as the production of novel non-mitomycin related compounds. For example, combinational biosynthetic-based modification of mitomycin antibiotics may be accomplished by selective activation or disruption of specific genes within the cluster or incorporation of the genes into biased biosynthetic libraries which are assayed for a wide range of biological activities, to derive greater chemical diversity in the mitomycins. A further example includes the introduction of a mitomycin biosynthetic gene(s) into a particular host cell so as to result in the production of a novel non-mitomycin related compound due to the activity of the mitomycin biosynthetic gene(s) on other metabolites, intermediates or components of the host cells. The in vitro expression of polypeptides from this gene cluster also provides an enzymatic route to the production of known mitomycin compounds that are produced in low quantities, or conversion of currently available mitomycins to other known or novel mitomycins, e.g., the bioconversion of mitomycin C to porfiromycin.

The mitomycin resistance genes may also be used to provide higher mitomycin resistance to cancer patients undergoing treatment and for clonal selection purposes (e.g., using mrd). For example, the resistance gene(s) may be inserted into human bone marrow cell lines to confer higher resistance to non-cancerous cells, thus allowing higher doses of mitomycins to be administered to cancer patients. Moreover, because mitomycin acts directly upon DNA itself, its toxicity is extremely broad, and therefore the resistance genes could be used for efficient selection in prokaryotes, fungi, plants, mammalian cell culture, and insect cell culture. Further, the regulatory resistance and transport genes may be used to create higher producing strains capable of synthesizing more mitomycin than can currently be obtained through traditional fermentation strategies.

In addition, the invention described herein can bemused for the production of novel compounds which include a diverse range of biodegradable PHA polymers through genetic redesign of DNA such as that found in Streptomyces spp. Different PHA synthases can then be tested for their ability to polymerize the monomers produced by the recombinant PHA synthase into a biodegradable polymer. PHA synthases can be tested for their specificity with respect to different monomer substrates by methods well known to the art.

The potential uses and applications of PHAs produced by PHA monomer synthases and PHA synthases include both medical and industrial applications. Medical applications of PHAs include surgical pins, sutures, staples, swabs, wound dressings, blood vessel replacements, bone replacements and plates, stimulation of bone growth by piezoelectric properties, and biodegradable carrier for long-term dosage of pharmaceuticals. Industrial applications of PHAs include disposable items such as baby diapers, packaging containers, bottles, wrappings, bags, and films, and biodegradable carriers for long-term dosage of herbicides, fungicides, insecticides, or fertilizers.

In animals, the biosynthesis of fatty acids de novo from malonyl-CoA is catalyzed by FAS. For example, the rat FAS is a homodimer with a subunit structure consisting of 2505 amino acid residues having a molecular weight of 272,340 Da. Each subunit consists of seven catalytic activities in separate physical domains (Amy et al., Proc. Natl. Acad. Sci. USA, 86, 3114 (1989)). The physical location of six of the catalytic activities, ketoacyl synthase (KS), malonyl/acetyltransferase (M/AT), enoyl reductase (ER), ketoreductase (KR), acyl carrier protein (ACP), and thioesterase (TE), has been established by (1) the identification of the various active site residues within the overall amino acid sequence by isolation of catalytically active fragments from limited proteolytic digests of the whole FAS, (2) the identification of regions within the FAS that exhibit sequence similarity with various monofunctional proteins, (3) expression of DNA encoding an amino acid sequence with catalytic activity to produce recombinant proteins, and (4) the identification of DNA that does not encode catalytic activity, i.e., DNA encoding a linker region. (Smith et al., Proc. Natl. Acad. Sci. USA, 73, 1184 (1976); Tsukamoto et al., J. Biol. Chem., 263, 16225 (1988); Rangan et al., J. Biol. Chem., 266, 19180 (1991)).

The seventh catalytic activity, dehydrase (DH), was identified as physically residing between AT and ER by an amino acid comparison of FAS with the amino acid sequences encoded by the three open reading frames of the eryA polyketide synthase (PKS) gene cluster of Saccharopolyspora erythraea. The three polypeptides that comprise this PKS are constructed from "modules" which resemble animal FAS, both in terms of their amino acid sequence and in the ordering of the constituent domains (Donadio et al., Gene, 111, 51 (1992); Benh et al., Eur. J. Biochem, 204, 39 (1992)).

One embodiment of the invention employs a FAS in which the DH is inactivated (FAS DH-). The FAS DH- employed in this embodiment of the invention is preferably a eukaryotic FAS DH- and, more preferably, a mammalian FAS DH-. The most preferred embodiment of the invention is a FAS where the active site in the DH has been inactivated by mutation. For example, Joshi et al. (J. Biol. Chem., 268, 22508 (1993)) changed the $His^{878}$ residue in the rat FAS to an alanine residue by site-directed mutagenesis. In vitro studies showed that a FAS with this change (ratFAS206) produced 3-hydroxybutyrylCoA as a premature termination product from acetyl-CoA, malonyl-CoA and NADPH.

A FAS DH- effectively replaces the β-ketothiolase and acetoacetyl-CoA reductase activities of the natural pathway by producing D(-)-3-hydroxybutyrate as a premature termination product, rather than the usual 16-carbon product, palmitic acid. This premature termination product can then be incorporated into PHB by a PHB synthase.

Another embodiment of the invention employs a recombinant Streptomyces spp. PKS to produce a variety of β-hydroxyCoA esters that can serve as monomers for a PHA synthase. One example of a DNA encoding a Type I PKS is the eryA gene cluster, which governs the synthesis of erythromycin aglycone deoxyerythronolide B (DEB). The gene cluster encodes six repeated units, termed modules or synthase units (SUs). Each module or SU, which comprises a series of putative FAS-like activities, is responsible for one of the six elongation cycles required for DEB formation. Thus, the processive synthesis of asymmetric acyl chains found in complex polyketides is accomplished through the use of a programmed protein template, where the nature of the chemical reactions occurring at each point is determined by the specificities in each SU.

Two other Type I PKS are encoded by the tyl (tylosin) and met (methymycin) gene clusters (see U.S. application Ser. No. 09/108,537, the disclosure of which is incorporated by reference herein). The macrolide multifunctional synthases encoded by tyl and met provide a greater degree of metabolic diversity than that found in the eryA gene cluster. The PKSs encoded by the eryA gene cluster only catalyze chain elongation with methylmalonylCoA, as opposed to tyl and met PKSs, which catalyze chain elongation with malonylCoA, methylmalonylCoA and ethylmalonylCoA. Specifically, the tyl PKS includes two malonylCoA extender units and one ethylmalonylCoA extender unit, and the met PKS includes one malonylCoA extender unit.

In order to manipulate the catalytic specificities within each module, DNA encoding a catalytic activity must remain undisturbed. To identify the amino acid sequences between the amino acid sequences with catalytic activity, the "linker regions," amino acid sequences of related modules, preferably those encoded by more than one gene cluster, are compared. Linker regions are amino acid sequences which are less well conserved than amino acid sequences with catalytic activity. Witkowski et al., *Eur. J. Biochem.*, 198, 571 (1991).

In an alternative embodiment of the invention, to provide a DNA encoding a Type I PKS module with a TE and lacking a functional DH, a DNA encoding a module F, containing KS, MT, KR, ACP, and TE catalytic activities, is introduced at the 3' end of a DNA encoding a first module. Module F introduces the final (R)-3-hydroxyl acyl group at the final step of PHA monomer synthesis, as a result of the presence of a TE domain. DNA encoding a module F is not present in the eryA PKS gene cluster (Donadio et al., supra, 1991).

A DNA encoding a recombinant monomer synthase is inserted into an expression vector. The expression vector employed varies depending on the host cell to be transformed with the expression vector. That is, vectors are employed with transcription, translation and/or post-translational signals, such as targeting signals, necessary for efficient expression of the genes in various host cells into which the vectors are introduced. Such vectors are constructed and transformed into host cells by methods well known in the art. See Sambrook et al., *Molecular Cloning: A Laboratory Manual*, Cold Spring Harbor (1989). Preferred host cells for the vectors of the invention include insect, bacterial, and plant cells. Preferred insect cells include *Spodoptera frugiperda* cells such as Sf21, and *Trichoplusia ni* cells. Preferred bacterial cells include *Escherichia coli*, Streptomyces and Pseudomonas. Preferred plant cells include monocot and dicot cells, such as maize, rice, wheat, tobacco, legumes, carrot, squash, canola, soybean, potato, and the like.

Moreover, the appropriate subcellular compartment in which to locate the enzyme in eukaryotic cells must be considered when constructing eukaryotic expression vectors. Two factors are important: the site of production of the acetyl-CoA substrate, and the available space for storage of the PHA polymer. To direct the enzyme to a particular subcellular location, targeting sequences may be added to the sequences encoding the recombinant molecules.

The baculovirus system is particularly amenable to the introduction of DNA encoding a recombinant FAS or a PKS monomer synthase because an increasing variety of transfer plasmids are becoming available which can accommodate a large insert, and the virus can be propagated to high titers. Moreover, insect cells are adapted readily to suspension culture, facilitating relatively large-scale recombinant protein production. Further, recombinant proteins tend to be produced exclusively as soluble proteins in insect. cells, thus, obviating the need for refolding, a task. that might be particularly daunting in the case of a large multifunctional protein. The Sf21/baculovirus system has routinely expressed milligram quantities of catalytically active recombinant fatty acid synthase. Finally, the baculovirus/insect cell system provides the ability to construct and analyze different synthase proteins for the ability to polymerize monomers into unique biodegradable polymers.

A further embodiment of the invention is the introduction of at least one DNA encoding a PHA synthase and a DNA encoding a PHA monomer synthase into a host cell. Such synthases include, but are not limited to, *A. eutrophus* 3-hydroxy, 4-hydroxy, and 5-hydroxy alkanoate synthases, *Rhodococcus ruber* $C_3$–$C_5$ hydroxyalkanoate synthases, *Pseudomonas oleororans* $C_6$–$C_4$ hydroxyalkanoate synthases, *P. putida* $C_6$–$C_4$ hydroxyalkanoate synthases, *P. aeruginosa* $C_5$–$C_{10}$ hydroxyalkanoate synthases, *P. resinovorans* $C_4$–$C_{10}$ hydroxyalkanoate synthases, *Rhodospirillum rubrum* $C_4$–$C_7$ hydroxyalkanoate syntheses, *R. gelatinorus* $C_4$–$C_7$, *Thiocapsa pfennigii* $C_4$–$C_8$ hydroxyalkanoate synthases, and *Bacillus megaterium* $C_4$–$C_5$ hydroxyalkanoate synthases.

The introduction of DNA(s) encoding more than one PHA synthase may be necessary to produce a particular PHA polymer due to the specificities exhibited by different PHA synthases. As multifunctional proteins are altered to produce unusual monomeric structures, synthase specificity may be problematic for particular substrates; Although the *A. eutrophus* PHB synthase utilizes only C4 and C5 compounds as substrates, it appears to be a good prototype synthase for initial studies since it is known to be capable of producing copolymers of 3-hydroxybutyrate and 4-hydroxybutyrate (Kunioka et al., *Macromolecules*, 22, 694 (1989)) as well as copolymers of 3-hydroxyvalerate, 3-hydroxybutyrate, and 5-hydroxyvalerate (Doi et al., *Macromolecules*, 19, 2860 (1986)). Other synthases, especially those of *Pseudomonas aeruginosa* (Timm et al., *Eur. J. Biochem.*, 209, 15 (1992)) and *Rhodococcus ruber* (Pieper et al., *FEMS Microbiol. Lett.*, 96, 73 (1992)), can also be employed in the practice of the invention. Synthase specificity may be alterable through molecular biological methods.

In yet another embodiment of the invention, a DNA encoding a FAS and a PHA synthase can be introduced into a single expression vector, obviating the need to introduce the genes into a host cell individually.

A further embodiment of the invention is the generation of a DNA encoding a recombinant multifunctional protein, which comprises a FAS, of either eukaryotic or prokaryotic origin, and a PKS module F. Module F will carry out the final chain extension to include two additional carbons and the reduction of the β-keto group, which results in a (R)-3-hydroxy acyl CoA moiety.

To produce this recombinant protein, DNA encoding the FAS TE is replaced with a DNA encoding a linker region which is normally found in the ACP-KS interdomain region of bimodular ORFs. DNA encoding a module F is then inserted 3' to the DNA encoding the linker region. Different linker regions, such as those described below which vary in length and amino acid composition, can be tested to determine which linker most efficiently mediates or allows the required transfer of the nascent saturated fatty acid intermediate to module F for the final chain elongation and keto reduction steps. The resulting DNA encoding the protein can then be tested for expression of long-chain β-hydroxy fatty acids in insect cells, such as Sf21 cells, or Streptomyces, or Pseudomonas. The expected 3-hydroxy C-18 fatty acid can serve as a potential substrate for PHA synthases which are able to accept long-chain alkyl groups. A preferred embodiment of the invention is a FAS that has a chain length specificity between 4–22 carbons.

Examples of linker regions that can be employed in this embodiment of the invention include, but are not limited to, the ACP-KS linker regions encoded by the tyl ORFI (ACP$_1$–KS$_2$; ACP$_2$–KS$_3$), and ORF3 (ACP$_5$–KS$_6$), and eryA ORFI (ACP$_1$–KS$_1$,; ACP$_2$–KS$_2$), ORF$_2$ (ACP$_3$–KS$_4$) and ORF3 (ACP$_5$–KS$_6$).

This approach can also be used to produce shorter chain fatty acid groups by limiting the ability of the FAS unit to generate long-chain fatty acids. Mutagenesis of DNA encoding various FAS catalytic activities, starting with the KS, may result in the synthesis of short-chain (R)-3-hydroxy fatty acids.

The PHA polymers are then recovered from the biomass. Large-scale solvent extraction can be used, but is expensive. An alternative method involving heat shock with subsequent enzymatic and detergent digestive processes is also available (Byron, *Trends Biotechnical*, 5, 246 (1987); Holmes, In: *Developments in Crystalline Polymers*, D. C. Bassett (ed.), pp. 1–65 (1988)). PHB and other PHAs are readily extracted from microorganisms by chlorinated hydrocarbons. Refluxing with chloroform has been extensively used; the resulting solution is filtered to remove debris and concentrated, and the polymer is precipitated with methanol or ethanol, leaving low-molecular-weight lipids in solution. Longer side-chain PHAs show a less restricted solubility than PHB and are, for example, soluble in acetone. Other strategies adopted include the use of ethylene carbonate and propylene carbonate as disclosed by Lafferty et al. (*Chem. Rundschau*, 30, 14 (1977)) to. extract PHB from biomass. Scandola et al. (*Int. J. Biol. Microbiol.*, 10, 373 (1988)) reported that 1 M HCl-chloroform extraction of Rhizobium meliloti yielded PHB of $M_w$=6×10$^4$ compared with 1.4×10$^6$ when acetone was used.

Methods are well known in the art for the determination of the PHB or PHA content of microorganisms, the composition of PHAs, and the distribution of the monomer units in the polymer. Gas chromatography and high-pressure liquid chromatography are widely used for quantitative PHB analysis. See Anderson et al., *Microbiol. Rev.*, 54, 450 (1990) for a review of such methods. NMR techniques can also be used to determine polymer composition, and the distribution of monomer units.

Variants of the Nucleic Acid Molecules of the Invention

The present invention contemplates nucleic acid sequences which hybridize under low, medium or high stringency hybridization conditions to the exemplified nucleic acid sequences set forth herein. Hybridization conditions are well known in the art. Thus, nucleic acid sequences encoding variant polypeptides, i.e., those having at least one amino acid substitution, insertion, addition or deletion, or nucleic acid sequences having conservative (e.g., silent) nucleotide substitutions (see FIGS. 24–25), are within the scope of the invention. Preferably, variant polypeptides encoded by the nucleic acid sequences of the invention are biologically active. The present invention also contemplates naturally occurring allelic variations and mutations of the nucleic acid sequences described herein.

As is well known in the art, because of the degeneracy of the genetic code, there are numerous other DNA and RNA molecules that can code for the same polypeptides as those encoded by the exemplified biosynthetic genes and fragments thereof. The present invention, therefore, contemplates those other DNA and RNA molecules which, on expression, encode the polypeptides of, for example, portions of SEQ ID NO:96. Having identified the amino acid residue sequence encoded by a mitomycin, sugar or polyketide biosynthetic gene, and with knowledge of all triplet codons for each particular amino acid residue, it is possible to describe all such encoding RNA and DNA sequences. DNA and. RNA molecules other than those specifically disclosed herein and,.which molecules are characterized simply by a change in a codon for a particular amino acid, are within the scope of this invention.

The 20 common amino acids and their representative abbreviations, symbols and codons are well known in the art (see, for example, *Molecular Biology of the Cell*, Second Edition, B. Alberts et al., Garland Publishing Inc., New York and London, 1989). As is also well known in the art, codons constitute triplet sequences of nucleotides in mRNA molecules and as such, are characterized by the base uracil (U) in place of base thymidine (T) which is present in DNA molecules. A simple change in a codon for the same amino acid residue within a polynucleotide will not change the structure of the encoded polypeptide. By way of example, it can be seen from SEQ ID NO:16 that a TCA codon for serine exists at nucleotide positions 146–148. However, serine can be encoded by a TCT codon, and a TCC codon. Substitution of the latter codons for serine with the TCA codon for serine or vice versa, does not substantially alter the DNA sequence of SEQ ID NO:16 and results in production of the same polypeptide. In a similar manner, substitutions of the recited codons with other equivalent codons can be made in a like manner without departing from the scope of the present invention.

A nucleic acid molecule, segment or sequence of the present invention can also be an RNA molecule, segment or sequence. An RNA molecule contemplated by the present invention corresponds to, is complementary to or hybridizes under low, medium or high stringency conditions to, any of the DNA sequences set forth herein. Exemplary and preferred RNA molecules are mRNA molecules that comprise at least one mitomycin, sugar or polyketide biosynthetic gene of this invention.

Mutations can be made to the native nucleic acid sequences of the invention and such mutants used in place of the native sequence, so long as the mutants are able to function with other sequences to collectively catalyze the synthesis of an identifiable sugar, polyketide or mitomycin. Such mutations can be made to the native sequences using conventional techniques such as by preparing synthetic oligonucleotides including the mutations and inserting the mutated sequence into the gene using restriction endonuclease digestion. (See, e.g., Kunkel, T. A. *Proc, Natl. Acad. Sci. USA* (1985) 82:448; Geisselsoder et al. *BioTechniques* (1987) 5:786. ) Alternatively, the mutations can be effected using a mismatched primer (generally 10–30 nucleotides in length) which hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. Zoller and Smith, *Methods Enzymol.*, (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al., *Proc. Natl. Acad. Sci. USA* (1982) 79:6409. PCR mutagenesis will also find use for effecting the desired mutations.

Random mutagenesis of the nucleotide sequence can be accomplished by several different techniques known in the art, such as by altering sequences within restriction endonuclease sites, inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants or by damaging plasmid DNA in vitro with chemicals. Chemical mutagens include, for example, sodium bisulfite, nitrous acid, hydroxylamine, agents which damage or remove bases thereby preventing normal base-pairing such as hydrazine or formic acid, analogues of nucleotide precursors such as nitrosoguanidine, 5-bromouracil, 2-aminopurine, or acridine intercalating agents such as proflavine, acriflavine, quinacrine, and the like. Generally, plasmid DNA or DNA fragments are treated with chemicals, transformed into E. coli and propagated as a pool or library of mutant plasmids.

Large populations of random enzyme variants can be constructed in vivo using "recombination-enhanced mutagenesis." This method employs two or more pools of, for example, $10^6$ mutants each of the wild-type encoding nucleotide sequence that are generated using any convenient mutagenesis technique and then inserted into cloning vectors.

Chimeric Expression Cassettes, Vectors and Host Cells of the Invention

As used herein, "chimeric" means that a vector comprises DNA from at least two different species, or comprises DNA from the same species, which is linked or associated in a manner which does not occur in the "native" or wild type of the species. The recombinant DNA sequence or segment, used for transformation herein, may be circular or linear, double-stranded or single-stranded. Generally, the DNA sequence or segment is in the form of chimeric DNA, such as plasmid DNA, that can also contain coding regions flanked by control sequences which promote the expression of the DNA present in the resultant transformed (recombinant) host cell. Aside from DNA sequences that serve as transcription units for the nucleic acid molecules of the invention or portions thereof, a portion of the DNA may be untranscribed, serving a regulatory or a structural function. For example, the preselected DNA may. itself comprise a promoter that is active in a particular host cell.

Other elements functional in the host cells, such as introns, enhancers, polyadenylation sequences and the like, may also be a part of the DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers. Other regulatory sequences may also be desirable which allow for regulation of expression of the genes relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

"Operably linked" is defined to mean that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Expression of the reporter gene is assayed at a suitable time after the DNA has been introduced into the recipient cells.

Prokaryotic expression systems are preferred, and in particular, systems compatible with Streptomyces spp. are of particular interest. Control elements for use in such systems include promoters, optionally containing operator sequences, and ribosome binding sites. Particularly useful promoters include control sequences derived from the gene clusters of the invention. However, other bacterial promoters, such as those derived from sugar metabolizing enzymes, such as galactose, lactose (lac) and maltose, will also find use in the expression cassettes encoding desosamine. Preferred promoters are Streptomyces promoters, including but not limited to the ermE*, pikA, and tipA promoters. Additional examples include promoter sequences derived from biosynthetic enzymes such as tryptophan (trp), the β-lactamase (bla) promoter system, bacteriophage lambda PL, and T5. In addition, synthetic promoters, such as the tac promoter (U.S. Pat. No. 4,551,433), which do not occur in nature, also function in bacterial host cells.

The various nucleic acid molecules of interest can be cloned into one or more recombinant vectors as individual cassettes, with separate control elements, or under the control of, e.g., a single promoter. The nucleic acid molecules can include flanking restriction sites to allow for the easy deletion and insertion of other sequences. The design of such unique restriction sites is known to those of skill in the art and can be accomplished using the techniques, such as site-directed mutagenesis and PCR.

For sequences generated by random mutagenesis, the choice of vector depends on the pool of mutant sequences, i.e., donor or recipient, with which they are to be employed. Furthermore, the choice of vector determines the host cell to be employed in subsequent steps of the claimed method. Any transducible cloning vector can be used as a cloning vector for the donor pool of mutants. It is preferred, however, that phagemids, cosmids, or similar cloning vectors be used for cloning the donor pool of mutant encoding nucleotide sequences into the host cell. Phagemids and cosmids, for example, are advantageous vectors due to the ability to insert and stably propagate therein larger fragments of DNA than in M13 phage and λ phage, respectively. Phagemids which will find use in this method generally include hybrids between plasmids and filamentous phage cloning vehicles. Cosmids which will find use in this method generally include λ phage-based vectors into which cos sites have been inserted. Recipient pool cloning vectors can be any suitable plasmid. The cloning vectors into which pools of mutants are inserted may be identical or may be constructed to harbor and express different genetic markers (see, e.g., Sambrook et al., supra). The utility of employing such vectors having different marker genes may be exploited to facilitate a determination of successful transduction.

Thus, for example, the cloning vector employed may be an *E. coli*/Streptomyces shuttle vector (see, for example, U.S. Pat. Nos. 4,416,994, 4,343,906, 4,477,571, 4,362,816, and 4,340,674), a cosmid, a plasmid, an artificial bacterial chromosome (see, e.g., Zhang and Wing, *Plant Mol. Biol.*, 35, 115 (1997); Schalkwyk et al., *Curr. Op. Biotech.*, 6, 37 91995); and Monaco and Lavin, *Trends in Biotech.*, 12, 280 (1994), or a phagemid, and the host cell may be a bacterial cell such as *E. coli, Penicillium patulum*, and Streptomyces spp. such as *S. lividans, S. venezuelae*, or *S. lavendulae*, or a eukaryotic cell such as fungi, yeast or a plant cell, e.g., monocot and dicot cells, preferably cells that are regenerable.

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual*, Cold Spring Harbor Laboratory Press (2d ed., 1989), provides suitable methods of construction.

The recombinant DNA can be readily introduced into the host cells by any procedure useful for the introduction into a particular cell, e.g., calcium phosphate precipitation, protoplast fusion, conjugation, lipofection, electroporation, and the like.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. In particular, the cell line or host cell may be of mammalian, plant, insect, yeast, fungal or bacterial origin.

"Transfected" or "transformed" is used herein to include any host cell or cell line, the genome of which has been altered or augmented by the presence of at least one DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering. The transfected DNA may be maintained as an extrachromosomal element or as an element which is stably integrated into the host chromosome.

Moreover, recombinant polypeptides having a particular activity may be prepared via "gene-shuffling". See, for example, Crameri et al., *Nature*, 391, 288 (1998); Patten et al., *Curr. Op. Biotech.*, 8, 724 (1997), U.S. Pat. Nos. 5,837,458, 5,834,252, 5,830,727, 5,811,238, 5,605,793).

For phagemids, upon infection of the host cell which contains a phagemid, single-stranded phagemid DNA is produced, packaged and extruded from the cell in the form of a transducing phage in a manner similar to other phage vectors. Thus, clonal amplification of mutant encoding nucleotide sequences carried by phagemids is accomplished by propagating the phagemids in a suitable host cell.

Following clonal amplification, the cloned donor pool of mutants is infected with a helper phage to obtain a mixture of phage particles containing either the helper phage genome or phagemids mutant alleles of the wild-type encoding nucleotide sequence.

Infection, or transfection, of host cells with helper phage is generally accomplished by methods well known in the art (see., e.g., Sambrook et al., supra; and Russell et al. (1986) *Gene* 45:333–338).

The helper phage may be any phage which can be used in combination with the cloning phage to produce an infective transducing phage. For example, if the cloning vector is a cosmid, the helper phage will necessarily be a λ phage. Preferably, the cloning vector is a phagemid and the helper phage is a filamentous phage, and preferably phage M13.

If desired after infecting the phagemid with helper phage and obtaining a mixture of phage particles, the transducing phage can be separated from helper phage based on size difference (Barnes et al. (1983) *Methods Enzymol.* 101:98–122), or other similarly effective technique.

The entire spectrum of cloned donor mutations can now be transduced into clonally amplified recipient cells into which has been transduced or transformed a pool of mutant encoding nucleotide sequences. Recipient cells which may be employed in the method disclosed and claimed herein may be, for example, *E. coli*, or other bacterial expression systems which are not recombination deficient. A recombination deficient cell is a cell in which recombinatorial events is greatly reduced, such as rec⁻ mutants of *E. coli* (see, Clark et al. (1965) *Proc. Natl. Acad. Sci. USA* 53:451–459).

These transductants can now be selected for the desired expressed protein property or characteristic and, if necessary or desirable, amplified. Optionally, if the phagemids into which each pool of mutants is cloned are constructed to express different genetic markers, as described above, transductants may be selected by way of their expression of both donor and recipient plasmid markers.

The recombinants generated by the above-described methods can then be subjected to selection or screening by any appropriate method, for example, enzymatic or other biological activity.

The above cycle of amplification, infection, transduction, and recombination may be repeated any number of times using additional donor pools cloned on phagemids. As above, the phagemids into which each pool of mutants is cloned may be constructed to express a different marker gene. Each cycle could increase the number of distinct mutants by up to a factor of $10^6$. Thus, if the probability of occurrence of an inter-allelic recombination event in any individual cell is f (a parameter that is actually a function of the distance between the recombining mutations), the transduced culture from two pools of $10^6$ allelic mutants will express up to $10^{12}$ distinct mutants in a population of $10^{12}/f$ cells.

Preparation, Isolation and Modification of the Polypeptides of the Invention

The present isolated, purified polypeptides, variants or fragments thereof, can be synthesized in vitro, e.g., by the solid phase peptide synthetic method or by recombinant DNA approaches (see above). The solid phase peptide synthetic method is an established and widely used method, which is described in the following references: Stewart et al., *Solid Phase Peptide Synthesis*, W. H. Freeman Co., San Francisco (1969); Merrifield, *J. Am. Chem, Soc.*, 85 2149 (1963); Meienhofer in "Hormonal Proteins and Peptides," ed.; C. H. Li, Vol. 2 (Academic Press, 1973), pp. 48–267; Bavaay and Merrifield, "The Peptides," eds. E. Gross and F. Meienhofer, Vol. 2 (Academic Press, 1980) pp. 3–285; and Clark-Lewis et al., *Meth. Enzymol.*, 287, 233 (1997). These polypeptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

In particular, fusion polypeptides are prepared which comprise an amino acid sequence useful in purification, e.g., a His tag is useful to purify fusion polypeptides on nickel columns. Once isolated and characterized, derivatives, e.g., chemically derived derivatives, of a given polypeptide can be readily prepared. For example, amides of the polypeptides of the present invention may also be prepared by techniques well known in the art for converting a carboxylic acid group or precursor, to an amide. A preferred method for amide formation at the C-terminal carboxyl group is to cleave the polypeptide from a solid support with an appropriate amine, or to cleave in the presence of an alcohol, yielding an ester, followed by aminolysis with the desired amine.

Salts of carboxyl groups of a polypeptide or polypeptide variant of the invention may be prepared in the usual manner by contacting the polypeptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the polypeptide or polypeptide variants may be prepared by utilizing an N-acyl protected amino acid for the final condensation, or by acylating a protected or unprotected polypeptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

One or more of the residues of the polypeptide can be altered, so long as the polypeptide variant is biologically active. For example, it is preferred that the variant has at least about 1% of the biological activity of the corresponding non-variant polypeptide, e.g. Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional polypeptide can readily be determined by assaying the specific activity of the polypeptide variant.

Conservative substitutions are shown in FIG. 25 under the heading of exemplary substitutions. More preferred substitutions are under the heading of preferred substitutions. After the substitutions are introduced, the variants are screened for biological activity.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic; trp, tyr, phe.

The invention also envisions polypeptide variants with non-conservative substitutions. Non-conservative substitutions entail exchanging a member of one of the classes described above for another.

Acid addition salts of the polypeptide or variant polypeptide or of amino residues of the polypeptide or variant polypeptide may be prepared by contacting the polypeptide or amine with one or more equivalents of the desired inorganic or organic acid, such as, for example, hydrochloric acid. Esters of carboxyl groups of the polypeptides may also be prepared by any of the usual methods known in the art.

Antibodies of the Invention

The antibodies of the invention are prepared by using standard techniques. To prepare polyclonal antibodies or "antisera," an animal is inoculated with an antigen that is an isolated and purified polypeptide of the invention, and immunoglobulins are recovered from a fluid, such as blood serum, that contains the immunoglobulins, after the animal has had an immune response. For inoculation, the antigen is preferably bound to a carrier peptide and emulsified using a biologically suitable emulsifying agent, such as Freund's incomplete adjuvant. A variety of mammalian or avian host organisms may be used to prepare polyclonal antibodies Following immunization, Ig is purified from the immunized bird or mammal, e.g., goat, rabbit, mouse, rat, or donkey and the like. For certain applications, it is preferable to obtain a composition in which the antibodies are essentially free of antibodies that do not react with the immunogen. This composition is composed virtually entirely of the high titer, monospecific, purified polyclonal antibodies to the antigen. Antibodies can be purified by affinity chromatography. Purification of antibodies by affinity chromatography is generally known to those skilled in the art (see, for example, U.S. Pat. No. 4,533,630). Briefly, the purified antibody is contacted with the purified polypeptide, or a peptide thereof, bound to a solid support for a sufficient time and under appropriate conditions for the antibody to bind to the polypeptide or peptide. Such time and conditions are readily determinable by those. skilled in the art. The unbound, unreacted antibody is then removed, such as by washing. The bound antibody is then recovered from the column by eluting the antibodies, so as to yield purified, monospecific polyclonal antibodies.

Monoclonal antibodies can be also prepared, using known hybridoma cell culture techniques. In general, this method involves preparing an antibody-producing fused cell line, e.g., of primary spleen cells fused with a compatible continuous line of myeloma cells, and growing the fused cells either in mass culture or in an animal species, such as a murine species, from which the myeloma cell line used was derived or is compatible. Such antibodies offer many advantages in comparison to those produced by inoculation of animals, as they are highly specific and sensitive and relatively "pure" immunochemically. Immunologically active fragments of the present antibodies are also within the scope of the present invention, e.g., the F(ab) fragment, scFv antibodies, as are partially humanized monoclonal antibodies.

Thus, it will be understood by those skilled in the art that the hybridomas herein referred to may be subject to genetic mutation or other changes while still retaining the ability to produce monoclonal antibody of the same desired specificity. The present invention encompasses mutants, other derivatives and descendants of the hybridomas.

It will be further understood by those skilled in the art that a monoclonal antibody may be subjected to the techniques of recombinant DNA technology to produce other derivative antibodies, humanized or chimeric molecules or antibody fragments which retain the specificity of the original monoclonal antibody. Such techniques may involve combining DNA encoding the immunoglobulin variable region, or the complementarity determining regions (CDRs), of the monoclonal antibody with DNA coding the constant regions, or constant regions plus framework regions, of a different immunoglobulin, for example, to convert a mouse-derived monoclonal antibody into one having largely human immunoglobulin characteristics (see EP 184187A, 2188638A, herein incorporated by reference).

The antibodies of the invention are useful for detecting or determining the presence or amount of a polypeptide of the invention in a sample. The antibodies are contacted with the sample for a period of time and under conditions sufficient for antibodies to bind to the polypeptide so as to form a binary complex between at least a portion of said antibodies and said polypeptide. Such times, conditions and reaction media can be readily determined by persons skilled in the art.

For example, the cells are lysed to yield an extract which comprises cellular proteins. Alternatively, intact cells are permeabilized in a manner which permits macromolecules, i.e., antibodies, to enter the cell. The antibodies of the invention are then incubated with the protein extract, e.g., in a Western blot, or permeabilized cells, e.g., prior to flow cytometry, so as to form a complex. The presence or amount of the complex is then determined or detected.

The antibodies of the invention may also be coupled to an insoluble or soluble substrate. Soluble substrates include proteins such as bovine serum albumin. Preferably, the antibodies are bound to an insoluble substrate, i.e., a solid support. The antibodies are bound to the support in an amount and manner that allows the antibodies to bind the polypeptide (ligand). The amount of the antibodies used relative to a given substrate depends upon the particular antibody being used, the particular substrate, and the binding efficiency of the antibody to the ligand. The antibodies may be bound to the substrate in any suitable manner. Covalent, noncovalent, or ionic binding may be used. Covalent bonding can be accomplished by attaching the antibodies to reactive groups on the substrate directly or through a linking moiety.

The solid support may be any insoluble material to which the antibodies can be bound and which may be conveniently used in an assay of the invention. Such solid supports include permeable and semipermeable membranes, glass beads, plastic beads, latex beads, plastic microtiter wells or tubes, agarose or dextran particles, sepharose, and diatomaceous earth. Alternatively, the antibodies may be bound to any porous or liquid permeable material, such as a fibrous (paper, felt etc.) strip or sheet, or a screen or net. A binder may be used as long as it does not interfere with the ability of the antibodies to bind the ligands.

The invention will be further described by the following examples.

EXAMPLE 1

Molecular Characterization and Analysis of the mit/mmc Biosynthetic Gene Cluster Materials and Methods Bacterial Strains and Cloning Vectors

*S. lavendulae* NRRL 2564 was used as the source strain for cosmid library construction and the creation of gene disruption mutants. *E. coli* DH5α was used as the host strain for constructing the library and subsequent DNA manipulation. *E. coli* strain S17-1 (Mazodier et al., 1989) served as the conjugative host for introducing foreign DNA into *S. lavendulae*. The cosmid library was constructed with the *E. coli*/Streptomyces shuttle vector pNJ1 (Tuan et al., 1990), and pUC119 was routinely used as a vector for subcloning and sequencing. The conjugative *E. coli*/Streptomyces shuttle vector pKC1139 (Bierman et al., 1992) was used for gene disruption in *S. lavendulae*.

DNA Manipulation

Standard in vitro techniques were used for DNA manipulation (Sambrook et al., 1989). *S. lavendulae* genomic DNA was harvested by standard procedures (Hopwood et al., 1985).

A library of size-fractionated genomic DNA in pNJ1 (Tuan et al., 1990) was screened with the rifamycin AHBA synthase (rifK) gene probe from *Amycolatopsis mediterra-*

*nei* (Kim et al., 1998). Through subsequent cosmid walking, a contiguous 120 kb region of *S. lavendulae* chromosomal DNA containing the putative mitomycin biosynthetic genes was mapped. M13 forward and reverse primers were used for sequencing (Gibco BRL, Gaithersburg, Md.). To accomplish this, individual fragments of less than 5 kb were subcloned into pUC 119 and serial deletion subclones were generated using the exonuclease III Erase-a Base System (Promega, Madison, Wis.).

DNA Sequencing and Analysis

Automatic DNA sequencing was done with the ABI PRISM™ Dye Terminator Cycle Sequencing Ready Reaction Kit (Applied Biosystems, Warrington, U.K.), and analyzed on an Applied Biosystems mode 377 DNA Sequencer at the University of Minnesota Advanced Genetic Analysis Center. Both DNA strands were sequenced redundantly a minimum of three times. Sequence compilation was performed with MacVector (Oxford Molecular Group, Mountain View, Calif.) and GeneWorks (Oxford Molecular Group) software, and sequence homology analysis was accomplished with Blast (Altschul et al., 1990) and GCG programs (Devereux et al., 1984).

Disruption Mutants Construction

A 1.4 kb ApaL1-HindIII fragment from pFD666 (Denis and Brzezinski, 1998) containing the aphII gene for kanamycin resistance was routinely used as the selection marker for the creation of gene disruption constructs. The target genes were subcloned into pUC119, cut at a unique internal restriction site, blunt-ended, and ligated with the end-blunted selection marker. The inserts were then transferred from pUC119 to pKC1139, and conjugated into wild-type *S. lavendulae*. Transconjugants were selected on AS1 plates (Baltz, 1980), overlaid with apramycin, kanamycin, and nalidixic acid followed by propagation on R5T plates (g/L: sucrose 12 1.1, $K_2SO_4$ 0.3, $MgCl_2 \cdot 6H_2O$ 11.92, glucose 11.8, yeast extract 5.89, casamino acids 0.12, trace elements 2.35 ml (Hopwood et al., 1985), agar 25.9, after autoclaving the following solutions were added: 0.5% $KH_2PO_4$ 11.8 ml, 5 M $CaCl_2$ 4.71 ml, 1 N NaOH 8.25 ml) at 37° C. for several generations. Disruption mutants were selected based on the phenotype changing from apramycin and kanamycin resistant to apramycin sensitive and kanamycin resistant. Replacement of the chromosomal copy of the target gene with the disrupted plasmid-born copy was confirmed by Southern blot hybridization.

Mitomycin C Analysis

MC production was evaluated using 3-day cultures in Nishikohri media (Nishikohri and Fukui, 1978). The culture broth was extracted twice with equal volumes of ethyl acetate. After removing the chemical solvent by vacuum, the crude broth extract was dissolved in 50% methanol and 50% 50 mM pH 7.2 Tris buffer and monitored by HPLC ($C_{18}$ reverse phase column) at 363 mn. A continuous methanol gradient from 20% to 60% in methanol/50 mM pH 7.2 Tris buffer system over 24 minutes was employed to resolve MC from other crude extract components. A 90% $CHCl_3$/10% MeOH solvent system was used to resolve and detect MC on TLC plates.

Results

Identification of the Mitomycin Biosynthetic Gene Cluster

Figure 2:
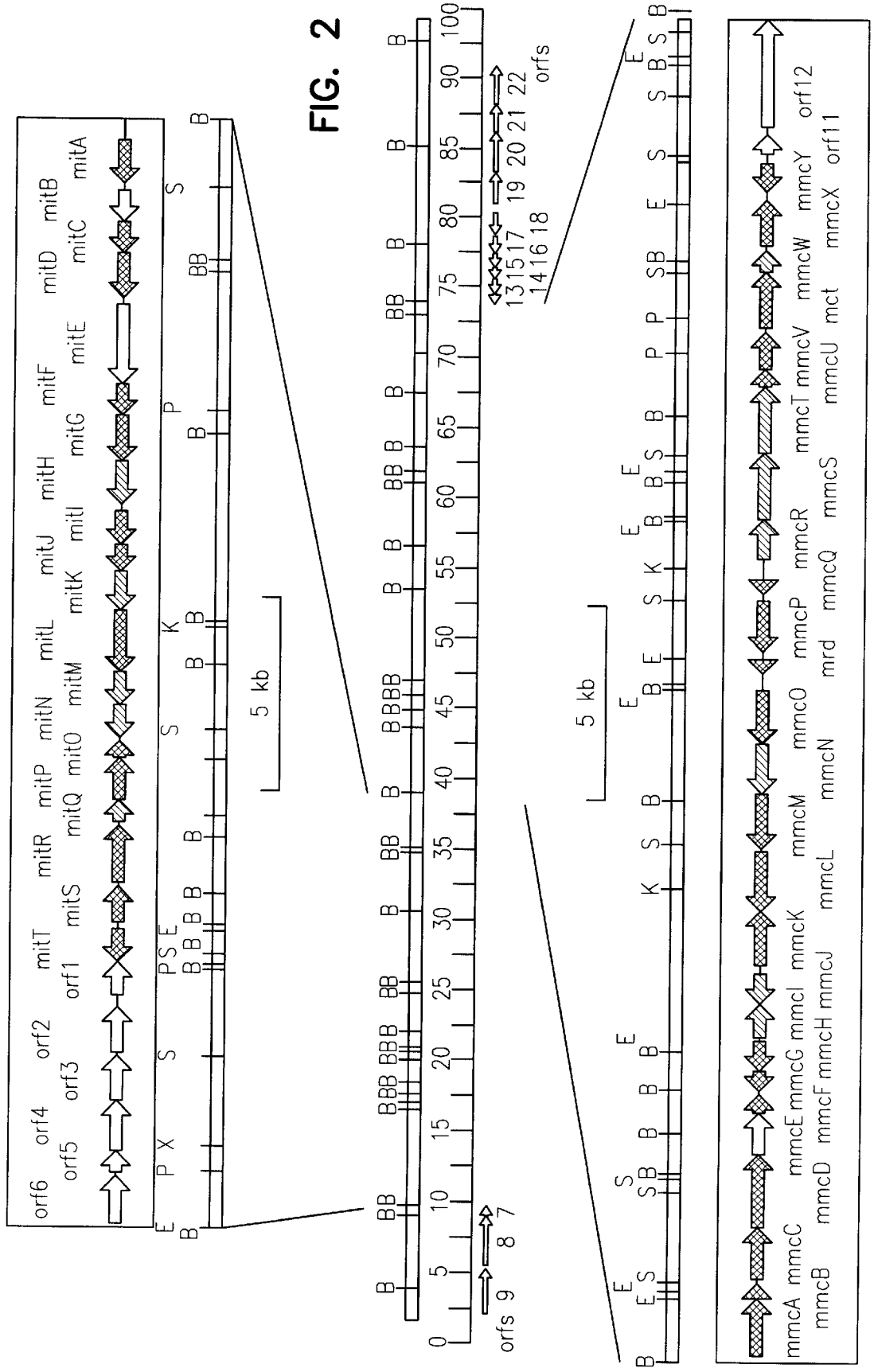
FIG. 2. Organization of the mitomycin gene cluster. The deduced ORFs are drawn to scale, and their corresponding genes are marked in italics. The filled bars indicate the location of the mitomycin cluster. Abbreviations of the restriction enzymes: B: BamHI, S: SphI, P: PstI, E: EcoRI, X: XhoI, K: KpnI.

The mitomycin cluster was identified by linkage of a cosmid clone containing mrd and a gene (mitA) that hybridized with the rifK-gene encoding the rifamycin AHBA synthase (Kim et al., 1998) from *Amycolatopsis mediterranei*. mitA was subsequently shown to be essential for mitomycin biosynthesis since genetic disruption of the chromosomal copy blocked MC production, and could be complemented with exogenous AHBA (Example 2). Linkage of mitA with one of the mitomycin resistance genes (mrd) implied that the corresponding biosynthetic genes were adjacent to mitA. Cosmid walking was used to obtain overlapping DNA fragments spanning more than 120 kb of the *S. lavendulae* chromosome adjacent to mitA. Subsequent nucleotide sequence analysis included 55-kb of contiguous DNA, revealing 47 genes involved in mitomycin assembly, regulation and resistance (FIGS. 2 and 5).

TABLE 1

MC production in wild-type *S. lavendulae* and gene disruption mutants

| No. | gene disrupted | MC production |
| --- | --- | --- |
| 0.0 | Wild-type control | ++ |
| 0.1 | additional copy of orf1 in wild-type | ++ |
| 1 | orf8 | ++ |
| 2 | orf4 | ++ |
| 3 | orf1 | ++ |
| 4 | mitR | + |
| 5 | mitM | – |
| 6 | mitI | – |
| 7 | mitH | – |
| 8 | mitE | – |
| 9 | mitB | – |
| 10 | mitA | – |
| 11 | mmcA | – |
| 12 | mmcB | – |
| 13 | mmcM | ++ |
| 14 | mmcP | – |
| 15 | mmcR | – |
| 16 | mmcT | – |
| 17 | mmcW | ++++ |
| 18 | mmcX | ++++ |
| 19 | orf11 | ++ |
| 20 | orf12 | ++ |
| 21 | orf16 | ++ |
| 22 | orf19 | ++ | mitT Defines the Left-hand Boundary of the Mitomycin Cluster

Nucleotide sequence analysis extended 30 kb downstream of mitA and revealed a set of genes corresponding to a type I polyketide synthase (PKS, orf9, SEQ ID NO:18, orf8, SEQ ID NO:19) and thioesterase (TEII, orf7, SEQ ID NO:20). MC is not derived from the polyketide pathway, and thus an orf8 disruption mutant showed normal MC production as expected (Table 1). Approximately 20 kb downstream of mitA, two genes (mitt, SEQ ID NO:29 and mitS, SEQ ID NO:30) encoding a putative aminoquinate dehydrogenase and glucose kinase, respectively, were located. Both are believed to be involved in AHBA biosynthesis since their equivalents are also present in the rifamycin biosynthetic gene cluster (rifcluster) (August et al., 1998). However, whether the six genes between orf7 and mitT are involved in MC biosynthesis remained unclear, since the two putative hydroxylases (orf3, SEQ ID NO:24 and orf4, SEQ ID NO:22) and the candidate activator gene (orf1, SEQ ID NO:26) could play a role in MC production. Both orf3 and orf4 are predicted to encode cytochrome P450 monooxygenases with Orf4 most similar to OleP and RapN (50% identity, 63% similarity) for oleandomycin and rapamycin biosynthesis, respectively (Rodriguez et al., 1995; Schwecke et al., 1995). Orf3 shows a high degree of similarity to cytochrome P450 105C1 (49% identity, 64% similarity) in Streptomyces sp. and cytochrome P450–SU2 in *Streptomyces griseolus* (Horii et al., 1990; Omer et al., 1990).

Database analysis revealed that Orf1 belonged to the ActII-ORF4, RedD, DnrI and CcaR family of Streptomyces antibiotic pathway specific activators regulating the production of actinorhodin, undecylprodigiosin, daunorubicin, and cephamycin, respectively (Fernandez-Moreno et al., 1991; Perez-Laraine et al., 1997; Takano et al., 1992; Tang et al., 1996; Wietzorrek and Bibb; 1997). A common feature of this group of activators is that disruption of the corresponding gene abolishes the production of the corresponding antibiotic while overexpression results in a several-fold increase in metabolite production. However, when orf1 was disrupted, the mutant strain showed normal MC production (Table 1). Moreover, the wild-type MC producer containing an additional copy of orf1 in pKC1139 also had a normal MC production profile (Table 1). Interestingly, orf4, one of the cytochrome P450 monooxygenase encoding genes adjacent to orf1 also showed normal MC production when disrupted (Table 1). Thus, mitT appears to map to the left-hand end of the mitomycin cluster, while orf1 to orf9 presumably specify biosynthesis of a polyketide product.

mmcY Defines the Right-hand Boundary of the Mitomycin Cluster

Nucleotide sequence analysis of the mitomycin biosynthetic gene cluster extended 30 kb upstream of mitA and several orfs corresponding to genes involved in sugar metabolism were identified. They included an acid trehalase (orf12, SEQ ID NO:28), one ABC type transporter (orf16, SEQ ID NO:79), and four adjacent α-amylases (orf19, SEQ ID NO:82; orf20, SEQ ID NO:83; orf21, SEQ ID NO:84; orf22, SEQ ID NO:85) for starch degradation spanning more than 18 kb (FIG. 2). Disruption of four genes (orf11, SEQ ID NO:27; orf12, SEQ ID NO:28; orf16, SEQ ID NO:79; orf19, SEQ ID NO:82) within this region resulted in mutants with wild-type level MC production profiles, indicating that they fall outside of the mitomycin cluster (Table 1). At the beginning of this group of sugar metabolism genes, a gene (mmcY, SEQ ID NO:73) encoding a presumed chitinase is proposed to be the upstream terminus of the mitomycin cluster. This is evident because mitomycin requires D-glucosamine as a biosynthetic precursor, and MmcY shows 75% identity (85% similarity) with the chitinase C gene (chiC) product from *S. griseus* that generates N-acetylglucosamine from chitin (Ohno et al., 1996). In addition, mutants with disrupted orf11 and orf12 genes had no effect on MC production, while disruption of mmcW (SEQ ID NO:71) and mmcX(SEQ ID NO:72) both affected MC production significantly (Table 1).

Mitomycin Resistance Genes

Antibiotic biosynthetic gene clusters typically include one or more genes for cellular self-protection (Seno and Baltz, 1989). Previous work has identified two mitomycin C resistance genes (mcr and mrd) with mrd linked to mitA (August et al., 1994; Sheldon et al., 1997; Example 2). Subsequent analysis showed that MRD is a resistance protein that binds mitomycin C with 1:1 stoichiometry (Sheldon et al., 1997). However, this resistance mechanism would be extremely inefficient unless the bound drug is transported out of the cell. Indeed, 5 kb upstream of mrd, the mct gene (SEQ ID NO:16, putative mitomycin translocase) encoding a presumed antibiotic transporter was found and shown to be a third resistance component (Example 3). mct encodes 484 amino-acid protein with 14 predicted transmembrane domains. Disruption of mct resulted in a mutant *S. lavendulae* strain substantially more sensitive to MC, while coexpression of mct with mrd in *E. coli* dramatically increased MC resistance levels compared to individual expression of the genes (Example 3). In contrast, the high-level MC resistance gene (mcrA) that encodes an MC oxidase (MCRA) capable of re-oxidizing activated MC (Johnson et al., 1997) is not linked with this cluster (August et al., 1990; Example 2). Interestingly, database searches identified two McrA homologues (MitR, MmcM) within the MC cluster, both of which encode putative flavoproteins conserved in the FMN/FAD binding motif. MitR displayed weak similarity with McrA (26% identity, 33% similarity), while MmcM showed end-to-end (54% identity, 69% similarity) alignment with the protein. mitR (SEQ ID NO:31) and mmcM (SEQ ID NO:61) were genetically disrupted giving substantially decreased MC production in the mitR mutant strain, in contrast to the mmcM mutant which displayed wild type MC production levels (Table 1).

Regulatory Genes

Two genes, mitQ (SEQ ID NO:32) and mmcW(SEQ ID NO:71), were identified in the mitomycin cluster and are presumed to be pathway-specific regulators. MitQ belongs to the OmpR-PhoB subfamily of DNA binding regulators in the two-component regulatory system, with the greatest similarity to members of the phosphate assimilation pathway (PhoR-PhoB) (Makino et al., 1986), ferric enterobactin response pair (PfeR-PfeS) (Dean et al., 1996), and one histidine protein kinase—response regulator system (HpkA-DrrA) from *Thermotoga maritima* (Lee and Stock, 1996). In contrast to the MitQ group of regulators that typically serve as transcriptional activators (Mizuno and Tanaka, 1997), MmcW showed high sequence similarity with the MarR groups of repressors. The most significant similarity corresponds to EmrR, the negative regulator of the *E. coli* multidrug resistance pump EmrAB (Lomovskaya et al., 1995), and Pacs, a repressor for pectinase, cellulase, and blue pigment production in *Erwinia chrysanthemi* (Praillet et al., 1996). Significantly, the mmcW disruption mutant displayed a several-fold increase in MC production (Table 1).

AHBA Biosynthetic Genes

Precursor incorporation studies previously demonstrated that AHBA is an intermediate for both the ansamycin and mitomycin natural products (Becker et al., 1983; Example 2). Combining the biochemical, enzymatic and molecular genetic results on the biosynthesis of the ansamycin antibiotic rifamycin, Floss has proposed that AHBA is derived from the ammoniated shikimate pathway via phosphenolpyruvate (PEP) and erythose 4-phosphate (E4P) by the early incorporation of nitrogen (Kim et al., 1996). In the shikimate pathway, PEP and E4P is first converted to 3-deoxy-D-arabino-heptulosonic acid-7-phosphate (DAHP) then stepwise transformed to 3-dehydroquinate (DHQ), 3-dehydroshikimate (DHS) and shikimate, catalyzed by DAHP synthase, DHQ synthase, DHQ dehydratase, and shikimate dehydrogenase, respectively (Dewick, 1998). Quinate can also enter the pathway by the action of quinate dehydrogenase to generate DHQ.

Evidence to support this new variant of the shikimate pathway includes the following experimental observations.

First, all proposed ammoniated shikimate pathway compounds including PEP, E4P, 3,4-dideoxy-4-amino-D-arabino-heptulosonic acid 7-phosphate (aminoDAHP), 5-deoxy-5-amino-3-dehydroquinic acid (aminoDHQ), and 5-deoxy-5-amino-3-dehydroshikimic acid (aminoDHS) can be readily converted into AHBA by cell-free extracts from the ansamycin producers, while none of the early shikimate pathway intermediates, DAHP, DHQ, DHS, quinic acid, shikimic acid can be incorporated into AHBA under the same conditions (Hornemann, 1981; Kim et al., 1996). Second, the rifamycin biosynthetic gene cluster (rif cluster) has been sequenced, and all of the genes encoding early shikimate pathway enzymes are found within the cluster (August et al., 1998). Finally, the ability of the rifamycin AHBA synthase (RifK) to catalyze dehydration of aminoDHS to AHBA has been previously demonstrated (Kim et al., 1998). As described in Example 2, the AHBA synthase gene (mitA) in S. lavendulae is required for AHBA biosynthesis.

A group of AHBA biosynthetic genes similar to those described for rif have been identified in the mitomycin cluster. In addition to AHBA synthase, six gene products in the cluster showed high sequence similarity (over 43% identity) with their rifamycin AHBA biosynthetic gene homologs. These gene products include aminoDHQ synthase (MitP, RifG equivalent), aminoquinate dehydrogenase (MitT, RifI equivalent), oxidoreductase (MitG, RifL equivalent), phosphatase (MitJ, RifM equivalent), kinase (MitS, RifN equivalent), and aminoDHQ dehydratase (MmcF, RifJ equivalent). In addition to the significant sequence similarity to rifamycin counterparts, all three putative mitomycin shikimate pathway enzymes displayed significant alignment with microbial primary shikimate metabolic enzymes including MitT with the quinate dehydrogenase (AroE) from Methanococcus jannaschii (28% identity, 46% similarity) (Bult et al., 1996), MitP with the DHQ synthase (AroB) from Mycobacterium tuberculosis (46% identity, 61% similarity) (Cole et al., 1998), and MmcF with the DHQ dehydratase from S. coelicolor (50% identity, 62% similarity) (White et al., 1990). Despite extensive sequencing of 15 kb on either side of the mapped right- and left-hand ends of the mitomycin cluster, an aminoDAHP synthase gene corresponding to RifH (the proposed first enzyme in the de novo biosynthesis from PEP and E4P in the rifcluster), was not found (FIG. 2). Interestingly, a rifH homologue has been cloned from S. lavendulae genomic DNA through Southern hybridization and shown to be unlinked to the mitomycin cluster.

The existence of non-shikimate pathway-related phosphatase/kinase pair in the mitomycin cluster (MitJ/MitS) and the -rif cluster (RifM/RifN) further support the finding that these two genes are required for AHBA biosynthesis (Floss, 1997). In addition to the strong homology to RifM, MitJ also showed 56% identity (69% similarity) with ORF8 from the ansamycin antibiotic ansamitocin producer Actinosynnema pretiosum auranticum. Other polypeptides with considerable sequence similarity belong to the CBBY family of phosphoglycolate phosphatases in glycolate oxidation (Schaferjohann et al., 1993). MitS, most similar to RifN (53% identity, 63% similarity), also showed significant similarity with the glucose kinase (involved in glucose repression) from S. coelicolor and Bacillus megaterium (Angell et al., 1992; Spath et al., 1997). mitG, the third non-shikimate pathway-related AHBA biosynthetic gene in this cluster is also worthy of note since it shows exclusive similarity (46% identity, 61% similarity) with oxidoreductase RifL and its equivalent in Actinosynnema pretiosum auranticum.

Mitosane Formation Genes

Precursor incorporation studies established that the mitosane core is assembled from the condensation of AHBA and D-glucosamine. Although no specific gene products can be assigned for forming the three bonds bridging AHBA and D-glucosamine, two genes downstream of mitA (SEQ ID NO:97), mitB (SEQ ID NO:98), and mitE (SEQ ID NO:44) likely encode enzymes that mediate one of these reactions. MitB shows local sequence similarity with a group of glycosyltransferases involved in glycopeptide antibiotic and polysaccharide biosynthesis, the typical function of which is to attach an activated sugar residue to a core compound (Yamazaki et al., 1996; Example 2). Meanwhile, MitE showed weak similarity (22% identity and 45% similarity) to the two cloned 4-hydroxybenzoate-CoA ligases from Rhodopseudomonas palustris in the anaerobic degradation of aromatic compounds (Gibson et al., 1994). It also showed similarity to a group of long chain fatty acid CoA ligases, as well as to the O-succinylbenzoic acid CoA synthetase in Vitamin K2 biosynthesis (Kwon et al., 1996). mitB and mitE disruption mutants. both had a MC deficient phenotype (Table 1).

The condensation of AHBA with D-glucosamine may be initiated in two different ways. This includes either initial formation of a $C_{8a}$–$C_9$ bond by an acylation or alkylation reaction, or formation of a Schiff base between the AHBA nitrogen and D-glucosamine C1 aldehyde, followed by the ring closure at $C_{8a}$–$C_9$. mitR (SEQ ID NO:31), one of the two McrA homologues may be involved in one of the ring closure reactions. Interesting, MitR showed high sequence homology with the plant berberine bridge enzyme. (BBE) (30% identity, 37% similarity) in benzophenanthridine alkaloid formation, where it catalyzes an unusual C-C bond formation of the berberine bridgehead carbon of (S)-scoulerine from the N-methyl carbon of (S)-reticuline (Dittrich and Kutchan, 1991). Using a mechanism similar to BBE, it is possible that MitB is involved in $C_{8a}$–$C_9$ bond formation. The decreased MC production in the mitR disruption mutant may be due to the existence of isoenzymes (e.g., MmcM) that could catalyze the reaction in the absence of a functional MitR.

Side Group Modification Genes

Complete assembly of MC requires functionalization of several sites on the core mitosane ring system. First, complete reduction of the carbonyl group at C-6 must occur. Second, hydroxylation at C-5 and C9a must proceed followed by methylation at C-9a. Third, amination at C-7 must occur presumably through initial hydroxylation followed by transamination. Fourth, oxidation of the hydroxyl groups at C-5 and C-8 to form the benzoquinone are required. Fifth, intramolecular amination of C-1 by N-1a to form the aziridine ring must be completed and finally, carbamoylation at C-10 completes assembly of the molecule. Several enzymes found in this cluster likely catalyze these modifications and are discussed below.

Methylation

Figure 1:
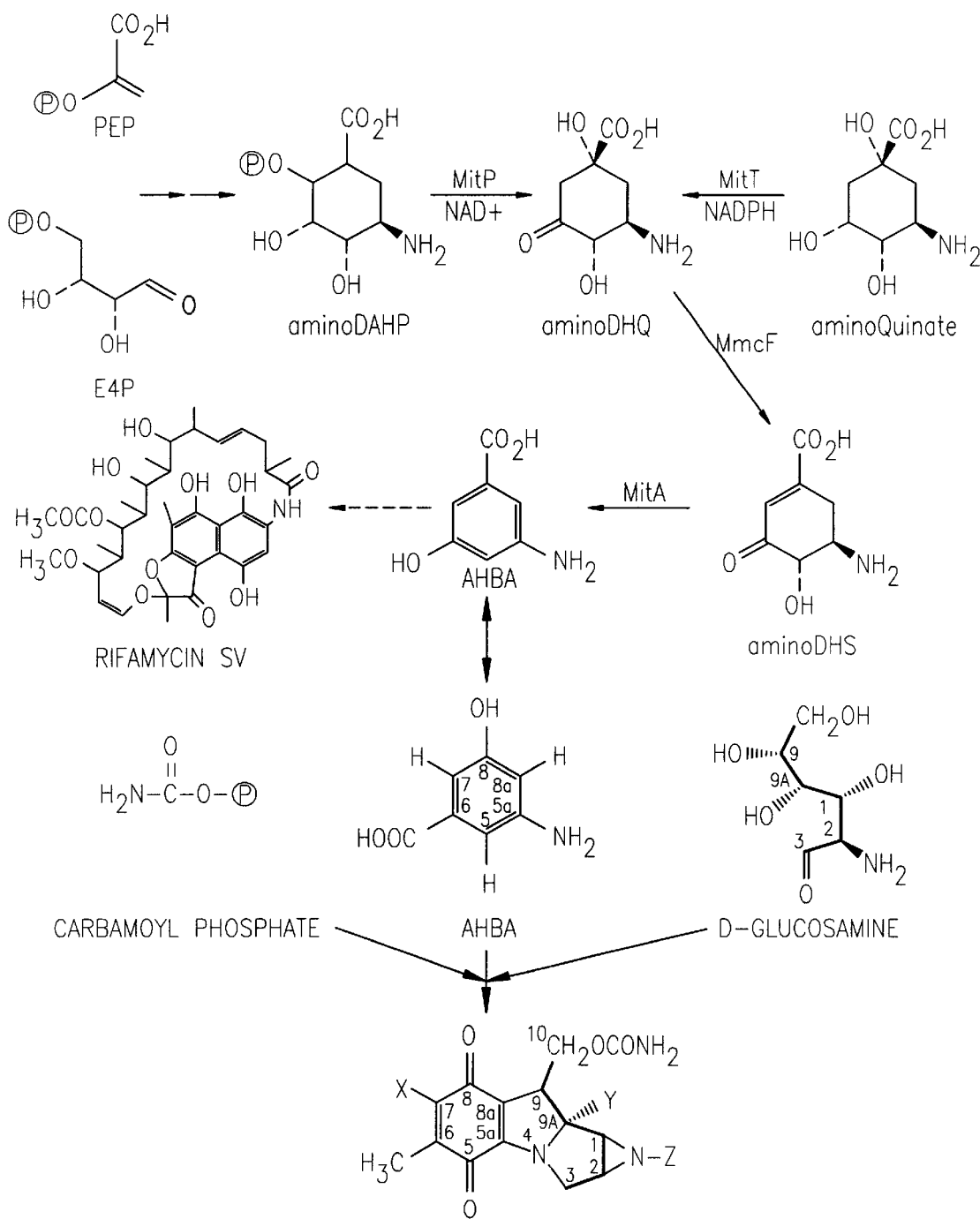
FIG. 1. The biosynthetic pathway for mitomycin antibiotics.
Figure 4:
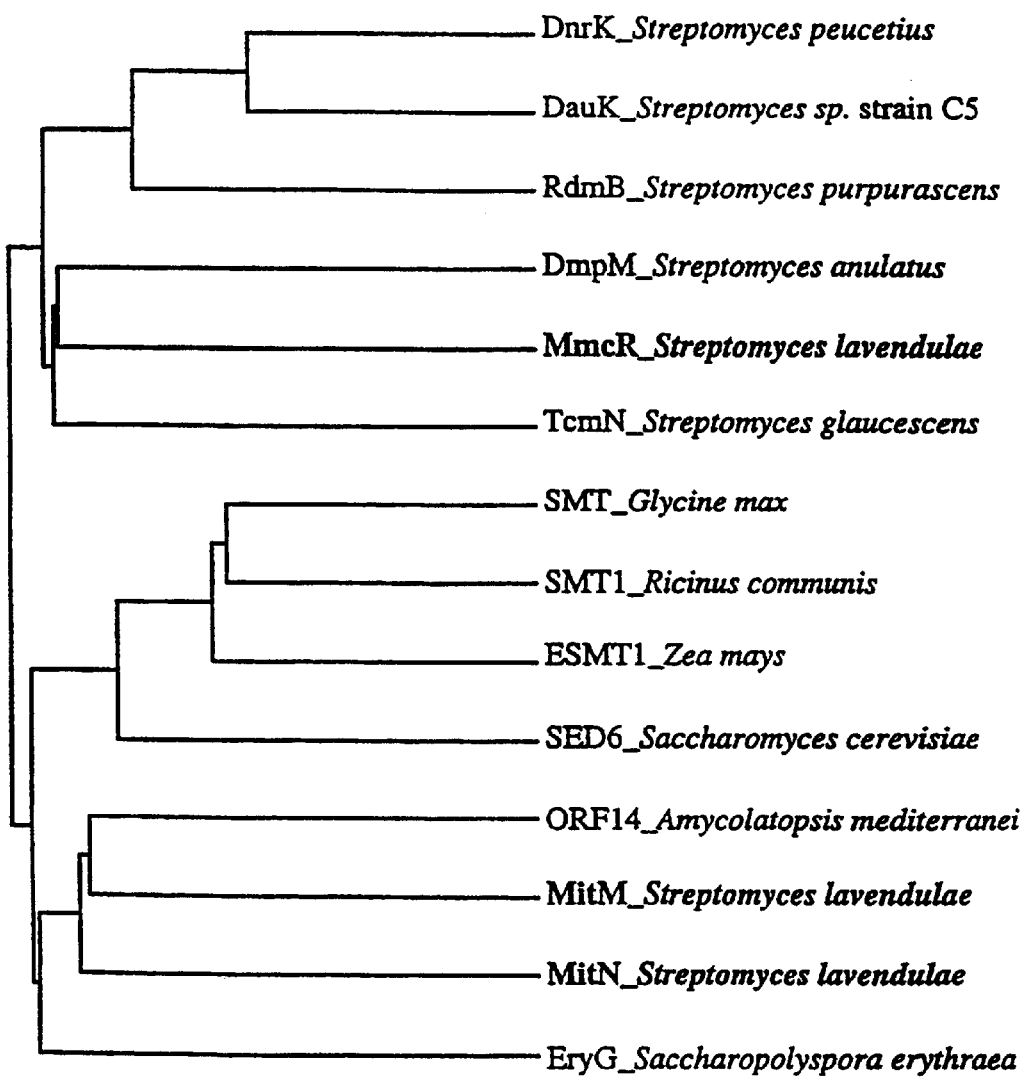
FIG. 4. Sequence similarity of MitM, MitN, and MmcR with other O-methyltransferases: DmpM (Kim et al., 1998), TcmN (Shikano et al., 1998), ORF14 (August et al., 1998), EryG (Hardwick and Pelham, 1994), RdmB (Mazodier et al., 1989), DnrK (Lee and Stock, 1996), and DauK (Devereux et al. 1984)); and C-methyltransferases: SMT (Schaferjohann et al., 1993), ESMT1 (Floss, 1997), SMT1 (Blattner et al., 1997), and SED6 (Guilfoile and Hutchinson, 1992)). The dendrogram was constructed with the program PILEUP (Denis and Brzezinki, 1992).

In contrast to MC which has an O-methyl group at C-9a, mitomycin A and mitomycin B also contain a C-7O-methyl group, while mitomycin B, mitomycin D and porfiromycin have an N-methyl on the aziridine ring (FIG. 1). Radiolabeled precursor incorporation studies showed that all of the O- and N-methyl (but not the C-methyl) groups in the mitomycin molecules are derived from L-methionine (Bezanson and Vining, 1971). Typically, the methyl donor for most C1 reactions is S-adenosyl-L-methionine (SAM), which can be formed through activation of L-methionine by ATP. Three SAM dependent methyltransferase genes were identified in this cluster (encoding MitM, MitN, and MmcR), all of which have three conserved S-adenosylmethionine or S-adenosylhomocysteine binding motifs (Kagan and Clarke, 1994) (FIG. 3). Interestingly, database searches of MitM and MitN (likely responsible for the MC C-9a side chain methylation) revealed a group of plant δ-(24)-sterol C-methyltransferases that have a closer phylogenetic relationship with the rifamycin O-methyltransferase (ORF14) and erythromycin O-methyltransferase (EryG) (5, 86) (FIG. 4). In contrast, protein database searches revealed that MmcR is most related to other Streptomyces antibiotic biosynthetic O-methyltransferases with greatest similarity to O-demethylpuromycin O-methyltransferase (44% identity, 60% similarity) from *S. anulatus* and carminomycin 4-O-methyltransferase from *S. peucetius* (Lacalle et al., 1991; Madduri et al., 1963). MmcR may be involved in the O-methylation of the phenol ring of MC before oxidation to the quinone. Both mmcR (SEQ ID NO:66) and mitM (SEQ ID NO:36) were shown to be essential for MC biosynthesis since disruption of each one completely abolished MC production (Table 1).

A SAM-independent methyltransferase, MmcD, was also identified in the mitomycin cluster. MmcD revealed strong sequence homology with the magnesium-protoporphyrin IX monomethyl ester oxidative cyclase (34% identity, 53% similarity) from *Methanobacterium thermoautotrophicum* (Accession Number 2622915), as well as the phosphonoacetaldehyde methyltransferase from *Streptomyces wedmorensis* (Hidaka et al., 1995), the P-methyltransferase from *Streptomyces hygroscopicus* (Hidaka et al., 1995) and the fortimicin KL methyltransferase from *Micromonospora olivasterospora* (Kuzuyama et al., 1995). Instead of SAM, this group of methyltransferases uses methylcobalamine or a structurally related protoporphyrin as the direct methyl donor. While the greatest number of matches were made to protoporphyrin methyltransferases, it is expected that this enzyme has another function in the mitomycin C biosynthetic pathway as all the O- and N-methyl groups of MC have been shown to be derived from SAM-dependent methyltransferases.

C-6 Carbonyl Reduction

The C-6 methyl group was previously shown to be derived from the reduction of the carboxylic acid of AHBA, since [carboxy-$^{13}$C] AHBA can be efficiently, and specifically incorporated into the C-6 methyl group of porfiromycin (Anderson et al., 1980). In the mitomycin cluster, four F420-dependent tetrahydromethanopterin (H$_4$MPT) reductase genes (encoding MitH, MitK, MmcI, MmcJ) and one H$_4$MPT:CoM methyltransferase gene (encoding MmcE) are candidates for the C-6 carbonyl reduction. In the methanogenesis pathway of *Methanobacterium thermoautotrophicum*, two cofactor F420-dependent H$_4$MPT reductases, and one cofactor CoM dependent methyltransferase are required in the seven step reduction from $CO_2$ to $CH_4$. Steps 4 to 6 from CH-H$_4$MPT to CH$_2$–H$_4$MPT, and CH$_3$–H$_4$MPT to CH$_3$-CoM are catalyzed by $N^5$, $N_{10}$-methylene-H$^4$MPT dehydrogenase, $N^5$, $N^{10}$-methylene-H$_4$MPT reductase, and $N^5$-methyl-H$_4$MPT:CoM methyltransferase, respectively (Deppenmeier et al., 1996; Thauer et al., 1993). All four enzymes (MitH, MitK, Mmcl, MmcJ) in this cluster showed local sequence similarity with the cloned F420 dependent H$_4$MPT reductase (42% identity, 62% similarity in several 50amino-acid fragments) (Nolling et al., 1995; Vaupel and Thauer 1995). One of these genes, mitH (SEQ ID NO:41) was disrupted, and the mutant strain displayed a MC deficient phenotype (Table 1). MmcE is notable since the deduced protein sequence contains two domains showing significant alignment (33% identity, 56% similarity) to the N-terminus of H$_4$MPT:CoM methyltransferase from *Methanobacterium the thermoautotrophicum* (Stupperich et al., 1993), while the remaining C-terminus is related to fatty acid biosynthetic acyl carrier proteins (ACP) (Morbidoni et al., 1996; Platt et al., 1990). The potential function of this ACP-like domain in MC biosynthesis remains unknown, as does the role of a distinct gene (mmcB, SEQ ID NO:50) encoding a putative ACP identified just upstream of mmcE (SEQ ID NO:53). Significantly, the disruption of mmcB resulted in total abrogation of MC production (Table 1).

Hydroxylation

The two putative hydroxylases (encoded by mmcN, SEQ ID NO:62; and mmcT, SEQ ID NO:68) identified in the mitomycin cluster are candidates for catalyzing hydroxylation at the C-5, C-7, and C-9a positions on the mitosane system. MmcN belongs to the cytochrome P450 family of monooxygenases, with greatest homology (37% identity, 56% similarity) to the two herbicide-inducible cytochrome P450s (P450-SU1 and P450-SU2) from *S. griseolus*, as well as to RapJ and RapN in the rapamycin biosynthetic gene cluster from *S. hygroscopicus* (Omer et al., 1990; Schwecke et al., 1995). MmcT showed highest similarity to the tetracenonmycin C hydroxylase (TcmG) in *Streptomyces glaucescens* (38% identity, 55% similarity), with lower but significant sequence similarity to a group of phenol or hydroxybenzoate hydroxylases (Decker et al., 1993). Genetic disruption of mmcT completely blocked MC biosynthesis (Table 1).

Carbamoylation

The carbamoyl group of MC is derived intact from L-citrulline or L-arginine with carbamoyl phosphate as the incorporated precursor (Hornemann, 1981). In eubacteria, carbamoyl phosphate can be generated from L-glutamine, $HCO_3^-$, and ATP by the enzyme carbamoyl phosphate synthetase, which is indispensable for pyrimidine biosynthesis. One candidate carbamoyl transferase gene (mmcS, SEQ ID NO:68) was identified directly upstream of mmcT. MmcS belongs to the NodU/CmcH family of O-carbamoylation enzymes, with the greatest similarity (35% identity, 44% similarity) to NolO from Rhizobium sp. (Jabbouri et al., 1998). Other members with significant alignment in this family include NolO from *Bradyrhizobium japonicum* (Luka et al., 1993) and NodU from Rhizobium sp. for 6-O-carbamoylation of Nod-factors (Jabbouri et al., 1995) and CmcH from *Nocardia lactamdurans* and *S. clavuligerus* for 3'-hydroxymethylcephem O-carbamoylation in cephamycin biosynthesis (Coque et al., 1995).

Discussion

Bridging Primary and Secondary Metabolism

The shikimate pathway is an essential metabolic route in microorganisms and plants for aromatic amino acid biosynthesis. Genes encoding the early shikimate pathway enzymes from various organisms have been well studied and are often dispersed along the chromosome as revealed by genome sequencing projects (Blattner et al., 1997; Bult et al., 1996; Cole et al., 1998). The finding that the ansamycin and mitomycin natural products are derived in part from an ammoniated shikimate pathway whose genes are clustered on the bacterial chromosome is a significant difference to the primary metabolic network, and may suggest an important evolutionary bridge leading to secondary metabolism. The lack of incorporation of early shikimate pathway intermediates into mitomycin and ansamycin metabolites indicated the existence and ultimate substrate specificity of the alternate ammoniated shikimate pathway enzymes. However, the conversion of aminoDAHP and aminoshikimic acid by the corresponding primary shikimate pathway enzymes to aminoDHQ and aminoDHS, respectively (Kim et al., 1996), suggested that the substrates specificity in primary metabolic shikimate pathway is mainly determined by the initial reaction step. This notion is further supported by the disruption results for rifG and rifI mutants showing only slightly affected rifamycin production (Floss, 1997).

In addition to the absence of an aminoDAHP synthase gene, the organization of the AHBA biosynthetic genes in the MC cluster is quite different compared to the rifcluster. In rif(with the exception rifJ), all AHBA biosynthetic genes are found within a defined sub-cluster that are organized into a single apparent operon. In contrast, almost all of the mit/mmc encoded AHBA genes are scattered within the 55 kb MC cluster. Thus, as opposed to the multifunctional polyketide gene clusters whose linearity of architecture reflects a precise pattern of biosynthesis, the MC cluster is biochemically less transparent based on a similar primary analysis. In addition, the MC cluster provides a good model for analyzing genetic evolution both vertically, from the primary metabolic shikimate pathway to the secondary shikimate pathway related route, and horizontally by comparing different groups of secondary metabolic biosynthetic clusters.

The MC Biosynthetic Network

In a typical liquid culture of *S. lavendulae*, MC production initiates 24 hours after inoculating the seed culture, reaches maximum production in two days, and maintains drug synthesis during stationary phase for another two days. Compared to high level MC resistance of the wild-type *S. lavendulae* (>150 $\mu$g/ml), MC production is relatively low (<5 $\mu$g/ml MC). The significant gap between the self-resistance and production levels makes it possible to improve drug production through genetic engineering. As described herein, disruption of the candidate repressor gene (mmcW) and downstream mmcX (encoding a putative membrane protein) in the mitomycin cluster resulted in a several-fold increase in MC production. The existence of a repressor gene(s) is not uncommon in Streptomyces antibiotic biosynthetic gene clusters. Previous examples include, mmyR from the methylenomycin cluster (Chater and Briton, 1985), actII-orfI in the actinorhodin cluster (Caballero et al., 1991),jadR (Anderson et al., 1980) injadomycin biosynthesis (Yang et al., 1995), and dnrO in the daunorubicin cluster (Otten, 1995). Disruption of jadR and mmyR also resulted in increased levels of the corresponding antibiotic (Chater and Bruton, 1985; Yang et al., 1995).

In order to avoid auto-toxicity, drug-producing microorganisms must evolve self-protection systems. Currently, three types of self-protection mechanisms have been identified in *S. lavendulae* for mitomycin resistance including, MC binding (MRD), efflux (MCT), and reversing MC reductive activation (MCRA). In principle, resistance genes must be expressed before drug formation. In this respect, it is interesting to note the linkage of the mitomycin resistance genes with the regulatory genes. Expression of the high-level resistance gene mcrA has been demonstrated to be regulated by the downstream gene mcrB which is presumably cotranscribed with mcrA (August et al., 1994). Though the function of the McrA homolog MitR in the mitomycin cluster remains unknown, mitR is also followed by a cotranscribed regulatory gene (mitQ). Meanwhile, the putative mitomycin translocase gene, mct is followed by the repressor gene, mmcW. Genetic linkage of membrane transporter/resistance and repressor genes have been described in a number of cases, including tetA/tetR in tetracycline resistance (Guilfoile and Hutchinson, 1992), tcmA/tcmR in tetracenomycin C resistance (Guilfoile and Hutchinson, 1992), actII-orj2/actII-orf1 in actinorhodin resistance (Caballero et al., 1991), and the qacA/qacR pair for multidrug resistance in *S. aureus* (Grkovic et al., 1998).

Conclusion

Although MC was first isolated more than 40 years ago and has been used in anti-cancer chemotherapy since the 1960s, the mechanistic details and order of its biosynthesis has remained unclear. The results described herein are clearly consistent with precursor incorporation studies gathered in the 1970s, showing that MC is biosynthetically derived from D-glucosamine, L-methionine, carbamoyl phosphate, and AHBA, and also support the use of the variant de novo shikimate pathway leading to AHBA (Hornemann, 1981; Kim et al., 1996). Many, if not all, of the genes responsible for the formation of the mitosane and aziridine rings are evidently located within the boundary of the 55 kb mitomycin cluster. These genes are of special interest since they may be useful as probes for identification of related natural product biosynthetic genes from other microorganisms and plants.

The cloned genes presented here are useful to study mitomycin biosynthesis and natural product assembly. The advantage of having this information has already been demonstrated through genetic disruption of the candidate repressor gene (mmcW) that provided a several-fold increase in MC production. In addition, expression and genetic disruption of selected genes should be useful for engineering the biosynthesis of clinically valuable mitomycin analogues, as well as more complex hybrid natural product systems. Finally, the MC resistance and regulatory genes identified in this cluster provide important insight into the mitomycin biosynthetic and regulatory network in the *S. lavendulae*.

EXAMPLE 2

Genetic Localization and Molecular Charactenzation of Two Genes Required for MC Biosynthesis

Materials and Methods

Strains and culture conditions. *E. coli* DH5α was grown in either Luria broth (LB) or tryptic soy broth (TSB) (Difco) as liquid medium or agar plates. *E. coli* DH5αF', the host for harvesting single-stranded DNA, was grown at 37° C. on TBG (1.2% tryptone, 2.4% yeast extract, 0.4% glycerol, 17 mM $KH_2PO_4$, 55 mM $K_2HPO_4$, and 20 mM glucose). *E. coli* S17-1 (Mazodier et al., 1989) used for conjugation was grown in TSB with 10 ug/ml of streptomycin. *S. lavendulae* was grown in TSB or on R5T plates. For MC production, *S. lavendulae* was grown in Nishikohri media (g/L: glucose 15, soluble starch 5, NaCl 5, $CaCO_3$ 3, yeast extract 5) for 72 hours from a 1% v/v inoculum of frozen mycelia. Pulse feeding of AHBA to the disruption mutant, MV 100, and the site-directed mutant, MV102, occurred with feedings of 2.5 mg of a 20 mg/mL solution of the sodium salt of AHBA at pH 7.1 in three pulses at 24, 43, and 57 hours of a culture that was harvested at 76 hours.

DNA Preparation and Amplification. Isolation and purification of DNA was performed using standard methods (Sambrook et al., 1989). S. lavendulae NRRL 2564 genomic DNA was isolated by using the modified Chater protocol (Hopwood et al., 1988). Plasmid DNA was isolated from E. coli by using the alkaline-sodium dodecyl sulfate method.

pDHS2002 was constructed as follows: The 1.1 kb thiostrepton resistance gene (tsr) fragment was removed from pDHS5000 with a SmaI-BamHI digestion, blunt-ended with the large fragment of DNA polymerase (Gibco BRL), and ligated to MscI restriction enzyme digested pDHS7601 to yield pDHS20001. MscI digestion of pDHS7601 resulted in the removal of 155 nucleotides at the C-terminus of the mitA gene, and ligation of the blunt-ended BamHI site of the tsr adjacent to the MscI site of pDHS7601 resulted in regeneration of the BamHI site in pDHS2001. The 4.9 kb EcoRI-HindIII fragment from pDHS2001 containing the tsr disrupted mitA gene was removed and ligated into EcoRI-HindIII digested pKC1139 to yield pDHS2002.

Primer-mediated site-directed mutagenesis (SDM) was employed to construct pDHS2015 containing a K191A mutation in mitA. Primer 1: 5'-GGCAAGGCATGCGAGGGTCGC-3' (SEQ ID NO:46) and primer 2: 5'-TTCCAGAACGGCGCCTGATGACCGCCGGC-3' (SEQ ID NO:47) were used to amplify the 691 bp fragment of the 5' end of mitA. The 3' end of mitA was amplified with primer 3: 5'-GCCGGCGGTCATCAGGGCGCCGTTCTGGAA-3' (SEQ ID NO:48) and primer 4: 5'-TCAGAATTCGGATCCGAGGGCCGGAGT-3' (SEQ ID NO:86) to generate a 1151 bp band (see amplification reaction conditions in Example 3). A second round of PCR was performed using the overlapping 691 and 1151 bp units as the initial templates with primer 1 and primer 4 to yield a 1.8 kb fragment. The final product containing mutagenized mitA was digested with EcoRI-Sph1, ligated to the 2.1 kb HindIII-SphI fragment from pDHS7601 and the EcoRI-HindIII digested pKC1139 to yield pDSH2015. The site-directed mutation of MitA K191A in pDHS2015 was confirmed by sequencing with forward primer: 5'-ACCTACTGCCTCGATGCC-3' (SEQ ID NO:87) and reverse primer: 5'-CTGATCCTTCAAGCG-3' (SEQ ID NO:88).

The mitB disruption vector pDHS7702 was constructed as follows. pDHS7601 was digested with BstBI, blunt-ended, and ligated with the 1.4 kb neomycin-resistant gene fragment from pFD666 (Denis and Brzezinski et al., 1992) (ApaL1-HindIII digestion, blunt-ended). The 5.2 kb EcoRI-HindIII fragment from the resulting construct pDHS7701 was subcloned into pKC1139 to create pDHS7702.

DNA library construction and screening. S. lavendulae NRRL 2564 genomic DNA was partially digested with Sau3AI, and a fraction containing 30–50 kb fragments was recovered by sucrose gradient centrifugation and ligated into the calf intestinal alkaline phosphatase (CIP) treated BglII site of the E. coli-Streptoyces shuttle vector pNJ1 (Tuan et al., 1990), then packaged with the Packagene Lambda DNA Packaging System (Promega). The cosmid library was constructed by transfecting E. coli DH5α, and colonies that appeared on the LB plates containing 100 ug/ml of ampicillin were transferred to a BioTrace NT nitrocellulose blotting membrane (Gelman Sciences, Ann Arbor, Mich.). Colony hybridization was performed as specified by the manufacturer. A PCR-amplified 0.7 kb DNA fragment from plasmid pKN108 (FIG. 6) was used to screen the library. The primers used for PCR were: 5'-GCGTCCGTGCTGCGCGCGCA-3' (SEQ ID NO:89), and 5'-TGCGCGCGCAGCACGGACGC-3' (SEQ ID NO:90). The cosmids from the positive colonies were confirmed by Southern blot hybridization, and a 1.7 kb AflII-BamHI fragment from pDHS3001 containing the mitomycin resistance determinant (mrd) (Sheldon et al., 1997) was used as a probe to establish genetic linkage.

DNA sequencing and analysis. Deletion subclones from pDHS7601 were made with exonuclease III Erase-a-Base System (Promega). Sequencing was accomplished with the ABI PRISM™ Dye Terminator Cycle Sequencing Ready Reaction Kit (Applied Biosystems), and analyzed on an Applied Biosystems 377 DNA Sequencer at the University of Minnesota Advanced Genetic Analysis Center. For generating single-stranded DNA, deletion subclones in pUC119 were transformed into E. coli DH5αF', and M13K07 Helper Phage was used (GIBCO BRL). Nucleotide sequence data were analyzed using Wisconsin Genetics Computer Group software (version 9.0) (Devereux et al., 1984), and Gene-Works software version 2.51 (Oxford Molecular Group). The GenBank accession number for mitABC is AFI 15779.

Conjugation from E. coli S17-1 to S. lavendulae. The procedure of Bierman et al. (Bierman et al., 1992) was used with the following modification. A single colony of E. coli S17-1/pDHS2002 was used to inoculate 2 ml of TSB containing 100 μg/ml of apramycin and 10 μg/ml of streptomycin. Following overnight incubation at 37° C. a 1:100 inoculation was made into TSB broth with 100 μg/ml of apramycin and 10 μg/ml of streptomycin. This culture was grown for 3 hours at 37° C., and the cells were washed twice with TSB and resuspended in 2 ml of TSB to provide the donor E. coli culture. The recipient S. lavendulae culture was generated by inoculating 9 ml of TSB with 1 ml of frozen wild-type culture. Following overnight (16 hour) incubation at 29° C., the culture was homogenized by sonication and 2 ml of this culture was used to inoculate 18 ml of TSB. Following overnight growth at 29° C. and sonication treatment to homogenize the culture, a 1 ml inoculum was placed in 9 ml of TSB. This culture was grown for 3 hours, the mycelia were washed with TSB and resuspended in 2 ml of TSB to provide the stock recipient culture.

The donor and recipient cultures were mixed together in 9:1, 1:1, and 1:1/10 donor:recipient ratios, and 100 μl of the cell mixture was spread on AS1 plates (Baltz, 1980). The plates were incubated overnight at 29° C. and overlaid with 1 ml of water containing a suspension of 500 μg/ml each of thiostrepton, apramycin and nalidixic acid. For the pKC1139 control, only apramycin and nalidixic acid were overlaid, while for pDHS7702, 500 μg/ml of kanamycin was used instead of thiostrepton. S. lavendulae exconjugates appeared in approximately 11–13 days at a frequency ranging from $10^{-7}$–$10^{-5}$. pKC1139 has a temperature-sensitive Streptomyces replication origin, which is unable to replicate at temperatures above 34° C. (Muth et al., 1989), while the S. lavendulae host grows well at 42° C. Thus, after propagating the conjugants at 39° C. for several generations, double crossover mutants were readily generated. Presence of plasmid was determined by transformation of E. coli DH5α with plasmid extracts from S. lavendulae transconjugants.

Double-crossover selection procedure. A single colony of S. lavendulae/pDHS2002 grown on R5T plates (50 μg/ml of thiostrepton and apramycin) was used to inoculate TSB broth containing 20 μg/ml of thiostrepton. After 72 hours of incubation at 39° C., $10^{-4}$, $10^{-5}$ and $10^{-6}$ diluted aliquots were used to inoculate R5T plates containing 50 μg/ml of thiostrepton. Following 48 hours of growth at 39° C., 84 colonies were picked randomly and each colony was patched out on separate 50 μg/ml of thiostrepton and 50 μg/ml of apramycin containing R5T plates. One of the 84 colonies displayed the double crossover phenotype of thiostrepton resistance and apramycin sensitivity. Integration of the tsr disrupted mitA gene and loss of plasmid pDHS2002 was confirmed by Southern hybridization analysis.

MitA K191A site-directed mutants (MV102) were selected by propagating MV100/pDHS2015 on R5T plates for two generations at 37° C. Colonies were replicated to plates containing 50 μg/ml of thiostrepton and plates without antibiotics. Of the 108 colonies replicated in the first round, one had the correct (thiostrepton sensitive) phenotype. To confirm the K191A mutation, the mitA gene was amplified from the chromosome with primers 1 and 4. Mutation of the conserved lysine codon (AAG) to an alanine codon (GCC) was verified with the same sequencing primers employed to confirm the correct construction of pDHS2015. The alanine codon was observed in both the forward and reverse sequence data.

Mutants for mitB (MM101) were selected as follows: S. lavendulae/pDHS7702 was propagated on R5T plates for five generations at 39° C. before single colonies were replicated on R5T plates as described above. Of the 300 colonies tested, 12 clones displayed the correct phenotype (kanamycin resistance and apramycin sensitivity). The genotype of selected mitB mutants was confirmed by Southern blot hybridization of S. lavendulae genomic DNA.

Analysis of MC production. All cultures intended for MC extraction were grown in Nishikohri media (Nishikohri and Fukui, 1975) for a period of 72 hours. In all cases a wild-type S. lavendulae culture was grown concurrently with the mutant cultures to provide a MC production reference point. A 72 hours, 50 ml culture (250 ml flask) of the MitA K191 A MV 102 mutant strain was supplemented with 125 μl of a 20 mg/ml solution of the sodium salt of AHBA (pH 7.05) at 24, 43 and 55 hours. In each case, the culture broth was separated from mycelia by centrifugation and then extracted three times with equal volumes of ethyl acetate. The ethyl acetate extracts were pooled and solvent was removed by vacuum to provide the crude broth extract. The preliminary screen for MC production involved thin layer chromatography (TLC) on silica gel plates (Whatman K6) eluted with 9:1 chloroform:methanol. Production of MC was monitored by HPLC($C_{18}$ reverse phase column) using a gradient of 80% 50 mM Tris buffer (pH. 7.1)/20% methanol to 40% 50 mM Tris buffer (pH 7.2)/60% methanol with the UV detector set to 363 nm.

Bioassay. detection of MC was performed by loading a 1 cm disk with fractions eluting at the mitomycin retention time from HPLC injections of wild-type, MV100, pKC1139 vector control crude extracts and MC standards. The disks were placed on antibiotic media number 2agar plates (Difco) with Bacillus subtilis spores added directly to the media. The plates were incubated overnight at 29° C. and examined for zones of inhibition. To confirm the production of MC by MV102 in the presence of exogenous AHBA the fraction eluting at the MC retention time was collected, dried down, desalted and submitted for desorption ionization mass spectrometric analysis on a Bio-Ion 20R DS-MS instrument (Applied Biosystems). The MC (M.W.=334)-sodium (M.W.=23) adduct peak, $[M+Na]^+=357$, was diagnostic for the presence of MC in the AHBA supplemented culture.

Results

Figures 8A, 8B:
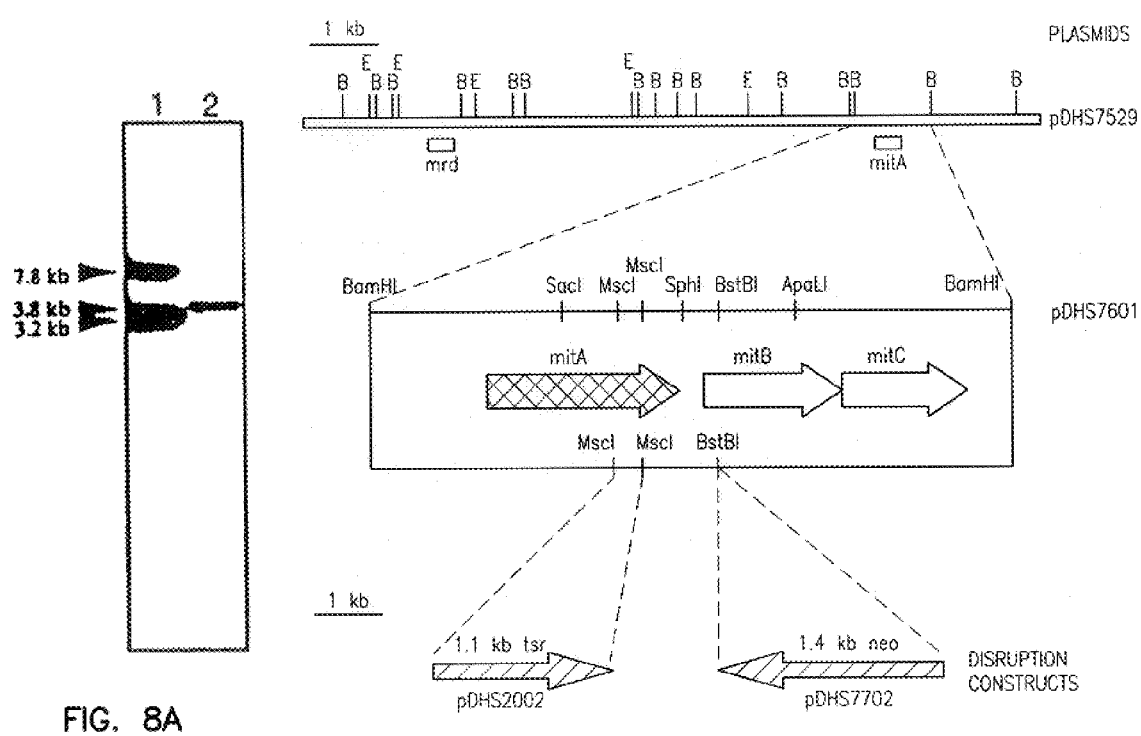
FIG. 8. Southern hybridization and restriction-enzyme map of the mrd and rifK hybridizing regions from S. lavendulae. A) Southern hybridization with the rifK gene probe (Kim et al., 1998). Lane 1, A. mediterranei ATCC 27643 genomic DNA digested with BamHI; Lane 2, S. lavendulae NRRL 2564 genomic DNA digested with BamHI; B) Physical map showing the mitABC genes. The location of mrd and rifK hybridizing genes in cosmid pDHS7529are indicated by solid bars. Enzymes: E, EcoRI; B, BamHI. The sequenced 3.8 kb BamHI fragment containing mitA, mitB, mitC is enlarged (wide arrows). Thin arrows below show sites of resistance gene integration for disruption experiments.

The mrd and ahbas genes are linked in the S. lavendulae genome. Southern blot analysis with the A. mediterranei AHBA synthase (rifK) gene probe (Kim et al., 1998) showed a single 3.8 kb band that hybridized with BamHI digested S. lavendulae genomic DNA (FIG. 8). Subsequently, a S. lavendulae genomic DNA library was constructed using the E. coli-Streptomyces shuttle cosmid pNJ1. Of the 5,000 colonies screened, 21 positive clones were identified with six of these hybridizing with the mrd gene probe (none hybridized with the mcr gene probe described in August et al., 1994). Restriction-enzyme mapping and reciprocal hybridization of the cosmid clones established that the mrd and S. mediterranei AHBA synthase homologous genes were about 20 kb apart in the S. lavendulae genome. The 3.8 kb BamHI fragment bearing a putative S. lavendulae AHBA synthase gene was subcloned and its nucleotide sequence determined.

Three ORFs are identified within the 3.8 kb BamHI fragrnent. Three ORFs (mitA, mitB, mitC) were identified within the sequenced 3.8 kb BamHI fragment (FIGS. 8 and 9). mitA comprises 1164 nucleotides and starts from ATG (position 579 of the sequenced fragment) that is preceded by a potential ribosome binding site (RBS), GAAAGG (SEQ ID NO:91). The deduced product of the mitA gene encodes a hydrophilic protein of 388 amino acids with a predicted $M_r$ of 41,949 Da and a calculated pI of 5.62. A BLAST (Altschul et al., 1990) search showed that the predicted MitA protein has high sequence similarity (about 71% identity, 80% similarity) with AHBA synthases (AHBASs), both from the rifamycin producer A. mediterranei (Kim et al., 1998) and other ansamycin-producing actinomycetes, including Actinosynnema pretiosum (ansamitocin) and Streptomyces collinus (naphthomycin A and ansatrienin) (FIG. 10). A conserved pyridoxal phosphate (PLP) coenzyme binding motif ($GX_3DX_7AX_8EDX_{14}GX_{13}KX_{4-5}geGGX_{19}G$) (SEQ ID NO:92) including the conserved lysine residue can also be found in these four proteins (Piepersberg, 1994).

The mitB gene is predicted to start at a GTG (position 1879) that is preceded by a presumed RBS (GGAACG) (SEQ ID NO:93). This gene encodes a 272 amino acid protein with a deduced $M_r$ or 28,648 Da and a deduced pI of 6.06. Database sequence homology searches revealed that the product of mitB shows local sequence similarity with a group of O-glycosyltransferases involved in polysaccharide biosynthesis. One segment of 70 amino acid residues at the N-terminus of MitB has 43% similarity (36% identity) with the two glycosyltransferases SpsL and SpsQ from Sphingomonas S88, and ExoO form Rhizobium meliloti involved in polysaccharide (S88) and succinoglycan biosynthesis, respectively (Becker et al., 1963). Another 60 amino acid residues located at the C-terminus displayed 30% identity with UDP-GalNAc:polypeptide N-acetylgalactosaminyltransferase from Mus musculus and Homo sapiens (Bennett et al., 1996).

The third ORF, mitC, starts from the ATG at position 2694, which is coupled to the stop codon TGA of mitB and encodes a putative protein of 260 amino acids with a molecular mass of 27,817 Da and a pI of 10.45. Database searches with the deduced protein product showed significant similarity over the first 90 amino acids (38% identity, 40% similarity) with the lmbE gene product (unknown function) from *Mycobacterium leprae* (U15183).

Insertional disruption of the mitA and mitB genes in *Streptomyces lavendulae*. To test the dependence of functional mitA and mitB genes for MC biosynthesis, gene disruption constructs were generated for subsequent isolation of the corresponding *S. lavendulae* isogenic mutant strains.

Figure 11A:
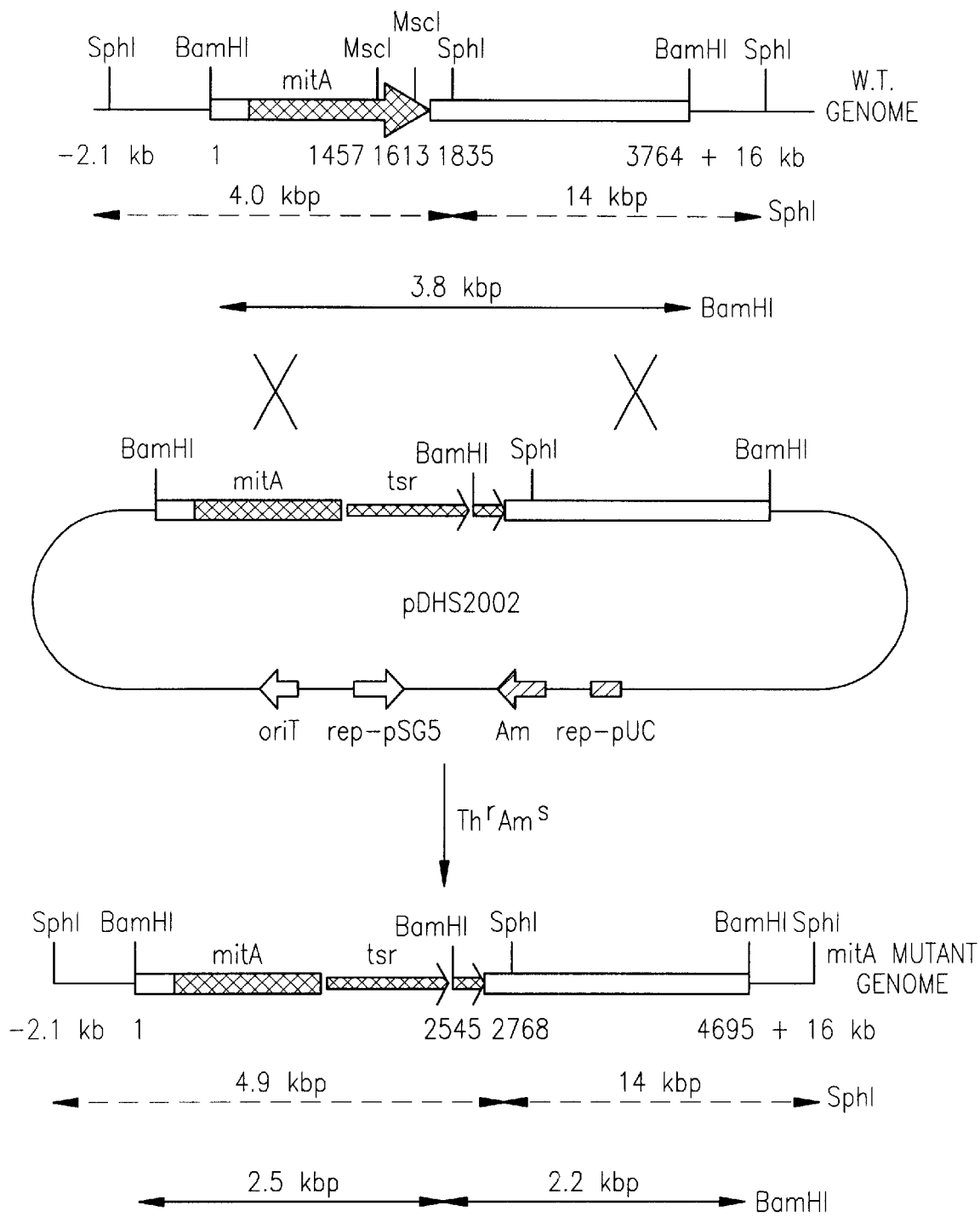
FIG. 11. Southern blot analysis of the mitA mutant strain. A) Construction of mitA disruption mutant and restriction map of the wild-type and mitA disruption mutant showing expected band sizes in the Southern blot. Maps are not drawn to scale. B) S. lavendulae genomic DNA from wild-type (lanes 1 and 2) and double crossover mutant (lanes 3 and 4) were digested with BamHI (lane 1 and 3) and SphI (lane 2 and lane 4), respectively. The 4.9 kb EcoRI-HindIII fragment from pDHS2001 containing tsr-disrupted mitA was used as the probe.
Figure 11B:
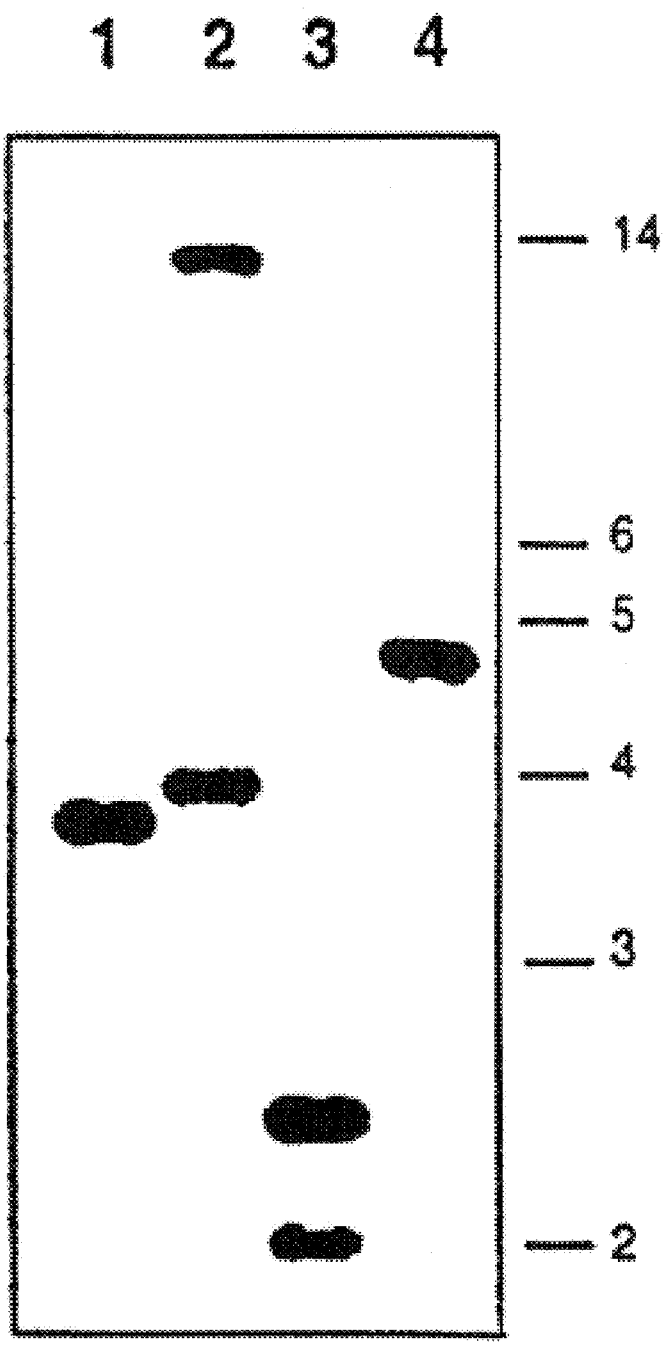

The mitA disruption construct was made by replacing a 155 bp fragment between the two MscI sites (located at the C-terminus of the mitA gene in pDHS7601) with the 1.1 kb SmaI-BamHI fragment containing a thiostrepton resistance gene from pDHS5000 (FIG. 11A). This replacement regenerated a BamHI site at the junction and the resulting construct was then subcloned into the *E. coli*-Streptomyces conjugative shuttle plasmid pKC1139, followed by conjugation into *S. lavendulae*. A double crossover mutant strain (MV100) was selected based on the expected phenotype (thiostrepton resistant, apramycin sensitive), and further confirmed by Southern blot hybridization. Genomic DNA from wild-type *S. lavendulae* and MV100 was digested with BamHI and SphI, and hybridized with the 4.9 kb EcoRI-HindIII tsr-disrupted mitA fragment from pDHS2001. As expected, the 4.0 kb SphI hybridized band in the wild-type strain was shifted to 4.9 kb in MV100, whereas the 3.8 kb BamHI hybridization and in the wild-type was converted to two bands (2.2 kb and 2.5 kb) in the mutant (FIG. 11B).

Figure 12A:
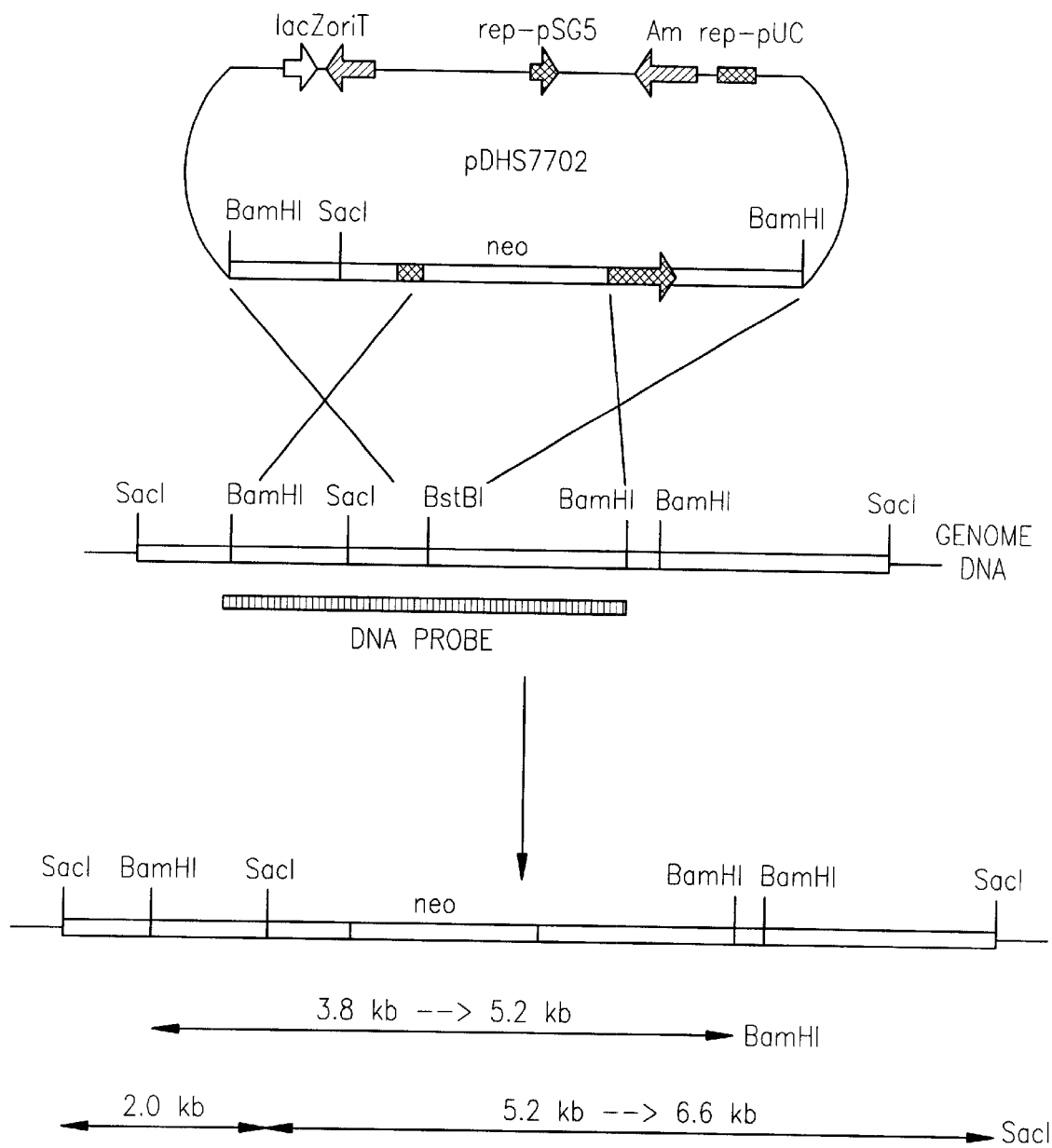
FIG. 12. Southern blot analysis of mitB mutant MM101. A) Construction of mitB disruption mutant and restriction map of the wild-type and mitB disruption mutant showing the expected sites in the Southern blot. B) S. lavendulae genomic DNA from wild-type (lane 1 and 3) and mitB mutant (lane 2 and 4) were digested with BamHI (lane 1 and 2) and SacI (lane 3 and 4). DNA probe: 3.8 kb BamHI fragment insert from pDHS7601.
Figure 12B:
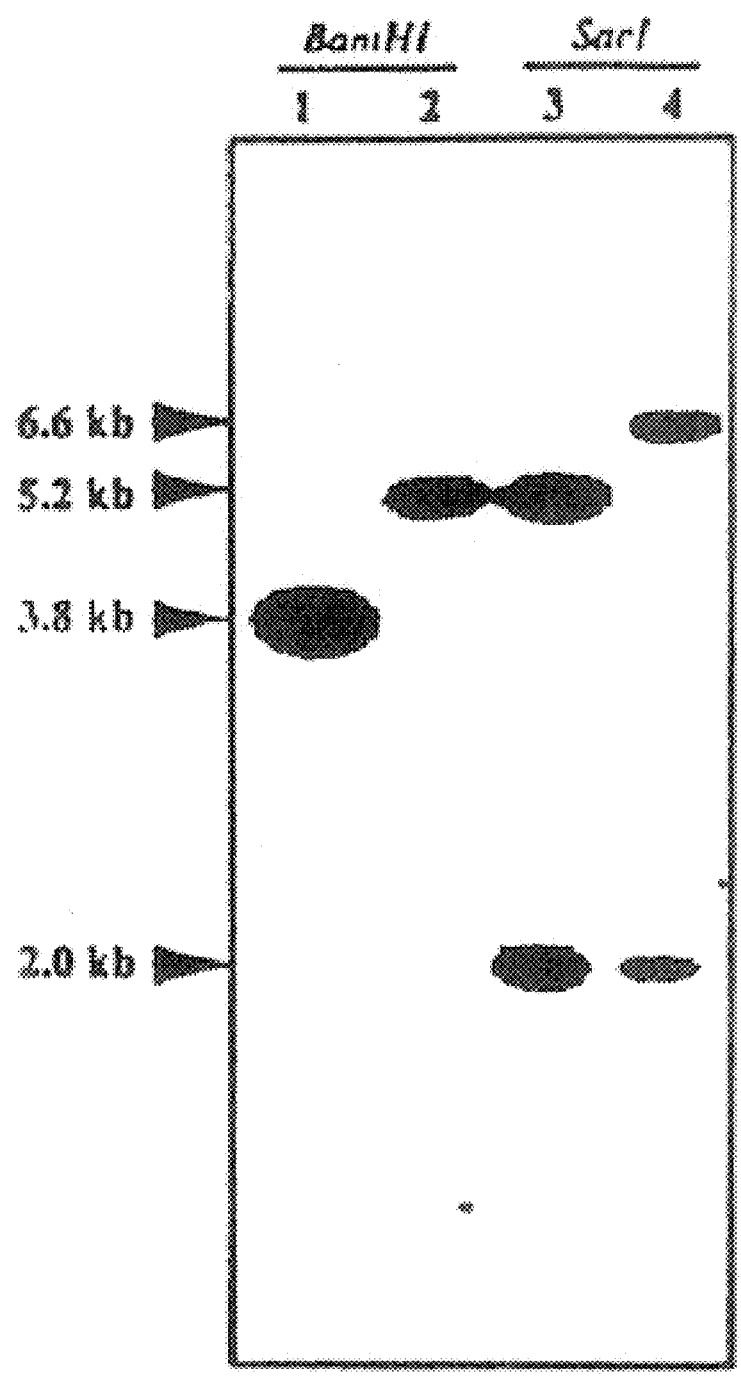
Figure 13A:
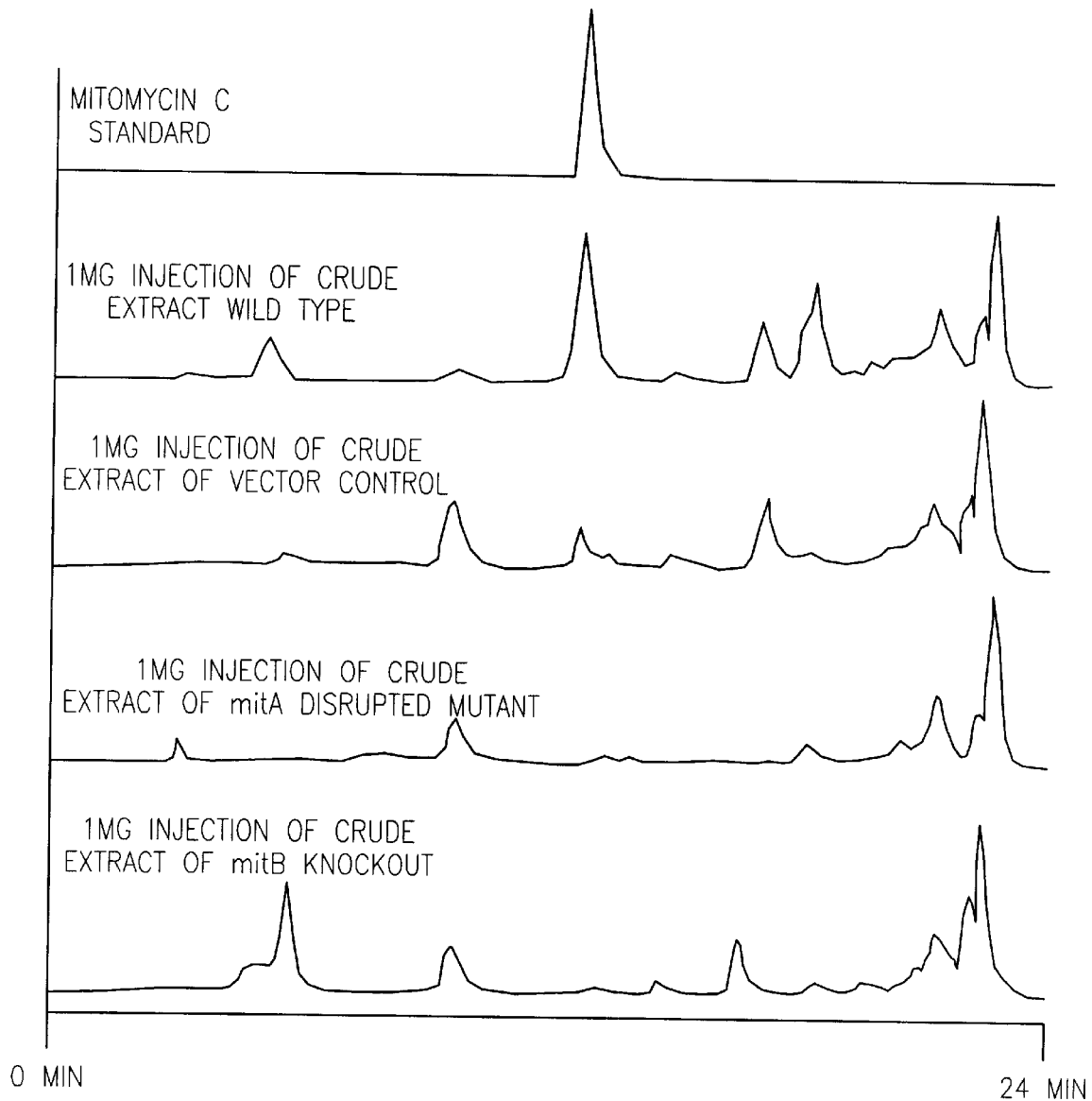
FIG. 13. Chemical analysis and biological activity of extracts from S. lavendulae wild-type and mutant strains. A) HPLC analysis of authentic mitomycin C standard, mitomycin C production in the wild-type S. lavendulae, mitA (AHBAS) and mitB (gtf) disruption mutants of S. laven-
Figure 13B:
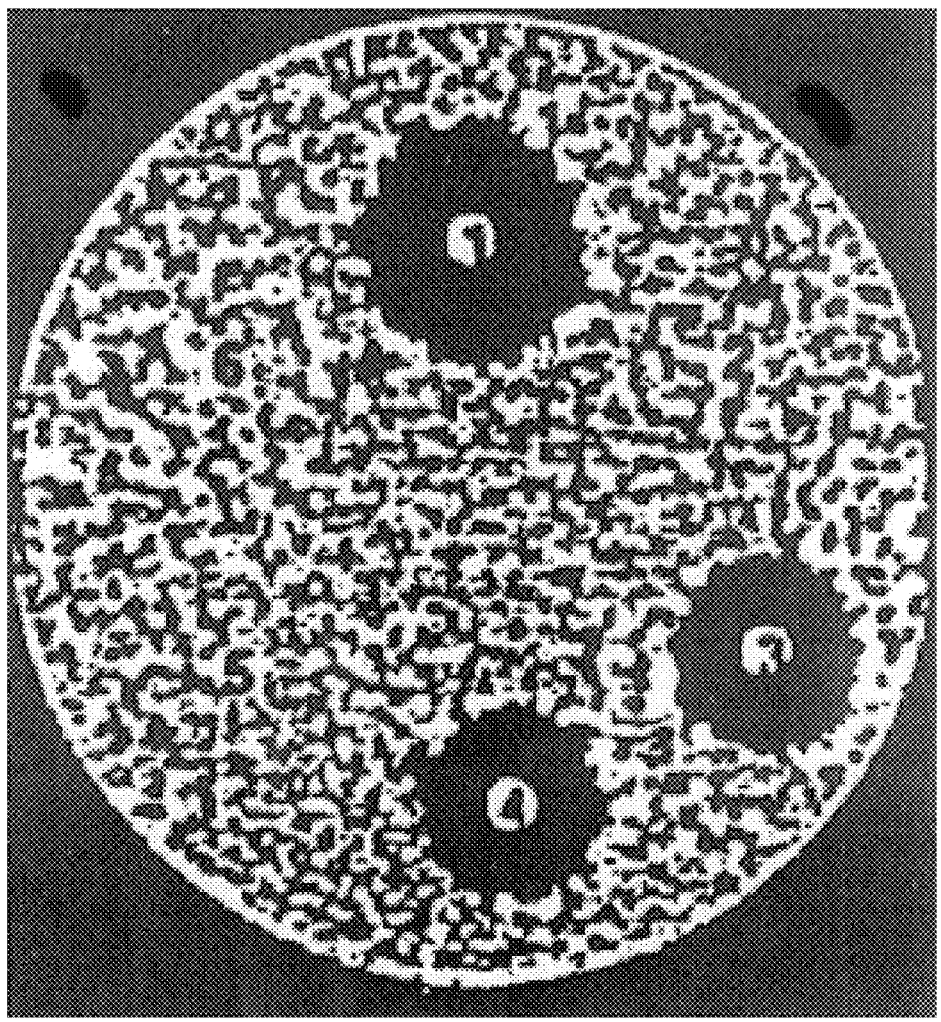

The mitB gene was disrupted by inserting a neomycin resistance gene (aphII) into the BstBI site (located at the 5'-end of mitB) (FIG. 12A). Transconjugants were selected on kanamycin/apramycin plates, and a double crossover mutant strain (MM101) was identified with a kanamycin-resistant, apramycin-sensitive phenotype and subsequently confirmed by Southern blot hybridization. As expected, the 3.8 kb BamHI hybridization band in wild-type *S. lavendulae* was shifted to 5.2 kb in MM101, whereas a 5.2 kb SacI hybridization band was shifted to 6.6 kb (FIG. 12B).

mitA and mitB disrupted strains (MV100, MM101) are blocked in MC biosynthesis The growth characteristics and morphology of MV100 and MM100 in liquid media and on agar plates was identical to wild-type *S. lavendulae*. HPLC was used to quantify production of MC in MV101 and MM101 (FIG. 13A), and culture extracts were used in a biological assay to test for presence of the drug (FIG. 13B). Injection of one mg of wild-type *S. lavendulae* culture extract gave a peak in the HPLC that eluted with the same retention time as the MC standard. Upon injection of one .mg of culture extract from the mitA or mitB disrupted strains (MV100, MM101) no MC peak was observed. To corroborate the lack of production of MC, the HPLC eluant obtained from the MV100 culture extracts was collected over the retention time range determined for MC. This eluant completely lacked biological activity against *Bacillus subtilis* (the MC target strain) while the fraction collected from the same retention time region of wild-type *S. lavendulae* and the vector control strain culture extracts showed substantial levels of biological activity (FIG. 13B).

It is important to note that the presence of the vector pKC1139 in *S. lavendulae* reduced the percentage of MC in the total crude extract while simultaneously increasing the total amount of material extractable by ethyl acetate. The combination of these two effects reduces the absolute amount of MC by approximately 25% in the vector control culture crude extract compared to the wild-type crude extract.

Exogenous AHBA can restore MC production in the MC-deficient MitA K191A mutant. Although complementation of MV100 (mitA insertional disruptant) was attempted by providing exogenous 3-amino-5-hydroxybenzoic acid in the culture medium, MC production was not restored as measured by HPLC or biological assay. A polar effect on genes downstream of tsr-disrupted mitA in MV100 appeared likely since supplying mitA in trans on a medium copy number plasmid (MV103) also failed to restore MC production. Therefore, site-directed mutagenesis was employed to generate a MitA K191A mutant resulting in strain MV102. Kim et al. (1998) had demonstrated that the AHBA synthase from *A. mediterranei* is PLP dependent and catalyzes the aromatization of 5-deoxy-5-amino-3-dehydroshikimic acid (aminoDHS). Thus, the nitrogen of the conserved lysine 191 is supposed to form a Schiff base with the PLP cofactor. Replacement of lysine 191 with alanine prevents binding of the cofactor and eliminates enzymatic activity. Replacement of the AGG encoding lysine 191 in wild-type *S. lavendulae* with a GCC codon in MV102 was confirmed by nucleotide sequence analysis. As expected, MV102 did not produce MC, however, when the culture medium was supplemented with exogenous AHBA, MC production was restored as determined by MS ([M+Na]$^+$=357), HPLC and TLC analysis (Table 2).

TABLE 2

Complementation results with (+) or without (−) AHBA.

| S. lavendulae strains | MC production | |
|---|---|---|
| | −AHBA | +AHBA |
| Wild-type | + | + |
| MV100 | − | − |
| MV103 | − | − |
| MV102 | − | + |

Discussion

An effective strategy for the identification of natural product biosynthetic gene clusters in actinomycetes has included cloning of antibiotic resistance genes followed by investigation of adjacent DNA for the presence of structural and regulatory genes (Butler et al., 1989, Donadio et al., 1991; Motamedi and Hutchinson, 1987; Vara et al., 1985). Although linkage of antibiotic resistance and biosynthetic genes appears to be a general feature in prokaryotes, a growing number of examples involve the existence of multiple resistance loci that may be linked or unlinked to the biosynthetic gene cluster (Vara et al., 1985; Seno and Baltz, 1989; Smith et al., 1995). The identification and characterization of two genetically unlinked resistance loci (August et al, 1994; Sheldon et al., 1997) for MC created a dilemma for mounting an effective search for the MC biosynthetic gene cluster. However, the use of the AHBA synthase gene from *A. mediterranei* provided an effective probe to identify cosmid clones bearing a linked MC resistance gene. Thus, the isolation of several cosmid clones form an *S. lavenduale* genomic DNA library that hybridized to both the *A. mediterranei* AHBA synthase gene and the *S. lavendulae* mrd gene indicated that the MC biosynthetic gene cluster resided on DNA adjacent to mrd. DNA sequence analysis of the 3.8 kb BamHI fragment revealed three ORFs whose deduced protein sequences corresponded to an AHBA synthase, a glycosyltransferase, and a ImbE-like product.

Figure 7:
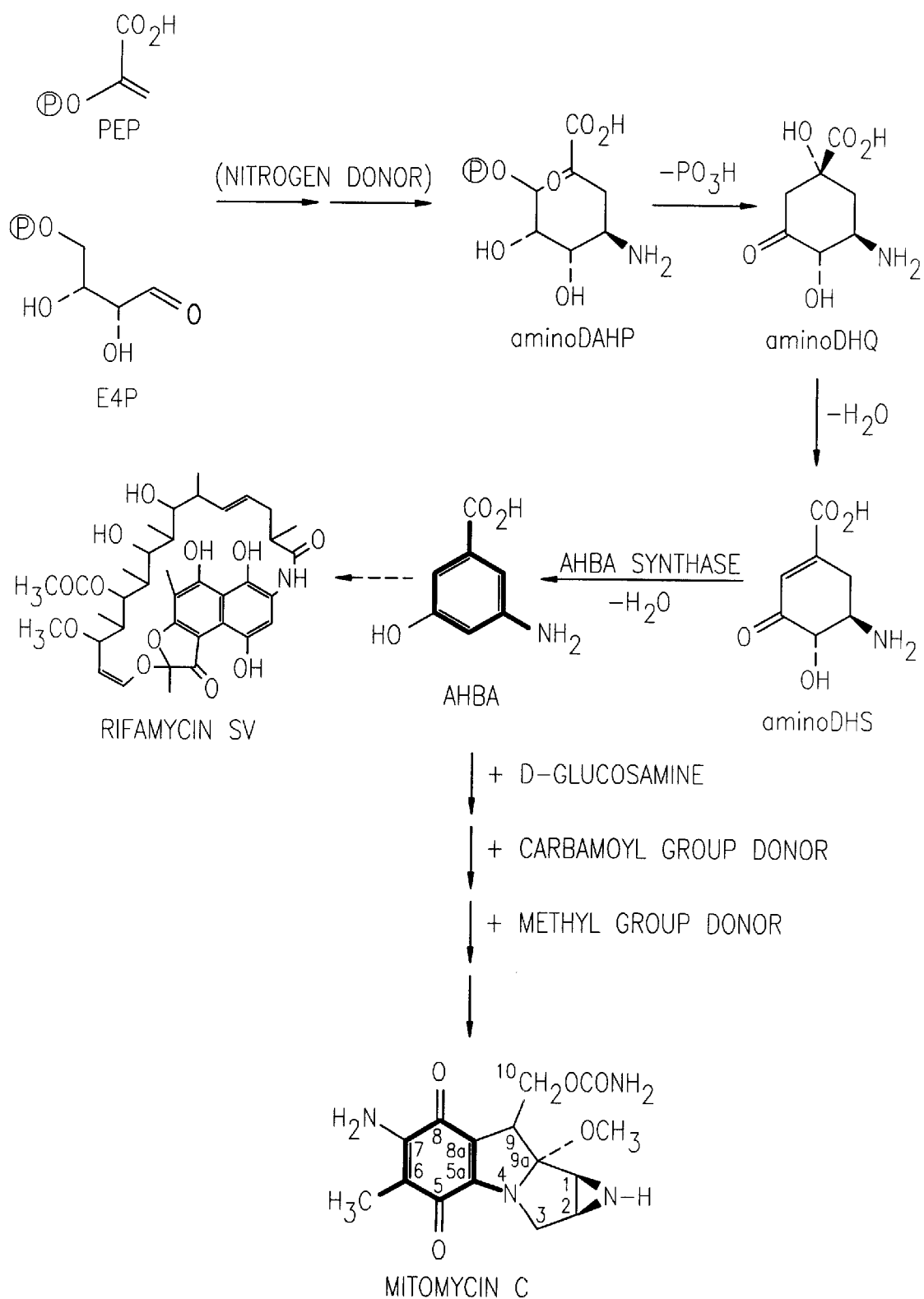
FIG. 7. Biosynthetic pathway leading to mitomycin C.

As determined by precursor feeding experiments, the mitosane core is formed through the condensation of AHBA and D-glucosamine (Hornemann, 1981). AHBA is thought to be derived from the ammoniated shikimate pathway from PEP and E4P, in which the last step from aminoDHS to AHBA is catalyzed by AHBA synthase (FIG. 7) (Kim et al., 1996; Kim et al., 1998). Meanwhile, the reaction of attaching an activated sugar residue to a core compound is usually catalyzed by a group of enzymes called glycosyltransferases as specified by macrolide, glycopeptide antibiotic and polysaccharide biosynthesis (Kahler et al., 1996; Otten et al., 1995b; Solenberg et al., 1997; Yamazaki et al., 1996). In principle, the condensation of AHBA with D-glucosamirie can be initiated in two different ways (FIG. 7). One would involve the formation of the $C_{8a}$–$C_9$ bond by an electrophilic aromatic alkylation or acylation. A second possibility would be formation of a Schiff base between the nitrogen of AHBA and the D-glucosamine C1 aldehyde, followed by ring closure at $C_{8a}$–$C_9$. In either case, a C- or N- instead of O-glycosyltransferase is expected. Although previously described glycosyltransferases display a high degree of sequence divergence (Yamazaki et al., 1996), the mechanistic similarity with O-glycosyl transfer may suggest that mitB encodes a N-glycosyltransferase that initiates the formation of the mitosane system by linking glucosamine to AHBA. The mitA and mitB genes and their corresponding products are likely candidates to mediate formation of AHBA and the mitosane ring system, respectively. However, the possible function of the ImbE-like protein remains unclear, since its current role within lincomycin biosynthetic pathway of *S. lincolnensis* is not known (Peschke, 1995).

The involvement of AHBA synthase (mitA) and the putative glycosyltransferase (mitB) in MC biosynthesis was established by gene disruption to create mutants blocked in MC biosynthesis. This required development of a method to introduce DNA into *S. lavendulae* NRRL 2564 since the strain remains refractory to traditional Streptomyces protoplast and electroporation-mediated transformation procedures. Other such refractory strains include, but are not limited to, ATCC 27422. The modified Bierman protocol (Bierman et al., 1992) was used to affect efficient conjugative transfer into *S. lavendulae* using the *E. coli*-Streptomyces shuttle plasmid pKC1139. This result is significant because it permits the development of an effective system for analyzing in detail the genes involved in mitomycin biosynthesis.

The function of mitA was probed by providing strains MV100 and MV102 with exogenous 3-amino-5-hydroxybenzoic acid in the culture medium. Despite repeated attempts to complement MV100, MC production was not restored as measured by HPLC or biological assay. It is believed that insertion of the tsr gene into mitA resulted in disruption of biosynthetic genes immediately downstream, since supplying mitA in trans on a medium copy number plasmid also failed to restore MC production to MV100. This putative polar effect was eliminated by generating the MitA K191A mutant strain MV102. Providing exogenous 3-amino-5-hydroxybenzoic acid to this mutant strain of *S. lavendulae* restored production of MC as shown by TLC, HPLC and mass spectrometry. When MV102 was grown in the absence of AHBA, there was no detectable production of MC. The ability of 3-amino-5-hydroxybenzoic acid to complement the mutant MitA protein further supports the function of MitA as an AHBA synthase as indicated by the database protein sequence alignment and previous studies on rifK (Kim et al., 1998).

EXAMPLE 3

Mitomycin Resistance in *Streptomyces lavendulae* Includes a Drug-Binding Protein-Dependent Export System As a prodrug, MC is unreactive until chemical or enzymatic reduction renders the molecule a highly effective alkylating agent (Iyer and Szybalski, 1964). The molecular basis of MC bioactivity derives mainly from its propensity to covalently interact with DNA at 5'-CpG sequences, causing lethal intra- and inter-strand crosslinks as well as monofunctional alkylation (Tomasz, 1995).

*S. lavendulae* encounters a daunting challenge in avoiding potentially lethal MC-mediated crosslinks since it has a chromosomal G+C content of over 70%, which translates into at least one million potential drug target sites per cell. Indeed, two genetic loci that mediate mitomycin resistance have been reported in this organism. One locus (mcr) encodes a protein (MCRA) that catalyzes oxidation of the reduced, bioactivated species of MC via a redox relay mechanism (August et al., 1994; Johnson et al., 1997). The second locus (mrd) encodes MRD that functions to sequester the prodrug by a specific mitomycin-binding protein (Sheldon et al., 1997). A paradox of current knowledge regarding mitomycin resistance has been the lack of a clear mechanism for drug transport. Indeed, the observed stoichiometry suggests that it would be ineffective for *S. lavendulae* to utilize MRD as a solo mechanism for cellular self-protection. Pathogenic bacteria (Nikaido, 1994), and antibiotic-producing microorganisms (Cundliffe, 1992; Mendez and Salas, 1998), employ export of toxic compounds as a means of resistance.

Materials and Methods

Bacterial strains, culture conditions, and media. *E. coli* DH5α used as a host for generation of double-stranded plasmid DNA, was grown at 37° C. on LB medium. *E. coli* BL21 (DE3), used as host for protein expression, was grown at 37° C. in NZCYM medium (Sambrook et al., 1989). *S. lavendulae* NRRL 2564 was grown on YEME medium (Hopwood et al., 1985) at 30° C. for preparation of genomic DNA.

DNA preparation and amplification. *S. lavendulae* genomic DNA was isolated by the lysozyme-2×Kirby mix method (Hopwood et al.,. 1988). General DNA manipulation was performed as described previously (August et al., 1994). Oligonucleotides for PCR and sequencing were obtained from Gibco BRL. PCR amplifications were carried out using a Hybaid thermal cycler (Hybaid Ltd., Teddington, U.K.).

Cloning and sequencing of mct. A *S. lavendulae* NRRL 2564 genomic DNA library was constructed in the cosmid vector pNJ1 (Tuan et al., 1990) as previously described (August et al., 1994). The insert DNA of a cosmid clone containing sequences flanking mrd was digested with BamHI and subcloned into the BamHI site of pUC 19. Using exonuclease III (Erase-A-Base kit, Promega, Madison, Wis.), a set of nested deletion clones was generated and both strands of the insert DNA were sequenced by the dideoxy chain termination method using the ABI Prism kit (PE Applied Biosystems) in coordination with an ABI 373automated sequencer. 10% DMSO was added to the reactions to reduce compressions. Sequence data was analyzed using the GeneWorks (Oxford Molecular) software package. Deduced amino acid sequence data were compared to the available databases using the BLAST program of the Genetics Computer Group version 9.0 software (Oxford Molecular Group). The mct gene has been deposited in the GenBank database under Accession No. AF120930.

Construction of the mct mutant strain of *S. lavendulae*. The mct disruption vector pDHS7704 was constructed as follows. pDHS7661 was digested with EcoRI, blunt-ended, and ligated with the 1.4 kb neomycin resistance gene fragment from pFD666 (ApaLI-HindIII digestion, blunt-ended)

(Ames, 1986). The 5.4 kb EcoRI-HindIII fragment from the resulting construct (pDHS7703) was subcloned into pKC1139 to create pDHS7704, and conjugated into *S. lavendulae* according to Bierman et al. (1992). A met double crossover mutant was selected after propagating transconjugants on R5T plates for five generations at 39° C. Kanamycin-resistant and apramycin-sensitive colonies were further tested by. Southern blot to confirm the desired double crossover genotype.

Construction of mct expression plasmid. For the construction of the *E. coli* expression plasmid NdeI and HindIII sites were introduced at the translational start codon and downstream of the translational stop codon of met, respectively. The primers used for PCR were 5'-GGGAATTCCATATGATGCAGTCCATGTCAC-3' (SEQ ID NO:94) and 5'-GGGAATTCAAGCTTTCATTCCGCCGGGGTC-3' (SEQ ID NO:95). The PCR was carried out using 2.5 U of Taq polymerase, 0.4 µg of each primer, 1 µg of pDHS7661 DNA as template, 10 mM each of dATP-dGTP-dCTP-dTTP, 1.5 mM $MgCl_2$, and 10 µl of 10×Promega PCR buffer in a total volume of 100 µl. Amplification was achieved with 30 cycles of denaturation at 94° C. for 30 seconds, annealing at 37° C. for 1 minute, and extension at 70° C. for 2 minutes. The 1.45 kb PCR product was recovered by 0.8% agarose gel electrophoresis, digested with NdeI-HindIII and ligated into the T7 expression plasmid pET17b (Novagen), which had been similarly cut with EcoRI-HindIII, to give pDHS7023. pDHS7023 was introduced by transformation into *E. coli* BL21(DE3) to provide strain PJS102.

Construction of mct-mrd co-expression plasmid. From plasmid pDHS7006 (Sheldon et al., 1997), a 2.1 kb SspI fragment was isolated. The fragment contained the mrd gene under the control of the T7 promoter, including transcriptional terminator sequences (rrnB T1) upstream and downstream of mrd. The fragment was ligated into the MC-translocase construct pDHS7023, which had been cut with MscI, to give pDHS7024. pDHS7024 was introduced by transformation into *E. coli* BL21 (DE3) to result in strain PJS103.

MC resistance phenotype of *E. coli*. To analyze resistance conferred by the expression of the MC-translocase in *E. coli*, 10 µl of strain PJS102 was spread on LB agar medium containing 100 µg/ml of ampicillin, IPTG to a final concentration of 1.0 mM, and various concentrations of MC. The cultures were grown overnight at 37° C. and colony-forming units (CFUS) were determined. Similarly, the MC resistance phenotype of strain PJS103 (mcr-mrd co-expression strain) was quantified.

[$^3$H]-MC uptake assay of strain PJ102 and PJS103, [$^3$H]-MC was obtained from Kyowa Hakko Kogyo, Ltd. Uptake studies were performed for whole cells of PJS100, PJS102, PJS103 and *E. Coli* BL21(DE3)::pT7SC and pET17b. PJS100, PJS102, and PJS103 as well as vector-only cultures were cultured (37° C.) in 5 ml of NCZYM medium with IPTG added to a final concentration of 1 mM (at approximately 3 hours growth). At 9 hours (late exponential phase), cells were harvested by centrifugation and resuspended in 1 ml NCZYM broth (5× concentration). The concentrated suspension of late-exponential growth phase cells was exposed to [$^3$H]-MC (59 Ci/mmol) at a final concentration of 0.022 µg/ml (0.0655 nmol). Aliquots (100 µl) were removed at frequent intervals, placed on 1.2 µM GF/C filters (Whatman International, Maidstone, U.K.) and washed once with 6 ml of 0.85% NaCl poured over the filters under vacuum pressure. Additional aliquots were simultaneously removed for determination of protein content (protein assay kit, Bio-Rad Laboratories, Richmond, Calif.). Radioactivity on the filters was quantified using a Beckman LS7000 scintillation counter. Results were expressed as nanograms of mitomycin per milligram of cell protein.

Results

A gene encoding a transmembrane protein is physically linked to mrd. DNA sequence analysis of a cosmid clone containing the mrd locus, a previously characterized MC resistance determinant (Sheldon et al., 1997), identified an open reading frame (ORF) encoding a polypeptide predicted to be highly hydrophobic that shows similarity to a variety of antibiotic export proteins in drug-producing actinomycetes. Significantly, the gene (mct, SEQ ID NO:16) encoding the putative mitomycin exporter (MC-translocase; MCT) protein is located within 5 kb of mrd (SEQ ID NO:143) and is physically linked to the mitomycin biosynthetic gene cluster (FIG. 15).

Sequence analysis of the mct locus. Nucleotide sequence analysis of cosmid clone pDHS7547 revealed an ORF predicted to start with the ATG codon at position 132 and end with the TGA codon at nucleotide 1587 (FIG. 16), resulting in a 484 amino acid polypeptide with a predicted molecular weight of 50,023 daltons. Comparison of the deduced amino acid sequence of the mct gene with proteins in the available databases revealed significant similarity to several integral membrane proteins that confer drug resistance. These include the CmcT protein from the cephamycin producer, *Nocardia lactamdurans* (Coque et al., 1993), the Pur8 protein from the puromycin producer, *Streptomyces alboniger* (Tercero et al., 1993), the Mmr protein from the methylenomycin producer, *Streptomyces coelicolor* (Neal and Chater, 1987), and the LmrA protein from the lincomycin producer, *Streptomyces lincolnensis* (Zhang et al., 1992). The similarities of the mct gene product and related proteins extend over the entire sequences, with the highest levels of similarity found within the amino-terminal regions (FIG. 17).

Within the N-terminal regions of several antibiotic efflux proteins, including Mmr and LmrA, several highly conserved structural motifs have been noted. The β-turn motif (VxGxLxDxxGRKxxxL) (SEQ ID NO:144) found within the highly conserved cytoplasmic loop sequence separating transmembrane domains two and three of most eukaryotic and prokaryotic transport proteins, is clearly evident in MCT at positions 79–95 (FIG. 16). A motif (LDxTVxNVALP) (SEQ ID NO:145) found at the end of transmembrane domain one, specific to the 14 transmembrane segment family (Paulson and Skurray (1993)) is present in MCT at positions 41–51 (FIG. 16). In addition, several other invariant motifs are apparent in the MCT sequence.

Transmembrane proteins that mediate resistance to antibiotics and antiseptics by active efflux are highly related, usually containing 12 or 14 transmembrane regions. Notably, the actinomycete drug transport proteins that share homology with MCT appear to contain 14 transmembrane spanning regions and constitute a family of drug resistance translocases. Utilizing the membrane structure and topology program MEMSAT (University College, London), and hydropathy analyses based on the algorithm of Kyte and Doolittle (1982), a prediction of 14 transmembrane spanning domains was made for the deduced amino acid sequence of MCT (FIG. 18).

Inactivation of met results in greater sensitivity to MC. To establish a physiological role for MCT in *S. lavendulae*, the corresponding gene (mct) was inactivated by insertion of the aphII gene from transposon Tn5 to give pDHS7704. After conjugal transfer of pDHS7704 from E. coli to S. lavendulae and growth of the transconjugants under selective conditions, targeted replacement of native mct was achieved by double crossover homologous recombination. Gene disruption was confirmed by Southern blot hybridization of total DNA from the S. lavendulae wild-type and mutant with a DNA probe that included the mct locus. Analytical digests of the genomic DNA resulted in detection of the predicted band shifts in the mutant and wild-type strains (FIG. 19). The S. lavendulae met disruption mutant strain (MM105) exhibited an approximately 25-fold reduction in resistance to MC when exposed to 100 μg of MC per ml of medium (Table 3). In media lacking MC, the growth kinetics of the strain MM105 was comparable to the wild-type S. lavendulae strain.

TABLE 3

Resistance of S. lavendulae strains to varying concentrations of MC

| Concentration of MC (μg/ml) | Plate count CFU/ml Strain | |
|---|---|---|
| | S. lavendulae wild-type | S. lavendulae mct mutant (MM 105) |
| 10 | >$10^7$ | >$10^7$ |
| 20 | >$10^7$ | >$10^7$ |
| 40 | 5.3 × $10^3$ | 2.6 × $10^3$ |
| 80 | 2.6 × $10^3$ | 2.4 × $10^2$ |
| 100 | 2.0 × $10^3$ | 8.0 × $10^1$ |

Expression of mct in E. coli. To investigate further the function of mct, heterologous expression of the gene in E. coli was pursued. met was amplified by PCR and cloned into the protein expression vector pET17b to give pDHS7023. pDHS7023 was then introduced into E. coli BL21(DE3) to give strain PJS102. After disruption of the cells by sonication, MCT was found to be associated mainly with the membrane fraction of the cell lysate, as expected for an integral membrane protein. To determine if strain PJS102 was resistant to MC, cultures were grown up and plated on agar medium containing various concentrations of MC. Significantly, IPTG-induced cultures of PJS102 exhibited resistance to MC at drug concentrations 5-fold greater than those for E. coli BL21 (DE3) containing vector alone (Table 4).

TABLE 4

MC resistance of mct, mrd expressing E. coli strains

| Concentration of MC (μg/ml) | Plate count CFU/ml Strain | | | |
|---|---|---|---|---|
| | BL21 (DE3):: pET17b | PJS100 | PJS102 | PJS103 |
| 0.0 | >$10^7$ | >$10^7$ | >$10^7$ | >$10^7$ |
| 0.01 | >$10^7$ | >$10^7$ | >$10^7$ | >$10^7$ |
| 0.1 | 7.3 × $10^3$ | >$10^7$ | >$10^7$ | >$10^7$ |
| 0.5 | 3.2 × $10^2$ | >$10^7$ | 2.1 × $10^5$ | >$10^7$ |
| 1.0 | 0.0 | 3.3 × $10^6$ | 5.9 × $10^4$ | >$10^7$ |
| 2.5 | — | NA[a] | 2.0 × $10^2$ | >$10^7$ |
| 5.0 | — | 2.7 × $10^6$ | 0.0 | >$10^7$ |
| 10 | — | 6.1 × $10^5$ | — | >$10^7$ |
| 20 | — | 2.5 × $10^5$ | — | >$10^7$ |
| 30 | — | 5.0 × $10^2$ | — | >$10^7$ |
| 60 | — | 0.0 | — | >$10^7$ |
| 80 | — | — | — | 1.4 × $10^5$ |

TABLE 4-continued

MC resistance of mct, mrd expressing E. coli strains

| Concentration of MC (μg/ml) | Plate count CFU/ml Strain | | | |
|---|---|---|---|---|
| | BL21 (DE3):: pET17b | PJS100 | PJS102 | PJS103 |
| 100 | — | — | — | 9.6 × $10^3$ |
| 150 | — | — | — | 3.0 × $10^1$ |
| Mitomycin B | — | >$10^{7b}$ | NA[c] | >$10^{7d}$ |

[a]Did not test strain against this concentration of MC
[b]Mitomycin B tested at a concentration of 1.0 μg/ml
[c]Did not test strain against mitomycin B
[d]Mitomycin B tested at a concentration of 15 μg/ml Co-expression of mct and mrd in E. coli. To address the notion that MRD and MCT proteins participate as components of a binding protein-dependent drug export system, the mct and mrd genes were co-expressed in E. coli. From plasmid pDHS7006 (mrd expression construct) (Sheldon et al., 1997), a DNA fragment containing the mrd gene under the control of the T7 promoter was ligated into pDHS7023 to give pDHS7024. pDHS7024 was then introduced into E. coli BL21(DE3) to give strain PJS103. To determine if strain PJS103 was resistant to MC, cultures were grown up and plated on agar medium containing various concentrations of MC. Significantly, IPTG-induced cultures of PJS103 exhibited resistance to MC at drug concentrations 300-fold greater than those for E. coli BL21(DE3) containing vector alone (150 μg/ml vs. 0.5 μg/ml of MC; Table 4). In addition to PJS103 maintaining levels of resistance over that of the vector control strain, co-expression of mct and mrd confers MC-resistance at drug concentrations 5 and 60-fold greater compared to PJS100 (containing the mrd gene alone) (Sheldon et al., 1997) or strain PJS102 (containing the mct gene alone), respectively. Strain PJS103 also displayed high-level resistance to mitomycin B (Table 4), a mitomycin also produced by S. lavendulae.

MC uptake by E. coli cells expressing mct, mrd or mct/mrd. Since the deduced amino acid sequence of the mct gene was similar to antibiotic export proteins, reduced accumulation of MC in MCT-expressing cells would be expected. An assay, modeled after experiments used to study tetracycline efflux-mediated resistance in E. coli (Levy and McMurry, 1978), was designed to study the uptake of [$^3$H]-MC by the susceptible vector control and resistant mct, mrd and mct/mrd expressing E. coli strains.

MC accumulation by the susceptible vector control strain (BL21 (DE3)::pET17b) was found to reach a maximum level at 5 minutes and thereafter maintained at constant concentrations. In contrast, the quantity of MC accumulation in the resistant, met-expressing strain (PJS102) was only 25% of the susceptible control at 5 minutes, and thereafter remained at reduced concentrations (FIG. 21). Reduced accumulation of drug in PJS102 suggests that mct encodes a protein that facilitates MC export from the cell. To determine if the co-expression of mct and mrd in E. coli also resulted in reduced accumulation of MC, strain PJS103 was analyzed using the [$^3$H]-MC uptake assay. Analyses of drug uptake by cultures of strain PJS101 (Sheldon et al., 1997) were also performed to determine drug accumulation levels in this MC resistant E. coli strain.

The results show a clear difference in MC accumulation between the MC sensitive and resistant strains. Compared to E. coli cells bearing vector alone, MC accumulation in PJS103 was only 35% at 5 minutes and thereafter remained at reduced concentrations. The accumulation of drug in strain PJS103 was found to parallel that of strain PJS102, albeit at slightly higher levels (about 23% greater) of drug over the course of the experiment. Interestingly, strain PJS100, although resistant to significant concentrations of MC, accumulated drug to levels 42% higher than the drug-sensitive vector control at 30 minutes (FIG. 20).

Discussion

Most antibiotics inhibit bacterial growth by binding to proteins or other macromolecular components that involve essential metabolic processes of the cell (Cundliffe, 1992). For instance, DNA alkylation by MC results in disruption of chromosomal replication leading to cell death (Iyer and Szybalski, 1964). In many antibiotic-producing streptomycetes, macromolecular target site(s) are likewise susceptible to endogenous cytotoxic compounds (that is certainly the case in S. lavendulae). Thus, pumping the antibiotic out of the cell at a rate equal to its production and/or re-uptake would prevent drug access to intracellular target sites. Based on the levels of drug found in most antibiotic fermentation broths (concentrations of intracellular drug being low), it is apparent that drug-producing organisms often depend on efficient antibiotic transport mechanisms. Indeed, a growing number of membrane systems implicated in transport (and therefore resistance) of a variety of antibiotics have been discovered in drug-producing streptomycetes (Mendez and Salas, 1998; Paulsen et al., 1996).

In general, genes coding for drug export proteins are physically linked to the corresponding biosynthetic genes within the genome of the antibiotic-producing microorganism. Presumably, the tight linkage of antibiotic export and biosynthetic genes ensures coordinate gene regulation. Interestingly, the presence of back-to-back and overlapping divergent promoters of antibiotic export and regulatory genes has been observed within the tetracenomycin (Guilfoile and Hutchinson, 1992) and actinorhodin (Caballero et al, 1991) biosynthetic gene clusters. Conforming to this example, S. lavendulae possesses a gene coding for an integral membrane drug export protein within the mitomycin biosynthetic gene cluster. Analysis of the deduced amino acid sequence of MCT revealed several similarities with actinomycete proteins predicted to function as drug exporters. By virtue of homology to tetracycline resistance proteins, which have been shown to use proton motive force to energize transport (Littlejohn et al., 1992), the actinomycete drug resistance translocases cited in this study are predicted to power excretion by a proton-dependent electrochemical gradient. It has been suggested that highly conserved sequences within the amino-terminal regions of these proteins play a role in proton translocation (Rouch et al., 1990), while the less well-conserved C-terminal regions may be involved in drug binding (Paulsen et al., 1996; and references therein) or recognition of a protein-drug complex.

Disruption of mct in S. lavendulae resulted in a 25-fold increase in sensitivity to exogenously added MC, providing evidence that MCT maintains a role in providing drug resistance in S. lavendulae. Although the effect is significant, alternative mechanisms of cellular self-protection clearly continue to operate. This evidently includes MCRA, the novel redox-relay protein that re-oxidizes activated MC in S. lavendulae. It is also likely that unidentified xenobiotic transporters provide an alternative mode of drug transport in the absence of MCT, albeit with lower efficiency.

In order to probe the ability of MCT to transport drug in the presence and absence of the MC binding protein, accumulation of [$^3$H]-MC in E. coli was analyzed. Expression of mct in E. coli resulted in MC-resistant cultures that accumulated lower levels of drug than strains bearing vector control (FIG. 20). Interestingly, strain PJS102 (expressing mct only) accumulates less drug intracellularly than strain PJS103 (expressing mrd and mct) (FIG. 20). Increased drug accumulation in strain PJS100 may lend support to the model of equimolar binding between MRD and MC (Sheldon et al., 1997). Significantly higher levels of drug accumulation in strain PJS100 may be the result of intracellular sequestration of MC by MRD. Accordingly, the presence of MRD could also account for the slightly greater levels of MC accumulation in strain PJS103 (co-expressing mct-mrd) as compared to strain PJS102 (expressing mci alone). Comparable to binding protein-dependent import systems (Miller et al., 1983), the binding of MC by MRD may be rate-limiting in the drug excretion process.

Taken together, these results suggest that cellular protection afforded by MCT is a function of drug transport from the cytoplasm. Interestingly, co-expression of mrd and mct in E. coli led to cultures that are dramatically more resistant to exogenously added drug. While normally required for the transport systems with which they are associated, in many instances binding proteins are not integral to the process of solute translocation (Higgins et al., 1990). Similarly, the presence of MRD is not required for MC translocation but dramatically enhances drug tolerance. Hence, the binding protein (MRD) may be considered an accessory component, a rather specific adaptation required for optimal drug resistance. The drug-resistance phenotype of E. coli strains expressing mct alone and in combination with mrd along with the MC uptake analysis of these strains provides evidence that MRD and MCT are components of a novel drug transport system. Such a resistance mechanism, sequestering the intact drug for efficient excretion to the environment, represents a unique cellular strategy for self-preservation by the MC-producing organism.

REFERENCES

Alderson, G., D. A. Ritchie, C. Caballero, R. H. Cool, N. M. Ivanova, A. S. Huddleston, C. S. Flaxman, V. Kristufek, and A. Lounes. Physiology and genetics of antibiotic production and resistance. Res. Microbiol., 44, 665–672 (1993).

Altschul, S. F., Gish, W., Miller, W., Myers, E. W. and D. J. Lipman. Basic local alignment search tool, J. Mol. Biol., 215, 403–410 (1990).

Ames, G. Bacterial periplasmic transport systems: structure, mechanism, and evolution. Ann. Rev. Biochem., 55, 397–425 (1986).

Anderson, M. G., Kibby, J. J., Rickards, R. W. and J. M. Rothschild. Biosynthesis of the mitomycin antibiotics from 3-amino-5-hydroxybenzoic acid, J. Chem. Soc. Chem. Commun., 1277–1278 (1980).

Angell, S., Schwarz, A., and M. J. Bibb. The glucose kinase gene of Streptomyces coelicolor A3(2): its nucleotide sequence, transcriptional analysis and role in glucose repression, Mol. Microbiol., 6, 2833–2844 (1992).

August, P. R., Flickinger, M. C. and D. H. Sherman. Cloning and analysis of a locus (mcr) involved in mitomycin C resistance in Streptomyces lavendulae, J. Bacteriol., 176, 4448–4454 (1994).

August, P. R., Tang, L., Yoon, Y. J., Ning, S., Muller, R., Yu, T. W., Taylor, M., Hoffmann, D., Kim, C. G., Zhang, X., Hutchinson, C. R. and H. G. Floss. Biosynthesis of the ansarnycin antibiotic rifamycin: deductions from the molecular analysis of the rif biosynthetic gene cluster of *Amycolatopsis mediterranei* S699, *Chem. Biol.*, 5, 69–70 (1998).

Baltz, R. H. Genetic recombination in *Streptomyces fradiae* by protoplast fusion and cell regeneration, *Dev, Ind. Microbiol.*, 21, 43–54 (1980).

Baltz, R. H., and T. J. Hosted. Molecular genetic methods for improving secondary-metabolite production in actinomycetes, *Trends Biotech.*, 14:245–250 (1996).

Beck, A., A. Kleickmann, M. Keller, W. Arnold, and A. Puhler. Identification and analysis of the *Rhizobium meliloti* exoAMONP genes involved in exopolysaccharide biosynthesis and mapping of promoters located on the exoHKLAMONP fragment, *Mol. Gen. Genet.*, 241, 367–379 (1993).

Becker, A. M., Herlt, A. J., Hilton, G. L., Kibby, J. J. and R. W. Rickards. 3-Amino-5-hydroxybenzoic acid in antibiotic biosynthesis, VI. Directed biosynthesis studies with ansamycin antibiotics, *J. Antibiot.*, 36, 1323–1328 (1983).

Bennett, E. P., H. Hassan, and H. Clausen. cDNA cloning and expression of a novel human UDP-N-acetyl-alpha-D-galactosamine. Polypeptide N-acetylgalatosaminyltransferase, GalNAc-t3. *J. Biol. Chem.*, 271, 17006–17012 (1996).

Berdy, J. Are actinomycetes exhausted as a source of secondary metabolites?, p. 13–14. In V. Debabov, Dudnik, Y. And Danlienko, V. (eds.), Ninth International Symposium on the Biology of Actinomycetes. All-Russia Scientific Research Institute for Genetics and Selection of Industrial Microorganisms, Moscow (1995).

Bezanson, G. S. and L. C. Vining. Studies on the biosynthesis of mitomycin C by *Streptomyces verticillatus*, *Can. J. Biochem.*, 49, 911–918 (1971).

Bierman, M.,.Logan, R., O'Brien, K., Seno, E. T., Rao, R. N. and B. E. Schoner. Plasmid cloning vectors for the conjugal transfer of DNA from *Escherichia coli* to Streptomyces spp., *Gene*, 116, 43–49 (1992).

Blattner, F. R., Plunkett, G. R. Bloch, C. A., Perna, N. T., Burland, V., Riley, M., Collado-Vides, J., Glasner; J. D., Rode, C. K., Mayhew, G. F., Gregor, J., Davis, N. W., Kirkpatrick, H. A., Goeden, M. A., Rose, D. J., Mau, B. and Shao, Y., the complete genome sequence of *Escherichia coli* K-12, *Science*, 277, 1453–74 (1997).

Bouvier-Nave, P., Husselstein, T., Desprez, T. and Benveniste, P., Identification of cDNAs encoding sterol methyl-transferases involved in the second methylation step of plant sterol biosynthesis, *Euro. J. Biochem*, 246, 518–29 (1997).

Boyer, M. J., Bioreductive agents: a clinical update, *Oncol. Res.*, 9, 391–395 (1997).

Brown, W. C., and J. L. Campbell. A new cloning vector and expression strategy for genes encoding proteins toxic to *Escherichia coli*, *Gene*, 127:99–103 (1993).

Bult, C. J., White, O., Olsen, G. J., Zhou, L., Flesichmann, R. D., Sutton, G. G., Blake, J. A., FitzGerald, L. M., Clayton, R. A., Gocayne, J. D., Kerlavage, A. R., Dougherty, B. A., Tomb, J. F., Adams, M. D., Reich, C. I., Overbeek, R., Kirkness, E. F., Weinstock, K. G., Merrick, J. M., Glodek, A., Scott, J. L., Geoghagen, N. and J. C. Venter. Complete genome sequence of the methanogenic archaeon, *Methanococcus jannaschii*, *Science*, 273, 1058–1073 (1996).

Butler, M. J., E. J. Friend, I. S. Hunter, F. S. Kaczmarek, D. A. Sugden, and M. Warren. Molecular cloning of resistance genes and architecture of a linked gene cluster involved in biosynthesis of oxytetracycline by Streptomyces rimosus. Mol. Gen. Genet., 215, 231–238 (1989).

Caballero, J. L., Malpartida, F. and D. A. Hopwood. Transcriptional organization and regulation of an antibiotic export complex in the producing Streptomyces culture, *Mol. Gen. Genet.*, 228, 372–380 (1991).

Chater, K. F. Genetic regulation of secondary metabolic pathways in Streptomyces. *Ciba Foundation Symposium*, 171, 144–156 (1992).

Chater, K. F. and C. J. Bruton. Resistance, regulatory and production genes for the antibiotic methylenomycin are clustered, *Embo Journal*, 4, 1893–7 (1985).

Chiao, J. S., T. H. Xia, B. G. Mei, Z. K. Jin, and W. L. Gu. Rifamycin SV and related ansamycins, p. 477–498. In L. C. Vining and Stuttard, C. (Eds.), Genetics and biochemistry and antibiotic production. Butterworth-Hornemann, Newton, Mass. (1995).

Cole, S. T., Brosch, R., Parkhill, J., Garnier, T., Churcher, C., Harris, D., Gordon, S. V., Eiglmeier, K., Gas, S., Barry, C. R., Tekaia, F., Badcock, K., Basham, D., Brown, D., Chillingworth, T., Connor, R., Davies, R., Devlin, K., Feltwell, T., Gentles, S., Hamlin, N., Holroyd, S., Hornsby, T., Jagels, K., Barrell, B. G. and et al., Deciphering the biology of *Mycobacterium tuberculosis* from the complete genome sequence, *Nature*, 393, 537–544 (1998).

Coque, J., P. Liras, and J. Martin. Genes for a β-lactamase, a penicillin-binding protein and a transmembrane protein are clustered with the cephamycin biosynthetic genes in *Nocardia lactamdurans*. *EMBO. J.*, 12, 631–639 (1993).

Coque, J. J., Perez-Laraine, F. J., Enguita, F. J., Fuente, J. L., Martin, J. F. and P. Liras. Characterization of the cmcH genes of *Nocardia lactamdurans* and *Streptomyces clavuligerus* encoding a functional 3'-hydroxymethylcephem O-carbamoyltransferase for cephamycin biosynthesis, *Gene*, 162, 21–27 (1995).

Cummings, J., Spanswick, V. J., Tomasz, M. and J .F. Smyth. Enzymology of mitomycin C metabolic activation in tumor tissue—implications for enzyme—directed bioreductive drug development, *Biochemical Pharmacology*, 56, 405–414 (1998).

Cundliffe, E. Self-protection mechanisms in antibiotic producers. *Ciba Found. Symp.*, 171, 199–208 (1992).

Cundliffe, E., L. A. Merson-Davies, and G. H. Keleman. Aspects of tylosin production and resistance in *Streptomyces fradiae*, p. 235–243, Industrial microorganisms: basic and applied molecular genetics. American Society for Microbiology, Washington, D. C. (1993).

Dean, C. R., Neshat, S. and K. Poole. PfeR, an enterobactin-responsive activator of ferric enterobactin receptor gene expression in *Pseudomonas aeruginosa, J. Bacteriol.*, 178, 5361–5369 (1996).

Decker, H., Motamedi, H. and C. R. Hutchinson. Nucleotide sequences and heterologous expression of tcmG and tcmP, biosynthetic genes for tetracenomycin C in *Streptomyces glaucescens*, *J. Bacteriol.*, 175, 3876–3886 (1993).

Denis, F. and R. Brzezinski. A versatile shuttle cosmid vector for use in *Escherichia coli* and *Actinomycetes, Gene*, 111, 115–118 (1992).

Deppenmeier, U., Muller, V. and G. Gottschalk. Pathways of energy conservation in methanogenic archaea, *Arch. Microbiol.*, 165, 149–163 (1996).

Devereux, J., Haeberli, P. and O. Smithies. A comprehensive set of sequence analysis programs for the VAX, *Nucleic Acids Res.* 12, 387–395 (1984).

Dewick, P. M., The biosynthesis of shikimate metabolites, *Nat. Prod. Rep.*, 15, 17–58 (1995).

Dickens, M. L., Ye, J. and W. R. Strohl. Analysis of clustered genes encoding both early and late steps in daunomycin biosynthesis by Streptomyces sp. strain C5. *J. Bacteriol.*, 177 , 536–543 (1995).

Dittrich, H. and T. M. Kutchan. Molecular cloning, expression, and induction of berberine bridge enzyme, an enzyme essential to the formation of benzophenanthridine alkaloids in the response of plants to pathogenic attach, *Proc. Natl, Acad, Sci. USA*, 88, 9969–9973(1991).

Donadio, S., M. J. Staver, J. B. McAlpine, S. J. Swanson, and L. Katz. Modular organization of genes required for complex polyketide biosynthesis. *Science*, 252, 675–679 (1991).

Evans, J. W., Yudoh, K., Delahoussaye, Y. M. and J. M. Brown. Tirpazamine is metabolized to its DNA-damaging radical by intranuclear enzymes, *Cancer Research*, 58, 2098–2101 (1998).

Fernandez-Moreno, M. A., Caballero, J. L., Hopwood, D. A. and F. Malpartida. The act cluster contains regulatory and antibiotic export genes, direct targets for translational control by the bldA tRNA gene of Streptomyces, *Cell*, 66, 769–80 (1991).

Floss, H. G. Natural products derived from unusual variants of the shikimate pathway, *Nat. Prod. Rep.*, 14, 433–52 (1997).

Ghisalba, O., and N. Nuesch. A genetic approach to the biosynthesis of the rifamycin-chromophore in *Nocardia mediterraniae*. IV. Identification of 3-amino-5-hydroxybenzoic acid as a direct precursor of the seven-carbon amino starter-unit. *J. Antibiot.*, 34, 64–71 (1981).

Gibson, J., Dispensa, M., Fogg, G. C., Evans, D. T. and C. S. Harwood. 4-Hydroxybenzoate-coenzyme A ligase from *Rhodopseudomonas palustris*: purification, gene sequence, and role in anaerobic degradation, *J. Bacteriol.*, 176, 634–641 (1994).

Grebenok, R. J., Galbraith, D. W. and D. D. Penna. Characterization of Zea mays endosperm C-24 sterol methyltransferase: one of two types of sterol methyltransferase in higher plants, *Plant Mol. Biol.*, 34, 891–6 (1997).

Grkovic, S., Brown, M. H., Roberts, N. J., Paulsen, I. T. and R. A. Skurray. QacR is a repressor protein that regulates expression of the *Staphylococcus aureus* multidrug efflux pump QacA, *J. Biol. Chem.*, 273, 18665–73 (1998).

Guilfoile, P. G. and C. R. Hutchinson. Sequence and transcriptional analysis of the *Streptomyces glaucescens* tcmAR tetracenomycin C resistance and repressor gene loci, *Journal of Bacteriology*, 174, 3651–3658 (1992).

Guilfoile, P. G. and C. R. Hutchinson. The *Streptomyces glaucescens* TcmR protein represses transcription of the divergently oriented tcmR and tcmA genes by binding to an intergenic operator region, *Journal of Bacteriology*, 174, 3659–66 (1992).

Hardwick, K. G. and H. R. Pelham. SED6 is identical to ERG6, and encodes a putative methyltransferase required for ergosterol synthesis, *Yeast*, 10, 265–269 (1994).

Hata, T., Sano, Y., Sugawara, R., Matsumae, A., Kanamori, K., Shima, T. and T. Hoshi. Mitomycin, a new antibiotic from Streptomyces, *J. Antibiot. Ser. A*, 9, 141–146 (1956).

Hatano, K., S. Akiyama, M. Asai, and R. W. Richards. Biosynthetic origin of amino benzenoid nucleus ($C_7$N-unit) of ansamitocin, a group of novel maytansinoid antibiotics. *J. Antibiot.*, 35, 1415–1417 (1982).

Haydock, S. F., Dowson, J. A., Dhillon, N., Roberts, G. A., Cortes, J. and P. F. Leadlay. Cloning and sequence analysis of genes involved in erythromycin biosynthesis in *Saccharopolyspora erythraea*: sequence similarities between EryG and a family of S-adenosylmethionine-dependent methyltransferases, *Mol. Gen. Genet.*, 230, 120–128 (1991).

Henderson, I. C., Recent Advances in the Usage of Mitomycin, Proceedings of a symposium, Hawaii, March 21–24, *Oncology*, 1, 1–83 (1993).

Henderson, C. I., Recent advances in the usage of mitomycin, *Oncology*, 50:(Suppl. 1), 1–84 (1993).

Hidaka, T., Goda, M., Kuzuyama, T., Takei, N., Hidaka, M. and H. Seto. Cloning and nucleotide sequence of fosfomycin biosynthetic genes of *Streptomyces wedmorensis*, *Mol. Gen. Genet.*, 249, 274–280 (1995).

Hidaka, T., Hidaka, M., Kuzuyama, T. and H. Seto. Sequence of a P-methyltransferase-encoding gene isolated from a bialaphos-producing *Streptomyces hygroscopicus*, *Gene*, 158, 149–150 (1995).

Higgins, C., S. Hyde, M. Mimmack, U. Gileadi, D. Gill, and M. Gallagher. Binding protein-dependent transport systems. *J. Bioenerg. Biomem.*, 22, 571–592 (1990).

Hirai, O., Miyamae, Y., Hattori, Y., Takashima, M., Miyamoto, A., Zaizen, K. and Y. Mine. Microbial mutagenicity an in vitro chromosome aberration induction by fk973, a new antitumor agent, *Mutation Res.*, 324, 43–50 (1994).

Hopwood, D. A. Genetic contributions to understanding polyketide synthases. *Chem. Rev.*, 97, 2465–2497 (1997).

Hopwood, D. A., Bibb, M. J., Chater, K. F., Kieser, T., Bruton, C. J., Kieser, H. M., Lydiate, D. J., Smith, C. P., Ward, J. M. and H. S. Schrempf. *Genetic manipulation of Stretomyces: a laboratory manual*, John Innes Institute, Norwich, United Kingdom, 1985.

Horii, M., Ishizaki, T., Paik, S. Y., Manome, T. and Y. Murooka. An operon containing the genes for cholesterol oxidase and a cytochrome P-450-like protein from a Streptomyces sp., *J. Bacteriol.*, 172, 3644–3653 (1990).

Hornemann, U., *Biosynthesis of the mitomycins*, 1981.

Hornemann, U. and J. H. Eggert. Utilization of the intact carbamoyl group of L—($NH_2CO$—$^{13}C,^{15}N$) citrulline in mitomycin biosynthesis by *Streptomyces verticillatus*, *Journal of Antibiotics*, 28, 841–843 (1975).

Hornemann, Y., Kehrer, J. P., Nunez, C. S. and R. L. Ranieri. D-glucosamine and L-citrulline, precursors in mitomycin biosynthesis by *Streptomyces verticillatus*, *Journal of the American Chemical Society*, 96, 320–322 (1974).

Iyer, N., and W. Szybalski. Mitomycin or porfiromycin: chemical mechanism of activation and cross-linking of DNA. *Science*, 145, 55–56 (1964).

Jabbouri, S., Fellay, R., Talmont, F., Kamalaprija, P., Burger, U., Relic, B., Prome, J. C. and W. J. Broughton. Involvement of nodS in N-methylation and nodU in 6-O-carbamoylation of Rhizobium sp. NGR234 nod factors, *J. Biol. Chem.*, 270, 22968–22073 (1995).

Jabbouri, S., Relic, B., Hanin, M., Kamalaprija, P., Burger, U., Prome, D., Prome, J. C. and W. J. Broughton. nolO and noeI (HsnIII) of Rhizobium sp. NGR234 are involved in 3-O-carbamoylation and 2-O-methylation of Nod factors, *J. Biol. Chem.*, 273, 12047–12055 (1998).

Johnson, D. A., August, P. R., Shackleton, C., Liu, H. W. and D. H. Sherman. Microbial resistance to mitomycins involves a redox relay mechanism, *J. Am. Chem. Soc.*, 119, 2576–2577 (1997).

Kagan, R. M. and S. Clarke. Widespread occurrence of three sequence motifs in diverse S-adenosylmethioninedependent methyltransferases suggests a common structure for these enzymes, Arch. Biochem. Biophy., 310, 417–27 (1994).

Kahler, C. M., R. W. Carlson, M. M. Rahman, L. E. Martin, D. S. Stephens. Two glycosyltransferase genes, IgtF and rfaK, constitute the lipooligosaccharide ice (inner core extension) biosynthesis operon of *Neisseria meningitidis*. *J. Bacteriol.*, 178, 6677–6684 (1996).

Kasai, M. and H. Arai. Novel mitomycin derivatives, *Exp. Opin. Ther. Patents*, 5, 757–770 (1995).

Kibby, J. J., I. A. McDonald, and R. W. Rickards. 3-amino-5-hydroxybenzoic acid as a key intermediate in ansamycin and maytansinoid biosynthesis. *J. Chem. Soc. Chem. Comm.*, 1980, 768–769 (1980).

Kibby, J. J. and R. W. Rickards. The identification of 3-amino-5-hydroxybenzoic acid as a new natural aromatic amino acid, *J. Antibiot.*, 34, 605–607 (1981).

Kim, C. G., Kirschning, A., Bergon, P., Zhou, P., Su, E., Sauerbrei, B., Ning, S., Ahn, Y., Breuer, M., Leistner, E. and H. G. Floss. Biosynthesis of 3-amino-5-hydroxybenzoic acid, the precursor of $mC_7N$ units in ansamycin antibiotics, *J. Am. Chem. Soc.*, 188, 7486–7491 (1996).

Kim, C. G., A. Kirschning, P. Bergon, Y. Ahn, J. J. Wang, M. Shibuya, and H. G. Floss. Formation of 3-amino-5-hydroxybenzoic acid, the precursor of $mC_7N$ units in ansamycin antibiotics, by a new variant of the shikimate pathway. *J. Am. Chem. Soc.*, 114, 4941–4943 (1992).

Kim, C. G., Yu, T. W., Fryhle, C. B., Handa, S. and H. G. Floss. 3-Amino-5-hydroxybenzoic acid synthase, the terminal enzyme in the formation of the precursor of $mC_7N$ units in rifamycin and related antibiotics, *J. Biol. Chem.*, 22, 6030–6040 (1998).

Kuzuyama, T., Seki, T., Dairi, T., Hidaka, T. and H. Seto. Nucleotide sequence of fortimicin KL1 methyltransferase gene isolated from *Micromonospora olivasterospora* and comparison of its deduced amino acid sequence with those of methyltransferases involved in the biosynthesis of bialaphos and fosfomycin, *J. Antibiot.*, 48, 1191–3 (1995).

Kwon, O., Bhattacharyya, D. K. and R. Meganathan. Menaquinone (vitamin K2) biosynthesis: overexpression, purification, and properties of o-succinylbenzoyl-coenzyme A synthetase from *Escherichia coli, J. Bacteriol.*, 178, 6778–6781 (1996).

Kyte, J., and R. F. Doolittle. A simple method for displaying the hydropathic character of a protein. *J. Mol. Biol.*, 105–132 (1982).

Lacalle, R. A., Ruiz, D. and A. Jimenez. Molecular analysis of the dmpM gene encoding an O-dimethyl puromycin O-methyltransferase from *Streptomyces alboniger, Gene*, 109, 55–61 (1991).

Lee, J. P., S. W. Tsao, C. J. Chang, X. G. He, and H. G. Floss. Biosynthesis of naphthomycin A in *Streptomyces collinus. Can. J. Chem.*, 72, 182–187 (1994).

Lee, P. J. and A. M. Stock. Characterization of the genes and proteins of a two-component system from the hyperthermophilic bacterium *Thermotoga maritima, J. Bacteriol.*, 178, 5579–5585 (1996).

Levy, S., and L. McMurry. Plasmid-mediated tetracycline resistance involves alternative transport systems for tetracycline. *Nature*, 276, 90–92 (1978).

Littlejohn, T., I. Paulsen, M. Gillespie, J. Tennant, M. Midgley, I. Jones, A. Purewal, and R. Skurray. Substrate specificity and energetics of antiseptic and disinfectant resistance in *Staphylococcus aureus. FEMS Microbiol. Lett.*, 95, 259–266 (1992).

Lomovskaya, O., Lewis, K. and A. Matin. EmrR is a negative regulator of the *Escherichia coli* multidrug resistance pump EmrAB, *J. Bacteriol.*, 122, 2328–2334 (1995).

Luka, S., Sanjuan, J;, Carlson, R. W. and G. Stacey. nolMNO genes of *Bradyrhizobium japonicum* are co-transcribed with nodYABCSUIJ, and nolO is involved in the synthesis of the lipo-oligosaccharide nodulation signals, *J. Biol. Chem.*, 268, 27053–27059 (1993).

Madduri, K., Torti, F., Colombo, A. L. and C. R. Hutchinson. Cloning and sequencing of a gene encoding carminomycin 4-O-methyltransferase from *Streptomyces peucetius* and its expression in *Escherichia coli, J. Bacteriol.*, 175, 3900–3904 (1993).

Makino, K., Shinagawa, H., Amemura, M. and A. Nakata. Nucleotide sequence of the phoB gene, the positive regulatory gene for the phosphate regulon of *Escherichia coli* K-12, *J. Mol. Biol.*, 190, 37–44 (1986).

Martin, J. F. Clusters of genes for the biosynthesis of antibiotics: regulatory genes and overproduction of pharmaceuticals. *J. Ind. Microbiol.*, 9, 73–90 (1992).

Mazodier, P., Petter, R. and C. Thomson. Intergeneric conjugation between *Escherichia coli* and Streptomyces species, *J. Bacteriol.*, 171, 3583–3585 (1989).

Mendez, C., and J. A. Salas. ABC transporters in antibiotic-producing actinomycetes. *FEMS Microb. Lett.*, 158, 1–8 (1998).

Miller, J., J. Olson, J. Plfugrath, and F. Quiocho. Rates of ligand binding to periplasmic proteins involved in bacterial transport and chemotaxis. *J. Biol. Chem.*, 238, 13665–13672 (1983).

Mizuno, T. and I. Tanaka. Structure of the DNA-binding domain of the OmpR family of response regulators, *Mol. Microbiol.*, 24, 665–667 (1997).

Morbidoni, H. R., de Mondoza, D. and J. Cronan Jr. *Bacillus subtilis* acyl carrier protein is encoded in a cluster of lipid biosyiithesis genes, *J. Bacteriol.*, 178, 4794–800 (1996).

Motamedi, H., and C. R. Hutchinson. Cloning and heterologous expression of a gene cluster for the biosynthesis of tetracenomycin C, the anthracycline antitumor antibiotic of *Streptomyces glaucescens. Proc. Natl. Acad. Sci. USA*, 84, 4445–4449 (1987).

Muth, G., B. Nussbaumer, W. Wohlleben, and A. Publer. A vector system with temperature-sensitive replication for gene disruption and mutational cloning in streptomycetes. *Mol. Gen. Genet.*, 219, 341–348 (1989).

Naoe, Y., Inami, M., Matsumoto, S., Nishigaki, F., Tsujimoto, S., Kawamura, I., Miyayasu, K., Manda, T. and K. Shimomura. Fk317—a novel substituted dihydrobenzoxazine with potent antitumor activity which does not induce vascular leak syndrome, *Cancer Chemo. Pharmacol.*, 42, 31–36 (1998).

Neal, R. J., and K. F. Chater. Nucleotide sequence analysis reveals similarities between proteins determining methylenomycin A resistance in Streptomyces and tetracycline resistance in eubacteria. *Gene*, 58, 229–241 (1987).

Niemi, J. and Mantsala, P., Nucleotide sequences and expression of genes from *Streptomyces purpurascens* that cause the production of new anthracyclines in *Streptomyces galilaeus, J. Bacteriol.*, 177, 2942–2945 (1995).

Nikaido, H. Prevention of drug access to bacterial targets: Permeability barriers and active efflux. *Science*, 264, 382–388 (1994).

Nishikohri, K. and S, Fukui. Biosynthesis of mitomycin in *Streptomyces caespitosus*. Relationship of intracellular vitamin B$_{12}$ level to mitomycin synthesis and enzymatic methylation of a demethylated derivative of mitomycin, *Eur. J. Appl. Microbiol.*, 2, 129–145 (1975).

Nolling, J., Pihl, T. D. and J. N. Reeve. Cloning, sequencing, and growth phase-dependent transcription of the coenzyme F420-dependent N5, N10-methylenetetrahydromethanopterin reductase-encoding genes from *Methanobacterium thermoautotrophicum* delta H and *Methanopyrus kandleri*, *J. Bacteriol.*, 177, 7238–7244 (1995).

Ohno, T., Armand, S., Hata, T., Nikaidou, N., Henrissat, B., Mitsutomi, M. and T. Watanabe. A modular family- 19 chitinase found in the prokaryotic organism *Streptomyces griseus* HUT 6037, *J. Bacteriol.*, 178, 5065–5070 (1996).

Omer, C. A., Lenstra, R., Little, P. J., Dean, C., Tepperman, J. M., Leto, K. J., Romesser, J. A. and D. P. O'Keefe. Genes for two herbicide-inducible cytochromes P-450 from *Streptomyces griseolus*, *J. Bacteriol.*, 172, 3335–3345 (1990).

Otten, S. L., X. Liu, J. Ferguson, and C. R. Hutchinson. Cloning and characterization of the *Streptomyces peucetius* dnrQS genes encoding a daunosamine biosynthesis enzyme and a glycosyl transferase involved in daunorubicin biosynthesis. *J. Bacteriol.*, 177, 6688–6692 (1995b).

Otten, S. L., Ferguson, J. and C. R. Hutchinson. Regulation of daunorubicin production in *Streptomyces peucetius* by the dnrR2 locus, *J. Bacteriol.*, 177, 1216–1224 (1995a).

Pan, S. S. and T. Iracki. Metabolites and DNA adduct formation from flavoenzyme-activated porfiromycin, *Molecular Pharmacology*, 34, 223–228 (1988).

Paulsen, I., and R. Skurray. Topology, structure and evolution of two families of proteins involved in antibiotic and antiseptic resistance in eukaryotes and prokaryotes—an analysis. *Gene*, 124:1–11 (1993).

Paulsen, I., M. Brown, and R. Skurray. Proton-dependent multidrug efflux pumps. *Microbiol. Rev.*, 60, 575–608 (1996).

Paz, M. M. and P. B. Hopkins. DNA-DNA interstrand cross-linking by FR66979-intermediates in the activation cascade, *J. Am. Chem. Soc.*, 119, 5999–6005 (1997).

Perez-Laraine, F. J., Liras, P., Rodriguez-Garcia, A. and J. F. Martin. A regulatory gene (ccaR) required for cephamycin and clavulanic acid production in *Streptomyces clavuligerus*: amplification results in overproduction of both beta-lactam compounds, *J. Bacteriol.*, 179, 2053–2059 (1997).

Peschke, U., H. Schmidt, H. Z. Zhang, and W. Piepersberg. Molecular characterization of the lincomycin-production gene cluster of *Streptomyces lincolnensis*. 78–11. *Mol. Microbiol.*, 16, 1137–1156 (1995).

Piepersberg, W. Pathway engineering in secondary metabolite-producing actinomycetes, *Crit. Rev. Biotechnol.*, 4:251–285 (1994).

Platt, M. W., Miller, K. J., Lane, W. S. and E. P. Kennedy. Isolation and characterization of the constitutive acyl carrier protein from *Rhozobium meliloti*, *J. Bacteriol.*, 172, 5440–4 (1990).

Potgieter, M. Biosynthetic studies on geldanamycin and pactamycin. Ph.D. thesis. Univ. Illinois (1983).

Praillet, T., Nasser, W., Robert-Baudouy, J. and S. Reverchon. Purification and functional characterization of Pacs, a regulator of virulence-factor synthesis in *Erwinia chrysanthemi*, *Molecular Microbiology*, 20, 391–402 (1996).

Rodriguez, A. M., Olano, C., Mendez, C., Hutchinson, C. R. and J. A. Salas. A cytochrome P450-like gene possibly involved in oleandomycin biosynthesis by *Streptomyces antibioticus*, *FEMS Microbiol. Lett.*, 127, 117–20 (1995).

Rouch, D., D. Cram, D. DiBerardino, T. Littlejohn and R. Skurray. Efflux-mediated antiseptic resistance gene qacA from *Staphylococcus aureus*: common ancestry with tetracycline and sugar-transport proteins. *Mol. Microbiol.*, 4, 2051–2062 (1990).

Sambrook, J., Fritsch, E. F. and Maniatis, T., *Molecular cloning: a laboratory manual*, 2nd ed, Cold Spring Harbor Laboratory Press, Cold Spring Harbor, N.Y. (1989).

Sartorelli, A. C., W. F. Hodnick, M. F. Belcourt, M. Tomasz, B. Haffly, J. J. Fischer, and S. Rockwell. Mitomycin C: a prototype bioreductive agent, *Oncol. Res.*, 6:501–508 (1994).

Schaferjohann, J., Yoo, J. G., Kusian, B. and B. Bowien. The cbb operons of the facultative chemoautotroph *Alcaligenes eutrophus* encode phosphoglycolate phosphatase, *J. Bacteriol.*, 175, 7329–40 (1993).

Schwecke, T., Aparicio, J. F., Molnar, I., Konig, A., Khaw, L. E., Haydock, S. F., Oliynyk, M., Caffrey, P., Cortes, J., Lester, J. B. and et al., The biosynthetic gene cluster for the polyketide immunosuppressant rapamycin, *Proc. Natl. Acad. Sci. USA*, 92, 7839–43 (1995).

Seno, E. T. and R. H. Baltz. *Structural organization and regulation of antibiotic biosynthesis and resistance genes in actinomycetes*, CRC Press, Boca Raton, Fla. (1989).

Sheldon, P. J., Johnson, D. A., August, P. J., Liu, H. W. and D. H. Sherman. Characterization of a mitomycin-binding drug resistance mechanism from the producing organism, *Streptomyces lavendulae*, *J. Bacteriol.*, 179, 1796–1804 (1997).

Shi, J., Gonzales, R. A. and Bhattacharyya, M. K., Identification and characterization of an S-adenosyl-L-methionine: delta 24-sterol-C-methyltransferase cDNA from soybean, *J. Biol. Chem.*, 271, 9384–9389 (1996).

Shikano, M., Onimura, K., Fukai, Y., Hori, M., Fukazawa, H., Mizuno, S., Yazawa, K. and Y. Uehara. 1a-docosahexaenoyl mitomycin C: a novel inhibitor of protein tyrosine kinase, *Biochem. Biophys. Res. Commun.*, 248, 858–863 (1998).

Simon, R., U. Priefer, and A. Puhler, A broad host range mobilization system for in vivo genetic engineering: Transposon mutagenesis in Gram negative bacteria, *Bio/Technology*, 1:784–791 (1983).

Smith, T. M., Y. F. Jiang, P. Shipley, and H. G. Floss. The thiostrepton-resistance encoding gene in *Streptomyces laurentii* is located within a cluster of ribosomal protein operons. *Gene*, 164, 137–142 (1995).

Smitskampwilms, E., Hendriks, H. R. and Peters, G. J., Development, pharmacology, role of DT-diaphorase and prospects of the indoloquinone EO9, *Gen Pharmacol.*, 27, 421–429 (1996).

Solenberg, P. J., P. Matsushima, D. R. Stack, S. C. Wilkie, R. C. Thompson, and R. H. Baltz. Production of hybrid glycopeptide antibiotics in vitro and in *Streptomyces toyocaensis*. *Chem. Biol.*, 4, 195–202 (1997).

Spanswick, V. J., Cummings, J. and J. F. Smyth. Current issues in the enzymology of mitomycin C metabolic activation, *Gen. Pharmacol.*, 31, 539–544 (1998).

Spath, C., Kraus, A. and W. Hillen. Contribution of glucose kinase to glucose repression of xylose utilization in *Bacillus megaterium*, *J. Bacteriol.*, 179, 7603–7605 (1997).

Stackebrandt, E., and C. R. Woese. Towards a phylogeny of the actinomycetes and related organisms. *Curr. Microbiol.*, 5, 197–202 (1981).

Staley, A. L., and K. L. Rinehart. Biosynthesis of the streptovaricins: 3-amino-5-hydroxybenzoic acid as a precursor to the meta-$C_7N$ unit. *J. Antibiot.*, 44, 218–224 (1991).

Stupperich, E., Juza, A., Hoppert, M. and F. Mayer. Cloning, sequencing and immunological characterization of the corrinoid-containing subunit of the N5-methyltetrahydromethanopterin: coenzyme-M methyltransferase from *Methanobacterium thermoautotrophicum, Euro. J Biochem.*, 217, 115–121 (1993).

Summers, R. G., Wendt-Pienkowski, E., Motamedi, H. and C. R. Hutchinson. Nucleotide sequence of the tcmII-tcmIV region of the tetracenomycin C biosynthetic gene cluster of *Streptomyces glaucescens* and evidence that the tcmN gene encodes a multifunctional cyclase-dehydratase-O-methyl transferase, *J. Bacteriol.*, 174, 1810–1820 (1992).

Takano, E., Gramajo, H. C., Strauch, E., Andres, N., White, J. and M. J. Bibb. Transcriptional regulation of the redD transcriptional activator gene accounts for growth-phase-dependent production of the antibiotic undecylprodigiosin in *Streptomyces coelicolor* A3(2), *Molecular Microbiology*, 6, 2797–2804 (1992).

Tang, L., Grimm, A., Zhang, Y. X. and C. R. Hutchinson. Purification and characterization of the DNA-binding protein DnrI, a transcriptional factor of daunorubicin biosynthesis in *Streptomyces peucetius, Molecular Microbiology*, 22, 801–13 (1996).

Tercero, J., R. Lacalle, and A. Jimenez. The pur8 gene from the pur cluster of *Streptomyces alboniger* encodes a highly hydrophobic polypeptide which confers resistance to puromycin. *Eur. J. Biochem.*, 218, 963–971 (1993).

Thauer, R. K., Hedderich, R. and R. Fischer. *Reactions and enzymes involved in methanogenesis from $CO_2$ and $H_2$,* Chapman and Hall, New York, N.Y., 1993.

Tomasz, M. Mitomycin C: small fast and deadly (but very selective), *Chemistry and Biology*, 2, 575–579 (1995).

Tomasz, M. and Y. Palom. The mitomycin bioreductive antitumor agents: cross-linking and alkylation of DNA as the molecular basis of their activity, *Pharmacol. Therap.*, 76, 73–87 (1997).

Tuan, J. S., Weber, J. M., Staver, M. J., Leung, J. O., Donadio, S. and L. Katz. Cloning of the genes involved in erythromycin biosynthesis from *Saccaropolyspora erythraea* using a novel Actinomycete-*Escherichia coli* cosmid, *Gene*, 90, 21–29 (1990).

Turgay, K., and M. A. Marahiel. A general approach for identifying and cloning peptide synthetase genes. *Peptide Res.*, 7, 238–241 (1994).

Vara, J., F. Malpartida, D. A. Hopwood, and A. Jimenez. Cloning and expression of a puromycin N-acetyl transferase gene from *Streptomyces alboniger* in *Streptomyces lividans* and *Escherichia coli Gene*, 33, 197–206 (1985).

Vaupel, M. and R. K. Thauer. Coenzyme F420-dependent N5, N10-methylenetetrahydromethanopterin reductase (Mer) from *Methanobacterium thermoautotrophicum* strain Marburg. Cloning, sequencing, transcriptional analysis, and functional expression in *Escherichia coli* of the mer gene, *Euro. J. Biochem.*, 231, 773–8 (1995).

Verweij, J. Mitomycins, *Cancer Chemotherapy and Biological Response Modifiers*, 17, 46–58 (1997).

Wakaki, K., Harumo, H., Tomioka, K., Shimizu, G., Kato, E., Kamada, H., Kudo, S. and Y. Fujimoto. Isolation of new fractions of antitumor mitomycins, *Antibiot. Chemother.*, 8, 228–240 (1958).

Webb, J. S., D. B. Cosalich, T. H. Mowat, J. B. Patrick, R. W. Broschard, W. E. Meyor, R. P. Williams, C. F. Wolf, W. Fulmore, C. Pidacks, and J. E. Lancaster. The structure of Mitomycins A, B, and C and Porfiromycin-Part 1. *J. Am. Chem. Soc.*, 84, 3185–3188 (1962).

White, P. J., Young, J., Hunter, I. S., Nimmo, H. G. and J. R. Coggins. The purification and characterization of 3-dehydroquinase from *Streptomyces coelicolor, Biochem. J.*, 265, 735–8 (1990).

Wietzorrek, A. and M. Bibb. A novel family of proteins that regulates antibiotic production in streptomycetes appears to contain an OmpR-like DNA-binding fold, *Molecular Microbiology*, 25, 1181–4 (1997).

Williams, R. M., Rajski, S. R. and S. B. Rollins. FR900482, a close cousin of mitomycin C that exploits mitosene-based DNA cross-linking, *Chemistry and Biology*, 4, 127–137 (1997).

Wu, T. S., J. Duncan, S. W. Tsao, C. J. Chang, P. J. Keller, and H. G. Floss. Biosynthesis of the ansamycin antibiotic assatrienin (mycotrienin) by *Streptomyces collinus. J. Natl. Prod.*, 50, 108–118 (1987).

Yamazaki, M., Thome, L., Mikolajczak, M., Armentrout, R. W. and T. J. Pollock. Linkage of genes essential for synthesis of a polysaccharide capsule in Sphingomonas strain S88, *J. Bacteriol.*, 178, 2676–87 (1996).

Yang, K., Han, L. and L. C. Vining. Regulation of jadomycin B production in *Streptomyces venezuelae* ISP5230: involvement of a repressor gene, jadR2, *Journal of Bacteriology*, 177, 6111–7 (1995).

Yanisch-Perron, C., J. Vieira, and J. Messing. Improved M13 phage cloning vectors and host strains: nucleotide sequences of the M13mp18 and pUC19 vectors, *Gene*, 33:103–119 (1985).

Zhang, H. Z., H. Schmidt, and W. Piepersberg. Molecular cloning and characterization of two lincomycin-resistance genes, ImrA and lmrB, from *Streptomyces lincolnensis* 78–11. *Mol. Microbiol.*, 6, 2147–2157 (1992).

While the present invention has been described in connection with the preferred embodiment thereof, it will be understood many modifications will be readily apparent to those skilled in the art, and this application is intended to cover any adaptations or variations thereof. It is manifestly intended this invention be limited only by the claims and equivalents thereof.

What is claimed is:

1. An isolated and purified nucleic acid molecule comprising at least a fragment of a nucleic acid sequence comprising a mitomycin biosynthetic gene cluster (mit/mmc),
   which fragment encodes a methyltransferase or a carbamoyltransferase that catalyzes a step in mitomycin biosynthesis, and which fragment has at least 80% nucleic acid sequence identity with at least one of SEQ ID NOs:35, 36, 52, 66, or 67, or
   comprising the complement of the fragment.

2. An isolated and purified nucleic acid molecule comprising a nucleic acid sequence encoding a gene product selected from the group consisting of MitN (SEQ ID NO:110), MitM (SEQ ID NO:109), MmcD (SEQ ID NO:119), MmcR (SEQ ID NO:133), and MmcS (SEQ ID NO:134).

3. The isolated and purified nucleic acid molecule of claim 1 which encodes MitN having SEQ ID NO:110 or MitM having SEQ ID NO:109.

4. The isolated and purified nucleic acid molecule of claim 1 which encodes MmcD having SEQ ID NO:119, MmcR having SEQ ID NO:133, or MmcS having SEQ ID NO:134.

5. The isolated and purified nucleic acid molecule of claim 1 which is from a naturally-occurring Streptomyces spp.

6. An isolated and purified nucleic acid molecule comprising a nucleic acid sequence encoding at least one gene product necessary for mitomycin biosynthesis wherein the nucleic acid sequence is selected from the group consisting of SEQ ID NO:35, SEQ ID NO:36, SEQ ID NO:52, SEQ ID NO:66 and SEQ ID NO:67.

7. An expression cassette comprising the nucleic acid molecule of claim 1, 2, 3, 4, 5 or 6 operably linked to a promoter fuctional in a host cell.

8. A recombinant host cell comprising a recombinant nucleic acid molecule comprising at least a fragment of a mitomycin biosynthetic gene cluster (mit/mmc) operably linked to a promoter functional in the host cell, wherein the fragment encodes a methyltransferase or a carbamoyltransferase that catalyzes a step in mitomycin biosynthesis, and wherein the fragment has at least 80% sequence identity with at least one of SEQ ID NOs:35, 36, 52, 66, or 67, or comprising the complement of the fragment.

9. The recombinant host cell of claim 8 wherein the fragment encodes MitN having SEQ ID NO:110 or MitM having SEQ ID NO:109.

10. The recombinant host cell of claim 8 wherein the fragment encodes MmcD having SEQ ID NO:119, MmcR having SEQ ID NO:133, or MmcS having SEQ ID NO:134.

11. The recombinant host cell of claim 8 in which levels of the methyltransferase or carbamoyltransferase in the recombinant cell are increased relative to the levels in a corresponding cell which does not comprise the recombinant nucleic acid molecule.

12. The recombinant host cell of claim 8 in which mitomycin levels are increased relative to the levels in a corresponding cell which does not comprise the recombinant nucleic acid molecule.

13. The recombinant host cell of claim 8 wherein the methyltransferase or carbamoyltransferase catalyzes a step in the production of a biologically active agent in the recombinant host cell that is not produced by a corresponding host cell which does not comprise the recombinant nucleic acid molecule.

14. A method for preparing a biologically active agent or a pharmaceutically acceptable salt thereof comprising culturing the host cell of claim 8 in a culture medium containing assimilable sources of carbon, nitrogen and inorganic salts under aerobic fermentation conditions so as to yield an increase in the agent relative to the level of the agent produced by a corresponding host cell which does not comprise the recombinant nucleic acid molecule.

15. A method for preparing a mitomycin or a pharmaceutically acceptable salt thereof comprising culturing the host cell of claim 8 in a culture medium containing assimilable sources of carbon, nitrogen and inorganic salts under aerobic fermentation conditions so as to yield an increase in the mitomycin relative to the level of the mitomycin produced by a corresponding host cell which does not comprise the recombinant nucleic acid molecule.

16. A recombinant bacterial host cell in which at least a portion of a nucleic acid molecule comprising a gene in the mitomycin biosynthetic gene cluster (mit/mmc) is disrupted relative to a corresponding bacterial host cell which lacks the disruption and produces mitomycin, so as to result in the recombinant bacterial host cell
    i) having decreased activity of a methyltransferase or a carbamoyltransferase relative to the corresponding bacterial host cell, and/or
    ii) producing a mitomycin not produced by the corresponding bacterial host cell, wherein the gene which is disrupted corresponds to a gene having at least 80% nucleic acid sequence identity with at least one of SEQ ID NOs:35, 36, 52, 66, or 67.

17. The host cell of claim 16 wherein the nucleic acid molecule which is disrupted encodes MitN having SEQ ID NO:110 or MitM having SEQ ID NO:109.

18. The host cell of claim 16 wherein the nucleic acid molecule which is disrupted encodes MmcD having SEQ ID NO:119, MmcR having SEQ ID NO:133, or MmcS having SEQ ID NO:134.

19. The recombinant bacterial host cell of claim 16 which is a recombinant *S. lavendulae* cell.

20. The recombinant host cell of claim 16 in which mitomycin levels are decreased relative to the levels in wild type *Streptomyces lavendulae*.

21. A method for preparing a biologically active agent or a pharmaceutically acceptable salt thereof comprising culturing the host cell of claim 16 in a culture medium containing assimilable sources of carbon, nitrogen and inorganic salts under aerobic fermentation conditions so as to yield an increase in the agent relative to the level of the agent produced by the corresponding host cell which lacks the disruption.

22. A method for preparing a mitomycin or a pharmaceutically acceptable salt thereof comprising culturing the host cell of claim 16 in a culture medium containing assimilable sources of carbon, nitrogen and inorganic salts under aerobic fermentation conditions so as to yield an increase in the mitomycin relative to the level of the mitomycin produced by the corresponding host cell which lacks the disruption.

23. A method to prepare a methyltransferase or a carbanoyltransferase, comprising: expressing a recombinant DNA molecule in a host cell so as to yield a methyltransferase or a carbamoyltransferase that catalyzes a step in mitomycin biosynthesis, wherein the recombinant DNA molecule comprises a promoter operably linked to a DNA sequence which encodes the methyltransferase or the carbamoyltransferase, and wherein the DNA sequence has at least 80% nucleic acid sequence identity with at least one of SEQ ID NOs:35, 36, 52, 66, or 67.

24. A method of preparing an expression cassette comprising DNA encoding a methyltransferase or a carbamoyltransferase comprising:
    a) providing an isolated Streptomyces DNA molecule that encodes a methyltransferase or a carbamoyltransferase which catalyzes a step in mitomycin biosynthesis, which DNA has at least 80% nucleic acid sequence identity with at least one of SEQ ID NOs:35, 36, 52, 66, or 67, or that comprises the complement of the DNA molecule; and
    b) linking the DNA molecule to a promoter functional in a host cell so as to yield an expression cassette.

25. The method of claim 24 wherein the expression cassette is in a vector.

* * * * *

UNITED STATES PATENT AND TRADEMARK OFFICE
CERTIFICATE OF CORRECTION

PATENT NO.   : 6,495,348 B1
DATED         : December 17, 2002
INVENTOR(S)  : David H. Sherman et al.

It is certified that error appears in the above-identified patent and that said Letters Patent is hereby corrected as shown below:

<u>Title page, Item [54] and Column 1, lines 1 and 2,</u>
In the title, delete "MITOMYCIN BIOSYNTHETIC GENE CLUSTER" and insert -- NUCLEIC ACID SEQUENCES ENCODING METHYLATION AND CARBAMOYLATION ENZYMES INVOLVED IN MITOMYCIN BIOSYNTHESIS -- therefor.

<u>Column 346,</u>
Line 18, delete "carbanoyltransferase" and insert -- carbamoyltransferase -- therefor.

Signed and Sealed this

Twelfth Day of August, 2003

JAMES E. ROGAN
*Director of the United States Patent and Trademark Office*